US012709612B2

(12) United States Patent
Braun et al.

(10) Patent No.: US 12,709,612 B2
(45) Date of Patent: Aug. 18, 2026

(54) PYRIDO-PYRIMIDINYL COMPOUNDS AND METHODS OF USE

(71) Applicant: Genentech, Inc., South San Francisco, CA (US)

(72) Inventors: Marie-Gabrielle Braun, San Francisco, CA (US); Joachim Rudolph, Burlingame, CA (US); Yao Wu, Beijing (CN); Guosheng Wu, Beijing (CN)

(73) Assignee: Genentech, Inc., South San Francisco, CA (US)

(*) Notice: Subject to any disclaimer, the term of this patent is extended or adjusted under 35 U.S.C. 154(b) by 961 days.

(21) Appl. No.: 17/404,568

(22) Filed: Aug. 17, 2021

(65) Prior Publication Data

US 2022/0204498 A1 Jun. 30, 2022

Related U.S. Application Data

(63) Continuation of application No. PCT/US2020/018499, filed on Feb. 17, 2020.

(30) Foreign Application Priority Data

Feb. 18, 2019 (WO) ................ PCT/CN2019/075328

(51) Int. Cl.
*C07D 471/04* (2006.01)
*A61P 35/00* (2006.01)
*C07D 471/00* (2006.01)

(52) U.S. Cl.
CPC ............ *C07D 471/04* (2013.01); *A61P 35/00* (2018.01); *C07D 471/00* (2013.01)

(58) Field of Classification Search
CPC ............................ C07D 471/04; C07D 471/00
See application file for complete search history.

(56) References Cited

U.S. PATENT DOCUMENTS

| | | | |
|---|---|---|---|
| 3,773,919 | A | 11/1973 | Boswell et al. |
| 7,868,177 | B2 | 1/2011 | Cee et al. |
| 7,880,000 | B2 | 2/2011 | Geuns-Meyer et al. |
| 8,476,434 | B2 | 7/2013 | Geuns-Meyer et al. |
| 8,815,885 | B2 | 8/2014 | Walter et al. |
| 9,382,230 | B2 | 7/2016 | Walter et al. |
| 2010/0048597 | A1 | 2/2010 | Beckwith et al. |
| 2016/0024094 | A1 | 1/2016 | Backes et al. |

FOREIGN PATENT DOCUMENTS

| | | | |
|---|---|---|---|
| JP | 2007/536280 | 12/2007 | |
| JP | 2010/514689 | 5/2010 | |
| JP | 6925435 | 8/2021 | |
| JP | 2021/536496 | 12/2021 | |
| WO | WO 96/15111 | 5/1996 | |
| WO | WO 01/19825 A1 | 3/2001 | |
| WO | WO 02/18380 | 3/2002 | |
| WO | WO 2004/063195 | 7/2004 | |
| WO | WO 2005/034869 A2 | 4/2005 | |
| WO | WO 2005/113494 A2 | 12/2005 | |
| WO | WO 2006/002367 | 1/2006 | |
| WO | WO 2006/039718 A2 | 4/2006 | |
| WO | WO 2006/056863 A1 | 6/2006 | |
| WO | WO 2007/100646 A1 | 9/2007 | |
| WO | WO 2007/136465 A2 | 11/2007 | |
| WO | WO-2008009076 A2 * | 1/2008 | ........... C07D 471/04 |
| WO | WO 2008/033999 A1 | 3/2008 | |
| WO | WO 2008/055842 | 5/2008 | |
| WO | WO 2010/031056 A2 | 3/2010 | |
| WO | WO 2011/097526 A1 | 8/2011 | |
| WO | WO 2013/067423 A1 | 5/2013 | |
| WO | WO 2013/090840 A1 | 6/2013 | |
| WO | WO 2014/052669 A1 | 4/2014 | |
| WO | WO 2014/179496 A1 | 11/2014 | |
| WO | WO 2014/179498 A1 | 11/2014 | |
| WO | WO 2014/182829 | 11/2014 | |
| WO | WO 2018/102751 A1 | 6/2018 | |
| WO | WO 2018/222918 A1 | 12/2018 | |
| WO | WO-2020117635 A1 * | 6/2020 | .............. A61P 35/00 |
| WO | WO-2020142612 A1 * | 7/2020 | ........... C07D 471/04 |
| WO | WO 2020/227020 A1 | 11/2020 | |
| WO | WO 2021/145521 | 7/2021 | |

OTHER PUBLICATIONS

Chusri et al., "HCV induces transforming growth factor β1 through activation of endoplasmic reticulum stress and the unfolded protein response", 2016, Scientific Reports, 6, 13 pgs. (Year: 2016).*

Han et al., "Synthesis and structure-activity relationships of PI3K/mTOR dual inhibitors from a series of 2-amino-4-methylpyrido[2,3-d]pyrimidine derivatives", 2014, Bioorganic & Medicinal Chemistry Letters, 24, pp. 4538-4541 (Year: 2014).*

Adachi et al., "ATF6 Is a Transcription Factor Specilaizing in the Regulation of Quality Control Proteins in the Endoplasmic Reticulum," Cell Struct. Func., 33:75-89, (2008).

Arai et al., "Transformation-associated gene regulation by ATF6α during hepatocarcinogenesis," FEBS Letts., 580:184-190, (2006).

Baek et al., "Involvement of Endoplasmic Reticulum Stress in Myofibroblastic Differentiation of Lung Fibroblasts," Am J. Resp. Cell Mol. Bio., 46:731-739, (2012).

Bogaert, S. et al., "Involvement of Endoplasmic Reticulum Stress in Inflammatory Bowel Disease: A Different Implication for Colonic and Ileal Disease?" PLoS One, 6(10):e25589, (2011).

Cao, S.S. et al., "The Unfolded Protein Response and Chemical Chaperones Reduce Protein Misfolding and Colitis in Mice," Gastroent, 144:989-1000, (2013).

Chiang, C-K. et al., "Endoplasmic Reticulum Stress Implicated in the Development of Renal Fibrosis," Mol. Med., 17:1295-1305, (2011).

(Continued)

*Primary Examiner* — Brenda L Coleman
*Assistant Examiner* — Madeline E Braun
(74) *Attorney, Agent, or Firm* — Alston & Bird LLP

(57) ABSTRACT

Provided herein are compounds and pharmaceutically acceptable salts thereof useful in the treatment of IRE1-related diseases and disorders described herein.

25 Claims, No Drawings

Specification includes a Sequence Listing.

(56) References Cited

OTHER PUBLICATIONS

Cross et al., "The molecular basis for selective inhibition of unconventional mRNA splicing by an IRE1-binding small molecule," PNAS, 109(15):E869-E878, (Apr. 10, 2012).
Galligan et al., "Oxidative Stress and the ER Stress Response in a Murine Model for Early-Stage Alcoholic Liver Disease," J. Toxicol., 2012(207594), 12 pgs., (2012).
Ghosh, et al., "Allosteric inhibition of the IRE1α Rnase preserves cell viability and function during endoplasmic reticulum stress," Cell, 158(3):534-548 (2014).
Harrington et al., "Unfolded Protein Response in Cancer: IRE1α Inhibition by Selective Kinase Ligands Does Not Impair Tumor Cell Viability," ACS Medicinal Chemistry Letters, 6(1):68-72, (2015).
Ji, C., "New Insights into the Pathogenesis of Alcholol-Induced Er Stress and Liver Diseases," Int. J. Hepatol., 2014(513787):1-11, (2014).
Ranatunga et al., "Synthesis of Novel Tricyclic Chromenone-Based Inhibitors of IRE-1 RNase Activity" Journal of Medicinal Chemistry, 57:4289-4301, (2014).
Schröder et al., "ER stress and the unfolded protein response," Mutation Research, 569:29-63, (2005).
Shin et al., "SIRT7 Represses Myc Activity to Suppress ER Stress and Prevent Fatty Liver Disease," Cell Reports, 5:654-665, (2013).
Sovolyova et al., "Stressed to death—mechanisms of ER stress-induced cell death," Biol Chem, 395:1-13, (2014).
Spitler et al., "Endoplasmic Reticulum Stress Contributes to Aortic Stiffening via Proapoptotic and Fibrotic Signaling Mechanismis," Hypertension, 63:e40-45, (2014).
Tanjore, H. et al., "Endoplasmic Reticulum Stress as a Pro-Fibrotic Stimulus," Biochim Biophys Acta, 1832:940-947, (2013).
Volkmann et al., "Potent and Selective Inhibitors of the Inositol-requiring Enzyme 1 Endoribonuclease," Journal of Biological Chemistry, 286(14):12743-12755, (Apr. 8, 2011).
Walter, P. et al., "The Unfolded Protein Response: From Stress Pathway to Homeostatic Regulation," Science, 334:1081-1086, (2011).
Wang et al., "Divergent allosteric control of the IRE1α endoribonuclease using kinase inhibitors," Nature Chemical Biology, 8:982-989, (Dec. 2012).
Wang et al., "Protein misfolding in the endoplasmic reticulum as a conduit to human disease," Nature, 529:326-335 (Jan. 21, 2016).
Yamamoto et al., "Differential Contributions of ATF6 and XBP1 to the Activation of Endoplasmic Reticulum Stress-Responsive cis-Acting Elements ERSE, UPRE and ERSE-II," J. Biochem., 136:343-50, (2004).
GC Application No. 2019-38265, Examination Report dated Jul. 28, 2021.
Taiwanese Application No. 108132813, Office Action dated Oct. 29, 2020. .
WIPO Application No. PCT/US2019/050698, PCT International Preliminary Report on Patentability mailed Mar. 25, 2021.
WIPO Application No. PCT/US2019/050698, PCT International Search Report and Written Opinion of the International Searching Authority mailed Nov. 18, 2019.
WIPO Application No. PCT/US2019/050749, PCT International Preliminary Report on Patentability mailed Mar. 25, 2021.
WIPO Application No. PCT/US2019/050749, PCT International Search Report and Written Opinion of the International Searching Authority mailed Nov. 21, 2019.
WIPO Application No. PCT/US2020/018499, PCT International Search Report and Written Opinion of the International Searching Authority mailed Jun. 17, 2020.
Beveridge et al., "Identification of BRaf-Sparing Amino-Thienopyrimidines with Potent IRE1a Inhibitory Activity," ACS Medicinal Chemistry Letters, 11(12):2389-2396, (Oct. 16, 2020).
REGISTRY(STN) [online], Dec. 7, 2011, [search date: Jan. 5, 2024] CAS No. 1348150-26-4.
REGISTRY(STN) [online], Dec. 7, 2011, [search date: Jan. 5, 2024] CAS No. 1350015-88-1.
EP Application No. 20702937.2, Office Action mailed Oct. 30, 2023.
JP Application No. 2021-539020, Reason for Refusal mailed Feb. 6, 2024.
JP Application No. 2021-548153, Reason for Refusal mailed Jan. 16, 2024.
EP Application No. 20711446.3, Office Action mailed May 19, 2023.
WIPO Application No. PCT/US2020/037233, PCT International Preliminary Report on Patentability mailed Dec. 23, 2021.
Binet, F. et al., "Neuronal ER Stress Impedes Myeloid-Cell-Induced Vascular Regeneration through IRE1α Degradation of Netrin-1," Cell Metabol., 17:353-371, (2013).
Bowen, T. et al., "MicroRNAs, transforming growth factor beta-1, and tissue fibrosis," J. Pathol., 229:274-285, (2013).
Cee, Victor J. et al., "Pyridyl-pyrimidine benzimidazole derivatives as potent, selective, and orally bioavailable inhibitors of Tie-2 kinase," Bioorganic & Medicinal Chemistry Letters, 19:424-427, (2009).
Cheng, A. C. et al., "Analysis of Kinase Inhibitor Selectivity using a Thermodynamics-Based Partition Index," J. Med. Chem. 53(11):4502-4510, (2010).
Davis, M., "Comprehensive analysis of kinase inhibitor selectivity," Nature Biotechnology, 29(11):1046-1051, (Nov. 1, 2011).
Heindryckx, F. et al., "Endoplasmic reticulum stress enhances fibrosis through IRE1α-mediated degradation of miR-150 and XBP-1 splicing," EMBO Molecular Medicine, 8(7):729-744, 2016.
Hollien, J. et al., "Decay of Endoplasmic Reticulum-Localized mRNAs During the Unfolded Protein Response," Science, 313:104-107, (2006).
Lu, M. et al., "Opposing unfolded-protein-response signals converge on death receptor 5 to control apoptosis," Science, 345:98-101, (2014).
Ren, L. et al., "The discovery of potent and selective pyridopyrimidin-7-one based inhibitors of B-RafV600E kinase," Bioorganic & Medicinal Chemistry Letters, 22:3387-3391, (2012).
Sriburi, R. et al., "XBP1: a link between the unfolded protein response, lipid biosynthesis, and biogenesis of the endoplasmic reticulum," J. Cell. Bio., 167:35-41, (2004).
Tirasophon, W. et al., "The endoribonuclease activity of mammalian IRE1 autoregulates its mRNA and is required for the unfolded protein response," Genes & Develop., 14:2725-2736, (2000).
Upton, J-P et al., "IRE1α cleaves select microRNAs during ER stress to derepress translation of proapoptotic Caspase-2," Science, 338:818-822, (2012).
EP Application No. 20 702 937.2, Communication pursuant to Article 94(3) EPC mailed Nov. 18, 2022.
JP Application No. 2021-513790, Office Action and Search Report issued Mar. 15, 2022.

* cited by examiner

PYRIDO-PYRIMIDINYL COMPOUNDS AND METHODS OF USE

CROSS-REFERENCE TO RELATED APPLICATIONS

This application is a Continuation of International Application No. PCT/US2020/018499, filed Feb. 17, 2020, which claims the benefit of priority to International Application No. PCT/CN2019/075328 filed Feb. 18, 2019, both of which are herein incorporated by reference in their entirety for all purposes.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 560909_SEQUENCE.TXT, created on Aug. 17, 2021, and having a size of 470 bytes and is filed concurrently with the specification. The sequence listing contained in this ASCII formatted document is part of the specification and is herein incorporated by reference in its entirety.

FIELD OF THE INVENTION

Provided herein are compounds or pharmaceutically acceptable salt thereof and methods of using such compounds for treating a cancer.

BACKGROUND

The kinase/endoribonuclease inositol requiring enzyme 1 (IRE1α), one of the key sensors of misfolded protein accumulation in the endoplasmic reticulum that triggers the unfolded protein response (UPR), is a potential therapeutic target for diverse diseases including cancer for inhibitors that bind to the ATP-binding site on the kinase moiety of IRE1α and block its endoribonuclease activity. IRE1α is a transmembrane, bifunctional protein with a luminal domain that binds to misfolded proteins, a transmembrane segment, and a cytoplasmic portion consisting of a kinase moiety and a tandem endoribonuclease domain. Structure-activity relationship (SAR) studies led to compounds selective in recombinant IRE1α kinase screens and potent against endoribonuclease activity of recombinant IRE1α as well as cellular IRE1α. IRE1α activity mediates certain cytoprotective and pro-survival functions of the UPR, increases viability and growth in certain tumor cell lines, and can be an effective therapeutic target for specific small molecule inhibitors that block malignant tumor growth, contrary to an earlier report (Harrington, P. E. et al (2015) ACS Med. Chem. Lett. 6:68-72). In addition, inhibitors of IRE1α can be therapeutically useful for other types of diseases besides cancer including certain autoimmune, neurodegenerative, fibrotic and metabolic disorders (Wang M. and Kaufman, R. J. (2016) Nature 529:326-335).

Homeostatic regulation of protein folding in the endoplasmic reticulum (ER) is under the control of three key intracellular signaling pathways: IRE1α, PERK, and ATF6, which together orchestrate the unfolded protein response (UPR) (Schroder, et al (2005) Mutat Res-Fund Mol Mech Metagenesis 569:29-63). An increase in demand for protein folding in the ER or certain types of cellular injury or stress lead to the accumulation of unfolded proteins in the ER—a condition called ER stress. Cells respond to ER stress by activating the UPR to help adjust or maintain their high-fidelity protein synthetic capacity (Walter, P. and Ron, D. (2011) Science, 334:1081-1086). IRE1α is the most evolutionarily conserved of the three branches of the UPR. Importantly, the UPR makes life/death decisions for the cell, depending on the severity and duration of ER stress, and the final outcome is either cell survival and recovery or programmed cell death (apoptosis) (Sovolyova et al, (2014) Biol Chem 395: 1-13). All three pathways of the UPR form a coordinated reaction to the accumulation of unfolded proteins; and several studies have demonstrated that there is cross talk between the different pathways (Yamamoto et al, J. Biochem. (2004) 136:343-350); Arai et al, FEBS Letts. (2006) 580:184-190; Adachi et al, Cell Struct. Func. (2008) 33:75-89). ER stress and activation of the UPR can be caused by mechanical injury, inflammation, genetic mutations, infections, oxidative stress, metabolic stress, and other types of cellular stress associated with malignancy. ER stress has also been implicated in diseases that result in fibrotic remodeling of internal organs, such as chronic liver diseases (Galligan et al, J. Toxicol. (2012) Vol. 2012, Article ID 207594, 12 pgs.; Shin et al, Cell Reports (2013) 5:654-665; Ji, Int. J. Hepatol. (2014) Vol. 2014, Article ID 513787, 11 pages), pulmonary fibrosis (Baek et al, Am. J. Resp. Cell Mol. Bio. (2012) 46:731-739); Tanjore et al, Biochim Biophys Acta (2012, online), (2013) 1832:940-947), kidney fibrosis (Chiang et al, Mol. Med. (2011) 17:1295-1305), cardiovascular disease (Spitler & Webb, Hypertension (2014) 63:e40-e45), and inflammatory bowel disease (Bogaert et al, PLoS One (2011) 6(10) e25589; Cao et al, Gastroent (2013) 144:989-1000).

Activation of the UPR has been shown to be an important survival pathway for tumors of secretory cell origin like multiple myeloma that have a very high protein synthesis burden. Therefore, efforts to disrupt the UPR by blocking the IRE1α endoribonuclease cleavage and activation of XBP1 have been an active area of cancer research. As a specific IRE1α RNase product, XBP1s is a direct indicator of functional IRE1 inhibition. A potent and selective IRE1α inhibitor would serve as an important tool to test the hypothesis that, without full UPR activation, tumor cells would be driven to apoptosis. IRE1α inhibitors and activating compounds have been reported (Harrington, P. E. et al (2015) ACS Med. Chem. Lett. 6:68-72; Volkmann, K., et al (2011) J. Biol. Chem., 286:12743-12755; Cross, B. C. S., et al (2012) Proc. Natl. Acad. Sci. U.S.A., 109:E869-E878; Wang, L., et al (2012) Nat. Chem. Biol., 8:982-989; Ghosh, R., et al (2014) Cell, 158:534-548; Ranatunga, S., et al (2014) J. Med. Chem., 57, 4289-4301; U.S. Pat. Nos. 9,382,230; 8,815,885).

Accordingly, there is a need for potent and selective inhibitors having suitable pharmacological properties for the treatment of IRE1-related diseases or disorders in patients.

SUMMARY

Provided herein are solutions to the problems above and other problems in the art.

Disclosed herein are compounds of Formula (I) or a stereoisomer, tautomer, or pharmaceutically acceptable salt thereof as described herein, including pharmaceutical compositions of the same that are inhibitors of IRE1α. The compounds described herein are useful in treating diseases and disorders mediated by IRE1α.

In a first aspect provided herein is a compound or pharmaceutically acceptable salt thereof of formula (I) as described herein, wherein $X^1$, $X^2$, $X^3$, ring B, $L^1$, $R^1$, $R^4$, $R^5$, $R^{13}$ and n are as described herein.

In another aspect provided herein is a compound of formula (II) as described herein, wherein $X^1$, $X^2$, $X^3$, ring A, ring B, $L^1$, $R^4$, $R^5$, $R^6$, and $R^{13}$ are as described herein.

In still another aspect provided herein is a compound or pharmaceutically acceptable salt thereof of Table 1 or Table 2.

In yet another aspect provided herein is a pharmaceutical composition comprising a compound or pharmaceutically acceptable salt thereof as described herein.

In another aspect provided herein is a method of treating an IRE1-related disease or disorder described herein by administering an effective amount of a compound or pharmaceutically acceptable salt thereof described herein.

In another aspect provided herein is a use of a compound or pharmaceutically acceptable salt thereof in the manufacture of a medicament for the treatment of an IRE1-related disease or disorder described herein.

In another aspect provided herein is a compound or pharmaceutically acceptable salt thereof described herein for use in a method of treating an IRE1-related disease or disorder described herein.

In still another aspect provided herein is a method of inhibiting or killing a cancer cell expressing Ire1 by contacting the cancer cell expressing Ire1 with a compound or pharmaceutically acceptable salt thereof as described herein.

In another aspect provided herein is a method of modulating Ire1 activity by contacting Ire1 with a compound or pharmaceutically acceptable salt thereof as described herein.

In another aspect provided herein is a kit for treating condition mediated by IRE1, where the kit comprises a compound or pharmaceutically acceptable salt thereof as described herein.

The present embodiments can be understood more fully by reference to the detailed description and examples, which are intended to exemplify non-limiting embodiments.

DETAILED DESCRIPTION

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

"Alkyl" as used herein refers to a saturated linear (i.e. unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having a 1 to 8 carbon atoms (a "$C_{1-8}$ alkyl"), having 1 to 6 carbon atoms (a "$C_{1-6}$ alkyl"), having 2 to 6 carbon atoms (a "$C_{2-6}$ alkyl"), having 1 to 4 carbon atoms (a "$C_{1-6}$ alkyl") or having 1 to 3 carbon atoms (a "$C_{1-3}$ alkyl"). Examples of alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Cycloalkyl" as used herein refers to non-aromatic, saturated or unsaturated cyclic univalent hydrocarbon structures having the number of carbon atoms designated (i.e., ($C_{3-10}$ means three to ten carbon atoms). Cycloalkyl can consist of one ring, such as cyclohexyl, or multiple rings, such as adamantly, but excludes aryl groups. A cycloalkyl comprising more than one ring can be fused, spiro, or bridged, or combinations thereof. Particular cycloalkyl groups are those having from 3 to 12 annular carbon atoms. A preferred cycloalkyl is a cyclic hydrocarbon having from 3 to 7 annular carbon atoms (a "$C_{3-7}$ cycloalkyl"), or having 3 to 6 carbon atoms (a "$C_{3-6}$ cycloalkyl"). Examples of cycloalkyl include, but are not limited to, cyclopropyl, cyclobutyl, cyclopentyl, cyclohyxyl, 1-cyclohexenyl, 3-cyclohexenyl, cycloheptyl, norbornyl, and the like.

"Heterocycloalkyl" as used herein refers to a cycloalkyl as defined herein where one or more of the ring carbon atoms have been replaced by a heteroatom such as, for example, nitrogen, oxygen, or sulfur. Representative examples of a heterocycloalkyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, pyrrolinyl, imidazolinyl, pyrazolinyl, thiazolinyl, piperidyl, piperidinyl, piperazinyl, piperazin-2-onyl, morpholinyl, thiomorpholinyl, tetrahydropyranyl (e.g., tetrahydro-2H-pyranyl), tetrahydrothiopyranyl, oxathianyl, dioxyl, dithianyl, pyranyl, dihydrodithiinyl, 1,4-dioxaspiro[4.5]decanyl, homopiperazinyl, quinuclidyl, and tetrahydropyrimidin-2(1H)-one groups.

"Aryl" as used herein refers to an unsaturated aromatic carbocyclic group having a single ring (e.g., phenyl) or multiple condensed rings (e.g., naphthyl or anthryl) which condensed rings can or cannot be aromatic. Particular aryl groups are those having from 6 to 14 annular (i.e., ring) carbon atoms (a "$C_{6-14}$ aryl"). Preferred aryl groups include those having 5 to 6 ring carbons. An aryl group having more than one ring where at least one ring is non-aromatic can be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, phosphorus, oxygen and sulfur. A heteroaryl group can have a single ring (e.g., pyridyl, furyl) or multiple condensed rings (e.g., indolizinyl, benzothienyl) which condensed rings can or cannot be aromatic. Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur. Still further, a heteroaryl as described herein can include rings have 5 or 6 members. A heteroaryl group having more than one ring where at least one ring is non-aromatic can be connected to the parent structure at either an aromatic ring position or at a non-aromatic ring position. In one variation, a heteroaryl group having more than one ring where at least one ring is non-aromatic is connected to the parent structure at an aromatic ring position.

"Halo" or Halogen" refers to fluoro, chloro, bromo and/or iodo. Where a residue is substituted with more than one halogen, it can be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which can be but are not necessarily the same halo; thus 4-chloro-3-fluorophenyl is within the scope of dihaloaryl.

An alkyl group in which one or more hydrogen is replaced with a halo group is referred to as a "haloalkyl", for example, "$C_{1-6}$ haloalkyl." An alkyl group in which each hydrogen is replaced with a halo group is referred to as a "perhaloalkyl." A preferred perhaloalkyl group is trifluoroalkyl ($—CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($—OCF_3$).

"Carbonyl" refers to the group C═O.

"Oxo" refers to the moiety ═O.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds or pharmaceutically acceptable salts thereof as described herein can contain asymmetric or chiral centers, and therefore exist in different stereoisomeric forms. It is intended that all stereoisomeric forms of the compounds or pharmaceutically acceptable salts thereof as described herein, including but not limited to, diastereomers, enantiomers and atropisomers, as well as mixtures thereof such as racemic mixtures, are included herein. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity. Enantiomers can be separated from a racemic mixture by a chiral separation method, such as supercritical fluid chromatography (SFC). Assignment of configuration at chiral centers in separated stereoisomers can be tentative, and depicted in Table 1 structures for illustrative purposes, before stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound or pharmaceutically acceptable salt thereof as described herein. Examples of solvents that form solvates include, but are not limited to, water (i.e., "hydrate"), isopropanol, ethanol, methanol, DMSO, ethylacetate (EtOAc), acetic acid (AcOH), and ethanolamine.

The term "administering" refers to the act of delivering a compound, pharmaceutically acceptable salt thereof, or pharmaceutical composition described herein into a patient by such routes as, for example, oral, mucosal, topical, suppository, intravenous, parenteral, intraperitoneal, intramuscular, intralesional, intrathecal, intranasal or subcutaneous administration. Parenteral administration includes intravenous, intramuscular, intra-arterial, intradermal, subcutaneous, intraperitoneal, intraventricular, and intracranial administration. Administration generally occurs after the onset of the cancer described herein, or its symptoms but. The term includes administering a chemotherapeutic agent or a therapy as described herein.

The term "coadministration" refers to administration of two or more agents (e.g., a compound, pharmaceutically acceptable salt thereof, or pharmaceutical composition with another active agent such as a chemotherapeutic agent described herein). The timing of coadministration depends in part of the compositions administered and can include administration at the same time, just prior to, or just after the administration of one or more additional therapies, for example cancer therapies such as chemotherapy, hormonal therapy, radiotherapy, or immunotherapy. Compounds, pharmaceutically acceptable salts thereof, and pharmaceutical compositions described herein may be administered alone or may be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation). The compounds described herein may be used in combination with one another, with other active agents known to be useful in treating a cancer described herein or associated with cells expressing a particular kinase as described herein, or with adjunctive agents that cannot be effective alone, but can contribute to the efficacy of the active agent.

A "1 L therapy" refers to the first line therapy administered to a treatment naïve cancer patient. Likewise, a 2 L, 3 L, and the like refer to subsequent therapies administered to a patient.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

"Metastatic" refers to cancer that has spread to tissues beyond the local tissue and regional lymph nodes. "Locally Advanced" refers to cancer that has spread from the immediate tissue only to surrounding tissue.

The term "clinical response" refers to inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. In general, clinical response refers to primary or secondary measures of efficacy known and understood in the art. Treatment and clinical response as described herein can be assessed using international standards for a given condition.

"Overall survival" or "OS" refers to the time from enrollment to death from any cause.

"Objective response rate" or "ORR" refers the proportion of patients with a confirmed complete response or partial response on two consecutive occasions ≥4 weeks apart, as determined by the investigator according to RECIST v1.1

"Time to progression" or "TTP" refers to the time from randomization until objective tumor progression.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

"Clinical benefit rate" or "CBR" refers to the proportion of patients with stable disease for at least 24 weeks or with confirmed complete or partial response, as determined by the investigator according to RECIST v1.1.

"Complete response" or "CR" refers to the disappearance of all target lesions and non-target lesions and (if applicable) normalization of tumor marker level.

"Partial response" or "non-CR/Non-PD" refers to persistence of one or more non-target lesions and/or (if applicable) maintenance of tumor marker level above the normal limits. A PR can also refer to ≥30% decrease in sum of diameters of target lesions, in the absence of CR, new lesions, and unequivocal progression in non-target lesions.

"Progressive disease" or "PD" refers to ≥20% increase in sum of diameters of target lesions, unequivocal progression in non-target lesions, and/or appearance of new lesions.

"Stable disease" or "SD" refers to neither sufficient shrinkage to qualify for CR or PR nor sufficient increase growth of tumor to qualify for PD.

The term "treatment" refers to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with the disease described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients. In certain embodiments, treatment can refer to a measured clinical outcome (e.g. increased OS, ORR, TTP, DOR, PFS, CBR, PR, CR, or SD).

The term "delaying progression" of a disease refers to deferring, hindering, slowing, retarding, stabilizing, and/or postponing development of a disease described herein. This delay can be of varying lengths of time, depending on the history of the cancer and/or patient being treated. As is evident to one skilled in the art, a sufficient or significant delay can, in effect, encompass prevention, in that the patient does not develop cancer.

An "effective amount" is at least the minimum amount required to effect a measurable improvement or prevention of a described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. An "effective amount" may be considered in the context of administering one or more therapeutic agents, and a single agent may be considered to be given in an effective amount if, in conjunction with one or more other agents, a desirable result may be or is achieved.

An "administration period" or "cycle" refers to a period of time comprising administration of a compound or pharmaceutically acceptable salt thereof described herein and an optional period of time comprising no administration of the compound or pharmaceutically acceptable salt thereof described herein. For example, a cycle can be 28 days in total length and include administration for 21 days and a rest period of 7 days. A "rest period" refers to a period of time where the compound or pharmaceutically acceptable salt thereof described herein is not administered. A rest period as provided herein can in some instances include administration of another agent that is not compound or pharmaceutically acceptable salt thereof described herein (e.g. an anticancer agent described herein). In such instances, administration of another agent during a rest period should not interfere or detriment administration of a compound or pharmaceutically acceptable salt thereof described herein.

A "dosing regimen" refers to a period of administration of a compound or pharmaceutically acceptable salt thereof described herein comprising one or more cycles, where each cycle can include administration of the compound or pharmaceutically acceptable salt thereof described herein at different times or in different amounts.

"QD" refers to administration of a compound or pharmaceutically acceptable salt thereof described herein once daily.

"BID", "TID", "and "QID" refer to administration of a compound or pharmaceutically acceptable salt thereof described herein 2, 3, and 4 times daily.

QW refers to administration of a compound or pharmaceutically acceptable salt thereof described herein once weekly.

"Q2W", "Q3W", and "Q4W" refer to administration of a compound or pharmaceutically acceptable salt thereof described herein once every 2, 3, and 4 weeks, respectively.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms (i.e. cancer), and they are generally treated by specialists in hematology and/or oncology. Hematological malignancies can derive from either of the two major blood cell lineages: myeloid and lymphoid cell lines. Lymphomas, lymphocytic leukemias, and myeloma are from the lymphoid line, while acute and chronic myelogenous leukemia, myelodysplastic syndromes and myeloproliferative diseases are myeloid in origin. Exemplary leukemias include acute lymphoblastic leukemia (ALL), acute myelogenous leukemia (AML), chronic lymphocytic leukemia (CLL), chronic myelogenous leukemia (CML), acute monocytic leukemia (AMOL) and small lymphocytic lymphoma (SLL). Exemplary lymphomas include Hodgkin's lymphomas (all four subtypes) and Non-Hodgkin's lymphomas (NHL, all subtypes).

An "IRE1-related disease" and the like refer to a disease described herein (e.g. a cancer described herein) having symptoms or requiring treatment as set forth herein that is/are wholly or partly associated with, a result of, a function of, or otherwise correlated to IRE1 activity as described herein.

A "anti-cancer agent" is a chemical compound useful in the treatment of cancer, regardless of mechanism of action. Classes of anti-cancer agents include, but are not limited to: alkylating agents, antimetabolites, anti-hormone therapies, endocrine therapies, immunomodulatory agents, spindle poison plant alkaloids, cytotoxic/antitumor antibiotics, topoisomerase inhibitors, antibodies, photosensitizers, and kinase inhibitors. Anti-cancer agents include compounds used in targeted therapy and conventional chemotherapy.

Exemplary anti-cancer agents include proteasome inhibitors such as bortezomib (VELCADE), carfilzomib (KYPROLIS) and ixazomib (NINLARO). Other examples include immunomodulatory agents such as lenalidomide (REVLIMID) and pomalidomide (POMALYST).

Other exemplary anti-cancer agents include inhibitors of B-cell receptor targets such as BTK, Bcl-2 and JAK inhibitors and include, for example, venetoclax (VENCLEXTA) and ibrutinib (IMBRUVICA).

Additional anti-cancer agents include, for example, Abemaciclib (VERZENIO); abiraterone (ZYTIGA, YONSA); aclarubicin; acivicin; acodazole; acronine; actinomycin; acylfulvene; adecypenol; adozelesin; adriamycin; aldesleukin; altretamine; ambamustine; ambomycin; ametantrone; amidox; amifostine; aminoglutethimide; aminolevulinic acid; amrubicin; amsacrine; anagrelide; anastrozole; andrographolide; antarelix; anthramycin; aphidicolin glycinate; apurinic acid; ARRY-300; arabinoside; asperlin; asulacrine; atamestane; atrimustine; azasetron; azatoxin; azatyrosine; azacitidine; AZD6244; AZD8330; azetepa; azotomycin; balanol; batimastat; bendamustine; benzochlorins; benzodopa; benzoylstaurosporine; beta-alethine; betaclamycin B; betulinic acid; bicalutamide; binimetinib; bisantrene; bisaziridinylspermine; bisnafide; bistratene; bleomycin; busulfan; bizelesin; breflate; bortezomib; brequinar; bropirimine; budotitane; buthionine; bryostatin; cactinomycin; calusterone; calcipotriol; calphostin C; camptothecin; capecitabine (XELODA); caracemide; carbetimer; carboplatin; carboquone; carmustine; carubicin; carzelesin; castanospermine; celecoxib; cetrorelix; cetuximab (ERBITUX); chloroquinoxaline; cicaprost; chlorambucil; chlorofusin; cisplatin; cladribine; clomifene; clotrimazole; crisnatol; crisnatol; cypemycin; cyclophosphamide; cytarabine; cytostatin; dacarbazine; dactinomycin; daratumamab; daunorubicin; decarbazine; dacliximab; dasatinib; decitabine; deslorelin; dexamethasone; dexifosfamide; dexrazoxane; dexverapamil; dexormaplatin; dezaguanine; diaziquone; dihydrotaxol; docosanol; dolasetron; docetaxel; doxorubicin; doxifluridine; droloxifene; dromostanolone; dronabinol; duazomycin; ebselen; ecomustine; edelfosine; edrecolomab; edatrexate; eflornithine; elemene; emitefur; elsamitrucin; enloplatin; enpromate; epipropidine; epirubicin; epristeride; erbulozole; erlotinib (TARCEVA); esorubicin; estramustine; etanidazole; etoposide; etoprine; exemestane; fadrozole; fazarabine; fenretinide; filgrastim; finasteride; flavopiridol; flezelastine; fluasterone; floxuridine; fludarabine; fludarabine; fluorodaunorubicin; forfenimex; formestane; fluorouracil; floxouridine; flurocitabine; fosquidone; fostriecin; fotemustine; fulvestrant (FASLODEX); gadolinium; gallium; galocitabine; ganirelix; gemcitabine; geldanamycin; gefitinib; gossyphol; hydroxyurea; hepsulfam; heregulin; ibandronate; ibrutinib; idarubicin; idelalisib (ZYDELIG), ifosfamide; canfosfamide; ilmofosine; iproplatin; idoxifene; idramantone; ilmofosine; ilomastat; imatinib mesylate (GLEEVEC); imiquimod; iobenguane; iododoxorubicin; ipomeanol; irinotecan; itasetron; iimofosine; lanreotide; lapatinib (TYKERB); leinamycin; lenograstim; lentinan; leptolstatin; letrozole; leuprorelin; levamisole; liarozole; lobaplatin; lombricine; lometrexol; lonidamine; lonafarnib (SARASAR); losoxantrone; lovastatin; loxoribine; lurtotecan; lapatinib; leucovorin; lometrexol; lomustine; maitansine; marimastat; masoprocol; maspin; menogaril; merbarone; meterelin; methioninase; metoclopramide; mifepristone; miltefosine; mirimostim; mitoguazone; mitolactol; mitonafide; mitoxantrone; mofarotene; molgramostim; mopidamol; maytansine; megestrol acetate; melengestrol acetate; melphalan; mercaptopurine; methotrexate; methotrexate sodium; metoprine; meturedepa; mitinmitomycin; mitosper; mitotane; mitoxantrone; mycophenolic acid; nafarelin; nagrestip; napavin; nedaplatin; nemorubicin; neridronic acid; nilutamide; nisamycin; oblimersen (GENASENSE); octreotide; okicenone; onapristone; ondansetron; ormaplatin; oxisuran; oxaloplatin; osaterone; oxaliplatin; oxaunomycin; palauamine; palbociclib (IBRANCE); panitumumab (VECTIBIX); panomifene; pegaspargase; picibanil; pirarubicin; piritrexim; prednisone; prednisolone, paclitaxel; nab-paclitaxel (ABRAXANE); prednimustine; procarbazine; puromycin; raltitrexed; ramosetron; rapamycin (RAPAMUNE); rhizoxin; ribociclib (KISQALI), rituximab; rogletimide; rohitukine; romurtide; roquinimex; romidepsin; safingol; saintopin; sargramostim; semustine; sizofiran; sobuzoxane; sorafenib (NEXAVAR); sunitinib; spiromustine; squalamine; suradista; suramin; swainsonine; spiroplatin; streptonigrin; streptozocin; sulofenur; tallimustine; tamoxifen; tauromustine; tazarotene; tellurapyrylium; temoporfin; temozolomide; teniposide; tetrachlorodecaoxide; tetrazomine; thrombopoietin; thymalfasin; thymotrinan; tirapazamine; toremifene; tretinoin; trimetrexate; triptorelin; tropisetron; talisomycin; taxotere; teroxirone; testolactone; thiamiprine; thiotepa; tirapazamine; toremifene; trastuzumab; trastuzumab emtansine; trestolone acetate; triciribine phosphate; trimetrexate; uracil mustard; vandetanib (CAPRELSA); variolin B; velaresol; veramine; verteporfin; vemurafenib; vinorelbine; vinxaltine; vitaxin; vinblastine; vincristine; vindesine; vinepidine; vinglycinate; vinleurosine; vinorelbine; vinrosidine; vinzolidine; vorozole; wortmannin; zanoterone; zeniplatin; zilascorb; zinostatin stimalamer; zinostatin; and zorubicin.

In some embodiments, an anti-cancer agent includes, for example, idelalisib (ZYDELIG), docetaxel, fluorouracil, gemcitabine (GEMZAR), cisplatin, cis-diamine, carboplatin, paclitaxel, nab-paclitaxel, trastuzumab (HERCEPTIN), temozolomide, tamoxifen, 4-hydroxytamoxifen, and doxorubicin.

Also included in the definition of anti-cancer agent are: (i) anti-estrogens and selective estrogen receptor modulators (SERMs), including, for example, tamoxifen, raloxifene, droloxifene, 4-hydroxytamoxifen, trioxifene, ketoxifene, LY117018, onapristone, and toremifine citrate; (ii) selective estrogen receptor modulators (SERDs) such as brilanestrant, GDC-0927, GDC-9545, AZ9496, AZ9833, GNE-274, and fulvestrant (FASLODEX); (iii) aromatase inhibitors such as, for example, 4(5)-imidazoles, aminoglutethimide, megestrol acetate, exemestane, formestanie, fadrozole, vorozole, letrozole, and anastrozole; (iv) anti-androgens such as apalutamide, abiraterone, enzalutamide, flutamide, nilutamide, bicalutamide, leuprolide, and goserelin.

Further included in the definition of anti-cancer agents are: (iv) MEK inhibitors such as cobimetinib; (v) lipid kinase inhibitors, such as taselisib; (vi) antisense oligonucleotides such as oblimersen; (vii) ribozymes such as VEGF expression inhibitors such as angiozyme; (viii) vaccines such as gene therapy vaccines, for example, ALLOVECTIN, LEUVECTIN, and VAXID; (ix) topoisomerase 1 inhibitors such as LURTOTECAN; ABARELIX rmRH; and (x) anti-angiogenic agents such as bevacizumab.

In some embodiments herein, the anti-cancer agent is a therapeutic antibody such as atezolizumab, nivolumab, daratumumab, pembrolizumab, alemtuzumab, bevacizumab; cetuximab; panitumumab, rituximab, pertuzumab, trastuzumab, trastuzumab emtansine, or tositumomab.

A "metabolite" is a product produced through metabolism in the body of a specified compound or salt thereof. Metabolites of a compound can be identified using routine techniques and their activities determined using tests such as those described herein. Such products can result for example from the oxidation, reduction, hydrolysis, amidation, deamidation, esterification, deesterification, enzymatic cleavage, and the like, of the administered compound. Accordingly, further provided herein are metabolites of compounds or pharmaceutically acceptable salts thereof described herein, including compounds produced by a process comprising contacting a compound of pharmaceutically acceptable salt thereof described herein with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., can be calculated.

A graded adverse event refers to the severity grading scale as established for by NCI CTCAE. In one embodiment, the adverse event is graded in accordance with the table below.

| Grade | Severity |
|---|---|
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living[a] |
| 3 | Severe or medically significant, but not immediately life-threatening; hospitalization or prolongation of hospitalization indicated; disabling; or limiting self-care activities of daily living[b,c] |
| 4 | Life-threatening consequences or urgent intervention indicated[d] |
| 5 | Death related to adverse event[d] |

Any formula or structure given herein, including Formula I compounds, is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds or pharmaceutically acceptable salts thereof as described herein include isotopes of hydrogen, carbon, nitrogen, oxygen, phosphorous, fluorine, and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds or pharmaceutically acceptable salts thereof as described herein, for example those into which radioactive isotopes such as $^{3}H$ and $^{14}C$ are incorporated. Such isotopically labeled compounds can be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds or pharmaceutically acceptable salts thereof as described herein can have improved DMPK (drug metabolism and pharmacokinetics) properties, relating to distribution, metabolism, and excretion (ADME). Substitution with heavier isotopes such as deuterium can afford certain therapeutic advantages resulting from greater metabolic stability, for example increased in vivo half-life or reduced dosage requirements. An 18F labeled compound can be useful for PET or SPECT studies. Isotopically labeled compounds or pharmaceutically acceptable salts thereof as described herein can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}H$ or D) can afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, can be defined by an isotopic enrichment factor. In the compounds or pharmaceutically acceptable salts thereof as described herein any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or pharmaceutically acceptable salts thereof as described herein any atom specifically designated as a deuterium (D) is meant to represent deuterium.

Compounds

Provided herein are compounds having the formula:

(I)

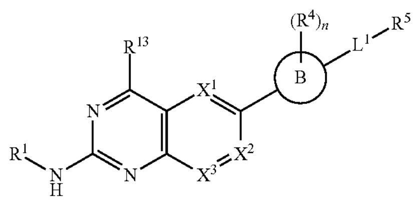

or a stereoisomer, tautomer or pharmaceutically acceptable salt thereof, wherein:

Ring B is $R^4$-substituted or unsubstituted $C_{3-7}$ cycloalkyl, $R^4$-substituted or unsubstituted 3 to 7 membered heterocycloalkyl, $R^4$-substituted or unsubstituted $C_{5-7}$ aryl, or $R^4$-substituted or unsubstituted 5 to 7 membered heteroaryl;

$L^1$ is —$NHSO_2$—, —$SO_2NH$—, —NH—, —NHC(O)—, —C(O)NH—, or pyrrolidin-2-one;

$X^1$ and $X^2$ are independently —N— or —$CR^2$—;

$X^3$ is —N— or —$CR^3$—, wherein one of $X^1$, $X^2$, and $X^3$ is —N—;

$R^1$ is $R^6$-substituted or unsubstituted $C_{1-6}$ alkyl, $R^6$-substituted or unsubstituted $C_{1-6}$ haloalkyl, $R^6$-substituted or unsubstituted $C_{3-7}$ cycloalkyl, or $R^6$-substituted or unsubstituted 3 to 7 membered heterocycloalkyl;

each $R^2$ is independently hydrogen, halogen, —$OR^7$, $R^{10}$-substituted or unsubstituted $C_{1-6}$ alkyl, $R^{10}$-substituted or unsubstituted $C_{3-7}$ cycloalkyl, or $R^{10}$-substituted or unsubstituted 3 to 7 membered heterocycloalkyl;

$R^3$ is hydrogen, halogen, —CN, —$OR^7$, —$NO_2$, —C(O)$R^7$, —C(O)$OR^7$, —C(O)$OR^7$, —C(O)$NR^{7A}R^{7B}$, —OC(O)$R^7$, —OC(O)$NR^{7A}R^{7B}$, —$SR^{7A}$, —S(O)$R^7$, —$S(O)_2R^7$, —S(O)(=$NR^{7A}$)$R^{7B}$, —$S(O)_2NR^{7A}R^{7B}$, —$NR^{7A}R^{7B}$, —$NR^{7A}C(O)R^7$, —$NR^{7A}C(O)OR^7$, —$N(R^{7A})C(O)NR^{7A}R^{7B}$, —$NR^{7A}S(O)_2R^7$, —$NR^{7A}S(O)_2NR^{7A}R^{7B}$, —$P(O)(R^7)_2$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, $R^{10}$-substituted or unsubstituted 3 to 7 membered heterocycloalkyl; $R^{10}$-substituted or unsubstituted $C_{5-7}$ aryl, or $R^{10}$-substituted or unsubstituted 5 to 7 membered heteroaryl;

each $R^4$ is hydrogen, halogen, —$OR^7$, —CN, —$S(O)_2R^7$, $R^{10}$-substituted or unsubstituted $C_{1-6}$ alkyl, $R^{10}$-substituted or unsubstituted $C_{1-6}$ haloalkyl, or $R^{10}$-substituted or unsubstituted $C_{3-7}$ cycloalkyl;

n is 0, 1, 2, 3, or 4;

$R^5$ is $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, $R^{10}$-substituted or unsubstituted 3 to 7 membered heterocycloalkyl, $R^{10}$-substituted or unsubstituted $C_{5-7}$ aryl, or $R^{10}$-substituted or unsubstituted 5 to 7 membered heteroaryl;

or, wherein an atom on $R^5$, together with $L^1$ and an atom on ring B, form a 4 to 7 membered heterocycloalkyl or 5 to 7 membered heteroaryl;

each $R^6$ is independently hydrogen, halogen, —$OR^7$, —$NR^{6A}R^{6B}$, $R^{10}$-substituted or unsubstituted $C_{1-6}$ alkyl, or $R^{10}$-substituted or unsubstituted $C_{1-6}$ haloalkyl;

$R^{6A}$ and $R^{6B}$ are independently hydrogen or $R^{10}$-substituted or unsubstituted $C_{1-6}$ alkyl, or $R^{6A}$ and $R^{6B}$ are taken together with the nitrogen atom to which they are attached to form a $R^{10}$-substituted or unsubstituted 4 to 7 membered heterocycloalkyl;

each $R^7$ is independently hydrogen, $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl;

each $R^{7A}$ and $R^{7B}$ is independently hydrogen, $R^{8A}$-substituted or unsubstituted $C_{1-6}$ alkyl, $R^{8A}$-substituted or unsubstituted $C_{1-6}$ haloalkyl, $R^{8A}$-substituted or unsubstituted $C_{3-7}$ cycloalkyl, or $R^{8A}$-substituted or unsubstituted 3 to 7 membered heterocycloalkyl;

each $R^{8A}$ is independently hydrogen, halogen, oxo, —CN, —$NO_2$, —C(O)H, —C(O)$CH_3$, —C(O)OH, —C(O)$OCH_3$, —C(O)$NH_2$, —OH, —$OCH_3$, —$OCF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)OH, —N(H)C(O)$NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl;

each $R^8$ is independently hydrogen, halogen, oxo, —CN, —$OR^{8B}$, —$NO_2$, —C(O)$R^{8B}$, —C(O)$OR^{8B}$, —C(O)$OR^{8B}$, —C(O)$NR^{8C}R^{8D}$, —OC(O)$R^{8B}$, —OC(O)$NR^{8C}R^{8D}$, —$SR^{8C}$, —S(O)$R^{8B}$, —$S(O)_2R^{8B}$, —S(O)(=$NR^{8C}$)$R^{8D}$, —$S(O)_2NR^{8C}R^{8B}$, —$NR^{8C}R^{8D}$, —$NR^{8C}C(O)R^{8B}$, —$NR^{8C}(O)OR^{8B}$, —$N(R^{8C})C(O)NR^{8C}R^{8D}$, —$NR^{8C}S(O)_2R^{8B}$, —$NR^{8C}S(O)_2NR^{8C}R^{8D}$, —$P(O)(R^{8B})_2$, $R^9$-substituted or unsubstituted $C_{1-6}$ alkyl, $R^9$-substituted or unsubstituted $C_{1-6}$ haloalkyl, $R^9$-substituted or unsubstituted $C_{3-7}$ cycloalkyl, $R^9$-substituted or unsubstituted 3 to 6 membered heterocycloalkyl; $R^9$-substituted or unsubstituted $C_{5-7}$ aryl, or $R^9$-substituted or unsubstituted 5 to 7 membered heteroaryl;

each $R^{8b}$, $R^{8C}$, and $R^{8D}$ is independently hydrogen, $R^{9A}$-substituted or unsubstituted $C_{1-6}$ alkyl, $R^{9A}$-substituted or unsubstituted $C_{1-6}$ haloalkyl, $R^{9A}$-substituted or unsubstituted $C_{3-7}$ cycloalkyl, or $R^{9'}$-substituted or unsubstituted 3 to 7 membered heterocycloalkyl;

each $R^{9A}$ is independently hydrogen, halogen, oxo, —CN, —$NO_2$, —C(O)H, —C(O)$CH_3$, —C(O)OH, —C(O)$OCH_3$, —C(O)$NH_2$, —OH, —$OCH_3$, —$OCF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)OH, —N(H)C(O)$NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl;

each $R^9$ is independently hydrogen, halogen, oxo, —CN, —$OR^{9B}$, —$NO_2$, —C(O)$R^{9B}$, —C(O)$OR^{9B}$, —C(O)$OR^{9B}$, —C(O)$NR^{9C}R^{9D}$, —OC(O)$R^{9B}$, —OC(O)

$NR^{9C}R^{9D}$, —$SR^{9C}$, —$S(O)R^{9B}$, —$S(O)_2R^{9B}$, —S(O)(═$NR^{9C}$)$R^{9D}$, —$S(O)_2NR^{9C}R^{9D}$, —$NR^{9C}R^{9D}$, —$NR^{9C}(O)R^{9B}$, —$NR^{9C}(O)OR^{9B}$, —$N(R^{9C})C(O)NR^{9C}R^{9D}$, —$NR^{9C}S(O)_2R^{9B}$, —$NR^{9C}S(O)_2NR^{9C}R^{9D}$, —$P(O)(R^{9B})_2$, $R^{12}$-substituted or unsubstituted $C_{1-6}$ alkyl, $R^{12}$-substituted or unsubstituted $C_{1-6}$ haloalkyl, $R^{12}$-substituted or unsubstituted $C_{3-7}$ cycloalkyl, $R^{12}$-substituted or unsubstituted 3 to 6 membered heterocycloalkyl; $R^{12}$-substituted or unsubstituted $C_{5-7}$ aryl, or $R^{12}$-substituted or unsubstituted 5 to 7 membered heteroaryl;

each $R^{9b}$ $R^{9C}$, and $R^{9D}$ is independently hydrogen, $R^{10A}$-substituted or unsubstituted $C_{1-6}$ alkyl, $R^{10A}$-substituted or unsubstituted $C_{1-6}$ haloalkyl, $R^{10A}$-substituted or unsubstituted $C_{3-7}$ cycloalkyl, or $R^{10A}$-substituted or unsubstituted 3 to 7 membered heterocycloalkyl;

each $R^{10A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl;

each $R^{10}$ is independently hydrogen, halogen, oxo, —CN, —$OR^{11A}$, —$NO_2$, —$C(O)R^{11A}$, —$C(O)OR^{11A}$, —$C(O)OR^{11A}$, —$C(O)NR^{11B}R^{11C}$, —$OC(O)R^{11A}$, —$OC(O)NR^{11B}R^{11C}$, —$SR^{11B}$, —$S(O)R^{11A}$, —$S(O)_2R^{11A}$, —S(O)═$NR^{11B}$)$R^{11C}$, —$S(O)_2NR^{11B}R^{11C}$, —$NR^{11B}R^{11C}$, —$NR^{11B}C(O)R^{11A}$, —$NR^{11B}C(O)OR^{11A}$, —$N(R^{11B})C(O)NR^{11B}R^{11C}$, —$NR^{11B}S(O)_2R^{11A}$, —$NR^{11B}S(O)_2NR^{11B}R^{11C}$, —$P(O)(R^{11A})_2$, $R^{11}$-substituted or unsubstituted $C_{1-6}$ alkoxy, $R^{11}$-substituted or unsubstituted $C_{1-6}$ alkyl, $R^{11}$-substituted or unsubstituted $C_{1-6}$ haloalkyl, $R^{11}$-substituted or unsubstituted $C_{3-7}$ cycloalkyl, $R^{11}$-substituted or unsubstituted 3 to 6 membered heterocycloalkyl; $R^{11}$-substituted or unsubstituted $C_{5-7}$ aryl, or $R^{11}$-substituted or unsubstituted 5 to 7 membered heteroaryl;

each $R^{11A}$, $R^{11B}$ and $R^{11C}$ is independently hydrogen, $R^{12A}$-substituted or unsubstituted $C_{1-6}$ alkyl, $R^{12A}$-substituted or unsubstituted $C_{1-6}$ haloalkyl, $R^{12A}$-substituted or unsubstituted $C_{3-7}$ cycloalkyl, or $R^{12A}$-substituted or unsubstituted 3 to 7 membered heterocycloalkyl;

each $R^{12A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl;

each $R^{11}$ is independently hydrogen, halogen, oxo, —CN, —$OR^{12B}$, —$NO_2$, —$C(O)R^{12B}$, —$C(O)OR^{12B}$, —$C(O)OR^{12B}$, —$C(O)NR^{12C}R^{12D}$, —$OC(O)R^{12B}$, —$OC(O)NR^{12C}R^{12D}$, —$SR^{12C}$, —$S(O)R^{12B}$, —$S(O)_2R^{12B}$, —S(O)(═$NR^{12C}$)$R^{12D}$, —$S(O)_2NR^{12C}R^{12D}$, —$NR^{12C}R^{12D}$, —$NR^{12C}C(O)R^{12B}$, —$NR^{12C}C(O)OR^{12B}$, —$N(R^{12C})C(O)NR^{12C}R^{12D}$, —$NR^{12C}S(O)_2R^{12B}$, —$NR^{12C}S(O)_2NR^{12C}R^{12D}$, —$P(O)(R^{12B})_2$, $R^{12}$-substituted or unsubstituted $C_{1-6}$ alkyl, $R^{12}$-substituted or unsubstituted $C_{1-6}$ haloalkyl, $R^{12}$-substituted or unsubstituted $C_{3-7}$ cycloalkyl, $R^{12}$-substituted or unsubstituted 3 to 6 membered heterocycloalkyl; $R^{12}$-substituted or unsubstituted $C_{5-7}$ aryl, or $R^{12}$-substituted or unsubstituted 5 to 7 membered heteroaryl;

each $R^{12B}$, $R^{12C}$ and $R^{12D}$ is independently hydrogen, unsubstituted $C_{1-6}$ alkyl, unsubstituted $C_{1-6}$ haloalkyl, unsubstituted $C_{3-7}$ cycloalkyl, or unsubstituted 3 to 7 membered heterocycloalkyl;

each $R^{12}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —$OC(O)CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$, unsubstituted $C_{1-6}$ alkoxy, unsubstituted $C_{1-6}$ alkyl, unsubstituted $C_{1-6}$ alkoxy, unsubstituted $C_{1-6}$ haloalkyl, unsubstituted $C_{1-6}$ haloalkoxy, unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl; and $R^{13}$ is hydrogen, halogen, or $R^{10}$-substituted or unsubstituted $C_{1-6}$ alkyl.

In one embodiment, $R^1$ is $R^6$-substituted or unsubstituted $C_{1-6}$ alkyl, $R^6$-substituted or unsubstituted $C_{1-6}$ haloalkyl, $R^6$-substituted or unsubstituted $C_{3-7}$ cycloalkyl, or $R^6$-substituted or unsubstituted 3 to 7 membered heterocycloalkyl. In one preferred embodiment, $R^1$ is $R^6$-substituted or unsubstituted $C_{1-6}$ alkyl.

In a preferred embodiment, $R^1$ is $R^6$-substituted $C_{3-6}$ cycloalkyl or $R^6$-substituted 3 to 6 membered heterocycloalkyl. In a preferred embodiment, $R^1$ is $R^6$-substituted cyclohexyl or $R^6$-substituted piperidinyl.

$R^1$ can have formula:

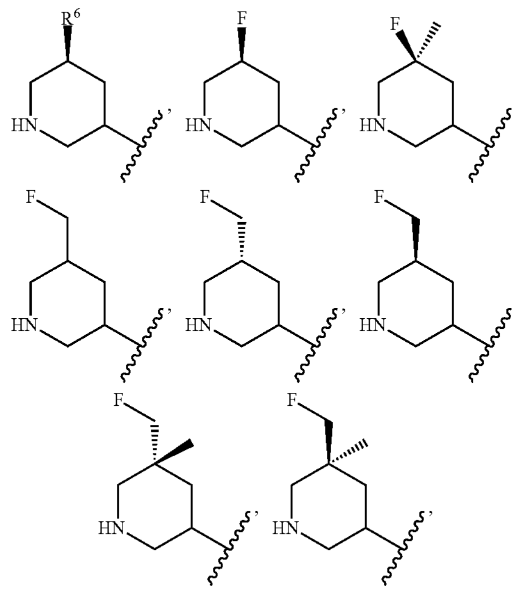

-continued

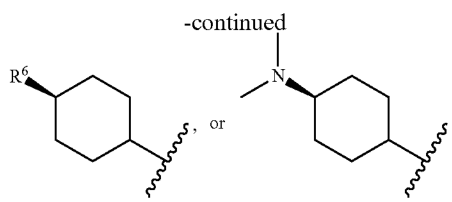

In one embodiment, $R^1$ is halogen-substituted piperidinyl. In another embodiment, $R^1$ is piperidinyl substituted by methyl, ethyl, halogen, or a combination thereof. In one embodiment, $R^1$ is halogen-substituted cyclohexyl. In another embodiment, $R^1$ is cyclohexyl substituted by one —$NR^{6A}R^{6B}$ moiety, where $R^{6A}$ and $R^{6B}$ are each $R^{10}$-substituted or unsubstituted $C_{1-6}$ alkyl.

In one preferred embodiment, $R^1$ is Ring A forming a compound or pharmaceutically acceptable salt thereof having formula II:

(II)

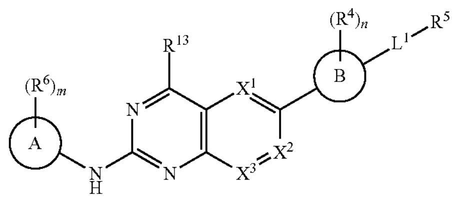

where $X^1$, $X^2$, $X^3$, $L^1$, $R^4$, $R^5$, $R^6$, and $R^{13}$ are as defined herein;

ring A is $R^6$-substituted or unsubstituted $C_{3-7}$ cycloalkyl, or $R^6$-substituted or unsubstituted 3 to 7 membered heterocycloalkyl, as defined herein for, for example, $R^1$;

and m is 0, 1, 2, 3, 4, or 5.

In one embodiment, each $R^2$ is independently hydrogen, halogen, or —$OR^7$. In another embodiment, each $R^2$ is independently $R^{10}$-substituted or unsubstituted $C_{1-6}$ alkyl. In another embodiment, each $R^2$ is independently $R^{10}$-substituted or unsubstituted $C_{3-7}$ cycloalkyl or $R^{10}$-substituted or unsubstituted 3 to 7 membered heterocycloalkyl.

In one embodiment, each $R^2$ is independently hydrogen, —$OR^7$, or $R^{10}$-substituted or unsubstituted $C_{1-6}$ alkyl. Where $R^2$ is independently —$OR^7$, $R^7$ can be hydrogen, $R^8$-substituted or unsubstituted $C_{1-6}$ alkyl, or $R^8$-substituted or unsubstituted $C_{1-6}$ haloalkyl. In another embodiment, where $R^2$ is independently —$OR^7$, $R^7$ is unsubstituted $C_{1-6}$ alkyl, or unsubstituted $C_{1-6}$ haloalkyl. In another embodiment, where $R^2$ is independently —$OR^7$, $R^7$ is $R^{10}$-substituted $C_{1-6}$ alkyl, or $R^{11}$-substituted $C_{1-6}$ haloalkyl and where $R^{10}$ can be halogen, oxo, —CN, —$NH_2$, —$NH(CH_3)$, —$N(CH_3)_2$, —$CF_3$, —$CHF_2$, —$CH_2F$, —$C(CH_3)_2F$, —$C(CH_3)F_2$, $R^{11}$-substituted or unsubstituted $C_{1-6}$ alkyl, $R^{11}$-substituted or unsubstituted $C_{1-6}$ haloalkyl, $R^{11}$-substituted or unsubstituted $C_{3-7}$ cycloalkyl, or $R^{11}$-substituted or unsubstituted 3 to 6 membered heterocycloalkyl.

In still another embodiment, where $R^2$ is independently —$OR^7$, $R^7$ is $R^8$-substituted or unsubstituted $C_{3-7}$ cycloalkyl or $R^8$-substituted or unsubstituted 3 to 7 membered heterocycloalkyl. In another aspect provided herein is where $R^2$ is independently —$OR^7$, $R^7$ is $R^8$-substituted or unsubstituted 3 to 7 membered heterocycloalkyl. In one embodiment, $R^7$ is $R^8$-substituted or unsubstituted oxetanyl, tetrahydrofuranyl, furanyl, oxazolyl, isoxazolyl, azetidinyl, pyrrolidinyl, pyrrolyl, or imidazolyl.

In a preferred embodiment, $R^2$ and $R^3$ are not both hydrogen. In one embodiment, $R^2$ is hydrogen and $R^3$ is not hydrogen. In another embodiment, $R^2$ is not hydrogen and $R^3$ is not hydrogen where $X^1$ is —N—. In another embodiment, $R^2$ is hydrogen and $R^3$ is not hydrogen where $X^1$ is —N—.

In one embodiment, $R^3$ is hydrogen, halogen, —$OR^7$, —$NR^{7A}R^{7B}$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, or $R^{10}$-substituted or unsubstituted 3 to 7 membered heterocycloalkyl.

In one embodiment, $R^3$ is hydrogen. In another embodiment, when $X^1$ is N, $R^3$ is not hydrogen. In another embodiment, $R^3$ is —$OR^7$ or —$NR^{7A}R^{7B}$. In one embodiment, where $R^3$ is —$OR^7$, $R^7$ is $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl. In one embodiment, where $R^3$ is —$NR^{7A}R^{7B}$, $R^{7A}$ and $R^{7B}$ are independently hydrogen or $R^{8A}$-substituted or unsubstituted $C_{1-6}$ alkyl.

In another embodiment, $R^3$ is $R^{10}$-substituted or unsubstituted $C_{1-6}$ alkyl or $R^{10}$-substituted or unsubstituted $C_{1-6}$ haloalkyl. In one preferred embodiment, $R^3$ is methyl, ethyl, propyl, or isopropyl. In one preferred embodiment, $R^3$ is —$C(CH_3)_2F$, —$C(CH_3)F_2$, —$CH_2F$, —$CHF_2$, or —$CF_3$.

In another embodiment, $R^3$ is $R^{10}$-substituted or unsubstituted $C_{3-7}$ cycloalkyl or $R^{10}$-substituted or unsubstituted 3 to 7 membered heterocycloalkyl. In one embodiment, $R^3$ is $R^{10}$-substituted or unsubstituted 3 to 7 membered heterocycloalkyl. In one embodiment, $R^3$ is $R^{10}$-substituted or unsubstituted 4-membered heterocycloalkyl. In one embodiment, $R^3$ is $R^{10}$-substituted or unsubstituted azetidinyl or oxetanyl. In one embodiment, $R^3$ is $R^{10}$-substituted or unsubstituted 5-membered heterocycloalkyl. In a preferred embodiment, $R^3$ is $R^{10}$-substituted or unsubstituted pyrrolidinyl, pyrrolyl, imidazolyl, tetrahydrofuranyl, furanyl, oxazolyl, oxazolidinyl, or isoxazolyl. In one embodiment, $R^3$ is $R^{10}$-substituted or unsubstituted pyrrolidinyl, pyrrolyl, imidazolyl, tetrahydrofuranyl, furanyl, oxazolyl, oxazolidinyl, or isoxazolyl, where $R^{10}$ is halogen, oxo, —CN, —$NO_2$, —C(O)H, —$C(O)CH_3$, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, —$C(CH_3)F_2$, unsubstituted $C_{1-6}$ alkyl, or unsubstituted $C_{1-6}$ haloalkyl, In one embodiment, $R^3$ is $R^{10}$-substituted or unsubstituted 6-membered heterocycloalkyl. In one embodiment, $R^3$ is $R^{10}$-substituted or unsubstituted oxetanyl or oxazolidinyl. In one embodiment, $R^3$ is $R^{10}$-substituted or unsubstituted morpholino, piperidinyl, piperazinyl, pyranyl, tetrahydropyranyl, or dioxanyl. In one embodiment, $R^3$ is $R^{10}$-substituted or unsubstituted 7-membered heterocycloalkyl. In one embodiment, $R^3$ is $R^{10}$-substituted or unsubstituted oxazepanyl, azepanyl, or oxepanyl.

In one embodiment, each $R^4$ is hydrogen, halogen, —$OR^7$, —CN, or —$S(O)_2R^7$. In another embodiment, each $R^4$ is $R^{10}$-substituted or unsubstituted $C_{1-6}$ alkyl or $R^{10}$-substituted or unsubstituted $C_{1-6}$ haloalkyl. In still another embodiment, each $R^4$ is $R^{10}$-substituted or unsubstituted $C_{3-7}$ cycloalkyl.

In one embodiment, n is 0, 1, or 2. In another embodiment, n is 1, 2, or 3. In another embodiment, n is 2, 3, or 4.

In one embodiment, $R^4$ is halogen and n is 1, 2, or 3. In another embodiment, $R^4$ is halogen and n is 1. In one preferred embodiment, $R^4$ is F and n is 1, 2, or 3.

In another embodiment, $R^4$ is $—OR^7$ and n is 1. In one preferred embodiment, where $R^4$ is $—OR^7$, $R^7$ is $R^8$-substituted or unsubstituted $C_{1-6}$ alkyl or $R^8$-substituted or unsubstituted $C_{1-6}$ haloalkyl. In one embodiment, $R^4$ is $—O(C_{1-3}$ unsubstituted alkyl) or $—O(C_{1-3}$ unsubstituted haloalkyl). In another embodiment, $R^4$ is $—OCH_3$, $—OCH_2CH_3$, $—O(CH_2)_2CH_3$, $—OCH_2F$, $—OCHF_2$, $—OCF_3$, $—OC(CH_3)_2F$, $—OC(CH_3)F_2$, $—O(CH_2)CH_2F$, $—O(CH_2)CHF_2$, or $—OCH_2CF_3$.

In one embodiment, $L^1$ is $—NHSO_2—$, $—SO_2NH—$, —NHC(O)—, —C(O)NH—, or pyrrolidin-2-one. In another embodiment, $L^1$ is $—NHSO_2—$, —NHC(O)—, or pyrrolidin-2-one. In a preferred embodiment, $L^1$ is $—NHSO_2—$. In another preferred embodiment, $L^1$ is-NHC(O)—.

In one embodiment, $R^5$ is $R^{10}$-substituted or unsubstituted $C_{1-6}$ alkyl or $R^{10}$-substituted or unsubstituted $C_{1-6}$ haloalkyl. In one embodiment, $R^5$ is $R^{10}$-substituted or unsubstituted $C_{3-7}$ cycloalkyl or $R^{10}$-substituted or unsubstituted 3 to 7 membered heterocycloalkyl. In one embodiment, $R^5$ is $R^{10}$-substituted or unsubstituted 3 to 7 membered heterocycloalkyl. In one embodiment, $R^5$ is $R^{10}$-substituted or unsubstituted pyrrolidinyl, pyrazolinyl, tetrahydrofuranyl, piperidinyl, piperazinyl, tetrahydropyranyl, or morphino. In a particular embodiment, $R^5$ is $R^{10}$-substituted or unsubstituted 4 to 6 membered heterocycloalkyl comprising at least one nitrogen heteroatom.

In one embodiment, $R^5$ is $R^{10}$-substituted or unsubstituted $C_{5-7}$ aryl, or $R^{10}$-substituted or unsubstituted 5 to 7 membered heteroaryl. In one embodiment, $R^5$ is not phenyl.

In another embodiment, $R^5$ is $R^{10}$-substituted or unsubstituted benzyl, $R^{10}$-substituted or unsubstituted pyrrolidinyl, $R^{10}$-substituted or unsubstituted piperidinyl, or $R^{10}$-substituted or unsubstituted $C_{1-6}$ haloalkyl. $R^{10}$ can be halogen, —CN, $R^{11}$-substituted or unsubstituted $C_{1-6}$ alkoxy, $R^{11}$-substituted or unsubstituted $C_{1-6}$ alkyl, or $R^{11}$-substituted or unsubstituted $C_{1-6}$ haloalkyl.

In one embodiment, $R^5$ is $R^{10}$-substituted or unsubstituted benzyl. In a particular embodiment, $R^5$ is unsubstituted benzyl. In some embodiments, $R^5$ is $R^{10}$-substituted benzyl, where $R^{10}$ is hydrogen, halogen, —OH, —CN, $—CF_3$, $—CHF_2$, $—CH_2F$, $—C(CH_3)_2F$, $—C(CH_3)F_2$, methyl, propyl, or ethyl.

In another embodiment, $R^5$ is $R^{10}$-substituted or unsubstituted piperidinyl. In some embodiments, $R^5$ is $R^{10}$-substituted piperidinyl $R^{10}$ is hydrogen, halogen, —OH, —CN, $—CF_3$, $—CHF_2$, $—CH_2F$, $—C(CH_3)_2F$, $—C(CH_3)F_2$, methyl, propyl, or ethyl.

In still another embodiment, $R^5$ is $R^{10}$-substituted or unsubstituted $C_{1-6}$ alkyl, $R^{10}$-substituted or unsubstituted $C_{1-6}$ haloalkyl, or $R^{10}$-substituted or unsubstituted 3 to 6 membered cycloalkyl. In some embodiments, $R^{10}$ is halogen, —CN, $R^{11}$-substituted or unsubstituted $C_{1-6}$ alkoxy, $R^{11}$-substituted or unsubstituted $C_{1-6}$ alkyl, or $R^{11}$-substituted or unsubstituted $C_{1-6}$ haloalkyl. In another embodiment, $R^{10}$ is hydrogen, halogen, —OH, —CN, $—CF_3$, $—CHF_2$, $—CH_2F$, $—C(CH_3)_2F$, $—C(CH_3)F_2$, methyl, propyl, or ethyl.

In one embodiment, $R^5$ is $R^{10}$-substituted or unsubstituted $C_{1-6}$ alkyl or $R^{10}$-substituted or unsubstituted $C_{1-6}$ haloalkyl. In a particular embodiment, $R^5$ is $R^{10}$-substituted $C_{1-6}$ alkyl, where $R^{10}$ is hydrogen, halogen, —OH, —CN, $—CF_3$, $—CHF_2$, $—CH_2F$, $—C(CH_3)_2F$, $—C(CH_3)F_2$, methyl, propyl, or ethyl.

In one embodiment, each $R^6$ is independently hydrogen or halogen. In one embodiment, each $R^6$ is independently $—OR^7$ or $—NR^{6A}R^{6B}$. In another embodiment, each $R^6$ is independently $R^{10}$-substituted or unsubstituted $C_{1-6}$ alkyl or $R^{10}$-substituted or unsubstituted $C_{1-6}$ haloalkyl.

In one embodiment, each $R^6$ is independently hydrogen, halogen, $R^{10}$-substituted or unsubstituted $C_{1-6}$ alkyl, $R^{10}$-substituted or unsubstituted $C_{1-6}$ haloalkyl, or $—NR^{6A}R^{6B}$. In another embodiment, each $R^6$ is independently hydrogen, halogen, or $R^{10}$-substituted or unsubstituted $C_{1-6}$ alkyl.

In a preferred embodiment, each $R^6$ is independently hydrogen, halogen, methyl, ethyl, propyl, isopropyl, $—NH_2$, $—NH(CH_3)$, $—N(CH_3)_2$, $—O(CH_3)$, $—(CH_2)_2OCH_3$, $—CF_3$, $—CHF_2$, $—CH_2F$, $—C(CH_3)_2F$, or $—C(CH_3)F_2$. In another preferred embodiment, each $R^6$ is independently hydrogen, halogen, methyl, ethyl, $—NH_2$, $—NH(CH_3)$, $—N(CH_3)_2$, $—O(CH_3)$, $—(CH_2)_2OCH_3$, $—CHF_2$, or $—CH_2F$.

In one embodiment, each $R^6$ is independently hydrogen, $R^{10}$-substituted or unsubstituted $C_{1-6}$ alkyl, or $R^{10}$-substituted or unsubstituted $C_{1-6}$ haloalkyl. In another embodiment, each $R^6$ is independently hydrogen or $—NR^8R^9$, where at least one $R^6$ is $—NR^{6A}R^{6B}$ and where $R^{6A}$ and $R^{6B}$ are each $R^{10}$-substituted or unsubstituted $C_{1-6}$ alkyl.

In one embodiment, $R^{6A}$ and $R^{6B}$ are independently hydrogen. In a preferred embodiment, $R^{6A}$ and $R^{6B}$ are independently $R^{10}$-substituted or unsubstituted $C_{1-6}$ alkyl. In one embodiment, $R^{6A}$ and $R^{6B}$ are taken together with the nitrogen atom to which they are attached to form a $R^{10}$-substituted or unsubstituted 4 to 7 membered heterocycloalkyl. In one embodiment, $R^{6A}$ and $R^{6B}$ are taken together with the nitrogen atom to which they are attached to form a $R^{10}$-substituted or unsubstituted 5 membered heterocycloalkyl.

In one embodiment, each $R^7$ is independently $R^8$-substituted or unsubstituted $C_{1-6}$ alkyl or $R^8$-substituted or unsubstituted $C_{1-6}$ haloalkyl. In another embodiment, each $R^7$ is independently $R^8$-substituted or unsubstituted $C_{3-7}$ cycloalkyl or $R^8$-substituted or unsubstituted 3 to 7 membered heterocycloalkyl. In a particular embodiment, each $R^7$ is independently $R^8$-substituted or unsubstituted $C_{1-6}$ alkyl. In one embodiment, each $R^7$ is independently methyl, ethyl, or propyl. In another embodiment, each $R^7$ is independently $R^8$-substituted or unsubstituted $C_{1-6}$ haloalkyl. In one embodiment, each $R^7$ is independently $—CF_3$, $CHF_2$, or $CH_2F$.

In one embodiment, at least one $R^{7A}$ and $R^{7B}$ is hydrogen. In another embodiment, each $R^{7A}$ and $R^{7B}$ is independently $R^{8A}$-substituted or unsubstituted $C_{1-6}$ alkyl or $R^{8A}$-substituted or unsubstituted $C_{1-6}$ haloalkyl. In another embodiment, each $R^{1A}$ and $R^{7B}$ is independently $R^{8A}$-substituted or unsubstituted $C_{3-7}$ cycloalkyl or $R^{8A}$-substituted or unsubstituted 3 to 7 membered heterocycloalkyl.

In one embodiment, each $R^{8A}$ is independently hydrogen, halogen, oxo, —CN, $—NO_2$, —C(O)H, $—C(O)CH_3$, —C(O)OH, $—C(O)OCH_3$, $—C(O)NH_2$, —OH, $—OCH_3$, $—OCF_3$, —OC(O)H, $—OC(O)\ CH_3$, $—OC(O)NH_2$, —SH, —S(O)H, $—S(O)_2H$, —S(O)(=NH)H, $—S(O)_2NH_2$, $—NH_2$, $—NH(CH_3)$, $—N(CH_3)_2$, —NHC(O)H, —NHC(O)OH, $—N(H)C(O)NH_2$, $—NHS(O)_2H$, $—NHS(O)_2NH_2$, or $—P(O)(CH_3)_2$, $—CF_3$, $—CHF_2$, $—CH_2F$, $—C(CH_3)_2F$, or $—C(CH_3)F_2$. In another embodiment, each $R^{8A}$ is independently hydrogen, halogen, —CN, —C(O)H, $—C(O)CH_3$, —C(O)OH, $—C(O)OCH_3$, $—C(O)NH_2$, —OH, $—OCH_3$, $—OCF_3$, —OC(O)H, $—OC(O)CH_3$, $—OC(O)NH_2$, —SH, —S(O)H, $—S(O)_2H$, —S(O)(=NH)H, $—S(O)_2NH_2$, $—NH_2$, $—NH(CH_3)$, $—N(CH_3)_2$, $—CF_3$, $—CHF_2$, $—CH_2F$, —$C(CH_3)_2F$, or —$C(CH_3)F_2$. In another embodiment, each $R^{8A}$ is independently hydrogen, halogen, —CN, —OH, —$OCH_3$, —$OCF_3$, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{8A}$ is independently hydrogen, halogen, —CN, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, or —$C(CH_3)F_2$.

In another embodiment, each $R^{8A}$ is independently unsubstituted $C_{1-6}$ alkoxy, unsubstituted $C_{1-6}$ alkyl, or unsubstituted $C_{1-6}$ haloalkyl. In another embodiment, each $R^{8A}$ is independently unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl.

In one embodiment, each $R^8$ is independently hydrogen, halogen, oxo, —CN, —ORB, —$NO_2$, —$C(O)R^{8B}$, —C(O)$OR^{8B}$, —$C(O)OR^{8B}$, —$C(O)NR^{8C}R^{8D}$, —$OC(O)R^{8B}$, —$OC(O)NR^{8C}R^{8D}$, —$SR^{8C}$, —$S(O)R^{8B}$, —$S(O)_2R^{8B}$, —$S(O)(=NR^{8C})R^{8D}$, —$S(O)_2NR^{8C}R^{8D}$, —$NR^{8C}R^{8D}$, —$NR^{8C}C(O)R^{8B}$, —$NR^{8C}C(O)OR^{8B}$, —$N(R^{8C})C(O)NR^{8C}R^{8D}$, —$NRCS(O)_2R^{8B}$, —$NR^{8C}S(O)_2NR^{8C}R^{8D}$, or —$P(O)R^{8B}$ where $R^{8B}$, $R^{8C}$, and $R^{8D}$ are as defined herein. In one embodiment, each $R^8$ is $R^9$-substituted or unsubstituted $C_{1-6}$ alkyl or $R^9$-substituted or unsubstituted $C_{1-6}$ haloalkyl. In one embodiment, each $R^8$ is $R^9$-substituted or unsubstituted $C_{3-7}$ cycloalkyl, $R^9$-substituted or unsubstituted 3 to 6 membered heterocycloalkyl, $R^9$-substituted or unsubstituted $C_{5-7}$ aryl, or $R^9$-substituted or unsubstituted 5 to 7 membered heteroaryl.

In one embodiment, each $R^{8b}$ $R^{8C}$, and $R^{8D}$ is independently hydrogen or $R^{9A}$-substituted or unsubstituted $C_{1-6}$ alkyl. In another embodiment, each $R^{8b}$ $R^{8C}$, and $R^{8D}$ is independently $R^{9A}$-substituted or unsubstituted $C_{1-6}$ haloalkyl. In still another embodiment, each $R^{8b}$ $R^{8C}$, and $R^{8D}$ is independently $R^{9A}$-substituted or unsubstituted $C_{3-7}$ cycloalkyl or $R^{9A}$-substituted or unsubstituted 3 to 7 membered heterocycloalkyl.

In one embodiment, each $R^{9A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$. In one embodiment, each $R^{9A}$ is independently hydrogen, halogen, oxo, —CN, —$NO_2$, —C(O)H, —C(O)$CH_3$, —C(O)OH, —$C(O)OCH_3$, —$C(O)NH_2$, —OH, —$OCH_3$, —$OCF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —NHS(O)$_2NH_2$, or —$P(O)(CH_3)_2$, —$CF_3$, —$CHF_2$, —$CH_2F$, —$C(CH_3)_2F$, or —$C(CH_3)F_2$. In another embodiment, each $R^{9A}$ is independently hydrogen, halogen, —CN, —C(O)H, —$C(O)CH_3$, —C(O)OH, —$C(O)OCH_3$, —$C(O)NH_2$, —OH, —$OCH_3$, —$OCF_3$, —OC(O)H, —$OC(O)CH_3$, —OC(O)$NH_2$, —SH, —S(O)H, —$S(O)_2H$, —S(O)(=NH)H, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{9A}$ is independently hydrogen, halogen, —CN, —OH, —$OCH_3$, —$OCF_3$, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{9A}$ is independently hydrogen, halogen, —CN, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, or —$C(CH_3)F_2$.

In one embodiment, each $R^{9A}$ is independently unsubstituted $C_{1-6}$ alkoxy, unsubstituted $C_{1-6}$ alkyl, or unsubstituted $C_{1-6}$ haloalkyl. In one embodiment, each $R^{9A}$ is independently unsubstituted $C_{3-7}$ cycloalkyl, unsubstituted 3 to 6 membered heterocycloalkyl; unsubstituted $C_{5-7}$ aryl, or unsubstituted 5 to 7 membered heteroaryl.

In one embodiment, each $R^9$ is independently hydrogen, halogen, oxo, —CN, —$OR^{9B}$, —$NO_2$, —$C(O)R^{9B}$, —C(O)$OR^{9B}$, —$C(O)OR^{9B}$, —$C(O)NR^{9C}R^{9D}$, —$OC(O)R^{9B}$, —$OC(O)NR^{9C}R^{9D}$, —$SR^{9C}$, —$S(O)R^{9B}$, —$S(O)_2R^{9B}$, —$S(O)(=NR^{9C})R^{9D}$, —$S(O)_2NR^{9C}R^{9D}$, —$NR^{9C}R^{9D}$, —$NR^{9C}C(O)R^{9B}$, —$NR^{9C}C(O)OR^{9B}$, —$N(R^{9C})C(O)NR^{9C}R^{9D}$, —$NR^{9C}S(O)_2R^{9B}$, —$NR^{9C}S(O)_2NR^{9C}R^{9D}$, —$P(O)(R^{9B})$, where $R^{9B}$, $R^{9C}$, and $R^{9D}$ are as defined herein.

In one embodiment, each $R^9$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$. In one embodiment, each $R^9$ is independently hydrogen, halogen, oxo, —CN, —$NO_2$, —C(O)H, —C(O)$CH_3$, —C(O)OH, —$C(O)OCH_3$, —$C(O)NH_2$, —OH, —$OCH_3$, —$OCF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —NHS(O)$_2NH_2$, or —$P(O)(CH_3)_2$, —$CF_3$, —$CHF_2$, —$CH_2F$, —$C(CH_3)_2F$, or —$C(CH_3)F_2$. In another embodiment, each $R^9$ is independently hydrogen, halogen, —CN, —C(O)H, —$C(O)CH_3$, —C(O)OH, —$C(O)OCH_3$, —$C(O)NH_2$, —OH, —$OCH_3$, —$OCF_3$, —OC(O)H, —$OC(O)CH_3$, —OC(O)$NH_2$, —SH, —S(O)H, —$S(O)_2H$, —S(O)(=NH)H, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^9$ is independently hydrogen, halogen, —CN, —OH, —$OCH_3$, —$OCF_3$, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^9$ is independently hydrogen, halogen, —CN, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, or —$C(CH_3)F_2$.

In one embodiment, each $R^9$ is independently $R^{12}$-substituted or unsubstituted $C_{1-6}$ alkyl or $R^{12}$-substituted or unsubstituted $C_{1-6}$ haloalkyl. In one embodiment, each $R^9$ is independently $R^{12}$-substituted or unsubstituted $C_{3-7}$ cycloalkyl or $R^{12}$-substituted or unsubstituted 3 to 6 membered heterocycloalkyl. In another embodiment, each $R^9$ is independently $R^{12}$-substituted or unsubstituted $C_{5-7}$ aryl or $R^{12}$-substituted or unsubstituted 5 to 7 membered heteroaryl In one embodiment, each $R^{9b}$ $R^{9C}$, and $R^{9D}$ is independently hydrogen. In another embodiment, each $R^{9b}$ $R^{9C}$, and $R^{9D}$ is independently $R^{10A}$-substituted or unsubstituted $C_{1-6}$ alkyl, $R^{10A}$-substituted or unsubstituted $C_{1-6}$ haloalkyl, $R^{10A}$-substituted or unsubstituted $C_{3-7}$ cycloalkyl, or $R^{10A}$-substituted or unsubstituted 3 to 7 membered heterocycloalkyl In one embodiment, each $R^{10A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)

OH, —N(H)C(O)NH$_2$, —NHS(O)$_2$H, —NHS(O)$_2$NH$_2$, or —P(O)(CH$_3$)$_2$, —CF$_3$, —CHF$_2$, —CH$_2$F, —C(CH$_3$)$_2$F, —C(CH$_3$)F$_2$.

In one embodiment, each $R^{10A}$ is independently hydrogen, halogen, oxo, —CN, —NO$_2$, —C(O)H, —C(O)CH$_3$, —C(O)OH, —C(O)OCH$_3$, —C(O)NH$_2$, —OH, —OCH$_3$, —OCF$_3$, —OC(O)H, —OC(O) CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, —CF$_3$, —CHF$_2$, —CH$_2$F, —C(CH$_3$)$_2$F, or —C(CH$_3$)F$_2$. In another embodiment, each $R^{10A}$ is independently hydrogen, halogen, —CN, —C(O)H, —C(O)CH$_3$, —C(O)OH, —C(O)OCH$_3$, —C(O)NH$_2$, —OH, —OCH$_3$, —OCF$_3$, —OC(O)H, —OC(O)CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{10A}$ is independently hydrogen, halogen, —CN, —OH, —OCH$_3$, —OCF$_3$, —S(O)$_2$NH$_2$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{10A}$ is independently hydrogen, halogen, —CN, —OH, —OCH$_3$, —OCF$_3$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$.

In another embodiment, each $R^{9b}$ $R^{9C}$, and $R^{9D}$ is independently unsubstituted $C_{1-6}$ alkoxy. In another embodiment, each $R^{9b}$ $R^{9C}$, and $R^{9D}$ is independently unsubstituted $C_{1-6}$ alkyl, unsubstituted $C_{1-6}$ haloalkyl, or unsubstituted $C_{3-7}$ cycloalkyl. In still another embodiment, each $R^{9b}$ $R^{9C}$, and $R^{9D}$ is independently unsubstituted 3 to 6 membered heterocycloalkyl, unsubstituted $C_{5-7}$ aryl, or unsubstituted 5 to 7 membered heteroaryl.

In one embodiment, each $R^{10}$ is independently hydrogen, halogen, oxo, —CN, —OR$^{11A}$, —NO$_2$, —C(O)R$^{11A}$, —C(O)OR$^{11A}$, —C(O)OR$^{11A}$, —C(O)NR$^{11B}$R$^{11C}$, —OC(O)R$^{11A}$, —OC(O)NR$^{11B}$R$^{11C}$, —SR$^{11B}$, —S(O)R$^{11A}$, —S(O)$_2$R$^{11A}$, —S(O)(=NR$^{11B}$)R$^{11C}$, —S(O)$_2$NR$^{11B}$R$^{11C}$, —NR$^{11B}$R$^{11C}$, —NR$^{11B}$C(O)R$^{11A}$, —NR$^{11B}$C(O)OR$^{11A}$, —N(R$^{11B}$)C(O)NR$^{11B}$R$^{11C}$, —NR$^{11B}$S(O)$_2$R$^{11A}$, —NR$^{11B}$S(O)$_2$NR$^{11B}$R$^{11C}$, —P(O)(R$^{11A}$)$_2$, where $R^{11A}$, $R^{11B}$, and $R^{11C}$ are as defined herein.

In one embodiment, each $R^{10}$ is independently hydrogen, halogen, oxo, —CN, —NO$_2$, —C(O)H, —C(O)CH$_3$, —C(O)OH, —C(O)OCH$_3$, —C(O)NH$_2$, —OH, —OCH$_3$, —OCF$_3$, —OC(O)H, —OC(O) CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, —CF$_3$, —CHF$_2$, —CH$_2$F, —C(CH$_3$)$_2$F, —C(CH$_3$)F$_2$. In one embodiment, each $R^{10}$ is independently hydrogen, halogen, oxo, —CN, —NO$_2$, —C(O)H, —C(O)CH$_3$, —C(O)OH, —C(O)OCH$_3$, —C(O)NH$_2$, —OH, —OCH$_3$, —OCF$_3$, —OC(O)H, —OC(O) CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, —CF$_3$, —CHF$_2$, —CH$_2$F, —C(CH$_3$)$_2$F, or —C(CH$_3$)F$_2$. In another embodiment, each $R^{10}$ is independently hydrogen, halogen, —CN, —C(O)H, —C(O)CH$_3$, —C(O)OH, —C(O)OCH$_3$, —C(O)NH$_2$, —OH, —OCH$_3$, —OCF$_3$, —OC(O)H, —OC(O)CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{10}$ is independently hydrogen, halogen, —CN, —OH, —OCH$_3$, —OCF$_3$, —S(O)$_2$NH$_2$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{10}$ is independently hydrogen, halogen, —CN, —OH, —OCH$_3$, —OCF$_3$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{10}$ is independently hydrogen, halogen, —CN, —OH, —OCH$_3$, —OCF$_3$, —CF$_3$, —CHF$_2$, —CH$_2$F, —C(CH$_3$)$_2$F, or —C(CH$_3$)F$_2$. In still another embodiment, each $R^{10}$ is independently hydrogen, halogen, —OH, —OCH$_3$, —OCF$_3$, —CF$_3$, —CHF$_2$, —CH$_2$F, —C(CH$_3$)$_2$F, or —C(CH$_3$)F$_2$.

In another embodiment, each $R^{10}$ is independently $R^{11}$-substituted or unsubstituted $C_{1-6}$ alkoxy. In still another embodiment, each $R^{10}$ is independently $R^{11}$-substituted or unsubstituted $C_{1-6}$ alkyl or $R^{11}$-substituted or unsubstituted $C_{1-6}$ haloalkyl. In another embodiment, each $R^{10}$ is independently methyl, ethyl, propyl, or isopropyl. In yet another embodiment, each $R^{10}$ is independently $R^{11}$-substituted or unsubstituted $C_{3-7}$ cycloalkyl or $R^{11}$-substituted or unsubstituted 3 to 6 membered heterocycloalkyl. In still another embodiment, each $R^{10}$ is independently $R^{11}$-substituted or unsubstituted $C_{5-7}$ aryl, or $R^{11}$-substituted or unsubstituted 5 to 7 membered heteroaryl.

In one embodiment, each $R^{11A}$, $R^{11B}$ and $R^{11C}$ is independently hydrogen. In one embodiment, each $R^{11A}$, $R^{11B}$ and $R^{11C}$ is independently $R^{12A}$-substituted or unsubstituted $C_{1-6}$ alkyl, $R^{12A}$-substituted or unsubstituted $C_{1-6}$ haloalkyl, $R^{12A}$-substituted or unsubstituted $C_{3-7}$ cycloalkyl, or $R^{12A}$-substituted or unsubstituted 3 to 7 membered heterocycloalkyl.

In one embodiment, each $R^{11}$ is independently hydrogen, halogen, oxo, —CN, —OR$^{12B}$, —NO$_2$, —C(O)R$^{12B}$, —C(O)OR$^{12B}$, —C(O)OR$^{12B}$, —C(O)NR$^{12C}$R$^{12D}$, —OC(O)R$^{12B}$, —OC(O)NR$^{12C}$R$^{12D}$, —SR$^{12C}$, —S(O)R$^{12B}$, —S(O)$_2$R$^{12B}$, —S(O)(=NR$^{12C}$)R$^{12D}$, —S(O)$_2$NR$^{12C}$R$^{12D}$, —NR$^{12C}$R$^{12D}$, —NR$^{12C}$CC(O)R$^{12B}$, —NR$^{12C}$C(O)OR$^{12B}$, —N(R$^{12C}$)C(O)NR$^{12C}$R$^{12D}$, —NR$^{12C}$S(O)$_2$R$^{12B}$, —NR$^{12C}$S(O)$_2$NR$^{12C}$R$^{12D}$, —P(O)(R$^{12B}$)$_2$, where $R^{12B}$, $R^{12C}$, and $R^{12D}$ are as defined herein.

In one embodiment, each $R^{11}$ is independently hydrogen, halogen, oxo, —CN, —NO$_2$, —C(O)H, —C(O)CH$_3$, —C(O)OH, —C(O)OCH$_3$, —C(O)NH$_2$, —OH, —OCH$_3$, —OCF$_3$, —OC(O)H, —OC(O) CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, —CF$_3$, —CHF$_2$, —CH$_2$F, —C(CH$_3$)$_2$F, —C(CH$_3$)F$_2$. In one embodiment, each $R^{11}$ is independently hydrogen, halogen, oxo, —CN, —NO$_2$, —C(O)H, —C(O)CH$_3$, —C(O)OH, —C(O)OCH$_3$, —C(O)NH$_2$, —OH, —OCH$_3$, —OCF$_3$, —OC(O)H, —OC(O) CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —NHC(O)H, —NHC(O)OH, —N(H)C(O)NH$_2$, —NHS(O)$_2$H, —NHS(O)$_2$NH$_2$, or —P(O)(CH$_3$)$_2$, —CF$_3$, —CHF$_2$, —CH$_2$F, —C(CH$_3$)$_2$F, or —C(CH$_3$)F$_2$. In another embodiment, each $R^{11}$ is independently hydrogen, halogen, —CN, —C(O)H, —C(O)CH$_3$, —C(O)OH, —C(O)OCH$_3$, —C(O)NH$_2$, —OH, —OCH$_3$, —OCF$_3$, —OC(O)H, —OC(O)CH$_3$, —OC(O)NH$_2$, —SH, —S(O)H, —S(O)$_2$H, —S(O)(=NH)H, —S(O)$_2$NH$_2$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{11}$ is independently hydrogen, halogen, —CN, —OH, —OCH$_3$, —OCF$_3$, —S(O)$_2$NH$_2$, —NH$_2$, —NH(CH$_3$), —N(CH$_3$)$_2$, —CF$_3$, —CHF$_2$, —CH$_2$F, —C(CH$_3$)$_2$F, or —C(CH$_3$)F$_2$. In another embodiment, each $R^{11}$ is independently hydrogen, halogen, —CN, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, or —$C(CH_3)F_2$.

In another embodiment, each $R^{11}$ is independently $R^{12}$-substituted or unsubstituted $C_{1-6}$ alkyl (e.g. methyl, ethyl, propyl, or isopropyl). In another embodiment, each $R^{11}$ is independently $R^{12}$-substituted or unsubstituted $C_{1-6}$ haloalkyl. In still another embodiment, each $R^{11}$ is independently $R^{12}$-substituted or unsubstituted $C_{3-7}$ cycloalkyl, $R^{12}$-substituted or unsubstituted 3 to 6 membered heterocycloalkyl. In yet another embodiment, each $R^{11}$ is independently $R^{12}$-substituted or unsubstituted $C_{5-7}$ aryl or $R^{12}$-substituted or unsubstituted 5 to 7 membered heteroaryl.

In one embodiment, each $R^{12A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$. In one embodiment, each $R^{12A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$. In one embodiment, each $R^{12A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, or —$C(CH_3)F_2$. In another embodiment, each $R^{12A}$ is independently hydrogen, halogen, —CN, —C(O)H, —$C(O)CH_3$, —C(O)OH, —$C(O)OCH_3$, —$C(O)NH_2$, —OH, —$OCH_3$, —$OCF_3$, —OC(O)H, —$OC(O)CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{12A}$ is independently hydrogen, halogen, —CN, —OH, —$OCH_3$, —$OCF_3$, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{12A}$ is independently hydrogen, halogen, —CN, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, or —$C(CH_3)F_2$.

In another embodiment, each $R^{12A}$ is independently unsubstituted $C_{1-6}$ alkoxy. In still another embodiment, each $R^{12A}$ is independently unsubstituted $C_{1-6}$ alkyl (e.g. methyl, ethyl, propyl, or isopropyl). In yet another embodiment, each $R^{12A}$ is independently unsubstituted $C_{1-6}$ haloalkyl. In still another embodiment, each $R^{12A}$ is independently unsubstituted $C_{3-7}$ cycloalkyl or unsubstituted 3 to 6 membered heterocycloalkyl. In another embodiment, each $R^{12A}$ is independently unsubstituted $C_{5-7}$ aryl or unsubstituted 5 to 7 membered heteroaryl In one embodiment, each $R^{12B}$, $R^{12C}$ and $R^{12D}$ is independently hydrogen. In another embodiment, each $R^{12B}$, $R^{12C}$ and $R^{12D}$ is independently unsubstituted $C_{1-6}$ alkyl (e.g. methyl, ethyl, propyl, or isopropyl). In still another embodiment, each $R^{12B}$, $R^{12C}$ and $R^{12D}$ is independently unsubstituted $C_{1-6}$ haloalkyl. In still another embodiment, each $R^{12B}$, $R^{12C}$ and $R^{12D}$ is independently unsubstituted $C_{3-7}$ cycloalkyl or unsubstituted 3 to 7 membered heterocycloalkyl.

In one embodiment, each $R^{12}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —$OC(O)CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, —$C(CH_3)F_2$.

In one embodiment, each $R^{12}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —NHC(O)H, —NHC(O)OH, —$N(H)C(O)NH_2$, —$NHS(O)_2H$, —$NHS(O)_2NH_2$, or —$P(O)(CH_3)_2$, —$CF_3$, —$CHF_2$, —$CH_2F$, —$C(CH_3)_2F$, or —$C(CH_3)F_2$. In another embodiment, each $R^{12}$ is independently hydrogen, halogen, —CN, —C(O)H, —$C(O)CH_3$, —C(O)OH, —$C(O)OCH_3$, —$C(O)NH_2$, —OH, —$OCH_3$, —$OCF_3$, —OC(O)H, —$OC(O)CH_3$, —$OC(O)NH_2$, —SH, —S(O)H, —$S(O)_2H$, —S(O)(═NH)H, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{12}$ is independently hydrogen, halogen, —CN, —OH, —$OCH_3$, —$OCF_3$, —$S(O)_2NH_2$, —$NH_2$, —$NH(CH_3)$, —$N(CH_3)_2$, —$CF_3$, —$CHF_2$, —$CH_2F$, —$C(CH_3)_2F$, or —$C(CH_3)F_2$. In another embodiment, each $R^{12}$ is independently hydrogen, halogen, —CN, —OH, —$OCH_3$, —$OCF_3$, —$NH_2$, —$NH(CH_3)$, —$N(CH_3)_2$, —$CF_3$, —$CHF_2$, —$CH_2F$, —$C(CH_3)_2F$, or —$C(CH_3)F_2$.

In another embodiment, each $R^{12}$ is independently unsubstituted $C_{1-6}$ alkoxy. In another embodiment, each $R^{12}$ is independently unsubstituted $C_{1-6}$ alkyl. In one embodiment, each $R^{12}$ is independently hydrogen, methyl, ethyl, propyl, or isopropyl. In still another embodiment, each $R^{12}$ is independently unsubstituted $C_{1-6}$ alkoxy. In still another embodiment, each $R^{12}$ is independently unsubstituted $C_{1-6}$ haloalkyl (e.g. —$CF_3$, —$CHF_2$, —$CH_2F$, —$C(CH_3)_2F$, or —$C(CH_3)F_2$). In yet another embodiment, each $R^{12}$ is independently unsubstituted $C_{1-6}$ haloalkoxy. In yet another embodiment, each $R^{12}$ is independently unsubstituted $C_{3-7}$ cycloalkyl or unsubstituted 3 to 6 membered heterocycloalkyl. In another embodiment, each $R^{12}$ is independently unsubstituted $C_{5-7}$ aryl or unsubstituted 5 to 7 membered heteroaryl.

In one embodiment, $R^{13}$ is hydrogen or $R^{10}$-substituted or unsubstituted $C_{1-6}$ alkyl. In another embodiment, $R^{13}$ is halogen. In a preferred embodiment, $R^{13}$ is hydrogen.

In one embodiment, $X^1$ and $X^2$ are independently —$CR^2$—. In another embodiment, $X^1$ is —N—. In another embodiment, $X^2$ is —N—.

In one embodiment, $X^3$ is —$CR^3$—. In a preferred embodiment, $X^3$ is —N—.

$X^3$ is —N— or —$CR^3$—, wherein one of $X^1$, $X^2$, and $X^3$ is —N—

In one embodiment, Ring B is $R^4$-substituted or unsubstituted $C_{3-7}$ cycloalkyl. In another embodiment, Ring B is $R^4$-substituted or unsubstituted 3 to 7 membered heterocycloalkyl. In another embodiment, Ring B is $R^4$-substituted or unsubstituted $C_{5-7}$ aryl. In still another embodiment, Ring B is $R^4$-substituted or unsubstituted 5 to 7 membered heteroaryl.

In one embodiment, Ring B is $R^4$-substituted or unsubstituted $C_{5-7}$ aryl. In a preferred embodiment, Ring B is $R^4$-substituted or unsubstituted phenyl. In one embodiment, Ring B has formula:

(B1) , (B2) (B3) or (B4) ,

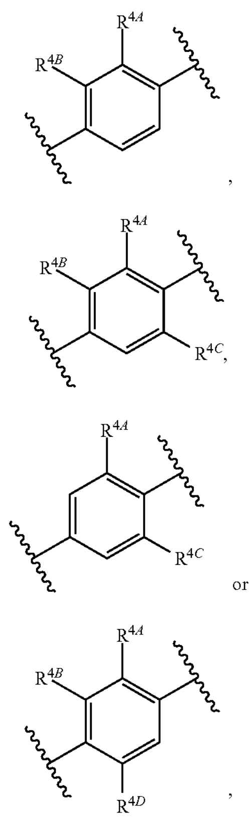

where $R^{4A}$, $R^{4B}$, $R^{4C}$, and $R^{4D}$ are each independently hydrogen, halogen, —CN, —$OR^7$, —$S(O)_2R^7$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-6}$ cycloalkyl, $R^{10}$-substituted or unsubstituted $C_{1-6}$ alkoxy, or $R^{10}$-substituted or unsubstituted $C_{1-6}$ haloalkoxy, where $R^7$ and $R^{10}$ are as defined herein (e.g. as for $R^4$).

In one embodiment, $R^{4A}$, $R^{4B}$, $R^{4C}$, and $R^{4D}$ are each independently hydrogen, halogen, —CN, —$OR^7$, or —$S(O)_2R^7$. In one embodiment, $R^{4A}$, $R^{4B}$, $R^{4C}$, and $R^{4D}$ are each independently hydrogen, halogen, or —CN. In another embodiment, $R^{4A}$, $R^{4B}$, $R^{4C}$, and $R^{4D}$ are each independently hydrogen, halogen, or —$OCF_3$. In another embodiment, $R^{4A}$, $R^{4B}$, $R^{4C}$, and $R^{4D}$ are each independently $R^{10}$-substituted or unsubstituted $C_{1-6}$ alkyl or $R^{10}$-substituted or unsubstituted $C_{1-6}$ haloalkyl. In still another embodiment, $R^{4A}$, $R^{4B}$, $R^{4C}$, and $R^{4D}$ are each independently $R^{10}$-substituted or unsubstituted $C_{3-6}$ cycloalkyl, $R^{10}$-substituted or unsubstituted $C_{1-6}$ alkoxy, or $R^{10}$-substituted or unsubstituted $C_{1-6}$ haloalkoxy.

In one embodiment, $R^{4A}$, $R^{4B}$, $R^{4C}$, and $R^{4D}$ are each independently hydrogen, halogen, —CN, $R^{10}$-substituted or unsubstituted $C_{1-6}$ alkyl, or $R^{10}$-substituted or unsubstituted $C_{1-6}$ haloalkyl. In another embodiment, $R^{4A}$, $R^{4B}$, $R^{4C}$, and $R^{4D}$ are each independently hydrogen or halogen.

In one embodiment, $R^{4A}$, $R^{4B}$, $R^{4C}$, and $R^{4D}$ are each independently hydrogen, halogen, —$OR^7$, —CN, or —$S(O)_2R^7$. In another embodiment, each $R^4$ is $R^{10}$-substituted or unsubstituted $C_{1-6}$ alkyl or $R^{10}$-substituted or unsubstituted $C_{1-6}$ haloalkyl. In still another embodiment, each $R^4$ is $R^{10}$-substituted or unsubstituted $C_{3-7}$ cycloalkyl.

In one embodiment, Ring B has formula (B1), where $R^{4A}$ is halogen (e.g. F) and $R^{4B}$ is hydrogen. In another embodiment, Ring B has formula (B1), where $R^{4A}$ is halogen (e.g. F) and $R^{4B}$ is hydrogen. In still another embodiment, Ring B has formula (B1), where $R^{4A}$ and $R^{4B}$ are halogen (e.g. F).

In one embodiment, Ring B has formula (B2), where $R^{4A}$, $R^{4B}$, and $R^{4C}$ are halogen (e.g. F). In another embodiment, Ring B has formula (B2), where $R^{4A}$ and $R^{4B}$ are halogen and $R^{4C}$ is hydrogen. In still another embodiment, Ring B has formula (B2), where $R^{4A}$ is halogen, $R^{4B}$ is hydrogen and $R^{4C}$ is halogen. In another embodiment, Ring B has formula (B2), where at least one of $R^{4A}$, $R^{4B}$, and $R^{4C}$ is F or —$OCF_3$.

In one embodiment, Ring B has formula (B3), where $R^{4A}$ and $R^{4C}$ are halogen. In one embodiment, Ring B has formula (B3), where at least one of $R^{4A}$ and $R^{4C}$ is F or —$OCF_3$.

In one embodiment, Ring B has formula (B4), where $R^{4A}$, $R^{4B}$, and $R^{4D}$ are halogen (e.g. F). In another embodiment, Ring B has formula (B4), where $R^{4A}$ and $R^{4B}$ are halogen and $R^{4D}$ is hydrogen. In still another embodiment, Ring B has formula (B4), where $R^{4A}$ is halogen, $R^{4B}$ is hydrogen and $R^{4D}$ is halogen. In another embodiment, Ring B has formula (B4), where at least one of $R^{4A}$, $R^{4B}$, and $R^{4D}$ is F or —$OCF_3$.

In another embodiment, at least one of $R^{4A}$, $R^{4B}$, $R^{4C}$, and $R^{4D}$ is —$OR^7$. In one preferred embodiment, where at least one of $R^{4A}$, $R^{4B}$, $R^{4C}$, and $R^{4D}$ is —$OR^7$, $R^7$ is $R^8$-substituted or unsubstituted $C_{1-6}$ alkyl or $R^8$-substituted or unsubstituted $C_{1-6}$ haloalkyl. In one embodiment, at least one of $R^{4A}$, $R^{4B}$, $R^{4C}$, and $R^{4D}$ is —O($C_{1-3}$ unsubstituted alkyl) or —O($C_{1-3}$ unsubstituted haloalkyl). In another embodiment, at least one of $R^{4A}$, $R^{4B}$, $R^{4C}$, and $R^{4D}$ is —$OCH_3$, —$OCH_2CH_3$, —$O(CH_2)_2CH_3$, —$OCH_2F$, —$OCHF_2$, —$OCF_3$, —$OC(CH_3)_2F$, —$OC(CH_3)F_2$, —$O(CH_2)CH_2F$, —$O(CH_2)CHF_2$, or —$OCH_2CF_3$.

In one embodiment, a compound or pharmaceutically acceptable salt thereof described herein comprises formula:

(IIA) , (IIB) , or

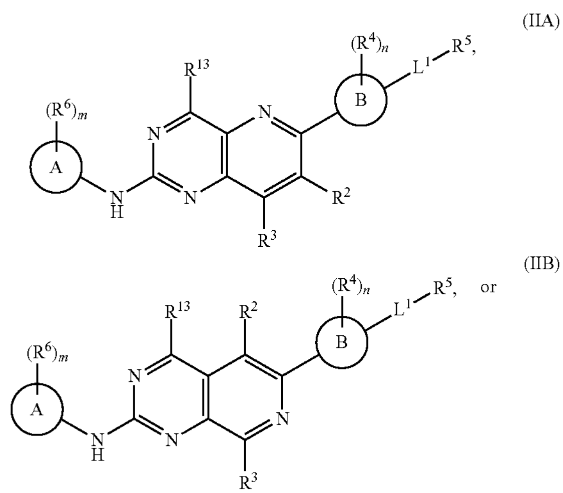

-continued (IIC)

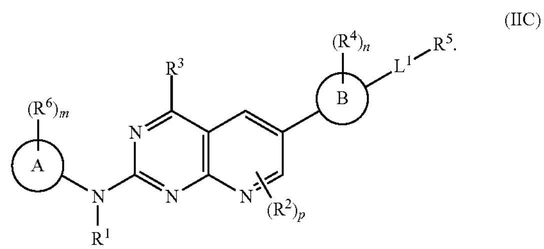

In one preferred embodiment, the compound or pharmaceutically acceptable salt thereof comprises formula (IIA).

In another embodiment, a compound or pharmaceutically acceptable salt thereof described herein comprises formula:

(IID)

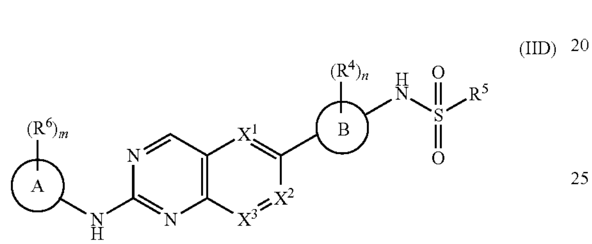

(IIE)

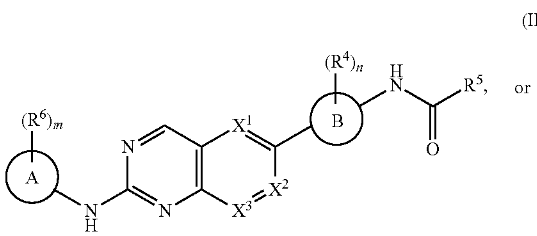

or (IIF)

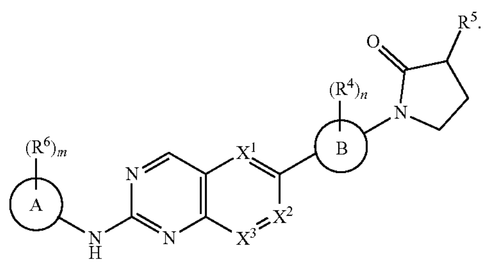

In one preferred embodiment, the compound or pharmaceutically acceptable salt thereof comprises formula (IID).

In one embodiment, a compound or pharmaceutically acceptable salt thereof described herein comprises formula:

(IA)

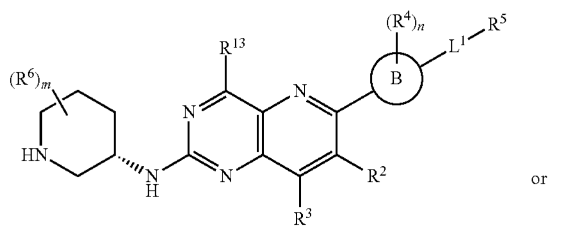

or

-continued (IB)

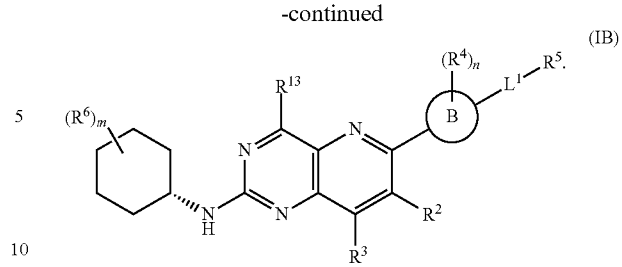

In one embodiment, a compound or pharmaceutically acceptable salt thereof described herein comprises the formula:

(IC)

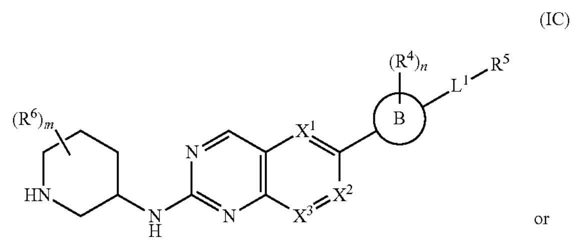

or (ID)

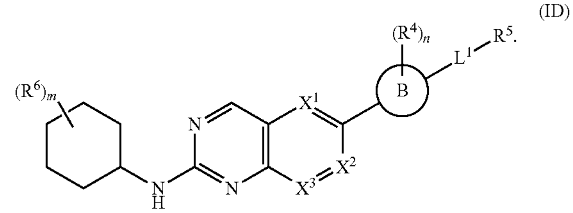

In another embodiment, a compound or pharmaceutically acceptable salt thereof described herein comprises the formula:

(IE)

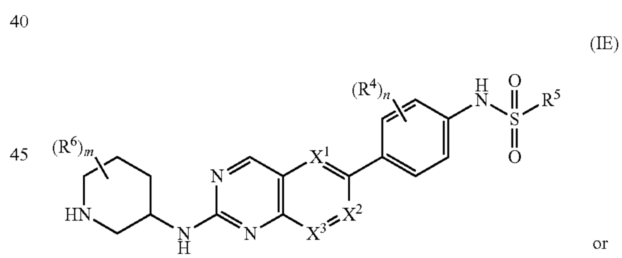

or (IF)

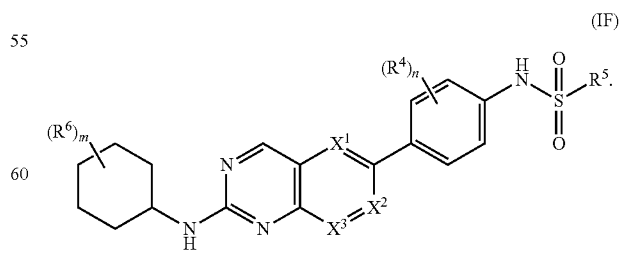

In another embodiment, a compound or pharmaceutically acceptable salt thereof described herein comprises the formula:

(IG)

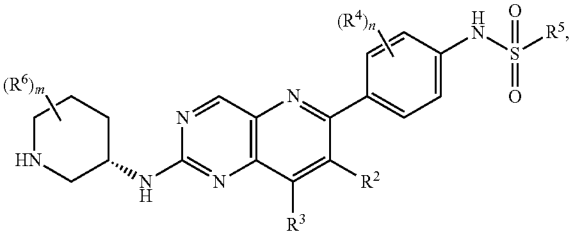

(IH)

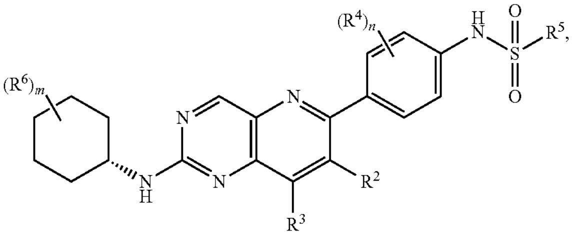

(IJ)

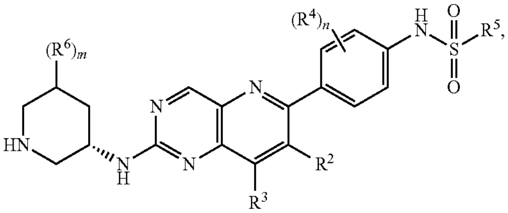

or (IK)

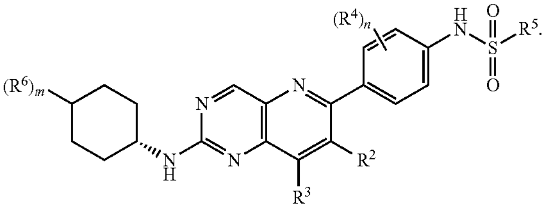

In still another embodiment, a compound or pharmaceutically acceptable salt thereof described herein comprises the formula:

(IL)

(IM)

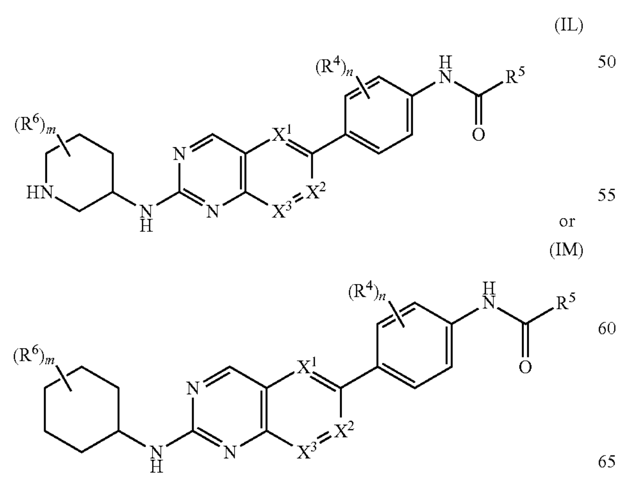

or

In yet another embodiment, a compound or pharmaceutically acceptable salt thereof described herein comprises the formula:

(IN)

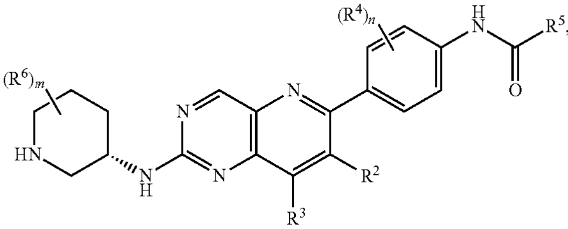

(IO)

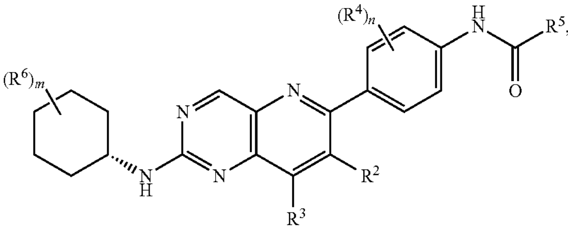

(IP)

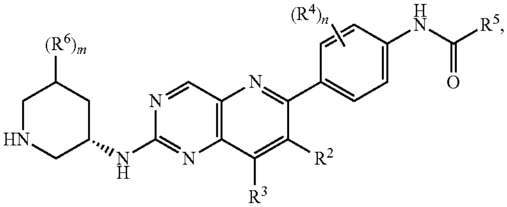

or (IQ)

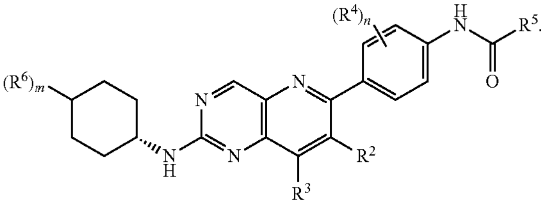

In still another embodiment, a compound or pharmaceutically acceptable salt thereof described herein comprises the formula:

(IR)

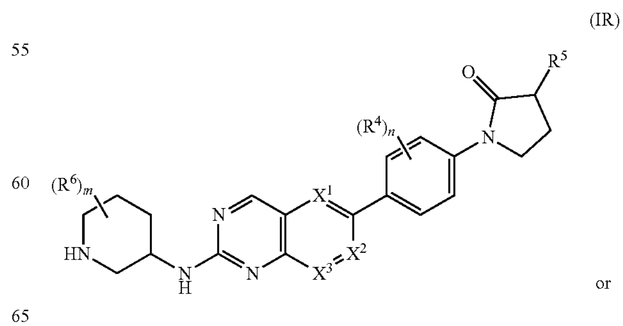

or

-continued (IS)

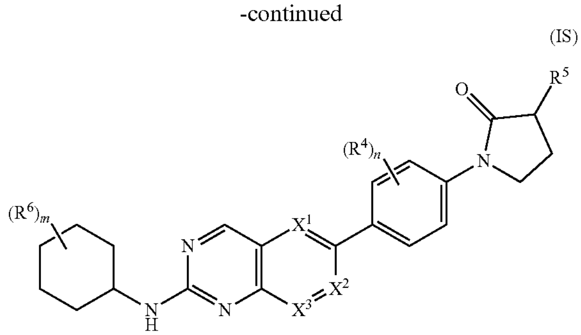

In another embodiment, a compound or pharmaceutically acceptable salt thereof described herein comprises the formula:

(IT)

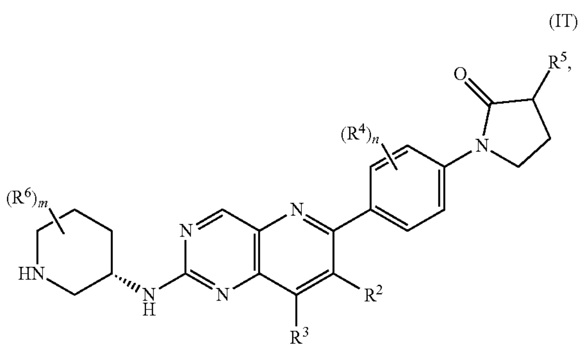

(IU)

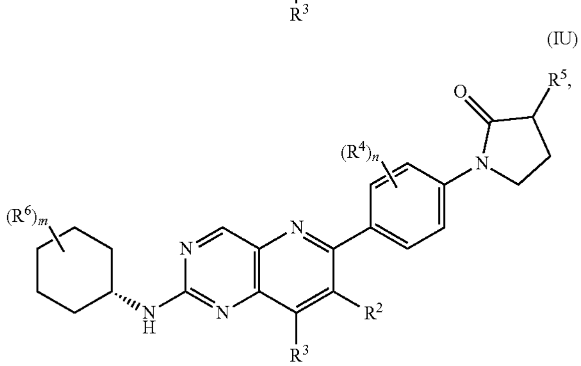

-continued (IV)

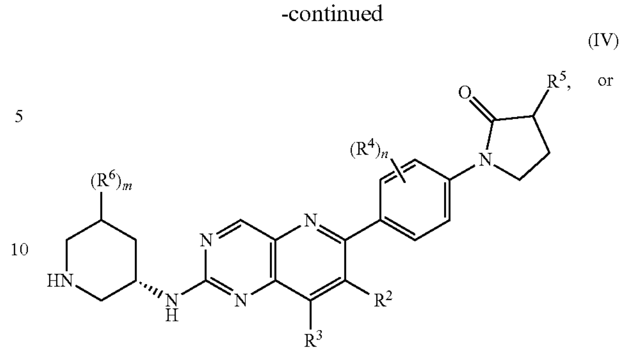

or (IW)

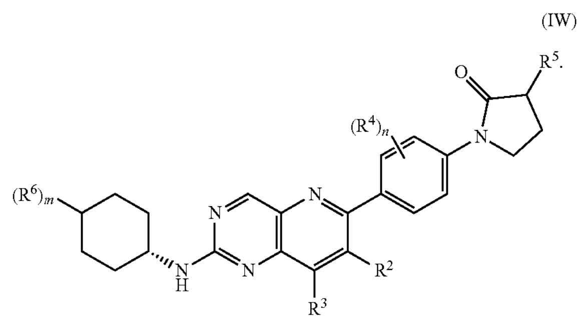

In one embodiment, the compound or pharmaceutically acceptable salt thereof is a compound set forth in Table 1. Compound structures that are otherwise identical but are numbered differently represent stereoisomeric mixtures.

TABLE 1

| Cmpd No. | Structure | Name | IRE1α (alpha) HTRF ($IC_{50}$) (μM) | Mass Spec. M + H/1 |
|---|---|---|---|---|
| 100 | 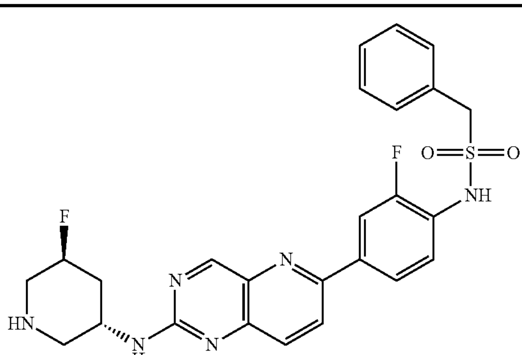 | N-(2-fluoro-4-(2-(((3S,5S)-5-fluoropiperidin-3-yl)amino)pyrido[3,2-d]pyrimidin-6-yl)phenyl)-1-phenyl-methanesulfonamide | 0.00089 | 511.2 |

TABLE 1-continued

| Cmpd No. | Structure | Name | IRE1α (alpha) HTRF ($IC_{50}$) (μM) | Mass Spec. M + H/1 |
|---|---|---|---|---|
| 101 | 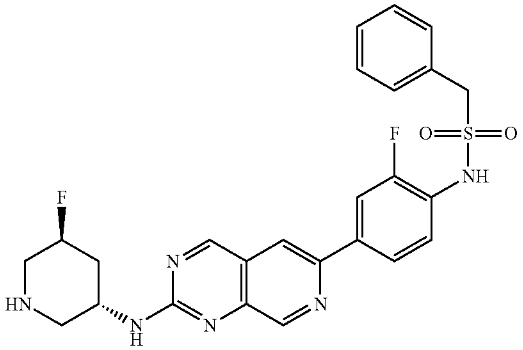 [SMILES: O=S(=O)(Cc1ccccc1)Nc1ccc(-c2cc3cnc(N[C@@H]4CNC[C@@H](F)C4)nc3cn2)cc1F] | N-(2-fluoro-4-(2-(((3S,5S)-5-fluoropiperidin-3-yl)amino)pyrido[3,4-d]pyrimidin-6-yl)phenyl)-1-phenyl-methanesulfonamide | 0.00300 | 511.2 |
| 102 | 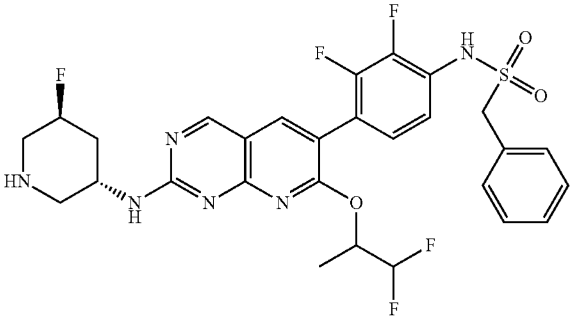 [SMILES: CC(Oc1nc2nc(N[C@@H]3CNC[C@@H](F)C3)ncc2cc1-c1ccc(NS(=O)(=O)Cc2ccccc2)c(F)c1F)C(F)F] | N-(4-(7-((1,1-difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide | 0.0011 | 623.2 |
| 103 | 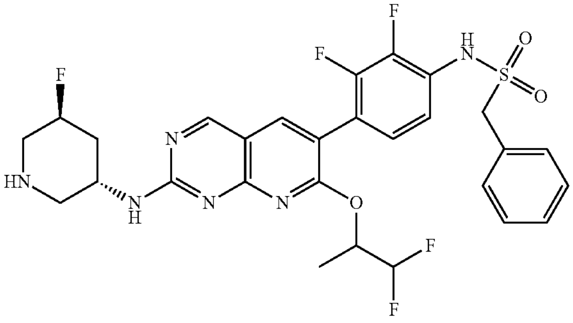 [SMILES: CC(Oc1nc2nc(N[C@@H]3CNC[C@@H](F)C3)ncc2cc1-c1ccc(NS(=O)(=O)Cc2ccccc2)c(F)c1F)C(F)F] | N-(4-(7-((1,1-difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide | 0.00110 | 623.2 |
| 104 | 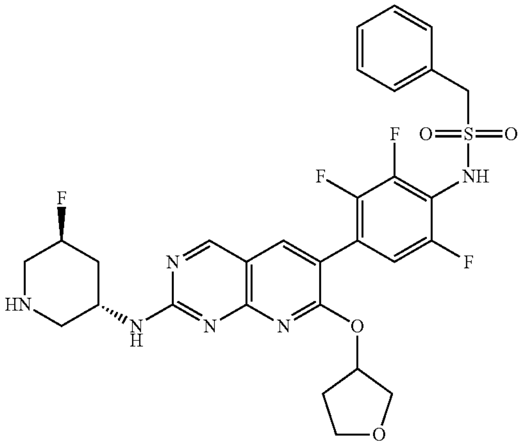 [SMILES: O=S(=O)(Cc1ccccc1)Nc1c(F)cc(-c2cc3cnc(N[C@@H]4CNC[C@@H](F)C4)nc3nc2OC2CCOC2)c(F)c1F] | 1-phenyl-N-(2,3,6-trifluoro-4-(2-(((3S,5S)-5-fluoropiperidin-3-yl)amino)-7-oxo-8-(tetrahydrofuran-3-yl)-7,8-dihydro-pyrido[2,3-d]pyrimidin-6-yl)phenyl)methanesulfonamide | 0.00066 | 633.2 |

TABLE 1-continued

| Cmpd No. | Structure | Name | IRE1α (alpha) HTRF ($IC_{50}$) (μM) | Mass Spec. M + H/1 |
|---|---|---|---|---|
| 105 | 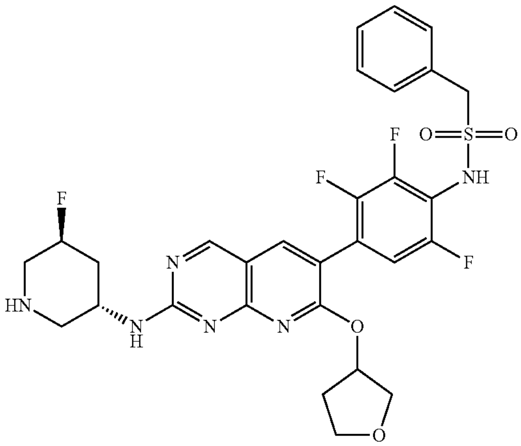 [SMILES: O=S(=O)(Cc1ccccc1)Nc1c(F)cc(-c2cc3cnc(N[C@@H]4CNC[C@@H](F)C4)nc3nc2OC2CCOC2)c(F)c1F] | 1-phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide | 0.00039 | 633.2 |
| 106 | 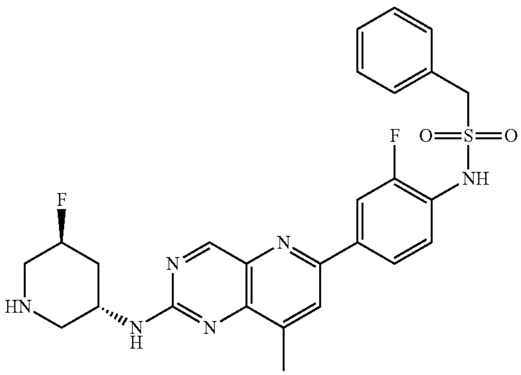 [SMILES: Cc1cc(-c2ccc(NS(=O)(=O)Cc3ccccc3)c(F)c2)nc2cnc(N[C@@H]3CNC[C@@H](F)C3)nc12] | N-(2-fluoro-4-(2-(((3S,5S)-5-fluoropiperidin-3-yl)amino)-8-methylpyrido[3,2-d]pyrimidin-6-yl)phenyl)-1-phenyl-methanesulfonamide | 0.0003 | 525.2 |
| 107 | 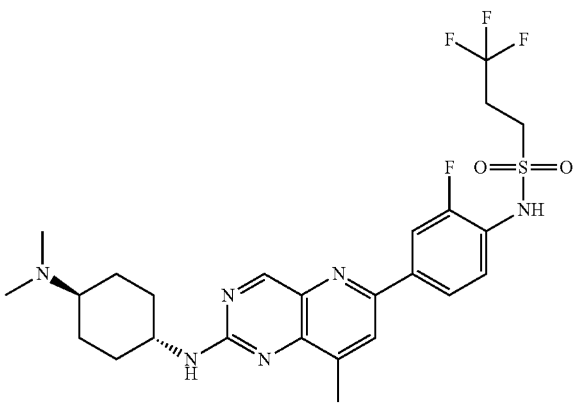 [SMILES: Cc1cc(-c2ccc(NS(=O)(=O)CCC(F)(F)F)c(F)c2)nc2cnc(N[C@H]3CC[C@H](N(C)C)CC3)nc12] | N-(4-(2-(((1r,4r)-4-(Dimethylamino)cyclohexyl)amino)-8-methylpyrido[3,2-d]pyrimidin-6-yl)-2-fluorophenyl)-3,3,3-trifluoropropane-1-sulfonamide | 0.0002 | 555.2 |

TABLE 1-continued

| Cmpd No. | Structure | Name | IRE1α (alpha) HTRF ($IC_{50}$) (μM) | Mass Spec. M + H/1 |
|---|---|---|---|---|
| 108 | 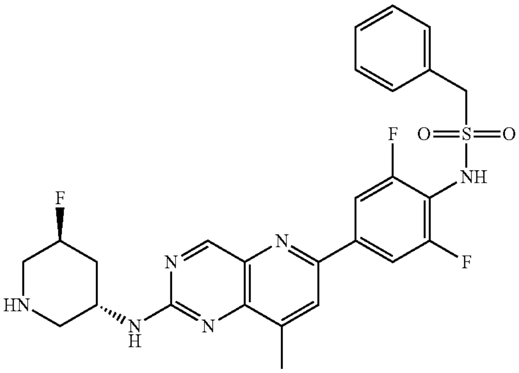 [SMILES: Cc1cc(-c2cc(F)c(NS(=O)(=O)Cc3ccccc3)c(F)c2)nc2cnc(N[C@@H]3CNC[C@@H](F)C3)nc12] | N-(2,6-difluoro-4-(2-(((3S,5S)-5-fluoropiperidin-3-yl)amino)-8-methylpyrido[3,2-d]pyrimidin-6-yl)phenyl)-1-phenylmethanesulfonamide | 0.0002 | 543.2 |
| 109 | 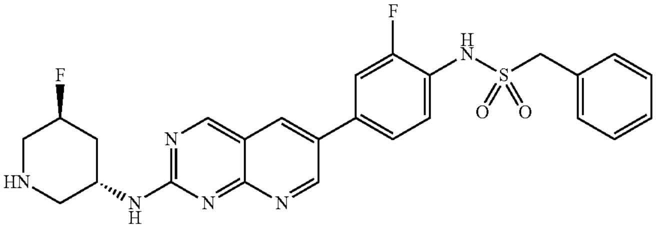 [SMILES: O=S(=O)(Cc1ccccc1)Nc1ccc(-c2cnc3nc(N[C@@H]4CNC[C@@H](F)C4)ncc3c2)cc1F] | N-(2-Fluoro-4-(2-(((3S,5S)-5-fluoropiperidin-3-yl)amino)pyrido[2,3-d]pyrimidin-6-yl)phenyl)-1-phenylmethanesulfonamide | 0.0057 | 510.8 |
| 110 | 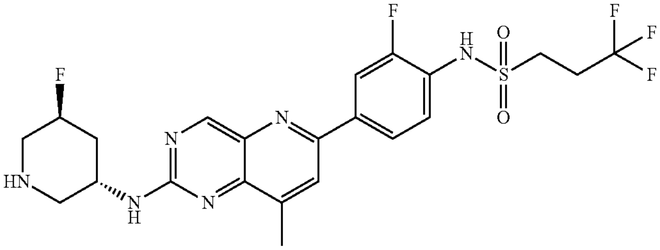 [SMILES: Cc1cc(-c2ccc(NS(=O)(=O)CCC(F)(F)F)c(F)c2)nc2cnc(N[C@@H]3CNC[C@@H](F)C3)nc12] | 3,3,3-Trifluoro-N-(2-fluoro-4-(2-(((3S,5S)-5-fluoropiperidin-3-yl)amino)-8-methylpyrido[3,2-d]pyrimidin-6-yl)phenyl)propane-1-sulfonamide | 0.0011 | 530.9 |
| 111 | 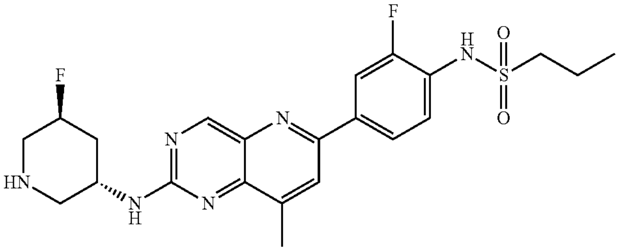 [SMILES: CCCS(=O)(=O)Nc1ccc(-c2cc(C)c3nc(N[C@@H]4CNC[C@@H](F)C4)ncc3n2)cc1F] | N-(2-Fluoro-4-(2-(((3S,5S)-5-fluoropiperidin-3-yl)amino)-8-methylpyrido[3,2-d]pyrimidin-6-yl)phenyl)propane-1-sulfonamide | 0.0021 | 476.9 |
| 112 | 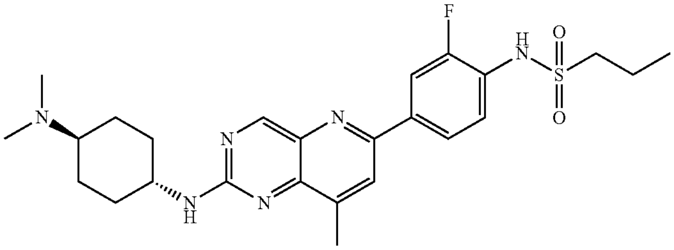 [SMILES: CCCS(=O)(=O)Nc1ccc(-c2cc(C)c3nc(N[C@H]4CC[C@H](N(C)C)CC4)ncc3n2)cc1F] | N-(4-(2-(((1,4-trans)-4-(Dimethylamino)cyclohexyl)amino)-8-methylpyrido[3,2-d]pyrimidin-6-yl)-2-fluorophenyl)propane-1-sulfonamide formate | 0.00032 | 501.0 |

TABLE 1-continued

| Cmpd No. | Structure | Name | IRE1α (alpha) HTRF ($IC_{50}$) (μM) | Mass Spec. M + H/1 |
|---|---|---|---|---|
| 113 | 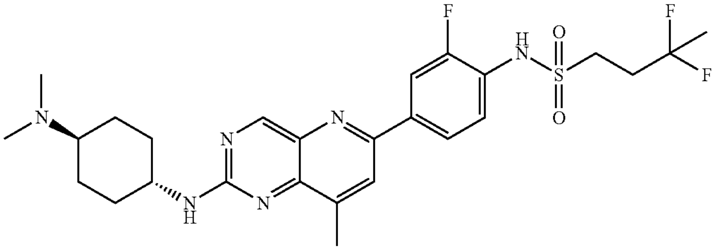 [SMILES: Cc1cc(-c2ccc(NS(=O)(=O)CCC(C)(F)F)c(F)c2)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2-fluorophenyl)-3,3-difluorobutane-1-sulfonamide formate | 0.00017 | 551.3 |
| 114 | 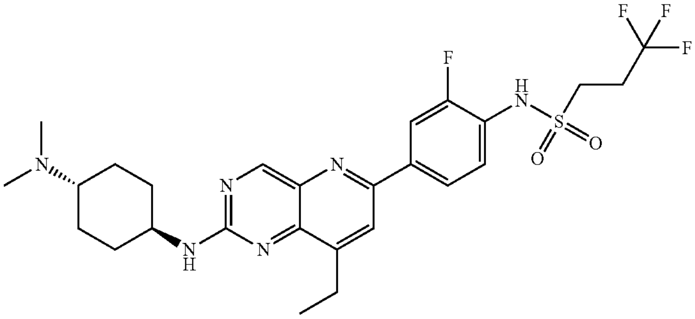 [SMILES: CCc1cc(-c2ccc(NS(=O)(=O)CCC(F)(F)F)c(F)c2)nc2cnc(N[C@H]3CC[C@H](N(C)C)CC3)nc12] | N-(4-(2-(((1,4-trans)-4-(Dimethylamino) cyclohexyl) amino)-8-ethylpyrido [3,2-d]pyrimidin-6-yl)-2-fluorophenyl)-3,3,3-trifluoropropane-1-sulfonamide | 0.00008 | 569.2 |
| 115 | 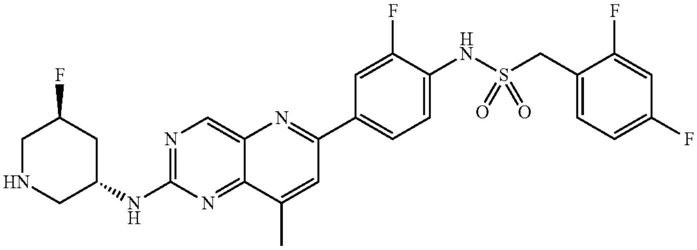 [SMILES: Cc1cc(-c2ccc(NS(=O)(=O)Cc3ccc(F)cc3F)c(F)c2)nc2cnc(N[C@@H]3CNC[C@@H](F)C3)nc12] | 1-(2,4-Difluorophenyl)-N-(2-fluoro-4-(2-(((3S,5S)-5-fluoropiperidin-3-yl)amino)-8-methylpyrido [3,2-d]pyrimidin-6-yl)phenyl) methanesulfonamide | 0.00026 | 560.9 |
| 116 | 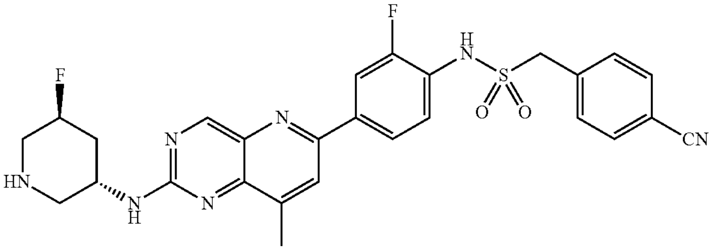 [SMILES: Cc1cc(-c2ccc(NS(=O)(=O)Cc3ccc(C#N)cc3)c(F)c2)nc2cnc(N[C@@H]3CNC[C@@H](F)C3)nc12] | 1-(4-Cyanophenyl)-N-(2-fluoro-4-(2-(((3S,5S)-5-fluoropiperidin-3-yl)amino)-8-methylpyrido [3,2-d]pyrimidin-6-yl)phenyl) methanesulfonamide formate | 0.00013 | 550.2 |
| 117 | 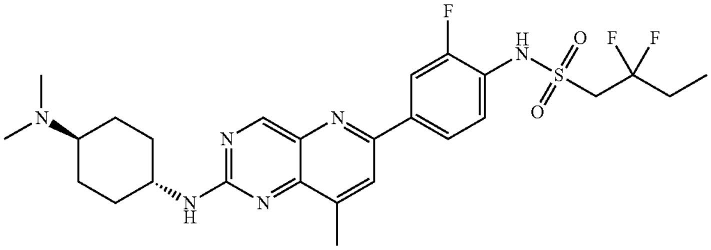 [SMILES: CCC(F)(F)CS(=O)(=O)Nc1ccc(-c2cc(C)c3nc(N[C@H]4CC[C@H](N(C)C)CC4)ncc3n2)cc1F] | N-(4-(2-(((1,4-trans)-4-(Dimethylamino) cyclohexyl) amino)-8-methylpyrido [3,2-d]pyrimidin-6-yl)-2-fluorophenyl)-2,2-difluorobutane-1-sulfonamide formate | 0.00011 | 551.0 |

TABLE 1-continued

| Cmpd No. | Structure | Name | IRE1α (alpha) HTRF ($IC_{50}$) (μM) | Mass Spec. M + H/1 |
|---|---|---|---|---|
| 118 | 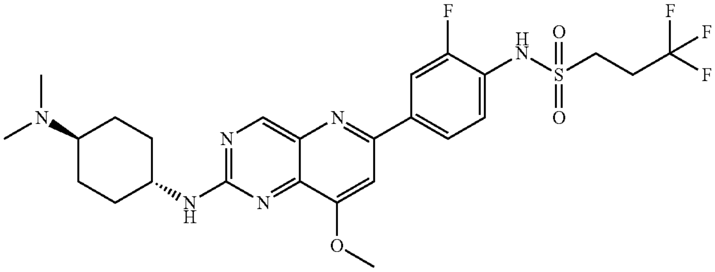 [SMILES: COc1cc(-c2ccc(NS(=O)(=O)CCC(F)(F)F)c(F)c2)nc2cnc(N[C@H]3CC[C@H](N(C)C)CC3)nc12] | N-(4-(2-(((1,4-trans)-4-(Dimethylamino) cyclohexyl) amino)-8-methoxypyrido [3,2-d]pyrimidin-6-yl)-2-fluorophenyl)-3,3,3-trifluoropropane-1-sulfonamide formate | 0.022 | 571.2 |
| 119 | 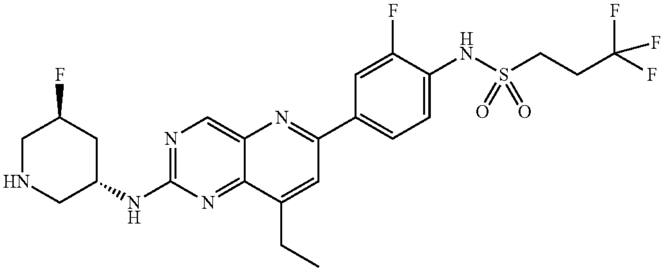 [SMILES: CCc1cc(-c2ccc(NS(=O)(=O)CCC(F)(F)F)c(F)c2)nc2cnc(N[C@@H]3CNC[C@@H](F)C3)nc12] | N-(4-(8-Ethyl-2-(((3S,5S)-5-fluoropiperidin-3-yl)amino)pyrido[3,2-d] pyrimidin-6-yl)-2-fluorophenyl)-3,3,3-trifluoropropane-1-sulfonamide formate | 0.00039 | 545.2 |
| 120 | 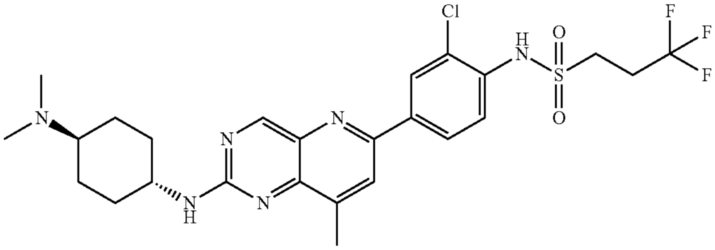 [SMILES: Cc1cc(-c2ccc(NS(=O)(=O)CCC(F)(F)F)c(Cl)c2)nc2cnc(N[C@H]3CC[C@H](N(C)C)CC3)nc12] | N-(2-Chloro-4-(2-(((1,4-trans)-4-(dimethylamino) cyclohexyl)amino)-8-methylpyrido[3,2-d] pyrimidin-6-yl)phenyl)-3,3,3-trifluoropropane-1-sulfonamide | 0.00025 | 571.0 |
| 121 | 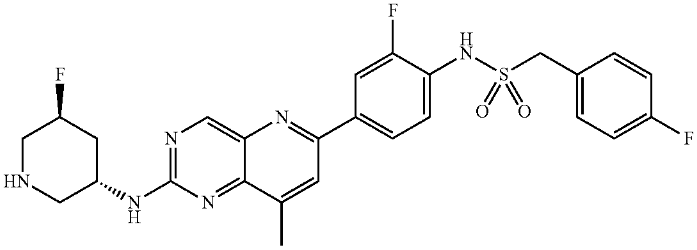 [SMILES: Cc1cc(-c2ccc(NS(=O)(=O)Cc3ccc(F)cc3)c(F)c2)nc2cnc(N[C@@H]3CNC[C@@H](F)C3)nc12] | N-(2-Fluoro-4-(2-(((3S,5S)-5-fluoropiperidin-3-yl)amino)-8-methylpyrido[3,2-d] pyrimidin-6-yl)phenyl)-1-(4-fluorophenyl) methanesulfonamide formate | 0.00027 | 543.0 |
| 122 | 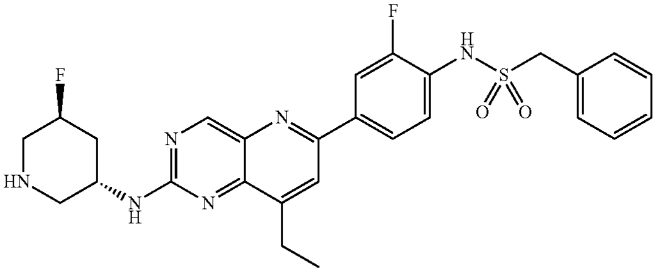 [SMILES: CCc1cc(-c2ccc(NS(=O)(=O)Cc3ccccc3)c(F)c2)nc2cnc(N[C@@H]3CNC[C@@H](F)C3)nc12] | N-(4-(8-Ethyl-2-(((3S,5S)-5-fluoropiperidin-3-yl)amino)pyrido[3,2-d] pyrimidin-6-yl)-2-fluorophenyl)-1-phenylmethanesulfonamide formate | 0.0002 | 539.0 |

TABLE 1-continued

| Cmpd No. | Structure | Name | IRE1α (alpha) HTRF ($IC_{50}$) (μM) | Mass Spec. M + H/1 |
|---|---|---|---|---|
| 123 | 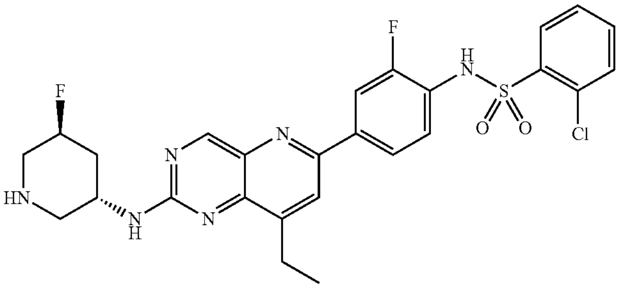 [SMILES: CCc1cc(-c2ccc(NS(=O)(=O)c3ccccc3Cl)c(F)c2)nc2cnc(N[C@@H]3CNC[C@@H](F)C3)nc12] | 2-Chloro-N-(4-(8-ethyl-2-(((3S,5S)-5-fluoropiperidin-3-yl)amino)pyrido[3,2-d]pyrimidin-6-yl)-2-fluorophenyl) benzenesulfonamide formate | 0.00018 | 558.9 |
| 124 | 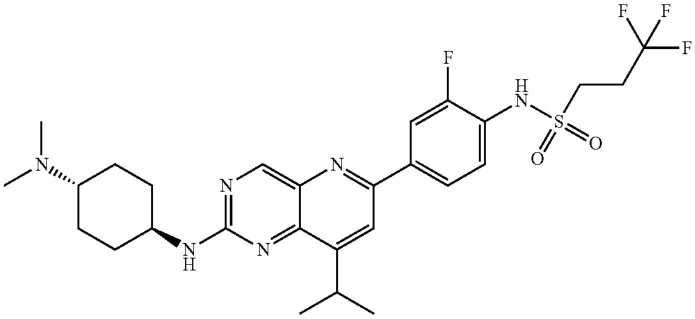 [SMILES: CC(C)c1cc(-c2ccc(NS(=O)(=O)CCC(F)(F)F)c(F)c2)nc2cnc(N[C@H]3CC[C@H](N(C)C)CC3)nc12] | N-(4-(2-(((1,4-trans)-4-(Dimethylamino) cyclohexyl)amino)-8-isopropylpyrido[3,2-d] pyrimidin-6-yl)-2-fluorophenyl)-3,3,3-trifluoropropane-1-sulfonamide | 0.00016 | 583.1 |
| 125 | 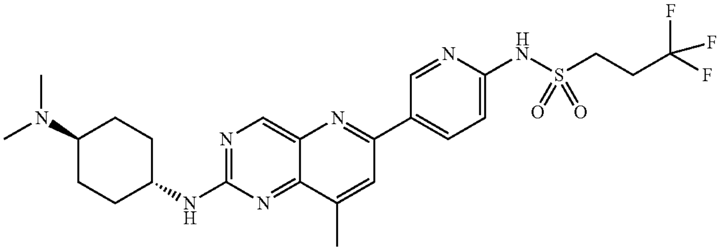 [SMILES: Cc1cc(-c2ccc(NS(=O)(=O)CCC(F)(F)F)nc2)nc2cnc(N[C@H]3CC[C@H](N(C)C)CC3)nc12] | N-(5-(2-(((1,4-trans)-4-(Dimethylamino) cyclohexyl) amino)-8-methylpyrido [3,2-d]pyrimidin-6-yl)pyridin-2-yl)-3,3,3-trifluoropropane-1-sulfonamide | 0.00044 | 538.3 |
| 126 | 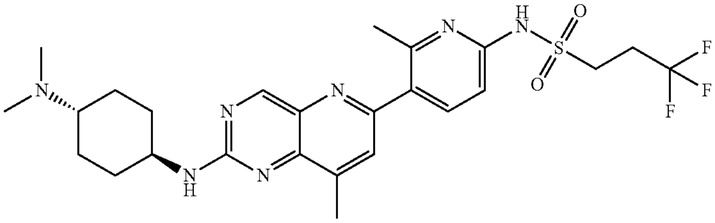 [SMILES: Cc1nc(NS(=O)(=O)CCC(F)(F)F)ccc1-c1cc(C)c2nc(N[C@H]3CC[C@H](N(C)C)CC3)ncc2n1] | N-(5-(2-(((1,4-trans)-4-(Dimethylamino) cyclohexyl) amino)-8-methylpyrido [3,2-d]pyrimidin-6-yl)-6-methylpyridin-2-yl)-3,3,3-trifluoropropane-1-sulfonamide | 0.018 | 552.0 |
| 127 | 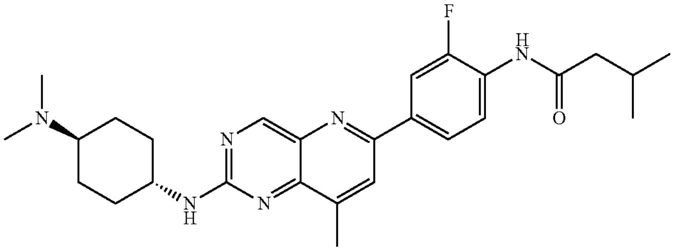 [SMILES: Cc1cc(-c2ccc(NC(=O)CC(C)C)c(F)c2)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2-fluorophenyl)-3-methylbutanamide | 0.14 | 479.1 |

TABLE 1-continued

| Cmpd No. | Structure | Name | IRE1α (alpha) HTRF ($IC_{50}$) (μM) | Mass Spec. M + H/1 |
|---|---|---|---|---|
| 128 | 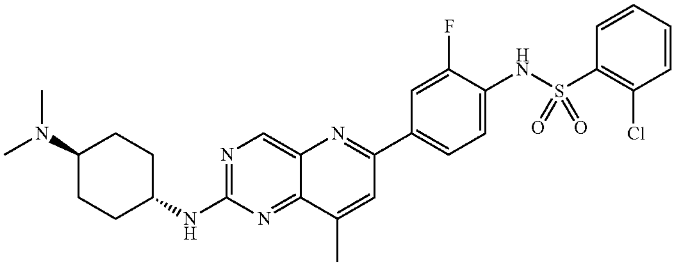 [SMILES: Cc1cc(-c2ccc(NS(=O)(=O)c3ccccc3Cl)c(F)c2)nc2cnc(N[C@H]3CC[C@H](N(C)C)CC3)nc12] | 2-Chloro-N-(4-(2-(((1,4-trans)-4-(dimethylamino) cyclohexyl)amino)-8-methylpyrido[3,2-d]-pyrimidin-6-yl)-2-fluorophenyl) benzenesulfonamide | 0.00016 | 569.0 |
| 129 | 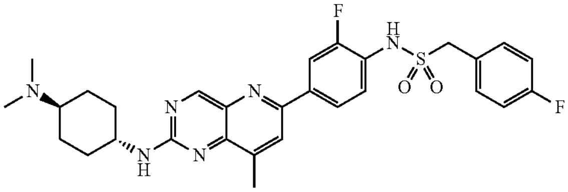 [SMILES: Cc1cc(-c2ccc(NS(=O)(=O)Cc3ccc(F)cc3)c(F)c2)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2-fluorophenyl)-1-(4-fluorophenyl) methanesulfonamide | 0.00008 | 567.1 |
| 130 | 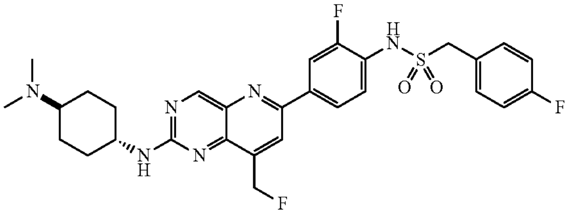 [SMILES: CN(C)[C@H]1CC[C@H](Nc2ncc3nc(-c4ccc(NS(=O)(=O)Cc5ccc(F)cc5)c(F)c4)cc(CF)c3n2)CC1] | N-[4-[2-[[(1,4-trans)-4-(Dimethylamino) cyclohexyl] amino]-8-(fluoromethyl) pyrido[3,2-d]pyrimidin-6-yl]-2-fluoro-phenyl]-1-(4-fluorophenyl) methanesulfonamide | 0.0002 | 585.2 |
| 131 | 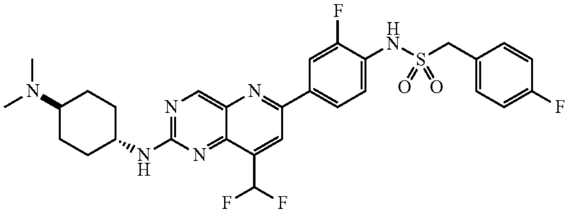 [SMILES: CN(C)[C@H]1CC[C@H](Nc2ncc3nc(-c4ccc(NS(=O)(=O)Cc5ccc(F)cc5)c(F)c4)cc(C(F)F)c3n2)CC1] | N-1,4-trans-[4-[8-(Difluoromethyl)-2-[[4-(dimethylamino) cyclohexyl]amino] pyrido[3,2-d] pyrimidin-6-yl]-2-fluorophenyl]-1-(4-fluorophenyl) methanesulfonamide | 0.00015 | 603.2 |
| 132 | 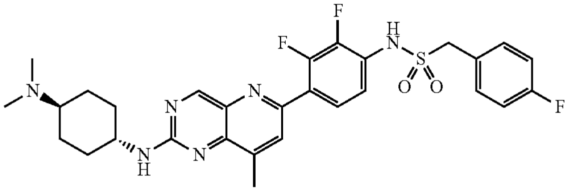 [SMILES: Cc1cc(-c2ccc(NS(=O)(=O)Cc3ccc(F)cc3)c(F)c2F)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2,3-difluorophenyl)-1-(4-fluorophenyl) methanesulfonamide | 0.00023 | 585.1 |
| 133 | 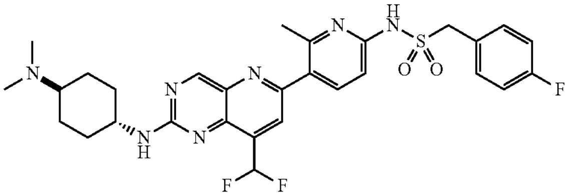 [SMILES: Cc1nc(NS(=O)(=O)Cc2ccc(F)cc2)ccc1-c1cc(C(F)F)c2nc(N[C@H]3CC[C@H](N(C)C)CC3)ncc2n1] | N-(5-(8-(Difluoromethyl)-2-(((1,4-trans)-4-(dimethylamino) cyclohexyl)amino) pyrido[3,2-d]pyrimidin-6-yl)-6-methylpyridin-2-yl)-1-(4-fluorophenyl) methanesulfonamide | 0.0052 | 600.3 |

TABLE 1-continued

| Cmpd No. | Structure | Name | IRE1α (alpha) HTRF ($IC_{50}$) (μM) | Mass Spec. M + H/1 |
|---|---|---|---|---|
| 134 | 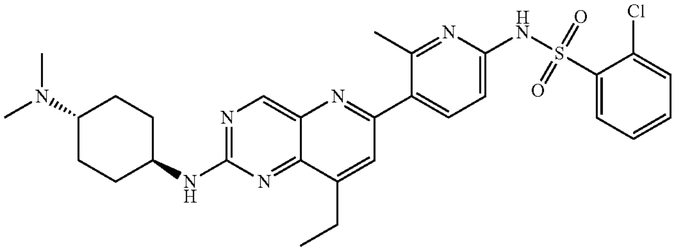 | 2-Chloro-N-(5-(2-(((1,4-trans)-4-(dimethylamino) cyclohexyl)amino)-8-ethylpyrido[3,2-d] pyrimidin-6-yl)-6-methylpyridin-2-yl)benzenesulfonamide | 0.00033 | 580.1 |
| 135 | 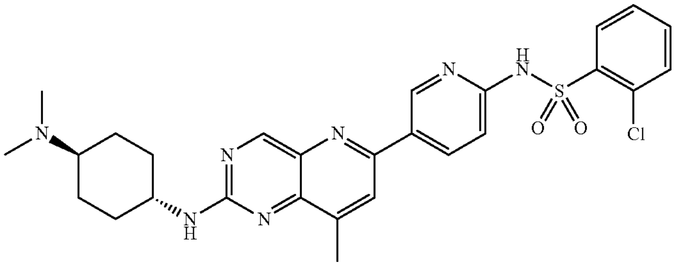 [SMILES: Cc1cc(-c2ccc(NS(=O)(=O)c3ccccc3Cl)nc2)nc2cnc(N[C@H]3CC[C@H](N(C)C)CC3)nc12] | 2-Chloro-N-(5-(2-(((1,4-trans)-4-(dimethylamino) cyclohexyl)amino)-8-methylpyrido[3,2-d] pyrimidin-6-yl)pyridin-2-yl)benzenesulfonamide | 0.00032 | 552.0 |
| 136 | 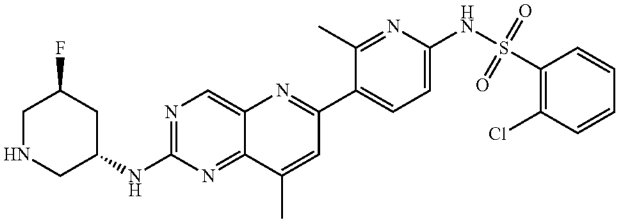 [SMILES: Cc1nc(NS(=O)(=O)c2ccccc2Cl)ccc1-c1cc(C)c2nc(N[C@@H]3CNC[C@@H](F)C3)ncc2n1] | 2-Chloro-N-(5-(2-(((3S,5S)-5-fluoropiperidin-3-yl)amino)-8-methylpyrido[3,2-d] pyrimidin-6-yl)-6-methylpyridin-2-yl) benzenesulfonamide | 0.014 | 542.0 |
| 137 | 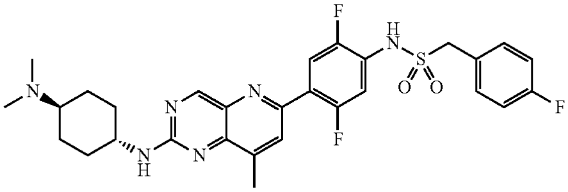 [SMILES: Cc1cc(-c2cc(F)c(NS(=O)(=O)Cc3ccc(F)cc3)cc2F)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2,5-difluorophenyl)-1-(4-fluorophenyl) methanesulfonamide | 0.00023 | 585.3 |
| 138 | 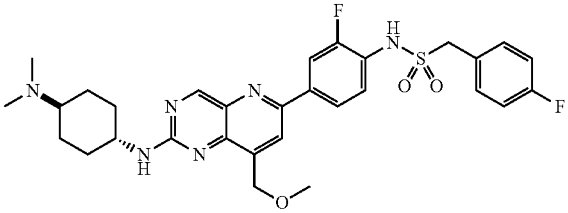 [SMILES: COCc1cc(-c2ccc(NS(=O)(=O)Cc3ccc(F)cc3)c(F)c2)nc2cnc(N[C@H]3CC[C@H](N(C)C)CC3)nc12] | N-(4-(2-(((1,4-trans)-4-(Dimethylamino) cyclohexyl)amino)-8-(methoxymethyl) pyrido[3,2-d]pyrimidin-6-yl)-2-fluorophenyl)-1-(4-fluorophenyl) methanesulfonamide | 0.00021 | 597.4 |
| 139 | 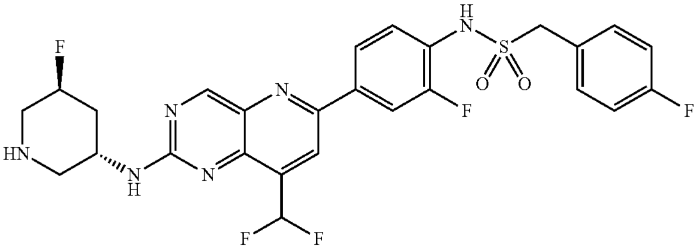 [SMILES: O=S(=O)(Cc1ccc(F)cc1)Nc1ccc(-c2cc(C(F)F)c3nc(N[C@@H]4CNC[C@@H](F)C4)ncc3n2)cc1F] | N-[4-[8-(Difluoromethyl)-2-[[(3S,5S)-5-fluoro-3-piperidyl]amino] pyrido[3,2-d] pyrimidin-6-yl]-2-fluorophenyl]-1-(4-fluorophenyl) methanesulfonamide hydrochloride | 0.00023 | 579.3 |

TABLE 1-continued

| Cmpd No. | Structure | Name | IRE1α (alpha) HTRF ($IC_{50}$) (μM) | Mass Spec. M + H/1 |
|---|---|---|---|---|
| 140 | 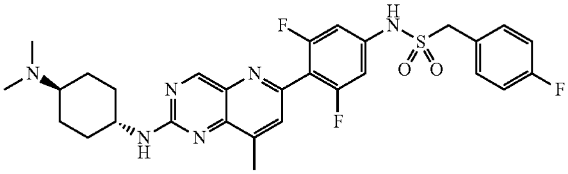 [SMILES: Cc1cc(-c2c(F)cc(NS(=O)(=O)Cc3ccc(F)cc3)cc2F)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-3,5-difluorophenyl)-1-(4-fluorophenyl) methanesulfonamide | 0.0045 | 585.1 |
| 141 | 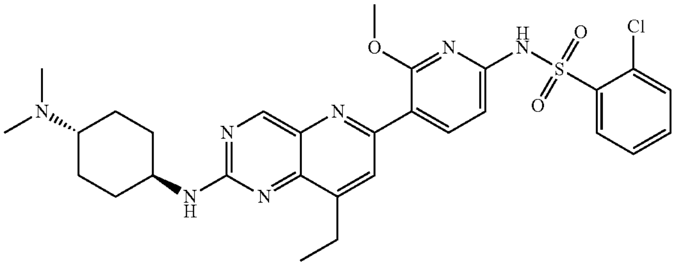 [SMILES: CCc1cc(-c2ccc(NS(=O)(=O)c3ccccc3Cl)nc2OC)nc2cnc(N[C@H]3CC[C@H](N(C)C)CC3)nc12] | 2-Chloro-N-(5-(2-(((1,4-trans)-4-(dimethylamino) cyclohexyl)amino)-8-ethylpyrido[3,2-d] pyrimidin-6-yl)-6-methoxypyridin-2-yl)benzenesulfonamide | 0.00043 | 596.1 |
| 142 | 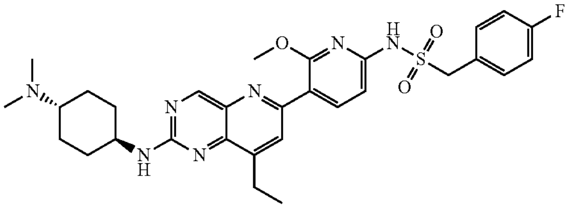 [SMILES: CCc1cc(-c2ccc(NS(=O)(=O)Cc3ccc(F)cc3)nc2OC)nc2cnc(N[C@H]3CC[C@H](N(C)C)CC3)nc12] | N-(5-(2-(((1,4-trans)-4-(Dimethylamino) cyclohexyl) amino)-8-ethylpyrido [3,2-d]pyrimidin-6-yl)-6-methoxypyridin-2-yl)-1-(4-fluorophenyl) methanesulfonamide | 0.00014 | 594.1 |
| 143 | 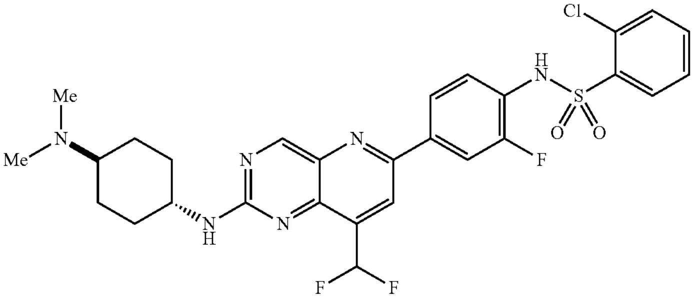 [SMILES: CN(C)[C@H]1CC[C@H](Nc2ncc3nc(-c4ccc(NS(=O)(=O)c5ccccc5Cl)c(F)c4)cc(C(F)F)c3n2)CC1] | 2-Chloro-N-[(1,4-trans)-4-[8-(difluoromethyl)-2-[[4-(dimethylamino) cyclohexyl] amino]pyrido[3,2-d]pyrimidin-6-yl]-2-fluorophenyl] benzenesulfonamide | 0.0002 | 605.3 |
| 144 | 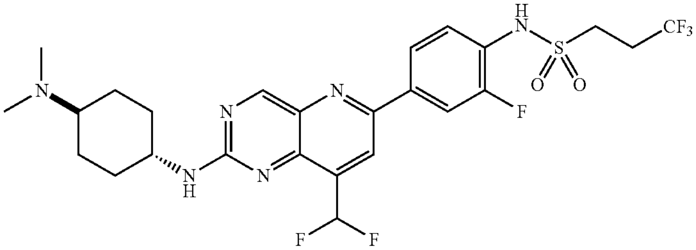 [SMILES: CN(C)[C@H]1CC[C@H](Nc2ncc3nc(-c4ccc(NS(=O)(=O)CCC(F)(F)F)c(F)c4)cc(C(F)F)c3n2)CC1] | N-[(1,4-trans)-4-[8-(Difluoromethyl)-2-[[4-(dimethylamino) cyclohexyl] amino]pyrido[3,2-d]pyrimidin-6-yl]-2-fluoro-phenyl]-3,3,3-trifluoro-propane-1-sulfonamide | 0.00016 | 591.3 |

TABLE 1-continued

| Cmpd No. | Structure | Name | IRE1α (alpha) HTRF ($IC_{50}$) (μM) | Mass Spec. M + H/1 |
|---|---|---|---|---|
| 145 | 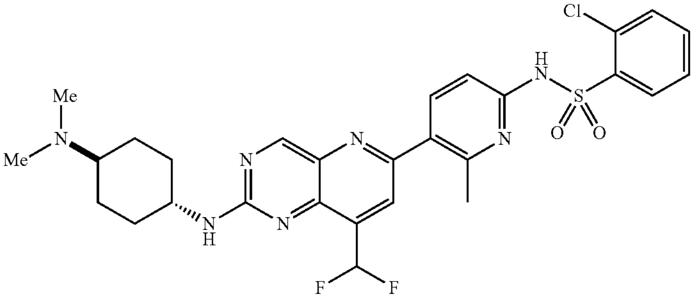 [SMILES: Cc1nc(NS(=O)(=O)c2ccccc2Cl)ccc1-c1cc(C(F)F)c2nc(N[C@H]3CC[C@H](N(C)C)CC3)ncc2n1] | 2-Chloro-N-[5-[8-(difluoromethyl)-2-[[(1,4-trans)-4-(dimethylamino) cyclohexyl] amino]pyrido[3,2-d]pyrimidin-6-yl]-6-methyl-2-pyridyl] benzenesulfonamide | 0.00025 | 602.3 |
| 146 | 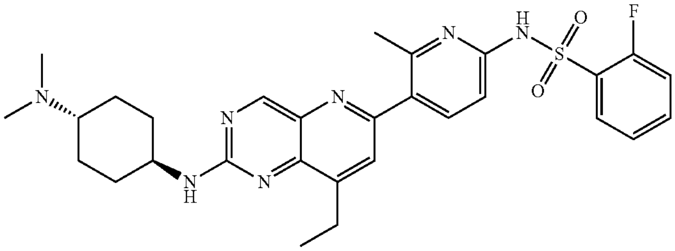 [SMILES: CCc1cc(-c2ccc(NS(=O)(=O)c3ccccc3F)nc2C)nc2cnc(N[C@H]3CC[C@H](N(C)C)CC3)nc12] | N-(5-(2-(((1,4-trans)-4-(dimethylamino) cyclohexyl) amino)-8-ethylpyrido [3,2-d]pyrimidin-6-yl)-6-methylpyridin-2-yl)-2-fluorobenzenesulfonamide | 0.00021 | 564.1 |
| 147 | 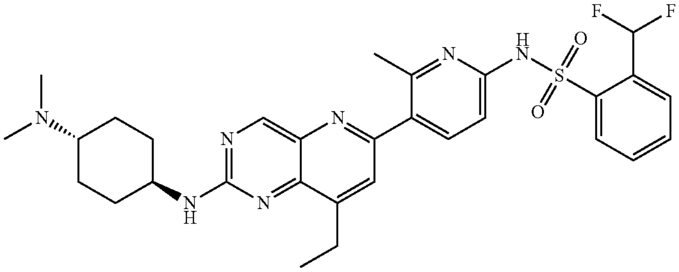 [SMILES: CCc1cc(-c2ccc(NS(=O)(=O)c3ccccc3C(F)F)nc2C)nc2cnc(N[C@H]3CC[C@H](N(C)C)CC3)nc12] | 2-(Difluoromethyl)-N-(5-(2-(((1,4- trans)-4-(dimethylamino) cyclohexyl) amino)-8-ethylpyrido [3,2-d]pyrimidin-6-yl)-6-methylpyridin-2-yl) benzenesulfonamide | 0.00028 | 596.1 |
| 148 | 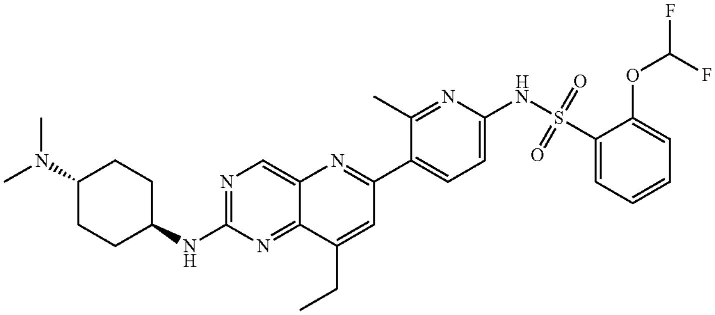 [SMILES: CCc1cc(-c2ccc(NS(=O)(=O)c3ccccc3OC(F)F)nc2C)nc2cnc(N[C@H]3CC[C@H](N(C)C)CC3)nc12] | 2-(Difluoromethoxy)-N-(5-(2-(((1,4-trans)-4-(dimethylamino) cyclohexyl) amino)-8-ethylpyrido [3,2-d]pyrimidin-6-yl)-6-methylpyridin-2-yl) benzenesulfonamide | 0.00051 | 612.2 |
| 149 | 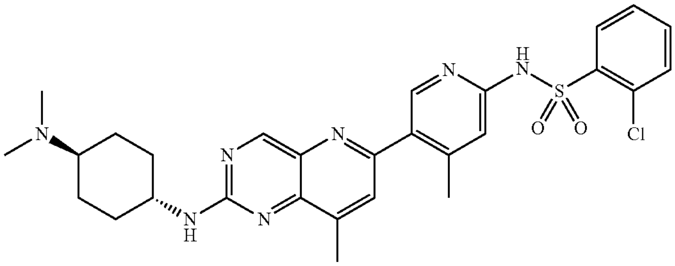 [SMILES: Cc1cc(NS(=O)(=O)c2ccccc2Cl)ncc1-c1cc(C)c2nc(N[C@H]3CC[C@H](N(C)C)CC3)ncc2n1] | 2-Chloro-N-(5-(2-(((1,4-trans)-4-(dimethylamino) cyclohexyl)amino)-8-methylpyrido[3,2-d] pyrimidin-6-yl)-4-methylpyridin-2-yl)benzenesulfonamide | 0.0033 | 566.1 |

TABLE 1-continued

| Cmpd No. | Structure | Name | IRE1α (alpha) HTRF ($IC_{50}$) (μM) | Mass Spec. M + H/1 |
|---|---|---|---|---|
| 150 | 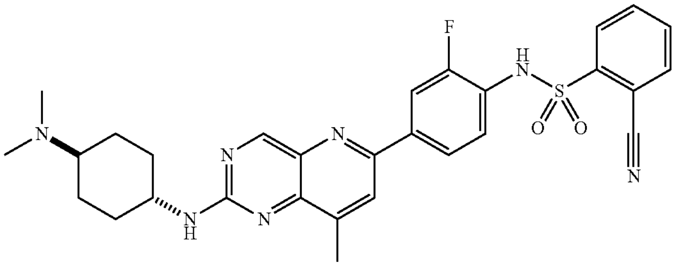 | 2-Cyano-N-[(1,4-trans)-4-[2-[[4-(dimethylamino) cyclohexyl]amino]-8-methylpyrido [3,2-d]pyrimidin-6-yl]-2-fluoro-phenyl] benzenesulfonamide | 0.00015 | 560.1 |
| 151 | 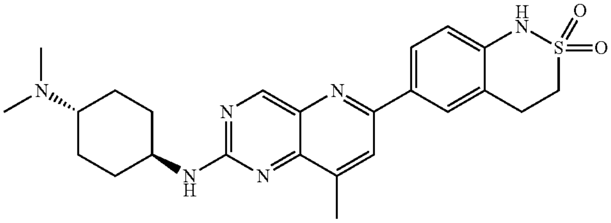 [SMILES: Cc1cc(-c2ccc3c(c2)CCS(=O)(=O)N3)nc2cnc(N[C@H]3CC[C@H](N(C)C)CC3)nc12] | 6-(2-(((1,4-trans)-4-(Dimethylamino) cyclohexyl) amino)-8-methylpyrido [3,2-d]pyrimidin-6-yl)-3,4-dihydro-1H-benzo[c][1,2]thiazine 2,2-dioxide | 0.039 | 467.1 |
| 152 | 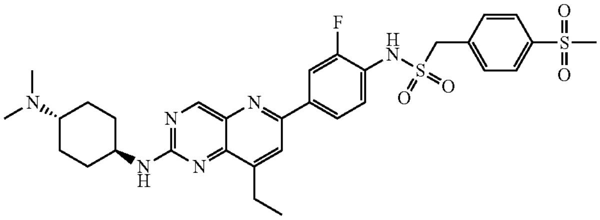 | N-(4-(2-(((1,4-trans)-4-(Dimethylamino) cyclohexyl) amino)-8-ethylpyrido [3,2-d]pyrimidin-6-yl)-2-fluorophenyl)-1-(4-(methylsulfonyl)phenyl) methanesulfonamide | 0.00012 | 641.2 |
| 153 | 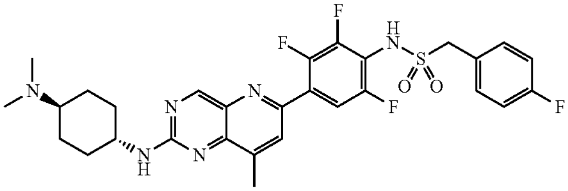 [SMILES: Cc1cc(-c2cc(F)c(NS(=O)(=O)Cc3ccc(F)cc3)c(F)c2F)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2,3,6-trifluorophenyl)-1-(4-fluorophenyl) methanesulfonamide | 0.00016 | 603.2 |
| 154 | 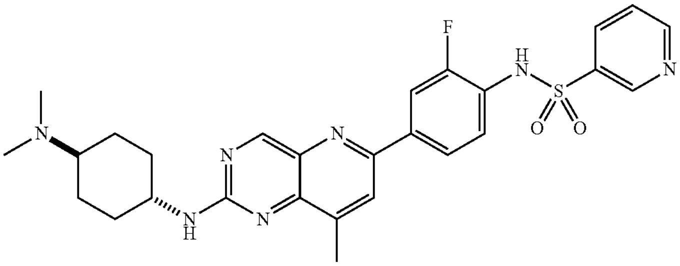 | N-[4-[2-[[(1,4-trans)-4-(Dimethylamino) cyclohexyl] amino]-8-methyl-pyrido[3,2-d]pyrimidin-6-yl]-2-fluoro-phenyl] pyridine-3-sulfonamide | 0.00021 | 608.3 |
| 155 | 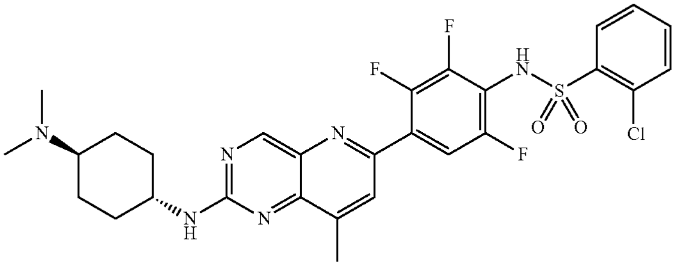 [SMILES: Cc1cc(-c2cc(F)c(NS(=O)(=O)c3ccccc3Cl)c(F)c2F)nc2cnc(N[C@H]3CC[C@H](N(C)C)CC3)nc12] | 2-Chloro-N-(4-(2-(((1,4-trans)-4-(dimethylamino) cyclohexyl)amino)-8-methylpyrido[3,2-d] pyrimidin-6-yl)-2,3,6-trifluorophenyl) benzenesulfonamide | 0.00019 | 605.4 |

TABLE 1-continued

| Cmpd No. | Structure | Name | IRE1α (alpha) HTRF ($IC_{50}$) (μM) | Mass Spec. M + H/1 |
|---|---|---|---|---|
| 156 | 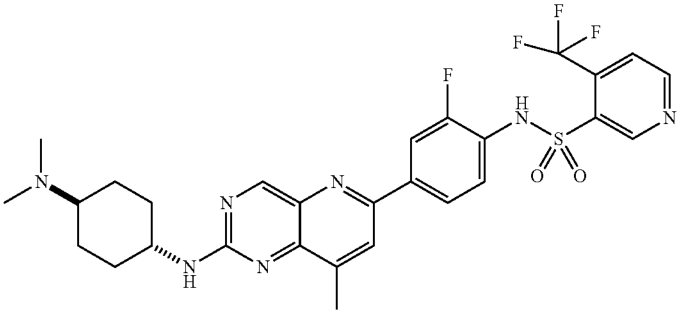 | N-[4-[2-[[(1,4-tans)-4-(Dimethylamino) cyclohexyl] amino]-8-methylpyrido [3,2-d]pyrimidin-6-yl]-2-fluoro-phenyl]-4-(trifluoromethyl) pyridine-3-sulfonamide | 0.00018 | 604.2 |
| 157 | 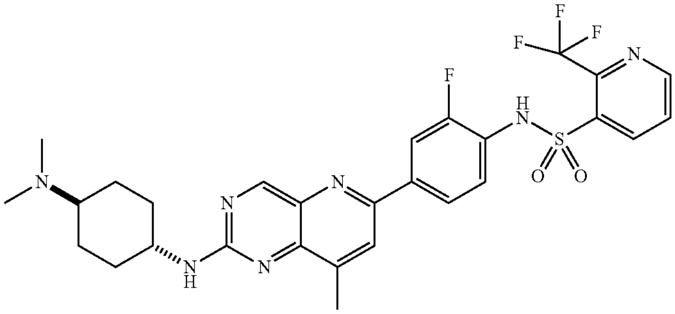 | N-[4-[2-[[(1,4-trans)-4-(Dimethylamino) cyclohexyl] amino]-8-methylpyrido [3,2-d]pyrimidin-6-yl]-2-fluoro-phenyl]-2-(trifluoromethyl) pyridine-3-sulfonamide | 0.00023 | 604.3 |
| 158 | 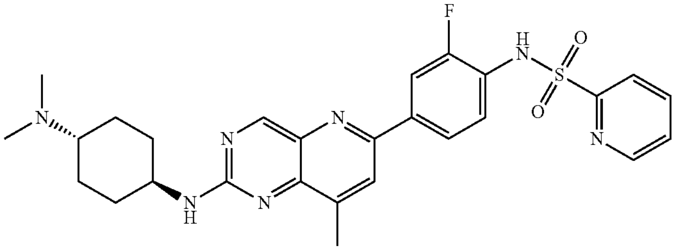 [SMILES: Cc1cc(-c2ccc(NS(=O)(=O)c3ccccn3)c(F)c2)nc2cnc(N[C@H]3CC[C@H](N(C)C)CC3)nc12] | N-(4-(2-(((1,4-trans)-4-(Dimethylamino) cyclohexyl) amino)-8-methylpyrido [3,2-d]pyrimidin-6-yl)-2-fluorophenyl) pyridine-2-sulfonamide | 0.0002 | 536.4 |
| 159 | 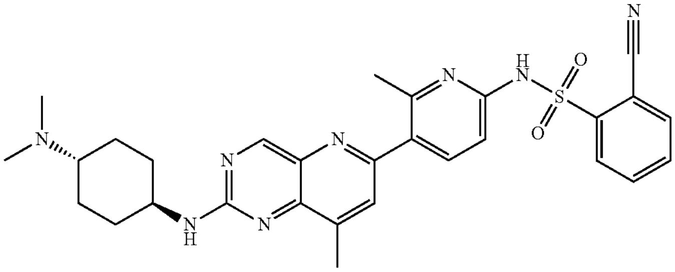 [SMILES: Cc1nc(NS(=O)(=O)c2ccccc2C#N)ccc1-c1cc(C)c2nc(N[C@H]3CC[C@H](N(C)C)CC3)ncc2n1] | 2-Cyano-N-(5-(2-(((1,4-trans)-4-(dimethylamino) cyclohexyl)amino)-8-methylpyrido[3,2-d] pyrimidin-6-yl)-6-methylpyridin-2-yl)benzenesulfonamide | 0.00033 | 557.2 |

In one embodiment, the compound or pharmaceutically acceptable salt thereof is a compound set forth in Table 2.

TABLE 2

| Cmpd No. | Structure | Name | Mw (m/z) |
|---|---|---|---|
| 201 | 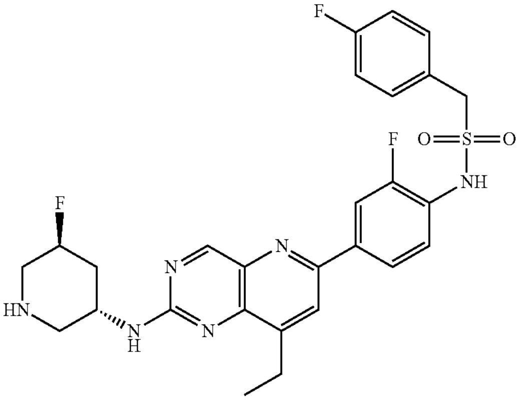 [SMILES: CCc1cc(-c2ccc(NS(=O)(=O)Cc3ccc(F)cc3)c(F)c2)nc2cnc(N[C@@H]3CNC[C@@H](F)C3)nc12] | N-(4-(8-ethyl-2-(((3S,5S)-5-fluoropiperidin-3-yl)amino)pyrido[3,2-d]pyrimidin-6-yl)-2-fluorophenyl)-1-(4-fluorophenyl) methanesulfonamide | 556.19 |
| 202 | 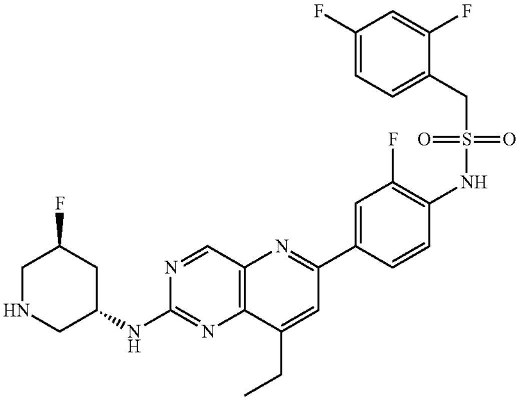 [SMILES: CCc1cc(-c2ccc(NS(=O)(=O)Cc3ccc(F)cc3F)c(F)c2)nc2cnc(N[C@@H]3CNC[C@@H](F)C3)nc12] | 1-(2,4-difluorophenyl)-N-(4-(8-ethyl-2-(((3S,5S)-5-fluoropiperidin-3-yl)amino)pyrido[3,2-d]pyrimidin-6-yl)-2-fluorophenyl)methanesulfonamide | 574.18 |
| 203 | 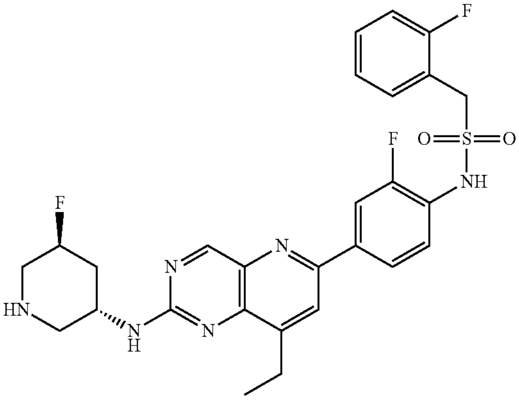 [SMILES: CCc1cc(-c2ccc(NS(=O)(=O)Cc3ccccc3F)c(F)c2)nc2cnc(N[C@@H]3CNC[C@@H](F)C3)nc12] | N-(4-(8-ethyl-2-(((3S,5S)-5-fluoropiperidin-3-yl)amino)pyrido[3,2-d]pyrimidin-6-yl)-2-fluorophenyl)-1-(2-fluorophenyl)methanesulfonamide | 556.19 |

TABLE 2-continued

| Cmpd No. | Structure | Name | Mw (m/z) |
|---|---|---|---|
| 204 | 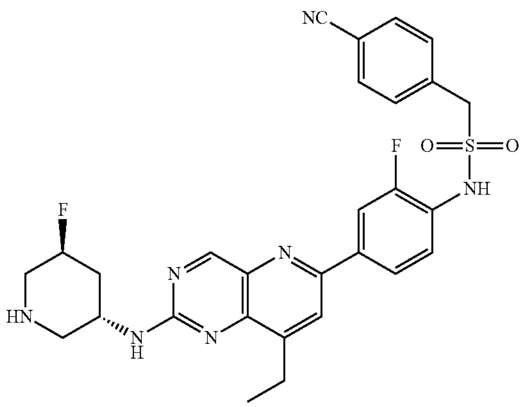 [SMILES: CCc1cc(-c2ccc(NS(=O)(=O)Cc3ccc(C#N)cc3)c(F)c2)nc2cnc(N[C@@H]3CNC[C@@H](F)C3)nc12] | 1-(4-cyanophenyl)-N-(4-(8-ethyl-2-(((3S,5S)-5-fluoropiperidin-3-yl) amino)pyrido[3,2-d]pyrimidin-6-yl)-2-fluorophenyl)methanesulfonamide | 563.19 |
| 205 | 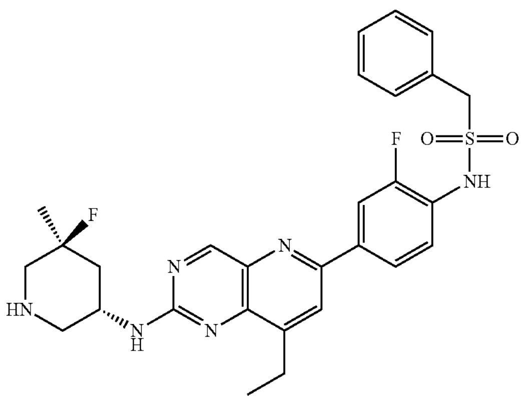 [SMILES: CCc1cc(-c2ccc(NS(=O)(=O)Cc3ccccc3)c(F)c2)nc2cnc(N[C@@H]3CNC[C@@](C)(F)C3)nc12] | N-(4-(8-ethyl-2-(((3S,5S)-4-fluoro-5-methylpiperidin-3-yl)amino)pyrido [3,2-d]pyrimidin-6-yl)-2-fluoro-phenyl)-1-phenylmethanesulfonamide | 552.21 |
| 206 | 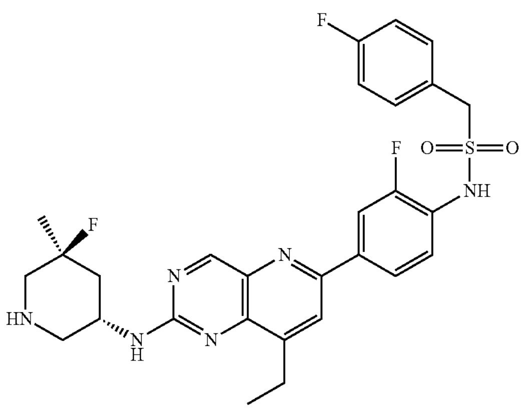 [SMILES: CCc1cc(-c2ccc(NS(=O)(=O)Cc3ccc(F)cc3)c(F)c2)nc2cnc(N[C@@H]3CNC[C@@](C)(F)C3)nc12] | N-(4-(8-ethyl-2-(((3S,5S)-5-fluoro-5-methylpiperidin-3-yl)amino)pyrido [3,2-d]pyrimidin-6-yl)-2-fluoro-phenyl)-1-(4-fluorophenyl) methanesulfonamide | 570.20 |

TABLE 2-continued

| Cmpd No. | Structure | Name | Mw (m/z) |
|---|---|---|---|
| 207 | 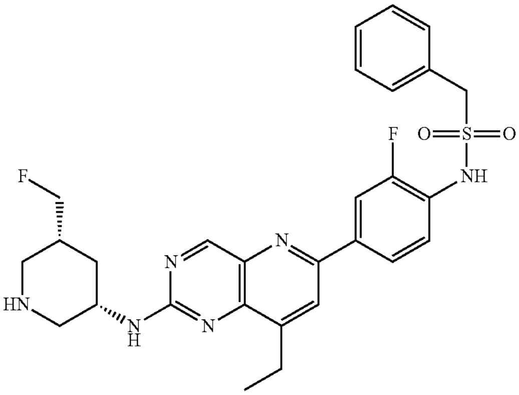 [SMILES: CCc1cc(-c2ccc(NS(=O)(=O)Cc3ccccc3)c(F)c2)nc2cnc(N[C@@H]3CNC[C@H](CF)C3)nc12] | N-(4-(8-ethyl-2-(((3S,5R)-5-(fluoro-methyl)piperidin-3-yl)amino)pyrido[3,2-d]pyrimidin-6-yl)-2-fluoro-phenyl)-1-phenylmethanesulfonamide | 552.21 |
| 208 | 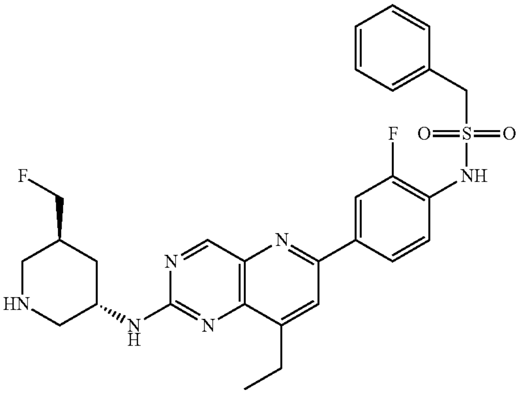 [SMILES: CCc1cc(-c2ccc(NS(=O)(=O)Cc3ccccc3)c(F)c2)nc2cnc(N[C@@H]3CNC[C@@H](CF)C3)nc12] | N-(4-(8-ethyl-2-(((3S,5S)-5-(fluoro-methyl)piperidin-3-yl)amino)pyrido[3,2-d]pyrimidin-6-yl)-2-fluoro-phenyl)-1-phenylmethanesulfonamide | 552.21 |
| 209 | 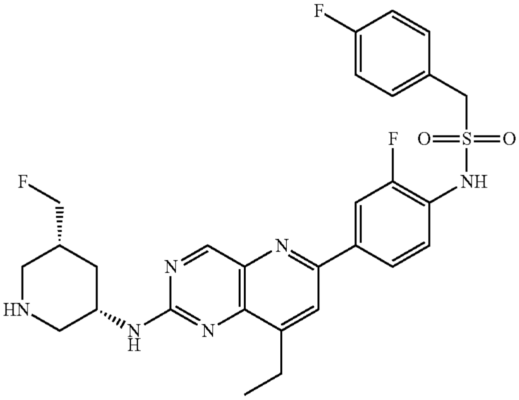 [SMILES: CCc1cc(-c2ccc(NS(=O)(=O)Cc3ccc(F)cc3)c(F)c2)nc2cnc(N[C@@H]3CNC[C@H](CF)C3)nc12] | N-(4-(8-ethyl-2-(((3S,5S)-5-(fluoro-methyl)piperidin-3-yl)amino)pyrido[3,2-d]pyrimidin-6-yl)-2-fluoro-phenyl)-1-(4-fluorophenyl)methanesulfonamide | 570.20 |

TABLE 2-continued

| Cmpd No. | Structure | Name | Mw (m/z) |
|---|---|---|---|
| 210 | 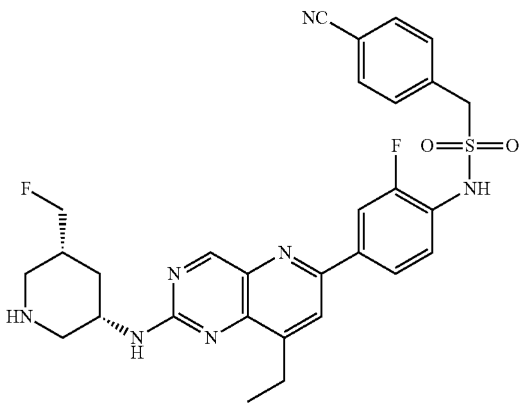 [SMILES: CCc1cc(-c2ccc(NS(=O)(=O)Cc3ccc(C#N)cc3)c(F)c2)nc2cnc(N[C@@H]3CNC[C@H](CF)C3)nc12] | 1-(4-cyanophenyl)-N-(4-(8-ethyl-2-(((3S,5S)-5-(fluoromethyl)piperidin-3-yl)amino)pyrido[3,2-d]pyrimidin-6-yl)-2-fluorophenyl)methanesulfonamide | 577.21 |
| 211 | 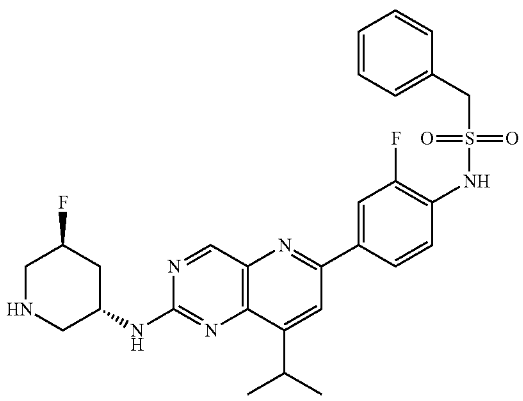 [SMILES: CC(C)c1cc(-c2ccc(NS(=O)(=O)Cc3ccccc3)c(F)c2)nc2cnc(N[C@@H]3CNC[C@@H](F)C3)nc12] | N-(2-fluoro-4-(2-(((3S,5S)-5-fluoro-piperidin-3-yl)amino)-8-iso-propylpyrido[3,2-d]pyrimidin-6-yl)phenyl)-1-phenylmethanesulfonamide | 552.21 |
| 212 | 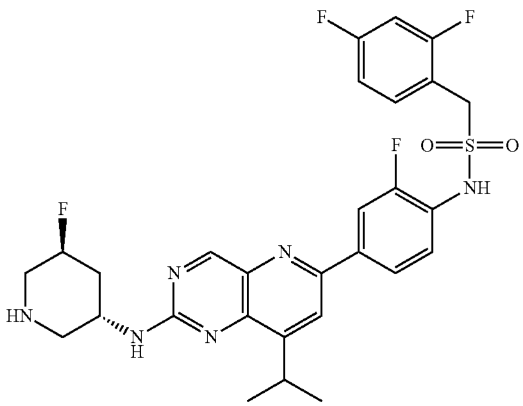 [SMILES: CC(C)c1cc(-c2ccc(NS(=O)(=O)Cc3ccc(F)cc3F)c(F)c2)nc2cnc(N[C@@H]3CNC[C@@H](F)C3)nc12] | 1-(2,4-difluorophenyl)-N-(2-fluoro-4-(2-(((3S,5S)-5-fluoropiperidin-3-yl)amino)-8-isopropylpyrido[3,2-d] pyrimidin-6-yl)phenyl) methanesulfonamide | 588.19 |

TABLE 2-continued

| Cmpd No. | Structure | Name | Mw (m/z) |
|---|---|---|---|
| 213 | 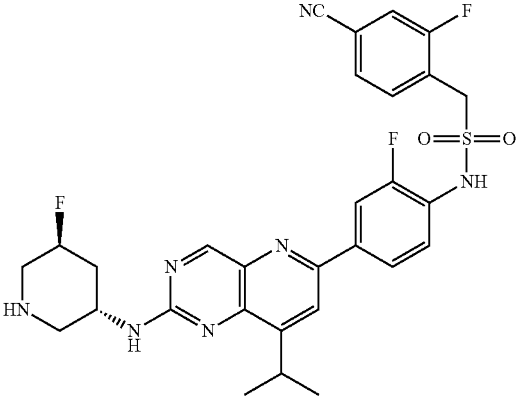 [SMILES: CC(C)c1cc(-c2ccc(NS(=O)(=O)Cc3ccc(C#N)cc3F)c(F)c2)nc2cnc(N[C@@H]3CNC[C@@H](F)C3)nc12] | 1-(4-cyano-2-fluorophenyl)-N-(2-fluoro-4-(2-(((3S,5S)-5-fluoropiperidin-3-yl)amino)-8-isopropylpyrido[3,2-d] pyrimidin-6-yl)phenyl)methanesulfonamide | 595.20 |
| 214 | 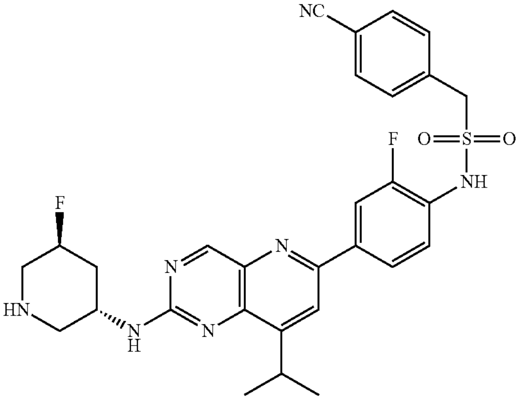 [SMILES: CC(C)c1cc(-c2ccc(NS(=O)(=O)Cc3ccc(C#N)cc3)c(F)c2)nc2cnc(N[C@@H]3CNC[C@@H](F)C3)nc12] | 1-(4-cyanophenyl)-N-(2-fluoro-4-(2-(((3S,5S)-5-fluoropiperidin-3-yl)amino)-8-isopropylpyrido[3,2-d] pyrimidin-6-yl)phenyl) methanesulfonamide | 577.21 |
| 215 | 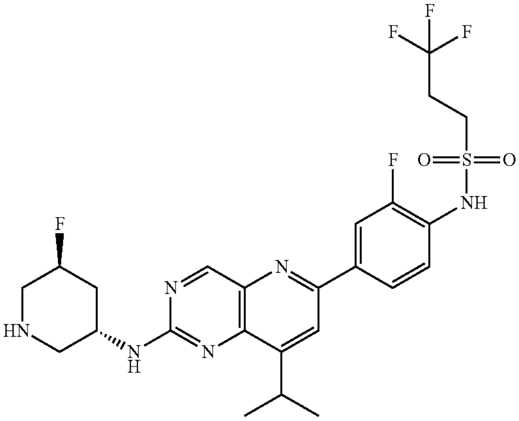 [SMILES: CC(C)c1cc(-c2ccc(NS(=O)(=O)CCC(F)(F)F)c(F)c2)nc2cnc(N[C@@H]3CNC[C@@H](F)C3)nc12] | 3,3,3-trifluoro-N-(2-fluoro-4-(2-(((3S,5S)-5-fluoropiperidin-3-yl)amino)-8-isopropylpyrido[3,2-d] pyrimidin-6-yl)phenyl)propane-1-sulfonamide | 558.18 |

TABLE 2-continued

| Cmpd No. | Structure | Name | Mw (m/z) |
|---|---|---|---|
| 216 | 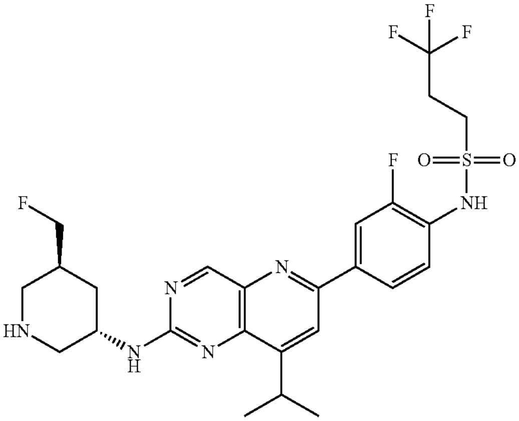 [SMILES: CC(C)c1cc(-c2ccc(NS(=O)(=O)CCC(F)(F)F)c(F)c2)nc2cnc(N[C@@H]3CNC[C@@H](CF)C3)nc12] | 3,3,3-trifluoro-N-(2-fluoro-4-(2-(((3S,5S)-5-(fluoromethyl)piperidin-3-yl)amino)-8-isopropylpyrido[3,2-d]pyrimidin-6-yl)phenyl)propane-1-sulfonamide | 570.20 |
| 217 | 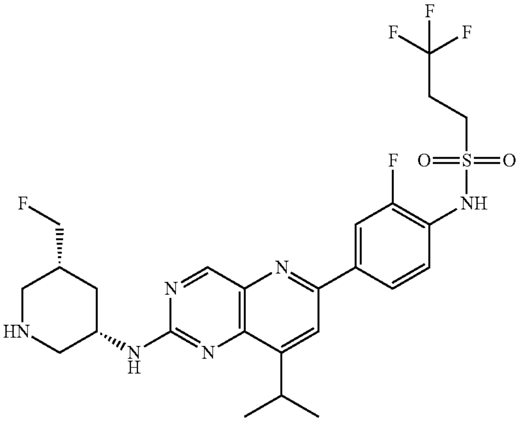 [SMILES: CC(C)c1cc(-c2ccc(NS(=O)(=O)CCC(F)(F)F)c(F)c2)nc2cnc(N[C@@H]3CNC[C@H](CF)C3)nc12] | 3,3,3-trifluoro-N-(2-fluoro-4-(2-(((3S,5R)-5-(fluoromethyl)piperidin-3-yl)amino)-8-isopropylpyrido[3,2-d]pyrimidine-6-yl)phenyl)propane-1-sulfonamide | 572.20 |
| 218 | 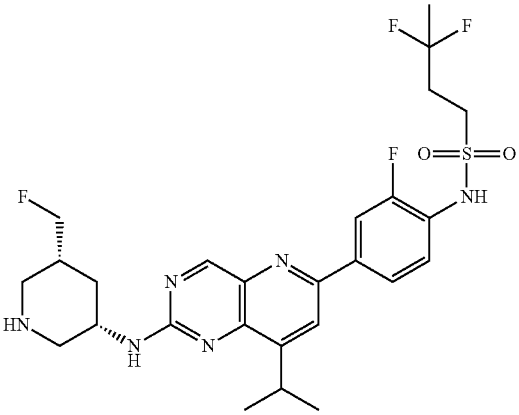 [SMILES: CC(C)c1cc(-c2ccc(NS(=O)(=O)CCC(C)(F)F)c(F)c2)nc2cnc(N[C@@H]3CNC[C@H](CF)C3)nc12] | 3,3-difluoro-N-(2-fluoro-4-(2-(((3S,5R)-5-(fluoromethyl)piperidin-3-yl)amino)-8-isopropylpyrido[3,2-d]pyrimidin-6-yl)phenyl)butane-1-sulfonamide | 568.22 |

TABLE 2-continued

| Cmpd No. | Structure | Name | Mw (m/z) |
|---|---|---|---|
| 219 | 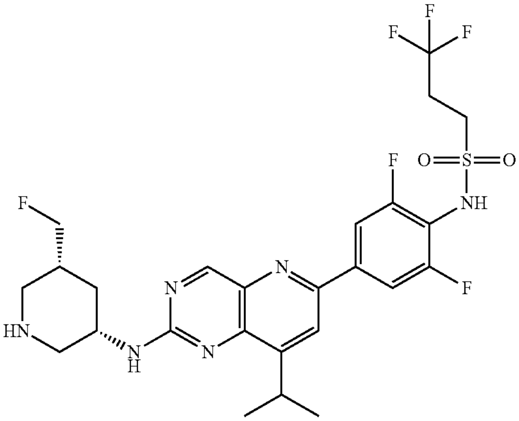 [SMILES: CC(C)c1cc(-c2cc(F)c(NS(=O)(=O)CCC(F)(F)F)c(F)c2)nc2cnc(N[C@@H]3CNC[C@H](CF)C3)nc12] | N-(2,6-difluoro-4-(2-(((3S,5R)-5-(fluoromethyl)piperidin-3-yl)amino)-8-isopropylpyrido[3,2-d]pyrimidin-6-yl)phenyl)-3,3,3-trifluoropropane-1-sulfonamide | 590.19 |
| 220 | 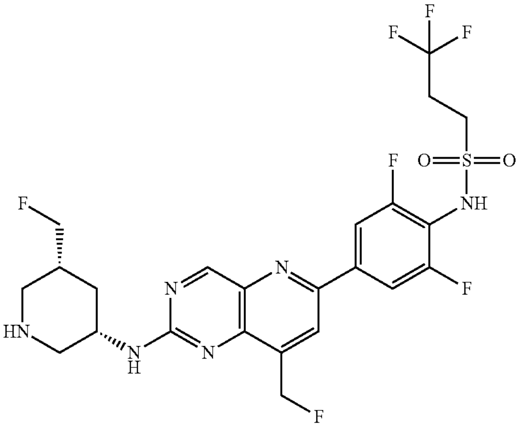 [SMILES: O=S(=O)(CCC(F)(F)F)Nc1c(F)cc(-c2cc(CF)c3nc(N[C@@H]4CNC[C@H](CF)C4)ncc3n2)cc1F] | N-(2,6-difluoro-4-(8-(fluoromethyl)-2-(((3S,5R)-5-(fluoromethyl)piperidin-3-yl)amino)pyrido[3,2-d]pyrimidin-6-yl)phenyl)-3,3,3-trifluoropropane-1-sulfonamide | 580.15 |
| 221 | 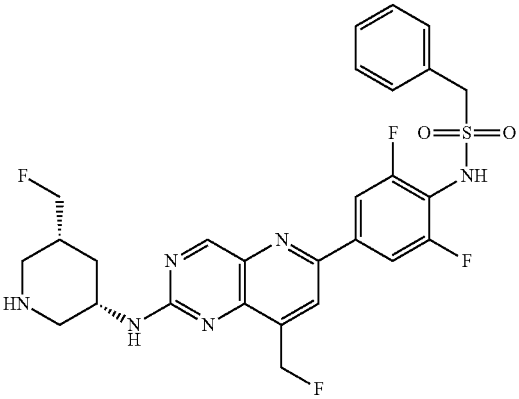 [SMILES: O=S(=O)(Cc1ccccc1)Nc1c(F)cc(-c2cc(CF)c3nc(N[C@@H]4CNC[C@H](CF)C4)ncc3n2)cc1F] | N-(2,6-difluoro-4-(8-(fluoromethyl)-2-(((3S,5S)-5-(fluoromethyl)piperidin-3-yl)amino)pyrido[3,2-d]pyrimidin-6-yl)phenyl)-1-phenylmethanesulfonamide | 574.18 |

TABLE 2-continued

| Cmpd No. | Structure | Name | Mw (m/z) |
|---|---|---|---|
| 222 | 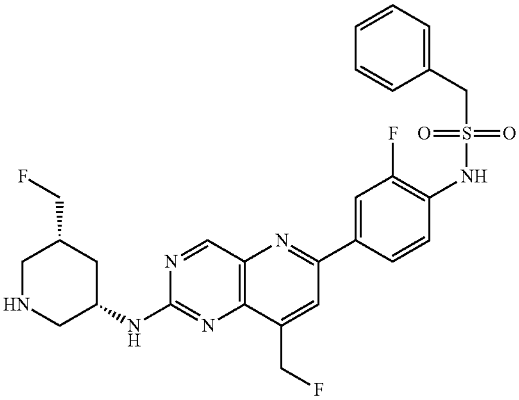 [SMILES: O=S(=O)(Cc1ccccc1)Nc1ccc(-c2cc(CF)c3nc(N[C@@H]4CNC[C@H](CF)C4)ncc3n2)cc1F] | N-(2-fluoro-4-(8-(fluoromethyl)-2-(((3S,5R)-5-(fluoromethyl)piperidin-3-yl)amino)pyrido[3,2-d]pyrimidin-6-yl)phenyl)-1-phenylmethanesulfonamide | 556.19 |
| 223 | 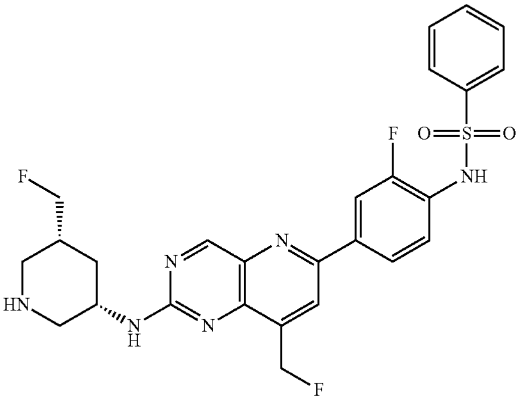 [SMILES: O=S(=O)(Nc1ccc(-c2cc(CF)c3nc(N[C@@H]4CNC[C@H](CF)C4)ncc3n2)cc1F)c1ccccc1] | N-(2-fluoro-4-(8-(fluoromethyl)-2-(((3S,5R)-5-(fluoromethyl)piperidin-3-yl)amino)pyrido[3,2-d]pyrimidin-6-yl)phenyl)benzenesulfonamide | 542.17 |
| 224 | 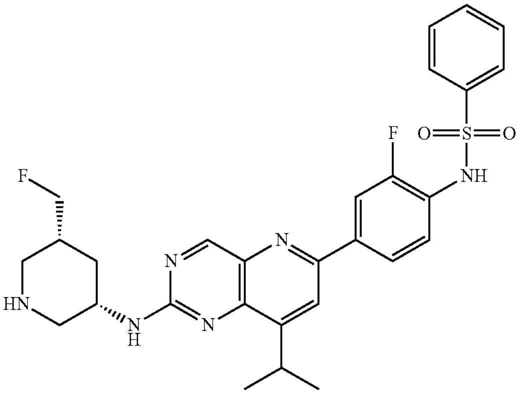 [SMILES: CC(C)c1cc(-c2ccc(NS(=O)(=O)c3ccccc3)c(F)c2)nc2cnc(N[C@@H]3CNC[C@H](CF)C3)nc12] | N-(2-fluoro-4-(2-(((3S,5R)-5-(fluoromethyl)piperidin-3-yl)amino)-8-isopropylpyrido[3,2-d]pyrimidin-6-yl)phenyl)benzenesulfonamide | 552.21 |

TABLE 2-continued

| Cmpd No. | Structure | Name | Mw (m/z) |
|---|---|---|---|
| 225 | 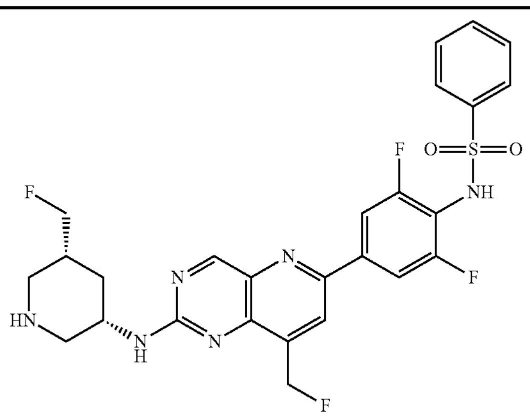 | N-(2,6-difluoro-4-(8-(fluoromethyl)-2-(((3S,5R)-5-(fluoromethyl)piperidin-3-yl)amino)pyrido[3,2-d]pyrimidin-6-yl)phenyl)benzenesulfonamide | 560.16 |
| 226 | 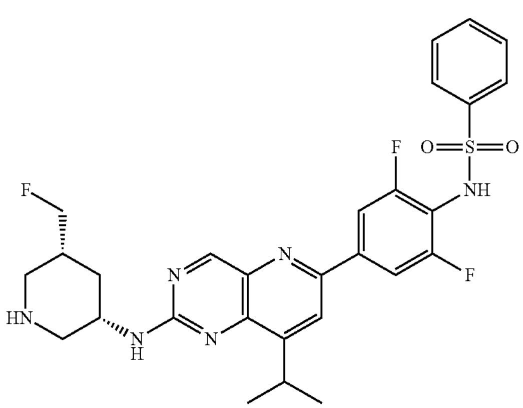 [SMILES: CC(C)c1cc(-c2cc(F)c(NS(=O)(=O)c3ccccc3)c(F)c2)nc2cnc(N[C@@H]3CNC[C@H](CF)C3)nc12] | N-(2,6-difluoro-4-(2-(((3S,5R)-5-(fluoromethyl)piperidin-3-yl)amino)-8-isopropylpyrido[3,2-d]pyrimidin-6-yl)phenyl)benzenesulfonamide | 570.20 |
| 227 | 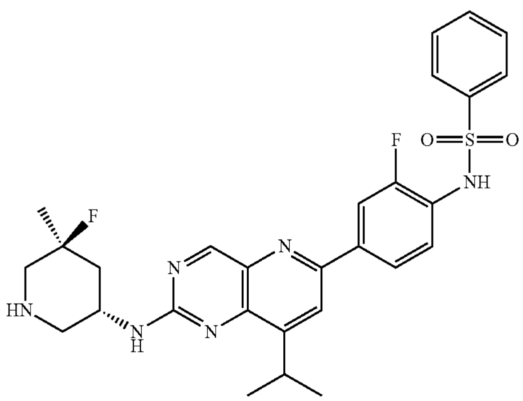 [SMILES: CC(C)c1cc(-c2ccc(NS(=O)(=O)c3ccccc3)c(F)c2)nc2cnc(N[C@@H]3CNC[C@@](C)(F)C3)nc12] | N-(2-fluoro-4-(2-(((3S,5S)-5-fluoro-5-methylpiperidin-3-yl)amino)-8-isopropylpyrido[3,2-d]pyrimidin-6-yl)phenyl)benzenesulfonamide | 552.21 |
| 228 | 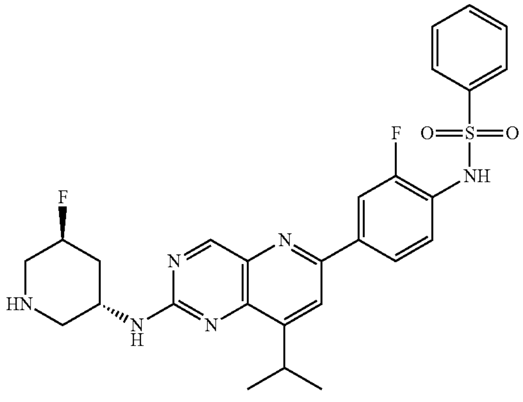 [SMILES: CC(C)c1cc(-c2ccc(NS(=O)(=O)c3ccccc3)c(F)c2)nc2cnc(N[C@@H]3CNC[C@@H](F)C3)nc12] | N-(2-fluoro-4-(2-(((3S,5S)-5-fluoropiperidin-3-yl)amino)-8-isopropylpyrido[3,2-d]pyrimidin-6-yl)phenyl)benzenesulfonamide | 538.20 |

TABLE 2-continued

| Cmpd No. | Structure | Name | Mw (m/z) |
|---|---|---|---|
| 229 | 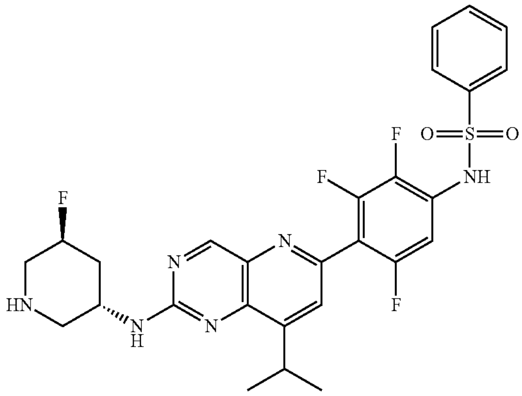 [SMILES: CC(C)c1cc(-c2c(F)cc(NS(=O)(=O)c3ccccc3)c(F)c2F)nc2cnc(N[C@@H]3CNC[C@@H](F)C3)nc12] | N-(2,3,5-trifluoro-4-(2-(((3S,5S)-5-fluoropiperidin-3-yl)amino)-8-isopropylpyrido[3,2-d]pyrimidin-6-yl)phenyl)benzenesulfonamide | 574.18 |
| 230 | 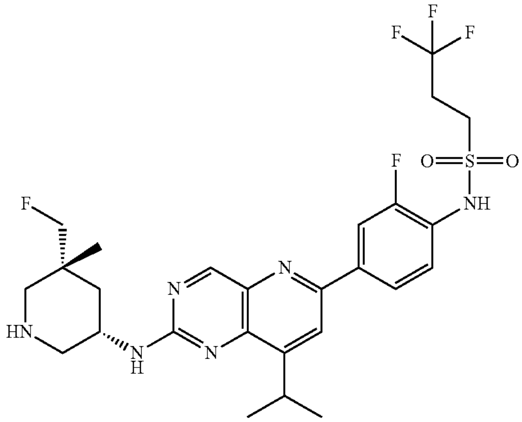 [SMILES: CC(C)c1cc(-c2ccc(NS(=O)(=O)CCC(F)(F)F)c(F)c2)nc2cnc(N[C@@H]3CNC[C@](C)(CF)C3)nc12] | 3,3,3-trifluoro-N-(2-fluoro-4-(2-(((3S,5R)-5-(fluoromethyl)-5-methylpiperidin-3-yl)amino)-8-isopropylpyrido[3,2-d]pyrimidin-6-yl)phenyl)propane-1-sulfonamide | 586.21 |
| 231 | 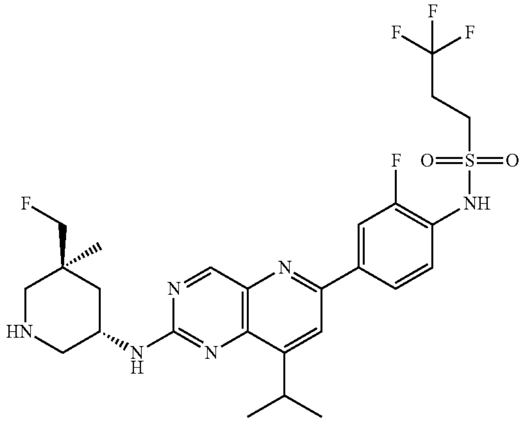 [SMILES: CC(C)c1cc(-c2ccc(NS(=O)(=O)CCC(F)(F)F)c(F)c2)nc2cnc(N[C@@H]3CNC[C@@](C)(CF)C3)nc12] | 3,3,3-trifluoro-N-(2-fluoro-4-(2-(((3S,5S)-5-(fluoromethyl)-5-methylpiperidin-3-yl)amino)-8-isopropylpyrido[3,2-d]pyrimidin-6-yl)phenyl)propane-1-sulfonamide | 586.21 |

TABLE 2-continued

| Cmpd No. | Structure | Name | Mw (m/z) |
|---|---|---|---|
| 232 | 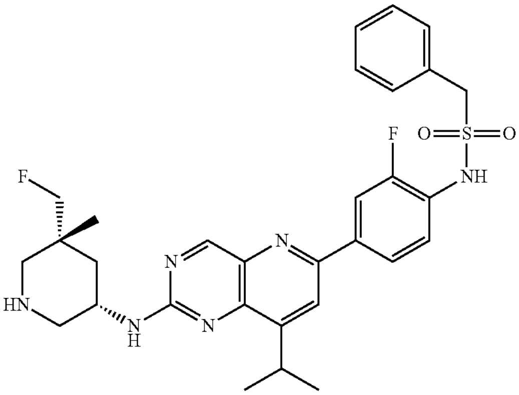 [SMILES: CC(C)c1cc(-c2ccc(NS(=O)(=O)Cc3ccccc3)c(F)c2)nc2cnc(N[C@@H]3CNC[C@](C)(CF)C3)nc12] | N-(2-fluoro-4-(2-(((3S,5R)-5-(fluoro-methyl)-5-methylpiperidin-3-yl)amino)-8-isopropylpyrido[3,2-d]pyrimidin-6-yl)phenyl)-1-phenyl-methanesulfonamide | 580.24 |
| 233 | 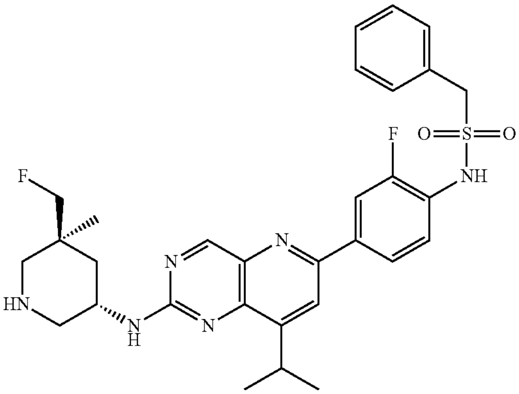 [SMILES: CC(C)c1cc(-c2ccc(NS(=O)(=O)Cc3ccccc3)c(F)c2)nc2cnc(N[C@@H]3CNC[C@@](C)(CF)C3)nc12] | N-(2-fluoro-4-(2-(((3S,5S)-5-(fluoro-methyl)-5-methylpiperidin-3-yl)amino)-8-isopropylpyrido[3,2-d]pyrimidin-6-yl)phenyl)-1-phenyl-methanesulfonamide | 580.24 |
| 234 | 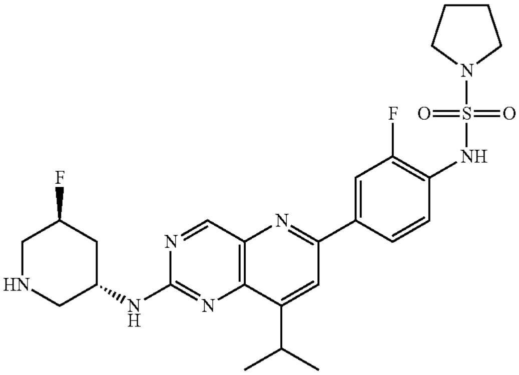 [SMILES: CC(C)c1cc(-c2ccc(NS(=O)(=O)N3CCCC3)c(F)c2)nc2cnc(N[C@@H]3CNC[C@@H](F)C3)nc12] | N-(2-fluoro-4-(2-(((3S,5S)-5-fluoro-piperidin-3-yl)amino)-8-iso-propylpyrido[3,2-d]pyrimidin-6-yl)phenyl)pyrrolidine-1-sulfonamide | 531.22 |
| 235 | 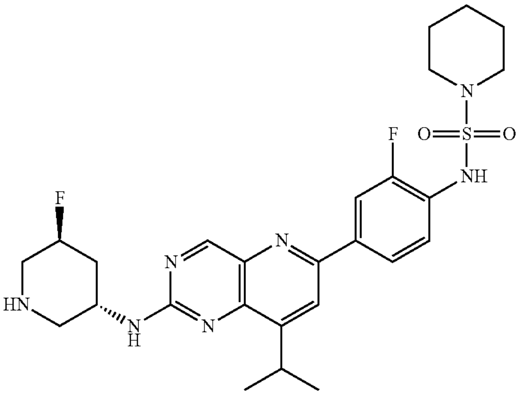 [SMILES: CC(C)c1cc(-c2ccc(NS(=O)(=O)N3CCCCC3)c(F)c2)nc2cnc(N[C@@H]3CNC[C@@H](F)C3)nc12] | N-(2-fluoro-4-(2-(((3S,5S)-5-fluoro-piperidin-3-yl)amino)-8-iso-propylpyrido[3,2-d]pyrimidin-6-yl)phenyl)piperidine-1-sulfonamide | 545.24 |

TABLE 2-continued

| Cmpd No. | Structure | Name | Mw (m/z) |
|---|---|---|---|
| 236 | 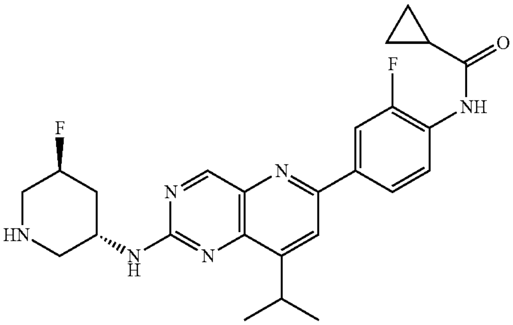 [SMILES: CC(C)c1cc(-c2ccc(NC(=O)C3CC3)c(F)c2)nc2cnc(N[C@@H]3CNC[C@@H](F)C3)nc12] | N-(2-fluoro-4-(2-(((3S,5S)-5-fluoro-piperidin-3-yl)amino)-8-iso-propylpyrido[3,2-d]pyrimidin-6-yl)phenyl)cyclopropanecarboxamide | 466.23 |
| 237 | 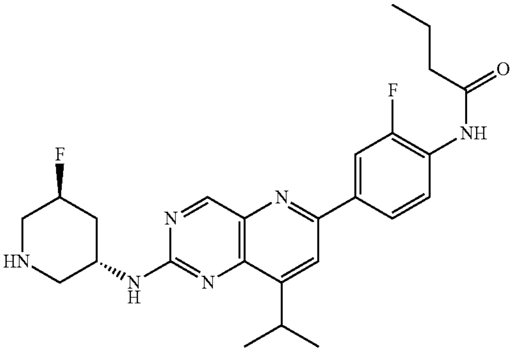 [SMILES: CCCC(=O)Nc1ccc(-c2cc(C(C)C)c3nc(N[C@@H]4CNC[C@@H](F)C4)ncc3n2)cc1F] | N-(2-fluoro-4-(2-(((3S,5S)-5-fluoro-piperidin-3-yl)amino)-8-iso-propylpyrido[3,2-d]pyrimidin-6-yl)phenyl)butyramide | 468.24 |
| 238 | 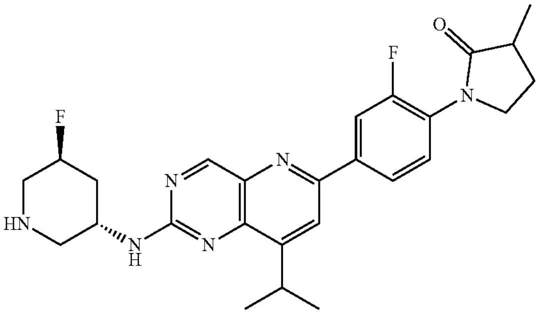 [SMILES: CC1CCN(c2ccc(-c3cc(C(C)C)c4nc(N[C@@H]5CNC[C@@H](F)C5)ncc4n3)cc2F)C1=O] | 1-(2-fluoro-4-(2-(((3S,5S)-5-fluoro-piperidin-3-yl)amino)-8-iso-propylpyrido[3,2-d]pyrimidin-6-yl)phenyl)-3-methylpyrrolidin-2-one | 480.24 |
| 239 | 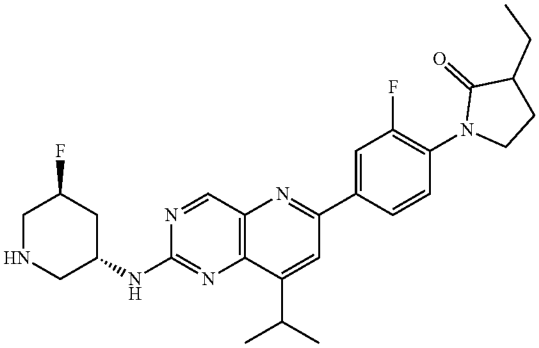 [SMILES: CCC1CCN(c2ccc(-c3cc(C(C)C)c4nc(N[C@@H]5CNC[C@@H](F)C5)ncc4n3)cc2F)C1=O] | 3-ethyl-1-(2-fluoro-4-(2-(((3S,5S)-5-fluoropiperidin-3-yl)amino)-8-iso-propylpyrido[3,2-d]pyrimidin-6-yl)phenyl)pyrrolidin-2-one | 494.26 |

TABLE 2-continued

| Cmpd No. | Structure | Name | Mw (m/z) |
|---|---|---|---|
| 240 | 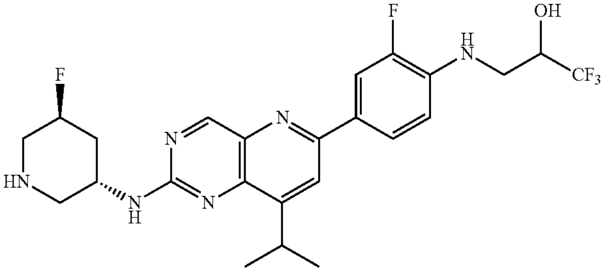 [SMILES: CC(C)c1cc(-c2ccc(NCC(O)C(F)(F)F)c(F)c2)nc2cnc(N[C@@H]3CNC[C@@H](F)C3)nc12] | 1,1,1-trifluoro-3-((2-fluoro-4-(2-(((3S,5S)-5-fluoropiperidin-3-yl)amino)-8-isopropylpyrido[3,2-d]pyrimidin-6-yl)phenyl)amino)propan-2-ol | 510.22 |
| 241 | 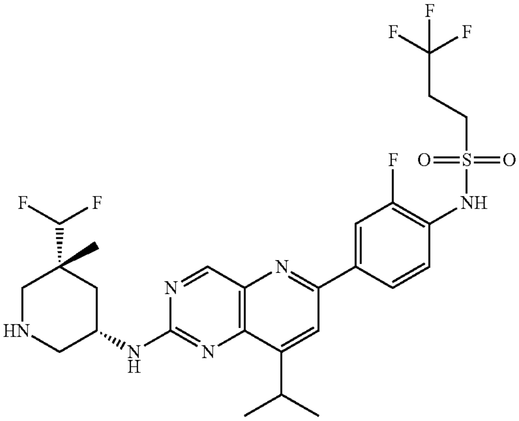 [SMILES: CC(C)c1cc(-c2ccc(NS(=O)(=O)CCC(F)(F)F)c(F)c2)nc2cnc(N[C@@H]3CNC[C@](C)(C(F)F)C3)nc12] | N-(4-(2-(((3S,5S)-5-(difluoromethyl)-5-methylpiperidin-3-yl)amino)-8-isopropylpyrido[3,2-d]pyrimidin-6-yl)-2-fluorophenyl)-3,3,3-trifluoropropane-1-sulfonamide | 604.21 |
| 242 | 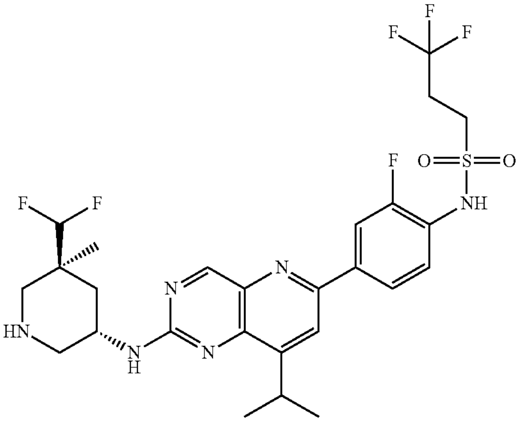 [SMILES: CC(C)c1cc(-c2ccc(NS(=O)(=O)CCC(F)(F)F)c(F)c2)nc2cnc(N[C@@H]3CNC[C@@](C)(C(F)F)C3)nc12] | N-(4-(2-(((3S,5S)-5-(difluoromethyl)-5-methylpiperidin-3-yl)amino)-8-isopropylpyrido[3,2-d]pyrimidin-6-yl)-2-fluorophenyl)-3,3,3-trifluoropropane-1-sulfonamide | 604.21 |
| 243 | 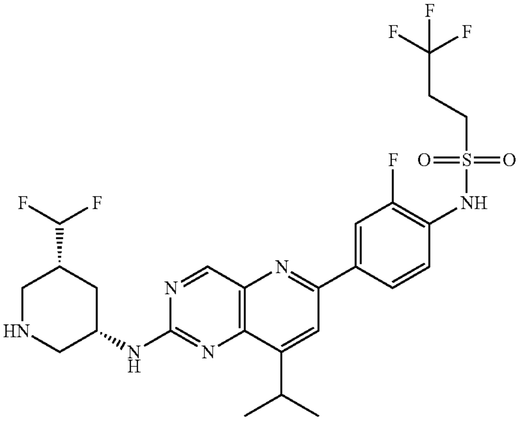 | N-(4-(2-(((3S,5S)-5-(difluoromethyl)piperidin-3-yl)amino)-8-isopropylpyrido[3,2-d]pyrimidin-6-yl)-2-fluorophenyl)-3,3,3-trifluoropropane-1-sulfonamide | 590.19 |

TABLE 2-continued

| Cmpd No. | Structure | Name | Mw (m/z) |
|---|---|---|---|
| 244 | 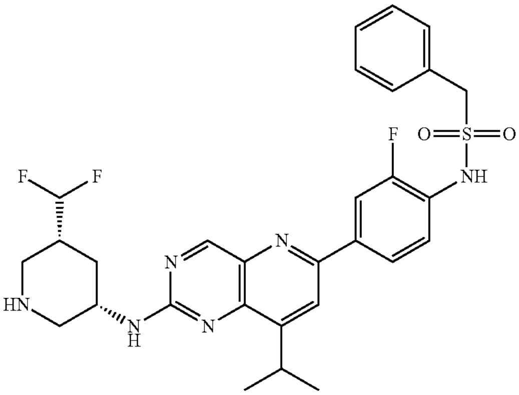 [SMILES: CC(C)c1cc(-c2ccc(NS(=O)(=O)Cc3ccccc3)c(F)c2)nc2cnc(N[C@@H]3CNC[C@H](C(F)F)C3)nc12] | N-(4-(2-(((3S,5S)-5-(difluoro-methyl)piperidin-3-yl)amino)-8-isopropylpyrido[3,2-d]pyrimidin-6-yl)-2-fluorophenyl)-1-phenylmethanesulfonamide | 584.22 |
| 245 | 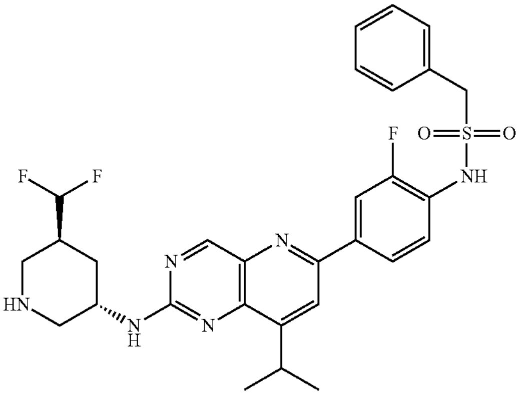 | N-(4-(2-(((3S,5S)-5-(difluoro-methyl)piperidin-3-yl)amino)-8-iso-propylpyrido[3,2-d]pyrimidin-6-yl)-2-fluorophenyl)-1-phenylmethane-sulfonamide | 584.22 |
| 246 | 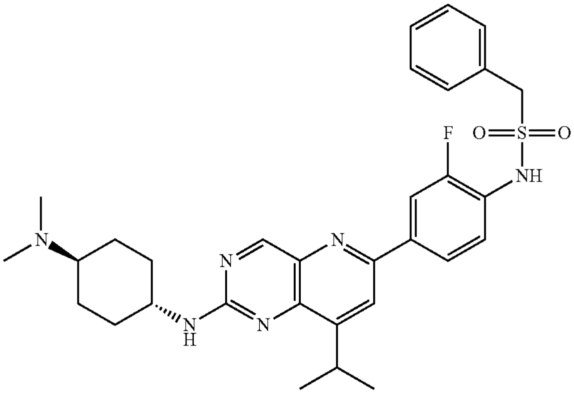 [SMILES: CC(C)c1cc(-c2ccc(NS(=O)(=O)Cc3ccccc3)c(F)c2)nc2cnc(N[C@H]3CC[C@H](N(C)C)CC3)nc12] | N-(4-(2-(((1r,4r)-4-(dimethylamino) cyclohexyl)amino)-8-isopropylpyrido [3,2-d]pyrimidin-6-yl)-2-fluorophenyl)-1-phenylmethanesulfonamide | 576.27 |
| 247 | 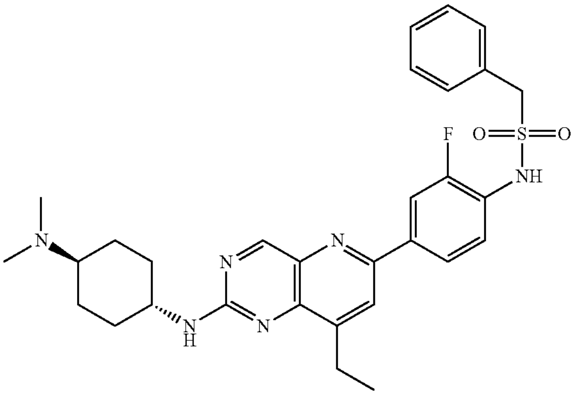 [SMILES: CCc1cc(-c2ccc(NS(=O)(=O)Cc3ccccc3)c(F)c2)nc2cnc(N[C@H]3CC[C@H](N(C)C)CC3)nc12] | N-(4-(2-(((1r,4r)-4-(dimethyl-amino)cyclohexyl)amino)-8-ethylpyrido [3,2-d]pyrimidin-6-yl)-2-fluoro-phenyl)-1-phenylmethanesulfonamide | 562.25 |

TABLE 2-continued

| Cmpd No. | Structure | Name | Mw (m/z) |
|---|---|---|---|
| 248 | 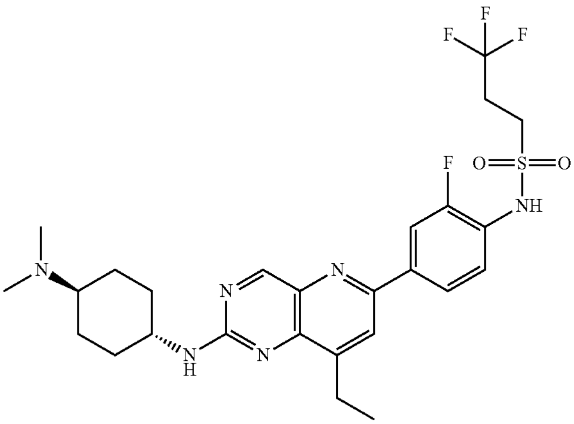 [SMILES: CCc1cc(-c2ccc(NS(=O)(=O)CCC(F)(F)F)c(F)c2)nc2cnc(N[C@H]3CC[C@H](N(C)C)CC3)nc12] | N-(4-(2-(((1r,4r)-4-(dimethylamino)cyclohexyl)amino)-8-ethylpyrido[3,2-d]pyrimidin-6-yl)-2-fluorophenyl)-3,3,3-trifluoropropane-1-sulfonamide | 568.22 |
| 249 | 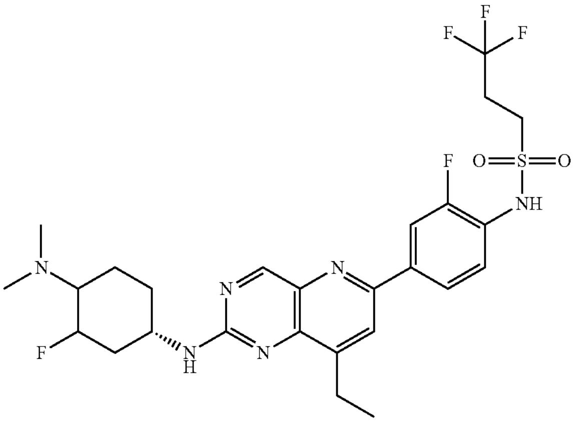 [SMILES: CCc1cc(-c2ccc(NS(=O)(=O)CCC(F)(F)F)c(F)c2)nc2cnc(N[C@H]3CCC(N(C)C)C(F)C3)nc12] | N-(4-(2-((4-(dimethylamino)-3-fluorocyclohexyl)amino)-8-ethylpyrido[3,2-d]pyrimidin-6-yl)-2-fluorophenyl)-3,3,3-trifluoropropane-1-sulfonamide | 586.21 |
| 250 | 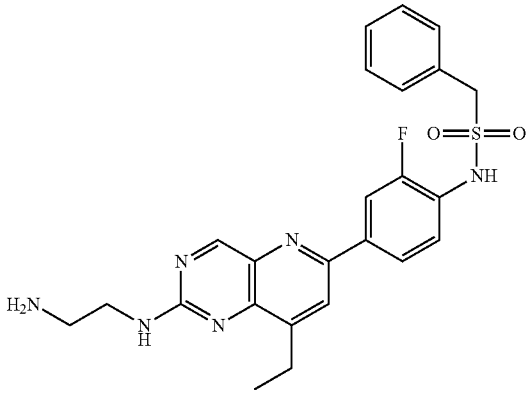 [SMILES: CCc1cc(-c2ccc(NS(=O)(=O)Cc3ccccc3)c(F)c2)nc2cnc(NCCN)nc12] | N-(4-(2-((2-aminoethyl)amino)-8-ethylpyrido[3,2-d]pyrimidin-6-yl)-2-fluorophenyl)-1-phenylmethanesulfonamide | 480.17 |

TABLE 2-continued

| Cmpd No. | Structure | Name | Mw (m/z) |
|---|---|---|---|
| 251 | 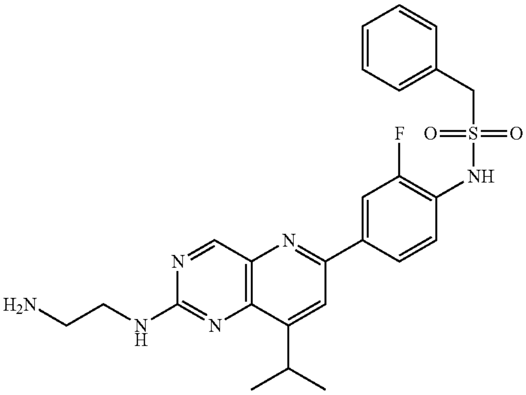 [SMILES: CC(C)c1cc(-c2ccc(NS(=O)(=O)Cc3ccccc3)c(F)c2)nc2cnc(NCCN)nc12] | N-(4-(2-((2-aminoethyl)amino)-8-isopropylpyrido[3,2-d]pyrimidin-6-yl)-2-fluorophenyl)-1-phenylmethane-sulfonamide | 494.19 |
| 252 | 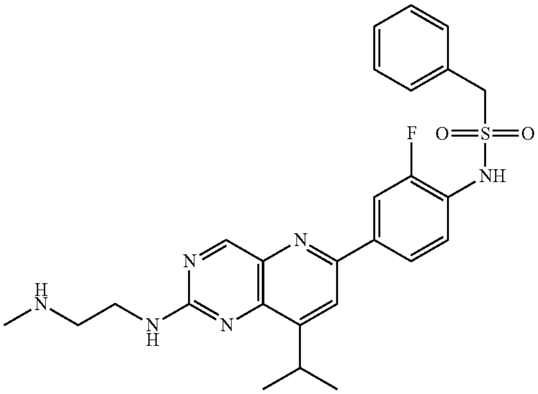 [SMILES: CNCCNc1ncc2nc(-c3ccc(NS(=O)(=O)Cc4ccccc4)c(F)c3)cc(C(C)C)c2n1] | N-(2-fluoro-4-(8-isopropyl-2-((2-(methylamino)ethyl)amino)pyrido[3,2-d]pyrimidin-6-yl)phenyl)-1-phenylmethanesulfonamide | 508.21 |
| 253 | 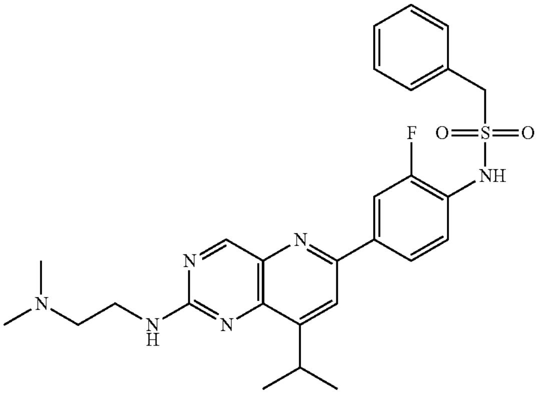 [SMILES: CC(C)c1cc(-c2ccc(NS(=O)(=O)Cc3ccccc3)c(F)c2)nc2cnc(NCCN(C)C)nc12] | N-(4-(2-((2-dimethylamino)ethyl)amino)-8-isopropylpyrido[3,2-d]pyrimidin-6-yl)-2-fluoro-phenyl)-1-phenylmethanesulfonamide | 502.22 |
| 254 | 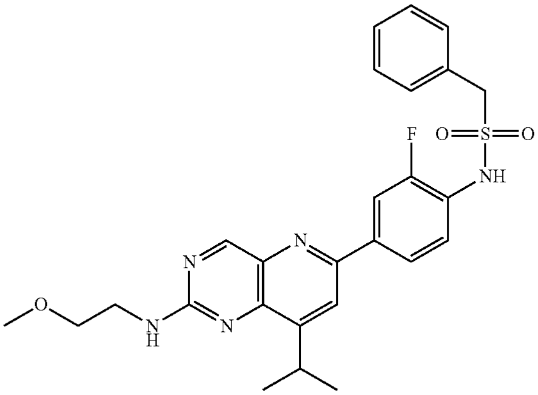 [SMILES: COCCNc1ncc2nc(-c3ccc(NS(=O)(=O)Cc4ccccc4)c(F)c3)cc(C(C)C)c2n1] | N-(2-fluoro-4-(8-isopropyl-2-((2-methoxyethyl)amino)pyrido[3,2-d]pyrimidin-6-yl)phenyl)-1-phenyl-methanesulfonamide | 509.19 |

TABLE 2-continued

| Cmpd No. | Structure | Name | Mw (m/z) |
|---|---|---|---|
| 255 | 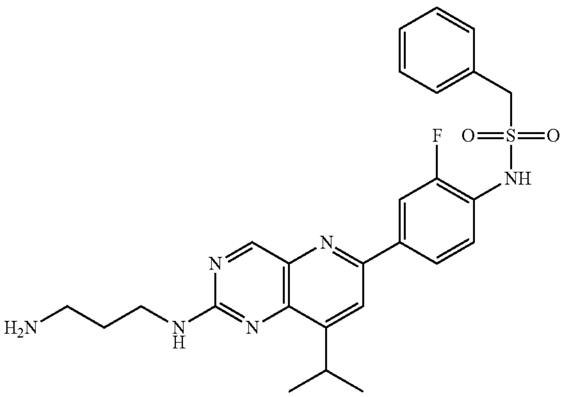 [SMILES: CC(C)c1cc(-c2ccc(NS(=O)(=O)Cc3ccccc3)c(F)c2)nc2cnc(NCCCN)nc12] | N-(4-(2-((3-aminopropyl)amino)-8-isopropylpyrido[3,2-d]pyrimidin-6-yl)-2-fluorophenyl)-1-phenylmethane-sulfonamide | 508.21 |
| 256 | 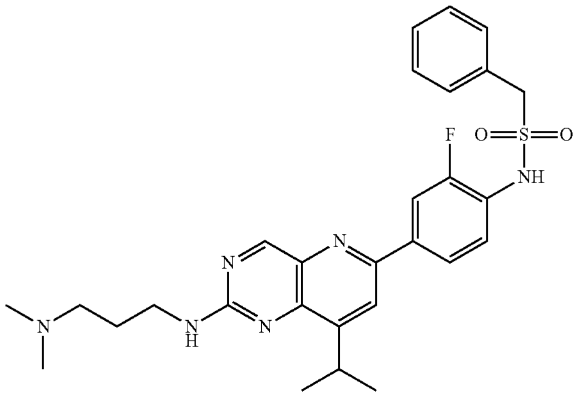 [SMILES: CC(C)c1cc(-c2ccc(NS(=O)(=O)Cc3ccccc3)c(F)c2)nc2cnc(NCCCN(C)C)nc12] | N-(4-(2-((3-(dimethylamino)propyl)amino)-8-isopropylpyrido[3,2-d]pyrimidin-6-yl)-2-fluorophenyl)-1-phenylmethanesulfonamide | 536.24 |
| 257 | 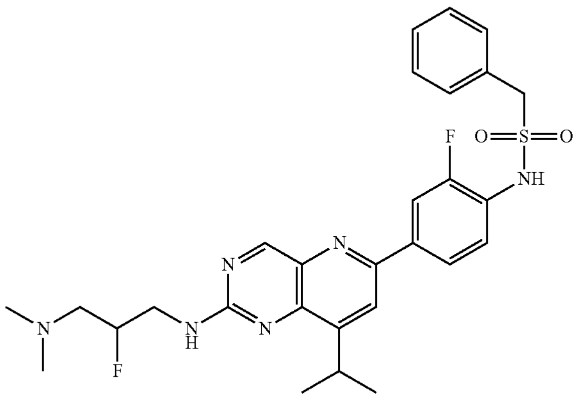 [SMILES: CC(C)c1cc(-c2ccc(NS(=O)(=O)Cc3ccccc3)c(F)c2)nc2cnc(NCC(F)CN(C)C)nc12] | N-(4-(2-((3-(dimethylamino)-2-fluoropropyl)amino)-8-isopropylpyrido[3,2-d]pyrimidin-6-yl)-2-fluorophenyl)-1-phenylmethanesulfonamide | 554.23 |

TABLE 2-continued

| Cmpd No. | Structure | Name | Mw (m/z) |
|---|---|---|---|
| 258 | 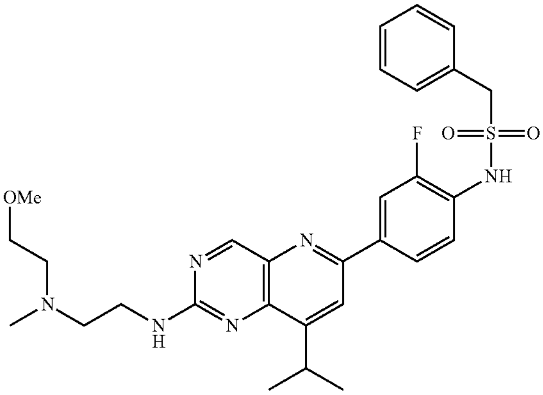 [SMILES: COCCN(C)CCNc1ncc2nc(-c3ccc(NS(=O)(=O)Cc4ccccc4)c(F)c3)cc(C(C)C)c2n1] | N-(2-fluoro-4-(8-isopropyl-2-((2-((2-methoxyethyl)(methyl)amino)ethyl)amino)pyrido[3,2-d]pyrimidin-6-yl)phenyl)-1-phenyl-methanesulfonamide | 566.25 |
| 259 | 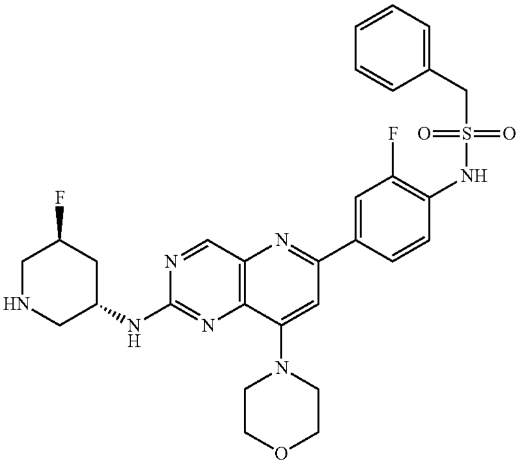 [SMILES: O=S(=O)(Cc1ccccc1)Nc1ccc(-c2cc(N3CCOCC3)c3nc(N[C@@H]4CNC[C@@H](F)C4)ncc3n2)cc1F] | N-(2-fluoro-4-(2-(((3S,5S)-5-fluoro-piperidin-3-yl)amino)-8-morpholino-pyrido[3,2-d]pyrimidin-6-yl)phenyl)-1-phenylmethanesulfonamide | 595.22 |
| 260 | 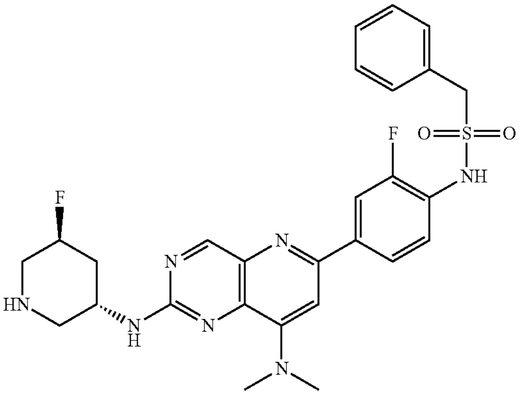 [SMILES: CN(C)c1cc(-c2ccc(NS(=O)(=O)Cc3ccccc3)c(F)c2)nc2cnc(N[C@@H]3CNC[C@@H](F)C3)nc12] | N-(4-(8-(dimethylamino)-2-(((3S,5S)-5-fluoropiperidin-3-yl)amino)pyrido[3,2-d]pyrimidin-6-yl)-2-fluorophenyl)-1-phenylmethane-sulfonamide | 553.21 |

TABLE 2-continued

| Cmpd No. | Structure | Name | Mw (m/z) |
|---|---|---|---|
| 261 | 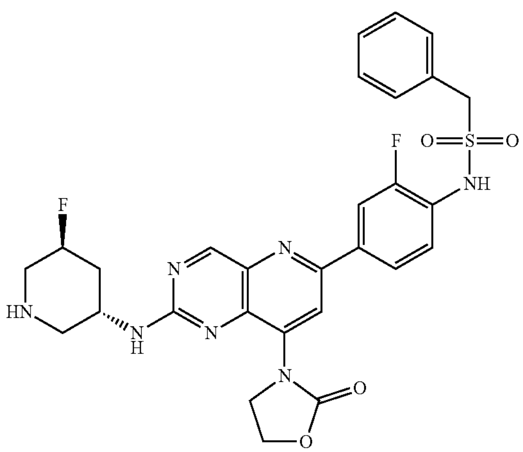 [SMILES: O=C1OCCN1c1cc(-c2ccc(NS(=O)(=O)Cc3ccccc3)c(F)c2)nc2cnc(N[C@@H]3CNC[C@@H](F)C3)nc12] | N-(2-fluoro-4-(2-(((3S,5S)-5-fluoro-piperidin-3-yl)amino)-8-(2-oxooxazolidin-3-yl)pyrido[3,2-d]pyrimidin-6-yl)phenyl)-1-phenylmethanesulfonamide | 595.18 |
| 262 | 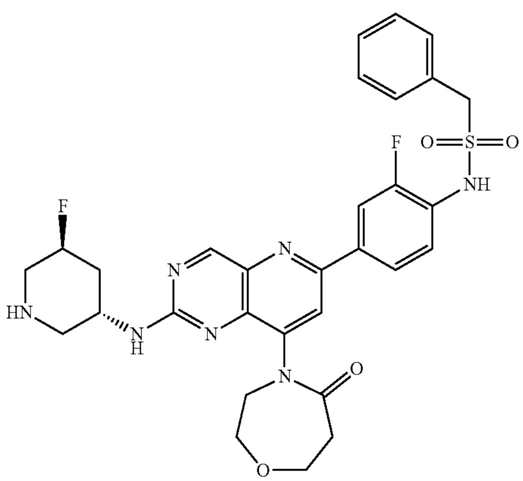 [SMILES: O=C1CCOCCN1c1cc(-c2ccc(NS(=O)(=O)Cc3ccccc3)c(F)c2)nc2cnc(N[C@@H]3CNC[C@@H](F)C3)nc12] | N-(2-fluoro-4-(2-(((3S,5S)-5-fluoro-piperidin-3-yl)amino)-8-(5-oxo-1,4-oxazepan-4-yl)pyrido[3,2-d]pyrimidin-6-yl)phenyl)-1-phenylmethanesulfonamide | 623.21 |
| 263 | 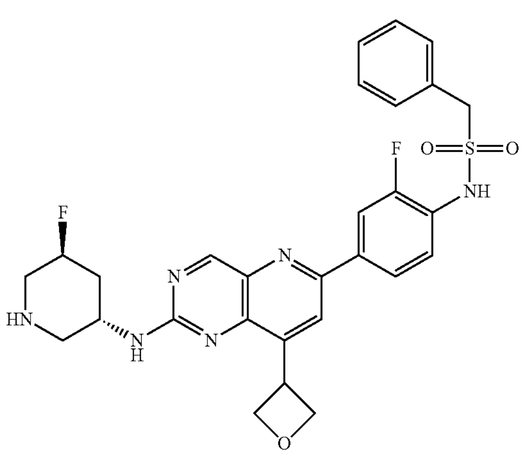 [SMILES: O=S(=O)(Cc1ccccc1)Nc1ccc(-c2cc(C3COC3)c3nc(N[C@@H]4CNC[C@@H](F)C4)ncc3n2)cc1F] | N-(2-fluoro-4-(2-(((3S,5S)-5-fluoro-piperidin-3-yl)amino)-8-(oxetan-3-yl)pyrido[3,2-d]pyrimidin-6-yl)phenyl)-1-phenylmethanesulfonamide | 566.19 |

TABLE 2-continued

| Cmpd No. | Structure | Name | Mw (m/z) |
|---|---|---|---|
| 264 | 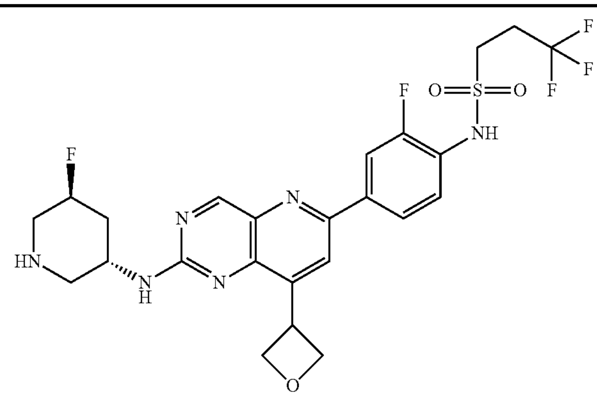 | 3,3,3-trifluoro-N-(2-fluoro-4-(2-(((3S,5S)-5-fluoropiperidin-3-yl)amino)-8-(oxetan-3-yl)pyrido[3,2-d]pyrimidin-6-yl)phenyl)propane-1-sulfonamide | 572.16 |
| 265 | 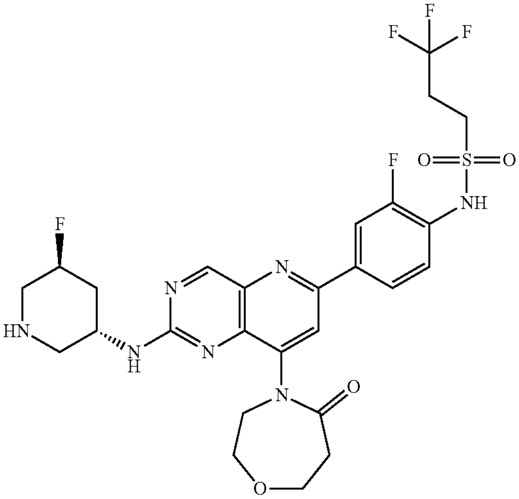 [SMILES: O=C1CCOCCN1c1cc(-c2ccc(NS(=O)(=O)CCC(F)(F)F)c(F)c2)nc2cnc(N[C@@H]3CNC[C@@H](F)C3)nc12] | 3,3,3-trifluoro-N-(2-fluoro-4-(2-(((3S,5S)-5-fluoropiperidin-3-yl)amino)-8-(5-oxa-1,4-oxazepan-4-yl)pyrido[3,2-d]pyrimidin-6-yl)phenyl)propane-1-sulfonamide | 629.18 |
| 266 | 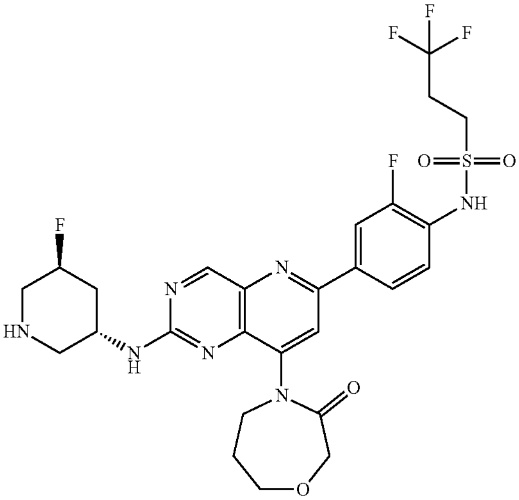 [SMILES: O=C1COCCCN1c1cc(-c2ccc(NS(=O)(=O)CCC(F)(F)F)c(F)c2)nc2cnc(N[C@@H]3CNC[C@@H](F)C3)nc12] | 3,3,3-trifluoro-N-(2-fluoro-4-(2-(((3S,5S)-5-fluoropiperidin-3-yl)amino)-8-(3-oxo-1,4-oxazepan-4-yl)pyrido[3,2-d]pyrimidin-6-yl)phenyl)propane-1-sulfonamide | 629.18 |

Synthesis of Compounds and Pharmaceutically Acceptable Salts Thereof

Compounds and pharmaceutically acceptable salts thereof as described herein can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, WI) or are readily prepared using methods (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie,* 4, Aufl. ed. Springer-Verlag, Berlin, including supplements (also available via the Beilstein online database). Compounds and pharmaceutically acceptable salts thereof as described herein can also be made following the procedures found in U.S. Pat. Nos. 8,476,434, 7,880,000, WO 2005/113494, U.S. Pat. No. 7,868,177, and WO 2007/100646.

Synthetic chemistry transformations and protecting group methodologies (protection and deprotection) useful in synthesizing compounds and pharmaceutically acceptable salts thereof as described herein and necessary reagents and intermediates include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds and pharmaceutically acceptable salts thereof as described herein can be prepared singly or as compound libraries comprising at least 2, for example 5 to 1,000 compounds, or 10 to 100 compounds. Libraries of compounds and pharmaceutically acceptable salts thereof as described herein can be prepared by a combinatorial split and mix approach or by multiple parallel syntheses using, for example, either solution phase or solid phase chemistry. Thus, according to a further aspect provided herein is a compound library comprising at least 2 compounds, or pharmaceutically acceptable salts thereof as described herein.

The Examples provide exemplary methods for preparing compounds and pharmaceutically acceptable salts thereof as described herein. Those skilled in the art will appreciate that other synthetic routes can be used to synthesize compounds and pharmaceutically acceptable salts thereof as described herein. Although specific starting materials and reagents are depicted and discussed in the Examples, other starting materials and reagents can be easily substituted to provide a variety of derivatives and/or reaction conditions. In addition, many of the exemplary compounds or pharmaceutically acceptable salts thereof as prepared by the described methods can be further modified in light of this disclosure using conventional chemistry.

In preparing compounds and pharmaceutically acceptable salts thereof as described herein, protection of remote functionality (e.g., primary or secondary amine) of intermediates can be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection can be readily determined. For a general description of protecting groups and their use, see T. W. Greene, Protective Groups in Organic Synthesis, John Wiley & Sons, New York, 1991.

In the methods of preparing compounds and pharmaceutically acceptable salts thereof as described herein, it can be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds or pharmaceutically acceptable salts thereof described herein can be atropisomers (e.g., substituted biaryls). Enantiomers can also be separated by use of a chiral HPLC column.

A single stereoisomer, e.g., an enantiomer, substantially free of its stereoisomer can be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds or pharmaceutically acceptable salts thereof described herein can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts can be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as methyl derivatives, followed by separation of the diastereomers and hydrolysis to yield the pure or enriched enantiomer. A method of determining optical purity involves making chiral esters, such as a methyl ester, e.g., (−) methyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^{1}H$ NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Administration of Compounds

Compounds or pharmaceutically acceptable salts thereof described herein can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. In one preferred embodiment, the compound or pharmaceutically acceptable salt thereof is formulated for oral administration as a pill, a capsule, or a tablet. Where the compound or pharmaceutically acceptable salt thereof is administered parenterally, it can be formulated with a pharmaceutically acceptable parenteral vehicle and in a unit dosage injectable form, as detailed below.

Thus, in one embodiment provided herein is a pharmaceutical composition comprising a compound or pharmaceutically acceptable salt thereof as described herein and one or more pharmaceutically acceptable excipients. In one embodiment, compounds or pharmaceutically acceptable salts thereof described herein are administered as pharmaceutical compositions capable of being administered to a subject orally or parenterally. The compounds described herein can be formulated for topical or parenteral use where the compound is dissolved or otherwise suspended in a solution suitable for injections, suspensions, syrups, creams, ointments, gels, sprays, solutions and emulsions.

Oral administration can promote patient compliance in taking the compound (e.g. formulated as a pharmaceutical composition), thereby increasing compliance and efficacy. Oral pharmaceutical compositions comprising a compound or pharmaceutically acceptable salt thereof described herein include, but are not limited to, tablets (e.g. coated, non-coated and chewable) and capsules (e.g. hard gelatin capsules, soft gelatin capsules, enteric coated capsules, and sustained release capsules). Tablets can be prepared by direct compression, by wet granulation, or by dry granulation. Oral pharmaceutical compositions comprising a compound described herein can be formulated for delayed or prolonged release. In one preferred embodiment, the oral pharmaceutical composition comprises a compound or pharmaceutically acceptable salt thereof formulated in a tablet.

A dose to treat human patients can range from about 10 mg to about 1000 mg of a compound or pharmaceutically acceptable salt thereof described herein. A typical dose can be about 100 mg to about 300 mg of the compound. A dose can be administered once a day (QD), twice per day (BID), or more frequently, depending on the pharmacokinetic and pharmacodynamic properties, including absorption, distribution, metabolism, and excretion of the particular compound. Administration as used herein refers to the frequency of dosing and not, for example, the number of individual units a patient described herein must take for a dose. Thus, in some embodiments, a patient may take two or more dosage units (e.g. two or more pills/tablets/capsules) QD. In addition, toxicity factors can influence the dosage and administration regimen. When administered orally, the pill, capsule, or tablet can be ingested daily or less frequently for a specified period of time. The regimen can be repeated for a number of cycles of therapy.

Methods of Treatment

In one aspect provided herein, compounds or pharmaceutically acceptable salts thereof are useful for treating a patient having a disease or disorder arising from: abnormal cell growth, function, or behavior associated with the UPR pathway such as cancer; an immune disorder; cardiovascular disease; viral infection; inflammation; a metabolism/endocrine disorder; or a neurological disorder by administering an effective amount of a compound or pharmaceutically acceptable salt thereof described herein. In one embodiment of the methods provided herein, compounds or pharmaceutically acceptable salts thereof are useful for treating a patient having an IRE1-related disease or disorder arising from: abnormal cell growth, function, or behavior associated with the UPR pathway such as cancer; an immune disorder; cardiovascular disease; viral infection; inflammation; a metabolism/endocrine disorder; or a neurological disorder by administering an effective amount of a compound or pharmaceutically acceptable salt thereof described herein.

Provided herein are methods of treating an IRE1-related disease or disorder by administering to a patient having an IRE1-related disease or disorder as described herein, an effective amount of a compound or a pharmaceutically acceptable salt thereof described herein. In another embodiment is a method of treating cancer by administering to a patient having cancer an effective amount of a compound or pharmaceutically acceptable salt thereof described herein. The cancer is an IRE1-related disease or disorder.

The methods provided herein include treatment of solid tumors/cancers by administering an effective amount of a compound or pharmaceutically acceptable salt thereof described herein to a patient having a solid tumor/cancer provided herein. For example, administration of an effective amount of a compound or pharmaceutically acceptable salt thereof described herein can be performed for patients having breast cancer, ovary cancer, cervix cancer, prostate cancer, testis cancer, genitourinary tract cancer, esophagus cancer, larynx cancer, glioblastoma, neuroblastoma, stomach cancer, skin cancer, keratoacanthoma, lung cancer, epidermoid carcinoma, large cell cancer, non-small cell lung cancer (NSCLC), small cell carcinoma, lung adenocarcinoma, bone cancer, colon cancer, adenoma, pancreatic cancer, adenocarcinoma, thyroid cancer, follicular carcinoma, undifferentiated carcinoma, papillary carcinoma, seminoma, melanoma, sarcoma, bladder carcinoma, liver carcinoma and biliary passages, kidney carcinoma, buccal cavity cancer, naso-pharyngeal cancer, pharynx cancer, lip cancer, tongue cancer, mouth cancer, small intestine cancer, colon-rectum cancer, large intestine cancer, rectum cancer, bronchial cancer, hepatocellular cancer, gastric cancer, endometrial cancer, melanoma, renal cancer, urinary bladder cancer, uterine corpus cancer, and uterine cervix cancer.

In another embodiment, the methods provided herein include treatment of cancer by administering to a patient having cancer an effective amount of a compound or pharmaceutically acceptable salt thereof where the cancer comprises squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

In certain embodiments, the cancer is breast cancer. The breast cancer can be Stage I, II, III, or IV as understood in the art. In one embodiment, the breast cancer is triple negative breast cancer (TNBC). In another embodiment, the breast cancer is Her2 negative breast cancer. In still another embodiment, the breast cancer is HR+ breast cancer.

Also provided herein are methods of treating a hematological cancer in a patient having such a hematological cancer by administering an effective amount of a compound or pharmaceutically acceptable salt thereof described herein. The hematological cancer can be, for example, lymphorrma, lymphocytic leukemia (acute (ALL) and chronic (CLL)), multiple myeloma (MM), acute myelogenous leukemia (AML), chronic myelogenous leukemia (CML), myelodysplastic syndrome (MDS), myeloproliferative disease (MPD), or non-Hodgkin lymphoma. In one embodiment, the methods herein include treating a patient having multiple myeloma (MM), acute myelogenous leukemia (AML), chronic myelogenous leukemia (CML), or myelodysplastic syndrome (MDS) by administering an effective amount of a compound or pharmaceutically acceptable salt thereof described herein.

In one embodiment is a method of treating MM by administering to a patient having MM an effective amount of compound or pharmaceutically acceptable salt thereof described herein. The MM can be stage I, II, III, or IV as understood in the art. In another embodiment is a method of treating AML by administering to a patient having AML an effective amount of a compound or pharmaceutically acceptable salt thereof described herein. The AML can be stage I, II, III, or IV as understood in the art. In another embodiment is a method of treating CML by administering to a patient having CML an effective amount of a compound or pharmaceutically acceptable salt thereof described herein. The CML can be stage I, II, III, or IV as understood in the art. In another embodiment is a method of treating MDS by administering to a patient having MDS an effective amount of a compound or pharmaceutically acceptable salt thereof described herein. It is further understood that such cancers can be relapsed or refractory as provided herein.

In one embodiment, the cancer is an IRE1-mediated cancer (i.e. a cancer having abnormal expression or activity of IRE1 relative to a control). In one embodiment, the IRE1-mediated cancer has increased expression of IRE1. In another embodiment, the IRE1-mediated cancer has increased activity of IRE1. Such increases can be measured against a control (e.g. against a patient having predetermined IRE1 function, expression, activity; or for example measure in a single patient before, during, or after treatment with a compound or pharmaceutically acceptable salt thereof described herein). Cancers as provided above include IRE1-mediated cancers.

The methods and uses described herein also include embodiments where a compound or pharmaceutically acceptable salt thereof is administered in combination with one or more additional therapeutic agent(s) selected from the group consisting of an anti-inflammatory agent, a corticosteroid, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, an agent for treating immunodeficiency disorders, and combinations thereof.

In one embodiment of the methods provided herein a compound or pharmaceutically acceptable salt thereof is administered in combination with one or more additional therapeutic agents comprising a corticosteroid, a proteasome inhibitor, an immunomodulatory agent, an anti-CD38 antibody, an anti-VEGF-A antibody, an anti-PD-1 antibody, an anti-PD-L1 antibody, or an anti-interleukin-6 antibody, or a combination thereof.

In another embodiment of the methods provided herein a compound or pharmaceutically acceptable salt thereof is administered in combination as described herein where the additional therapeutic agent is a corticosteroid, a proteasome inhibitor, an IMiD, an antibody, or a combination thereof.

In one embodiment, a compound or pharmaceutically acceptable salt thereof is administered in combination with a proteasome inhibitor. In one embodiment, the proteasome inhibitor comprises carfilzomib, bortezomib, or ixazomib. In one embodiment, a compound or pharmaceutically acceptable salt thereof is administered in combination with a IMiD, where the IMiD is lenalidomide or pomalidomide. In one embodiment of the methods provided herein a compound or pharmaceutically acceptable salt thereof is administered in combination with a corticosteroid where the corticosteroid comprises dexamethasone.

In another embodiment, a compound or pharmaceutically acceptable salt thereof is administered in combination with an anti-PD-L1 antibody. The anti-PD-L1 antibody can be avelumab, durvalumab, or atezolizumab. In still another embodiment, a compound or pharmaceutically acceptable salt thereof is administered in combination with an anti-PD-1 antibody. The anti-PD-1 antibody can be pembrolizumab or nivolumab.

The methods provided herein can also further comprise administration of radiotherapy. In certain embodiments, the radiotherapy can be administered before administration of a compound or pharmaceutically acceptable salt thereof described herein.

Further provided herein is a compound or pharmaceutically acceptable salt thereof described herein, for use in a method for treating an IRE1-related disease or disorder, where the IRE1-related disease or disorder is as set forth herein. In one embodiment the compound or pharmaceutically acceptable salt thereof as described herein is for use in a method of treating a cancer as set forth above. In a preferred embodiment, the cancer is MM, AML, CML, or MDS.

Further provided herein is a use of a compound or pharmaceutically acceptable salt thereof described herein in the manufacture of a medicament for the treatment of an IRE1-related disease or disorder, where the IRE1-related disease or disorder is as set forth herein. In one embodiment the IRE1-related disease or disorder is a cancer as set forth above. In a preferred embodiment, the cancer is MM, AML, CML, or MDS. It is to be understood that embodiments herein referring to a method (e.g. a method of treating) can further refer to a use or a compound for use as set forth herein.

The methods and uses described herein are also applicable to patients that have been previously treated with one or more therapies prior to receiving administration of a compound or pharmaceutically acceptable salt thereof described herein. It is well known in the art that patients may be treated with one or more treatment regimens—especially for hematological cancers such as those described herein. Cancers can be relapse or refractory (r/r) (e.g. a patient having rrMM, rrAML, rrCML, or rrMDS). A "refractory" cancer refers to cancer that progresses despite active treatment. A "relapse" cancer generally refers to cancer that occurs in the absence of therapy following successful treatment with one or more anticancer agents. Accordingly, in one embodiment provided herein are methods of treating r/r cancer (e.g. rrMM, rrAML, rrCML, or rrMDS) in a patient having such a cancer by administering a compound or pharmaceutically acceptable salt thereof described herein. Such methods can include co-administration with one or more anticancer agents described herein as set forth above.

Accordingly, in one embodiment, a patient may have been treated with one or more anticancer agents. In one particular embodiment, a patient has been treated with 2 or more anticancer agents as provided herein for the treatment of a hematological disease, such as for example MM or AML. In one embodiment, a patient treated according to the methods provided herein has been previously administered one or more proteasome inhibitors such as bortezomib, carfilzomib, or ixazomib. In one embodiment, a patient treated according to the methods provided herein has been previously administered one or more IMiDs such as thalidomide, lenalidomide, or pomalidomide. In another embodiment, a patient treated according to the methods provided herein has been previously administered chemotherapy (e.g. cytarbine, cladribine, fludarabine, mitoxantrone, etoposide, 6-TG, hydroxyurea, methotrexate, decitabine, or an anthracyclin). In another embodiment, a patient treated according to the methods provided herein has been previously administered one or more corticosteroids such as dexamethasone. Such corticosteroids are often administered with other anticancer agents as understood in the art. In still another embodiment, a patient treated according to the methods provided herein has been previously administered one or more antibodies such as, for example, daratumumab, gemtuzumab ozogamicin, atezolizumab, alemtuzumab, rituximab, obinutuzumab, or ofatumumab. In still another embodiment, a patient treated according to the methods provided herein has been previously administered one or more FLT3 inhibitor (e.g. midostaurin or gilteritinib). In yet another embodiment, a patient treated according to the methods provided herein has been previously administered one or more Bcl-2 inhibitors such as venetoclax or navitoclax. In yet another embodiment, a patient treated according to the methods provided herein has been previously administered one or more of ibrutinib, idelalisib, or duvelisib. In another embodiment, a patient treated according to the methods provided herein has been previously administered an IMiD as described herein in combination with a proteasome inhibitor and optionally a corticosteroid.

A compound or pharmaceutically acceptable salt thereof described herein can be administered as a first line (1 L) therapy (e.g. administration prior to administration of another anticancer agent, including chemotherapy). Thus, in certain instances a patient may be chemotherapy naïve.

It is understood that the methods described herein include administration of a pharmaceutical composition comprising a compound or pharmaceutically acceptable salt thereof as provided herein. Such pharmaceutical compositions also comprise one or more pharmaceutically acceptable carrier excipients. In some embodiments, the compound is selected from Table 1 or Table 2, or a pharmaceutically acceptable salt thereof. In one embodiment, the compound or pharmaceutically acceptable salt thereof is one set forth in Table 1. In one embodiment, the compound or pharmaceutically acceptable salt thereof is one set forth in Table 2.

Also provided herein is a method of treating a disease caused by abnormal levels of IRE1 activity in a human or animal patient in need of such treatment with a compound or a pharmaceutically acceptable salt thereof described herein. The disease can be caused by an amount of IRE1 activity that is too low or too high. For example, the disease can be caused by a deficiency in IRE1 activity or by abnormally high IRE1 activity (e.g., hyperactivity of IRE1). The method includes administering to the patient a effective amount of a compound or a pharmaceutically acceptable salt thereof described herein that modulates IRE1 activity (an IRE1 modulator compound).

IRE1 deficiency can be measured as a decreased amount of IRE1 activity compared to normal levels of IRE1 activity in a particular subject or a population of healthy subjects. The decreased amount of IRE1 activity results in excessive amounts of misfolded protein accumulation thereby causing the disease state.

IRE1 hyperactivity can be measured as an increased amount of IRE1 activity compared to normal levels of IRE1 activity in a particular subject or a population of healthy subjects. The increased amount of IRE1 activity can result in, for example, excessive amounts of cell proliferation thereby causing the disease state.

In some embodiments, the disease is associated with IRE1 deficiency. Such diseases include, but are not limited to, cystic fibrosis, retinitis pigmentosa, diabetes, or a neurodegenerative disease. The neurodegenerative disease can include Alexander's disease, Alper's disease, Alzheimer's disease, Amyotrophic lateral sclerosis, Ataxia telangiectasia, Batten disease (also known as Spielmeyer-Vogt-Sjogren-Batten disease). Bovine spongiform encephalopathy (BSF), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes *dorsalis.*

In other embodiments, the disease is associated with abnormally high IRE1. Such diseases include, but are not limited, to cancers, inflammatory diseases, and autoimmune diseases. Exemplary cancers include, but am not limited to, breast cancer and multiple myeloma. In one embodiment, the disease is multiple myeloma. In one embodiment, the disease is a triple-negative breast cancer. Exemplary inflammatory diseases include, but are not limited to, asthma, chronic inflammation, chronic prostatitis, glomerulonephritis, hypersensitivities, inflammatory bowel diseases, pelvic inflammatory disease; reperfusion injury, rheumatoid arthritis, transplant rejection, and vasculitis. Exemplary autoimmune diseases include, but are not limited to, XBP1-linked Crohn's disease, Coeliac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, and rheumatoid arthritis. In one embodiment, the disease is XBP1-linked. Crohn's disease.

Pharmaceutical Formulations

Compounds or pharmaceutically acceptable salts thereof as described herein can be formulated in accordance with standard pharmaceutical practice as a pharmaceutical composition. Thus, further provided herein is a pharmaceutical composition comprising a compound or pharmaceutically acceptable salt thereof and one or more pharmaceutically acceptable excipients.

A typical formulation is prepared by mixing a compound or pharmaceutically acceptable salt thereof as described herein and an excipient. Suitable carriers, diluents and excipients include, but are not limited to, materials such as carbohydrates, waxes, water soluble and/or swellable polymers, hydrophilic or hydrophobic materials, gelatin, oils, solvents, water and the like. The particular excipient used will depend upon the means and purpose for which the compound or pharmaceutically acceptable salt thereof as described herein is being applied. Solvents are generally selected based on solvents recognized as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound described herein or pharmaceutical composition thereof) or aid in the manufacturing of the pharmaceutical product (i.e., medicament).

The formulations can be prepared using conventional dissolution and mixing procedures. For example, the bulk drug substance (i.e., compound or pharmaceutically acceptable salt thereof as described herein or stabilized form thereof (e.g., complex with a cyclodextrin derivative or other known complexation agent) is dissolved in a suitable solvent in the presence of one or more of the excipients described above. The compound or pharmaceutically acceptable salt thereof as described herein is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations of the compounds or pharmaceutically acceptable salts thereof as described herein can be prepared for various routes and types of administration. For example, a compound or pharmaceutically acceptable salt thereof as described herein having the desired degree of purity can optionally be mixed with one or more pharmaceutically acceptable excipients (Remington's Pharmaceutical Sciences (1980) 16th edition, Osol, A. Ed.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. For example, formulation in an acetate buffer at pH 5 can be a suitable embodiment.

The pharmaceutical composition ordinarily can be stored as a solid composition, a lyophilized formulation or as an aqueous solution.

The pharmaceutical compositions described herein can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day. In another embodiment, a pharmaceutical composition described herein comprises an effective amount of a compound or pharmaceutically acceptable salt thereof in an amount of about: 1 mg-10 mg; 10 mg-25 mg; 20 mg-50 mg; 50 mg-75 mg; 70 mg-100 mg; 100 mg-150 mg; 100 mg-200 mg; 100 mg-500 mg; 200 mg-500 mg; 250 mg-500 mg; 500 mg-1000 mg; or 750 mg-1000 mg.

Acceptable pharmaceutically acceptable excipients are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds or pharmaceutically acceptable salts thereof as described herein may be prepared. Suitable examples of sustained-release preparations include semipermeable matrices of solid hydrophobic polymers containing a compound or pharmaceutically acceptable salt thereof as described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any methods. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound or pharmaceutically acceptable salt thereof as described herein suitable for oral administration can be prepared as discrete units such as pills, capsules, cachets or tablets each containing a predetermined amount of such compound or pharmaceutically acceptable salt thereof. Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs can be prepared for oral use. Formulations of compounds or pharmaceutically acceptable salts thereof as described herein intended for oral use can be prepared according to any method for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs. The oily phase of the emulsions of compositions provided herein can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of described herein include Tween® 60, Span® 80, cetostearyl alcohol, benzyl alcohol, myristyl alcohol, glyceryl mono-stearate and sodium lauryl sulfate.

Aqueous suspensions comprising compounds or pharmaceutically acceptable salts thereof as described herein can contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds or pharmaceutically acceptable salts thereof as described herein can be in the form of a sterile injectable preparation, such as a sterile injectable aqueous or oleaginous suspension. This suspension can be formulated using suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Formulations suitable for vaginal administration can be presented as pessaries, tampons, creams, gels, pastes, foams or spray formulations containing in addition to the active ingredient such carriers considered to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The compounds or pharmaceutically acceptable salts thereof as described herein can be used in veterinary compositions comprising at least one active ingredient as above defined together with a veterinary carrier. Veterinary carriers are materials useful for the purpose of administering the composition and can be solid, liquid or gaseous materials which are otherwise inert or acceptable in the veterinary field and are compatible with the active ingredient. These veterinary compositions can be administered parenterally, orally or by any other desired route.

Combination Therapy

The compounds and pharmaceutically acceptable salts thereof described herein can be employed alone or in combination with additional therapeutic agents for the treatment of a disease or disorder described herein, such as inflammation or a hyperproliferative disorder (e.g., cancer). In certain embodiments, a compound or a pharmaceutically acceptable salt thereof as described herein is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic can be a Bcl-2 inhibitor, a JAK inhibitor, a PI3K inhibitor, an mTOR inhibitor, an anti-inflammatory agent, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent can be an NSAID anti-inflammatory agent. The second therapeutic agent can be an anti-cancer agent as described herein. The second compound of the pharmaceutical combination formulation or dosing regimen preferably has complementary activities to the compound or pharmaceutically acceptable salt thereof described herein such that they do not adversely affect each other. Such compounds are suitably present in combination in amounts that are effective for the purpose intended. In one embodiment, a composition provided herein comprises a compound or a stereoisomer, tautomer, solvate, metabolite, or pharmaceutically acceptable salt thereof, in combination with a therapeutic agent such as an NSAID.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and can be lowered due to the combined action (synergy) of the newly identified agent and other therapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound or a or pharmaceutically acceptable salt thereof described herein can be combined with other therapeutic, hormonal or antibody agents such as those described herein, as well as combined with surgical therapy and radiotherapy. Combination therapies provided herein thus comprise the administration of at least one compound of or pharmaceutically acceptable salt thereof described herein, and the use of at least one other cancer treatment method as provided herein. The amounts of the compound(s) or pharmaceutically acceptable salts thereof described herein, and the other pharmaceutically active therapeutic agent(s) and the relative timings of administration will be selected in order to achieve the desired combined therapeutic effect.

In some embodiments, a compound or a pharmaceutically acceptable salt thereof described herein, is used in combination with an aromatase inhibitor, a phosphoinositide 3-kinase (PI3K)/mTOR pathway inhibitor, a CDK 4/6 inhibitor, a HER-2 inhibitor, a SERM, a SERD, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a pharmaceutical composition comprising a compound or a pharmaceutically acceptable salt thereof described herein, is administered in combination with a therapeutic agent selected from paclitaxel, anastrozole, exemestane, cyclophosphamide, epirubicin, fulvestrant, letrozole, palbociclib, gemcitabine, trastuzumab (HERCEPTIN®, Genentech), trastuzumab emtansine (KADCYLA®, Genentech), pegfilgrastim, filgrastim, tamoxifen, docetaxel, toremifene, vinorelbine, capecitabine, and ixabepilone.

In some embodiments, a compound or a pharmaceutically acceptable salt thereof described herein, is used in combination with hormone blocking therapy, chemotherapy, radiation therapy, monoclonal antibodies, or combinations thereof.

Also provided herein are methods of inhibiting or killing a cancer cell expressing Ire1 by contacting the cancer cell expressing Ire1 with a compound or pharmaceutically acceptable salt thereof described herein. In one embodiment of the methods, the contacting is performed in vivo (e.g. the contacting is a result of administration of a compound or pharmaceutically acceptable salt thereof described herein). Thus, in another embodiment of the methods the inhibition or killing of the cancer cell occurs in vivo. In still another embodiment, the cancer cell expressing IRE1 is in a human patient described herein.

Metabolites of Compounds of Described Herein

Also provided herein are in vivo metabolic products of compounds or pharmaceutically acceptable salts thereof described herein. Such products can result for example from the oxidation, reduction, hydrolysis, amidation, deamidation, esterification, deesterification, enzymatic cleavage, and the like, of the administered compound. Accordingly, provided herein are compounds produced by a process comprising contacting a compound or pharmaceutically acceptable salt thereof described herein with a mammal for a period of time sufficient to yield a metabolic product thereof.

Metabolite products typically are identified by preparing a radiolabelled (e.g., $^{14}C$ or $^{3}H$) isotope of a compound or pharmaceutically acceptable salt thereof as described herein, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies. The metabolite products, so long as they are not otherwise found in vivo, are useful in diagnostic assays for therapeutic dosing of the compounds or pharmaceutically acceptable salts thereof described herein.

Articles of Manufacture

Also provided herein is an article of manufacture, or kit, containing materials useful for the treatment of the diseases and disorders described above (e.g. cancer). In one embodiment, the kit comprises a container comprising a compound or pharmaceutically acceptable salt thereof described herein. The kit can further comprise a label or package insert on or associated with the container. Suitable containers include, for example, bottles, vials, syringes, blister pack, etc. The container can be formed from a variety of materials known in the art such as metal, glass, or plastic. The container can hold a compound or pharmaceutically acceptable salt thereof or a formulation thereof which is effective for treating the condition and can have a sterile access port (for example, the container can be an intravenous solution bag or a vial having a stopper pierceable by a hypodermic injection needle). At least one active agent in the composition is a compound or a pharmaceutically acceptable salt thereof described herein. The label or package insert indicates that the composition is used for treating the condition of choice, such as cancer. In addition, the label or package insert can indicate that the patient to be treated is one having a disorder such as a hyperproliferative disorder, atherosclerosis, neurodegeneration, cardiac hypertrophy, pain, migraine or a neurotraumatic disease or event. In one embodiment, the label or package inserts indicates that the composition comprising a compound or pharmaceutically acceptable salt thereof described herein can be used to treat a disorder resulting from abnormal cell growth. In one embodiment, the label or package inserts indicates that the composition comprising a compound or pharmaceutically acceptable salt thereof described herein can be used to treat a disorder resulting from atherosclerosis. The label or package insert can also indicate that the composition can be used to treat other disorders. Alternatively, or additionally, the article of manufacture can further comprise a second container comprising a pharmaceutically acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

The kit can further comprise directions for the administration of the compound or pharmaceutically acceptable salt thereof described herein and, if present, the second pharmaceutical formulation. For example, if the kit comprises a first composition comprising a compound or pharmaceutically acceptable salt thereof described herein and a second pharmaceutical formulation, the kit can further comprise directions for the simultaneous, sequential or separate administration of the first and second pharmaceutical compositions to a patient in need thereof (e.g. according to the co-administration routes discussed herein). Accordingly, in one embodiment is a kit for treating a condition mediated by IRE1 where the kit comprises a compound or pharmaceutically acceptable salt thereof (formulated as a pharmaceutical composition described herein) and instructions for use.

In another embodiment, the kits are suitable for the delivery of solid oral forms of a compound or pharmaceutically acceptable salt thereof described herein, such as tablets or capsules. Such a kit preferably includes a number of unit dosages. Such kits can include a card having the dosages oriented in the order of their intended use. An example of such a kit is a blister pack. Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit can comprise (a) a first container with a compound or pharmaceutically acceptable salt thereof described herein contained therein; and optionally (b) a second container with a second pharmaceutical formulation contained therein, wherein the second pharmaceutical formulation comprises a second compound with anti-hyperproliferative activity. Alternatively, or additionally, the kit can further comprise a third container comprising a pharmaceutically-acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

In certain other embodiments wherein the kit comprises a composition comprising a compound or a pharmaceutically acceptable salt thereof described herein and a second therapeutic agent, the kit can comprise a container for containing the separate compositions such as a divided bottle or a divided foil packet, however, the separate compositions can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EMBODIMENTS

Embodiment 1: A compound having formula (I):

(I)

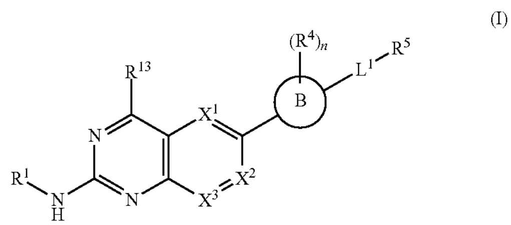

or a stereoisomer, tautomer or pharmaceutically acceptable salt thereof, wherein:

Ring B is $R^4$-substituted or unsubstituted $C_{3-7}$ cycloalkyl, $R^4$-substituted or unsubstituted 3 to 7 membered heterocycloalkyl, $R^4$-substituted or unsubstituted $C_{5-7}$ aryl, or $R^4$-substituted or unsubstituted 5 to 7 membered heteroaryl;

$L^1$ is —$NHSO_2$—, —$SO_2NH$—, —NH—, —NHC(O)—, —C(O)NH—, or pyrrolidin-2-one;

$X^1$ and $X^2$ are independently —N— or —$CR^2$—;

$X^3$ is —N— or —$CR^3$—, wherein one of $X^1$, $X^2$, and $X^3$ is —N—;

$R^1$ is $R^6$-substituted or unsubstituted $C_{1-6}$ alkyl, $R^6$-substituted or unsubstituted $C_{1-6}$ haloalkyl, $R^6$-substituted or unsubstituted $C_{3-7}$ cycloalkyl, or $R^6$-substituted or unsubstituted 3 to 7 membered heterocycloalkyl, each $R^2$ is independently hydrogen, halogen, —$OR^7$, $R^{10}$-substituted or unsubstituted $C_{1-6}$ alkyl, $R^{10}$-substituted or unsubstituted $C_{3-7}$ cycloalkyl, or $R^{10}$-substituted or unsubstituted 3 to 7 membered heterocycloalkyl, $R^3$ is hydrogen, halogen, —CN, —$OR^7$, —$NO_2$, —C(O)$R^7$, —C(O)$OR^7$, —C(O)$OR^7$, —C(O)$NR^{7A}R^{7B}$, —OC (O)$R^7$, —OC(O)$NR^{7A}R^{7B}$, —$SR^{7A}$, —S(O)$R^7$, —$S(O)_2R^7$, —S(O)(=$NR^{7A}$)$R^{7B}$, —$S(O)_2NR^{7A}R^{7B}$, —$NR^{7A}R^{7B}$, —$NR^{7A}$C(O)$R^7$, —$NR^{7A}$C(O)O$R^7$, —N($R^{7A}$)C(O)$NR^{7A}R^{7B}$, —$NR^{7A}S(O)_2R^7$, —$NR^{1A}$S(O)$_2NR^{7A}R^{7B}$, —P(O)$(R^7)_2$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, $R^{10}$-substituted or unsubstituted 3 to 7 membered heterocycloalkyl, $R^{10}$-substituted or unsubstituted $C_{5-7}$ aryl, or $R^{10}$-substituted or unsubstituted 5 to 7 membered heteroaryl;

each $R^4$ is hydrogen, halogen, —O$R^7$, —CN, —$S(O)_2R^7$, $R^{10}$-substituted or unsubstituted $C_{1-6}$ alkyl, $R^{10}$-substituted or unsubstituted $C_{1-6}$ haloalkyl, or $R^{10}$-substituted or unsubstituted $C_{3-7}$ cycloalkyl;

n is 0, 1, 2, 3, or 4;

$R^5$ is $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, $R^{10}$-substituted or unsubstituted 3 to 7 membered heterocycloalkyl, $R^{10}$-substituted or unsubstituted $C_{5-7}$ aryl, or $R^{10}$-substituted or unsubstituted 5 to 7 membered heteroaryl;

each $R^6$ is independently hydrogen, halogen, —O$R^7$, —$NR^{6A}R^{6B}$, $R^{10}$-substituted or unsubstituted $C_{1-6}$ alkyl, or $R^{10}$-substituted or unsubstituted $C_{1-6}$ haloalkyl;

$R^{6A}$ and $R^{6B}$ are independently hydrogen or $R^{10}$-substituted or unsubstituted $C_{1-6}$ alkyl, or $R^{6A}$ and $R^{6B}$ are taken together with the nitrogen atom to which they are attached to form a $R^{10}$-substituted or unsubstituted 4 to 7 membered heterocycloalkyl, each $R^7$ is independently hydrogen, $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl, each $R^{7A}$ and $R^{7B}$ is independently hydrogen, $R^{8A}$-substituted or unsubstituted $C_{1-6}$ alkyl, $R^{8A}$-substituted or unsubstituted $C_{1-6}$ haloalkyl, $R^{8A}$-substituted or unsubstituted $C_{3-7}$ cycloalkyl, or $R^{8A}$-substituted or unsubstituted 3 to 7 membered heterocycloalkyl, each $R^{8A}$ is independently hydrogen, halogen, oxo, —CN, —$NO_2$, —C(O)H, —C(O)$CH_3$, —C(O)OH, —C(O)O$CH_3$, —C(O)$NH_2$, —OH, —O$CH_3$, —O$CF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —NH($CH_3$), —N$(CH_3)_2$, —NHC(O)H, —NHC(O)OH, —N(H)C(O)$NH_2$, —NHS$(O)_2$H, —NHS$(O)_2NH_2$, or —P(O)$(CH_3)_2$, —$CF_3$, —$CHF_2$, —$CH_2F$, —C$(CH_3)_2$F, —C($CH_3$)$F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^8$ is independently hydrogen, halogen, oxo, —CN, —O$R^{8B}$, —$NO_2$, —C(O)$R^{8B}$, —C(O)O$R^{8B}$, —C(O)O$R^{8B}$, —C(O)$NR^{8C}R^{8D}$, —OC(O)$R^{8B}$, —OC(O)$NR^{8C}R^{8D}$, —$SR^{8C}$, —S(O)$R^{8B}$, —$S(O)_2R^{8B}$, —S(O)(=$NR^{8C}$)$R^{8D}$, —$S(O)_2NR^{8C}R^{8D}$, —$NR^{8C}R^{8D}$, —$NR^{8C}$C(O)$R^{8B}$, —$NR^{8C}$C(O)O$R^{8B}$, —N($R^{8C}$)C(O)$NR^{8C}R^{8D}$, —$NR^{8C}S(O)_2R^{8B}$, —$NR^{8C}S(O)_2NR^{8C}R^{8D}$, —P(O)$(R^{8B})_2$, $R^9$-substituted or unsubstituted $C_{1-6}$ alkyl, $R^9$-substituted or unsubstituted $C_{1-6}$ haloalkyl, $R^9$-substituted or unsubstituted $C_{3-7}$ cycloalkyl, $R^9$-substituted or unsubstituted 3 to 6 membered heterocycloalkyl, $R^9$-substituted or unsubstituted $C_{5-7}$ aryl, or $R^9$-substituted or unsubstituted 5 to 7 membered heteroaryl;

each $R^{8b}$ $R^{8C}$, and $R^{8D}$ is independently hydrogen, $R^{9A}$-substituted or unsubstituted $C_{1-6}$ alkyl, $R^{9A}$-substituted or unsubstituted $C_{1-6}$ haloalkyl, $R^{9A}$-substituted or unsubstituted $C_{3-7}$ cycloalkyl, or $R^{9A}$-substituted or unsubstituted 3 to 7 membered heterocycloalkyl, each $R^{9A}$ is independently hydrogen, halogen, oxo, —CN, —$NO_2$, —C(O)H, —C(O)$CH_3$, —C(O)OH, —C(O)O$CH_3$, —C(O)$NH_2$, —OH, —O$CH_3$, —O$CF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —NH($CH_3$), —N$(CH_3)_2$, —NHC(O)H, —NHC(O)OH, —N(H)C(O)$NH_2$, —NHS$(O)_2$H, —NHS$(O)_2NH_2$, or —P(O)$(CH_3)_2$, —$CF_3$, —$CHF_2$, —$CH_2F$, —C$(CH_3)_2$F, —C($CH_3$)$F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^9$ is independently hydrogen, halogen, oxo, —CN, —O$R^{9B}$, —$NO_2$, —C(O)$R^{9B}$, —C(O)O$R^{9B}$, —C(O)O$R^{9B}$, —C(O)$NR^{9C}R^{9D}$, —OC(O)$R^{9B}$, —OC(O)$NR^{9C}R^{9A}$, —$SR^{9C}$, —S(O)$R^{9B}$, —$S(O)_2R^{9B}$, —S(O)(=$NR^{9C}$)$R^{9D}$, —$S(O)_2NR^{9C}R^{9D}$, —$NR^{9C}$ $R^{9D}$, —$NR^{9C}$C(O)$R^{9B}$, —$NR^{9C}$C(O)O$R^{9B}$, —N($R^{9C}$)C(O)$NR^{9C}R^{9D}$, —$NR^{9C}S(O)_2R^{9A}R^{9B}$, —$NR^{9C}S(O)_2NR^{9C}R^{9D}$, —P(O)$(R^{9B})_2$, $R^{12}$-substituted or unsubstituted $C_{1-6}$ alkyl, $R^{12}$-substituted or unsubstituted $C_{1-6}$ haloalkyl, $R^{12}$-substituted or unsubstituted $C_{3-7}$ cycloalkyl, $R^{12}$-substituted or unsubstituted 3 to 6 membered heterocycloalkyl, $R^{12}$-substituted or unsubstituted $C_{5-7}$ aryl, or $R^{12}$-substituted or unsubstituted 5 to 7 membered heteroaryl;

each $R^{9b}$ $R^{9C}$, and $R^{9D}$ is independently hydrogen, $R^{10A}$-substituted or unsubstituted $C_{1-6}$ alkyl, $R^{10A}$-substituted or unsubstituted $C_{1-6}$ haloalkyl, $R^{10A}$-substituted or unsubstituted $C_{3-7}$ cycloalkyl, or $R^{10A}$-substituted or unsubstituted 3 to 7 membered heterocycloalkyl, each $R^{10A}$ is independently hydrogen, halogen, oxo, —CN, —$NO_2$, —C(O)H, —C(O)$CH_3$, —C(O)OH, —C(O)O$CH_3$, —C(O)$NH_2$, —OH, —O$CH_3$, —O$CF_3$, —OC(O)H, —OC(O) $CH_3$, —OC(O)$NH_2$, —SH, —S(O)H, —$S(O)_2H$, —S(O)(=NH)H, —$S(O)_2NH_2$, —$NH_2$, —NH($CH_3$), —N$(CH_3)_2$, —NHC(O)H, —NHC(O)OH, —N(H)C(O)$NH_2$, —NHS$(O)_2$H, —NHS$(O)_2NH_2$, or —P(O)$(CH_3)_2$, —$CF_3$, —$CHF_2$, —$CH_2F$, —C$(CH_3)_2$F, —C($CH_3$)$F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^{10}$ is independently hydrogen, halogen, oxo, —CN, —O$R^{11A}$, —$NO_2$, —C(O)$R^{11A}$C(O)O$R^{11A}$, —C(O)O$R^{11A}$, —C(O)$NR^{11B}R^{11C}$, —OC(O)$R^{11A}$, —OC(O)$NR^{11B}R^{11C}$, —$SR^{11B}$, —S(O)$R^{11A}$, —$S(O)_2R^{11A}$, —S(O)(=$NR^{11B}$)$R^{11C}$, —$S(O)_2NR^{11B}R^{11C}$, —$NR^{11B}R^{11C}$, —$NR^{11B}$C(O)$R^{11A}$, —$NR^{11B}$C(O)O$R^{11A}$, —N($R^{11B}$)C(O)$NR^{11B}R^{11C}$, —$NR^{11B}S(O)_2R^{11A}$, —$NR^{11B}S(O)_2NR^{11B}R^{11C}$, —P(O)$(R^{11A})_2$, $R^{11}$-substituted or unsubstituted $C_{1-6}$ alkoxy, $R^{11}$-substituted or unsubstituted $C_{1-6}$ alkyl, $R^{11}$-substituted or unsubstituted $C_{1-6}$ haloalkyl, $R^{11}$-substituted or unsubstituted $C_{3-7}$ cycloalkyl, $R^{11}$-substituted or unsubstituted 3 to 6 membered heterocycloalkyl, $R^{11}$- substituted or unsubstituted $C_{5-7}$ aryl, or $R^{11}$-substituted or unsubstituted 5 to 7 membered heteroaryl;

each $R^{11A}$, $R^{11B}$ and $R^{11C}$ is independently hydrogen, $R^{12A}$-substituted or unsubstituted $C_{1-6}$ alkyl, $R^{12A}$-substituted or unsubstituted $C_{1-6}$ haloalkyl, $R^{12A}$-substituted or unsubstituted $C_{3-7}$ cycloalkyl, or $R^{12A}$-substituted or unsubstituted 3 to 7 membered heterocycloalkyl, each $R^{12A}$ is independently hydrogen, halogen, oxo, —CN, —$NO_2$, —C(O)H, —C(O)$CH_3$, —C(O)OH, —C(O)O$CH_3$, —C(O)$NH_2$, —OH, —O$CH_3$, —O$CF_3$, —OC(O)H, —OC(O) $CH_3$, —OC(O)$NH_2$, —SH, —S(O)H, —S$(O)_2$H, —S(O)(=NH)H, —S$(O)_2NH_2$, —$NH_2$, —NH($CH_3$), —N$(CH_3)_2$, —NHC(O)H, —NHC(O)OH, —N(H)C(O)$NH_2$, —NHS$(O)_2$H, —NHS$(O)_2NH_2$, or —P(O)$(CH_3)_2$, —$CF_3$, —$CHF_2$, —$CH_2$F, —C$(CH_3)_2$F, —C($CH_3$)$F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^{11}$ is independently hydrogen, halogen, oxo, —CN, —$OR^{12B}$, —$NO_2$, —C(O)$R^{12B}$, —C(O)O$R^{12B}$, —C(O)O$R^{12B}$, —C(O)N$R^{12C}R^{12D}$, —OC(O)$R^{12B}$, —OC(O)N$R^{12C}R^{12D}$, —S$R^{12}$C, —S(O)$R^{12B}$, —S$(O)_2R^{12B}$, —S(O)(=N$R^{12C}$)$R^{12D}$, —S$(O)_2$N$R^{12C}R^{12D}$, —N$R^{12C}R^{12D}$, —N$R^{12C}$C(O)$R^{12B}$, N$R^{12C}$C(O)O$R^{12B}$, —N($R^{12C}$)C(O)N$R^{12C}R^{12D}$, —N$R^{12C}$S$(O)_2R^{12B}$, N$R^{12C}$S$(O)_2$N$R^{12C}R^{12D}$, —P(O)$(R^{12B})_2$, $R^{12}$-substituted or unsubstituted $C_{1-6}$ alkyl, $R^{12}$-substituted or unsubstituted $C_{1-6}$ haloalkyl, $R^{12}$-substituted or unsubstituted $C_{3-7}$ cycloalkyl, $R^{12}$-substituted or unsubstituted 3 to 6 membered heterocycloalkyl, $R^{12}$-substituted or unsubstituted $C_{5-7}$ aryl, or $R^{12}$-substituted or unsubstituted 5 to 7 membered heteroaryl;

each $R^{12B}$, $R^{12C}$ and $R^{12D}$ is independently hydrogen, unsubstituted $C_{1-6}$ alkyl, unsubstituted $C_{1-6}$ haloalkyl, unsubstituted $C_{3-7}$ cycloalkyl, or unsubstituted 3 to 7 membered heterocycloalkyl, each $R^{12}$ is independently hydrogen, halogen, oxo, —CN, —$NO_2$, —C(O)H, —C(O)$CH_3$, —C(O)OH, —C(O)O$CH_3$, —C(O)$NH_2$, —OH, —O$CH_3$, —O$CF_3$, —OC(O)H, —OC(O)$CH_3$, —OC(O)$NH_2$, —SH, —S(O)H, —S$(O)_2$H, —S(O)(=NH)H, —S$(O)_2NH_2$, —$NH_2$, —NH($CH_3$), —N$(CH_3)_2$, —NHC(O)H, —NHC(O)OH, —N(H)C(O)$NH_2$, —NHS$(O)_2$H, —NHS$(O)_2NH_2$, or —P(O)$(CH_3)_2$, —$CF_3$, —$CHF_2$, —$CH_2$F, —C$(CH_3)_2$F, —C($CH_3$)$F_2$, unsubstituted $C_{1-6}$ alkoxy, unsubstituted $C_{1-6}$ alkyl, unsubstituted $C_{1-6}$ alkoxy, unsubstituted $C_{1-6}$ haloalkyl, unsubstituted $C_{1-6}$ haloalkoxy, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl; and $R^{13}$ is hydrogen, halogen, or $R^{10}$-substituted or unsubstituted $C_{1-6}$ alkyl.

Embodiment 2: The compound of embodiment 1 having formula (II):

(II)

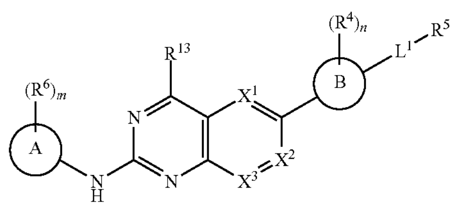

or a stereoisomer, tautomer, or pharmaceutically acceptable salt thereof, wherein:

Ring A is $R^6$-substituted or unsubstituted $C_{3-6}$ cycloalkyl or $R^6$-substituted or unsubstituted 3 to 6 membered heterocycloalkyl, and m is 0, 1, 2, 3, 4, or 5.

Embodiment 3: The compound or pharmaceutically acceptable salt thereof of embodiment 1 or 2, wherein the compound has the formula:

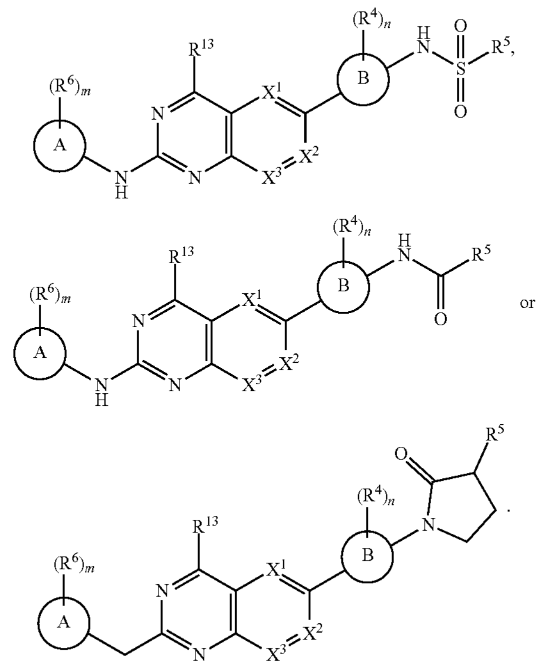

or

Embodiment 4: The compound or pharmaceutically acceptable salt thereof of embodiment 1 or 2, wherein the compound has formula:

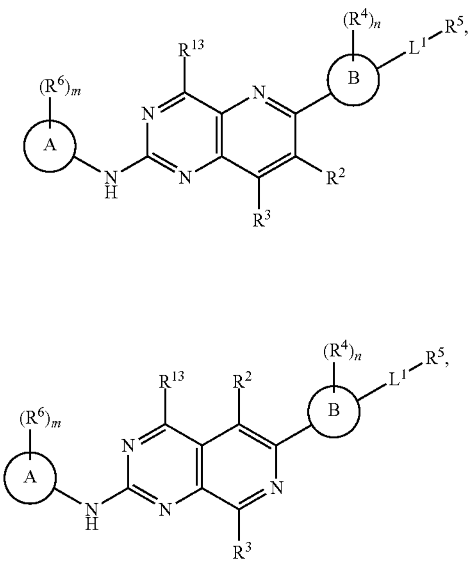

or

-continued

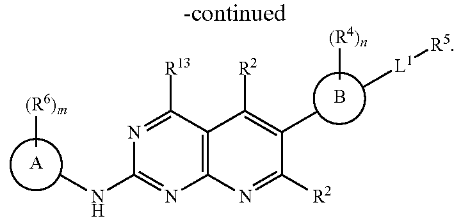

Embodiment 5: The compound or pharmaceutically acceptable salt thereof of any one of embodiments 1 to 4, wherein $R^2$ is independently hydrogen, $OR^7$, or $R^{10}$-substituted or unsubstituted $C_{1-6}$ alkyl.

Embodiment 6: The compound or pharmaceutically acceptable salt thereof of embodiment 5, wherein $R^7$ is hydrogen, $R^8$-substituted or unsubstituted $C_{1-6}$ alkyl, or $R^8$-substituted or unsubstituted $C_{1-6}$haloalkyl.

Embodiment 7: The compound or pharmaceutically acceptable salt thereof of embodiment 6, wherein $R^7$ is unsubstituted $C_{1-6}$ alkyl, or unsubstituted $C_{1-6}$ haloalkyl.

Embodiment 8: The compound or pharmaceutically acceptable salt thereof of embodiment 5, wherein $R^7$ is $R^8$-substituted or unsubstituted $C_{3-7}$ cycloalkyl or $R^8$-substituted or unsubstituted 3 to 7 membered heterocycloalkyl.

Embodiment 9: The compound or pharmaceutically acceptable salt thereof of embodiment 8, wherein $R^7$ is $R^8$-substituted or unsubstituted 3 to 7 membered heterocycloalkyl.

Embodiment 10: The compound or pharmaceutically acceptable salt thereof of any one of embodiments 1 to 4, wherein $R^2$ is hydrogen and $R^3$ is not hydrogen.

Embodiment 11: The compound or pharmaceutically acceptable salt thereof of any one of embodiments 1 to 9, wherein $R^3$ is hydrogen, halogen, —$OR^7$, —$NR^{7A}R^{7B}$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, or $R^{10}$-substituted or unsubstituted 3 to 7 membered heterocycloalkyl.

Embodiment 12: The compound or pharmaceutically acceptable salt thereof of any one of embodiments 1 to 9, wherein $R^3$ is hydrogen.

Embodiment 13: The compound or pharmaceutically acceptable salt thereof of any one of embodiments 1 to 9, wherein $R^3$ is —$OR^7$ or —$NR^{7A}R^{7B}$.

Embodiment 14: The compound or pharmaceutically acceptable salt thereof of embodiment 13, wherein $R^7$ is $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl.

Embodiment 15: The compound or pharmaceutically acceptable salt thereof of embodiment 13, wherein $R^{7A}$ and $R^{7B}$ are independently hydrogen or $R^{8A}$-substituted or unsubstituted $C_{1-6}$ alkyl.

Embodiment 16: The compound or pharmaceutically acceptable salt thereof of any one of embodiments 1 to 9, wherein $R^3$ is $R^{10}$-substituted or unsubstituted $C_{1-6}$ alkyl or $R^{10}$-substituted or unsubstituted $C_{1-6}$ haloalkyl.

Embodiment 17: The compound or pharmaceutically acceptable salt thereof of embodiment 16, wherein $R^3$ is methyl, ethyl, propyl, or isopropyl.

Embodiment 18: The compound or pharmaceutically acceptable salt thereof of embodiment 16, wherein $R^3$ is —$C(CH_3)_2F$, —$C(CH_3)F_2$, —$CH_2F$, —$CHF_2$, or —$CF_3$.

Embodiment 19: The compound or pharmaceutically acceptable salt thereof of any one of embodiments 1 to 9, wherein $R^3$ is $R^{10}$-substituted or unsubstituted $C_{3-7}$ cycloalkyl or $R^{10}$-substituted or unsubstituted 3 to 7 membered heterocycloalkyl.

Embodiment 20: The compound or pharmaceutically acceptable salt thereof of embodiment 19, wherein $R^3$ is $R^{10}$-substituted or unsubstituted 3 to 7 membered heterocycloalkyl.

Embodiment 21: The compound or pharmaceutically acceptable salt thereof of any one of embodiments 1 to 20, wherein $R^4$ is halogen and n is 1, 2, or 3.

Embodiment 22: The compound or pharmaceutically acceptable salt thereof of any one of embodiments 1 to 21, wherein $R^4$ is F and n is 1, 2, or 3.

Embodiment 23: The compound or pharmaceutically acceptable salt thereof of any one of embodiments 1 to 20, wherein $R^4$ is —$OR^7$ and n is 1.

Embodiment 24: The compound or pharmaceutically acceptable salt thereof of any one of embodiments 1 to 20, wherein $R^7$ is $R^8$-substituted or unsubstituted $C_{1-6}$ alkyl or $R^8$-substituted or unsubstituted $C_{1-6}$ haloalkyl.

Embodiment 25: The compound or pharmaceutically acceptable salt thereof of any one of embodiments 1 to 24, wherein $L^1$ is —$NHSO_2$—, —NHC(O)—, or pyrrolidin-2-one.

Embodiment 26: The compound or pharmaceutically acceptable salt thereof of any one of embodiments 1 to 25, wherein $L^1$ is —$NHSO_2$—.

Embodiment 27: The compound or pharmaceutically acceptable salt thereof of any one of embodiments 1 to 25, wherein $L^1$ is-NHC(O)—.

Embodiment 28: The compound or pharmaceutically acceptable salt thereof of any one of embodiments 1 to 27, wherein $R^5$ is $R^{10}$-substituted or unsubstituted benzyl, $R^{10}$-substituted or unsubstituted pyrrolidinyl, $R^{10}$-substituted or unsubstituted piperidinyl, or $R^{10}$-substituted or unsubstituted $C_{1-6}$ haloalkyl.

Embodiment 29: The compound or pharmaceutically acceptable salt thereof of any one of embodiments 1 to 27, wherein $R^5$ is $R^{10}$-substituted or unsubstituted $C_{1-6}$ alkyl, $R^{10}$-substituted or unsubstituted $C_{1-6}$ haloalkyl, or $R^{10}$-substituted or unsubstituted 3 to 6 membered cycloalkyl.

Embodiment 30: The compound or pharmaceutically acceptable salt thereof of embodiment 28 or 29, wherein $R^{10}$ is halogen, —CN, $R^{11}$-substituted or unsubstituted $C_{1-6}$ alkoxy, $R^{11}$-substituted or unsubstituted $C_{1-6}$ alkyl, or $R^{11}$-substituted or unsubstituted $C_{1-6}$ haloalkyl.

Embodiment 31: The compound or pharmaceutically acceptable salt thereof of embodiment 28 or 29, wherein $R^{10}$ is hydrogen, halogen, —OH, —CN, —$CF_3$, —$CHF_2$, —$CH_2F$, —$C(CH_3)_2F$, —$C(CH_3)F_2$, methyl, propyl, or ethyl.

Embodiment 32: The compound or pharmaceutically acceptable salt thereof of any one of embodiments 1 to 31, wherein $R^6$ is independently hydrogen, halogen, $R^{10}$-substituted or unsubstituted $C_{1-6}$ alkyl, $R^{10}$-substituted or unsubstituted $C_{1-6}$ haloalkyl, or —$NR^{6A}R^{6B}$.

Embodiment 33: The compound or pharmaceutically acceptable salt thereof of any one of embodiments 1 to 32, wherein $R^6$ is independently hydrogen, halogen, or $R^{10}$-substituted or unsubstituted $C_{1-6}$ alkyl.

Embodiment 34: The compound or pharmaceutically acceptable salt thereof of any one of embodiments 1 to 32, wherein $R^6$ is independently hydrogen, $R^{10}$-substituted or unsubstituted $C_{1-6}$ alkyl, or $R^{10}$-substituted or unsubstituted $C_{1-6}$ haloalkyl.

Embodiment 35: The compound or pharmaceutically acceptable salt thereof of any one of embodiments 1 to 32, wherein $R^6$ is independently hydrogen or —$NR^8R^9$.

Embodiment 36: The compound or pharmaceutically acceptable salt thereof of embodiment 35, wherein at least one $R^6$ is —$NR^{6A}R^{6B}$, wherein $R^{6A}$ and $R^{6B}$ are each $R^{10}$-substituted or unsubstituted $C_{1-6}$ alkyl.

Embodiment 37: The compound or pharmaceutically acceptable salt thereof of any one of embodiments 1 to 36, wherein $R^1$ is $R^6$-substituted or unsubstituted $C_{1-6}$ alkyl.

Embodiment 38: The compound or pharmaceutically acceptable salt thereof of any one of embodiments 1 to 36, wherein $R^1$ is $R^6$-substituted $C_{3-4}$ cycloalkyl or $R^6$-substituted 3 to 6 membered heterocycloalkyl.

Embodiment 39: The compound or pharmaceutically acceptable salt thereof of any one of embodiments 1 to 36, wherein $R^1$ is $R^6$-substituted cyclohexyl or $R^6$-substituted piperidinyl.

Embodiment 40: The compound or pharmaceutically acceptable salt thereof of any one of embodiments 1 to 36, wherein $R^1$ has formula:

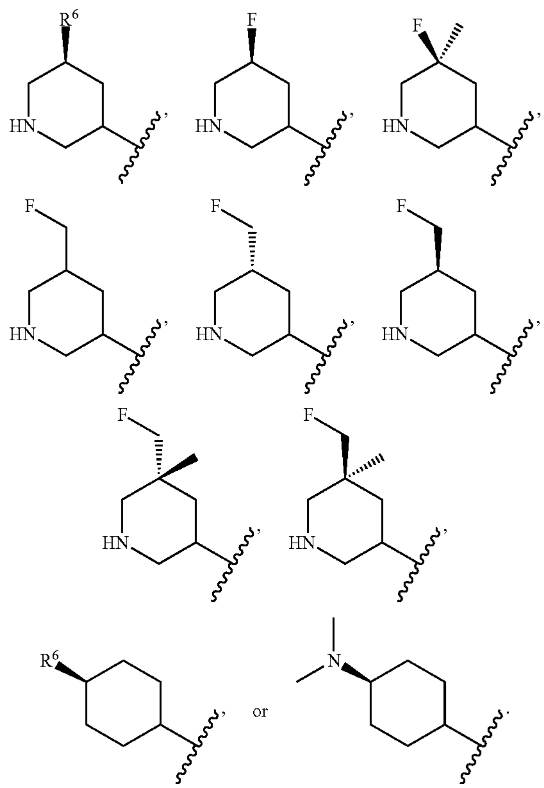

Embodiment 41: The compound or pharmaceutically acceptable salt thereof of any one of embodiments 1 to 40, wherein Ring B is $R^4$-substituted or unsubstituted $C_{5-7}$ aryl.

Embodiment 42: The compound or pharmaceutically acceptable salt thereof of any one of embodiments 1 to 41, wherein Ring B is $R^4$-substituted or unsubstituted phenyl.

Embodiment 43: The compound or pharmaceutically acceptable salt thereof of any one of embodiments 1 to 42, wherein Ring B has formula:

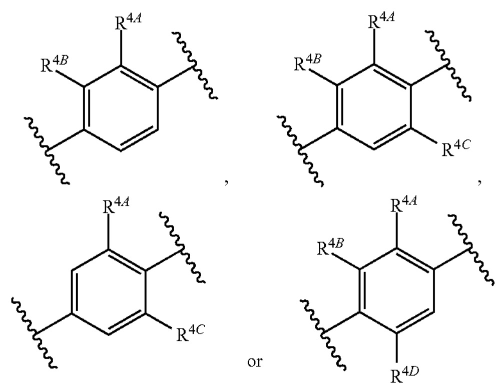

wherein $R^{4A}$, $R^{4B}$, $R^{4C}$, and $R^{4D}$ are each independently hydrogen, halogen, —CN, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-6}$ cycloalkyl, $R^{10}$-substituted or unsubstituted $C_{1-6}$ alkoxy, or $R^{10}$-substituted or unsubstituted $C_{1-6}$ haloalkoxy.

Embodiment 44: The compound or pharmaceutically acceptable salt thereof of embodiment 43, wherein $R^{4A}$, $R^{4B}$, $R^{4C}$, and $R^{4D}$ are each independently hydrogen, halogen, —CN, $R^{10}$-substituted or unsubstituted $C_{1-6}$ alkyl, or $R^{10}$-substituted or unsubstituted $C_{1-6}$ haloalkyl.

Embodiment 45: The compound or pharmaceutically acceptable salt thereof of embodiment 43 or 44, wherein $R^{4A}$, $R^{4B}$, $R^{4C}$, and $R^{4D}$ are each independently hydrogen or halogen.

Embodiment 46: The compound or pharmaceutically acceptable salt thereof of any one of embodiments 1 to 45, wherein $X^1$ is —N—.

Embodiment 47: The compound or pharmaceutically acceptable salt thereof of any one of embodiments 1 to 45, wherein $X^2$ is —N—.

Embodiment 48: The compound or pharmaceutically acceptable salt thereof of any one of embodiments 1 to 45, wherein $X^3$ is —N—.

Embodiment 49: The compound or pharmaceutically acceptable salt thereof of any one of embodiments 1 to 45, wherein the compound has the formula:

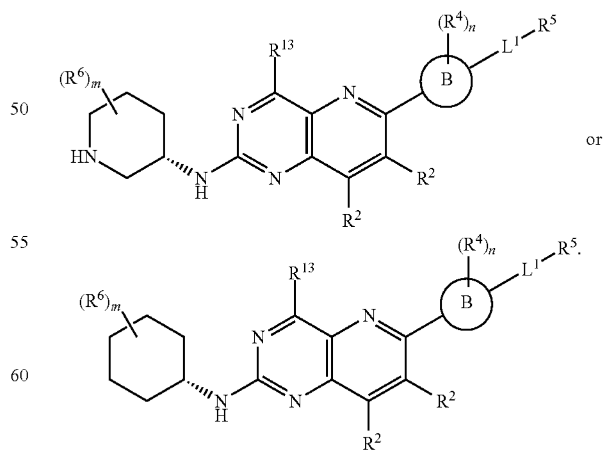

Embodiment 50: The compound or pharmaceutically acceptable salt thereof of any one of embodiments 1 to 45, wherein the compound has the formula:

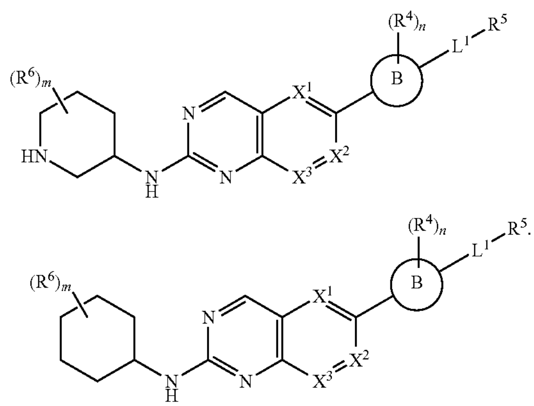

or

Embodiment 51: The compound or pharmaceutically acceptable salt thereof of any one of embodiments 1 to 50, wherein the compound has the formula:

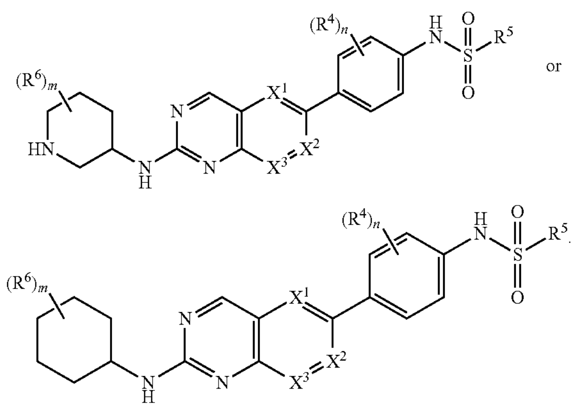

or

Embodiment 52: The compound or pharmaceutically acceptable salt thereof of any one of embodiments 1 to 51, wherein the compound has the formula:

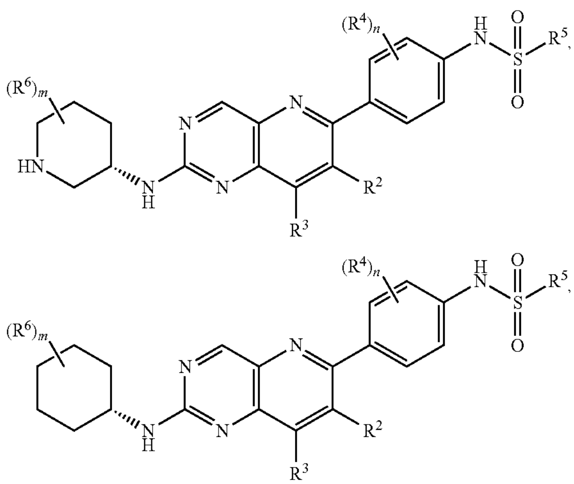

-continued

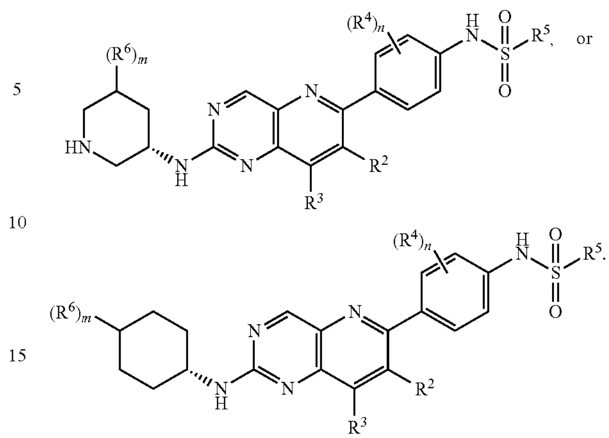

or

Embodiment 53: The compound or pharmaceutically acceptable salt thereof of any one of embodiments 1 to 50, wherein the compound has the formula:

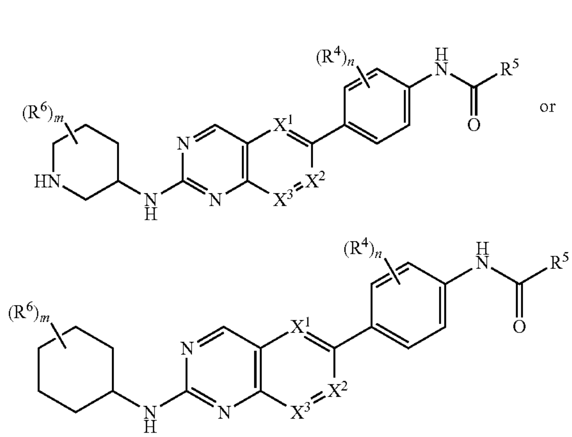

or

Embodiment 54: The compound or pharmaceutically acceptable salt thereof of any one of embodiments 1-50 or 53, wherein the compound has the formula:

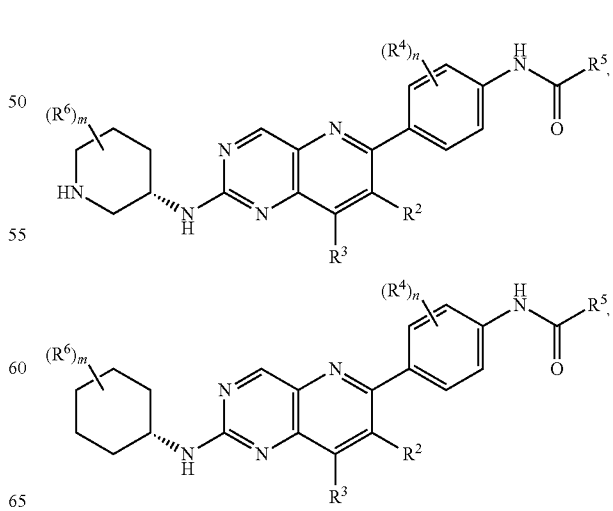

-continued

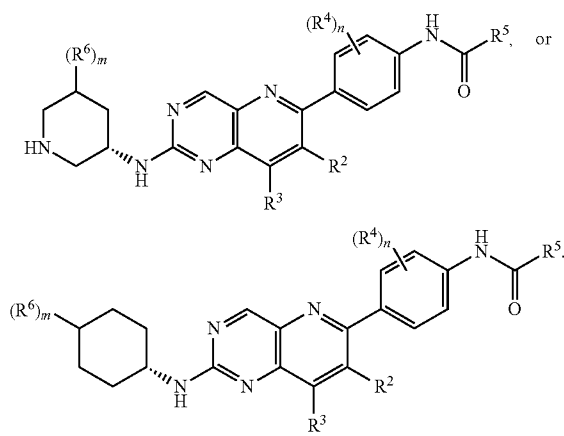

or

Embodiment 55: The compound or pharmaceutically acceptable salt thereof of any one of embodiments 1 to 50, wherein the compound has the formula:

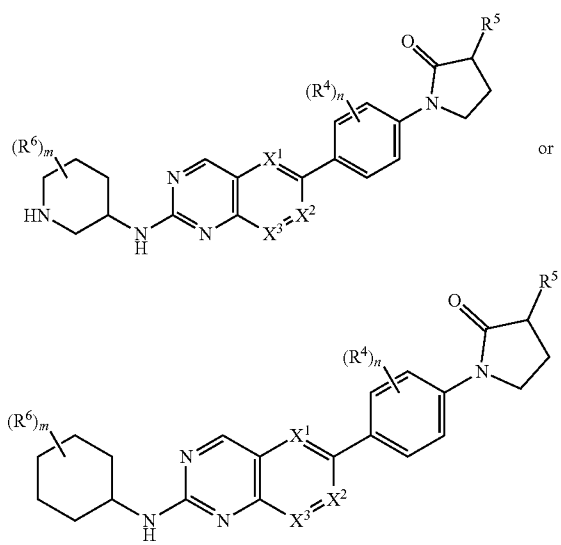

or

Embodiment 56: The compound or pharmaceutically acceptable salt thereof of any one of embodiments 1 to 50 or 55, wherein the compound has the formula:

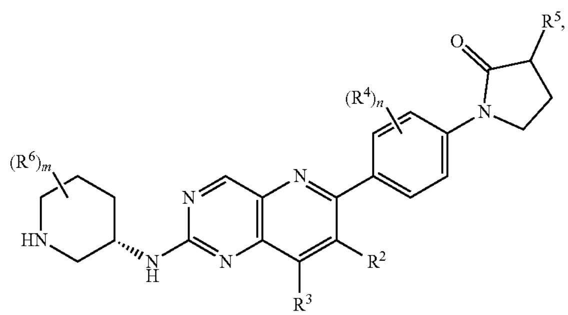

-continued

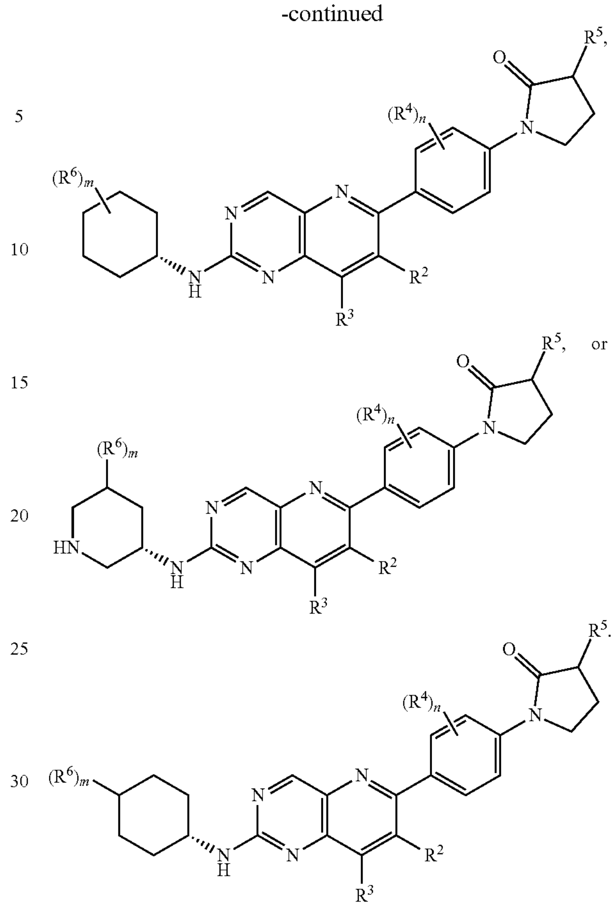

or

Embodiment 57: A compound or pharmaceutically acceptable salt thereof of Table 1.

Embodiment 58: A compound or pharmaceutically acceptable salt thereof of Table 2.

Embodiment 59: A pharmaceutical composition comprising a compound or pharmaceutically acceptable salt thereof of any one of embodiments 1 to 58 and one or more pharmaceutically acceptable excipients.

Embodiment 60: A method of treating an IRE1-related disease or disorder, the method comprising administering to the subject having an IRE1-related disease or disorder an effective amount of the compound of any of embodiments 1 to 58 or a pharmaceutically acceptable salt thereof, or the pharmaceutical composition of embodiment 59.

Embodiment 61: The method of embodiment 60, wherein the IRE1-related disease or disorder is cancer.

Embodiment 62: The method of embodiment 61, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 63: The method of embodiment 61, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 64: The method of embodiment 61, wherein the cancer is multiple myeloma.

Embodiment 65: The method of embodiment 61, wherein the cancer is a triple-negative breast cancer (TNBC).

Embodiment 66: The method of any one of embodiments 60 to 65, further comprising administering one or more additional therapeutic agent(s) selected from the group consisting of an anti-inflammatory agent, a corticosteroid, an immunomodulatory agent, anti-cancer agent, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, and an agent for treating immunodeficiency disorders.

Embodiment 67: The method of embodiment 66, wherein the additional therapeutic agent is a corticosteroid, a proteasome inhibitor, an immunomodulatory agent, an anti-CD38 antibody, an anti-VEGF-A antibody, an anti-PD-1 antibody, an anti-PD-L1 antibody, or an anti-interleukin-6 antibody, or a combination thereof.

Embodiment 68: The method of embodiment 67, wherein the corticosteroid comprises dexamethasone.

Embodiment 69: The method of embodiment 67, wherein proteasome inhibitor comprises carfilzomib, ixazomib or bortezomib.

Embodiment 70: The method of embodiment 67, wherein immunomodulatory agent comprises lenalidomide or pomalidomide.

Embodiment 71: The method of embodiment 67, wherein the anti-PD-L1 antibody comprises, avelumab, durvalumab, or atezolizumab.

Embodiment 72: The method of embodiment 67, wherein the anti-PD-1 antibody comprises pembrolizumab or nivolumab.

Embodiment 73: The method of any one of embodiments 60 to 72, further comprising administering radiotherapy.

Embodiment 74: Use of a compound according to any of embodiments 1 to 58 or a pharmaceutically acceptable salt thereof, or the pharmaceutical composition of embodiment 59, in the manufacture of a medicament for the treatment of an IRE1-related disease or disorder.

Embodiment 75: The use of embodiment 74 wherein the IRE1-related disease or disorder is cancer.

Embodiment 76: The use of embodiment 75, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 77: The use of embodiment 75, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 78: The use of embodiment 75, wherein the cancer is multiple myeloma.

Embodiment 79: The use of embodiment 75, wherein the cancer is a triple-negative breast cancer (TNBC).

Embodiment 80: A compound according to any of embodiments 1 to 58 or a pharmaceutically acceptable salt thereof, or the pharmaceutical composition of embodiment 59, for use in a method for treating an IRE1-related disease or disorder.

Embodiment 81: The compound for use of embodiment 80, wherein the IRE1-related disease or disorder is cancer.

Embodiment 82: The compound for use of embodiment 81, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 83: The compound for use of embodiment 81, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 84: The compound for use of embodiment 81, wherein the cancer is multiple myeloma.

Embodiment 85: The compound for use of embodiment 81, wherein the cancer is a triple-negative breast cancer (TNBC).

Embodiment 86: The compound for use of any one of embodiments 80 to 85, further comprising administering one or more additional therapeutic agent(s) selected from the group consisting of an anti-inflammatory agent, a corticosteroid, an immunomodulatory agent, anti-cancer agent, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, and an agent for treating immunodeficiency disorders.

Embodiment 87: The compound for use of embodiment 86, wherein the additional therapeutic agent is a corticosteroid, a proteasome inhibitor, an immunomodulatory agent, an anti-CD38 antibody, an anti-VEGF-A antibody, an anti-PD-1 antibody, an anti-PD-L1 antibody, or an anti-interleukin-6 antibody, or a combination thereof.

Embodiment 88: The compound for use of embodiment 87, wherein the corticosteroid comprises dexamethasone.

Embodiment 89: The compound for use of embodiment 87, wherein proteasome inhibitor comprises carfilzomib, ixazomib or bortezomib.

Embodiment 90: The compound for use of embodiment 87, wherein immunomodulatory agent comprises lenalidomide or pomalidomide.

Embodiment 91: The compound for use of embodiment 87, wherein the anti-PD-L1 antibody comprises, avelumab, durvalumab, or atezolizumab.

Embodiment 92: The compound for use of embodiment 87, wherein the anti-PD-1 antibody comprises pembrolizumab or nivolumab.

Embodiment 93: The compound for use of any one of embodiments 80 to 92, further comprising administering radiotherapy.

Embodiment 94: A method of inhibiting or killing a cancer cell expressing Ire1, the method comprising contacting the cancer cell expressing Ire1 with a compound or pharmaceutically acceptable salt thereof, of any one of embodiments 1 to 58 or a pharmaceutical composition of embodiment 59.

Embodiment 95: The method of embodiment 94, wherein the inhibiting or killing is performed in vivo.

Embodiment 96: The method of embodiment 94, wherein the cancer cell expressing Ire1 is in a human.

Embodiment 97: A method of modulating Ire1 activity, the method comprising contacting Ire1 with a compound or pharmaceutically acceptable salt thereof of any one of embodiments 1 to 58 or a pharmaceutical composition of embodiment 59.

Embodiment 98: A kit for treating a condition mediated by IRE1, comprising:

a) a pharmaceutical composition of embodiment 59; and b) instructions for use.

EXAMPLES

The following Examples are presented by way of illustration, not limitation.

Abbreviations

ACN: acetonitrile
DCM: dichloromethane
DMF: N,N-dimethylformamide
DMSO: dimethyl sulfoxide
EtOAc: ethyl acetate
EtOH: ethanol
h: hour
HCl: hydrochloric acid
HPLC: High-performance liquid chromatography
IPA: isopropyl acetate
LCMS: Liquid chromatography-mass spectrometry
$Na_2SO_4$: sodium sulfate
THF: tetrahydrofuran

Example 1: N-(2-Fluoro-4-(2-(((3S,5S)-5-fluoropiperidin-3-yl)amino)pyrido[3,2-d]pyrimidin-6-yl)phenyl)-1-phenylmethanesulfonamide (Compound 100)

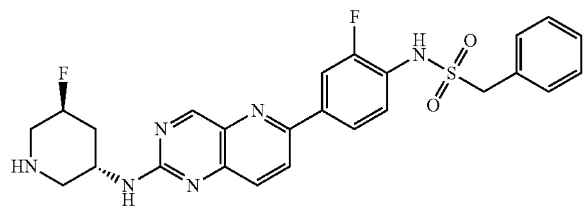 [SMILES: O=S(=O)(Cc1ccccc1)Nc1ccc(-c2ccc3nc(N[C@@H]4CNC[C@@H](F)C4)ncc3n2)cc1F]

Step 1: (3-Amino-6-chloro-2-pyridyl)methanol

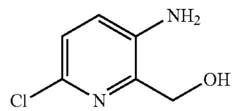

Under nitrogen, to a solution of 3-amino-6-chloropyridine-2-carboxylic acid (2.0 g, 11 mmol) in tetrahydrofuran (20 mL) was added borane (1 M in tetrahydrofuran, 100 mL) at 0° C. and stirred at room temperature for 24 h. The reaction was quenched with methyl alcohol and 2 M HCl. The reaction was adjusted to pH=8 with potassium carbonate solution. The resulting solution was extracted with dichloromethane, dried over anhydrous sodium sulfate and concentrated under vacuum. The residue was purified by silica flash chromatography eluting with ethyl acetate/petroleum ether (7:3) to afford the title compound (1.5 g, 81.6% yield) as a light green solid. LCMS (ESI): $[M+H]^+$=159.0.

Step 2: 3-Amino-6-chloro-pyridine-2-carbaldehyde

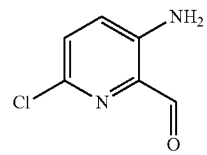

A mixture of (3-amino-6-chloro-2-pyridyl)methanol (1.4 g, 8.83 mmol) and manganese dioxide (2.3 g, 26 mmol) in 1,2-dichloroethane (150 mL) was stirred for 24 h at 80° C. After filtration, the filtrate was dried over anhydrous sodium sulfate and concentrated under vacuum. The residue was purified by silica flash chromatography eluting with ethyl acetate/petroleum ether (1/2) to afford the title compound (1.2 g, 86.8% yield) as a yellow solid. LCMS (ESI): $[M+H]^+$=157.0

Step 3: 6-Chloro-1H-pyrido[3,2-d]pyrimidin-2-one

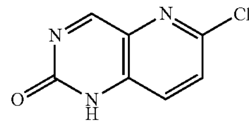 [SMILES: O=c1ncc2nc(Cl)ccc2[nH]1]

A mixture of 3-amino-6-chloro-pyridine-2-carbaldehyde (0.4 g, 2.57 mmol) and urea (2.32 g, 38.57 mmol) was stirred for 2 h at 135° C. The crude product was washed with water to afford the title compound (428 mg, 91.7% yield) as a yellow solid. LCMS (ESI): $[M+H]^+$=182.0.

Step 4: 2,6-Dichloropyrido[3,2-d]pyrimidine

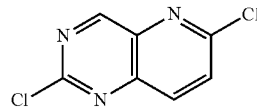 [SMILES: Clc1ccc2nc(Cl)ncc2n1]

A mixture of 6-chloro-1H-pyrido[3,2-d]pyrimidin-2-one (0.1 g, 0.55 mmol) in phosphorus oxychloride (10 mL) was stirred at 105° C. for 3 h. Most solvent was removed under vacuum, and the resulting mixture poured into ice water. The mixture was extracted with dichloromethane. The solvent was removed. The residue was purified by silica flash chromatography eluting with ethyl acetate/petroleum ether (30%) to afford the title compound (61 mg, 55.4% yield) as a pink solid. LCMS (ESI): $[M+H]^+$=200.0

Step 5: Mixture of 6-chloro-2-(methylthio)pyrido[3,2-d]pyrimidine & 2-chloro-6-(methylthio)pyrido[3,2-d]pyrimidine

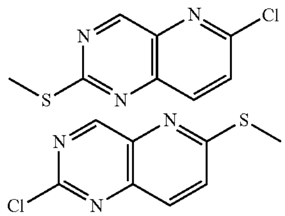

A solution of 2,6-dichloropyrido[3,2-d]pyrimidine (0.29 g, 1.45 mmol) in tetrahydrofuran (5 mL) was added sodium thiomethoxide (0.1 g, 1.45 mmol) at −10° C. and stirred for 2 h at the same temperature. The mixture was diluted with water, extracted with dichloromethane and concentrated under vacuum. The residue was purified by silica flash chromatography eluting with ethyl acetate/petroleum ether (30%) to afford the title compound (300 mg, 97.8% yield) as a white solid. LCMS (ESI): $[M+H]^+$=212.0

Step 6: 2-Fluoro-4-(2-methylsulfanylpyrido[3,2-d]pyrimidin-6-yl)aniline

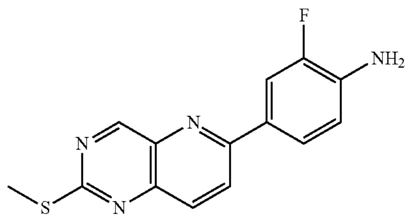 [SMILES: CSc1ncc2nc(-c3ccc(N)c(F)c3)ccc2n1]

Under nitrogen, a mixture of 6-chloro-2-(methylthio)pyrido[3,2-d]pyrimidine & 2-chloro-6-(methylthio)pyrido[3,2-d]pyrimidine (0.3 g, 1.42 mmol), 2-fluoro-4-(4,4,5,5-tetramethyl-1,3,2-dioxaborolan-2-yl)aniline (0.37 g, 1.56 mmol), 1,1'-bis(diphenylphosphino)ferrocene-palladium(II) dichloride dichloromethane complex (0.23 g, 0.28 mmol) and sodium carbonate (0.45 g, 4.25 mmol) in 1,4-dioxane (15 mL) and water (3 mL) was stirred for 2 h at 80° C. The reaction mixture was diluted with ethyl acetate, washed with water, dried over anhydrous sodium sulfate and concentrated under vacuum. The residue was purified by silica flash chromatography eluting with ethyl acetate/petroleum ether (18:82) to afford the title compound (100 mg, 24.6% yield) as a yellow solid. LCMS (ESI): $[M+H]^+$=287.1

Step 7: N-(2-Fluoro-4-(2-(methylthio)pyrido[3,2-d]pyrimidin-6-yl)phenyl)-1-phenylmethanesulfonamide

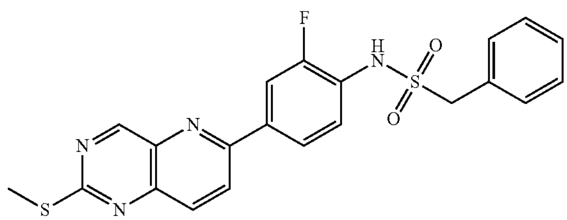 [SMILES: CSc1ncc2nc(-c3ccc(NS(=O)(=O)Cc4ccccc4)c(F)c3)ccc2n1]

A solution of 2-fluoro-4-(2-methylsulfanylpyrido[3,2-d]pyrimidin-6-yl)aniline (80 mg, 0.28 mmol) and alpha-toluenesulfonylchloride (80 mg, 0.42 mmol) in pyridine (2 mL) was stirred at room temperature for 2 h. The solvent was concentrated under vacuum. The residue was purified by silica flash chromatography eluting with ethyl acetate/petroleum ether (60%) to afford the title compound (63 mg, 51.2% yield) as a yellow solid. LCMS (ESI): $[M+H]^+$=441.1

Step 8: N-(2-Fluoro-4-(2-(methylsulfonyl)pyrido[3,2-d]pyrimidin-6-yl)phenyl)-1-phenylmethanesulfonamide

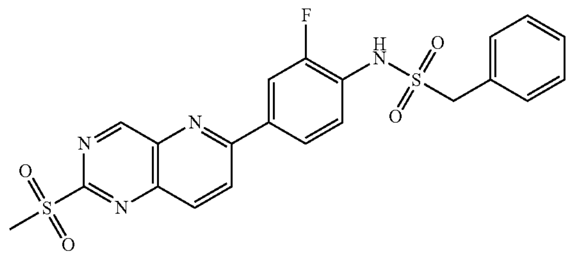 [SMILES: CS(=O)(=O)c1ncc2nc(-c3ccc(NS(=O)(=O)Cc4ccccc4)c(F)c3)ccc2n1]

To a mixture of N-(2-fluoro-4-(2-(methylthio)pyrido[3,2-d]pyrimidin-6-yl)phenyl)-1-phenylmethanesulfonamide (43 mg, 0.10 mmol) in dichloromethane (3 mL) was added 3-chloroperoxybenzoic acid (51 mg, 0.29 mmol) and stirred at rt for 1 h. The reaction was quenched with saturated sodium sulfite and extracted with ethyl acetate, washed with brine, dried over sodium sulfate. The solvent was removed under vacuum to afford the title compound (46 mg, 99.0% yield) LCMS (ESI): $[M+H]^+$=473.1.

Step 9: Benzyl (3S,5S)-3-fluoro-5-((6-(3-fluoro-4-((phenylmethyl)sulfonamido)phenyl)pyrido[3,2-d]pyrimidin-2-yl)amino)piperidine-1-carboxylate

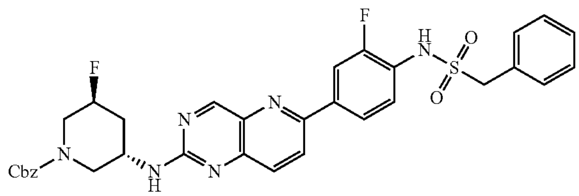 [SMILES: O=C(OCc1ccccc1)N1C[C@@H](F)C[C@H](Nc2ncc3nc(-c4ccc(NS(=O)(=O)Cc5ccccc5)c(F)c4)ccc3n2)C1]

Under nitrogen, a mixture of N-(2-fluoro-4-(2-(methylsulfonyl)pyrido[3,2-d]pyrimidin-6-yl)phenyl)-1-phenylmethanesulfonamide (46 mg, 0.10 mmol), benzyl (3S,5S)-3-amino-5-fluoro-piperidine-1-carboxylate (27 mg, 0.11 mmol), caesium fluoride (45 mg, 0.29 mmol) and N,N-diisopropylethylamine (38 mg, 0.29 mmol) in dimethyl sulfoxide (3 mL) was stirred at 80° C. for 2 h. The reaction mixture was diluted with ethyl acetate and washed with water. The solvent was removed under vacuum. The residue was purified by silica flash chromatography eluting with ethyl acetate/petroleum ether (60%) to afford the title compound (30 mg, 47.7% yield) as a yellow solid. LCMS (ESI): $[M+H]^+$=645.2

Step 9: N-(2-Fluoro-4-(2-(((3S,5S)-5-fluoropiperidin-3-yl)amino)pyrido[3,2-d]pyrimidin-6-yl)phenyl)-1-phenylmethanesulfonamide

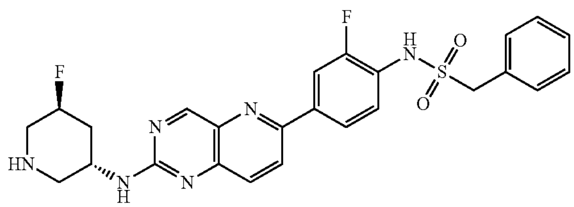 [SMILES: O=S(=O)(Cc1ccccc1)Nc1ccc(-c2ccc3nc(N[C@@H]4CNC[C@@H](F)C4)ncc3n2)cc1F]

To a solution of a solution of benzyl (3S,5S)-3-fluoro-5-((6-(3-fluoro-4-((phenylmethyl)sulfonamido)phenyl)pyrido[3,2-d]pyrimidin-2-yl)amino)piperidine-1-carboxylate (30 mg, 0.05 mmol) in dichloromethane (4 mL) was added 33% HBr in acetic acid (1 mL) and stirred for 1 h at room temperature. The solvent was concentrated under vacuum. The crude product was purified by Prep-HPLC to afford the title compound (7.2 mg, 30.3% yield) as a yellow solid.

Example 2: N-(2-Fluoro-4-(2-(((3S,5S)-5-fluoropiperidin-3-yl)amino)pyrido[3,4-d]pyrimidin-6-yl)phenyl)-1-phenylmethanesulfonamide (Compound 101)

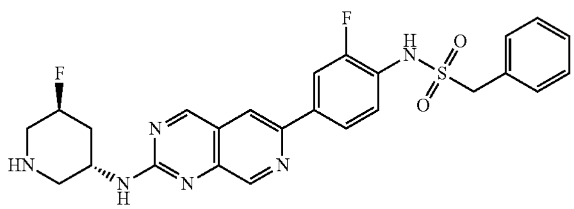 [SMILES: O=S(=O)(Cc1ccccc1)Nc1ccc(-c2cc3cnc(N[C@@H]4CNC[C@@H](F)C4)nc3cn2)cc1F]

Step 1: Methyl 2-chloro-5-((2,2,2-trichloroacetyl)carbamoylamino)pyridine-4-carboxylate

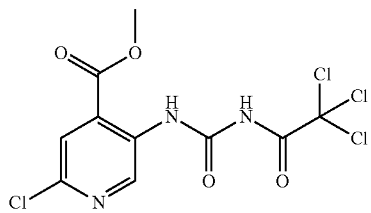 [SMILES: COC(=O)c1cc(Cl)ncc1NC(=O)NC(=O)C(Cl)(Cl)Cl]

A solution of methyl 5-amino-2-chloro-pyridine-4-carboxylate (1.0 g, 5.3 mmol) in tetrahydrofuran (30 mL) was added trichloroacetyl isocyanate (0.71 mL, 5.97 mmol). The solution was stirred at room temperature for 1.5 h. the solution was concentrated under vacuum and the residue was diluted with ether. The solid was collected by filtration to afford the title compound (1.9 g, 94.3% yield) as a white solid. LCMS (ESI) $[M+H]^+$=373.9.

Step 2: 6-Chloro-1H-pyrido[3,4-d]pyrimidine-2,4-dione

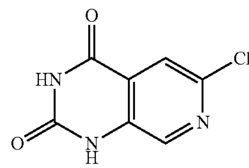 [SMILES: O=c1[nH]c(=O)c2cc(Cl)ncc2[nH]1]

Into the solution of methyl 2-chloro-5-((2,2,2-trichloroacetyl)carbamoylamino)pyridine-4-carboxylate (1.9 g, 5.07 mmol) in methyl alcohol (70 mL) was added 7 M ammonia in methanol (10 mL, 70 mmol). The mixture was stirred at room temperature for 4 h. The mixture was concentrated under vacuum. The solids were diluted with methanol. The mixture was stirred at 80° C. for 1.5 h. After most of solvent was removed, the mixture was cooled to room temperature. The solids were collected by filtration to afford the title compound (950 mg, 94.9% yield) as a white solid. $^1H$ NMR (300 MHz, DMSO-$d_6$) δ 11.72-11.52 (br s, 2H), 8.36 (s, 1H), 7.78 (s, 1H).

Step 3: 2,4,6-Trichloropyrido[3,4-d]pyrimidine

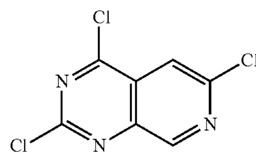 [SMILES: Clc1cc2c(Cl)nc(Cl)nc2cn1]

Into the mixture of 6-chloro-1H-pyrido[3,4-d]pyrimidine-2,4-dione (950 mg, 4.81 mmol) in N,N-diethylaniline (0.85 mL, 5.3 mmol) was added phosphorus oxychloride (6 mL, 65 mmol). The solution was stirred at 110° C. for 3 h. The solvent was removed under vacuum. The residue was diluted with dichloromethane and water. The mixture was extracted with dichloromethane and the organic layers were combined. The solvent was removed under vacuum. The residue was used directly into the next step.

Step 4: 2,6-Dichloropyrido[3,4-d]pyrimidine

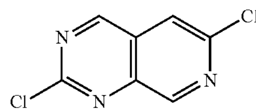 [SMILES: Clc1cc2cnc(Cl)nc2cn1]

Under nitrogen, into the mixture of 2,4,6-trichloropyrido[3,4-d]pyrimidine (1.1 g, 4.8 mmol) in tetrahydrofuran (20 mL) was added triphenylphosphine (1.27 g, 4.8 mmol), tri-n-butyltin hydride (1.5 ml, 5.6 mmol) and bis(triphenylphosphine)palladium(II) chloride (340 mg, 0.48 mmol). The mixture was stirred at rt for 1.5 h. The mixture was diluted with ethyl acetate and washed with sat. potassium fluoride solution. The solvent was removed under vacuum. The residue was purified by silica flash chromatography eluting with ethyl acetate/petroleum ether (15%) to afford the title compound (440 mg, 45.8% yield) as a red brown solid. $^1$H NMR (300 MHz, DMSO-$d_6$) δ 9.75 (s, 1H), 9.36 (s, 1H), 8.37 (s, 1H).

Step 5: Benzyl (3S,5S)-3-((6-chloropyrido[3,4-d]pyrimidin-2-yl)amino)-5-fluoropiperidine-1-carboxylate

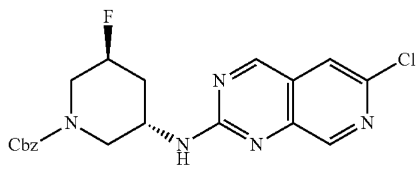 [SMILES: O=C(OCc1ccccc1)N1C[C@@H](F)C[C@H](Nc2ncc3cc(Cl)ncc3n2)C1]

Under nitrogen, into the solution of 2,6-dichloropyrido[3,4-d]pyrimidine (161 mg, 0.80 mmol) in ethanol (12 mL) was added benzyl (3S,5S)-3-amino-5-fluoro-piperidine-1-carboxylate hydrochloride (307 mg, 1.06 mmol) and N,N-diisopropylethylamine (0.46 mL, 2.78 mmol). The solution was stirred for 1 h at 100° C. with microwave. The solution was diluted with water and ethyl acetate. The solution was extracted with ethyl acetate. The solvent was removed under vacuum. The residue was purified by silica flash chromatography eluting with ethyl acetate/petroleum ether (60%) to afford the title compound (240 mg, 71.7% yield) as a yellow solid. LCMS (ESI): $[M+H]^+$=416.1.

Step 6: Benzyl (3S,5S)-3-((6-(4-amino-3-fluorophenyl)pyrido[3,4-d]pyrimidin-2-yl)amino)-5-fluoropiperidine-1-carboxylate

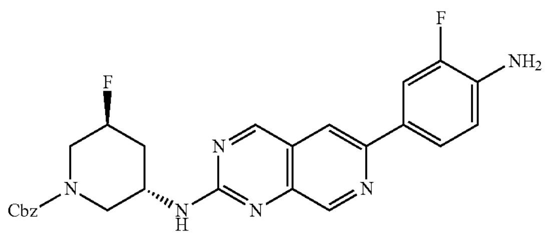 [SMILES: Nc1ccc(-c2cc3cnc(N[C@H]4C[C@H](F)CN(C(=O)OCc5ccccc5)C4)nc3cn2)cc1F]

Into the mixture of benzyl (3S,5S)-3-((6-chloropyrido[3,4-d]pyrimidin-2-yl)amino)-5-fluoropiperidine-1-carboxylate (240 mg, 0.58 mmol) and 4-amino-3-fluorophenylboronic acid pinacol ester (178 mg, 0.75 mmol) in 1,4-dioxane (6 mL) and water (1.2 mL) was added 1,1'-bis(diphenylphosphino)ferrocene-palladium(II)dichloride dichloromethane complex (48 mg, 0.06 mmol), sodium bicarbonate (146 mg, 1.7 mmol). The mixture was stirred at 90° C. for 1 h. The mixture was diluted with ethyl acetate, washed with water and brine. The solution was dried over anhydrous sodium sulfate and concentrated under vacuum. The residue was purified by silica flash chromatography eluting with ethyl acetate/petroleum ether (60%) to afford the title compound (180 mg, 63.6% yield) as a yellow solid. LCMS (ESI): $[M+H]^+$=491.2.

Step 7: Benzyl (3S,5S)-3-fluoro-5-((6-(3-fluoro-4-((phenylmethyl)sulfonamido)phenyl)pyrido[3,4-d]pyrimidin-2-yl)amino)piperidine-1-carboxylate

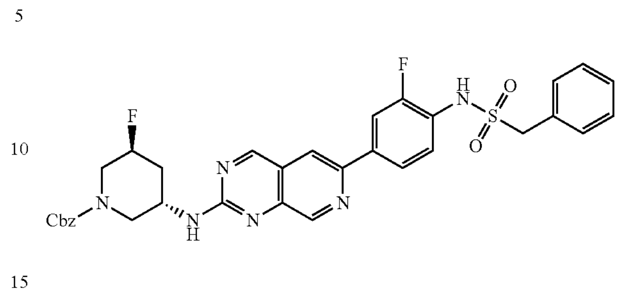

Into the solution of benzyl (3S,5S)-3-((6-(4-amino-3-fluorophenyl)pyrido[3,4-d]pyrimidin-2-yl)amino)-5-fluoropiperidine-1-carboxylate (93 mg, 0.19 mmol) in pyridine (1.2 mL) was added alpha-toluenesulfonylchloride (125 mg, 0.66 mmol). The solution was stirred at room temperature for 1 h. The reaction was diluted with dichloromethane and washed with water. The organic layer was dried over anhydrous sodium sulfate and concentrated under vacuum. The residue was purified by silica flash chromatography eluting with ethyl acetate/petroleum ether (60%) to afford the title compound (120 mg, 93.3% yield) as a yellow solid. LCMS (ESI): $[M+H]^+$=645.2.

Step 8: N-(2-Fluoro-4-(2-(((3S,5S)-5-fluoropiperidin-3-yl)amino)pyrido[3,4-d]pyrimidin-6-yl)phenyl)-1-phenylmethanesulfonamide (Compound 101)

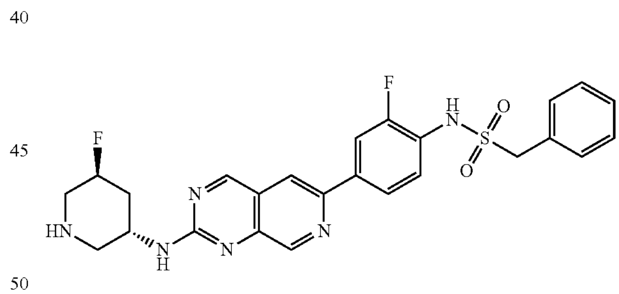

To the solution of benzyl (3S,5S)-3-fluoro-5-((6-(3-fluoro-4-((phenylmethyl)sulfonamido)phenyl)pyrido[3,4-d]pyrimidin-2-yl)amino)piperidine-1-carboxylate (120 mg, 0.18 mmol) in dichloromethane (5 mL) was added 33% HBr in acetic acid (4 mL). The mixture was stirred at room temperature for 0.5 h. The mixture was concentrated under vacuum and purified with Prep-HPLC to afford the title compound (27.5 mg, 30.5% yield) as a yellow solid.

Example 3: N-(4-(7-((1,1-Difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide & N-(4-(7-((1,1-difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide (Compound 102) & (Compound 103)

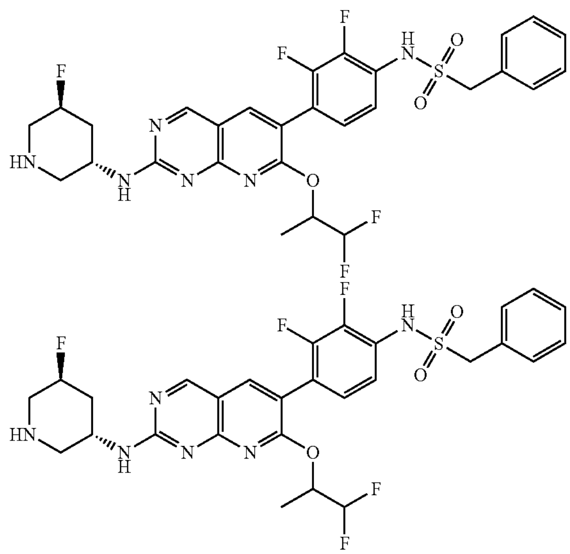

N-(4-(7-((1,1-Difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide
N-(4-(7-((1,1-Difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide

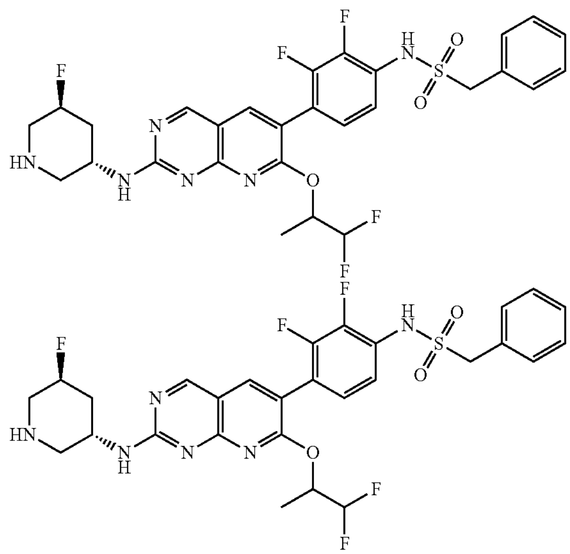

A solution of benzyl (3S,5S)-3-((6-(2,3-difluoro-4-((phenylmethyl)sulfonamido) phenyl)-8-(1,1-difluoropropan-2-yl)-7-oxo-7,8-dihydropyrido[2,3-d]pyrimidin-2-yl)amino)-5-fluoropiperidine-1-carboxylate & benzyl (3S,5S)-3-((6-(2,3-difluoro-4-((phenylmethyl) sulfonamido)phenyl)-7-((1,1-difluoropropan-2-yl)oxy)pyrido[2,3-d]pyrimidin-2-yl) amino)-5-fluoropiperidine-1-carboxylate (160 mg, 0.21 mmol) in trifluoroacetic acid (10 mL) was stirred for 16 h at 50° C. The solvent was removed under vacuum. The residue was purified by Prep-HPLC and Chiral HPLC to afford the title compound.

N-(4-(7-((1,1-Difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide (6.5 mg, 4.9% yield) as a white solid. (rt=4.179 min, chiralpak IG-3, 0.46×5 cm; 3 μm, (Hexanes:DCM=3:1)(0.1% DEA):EtOH=85:15, 1.0 ml/min).

N-(4-(7-((1,1-Difluoropropan-2-yl)oxy)-2-(((3S,5S)-5-fluoropiperidin-3-yl)amino)pyrido[2,3-d]pyrimidin-6-yl)-2,3-difluorophenyl)-1-phenylmethanesulfonamide (6.4 mg, 4.9% yield) as a white solid. (rt=5.029 min, chiralpak IG-3, 0.46×5 cm; 3 μm, (Hexanes:DCM=3:1)(0.1% DEA):EtOH=85:15, 1.0 ml/min).

Example 4: 1-Phenyl-N-(2,3,6-trifluoro-4-(2-(((3S,5S)-5-fluoropiperidin-3-yl)amino)-7-((tetrahydrofuran-3-yl)oxy)pyrido[2,3-d]pyrimidin-6-yl)phenyl) methanesulfonamide & 1-phenyl-N-(2,3,6-trifluoro-4-(2-(((3S,5S)-5-fluoropiperidin-3-yl)amino)-7-((tetrahydrofuran-3-yl)oxy)pyrido[2,3-d]pyrimidin-6-yl)phenyl)methanesulfonamide (Compound 104) & (Compound 105)

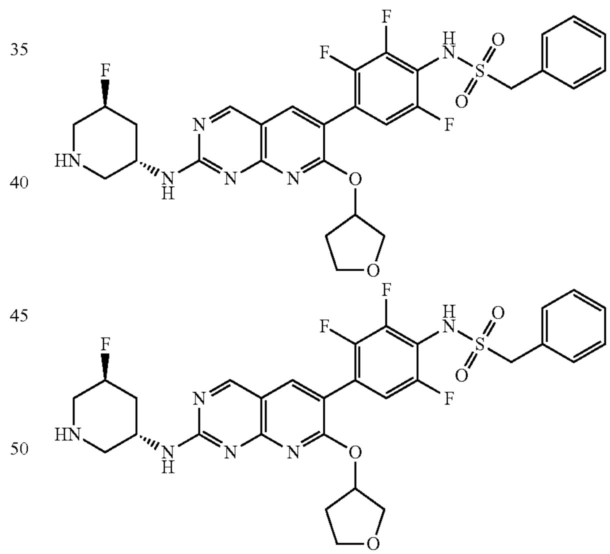

The title compound was prepared according to Example 3. This provides the title compound.

1-Phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide (12.4 mg, 12.4% yield) as white solid. (rt=3.566 min, chiral Cellulose-SB, 0.46*10 cm; 3 μm, MTBE (0.1% DEA):MeOH=80:20, 1.0 mL/min).

1-Phenyl-N-(2,3,6-trifluoro-4-(2-(((3S,5S)-5-fluoropiperidin-3-yl)amino)-7-oxo-8-(tetrahydrofuran-3-yl)-7,8-dihydropyrido[2,3-d]pyrimidin-6-yl)phenyl)methanesulfonamide (13.0 mg, 13.0% yield as white solid. (rt=4.258 min, chiral Cellulose-SB, 0.46*10 cm; 3 μm, MTBE (0.1% DEA):MeOH=80:20, 1.0 mL/min).

Example 5: N-(2-Fluoro-4-(2-(((3S,5S)-5-fluoropiperidin-3-yl)amino)-8-methylpyrido[3,2-d]pyrimidin-6-yl)phenyl)-1-phenylmethanesulfonamide (Compound 106)

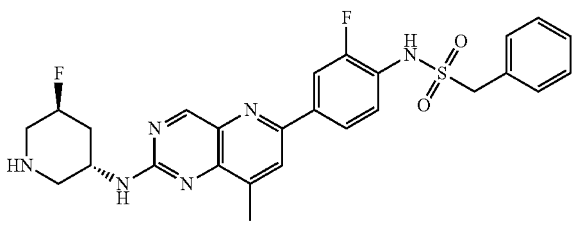 [SMILES: Cc1cc(-c2ccc(NS(=O)(=O)Cc3ccccc3)c(F)c2)nc2cnc(N[C@@H]3CNC[C@@H](F)C3)nc12]

Step 1: 6-Chloro-2-iodo-4-methylpyridin-3-amine

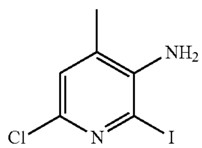

To a solution of 3-amino-6-chloro-4-picoline (5.0 g, 35 mmol) in N,N-dimethylformamide (70 mL) was added N-iodosuccinimide (8.7 g, 38 mmol) and stirred for 16 h at rt. The reaction was quenched with saturated sodium bicarbonate and extracted with ethyl acetate. The organic layer was washed with brine and the organic layers were combined. The solvent was removed under vacuum. The residue was purified by silica flash chromatography eluting with ethyl acetate/petroleum ether (30%) to afford the tittle compound (5.8 g, 61.6% yield) as a brown solid. LCMS (ESI): $[M+H]^+$=268.9.

Step 2: Methyl 3-amino-6-chloro-4-methylpicolinate

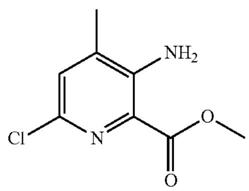

Under carbon monoxide, a mixture of 6-chloro-2-iodo-4-methyl-pyridin-3-amine (5.6 g, 21 mmol), triethylamine (6.44 g, 64 mmol) and 1,1'-bis(diphenylphosphino)ferrocene-palladium(II)dichloride dichloromethane complex (3.36 g, 4.1 mmol) in methyl alcohol (60 mL) was stirred for 1 h at 40° C. The solvent was concentrated under vacuum. The residue was purified by silica flash chromatography eluting with ethyl acetate/petroleum ether (30%) to afford the title compound (3.9 g, 93.2% yield) as a yellow solid. LCMS (ESI): [M+H]+=201.0

Step 3: (3-Amino-6-chloro-4-methylpyridin-2-yl)methanol

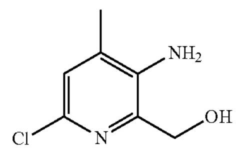

A solution of methyl 3-amino-6-chloro-4-methyl-pyridine-2-carboxylate (3.8 g, 19 mmol) in methyl alcohol (50 mL) was added sodium borohydride (4.5 g, 119 mmol) and stirred for 6 h at rt. The reaction was quenched with water. The solvent was concentrated under vacuum. The residue was purified by silica flash chromatography eluting with methyl alcohol/dichloromethane (5%) to afford the title compound (3.2 g, 97.9% yield) as a yellow solid. LCMS (ESI): [M+H]+=173.0

Step 4: 3-Amino-6-chloro-4-methylpicolinaldehyde

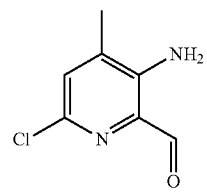

A mixture of (3-amino-6-chloro-4-methyl-2-pyridyl) methanol (3.2 g, 19 mmol) and manganese dioxide (4.8 g, 56 mmol) in 1,2-dichloroethane (50 mL) was stirred for 2 h at 80° C. After filtration, the filtrate was concentrated under reduced pressure to afford the title compound (2.8 g, 88% yield) as a yellow solid. LCMS (ESI): [M+H]+=171.0

Step 5: 6-Chloro-8-methylpyrido[3,2-d]pyrimidin-2 (11H)-one

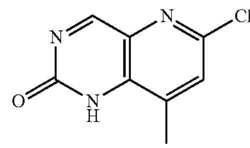

A mixture of 3-amino-6-chloro-4-methyl-pyridine-2-carbaldehyde (2.1 g, 12 mmol) and urea (52 g, 866 mmol) was stirred for 9 at 140° C. h. Then the reaction was quenched with water. After filtration, the solids were collected and washed with water to afford the title compound (1.8 g). The crude product would be directly used in the next step without further purification. LCMS (ESI): [M+H]+=196.0

Step 6: 2,6-Dichloro-8-methylpyrido[3,2-d]pyrimidine

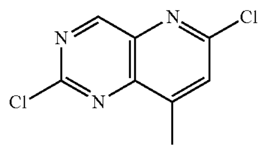

A mixture of 6-chloro-8-methyl-1H-pyrido[3,2-d]pyrimidin-2-one (1.8 g, 9.2 mmol) in phosphorus oxychloride (40 mL) was stirred for 16 h at 105° C. The solvent was concentrated under vacuum. The residue was purified by silica flash chromatography eluting with ethyl acetate/petroleum ether (10%) to afford the title compound (600 mg, 30.5% yield) as a white solid. LCMS (ESI): $[M+H]^+$=214.0.

Step 7: Benzyl (3S,5S)-3-((6-chloro-8-methylpyrido[3,2-d]pyrimidin-2-yl)amino)-5-fluoropiperidine-1-carboxylate

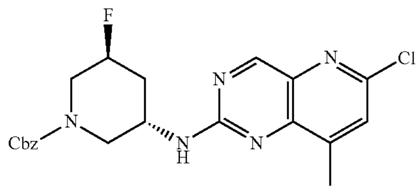 [SMILES: Cc1cc(Cl)nc2cnc(N[C@H]3C[C@H](F)CN(C(=O)OCc4ccccc4)C3)nc12]

Under nitrogen, a solution of 2,6-dichloro-8-methylpyrido[3,2-d]pyrimidine (0.2 g, 0.93 mmol), benzyl (3S,5S)-3-amino-5-fluoro-piperidine-1-carboxylate (0.26 g, 1.03 mmol) and N,N-diisopropylethylamine (0.4 g, 3.1 mmol) in ethanol (10 mL) was stirred for 6 h at 100° C. by microwave. The solvent was concentrated under vacuum. The residue was purified by silica flash chromatography eluting with ethyl acetate/petroleum ether (40%) to afford the title compound (252 mg, 62.7% yield) as a yellow solid. LCMS (ESI): $[M+H]^+$=430.1.

Step 8: Benzyl (3S,5S)-3-((6-(4-amino-3-fluorophenyl)-8-methylpyrido[3,2-d]pyrimidin-2-yl)amino)-5-fluoropiperidine-1-carboxylate

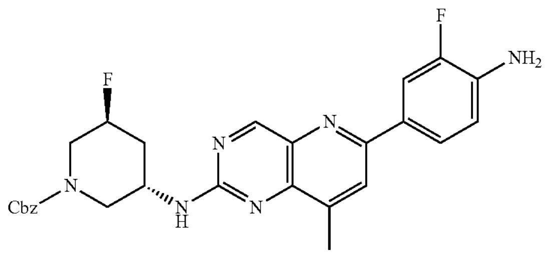 [SMILES: Cc1cc(-c2ccc(N)c(F)c2)nc2cnc(N[C@H]3C[C@H](F)CN(C(=O)OCc4ccccc4)C3)nc12]

Under nitrogen, a mixture of benzyl (3S,5S)-3-((6-chloro-8-methylpyrido[3,2-d]pyrimidin-2-yl)amino)-5-fluoropiperidine-1-carboxylate (0.23 g, 0.54 mmol), 4-amino-3-fluorophenylboronic acid pinacol ester (0.14 g, 0.59 mmol), 1,1'-bis(diphenylphosphino)ferrocene-palladium(II)dichloride dichloromethane complex (0.08 g, 0.11 mmol) and sodium carbonate (0.17 g, 1.6 mmol) in 1,4-dioxane (6 mL) and water (1 mL) was stirred for 2 h at 90° C. The solvent was concentrated under vacuum. The residue was purified by silica flash chromatography eluting with ethyl acetate/petroleum ether (70%) to afford the title compound (205 mg, 75.9% yield) as a yellow solid. LCMS (ESI): $[M+H]^+$=505.2.

Step 9: Benzyl (3S,5S)-3-fluoro-5-((6-(3-fluoro-4-((phenylmethyl)sulfonamido)phenyl)-8-methylpyrido[3,2-d]pyrimidin-2-yl)amino)piperidine-1-carboxylate

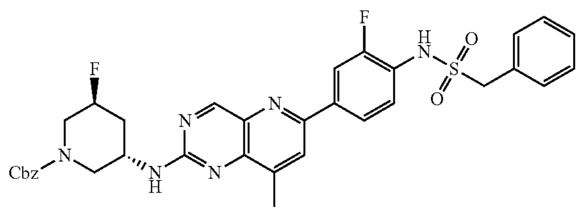 [SMILES: Cc1cc(-c2ccc(NS(=O)(=O)Cc3ccccc3)c(F)c2)nc2cnc(N[C@H]3C[C@H](F)CN(C(=O)OCc4ccccc4)C3)nc12]

To a solution of benzyl (3S,5S)-3-((6-(4-amino-3-fluorophenyl)-8-methylpyrido[3,2-d]pyrimidin-2-yl)amino)-5-fluoropiperidine-1-carboxylate (0.18 g, 0.36 mmol) in pyridine (2 mL) was added alpha-toluenesulfonylchloride (0.1 g, 0.54 mmol) and stirred for 1 h at rt. The solvent was removed under vacuum. The residue was purified by silica flash chromatography eluting with ethyl acetate/petroleum ether (55%) to afford the title compound (223 mg, 94.9% yield) as a yellow solid. LCMS (ESI): $[M+H]^+$=659.2.

Step 10: N-(2-Fluoro-4-(2-(((3S,5S)-5-fluoropiperidin-3-yl)amino)-8-methylpyrido[3,2-d]pyrimidin-6-yl)phenyl)-1-phenylmethanesulfonamide

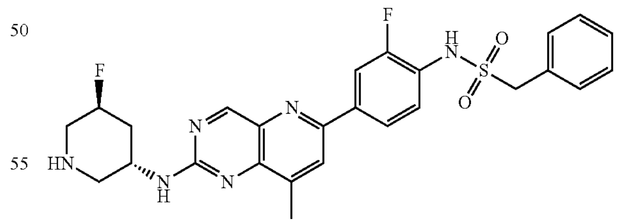

To a solution of benzyl (3S,5S)-3-fluoro-5-((6-(3-fluoro-4-((phenylmethyl)sulfonamido)phenyl)-8-methylpyrido[3,2-d]pyrimidin-2-yl)amino)piperidine-1-carboxylate (223 mg, 0.34 mmol) in dichloromethane (6 mL) was added 33% HBr in acetic acid (1.5 mL) and stirred for 1 h at rt. The solvent was concentrated under vacuum. The residue was purified by Prep-HPLC to afford the title compound (33.1 mg, 18.6% yield) as a yellow solid.

Example 6: N-(4-(2-(((1r,4r)-4-(Dimethylamino) cyclohexyl)amino)-8-methylpyrido[3,2-d]pyrimidin-6-yl)-2-fluorophenyl)-3,3,3-trifluoropropane-1-sulfonamide (Compound 107)

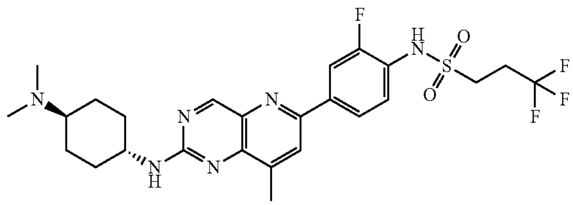 [SMILES: Cc1cc(-c2ccc(NS(=O)(=O)CCC(F)(F)F)c(F)c2)nc2cnc(N[C@H]3CC[C@H](N(C)C)CC3)nc12]

The title compound was prepared according to Example 5. This provides the title compound (29.5 mg, 18.6% yield) as a white solid.

Example 7: N-(2,6-Difluoro-4-(2-(((3S,5S)-5-fluoropiperidin-3-yl)amino)-8-methylpyrido[3,2-d]pyrimidin-6-yl)phenyl)-1-phenylmethanesulfonamide (Compound 108)

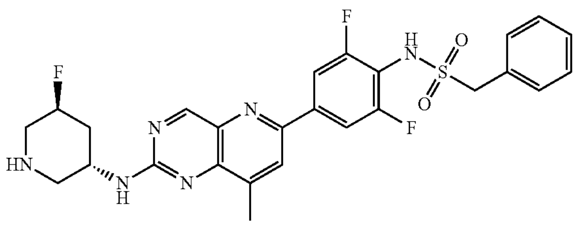 [SMILES: Cc1cc(-c2cc(F)c(NS(=O)(=O)Cc3ccccc3)c(F)c2)nc2cnc(N[C@@H]3CNC[C@@H](F)C3)nc12]

The title compound was prepared according to Example 5. This provides the title compound (52.7 mg, 32.9% yield) as a white solid.

Example 8: N-(2-Fluoro-4-(2-(((3S,5S)-5-fluoropiperidin-3-yl)amino)pyrido[2,3-d]pyrimidin-6-yl)phenyl)-1-phenylmethanesulfonamide (Compound 109)

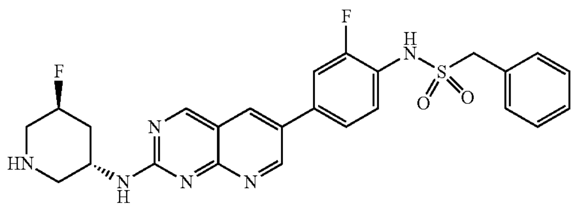 [SMILES: O=S(=O)(Cc1ccccc1)Nc1ccc(-c2cnc3nc(N[C@@H]4CNC[C@@H](F)C4)ncc3c2)cc1F]

Step 1: 6-Bromo-2-chloropyrido[2,3-d]pyrimidine

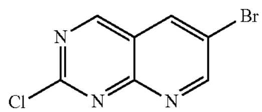 [SMILES: Clc1ncc2cc(Br)cnc2n1]

A solution of 6-bromopyrido[2,3-d]pyrimidin-2-ol (1.10 g, 4.87 mmol) and N,N-diisopropylethylamine (2.15 mL, 12.34 mmol), in $POCl_3$ (20.0 mL, 214 mmol), was heated for 5 h at 125° C. Most of the phosphoryl trichloride was then evaporated under reduced pressure. Ice water was added to the residue and the precipitate was filtered to provide a brown solid that was purified by flash chromatography through silica gel (15% $EtOAc/CH_2Cl_2$) to provide the title compound (242 mg, 20% yield). LCMS (ESI) $[M+H]^+$=243.9, 246.0.

Step 2: (3S,5S)-tert-Butyl 3-((6-bromopyrido[2,3-d]pyrimidin-2-yl)amino)-5-fluoropiperidine-1-carboxylate

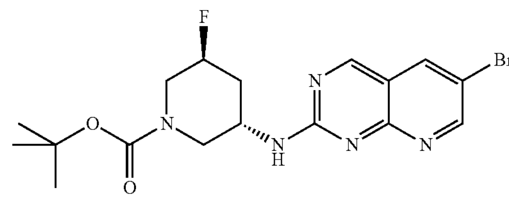

Triethylamine (0.14 mL, 1.04 mmol) was added to a solution of tert-butyl (3S,5S)-3-amino-5-fluoro-piperidine-1-carboxylate (112 mg, 0.51 mmol) and 6-bromo-2-chloropyrido[2,3-d]pyrimidine (100 mg, 0.41 mmol), in DMSO (3 mL). The resulting solution was stirred 2 h at 100° C. The reaction mixture was diluted with EtOAc, washed twice with $H_2O$, then twice with brine, dried over anhydrous $MgSO_4$, filtered and concentrated under reduced pressure. The crude material thus obtained was purified by flash chromatography through silica gel (0-100% EtOAc/heptanes) to provide the title compound (92 mg, 53% yield). LCMS (ESI) $[M+H]^+$=425.9, 427.8.

Step 3: (3S,5S)-tert-Butyl 3-((6-(4-amino-3-fluorophenyl)pyrido[2,3-d]pyrimidin-2-yl)amino)-5-fluoropiperidine-1-carboxylate

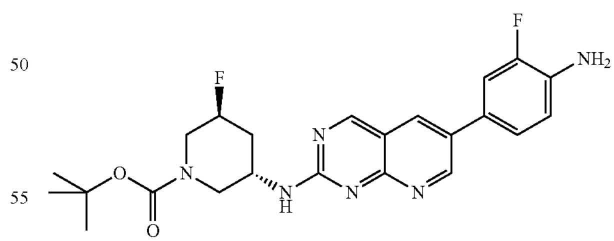

Prepared according to Example 14 (Compound 115) step 2 using (3S,5S)-tert-butyl 3-((6-bromopyrido[2,3-d]pyrimidin-2-yl)amino)-5-fluoropiperidine-1-carboxylate (90 mg, 0.21 mmol), 2-fluoro-4-(4,4,5,5-tetramethyl-1,3,2-dioxaborolan-2-yl)aniline (100 mg, 0.42 mmol), sodium carbonate (45 mg, 0.42 mmol) and tri-o-tolylphosphine (27 mg, 0.09 mmol) and palladium acetate (12 mg, 0.05 mmol) to provide the title compound (110 mg, 114% yield). LCMS (ESI) $[M+H]^+$=457.0.

Step 4: (3S,5S)-tert-Butyl 3-fluoro-5-((6-(3-fluoro-4-(phenylmethylsulfonamido)phenyl)pyrido[2,3-d]pyrimidin-2-yl)amino)piperidine-1-carboxylate

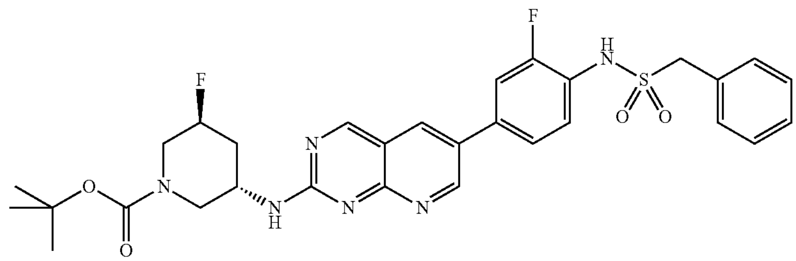 [SMILES: CC(C)(C)OC(=O)N1C[C@@H](F)C[C@H](Nc2ncc3cc(-c4ccc(NS(=O)(=O)Cc5ccccc5)c(F)c4)cnc3n2)C1]

Prepared according to Example 34 (Compound 135) step 1 using (3S,5S)-tert-butyl 3-((6-(4-amino-3-fluorophenyl)pyrido[2,3-d]pyrimidin-2-yl)amino)-5-fluoropiperidine-1-carboxylate (52 mg, 0.11 mmol) and phenylmethanesulfonyl chloride (29 mg, 0.15 mmol) to provide the title compound (55 mg, 79% yield). LCMS (ESI) $[M+H]^+$=611.2.

Step 5: N-(2-Fluoro-4-(2-(((3S,5S)-5-fluoropiperidin-3-yl)amino)pyrido[2,3-d]pyrimidin-6-yl)phenyl)-1-phenylmethanesulfonamide

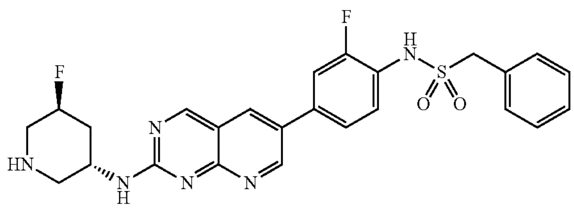 [SMILES: O=S(=O)(Cc1ccccc1)Nc1ccc(-c2cnc3nc(N[C@@H]4CNC[C@@H](F)C4)ncc3c2)cc1F]

To a solution of (3S,5S)-tert-butyl 3-fluoro-5-((6-(3-fluoro-4-(phenylmethylsulfonamido)phenyl)pyrido[2,3-d]pyrimidin-2-yl)amino)piperidine-1-carboxylate (55 mg, 0.09 mmol) in 1,4-dioxane (1 mL) was added 4M HCl in dioxane (1.0 mL, 4.0 mmol) and the mixture was stirred at rt. After 2 h, the solvent was evaporated under reduced pressure. The residue thus obtained was diluted with a $NaHCO_3$ saturated aqueous solution, and extracted four times with EtOAc. The organic extracts were combined and concentrated under reduced pressure. The crude material was purified by C18 reverse phase flash chromatography (10-50% MeCN/10 mM aqueous ammonium bicarbonate, pH=10) to provide 26 mg (57% yield) of the title compound.

Example 9: 3,3,3-Trifluoro-N-(2-fluoro-4-(2-(((3S,5S)-5-fluoropiperidin-3-yl)amino)-8-methylpyrido[3,2-d]pyrimidin-6-yl)phenyl)propane-1-sulfonamide (Compound 110)

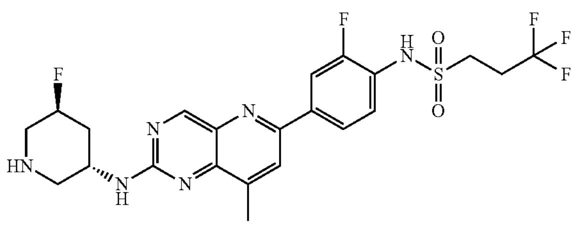 [SMILES: Cc1cc(-c2ccc(NS(=O)(=O)CCC(F)(F)F)c(F)c2)nc2cnc(N[C@@H]3CNC[C@@H](F)C3)nc12]

Step 1: (3S,5S)-tert-Butyl 3-((6-chloro-8-methylpyrido[3,2-d]pyrimidin-2-yl)amino)-5-fluoropiperidine-1-carboxylate

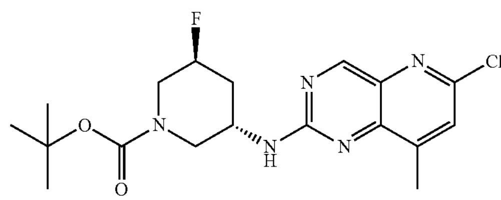 [SMILES: Cc1cc(Cl)nc2cnc(N[C@H]3C[C@H](F)CN(C(=O)OC(C)(C)C)C3)nc12]

tert-Butyl (3S,5S)-3-amino-5-fluoro-piperidine-1-carboxylate (122.4 mg, 0.56 mmol) and 2,6-dichloro-8-methyl-pyrido[3,2-d]pyrimidine (100 mg, 0.47 mmol) were combined in DMSO (1 mL) in a microwave vial. N,N-Diisopropylethylamine (0.12 mL, 0.70 mmol) was added and the vial was sealed and heated at 60° C. overnight. After 16 h, the mixture was diluted with EtOAc (50 mL) and washed with saturated $NaHCO_3$ (10 mL), then with $H_2O$ (3×10 mL), dried ($Na_2SO_4$), filtered through a 1 cm×1 cm Si plug topped with Celite and concentrated to provide the title compound (189 mg, 102% yield) as a yellow oil. LCMS (ESI) $[M+H]^+$=395.9.

Step 2: (3S,5S)-tert-Butyl 3-((6-(4-amino-3-fluorophenyl)-8-methylpyrido[3,2-d]pyrimidin-2-yl)amino)-5-fluoropiperidine-1-carboxylate

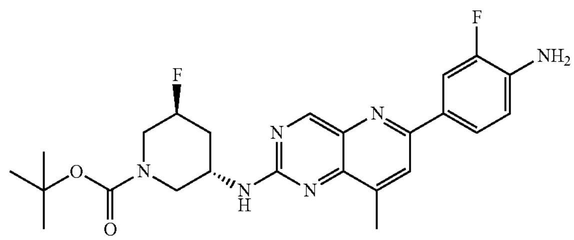 [SMILES: Cc1cc(-c2ccc(N)c(F)c2)nc2cnc(N[C@H]3C[C@H](F)CN(C(=O)OC(C)(C)C)C3)nc12]

A flask was charged with tert-butyl (3S,5S)-3-[(6-chloro-8-methyl-pyrido[3,2-d]pyrimidin-2-yl)amino]-5-fluoro-piperidine-1-carboxylate (185 mg, 0.47 mmol), DME (4 mL) and $H_2O$ (1 mL). To this mixture was then added 2-fluoro-4-(4,4,5,5-tetramethyl-1,3,2-dioxaborolan-2-yl)aniline (166 mg, 0.70 mmol), palladium acetate (10 mg, 0.05 mmol), tri-o-tolylphosphine (28 mg, 0.09 mmol) and sodium carbonate (99 mg, 0.93 mmol). The flask was capped and $N_2$ purged for 5 min then heated at 85° C. in an oil bath overnight. After 16 h, the mixture was diluted with EtOAc (40 mL) and $Na_2SO_4$ was added to remove $H_2O$ and the mixture filtered through a 1"×1" Si plug topped with Celite using EtOAc (2×20 mL) to wash/elute and concentrated to provide the title compound (267 mg, 121% yield) which was used in the next step without further purification. LCMS (ESI) $[M+H]^+$=471.1.

Step 3: (3S,5S)-tert-Butyl 3-fluoro-5-((6-(3-fluoro-4-(3,3,3-trifluoropropylsulfonamido)phenyl)-8-methylpyrido[3,2-d]pyrimidin-2-yl)amino)piperidine-1-carboxylate

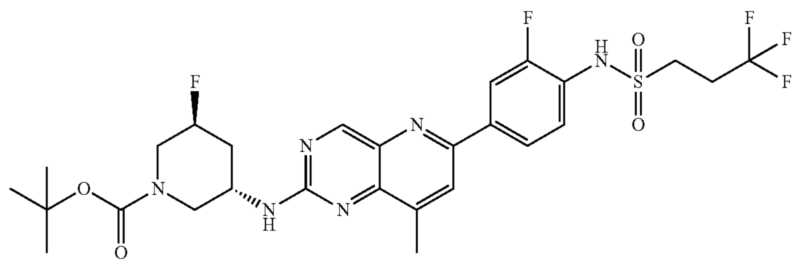 [SMILES: Cc1cc(-c2ccc(NS(=O)(=O)CCC(F)(F)F)c(F)c2)nc2cnc(N[C@H]3C[C@H](F)CN(C(=O)OC(C)(C)C)C3)nc12]

To a solution of tert-butyl (3S,5S)-3-[[6-(4-amino-3-fluoro-phenyl)-8-methyl-pyrido[3,2-d]pyrimidin-2-yl]amino]-5-fluoro-piperidine-1-carboxylate (100 mg, 0.21 mmol) in a mixture of $CH_2Cl_2$ (2.5 mL) and pyridine (0.5 mL) was added a solution of 3,3,3-trifluoropropane-1-sulfonyl chloride (147 mg, 0.45 mmol) in DCM (0.5 mL) and the mixture stirred at rt. After 20 h, the mixture was diluted with MeOH (10 mL) and volatiles removed under reduced pressure (repeated twice). The crude material was purified by flash chromatography through silica gel (0-100% EtOAc/heptanes) to provide the title product (64 mg, 48% yield). LCMS (ESI) $[M+H]^+$=631.0.

Step 4: 3,3,3-Trifluoro-N-(2-fluoro-4-(2-(((3S,5S)-5-fluoropiperidin-3-yl)amino)-8-methylpyrido[3,2-d]pyrimidin-6-yl)phenyl)propane-1-sulfonamide

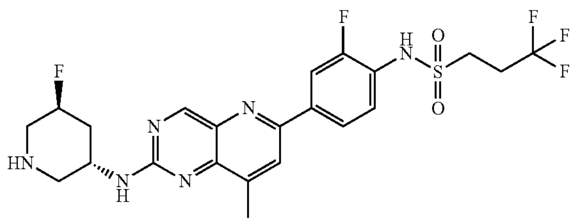 [SMILES: Cc1cc(-c2ccc(NS(=O)(=O)CCC(F)(F)F)c(F)c2)nc2cnc(N[C@@H]3CNC[C@@H](F)C3)nc12]

To tert-Butyl (3S,5S)-3-fluoro-5-[[6-[3-fluoro-4-(3,3,3-trifluoropropylsulfonylamino)phenyl]-8-methyl-pyrido[3,2-d]pyrimidin-2-yl]amino]piperidine-1-carboxylate (64 mg, 0.10 mmol) was added 4N HCl in dioxanes (2 mL) and stirred at rt for 3 days. The solvent was removed under reduced pressure and the crude residue was directly purified by C18 reverse phase flash chromatography (0-100% MeCN/10 mM aqueous ammonium formate, pH=3.8) to provide the title product (20 mg, 37% yield).

Example 10: N-(2-Fluoro-4-(2-(((3S,5S)-5-fluoropiperidin-3-yl)amino)-8-methylpyrido[3,2-d]pyrimidin-6-yl)phenyl)propane-1-sulfonamide (Compound 111)

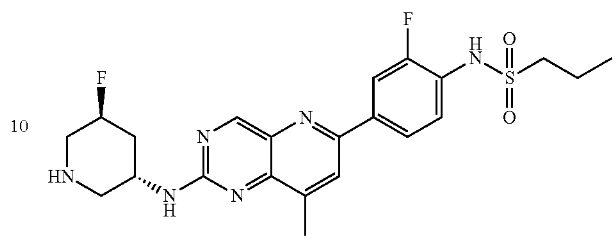

Step 1: (3S,5S)-tert-Butyl 3-fluoro-5-((6-(3-fluoro-4-(propylsulfonamido)phenyl)-8-methylpyrido[3,2-d]pyrimidin-2-yl)amino)piperidine-1-carboxylate

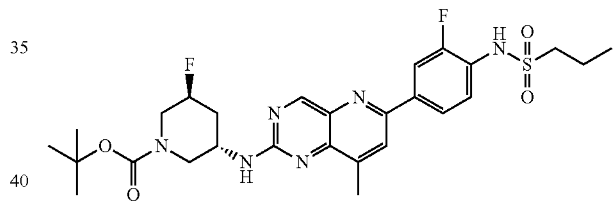

Prepared according to Example 9 (Compound 110) step 3 using tert-butyl (3S,5S)-3-[[6-(4-amino-3-fluoro-phenyl)-8-methyl-pyrido[3,2-d]pyrimidin-2-yl]amino]-5-fluoro-piperidine-1-carboxylate (100 mg, 0.21 mmol), pyridine (0.5 mL), 1-propanesulfonyl chloride (30 mg, 0.21 mmol) and $CH_2Cl_2$ (2.5 mL) to provide the title product (66 mg, 54% yield). LCMS (ESI) $[M+H]^+$=577.2.

Step 2: N-(2-Fluoro-4-(2-(((3S,5S)-5-fluoropiperidin-3-yl)amino)-8-methylpyrido[3,2-d]pyrimidin-6-yl)phenyl)propane-1-sulfonamide

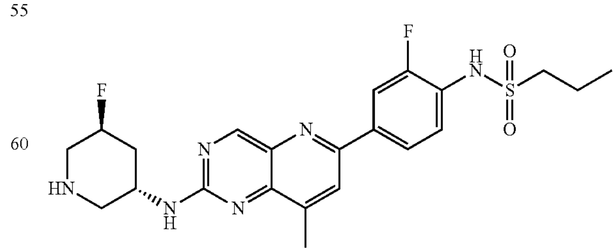

Prepared according to Example 9 (Compound 110) step 4 using tert-butyl (3S,5S)-3-fluoro-5-[[6-[3-fluoro-4-(propylsulfonylamino)phenyl]-8-methyl-pyrido[3,2-d]pyrimidin-2-yl]amino]piperidine-1-carboxylate (66 mg, 0.11 mmol) and 4N HCl in dioxanes (2 mL) to provide the title product (20 mg, 37% yield).

Example 11: N-(4-(2-(((1,4-trans)-4-(Dimethylamino)cyclohexyl)amino)-8-methylpyrido[3,2-d]pyrimidin-6-yl)-2-fluorophenyl)propane-1-sulfonamide formate (Compound 112)

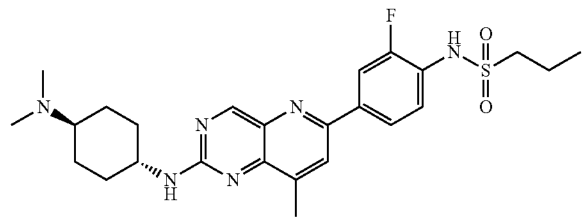 [SMILES: CCCS(=O)(=O)Nc1ccc(-c2cc(C)c3nc(N[C@H]4CC[C@H](N(C)C)CC4)ncc3n2)cc1F]

Step 1: tert-Butyl ((1,4-trans)-4-((6-(3-fluoro-4-(propylsulfonamido)phenyl)-8-methylpyrido[3,2-d]pyrimidin-2-yl)amino)cyclohexyl)carbamate

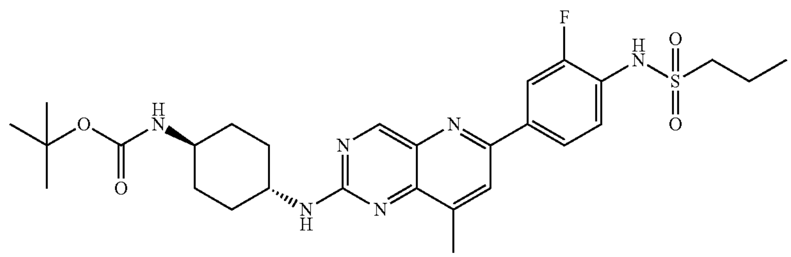 [SMILES: CCCS(=O)(=O)Nc1ccc(-c2cc(C)c3nc(N[C@H]4CC[C@H](NC(=O)OC(C)(C)C)CC4)ncc3n2)cc1F]

Prepared according to Example 9 (Compound 110) step 3 using tert-butyl N-[4-[[6-(4-amino-3-fluoro-phenyl)-8-methyl-pyrido[3,2-d]pyrimidin-2-yl]amino]cyclohexyl]carbamate (100 mg, 0.21 mmol), pyridine (1 mL), 1-propanesulfonyl chloride (135 mg, 0.96 mmol) and $CH_2Cl_2$ (4.5 mL) to provide the title compound (52 mg, 42% yield). LCMS (ESI) $[M+H]^+$=573.3.

Step 2: N-(4-(2-(((1,4-trans)-4-Aminocyclohexyl)amino)-8-methylpyrido[3,2-d]pyrimidin-6-yl)-2-fluorophenyl)propane-1-sulfonamide 2,2,2-trifluoroacetate

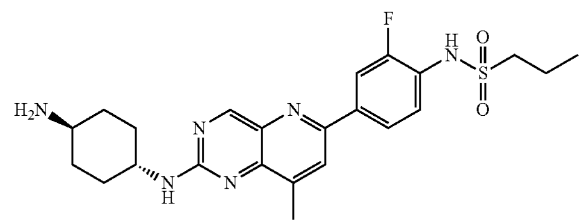 [SMILES: CCCS(=O)(=O)Nc1ccc(-c2cc(C)c3nc(N[C@H]4CC[C@H](N)CC4)ncc3n2)cc1F]

Prepared according to Example 12 (Compound 113) step 4 using tert-butyl N-[4-[[6-[3-fluoro-4-(propylsulfonylamino)phenyl]-8-methyl-pyrido[3,2-d]pyrimidin-2-yl]amino]cyclohexyl]carbamate (52 mg, 0.09 mmol), trifluoroacetic acid (0.5 mL) and $CH_2Cl_2$ (2 mL) to provide the crude title compound (54 mg, 100%). LCMS (ESI) $[M+H]^+$=472.9.

Step 3: N-(4-(2-(((1,4-trans)-4-(Dimethylamino)cyclohexyl)amino)-8-methylpyrido[3,2-d]pyrimidin-6-yl)-2-fluorophenyl)propane-1-sulfonamide formate

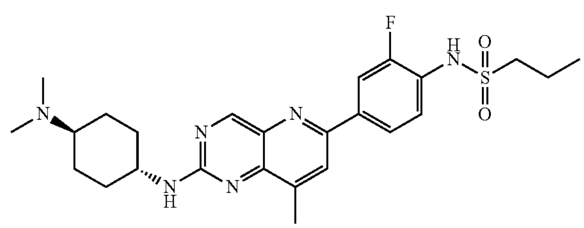 [SMILES: CCCS(=O)(=O)Nc1ccc(-c2cc(C)c3nc(N[C@H]4CC[C@H](N(C)C)CC4)ncc3n2)cc1F]

Prepared according to Example 12 (Compound 113) step 5 using N-[4-[2-[(4-aminocyclohexyl)amino]-8-methyl-pyrido[3,2-d]pyrimidin-6-yl]-2-fluoro-phenyl]propane-1-sulfonamide; 2,2,2-trifluoroacetic acid (53 mg, 0.09 mmol), sodium acetate (44 mg, 0.54 mmol), 37% w/w aqueous formaldehyde (110 mg, 1.36 mmol), sodium triacetoxyborohydride (76 mg, 0.36 mmol) and MeOH (2 mL) to provide the title compound (29 mg, 59% yield).

Example 12: N-(4-(2-(((1,4-trans)-4-(Dimethylamino)cyclohexyl)amino)-8-methylpyrido[3,2-d]pyrimidin-6-yl)-2-fluorophenyl)-3,3-difluorobutane-1-sulfonamide formate (Compound 113)

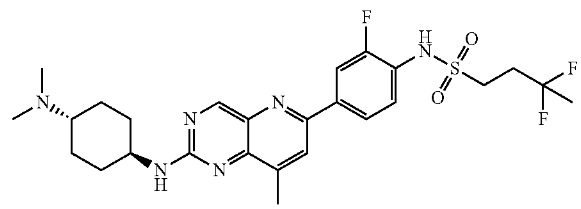 [SMILES: Cc1cc(-c2ccc(NS(=O)(=O)CCC(C)(F)F)c(F)c2)nc2cnc(N[C@H]3CC[C@H](N(C)C)CC3)nc12]

Step 1: tert-Butyl ((1,4-trans)-4-((6-chloro-8-methylpyrido[3,2-d]pyrimidin-2-yl)amino)cyclohexyl) carbamate

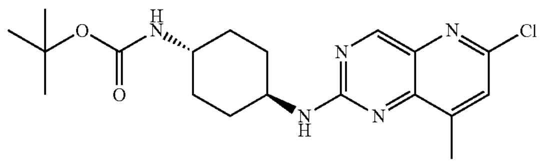 [SMILES: Cc1cc(Cl)nc2cnc(N[C@H]3CC[C@H](NC(=O)OC(C)(C)C)CC3)nc12]

A mixture of 2,6-dichloro-8-methyl-pyrido[3,2-d]pyrimidine (2.00 g, 9.34 mmol), N-Boc-trans-1,4-cyclohexanediamine (3.00 g, 14.0 mmol) and $NaHCO_3$ (3.14 g, 37.4 mmol) in DMSO (18.8 mL) was stirred at 60° C. for 2 h. The reaction was diluted with water (100 mL) and EtOAc (100 mL), acidified with $KHSO_4$ (1 M) to pH ~7. The phases were separated and the organic layer was washed twice with water followed by brine, dried over anhydrous $Na_2SO_4$, filtered, silica gel was added and concentrated. The crude material was purified by silica flash chromatography (20-100% EtOAc/Heptanes) to provide the title product (1.70 g, 46% yield). LCMS (ESI) $[M+H]^+$=392.2, 394.2.

Step 2: tert-Butyl ((1,4-trans)-4-((6-(4-amino-3-fluorophenyl)-8-methylpyrido[3,2-d]pyrimidin-2-yl) amino)cyclohexyl)carbamate

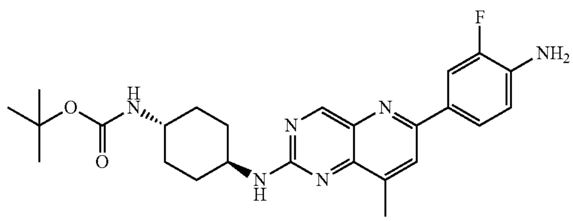 [SMILES: Cc1cc(-c2ccc(N)c(F)c2)nc2cnc(N[C@H]3CC[C@H](NC(=O)OC(C)(C)C)CC3)nc12]

A flask was charged with tert-butyl N-[4-[(6-chloro-8-methyl-pyrido[3,2-d]pyrimidin-2-yl)amino]cyclohexyl]carbamate (1.00 g, 2.55 mmol), 1,2-dimethoxyethane (20 mL) and water (5 mL) were added. The mixture was degassed for 10 min with nitrogen then to this mixture was added 2-fluoro-4-(4,4,5,5-tetramethyl-1,3,2-dioxaborolan-2-yl) aniline (907 mg, 3.83 mmol), palladium acetate (57 mg, 0.26 mmol), tri-o-tolylphosphine (155 mg, 0.51 mmol) and sodium carbonate (541 mg, 5.10 mmol). The reaction mixture was then stirred at 90° C. under nitrogen for 18 h. The reaction was then concentrated with silica gel, toluene was added and concentrated under reduced pressure again. The crude material was purified by silica flash chromatography through silica gel (30-90% EtOAc/Heptanes) to provide the title product (820 mg, 69% yield). LCMS (ESI) $[M+H]^+$=467.3.

Step 3: tert-Butyl ((1,4-trans)-4-((6-(4-(3,3-difluorobutylsulfonamido)-3-fluorophenyl)-8-methylpyrido[3,2-d]pyrimidin-2-yl)amino)cyclohexyl) carbamate

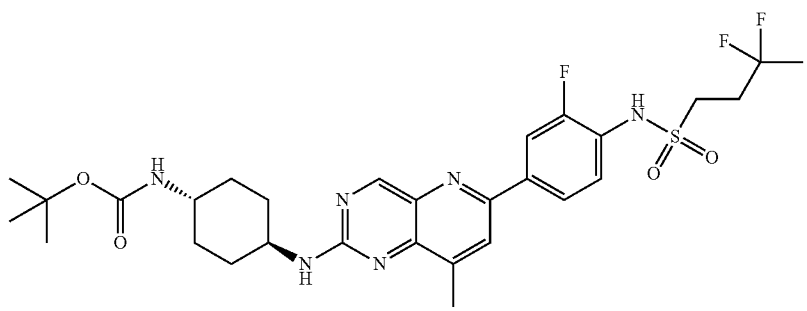 [SMILES: Cc1cc(-c2ccc(NS(=O)(=O)CCC(C)(F)F)c(F)c2)nc2cnc(N[C@H]3CC[C@H](NC(=O)OC(C)(C)C)CC3)nc12]

To a solution of tert-butyl N-[4-[[6-(4-amino-3-fluorophenyl)-8-methyl-pyrido[3,2-d]pyrimidin-2-yl]amino]cyclohexyl]carbamate (100 mg, 0.21 mmol) in $CH_2Cl_2$ (1.1 mL) was added 3,3-difluorobutane-1-sulfonyl chloride (58 mg, 0.30 mmol) and pyridine (345 μL, 4.29 mmol) and the mixture stirred at rt overnight. After 16 h, the reaction mixture was poured in $CH_2Cl_2$ and washed with 1 M aqueous $KHSO_4$. The organic extract was dried by passing through a phase cartridge separator and concentrated. The crude material was purified by silica flash chromatography (0-50% EtOAc/$CH_2Cl_2$) to provide the title product (81 mg, 61% yield). LCMS (ESI) $[M+H]^+$=623.3.

Step 4: N-(4-(2-(((1,4-trans)-4-Aminocyclohexyl) amino)-8-methylpyrido[3,2-d]pyrimidin-6-yl)-2-fluorophenyl)-3,3-difluorobutane-1-sulfonamide 2,2,2-trifluoroacetate

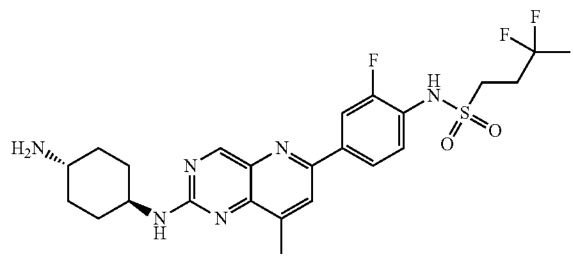 [SMILES: Cc1cc(-c2ccc(NS(=O)(=O)CCC(C)(F)F)c(F)c2)nc2cnc(N[C@H]3CC[C@H](N)CC3)nc12]

tert-Butyl N-[4-[[6-[4-(3,3-difluorobutylsulfonylamino)-3-fluoro-phenyl]-8-methyl-pyrido[3,2-d]pyrimidin-2-yl] amino]cyclohexyl]carbamate (81 mg, 0.13 mmol) was dissolved in $CH_2Cl_2$ (0.70 mL) and to the solution was added trifluoroacetic acid (0.3 mL, 3.95 mmol). The reaction was stirred at rt for 90 min. The reaction was concentrated to dryness, toluene was added and concentration again (repeated twice) to provide the crude title product (83 mg, 100% yield). LCMS (ESI) $[M+H]^+$=523.3.

Step 5: N-(4-(2-(((1,4-trans)-4-(Dimethylamino) cyclohexyl)amino)-8-methylpyrido[3,2-d]pyrimidin-6-yl)-2-fluorophenyl)-3,3-difluorobutane-1-sulfonamide formate

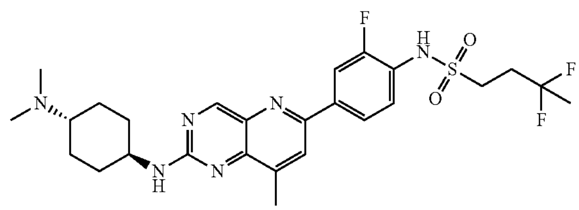 [SMILES: Cc1cc(-c2ccc(NS(=O)(=O)CCC(C)(F)F)c(F)c2)nc2cnc(N[C@H]3CC[C@H](N(C)C)CC3)nc12]

To a solution of N-[4-[2-[(4-Aminocyclohexyl)amino]-8-methyl-pyrido[3,2-d]pyrimidin-6-yl]-2-fluoro-phenyl]-3,3-difluoro-butane-1-sulfonamide; 2,2,2-trifluoroacetic acid (83 mg, 0.13 mmol) in methanol (1.1 mL) was added sodium acetate (64 mg, 0.78 mmol) followed by 37% w/w aqueous formaldehyde (0.16 mL, 1.96 mmol). The mixture was stirred at rt for 5 min then sodium triacetoxyborohydride (109 mg, 0.52 mmol) was added and the mixture was stirred at rt. After 1 h, ⅔ of volatiles removed under reduced pressure and the crude residue was purified by C18 reverse phase flash chromatography (20-80% MeCN/10 mM aqueous ammonium formate, pH=3.8) to provide the title product (50 mg, 69% yield).

Example 13: N-(4-(2-(((1,4-trans)-4-(Dimethylamino)cyclohexyl)amino)-8-ethylpyrido[3,2-d]pyrimidin-6-yl)-2-fluorophenyl)-3,3,3-trifluoropropane-1-sulfonamide (Compound 114)

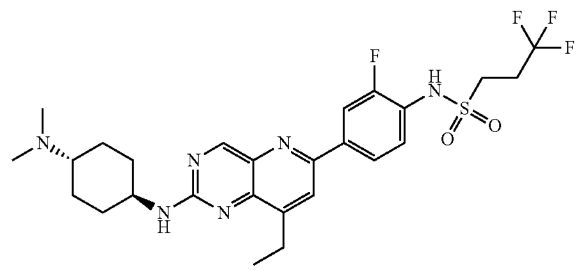 [SMILES: CCc1cc(-c2ccc(NS(=O)(=O)CCC(F)(F)F)c(F)c2)nc2cnc(N[C@H]3CC[C@H](N(C)C)CC3)nc12]

Step 1: 3-Amino-4-bromo-6-chloropicolinonitrile

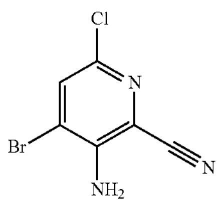 [SMILES: N#Cc1nc(Cl)cc(Br)c1N]

To a mixture of 3-amino-6-chloro-pyridine-2-carbonitrile (10.6 g, 69.4 mmol) in DMF (150 mL) was added N-Bromosuccinimide (16.4 g, 92.2 mmol). The mixture was stirred at rt for 2.5 h. To the mixture was added water (125 mL), the resulting solids filtered off and rinsed with water. The collected solids were dissolved in a mixture of $CH_2Cl_2$ and EtOAc, silica gel was added and concentrated. The crude material was purified by silica flash chromatography (10-70% EtOAc/heptanes) to provide the title product (11.0 g, 69% yield). $^1$H NMR (400 MHz, $CDCl_3$) δ 7.60 (s, 1H), 4.92 (s, 2H).

Step 2: 3-Amino-6-chloro-4-vinylpicolinonitrile

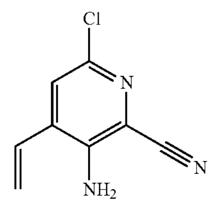

A flask was charged with 3-amino-4-bromo-6-chloro-pyridine-2-carbonitrile (5.00 g, 21.5 mmol), potassium; trifluoro(vinyl)boron (3.60 g, 26.9 mmol), $Na_2CO_3$ (4.56 g, 43.0 mmol) and tetrakis(triphenylphosphine)palladium(0) (1.24 g, 1.08 mmol). The flask was capped and purged with nitrogen then nitrogen degassed 1,2-dimethoxyethane (80 mL) and nitrogen degassed water (20 mL) were added. The mixture was heated at 100° C. for 3 h then partitioned between water and EtOAc. The phases were separated and the organic extract washed with brine, dried over anydrous $Na_2SO_4$, filtered and concentrated to ½ volume. Silica gel was added and concentrated to dryness and the crude material was purified by silica flash chromatography (0-10% EtOAc/$CH_2Cl_2$) to provide the title product (2.69 g, 69% yield). LCMS (ESI) $[M+H]^+$=180.1, 181.9.

Step 3: 3-Amino-6-chloro-4-ethylpicolinonitrile

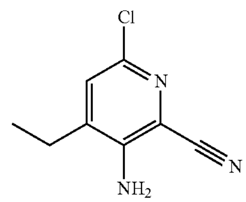

To 3-amino-6-chloro-4-vinyl-pyridine-2-carbonitrile (2.69 g, 15.0 mmol) in ethyl acetate (150 mL) under nitrogen was added Pd/C (260 mg). The flask was submitted to 5 cycles of vacuum hydrogen purge and stirred at rt for 18 h under hydrogen atmosphere. Nitrogen was then bubbled in the solution for 10 minutes. The solution was filtered through celite, rinsed with EtOAc and concentrated to give the title compound (2.52 g, 93% yield) as a yellow solid. LCMS (ESI) $[M+H]^+$=182.1, 184.1. $^1$H NMR (400 MHz, $CDCl_3$) δ 7.17 (s, 1H), 4.42 (bs, 2H), 2.52 (q, J=7.5 Hz, 2H), 1.31 (t, J=7.5 Hz, 3H).

Step 4: 3-Amino-6-chloro-4-ethylpicolinamide

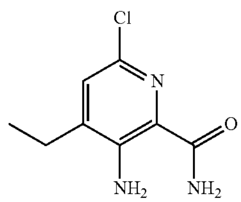

To 3-amino-6-chloro-4-ethyl-pyridine-2-carbonitrile (2.22 g, 12.2 mmol) was added concentrated sulfuric acid (35.5 mL, 666 mmol) and the reaction mixture was stirred for 2 h at 70° C. The mixture was then cooled to rt and slowly poured over ice. The precipitate formed was filtered off, washed with water and dried to provide the title compound (1.76 g, 72% yield) as a yellow solid. LCMS (ESI) $[M+H]^+$=201.0, 202.1.

Step 5: 6-Chloro-8-ethylpyrido[3,2-d]pyrimidine-2,4-diol

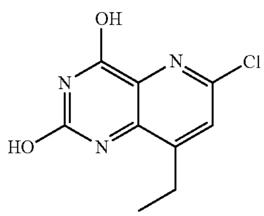

To 3-amino-6-chloro-4-ethyl-pyridine-2-carboxamide (1.76 g, 8.79 mmol) in 1,4-dioxane (57 mL) was added triphosgene (1.3 g, 4.4 mmol). The reaction mixture was then stirred at rt for 20 min and then at reflux for 1 h. The mixture was cooled down to rt and nitrogen was bubbled for 5 min. The mixture was then diluted with EtOAc and stirred at 0° C. for 30 min and the resulting precipitate was filtered off. The precipitate was washed with EtOAc and dried to provide the title compound (1.20 g, 60% yield). LCMS (ESI) $[M+H]^+$=226., 228.1.

Step 6: 2,6-Dichloro-8-ethylpyrido[3,2-d]pyrimidine

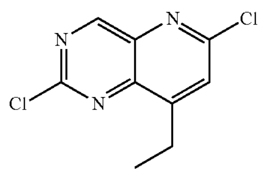

To a suspension of 6-chloro-8-ethyl-pyrido[3,2-d]pyrimidine-2,4-diol (1.32 g, 5.86 mmol) in phosphorus oxychloride (7.4 mL, 79 mmol) was added N,N-diisopropylethylamine (2.1 mL, 12 mmol). The reaction mixture was then stirred at 115° C. for 2 h and then concentrated. The residue was dissolved in toluene and concentrated under reduced pressure (repeated twice). The crude was used without any further purification and assumed to be quantitative to give crude 2,4,6-trichloro-8-ethylpyrido[3,2-d]pyrimidine which was used in the next step without further purification.

Crude 2,4,6-trichloro-8-ethyl-pyrido[3,2-d]pyrimidine (1.05 g, 4.0 mmol) was dissolved in toluene (36 mL) and the mixture was degassed with $N_2$ for 20 min. To the solution was added $Pd(PPh_3)_4$ (231 mg, 0.20 mmol) followed by tributyltin hydride (1.2 mL, 4.4 mmol) and the mixture was heated at 100° C. overnight. After 16 h, the solution was cooled down to rt, potassium fluoride (946 mg, 16 mmol) and 9.45 g of silica gel were added (10:1 ratio) and stirred at rt for 30 min then the solvent was removed under reduced pressure. The crude material was purified by flash chromatography through silica gel (0-40% EtOAc/heptane) to provide the title product (0.73 g, 79% yield). LCMS (ESI) $[M+H]^+$=228.0. $^1$H NMR (400 MHz, $CDCl_3$) δ 9.39 (s, 1H), 7.65 (s, 1H), 3.23 (q, J=7.1 Hz, 2H), 1.40 (t, J=7.5 Hz, 3H).

Step 7: tert-Butyl ((1,4-trans)-4-((6-chloro-8-ethylpyrido[3,2-d]pyrimidin-2-yl)amino)cyclohexyl) carbamate

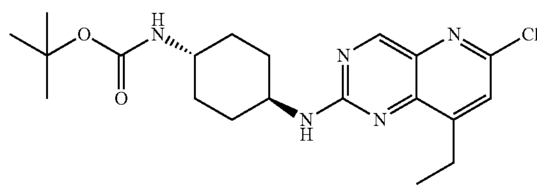 [SMILES: CCc1cc(Cl)nc2cnc(N[C@H]3CC[C@H](NC(=O)OC(C)(C)C)CC3)nc12]

Prepared according to Example 12 (Compound 113) step 1 using 2,6-dichloro-8-ethyl-pyrido[3,2-d]pyrimidine (100 mg, 0.44 mmol), N-Boc-trans-1,4-cyclohexanediamine (122 mg, 0.57 mmol), N,N-diisopropylethylamine (153 μL, 0.88 mmol) and DMSO (1.41 mL) to provide the title product (82 mg, 46% yield). LCMS (ESI) $[M+H]^+$=406.2, 408.2.

Step 8: tert-Butyl ((1,4-trans)-4-((6-(4-amino-3-fluorophenyl)-8-ethylpyrido[3,2-d]pyrimidin-2-yl) amino)cyclohexyl)carbamate

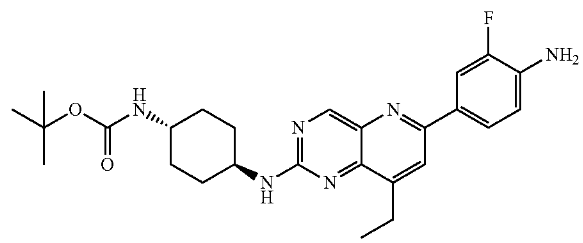 [SMILES: CCc1cc(-c2ccc(N)c(F)c2)nc2cnc(N[C@H]3CC[C@H](NC(=O)OC(C)(C)C)CC3)nc12]

Prepared according to Example 12 (Compound 113) step 2 using tert-butyl N-[4-[(6-chloro-8-ethyl-pyrido[3,2-d]pyrimidin-2-yl)amino]cyclohexyl]carbamate (82 mg, 0.20 mmol, 2-fluoro-4-(4,4,5,5-tetramethyl-1,3,2-dioxaborolan-2-yl)aniline (72 mg, 0.30 mmol), palladium acetate (4.5 mg, 0.02 mmol), tri-o-tolylphosphine (12 mg, 0.04 mmol) and sodium carbonate (43 mg, 0.40 mmol) to provide the title product (48 mg, 49% yield). LCMS (ESI) $[M+H]^+$=481.3.

Step 9: tert-Butyl ((1,4-trans)-4-((8-ethyl-6-(3-fluoro-4-(3,3,3-trifluoropropylsulfonamido)phenyl)pyrido[3,2-d]pyrimidin-2-yl)amino)cyclohexyl)carbamate

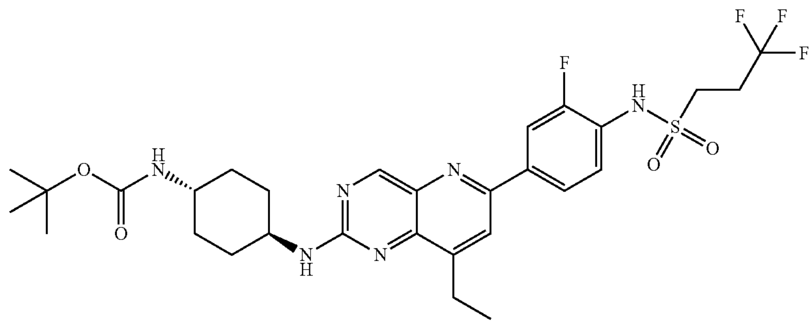 [SMILES: CCc1cc(-c2ccc(NS(=O)(=O)CCC(F)(F)F)c(F)c2)nc2cnc(N[C@H]3CC[C@H](NC(=O)OC(C)(C)C)CC3)nc12]

Prepared according to Example 12 (Compound 113) step 3 using tert-butyl N-[4-[[6-(4-amino-3-fluoro-phenyl)-8-ethyl-pyrido[3,2-d]pyrimidin-2-yl]amino]cyclohexyl]carbamate (48 mg, 0.10 mmol), pyridine (0.12 mL, 1.5 mmol) and 3,3,3-trifluoropropane-1-sulfonyl chloride (26 mg, 0.13 mmol) to provide the title product (41 mg, 64% yield). LCMS (ESI) $[M+H]^+$=641.3.

Step 10: N-(4-(2-(((1,4-trans)-4-Aminocyclohexyl)amino)-8-ethylpyrido[3,2-d]pyrimidin-6-yl)-2-fluorophenyl)-3,3,3-trifluoropropane-1-sulfonamide 2,2,2-trifluoroacetate

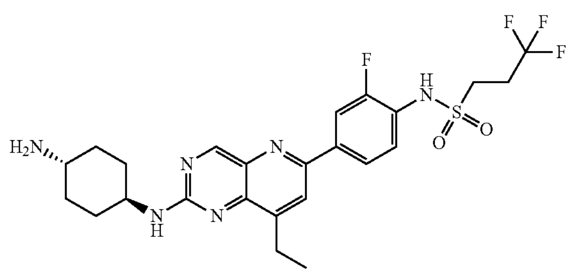 [SMILES: CCc1cc(-c2ccc(NS(=O)(=O)CCC(F)(F)F)c(F)c2)nc2cnc(N[C@H]3CC[C@H](N)CC3)nc12]

Prepared according to Example 12 (Compound 113) step 4 using tert-butyl N-[4-[[8-ethyl-6-[3-fluoro-4-(3,3,3-trifluoropropylsulfonylamino)phenyl]pyrido[3,2-d]pyrimidin-2-yl]amino]cyclohexyl]carbamate (40 mg, 0.06 mmol) trifluoroacetic acid (0.1 mL, 1.3 mmol) and $CH_2Cl_2$ (0.3 mL) to provide the crude title product (41 mg, 100% yield). LCMS (ESI) $[M+H]^+$=541.1.

Step 11: N-(4-(2-(((1,4-trans)-4-(Dimethylamino)cyclohexyl)amino)-8-ethylpyrido[3,2-d]pyrimidin-6-yl)-2-fluorophenyl)-3,3,3-trifluoropropane-1-sulfonamide

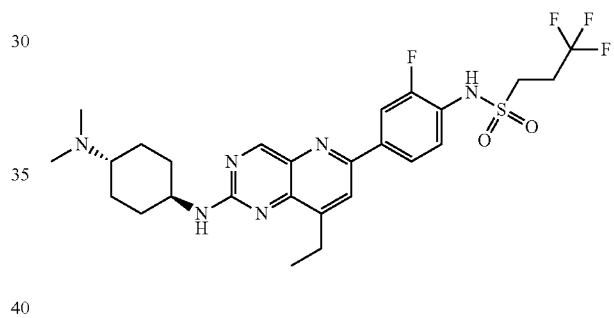

Prepared according to Example 12 (Compound 113) step 5 using N-[4-[2-[(4-aminocyclohexyl)amino]-8-ethyl-pyrido[3,2-d]pyrimidin-6-yl]-2-fluoro-phenyl]-3,3,3-trifluoro-propane-1-sulfonamide; 2,2,2-trifluoroacetic acid (40 mg, 0.06 mmol), sodium acetate (30 mg, 0.37 mmol), 37% w/w aqueous formaldehyde (70 μL, 0.92 mmol), sodium triacetoxyborohydride (51 mg, 0.24 mmol) and methanol (0.5 mL) to provide the title product (24 mg, 67% yield).

Example 14: 1-(2,4-Difluorophenyl)-N-(2-fluoro-4-(2-(((3S,5S)-5-fluoropiperidin-3-yl)amino)-8-methylpyrido[3,2-d]pyrimidin-6-yl)phenyl)methanesulfonamide (Compound 115)

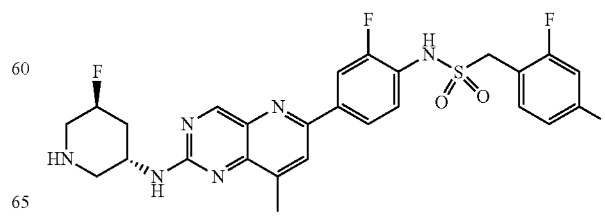

Step 1: (3S,5S)-tert-Butyl 3-((6-chloro-8-methylpyrido[3,2-d]pyrimidin-2-yl)amino)-5-fluoropiperidine-1-carboxylate

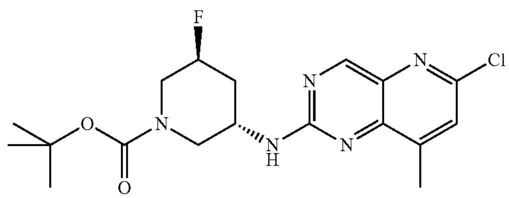 [SMILES: Cc1cc(Cl)nc2cnc(N[C@H]3C[C@H](F)CN(C(=O)OC(C)(C)C)C3)nc12]

To a solution of tert-butyl (3S,5S)-3-amino-5-fluoro-piperidine-1-carboxylate (1.22 g, 5.59 mmol) and 2,6-dichloro-8-methyl-pyrido[3,2-d]pyrimidine (1.00 g, 4.67 mmol) in DMSO (1 mL) was added N,N-diisopropylethylamine (1.25 mL, 7.18 mmol) and the mixture was stirred overnight at 60° C. After 16 h, the reaction mixture was diluted with EtOAc, washed three times with $H_2O$, then three times with saturated aqueous sodium chloride, dried ($MgSO_4$), filtered and concentrated under reduced pressure to provide the title compound (1.96 g, 105% yield). LCMS (ESI) [M+H]+=396.1.

Step 2: (3S,5S)-tert-Butyl 3-((6-(4-amino-3-fluorophenyl)-8-methylpyrido[3,2-d]pyrimidin-2-yl)amino)-5-fluoropiperidine-1-carboxylate

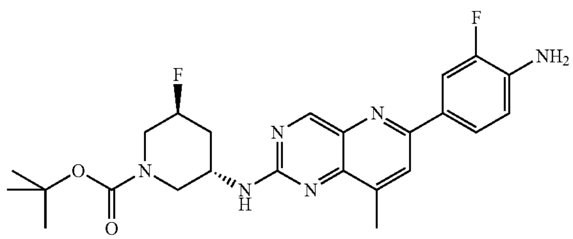 [SMILES: Cc1cc(-c2ccc(N)c(F)c2)nc2cnc(N[C@H]3C[C@H](F)CN(C(=O)OC(C)(C)C)C3)nc12]

A solution of (3S,5S)-tert-butyl 3-((6-chloro-8-methylpyrido[3,2-d]pyrimidin-2-yl)amino)-5-fluoropiperidine-1-carboxylate (600 mg, 1.52 mmol), 2-fluoro-4-(4,4,5,5-tetramethyl-1,3,2-dioxaborolan-2-yl)aniline (545 mg, 2.30 mmol), sodium carbonate (321 mg, 3.03 mmol) and tri-o-tolylphosphine (185 mg, 0.61 mmol) in a mixture of 1,2-dimethoxyethane (12 mL) and water (3 mL), was degassed 10 minutes before the addition of palladium acetate (85 mg, 0.38 mmol). The mixture was then stirred 10 h at 85° C. The reaction mixture was then diluted with EtOAc and filtered through celite. The filtrate was washed twice with $H_2O$, then twice with saturated aqueous sodium chloride, dried over anhydrous $MgSO_4$), filtered and concentrated under reduced pressure. The crude material was purified by flash chromatography through silica gel (85% EtOAc/heptanes) to provide the title compound (300 mg, 42% yield). LCMS (ESI) [M+H]+=471.0.

Step 3: (3S,5S)-tert-Butyl 3-((6-(4-((2,4-difluorophenyl)methylsulfonamido)-3-fluorophenyl)-8-methylpyrido[3,2-d]pyrimidin-2-yl)amino)-5-fluoropiperidine-1-carboxylate

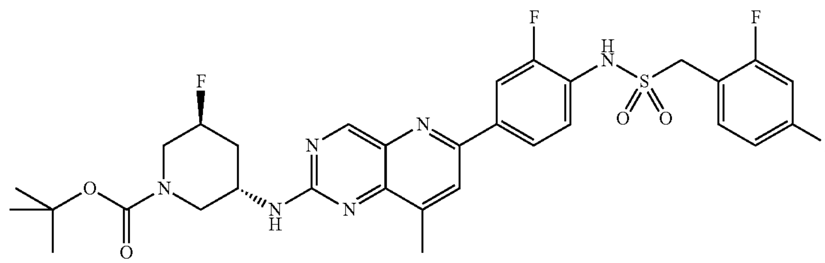

To a mixture of (3S,5S)-tert-butyl 3-((6-(4-amino-3-fluorophenyl)-8-methylpyrido[3,2-d]pyrimidin-2-yl)amino)-5-fluoropiperidine-1-carboxylate (75 mg, 0.16 mmol) and (2,4-difluorophenyl)methanesulfonyl chloride (47 mg, 0.21 mmol), in $CH_2Cl_2$ (1 mL), was added pyridine (0.32 mL, 3.97 mmol). The resulting solution was stirred overnight at rt. After 16 h, volatiles were removed under reduced pressure and the crude material was purified by flash chromatography through silica gel (20% EtOAc/$CH_2Cl_2$) to provide the title compound (50 mg, 47% yield). LCMS (ESI) [M+H]+=661.3.

Step 4: 1-(2,4-Difluorophenyl)-N-(2-fluoro-4-(2-(((3S,5S)-5-fluoropiperidin-3-yl)amino)-8-methylpyrido[3,2-d]pyrimidin-6-yl)phenyl)methanesulfonamide

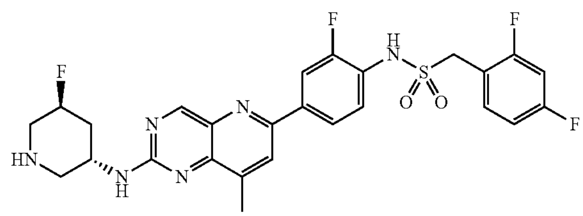 [SMILES: Cc1cc(-c2ccc(NS(=O)(=O)Cc3ccc(F)cc3F)c(F)c2)nc2cnc(N[C@@H]3CNC[C@@H](F)C3)nc12]

To a solution of (3S,5S)-tert-butyl 3-((6-(4-((2,4-difluorophenyl)methylsulfonamido)-3-fluorophenyl)-8-methylpyrido[3,2-d]pyrimidin-2-yl)amino)-5-fluoropiperidine-1-carboxylate (47 mg, 0.07 mmol) in 1,4-Dioxane (1 mL) was added 4M HCl in dioxane (1.0 mL, 4.0 mmol) and the mixture stirred at rt. After 2 h, volatiles were evaporated under reduced pressure. The residue was diluted with a saturated aqueous solution of $NaHCO_3$ and extracted twice with EtOAc. The organic extracts were dried ($MgSO_4$), filtered and concentrated under reduced pressure. The crude material was purified by C18 reverse phase flash chromatography (0-45% MeCN/10 mM aqueous ammonium formate, pH=3.8) to provide the title compound (24 mg, 60% yield).

Example 15: 1-(4-Cyanophenyl)-N-(2-fluoro-4-(2-(((3S,5S)-5-fluoropiperidin-3-yl)amino)-8-methylpyrido[3,2-d]pyrimidin-6-yl)phenyl)methanesulfonamide formate (Compound 116)

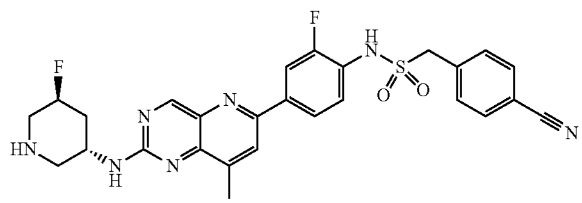 [SMILES: Cc1cc(-c2ccc(NS(=O)(=O)Cc3ccc(C#N)cc3)c(F)c2)nc2cnc(N[C@@H]3CNC[C@@H](F)C3)nc12]

Step 1: (3S,5S)-tert-Butyl 3-((6-(4-((4-cyanophenyl)methylsulfonamido)-3-fluorophenyl)-8-methylpyrido[3,2-d]pyrimidin-2-yl)amino)-5-fluoropiperidine-1-carboxylate

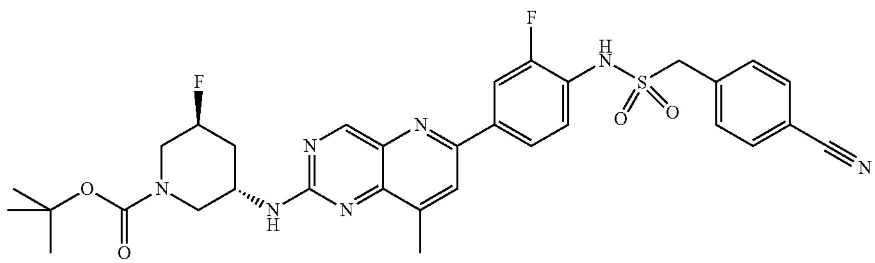 [SMILES: Cc1cc(-c2ccc(NS(=O)(=O)Cc3ccc(C#N)cc3)c(F)c2)nc2cnc(N[C@H]3C[C@H](F)CN(C(=O)OC(C)(C)C)C3)nc12]

Prepared according to Example 14 (Compound 115) step 3 using (3S,5S)-tert-butyl 3-((6-(4-amino-3-fluorophenyl)-8-methylpyrido[3,2-d]pyrimidin-2-yl)amino)-5-fluoropiperidine-1-carboxylate (75 mg, 0.16 mmol), (4-cyanophenyl) methanesulfonyl chloride (45 mg, 0.21 mmol) and pyridine (0.32 mL, 3.97 mmol) to provide the title product (50 mg, 48% yield). LCMS (ESI) [M+H]+=650.3.

Step 2: 1-(4-Cyanophenyl)-N-(2-fluoro-4-(2-(((3S,5S)-5-fluoropiperidin-3-yl)amino)-8-methylpyrido[3,2-d]pyrimidin-6-yl)phenyl)methanesulfonamide formate

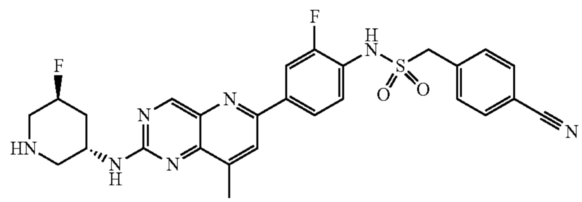 [SMILES: Cc1cc(-c2ccc(NS(=O)(=O)Cc3ccc(C#N)cc3)c(F)c2)nc2cnc(N[C@@H]3CNC[C@@H](F)C3)nc12]

Prepared according to Example 14 (Compound 115) step 4 using (3S,5S)-tert-butyl 3-((6-(4-((4-cyanophenyl)methylsulfonamido)-3-fluorophenyl)-8-methylpyrido[3,2-d]pyrimidin-2-yl)amino)-5-fluoropiperidine-1-carboxylate (50 mg, 0.08 mmol) and 4N HCl in dioxane (1.0 mL, 4.0 mmol) to provide the title product (27 mg, 59% yield).

Example 16: N-(4-(2-(((1,4-trans)-4-(Dimethylamino)cyclohexyl)amino)-8-methylpyrido[3,2-d]pyrimidin-6-yl)-2-fluorophenyl)-2,2-difluorobutane-1-sulfonamide formate (Compound 117)

Step 1: tert-Butyl ((1,4-trans)-4-((6-(4-(2,2-difluorobutylsulfonamido)-3-fluorophenyl)-8-methylpyrido[3,2-d]pyrimidin-2-yl)amino)cyclohexyl) carbamate

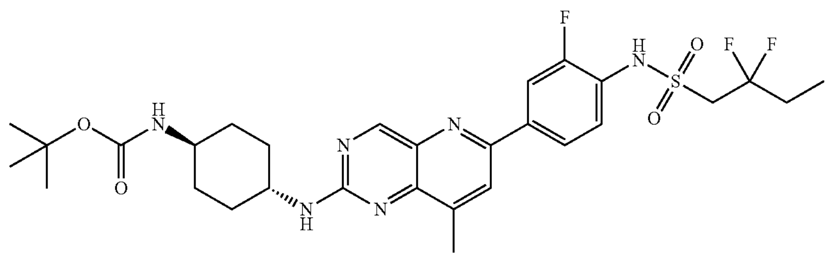 [SMILES: CCC(F)(F)CS(=O)(=O)Nc1ccc(-c2cc(C)c3nc(N[C@H]4CC[C@H](NC(=O)OC(C)(C)C)CC4)ncc3n2)cc1F]

Prepared according to Example 12 (Compound 113) step 3 using tert-butyl N-[4-[[6-(4-amino-3-fluoro-phenyl)-8-methyl-pyrido[3,2-d]pyrimidin-2-yl]amino]cyclohexyl]carbamate (70 mg, 0.15 mmol), pyridine (0.5 mL), 2,2-difluorobutane-1-sulfonyl chloride (86.7 mg, 0.45 mmol) and $CH_2Cl_2$ (3 mL) to provide the title compound (41 mg, 44% yield) as a yellow solid. LCMS (ESI) $[M+H]^+$=623.1.

Step 2: N-(4-(2-(((1,4-trans)-4-Aminocyclohexyl)amino)-8-methylpyrido[3,2-d]pyrimidin-6-yl)-2-fluorophenyl)-2,2-difluorobutane-1-sulfonamide 2,2,2-trifluoroacetate

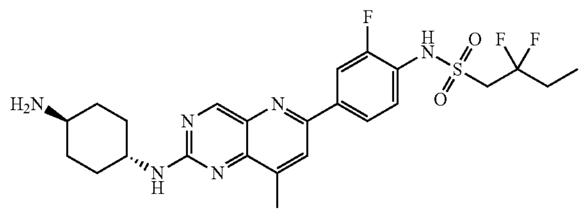 [SMILES: CCC(F)(F)CS(=O)(=O)Nc1ccc(-c2cc(C)c3nc(N[C@H]4CC[C@H](N)CC4)ncc3n2)cc1F]

Prepared according to Example 12 (Compound 113) step 4 using tert-butyl ((1,4-trans)-4-((6-(4-(2,2-difluorobutylsulfonamido)-3-fluorophenyl)-8-methylpyrido[3,2-d]pyrimidin-2-yl)amino)cyclohexyl)carbamate (41 mg, 0.07 mmol), TFA (0.5 mL) and $CH_2Cl_2$ (2 mL) to provide the title compound (42 mg, 100% yield).

Step 3: N-(4-(2-(((1,4-trans)-4-(Dimethylamino)cyclohexyl)amino)-8-methylpyrido[3,2-d]pyrimidin-6-yl)-2-fluorophenyl)-2,2-difluorobutane-1-sulfonamide formate

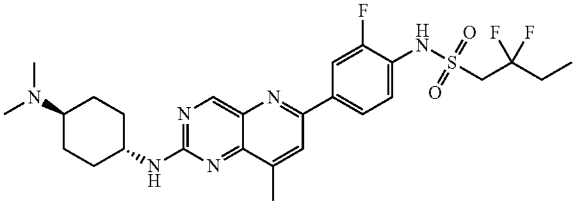 [SMILES: CCC(F)(F)CS(=O)(=O)Nc1ccc(-c2cc(C)c3nc(N[C@H]4CC[C@H](N(C)C)CC4)ncc3n2)cc1F]

Prepared according to Example 12 (Compound 113) step 5 using N-(4-(2-(((1,4-trans)-4-aminocyclohexyl)amino)-8-methylpyrido[3,2-d]pyrimidin-6-yl)-2-fluorophenyl)-2,2-difluorobutane-1-sulfonamide 2,2,2-trifluoroacetate (42 mg, 0.07 mmol), sodium acetate (32 mg, 0.40 mmol), 37% w/w aqueous formaldehyde (80 mg, 0.99 mmol), sodium triacetoxyborohydride (55 mg, 0.26 mmol) and MeOH (2 mL) to provide the title compound (17 mg, 43% yield).

Example 17: N-(4-(2-(((1,4-trans)-4-(Dimethylamino)cyclohexyl)amino)-8-methoxypyrido[3,2-d]pyrimidin-6-yl)-2-fluorophenyl)-3,3,3-trifluoropropane-1-sulfonamide formate (Compound 118)

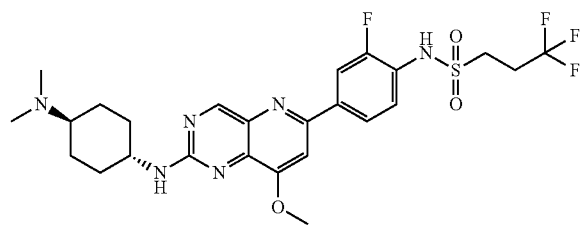 [SMILES: COc1cc(-c2ccc(NS(=O)(=O)CCC(F)(F)F)c(F)c2)nc2cnc(N[C@H]3CC[C@H](N(C)C)CC3)nc12]

Step 1: 3-Amino-4-bromo-6-chloro-pyridine-2-carboxylic acid

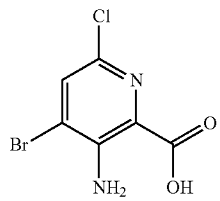 [SMILES: Nc1c(Br)cc(Cl)nc1C(=O)O]

3-Amino-4-bromo-6-chloro-pyridine-2-carbonitrile (6.20 g, 26.7 mmol) was dissolved in concentrated sulfuric acid (40 mL, 816 mmol) and stirred for 0.5 h at 100° C. The reaction mixture was cooled to room temperature in a water bath and water (40 mL) was very slowly added. After addition, the reaction mixture was heated for 1 h. After cooling to rt, water (200 mL) was added and the aqueous solution was extracted twice with EtOAc. The organic extracts were combined, washed with saturated aqueous sodium chloride, dried over magnesium sulfate and concentrated under reduced pressure to provide the crude title compound (6.0 g, 89% yield). LCMS (ESI) $[M+H]^+$=250.8.

Step 2: (3-Amino-4-bromo-6-chloro-2-pyridyl)methanol

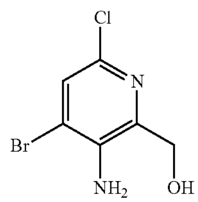 [SMILES: Nc1c(Br)cc(Cl)nc1CO]

3-Amino-4-bromo-6-chloro-pyridine-2-carboxylic acid (500 mg, 1.99 mmol) was suspended in tert-butyl methyl ether (20 mL) and the mixture was degassed with $N_2$ for 5 min. The solution was stirred at 50° C. and to the solution was added lithium aluminum hydride (196 mg, 5.96 mmol) in small portions. After complete addition, the reaction was stirred for another 20 min then cooled to 0° C. and to the solution was added $Na_2SO_4$ decahydrate portionwise. The mixture was concentrated under reduced pressure and to the residue was added MeOH and silica gel and volatiles removed under reduced pressure to dry load the crude material on silica gel and purified by flash column chromatography through silica gel (0-100% EtOAc/heptanes) to provide the title compound (330 mg, 70% yield). LCMS (ESI) $[M+H]^+$=238.6.

Step 3: 3-Amino-4-bromo-6-chloro-pyridine-2-carbaldehyde

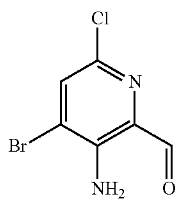

(3-Amino-4-bromo-6-chloro-2-pyridyl)methanol (330 mg, 1.39 mmol) was dissolved in 1,2-dichloroethane (10 mL) and to the solution was added manganese (IV) oxide activated (1.81 g, 20.8 mmol). The reaction mixture was then stirred at 80° C. for 1 h then filtered and the filtrate was concentrated to provide the title compound (310 mg, 95% in yield). LCMS (ESI) $[M+H]^+$=236.5.

Step 4: 8-Bromo-6-chloro-1H-pyrido[3,2-d]pyrimidin-2-one

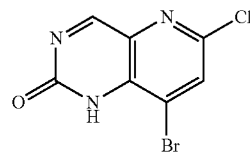 [SMILES: O=c1ncc2nc(Cl)cc(Br)c2[nH]1]

3-Amino-4-bromo-6-chloro-pyridine-2-carbaldehyde (2.60 g, 11.0 mmol) and urea (6.63 g, 110 mmol) is mixed thoroughly and heated at 180° C. for 20 min. The reaction mixture was then suspended in water and the precipitate filtered off and dried to provide the title compound (2.40 g, 83% yield). LCMS (ESI) $[M+H]^+$=261.9.

Step 5: 8-Bromo-2,6-dichloro-pyrido[3,2-d]pyrimidine

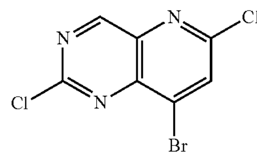 [SMILES: Clc1cc(Br)c2nc(Cl)ncc2n1]

8-Bromo-6-chloro-1H-pyrido[3,2-d]pyrimidin-2-one (500 mg, 1.92 mmol) was suspended in $POCl_3$ (15 mL, 1.92 mmol) and the mixture was heated at 105° C. for 4 h. The reaction was concentrated under reduced pressure and purified by flash column chromatography through silica gel (0-50% EtOAc/heptanes) to provide the title compound (120 mg, 22% yield). $^1H$ NMR (400 MHz, $CDCl_3$) 9.45 (s, 1H), 7.94 (s, 1H).

Step 6: 2,6-Dichloro-8-methoxy-pyrido[3,2-d]pyrimidine

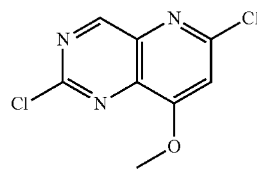

8-Bromo-2,6-dichloro-pyrido[3,2-d]pyrimidine (100 mg, 0.36 mmol) was suspended in methanol (3 mL) and to the mixture was added 30 wt % sodium methoxide in methanol (83 mg, 0.47 mmol). The reaction was stirred at rt for 1 h then diluted with water and EtOAc. The phases were separated and the organic layer was washed with saturated aqueous sodium chloride, dried over anhydrous $Na_2SO_4$, filtered and concentrated under reduced pressure to provide the crude title compound (69 mg, 84% yield). LCMS (ESI) $[M+H]^+$=230.0.

Step 7: tert-Butyl N-[4-[(6-chloro-8-methoxy-pyrido[3,2-d]pyrimidin-2-yl)amino]cyclohexyl]carbamate

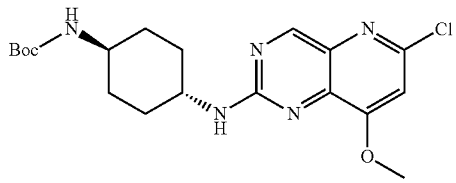 [SMILES: COc1cc(Cl)nc2cnc(N[C@H]3CC[C@H](NC(=O)OC(C)(C)C)CC3)nc12]

2,6-Dichloro-8-methoxy-pyrido[3,2-d]pyrimidine (69 mg, 0.30 mmol) was dissolved in DMSO (4 mL) and to the solution was added N-Boc-trans-1,4-cyclohexanediamine (77 mg, 0.36 mmol) followed by $NaHCO_3$ (100 mg, 1.2 mmol). The mixture was stirred at 60° C. for 2 days then diluted with water (20 mL) and extracted with EtOAc (30 mL). The organic layer was washed with water (20 mL), then saturated aqueous sodium chloride, concentrated under reduced pressure with silica gel and purified by silica flash column chromatography (0-70% EtOAc/heptanes) to provide the title compound (95 mg, 78% yield). LCMS (ESI) $[M+H]^+$=408.2.

Step 8: tert-Butyl N-[4-[[6-(4-amino-3-fluoro-phenyl)-8-methoxy-pyrido[3,2-d]pyrimidin-2-yl]amino]cyclohexyl]carbamate

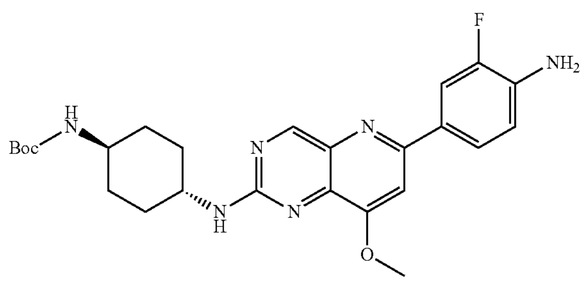 [SMILES: COc1cc(-c2ccc(N)c(F)c2)nc2cnc(N[C@H]3CC[C@H](NC(=O)OC(C)(C)C)CC3)nc12]

A flask was charged with tert-butyl N-[4-[(2-chloro-8-methoxy-pyrido[3,2-d]pyrimidin-6-yl)amino]cyclohexyl]carbamate (95 mg, 0.23 mmol) and 1,2-dimethoxyethane (1 mL) and $H_2O$ (0.25 mL). The mixture was degassed for 10 min with $N_2$ and to this mixture was then added 2-fluoro-4-(4,4,5,5-tetramethyl-1,3,2-dioxaborolan-2-yl)aniline (83 mg, 0.35 mmol), palladium acetate (10 mg, 0.05 mmol), tri-o-tolylphosphine (28 mg, 0.09 mmol) and sodium carbonate (49 mg, 0.47 mmol) and the mixture was stirred at 100° C. under $N_2$ with a condenser overnight. After 16 h, the mixture was then concentrated with silica gel and the crude was purified by silica flash column chromatography (30-90% EtOAc/heptanes) to provide the title compound (85 mg, 76% yield). LCMS (ESI) $[M+H]^+$=483.3.

Step 9: tert-Butyl N-[4-[[6-[3-fluoro-4-(3,3,3-trifluoropropylsulfonylamino)phenyl]-8-methoxy-pyrido[3,2-d]pyrimidin-2-yl]amino]cyclohexyl]carbamate

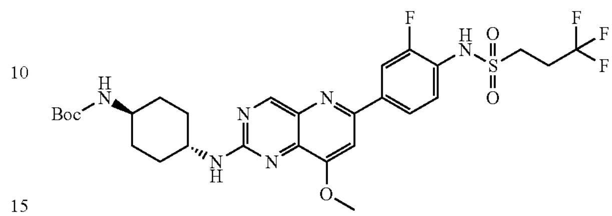

tert-Butyl N-[4-[[6-(4-amino-3-fluoro-phenyl)-8-methoxy-pyrido[3,2-d]pyrimidin-2-yl]amino]cyclohexyl]carbamate (85 mg, 0.18 mmol) was suspended in pyridine (1 mL, 1 mmol) and 3,3,3-trifluoropropane-1-sulfonyl chloride (104 mg, 0.53 mmol) was added. The reaction was stirred at rt for 2 h then concentrated under reduced pressure and directly purified by silica flash column chromatography (10-100% EtOAc/heptanes) to provide the title compound (53 mg, 47% yield). LCMS (ESI) $[M+H]^+$=643.3.

Step 10: N-(4-(2-(((1,4-trans)-4-(Dimethylamino)cyclohexyl)amino)-8-methoxypyrido[3,2-d]pyrimidin-6-yl)-2-fluorophenyl)-3,3,3-trifluoropropane-1-sulfonamide formate

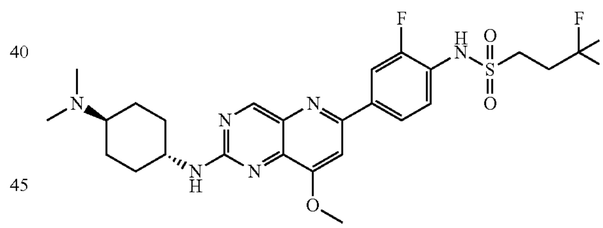

To tert-butyl N-[4-[[6-[3-fluoro-4-(3,3,3-trifluoropropylsulfonylamino)phenyl]-8-methoxy-pyrido[3,2-d]pyrimidin-2-yl]amino]cyclohexyl]carbamate (62 mg, 0.10 mmol) was added TFA (1 mL, 0.10 mmol) and the reaction was stirred at rt for 20 min. To the reaction was added toluene (5 mL) and the solvent was removed in vacuo to give the crude amine, which was dissolved in methanol (1 mL). To the solution was added NaOAc (158 mg, 1.93 mmol) followed by 37% w/w aqueous formaldehyde (96 mg, 0.96 mmol). The reaction was stirred for 5 min before addition of sodium triacetoxyborohydride (81 mg, 0.39 mmol) and stirred at rt for 20 min. The mixture was then directly purified by C18 reverse phase flash chromatography (10-100% MeCN/10 mM aqueous ammonium formate, pH=3.8) to provide the title compound (16 mg, 27% yield).

Example 18: N-(4-(8-Ethyl-2-(((3S,5S)-5-fluoropiperidin-3-yl)amino)pyrido[3,2-d]pyrimidin-6-yl)-2-fluorophenyl)-3,3,3-trifluoropropane-1-sulfonamide formate (Compound 119)

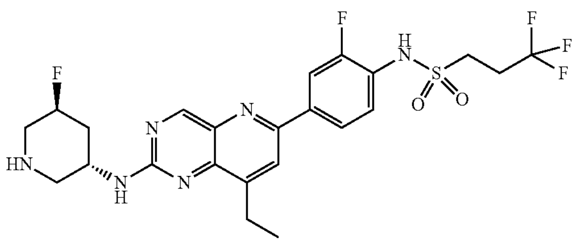 [SMILES: CCc1cc(-c2ccc(NS(=O)(=O)CCC(F)(F)F)c(F)c2)nc2cnc(N[C@@H]3CNC[C@@H](F)C3)nc12]

Step 1: (3S,5S)-tert-Butyl 3-((6-chloro-8-ethylpyrido[3,2-d]pyrimidin-2-yl)amino)-5-fluoropiperidine-1-carboxylate

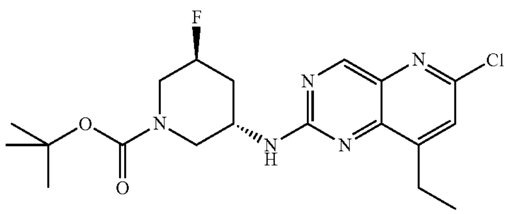 [SMILES: CCc1cc(Cl)nc2cnc(N[C@H]3C[C@H](F)CN(C(=O)OC(C)(C)C)C3)nc12]

Prepared according to Example 14 (Compound 115) step 1 using tert-butyl (3S,5S)-3-amino-5-fluoro-piperidine-1-carboxylate (345 mg, 1.58 mmol), 2,6-dichloro-8-ethyl-pyrido[3,2-d]pyrimidine (300 mg, 1.32 mmol) and N,N-diisopropylethylamine (0.35 mL, 2.01 mmol) to provide the title product (304 mg, 56% yield). LCMS (ESI) [M+H]+=410.2.

Step 2: (3S,5S)-tert-Butyl 3-((6-(4-amino-3-fluorophenyl)-8-ethylpyrido[3,2-d]pyrimidin-2-yl)amino)-5-fluoropiperidine-1-carboxylate

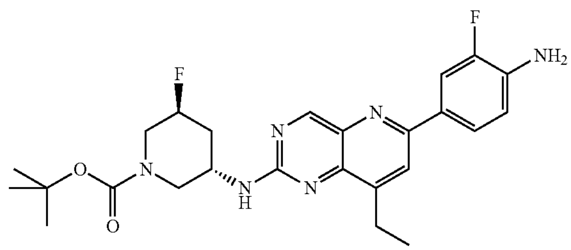 [SMILES: CCc1cc(-c2ccc(N)c(F)c2)nc2cnc(N[C@H]3C[C@H](F)CN(C(=O)OC(C)(C)C)C3)nc12]

Prepared according to Example 14 (Compound 115) step 2 using (3S,5S)-tert-butyl 3-((6-chloro-8-ethylpyrido[3,2-d]pyrimidin-2-yl)amino)-5-fluoropiperidine-1-carboxylate (304 mg, 0.74 mmol), 2-fluoro-4-(4,4,5,5-tetramethyl-1,3,2-dioxaborolan-2-yl)aniline (268 mg, 1.13 mmol), sodium carbonate (157 mg, 1.48 mmol), tri-o-tolylphosphine (46 mg, 0.15 mmol) and palladium acetate (17 mg, 0.08 mmol) to provide the title product (219 mg, 61% yield). LCMS (ESI) [M+H]+=485.1.

Step 3: (3S,5S)-tert-Butyl 3-((8-ethyl-6-(3-fluoro-4-(3,3,3-trifluoropropylsulfonamido)phenyl)pyrido[3,2-d]pyrimidin-2-yl)amino)-5-fluoropiperidine-1-carboxylate

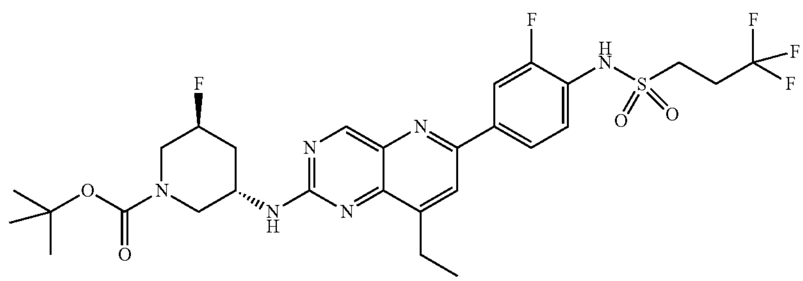 [SMILES: CCc1cc(-c2ccc(NS(=O)(=O)CCC(F)(F)F)c(F)c2)nc2cnc(N[C@H]3C[C@H](F)CN(C(=O)OC(C)(C)C)C3)nc12]

Prepared according to Example 14 (Compound 115) step 3 using (3S,5S)-tert-butyl 3-((6-(4-amino-3-fluorophenyl)-8-ethylpyrido[3,2-d]pyrimidin-2-yl)amino)-5-fluoropiperidine-1-carboxylate (72 mg, 0.15 mmol), 3,3,3-trifluoropropane-1-sulfonyl chloride (0.025 mL, 0.20 mmol) and pyridine (0.30 mL, 3.72 mmol) to provide the title product (69 mg, 72% yield). LCMS (ESI) [M+H]+=645.1.

Step 4: N-(4-(8-Ethyl-2-(((3S,5S)-5-fluoropiperidin-3-yl)amino)pyrido[3,2-d]pyrimidin-6-yl)-2-fluorophenyl)-3,3,3-trifluoropropane-1-sulfonamide formate

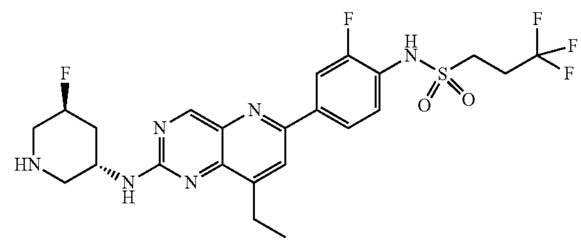 [SMILES: CCc1cc(-c2ccc(NS(=O)(=O)CCC(F)(F)F)c(F)c2)nc2cnc(N[C@@H]3CNC[C@@H](F)C3)nc12]

Prepared according to Example 14 (Compound 115) step 4 using (3S,5S)-tert-butyl 3-((8-ethyl-6-(3-fluoro-4-(3,3,3-trifluoropropylsulfonamido)phenyl)pyrido[3,2-d]pyrimidin-2-yl)amino)-5-fluoropiperidine-1-carboxylate (69 mg, 0.11 mmol) and 4M HCl in dioxane (1.0 mL, 4.0 mmol) to provide the title product (37 mg, 59% yield).

Example 19: N-(2-Chloro-4-(2-(((1,4-trans)-4-(dimethylamino)cyclohexyl)amino)-8-methylpyrido[3,2-d]pyrimidin-6-yl)phenyl)-3,3,3-trifluoropropane-1-sulfonamide (Compound 120)

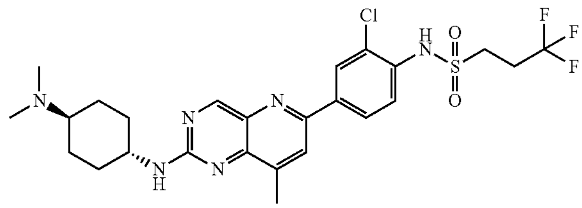 [SMILES: Cc1cc(-c2ccc(NS(=O)(=O)CCC(F)(F)F)c(Cl)c2)nc2cnc(N[C@H]3CC[C@H](N(C)C)CC3)nc12]

Step 1: tert-Butyl ((1,4-trans)-4-((6-(4-amino-3-chlorophenyl)-8-methylpyrido[3,2-d]pyrimidin-2-yl)amino)cyclohexyl)carbamate

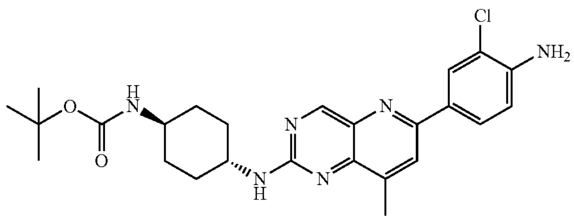 [SMILES: Cc1cc(-c2ccc(N)c(Cl)c2)nc2cnc(N[C@H]3CC[C@H](NC(=O)OC(C)(C)C)CC3)nc12]

Prepared according to Example 12 (Compound 113) step 2 using tert-butyl N-[4-[(6-chloro-8-methyl-pyrido[3,2-d]pyrimidin-2-yl)amino]cyclohexyl]carbamate (150 mg, 0.38 mmol) 2-chloro-4-(4,4,5,5-tetramethyl-1,3,2-dioxaborolan-2-yl)aniline (146 mg, 0.57 mmol), palladium acetate (8.6 mg, 0.04 mmol), tri-o-tolylphosphine (23 mg, 0.08 mmol) and sodium carbonate (81 mg, 0.77 mmol) to provide the title product (135 mg, 73% yield). LCMS (ESI) $[M+H]^+$=483.0.

Step 2: tert-Butyl ((1,4-trans)-4-((6-(3-chloro-4-(3,3,3-trifluoropropylsulfonamido)phenyl)-8-methylpyrido[3,2-d]pyrimidin-2-yl)amino)cyclohexyl)carbamate

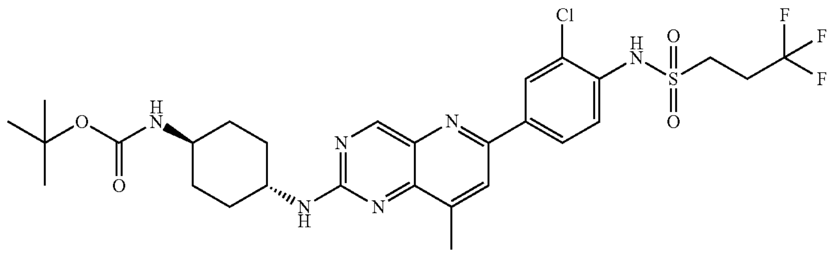 [SMILES: Cc1cc(-c2ccc(NS(=O)(=O)CCC(F)(F)F)c(Cl)c2)nc2cnc(N[C@H]3CC[C@H](NC(=O)OC(C)(C)C)CC3)nc12]

Prepared according to Example 12 (Compound 113) step 3 using tert-butyl ((1,4-trans)-4-((6-(4-amino-3-chlorophenyl)-8-methylpyrido[3,2-d]pyrimidin-2-yl)amino)cyclohexyl)carbamate (135 mg, 0.28 mmol), pyridine (0.5 mL), 3,3,3-trifluoropropane-1-sulfonyl chloride (165 mg, 0.84 mmol) and $CH_2Cl_2$ (0.5 mL) to provide the title product (69 mg, 38% yield). LCMS (ESI) $[M+H]^+$=643.0.

Step 3: N-(4-(2-(((1,4-trans)-4-Aminocyclohexyl)amino)-8-methylpyrido[3,2-d]pyrimidin-6-yl)-2-chlorophenyl)-3,3,3-trifluoropropane-1-sulfonamide 2,2,2-trifluoroacetate

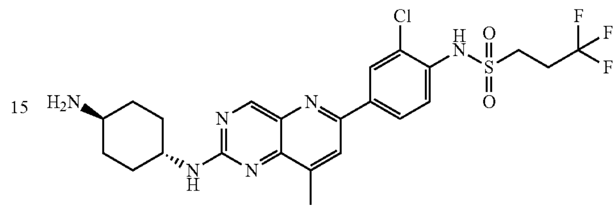

Prepared according to Example 12 (Compound 113) step 4 using tert-butyl ((1,4-trans)-4-((6-(3-chloro-4-(3,3,3-trifluoropropylsulfonamido)phenyl)-8-methylpyrido[3,2-d]pyrimidin-2-yl)amino)cyclohexyl)carbamate (69 mg, 0.11 mmol), trifluoroacetic acid (0.5 mL) and $CH_2Cl_2$ (0.5 mL) to provide the crude title product (72 mg, 100% yield).

Step 4: N-(2-Chloro-4-(2-(((1,4-trans)-4-(dimethylamino)cyclohexyl)amino)-8-methylpyrido[3,2-d]pyrimidin-6-yl)phenyl)-3,3,3-trifluoropropane-1-sulfonamide

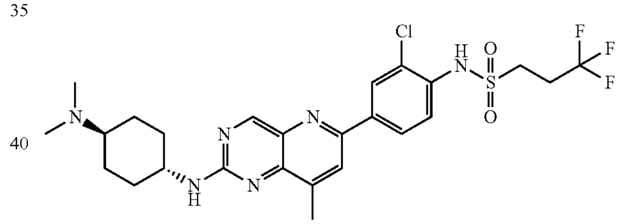

Prepared according to Example 12 (Compound 113) step 5 using N-(4-(2-(((1,4-trans)-4-aminocyclohexyl)amino)-8-methylpyrido[3,2-d]pyrimidin-6-yl)-2-chlorophenyl)-3,3,3-trifluoropropane-1-sulfonamide 2,2,2-trifluoroacetate (72 mg, 0.11 mmol), 37% w/w aqueous formaldehyde (130 mg, 1.61 mmol), sodium acetate (53 mg, 0.64 mmol) sodium triacetoxyborohydride (90 mg, 0.43 mmol) and methanol (3 mL) to provide the title product (16 mg, 26% yield).

Example 20: N-(2-Fluoro-4-(2-(((3S,5S)-5-fluoropiperidin-3-yl)amino)-8-methylpyrido[3,2-d]pyrimidin-6-yl)phenyl)-1-(4-fluorophenyl)methanesulfonamide formate (Compound 121)

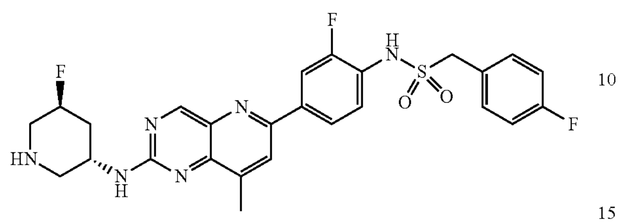

Step 1: (3S,5S)-tert-Butyl 3-fluoro-5-((6-(3-fluoro-4-((4-fluorophenyl)methylsulfonamido)phenyl)-8-methylpyrido[3,2-d]pyrimidin-2-yl)amino)piperidine-1-carboxylate

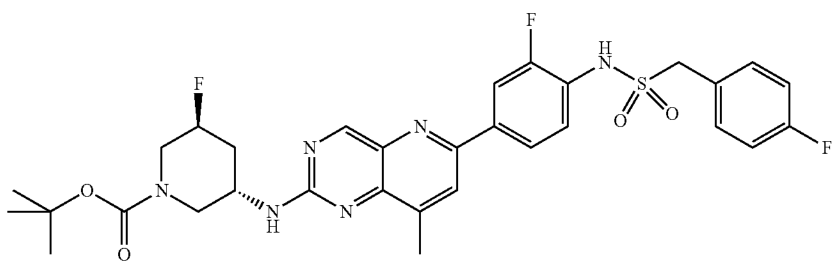 [SMILES: Cc1cc(-c2ccc(NS(=O)(=O)Cc3ccc(F)cc3)c(F)c2)nc2cnc(N[C@H]3C[C@H](F)CN(C(=O)OC(C)(C)C)C3)nc12]

Prepared according to Example 14 (Compound 15) step 3 using (3S,5S)-tert-butyl 3-((6-(4-amino-3-fluorophenyl)-8-methylpyrido[3,2-d]pyrimidin-2-yl)amino)-5-fluoropiperidine-1-carboxylate (50 mg, 0.11 mmol), (4-fluorophenyl) methanesulfonyl chloride (29 mg, 0.14 mmol) and pyridine (0.22 mL, 2.67 mmol) to provide the title product (20 mg, 29% yield). LCMS (ESI) [M+H]+=643.1.

Step 2: N-(2-Fluoro-4-(2-(((3S,5S)-5-fluoropiperidin-3-yl)amino)-8-methylpyrido[3,2-d]pyrimidin-6-yl)phenyl)-1-(4-fluorophenyl)methanesulfonamide formate

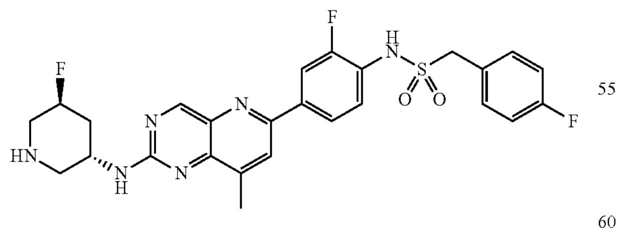

Prepared according to Example 14 (Compound 115) step 4 using (3S,5S)-tert-butyl 3-fluoro-5-((6-(3-fluoro-4-((4-fluorophenyl)methylsulfonamido)phenyl)-8-methylpyrido[3,2-d]pyrimidin-2-yl)amino)piperidine-1-carboxylate (40 mg, 0.06 mmol) and 4N HCl in dioxane (1.0 mL, 4.0 mmol) to provide the title product (14 mg, 38% yield).

-

Example 21: N-(4-(8-Ethyl-2-(((3S,5S)-5-fluoropiperidin-3-yl)amino)pyrido[3,2-d]pyrimidin-6-yl)-2-fluorophenyl)-1-phenylmethanesulfonamide formate (Compound 122)

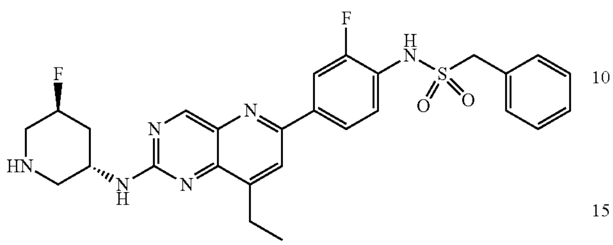

Step 1: (3S,5S)-tert-Butyl 3-((8-ethyl-6-(3-fluoro-4-(phenylmethylsulfonamido)phenyl)pyrido[3,2-d]pyrimidin-2-yl)amino)-5-fluoropiperidine-1-carboxylate

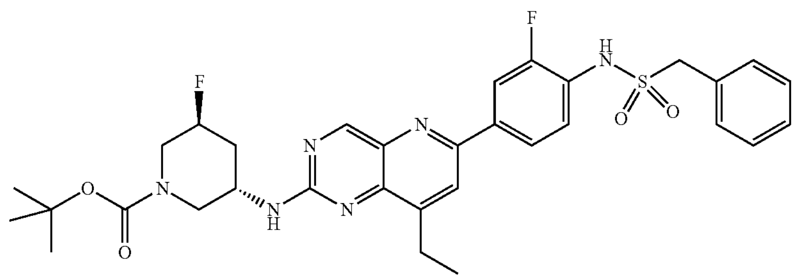 [SMILES: CCc1cc(-c2ccc(NS(=O)(=O)Cc3ccccc3)c(F)c2)nc2cnc(N[C@H]3C[C@H](F)CN(C(=O)OC(C)(C)C)C3)nc12]

Prepared according to Example 14 (Compound 115) step 3 using (3S,5S)-tert-butyl 3-((6-(4-amino-3-fluorophenyl)-8-ethylpyrido[3,2-d]pyrimidin-2-yl)amino)-5-fluoropiperidine-1-carboxylate (72 mg, 0.15 mmol), phenylmethanesulfonyl chloride (0.024 mL, 0.19 mmol) and pyridine (0.30 mL, 3.72 mmol) to provide the title product (68 mg, 72% yield). LCMS (ESI) [M+H]+=639.3.

Step 2: N-(4-(8-Ethyl-2-(((3S,5S)-5-fluoropiperidin-3-yl)amino)pyrido[3,2-d]pyrimidin-6-yl)-2-fluorophenyl)-1-phenylmethanesulfonamide formate

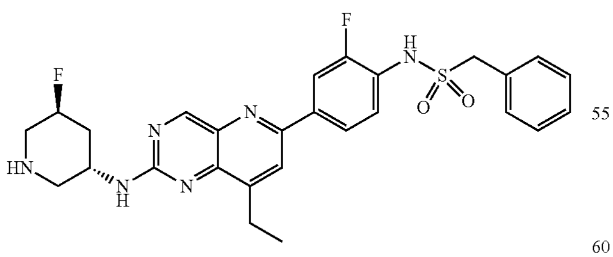

Prepared according to Example 14 (Compound 115) step 4 using (3S,5S)-tert-butyl 3-((8-ethyl-6-(3-fluoro-4-(phenylmethylsulfonamido)phenyl)pyrido[3,2-d]pyrimidin-2-yl)amino)-5-fluoropiperidine-1-carboxylate (68 mg, 0.11 mmol) and 4N HCl in dioxane (1.0 mL, 4.0 mmol) to provide the title product (33 mg, 53% yield).

Example 22: 2-Chloro-N-(4-(8-ethyl-2-(((3S,5S)-5-fluoropiperidin-3-yl)amino)pyrido[3,2-d]pyrimidin-6-yl)-2-fluorophenyl)benzenesulfonamide formate (Compound 123)

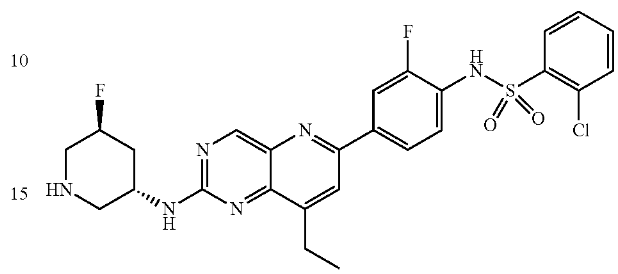

Step 1: (3S,5S)-tert-Butyl 3-((6-(4-(2-chlorophenylsulfonamido)-3-fluorophenyl)-8-ethylpyrido[3,2-d]pyrimidin-2-yl)amino)-5-fluoropiperidine-1-carboxylate

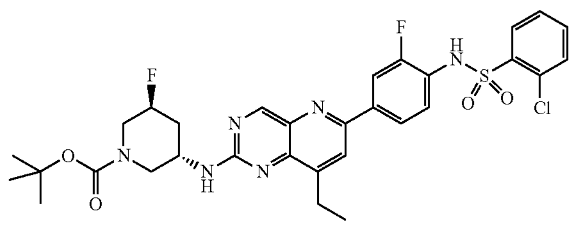 [SMILES: CCc1cc(-c2ccc(NS(=O)(=O)c3ccccc3Cl)c(F)c2)nc2cnc(N[C@H]3C[C@H](F)CN(C(=O)OC(C)(C)C)C3)nc12]

Prepared according to Example 14 (Compound 115) step 3 using (3S,5S)-tert-butyl 3-((6-(4-amino-3-fluorophenyl)-8-ethylpyrido[3,2-d]pyrimidin-2-yl)amino)-5-fluoropiperidine-1-carboxylate (72 mg, 0.15 mmol), 2-chlorobenzenesulfonyl chloride (41 mg, 0.19 mmol) and pyridine (0.30 mL, 3.72 mmol) to provide the title product (78 mg, 80% yield). LCMS (ESI) [M+H]+=659.0.

Step 2: 2-Chloro-N-(4-(8-ethyl-2-(((3S,5S)-5-fluoropiperidin-3-yl)amino)pyrido[3,2-d]pyrimidin-6-yl)-2-fluorophenyl)benzenesulfonamide formate

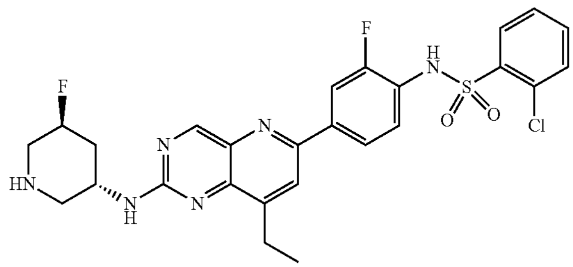 [SMILES: CCc1cc(-c2ccc(NS(=O)(=O)c3ccccc3Cl)c(F)c2)nc2cnc(N[C@@H]3CNC[C@@H](F)C3)nc12]

Prepared according to Example 14 (Compound 115) step 4 using (3S,5S)-tert-butyl 3-((6-(4-(2-chlorophenylsulfonamido)-3-fluorophenyl)-8-ethylpyrido[3,2-d]pyrimidin-2-yl)amino)-5-fluoropiperidine-1-carboxylate (78 mg, 0.12 mmol) and 4N HCl in dioxanes (1.0 mL, 4.0 mmol) to provide the title product (46 mg, 64% yield).

Example 23: N-(4-(2-(((1,4-trans)-4-(Dimethylamino)cyclohexyl)amino)-8-isopropylpyrido[3,2-d]pyrimidin-6-yl)-2-fluorophenyl)-3,3,3-trifluoropropane-1-sulfonamide (Compound 124)

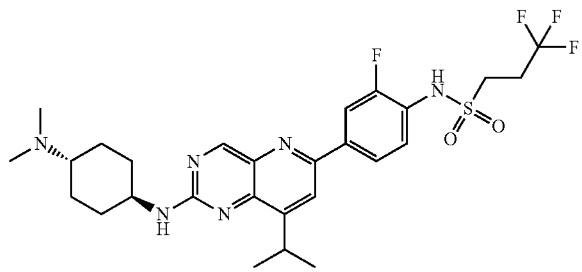 [SMILES: CC(C)c1cc(-c2ccc(NS(=O)(=O)CCC(F)(F)F)c(F)c2)nc2cnc(N[C@H]3CC[C@H](N(C)C)CC3)nc12]

Step 1: 3-Amino-6-chloro-4-(prop-1-en-2-yl)picolinonitrile

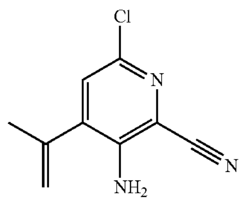

To 3-amino-4-bromo-6-chloro-pyridine-2-carbonitrile (3.50 g, 15.1 mmol), potassium isopropenyltrifluoroborate (1.91 g, 12.9 mmol), $Na_2CO_3$ (2.28 g, 21.5 mmol) and tetrakis(triphenylphosphine)palladium(0) (0.62 g, 0.54 mmol) were added degassed 1,2-dimethoxyethane (56 mL) and degassed water (14 mL). The mixture was heated at 100° C. for 3 h then partitioned between water and EtOAc. The phases were separated and the organic extract was washed with saturated aqueous sodium chloride, dried over $Na_2SO_4$, filtered and concentrated. The crude material was purified by silica flash chromatography (10-50% EtOAc/heptane) to provide the title product (2.53 g, 87% yield). LCMS (ESI) $[M+H]^+$=194.0.

Step 2: 3-Amino-6-chloro-4-isopropylpicolinonitrile

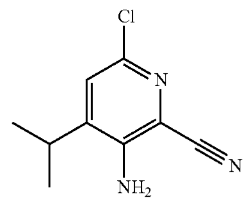

To 3-amino-6-chloro-4-isopropenyl-pyridine-2-carbonitrile (1.95 g, 10.1 mmol) in methanol (50 mL) under nitrogen was added 10% w/w Pd/C (400 mg). The flask was submitted to 5 cycles of vacuum hydrogen purge and stirred at rt under hydrogen atmosphere. After 18 h, nitrogen was bubbled in the solution for 10 minutes. The solution was filtered through Celite, rinsed with EtOAc and concentrated. The crude material was purified by flash chromatography through silica gel (10-100% EtOAc/heptane) to provide the title product (0.67 g, 35% yield). $^1H$ NMR (400 MHz, $CDCl_3$) δ 7.19 (s, 1H), 4.51 (s, 2H), 2.84 (hept, J=6.8 Hz, 1H), 1.29 (d, J=6.8 Hz, 6H).

Step 3: 3-Amino-6-chloro-4-isopropylpicolinamide

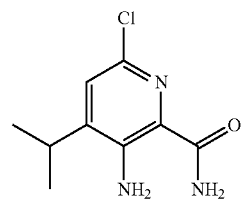

To 3-amino-6-chloro-4-isopropyl-pyridine-2-carbonitrile (0.67 g, 3.42 mmol) was added concentrated sulfuric acid (9.3 mL, 174 mmol) and the reaction mixture was stirred for 2 h at 70° C. then cooled down to rt and slowly added to ice. The aqueous mixture was extracted with $CH_2Cl_2$ (2×50 mL) then with 10% $MeOH/CH_2Cl_2$ (2×50 mL). The organic extracts were combined, dried over anhydrous $Na_2SO_4$, filtered and concentrated to provide the title compound (0.56 g, 77% yield). LCMS (ESI) $[M+H]^+$=214.1, 216.0.

Step 4: 6-Chloro-8-isopropylpyrido[3,2-d]pyrimidine-2,4-diol

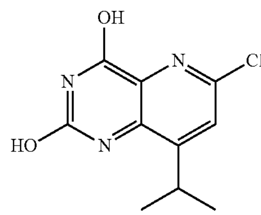 [SMILES: CC(C)c1cc(Cl)nc2c(O)nc(O)nc12]

Prepared according to Example 13 (Compound 114) step 5 using 3-amino-6-chloro-4-isopropyl-pyridine-2-carboxamide (0.56 g, 2.62 mmol), triphosgene (0.39 g, 1.31 mmol) and 1,4-dioxane (17 mL) to provide the title compound (614 mg, 97% yield). LCMS (ESI) $[M+H]^+$=240.0, 242.0.

Step 5: 2,6-Dichloro-8-isopropylpyrido[3,2-d]pyrimidine

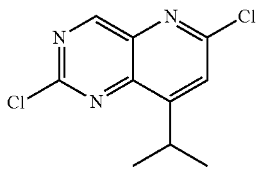

Following the procedure in Example 13 (Compound 114) step 6 using 6-chloro-8-isopropyl-pyrido[3,2-d]pyrimidine-2,4-diol (0.61 g, 2.56 mmol), phosphorus oxychloride (3.24 mL, 34.7 mmol) and N,N-diisopropylamine (0.89 mL, 5.12 mmol) provided crude 2,4,6-trichloro-8-isopropylpyrido[3,2-d]pyrimidine.

Following the procedure in Example 13 (Compound 114) step 6 using crude 2,4,6-trichloro-8-isopropyl-pyrido[3,2-d]pyrimidine (0.71 g, 2.56 mmol) prepared above, $Pd(PPh_3)_4$ (148 mg, 0.13 mmol) tri-butyltin hydride (0.76 mL, 2.82 mmol) and toluene (22.8 mL) provided the title compound (85 mg, 14% yield).

Step 6: tert-Butyl ((1,4-trans)-4-((6-chloro-8-isopropylpyrido[3,2-d]pyrimidin-2-yl)amino)cyclohexyl) carbamate

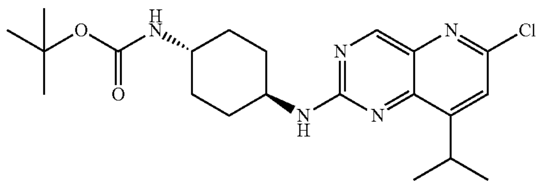 [SMILES: CC(C)c1cc(Cl)nc2cnc(N[C@H]3CC[C@H](NC(=O)OC(C)(C)C)CC3)nc12]

Prepared according to Example 13 (Compound 114) step 7 using 2,6-dichloro-8-isopropyl-pyrido[3,2-d]pyrimidine (80 mg, 0.33 mmol), N-Boc-trans-1,4-cyclohexanediamine (92 mg, 0.43 mmol), N,N-diisopropylethylamine (115 μL, 0.66 mmol) and DMSO (1.1 mL) to provide the title compound (82 mg, 59% yield). LCMS (ESI) $[M+H]^+$=420.3.

Step 7: tert-Butyl ((1,4-trans)-4-((6-(4-amino-3-fluorophenyl)-8-isopropylpyrido[3,2-d]pyrimidin-2-yl)amino)cyclohexyl)carbamate

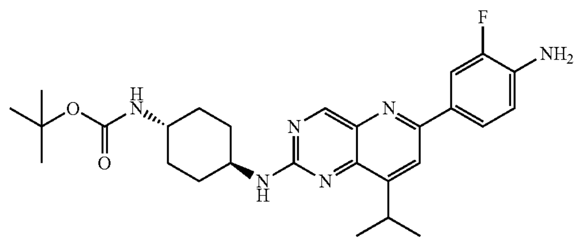 [SMILES: CC(C)c1cc(-c2ccc(N)c(F)c2)nc2cnc(N[C@H]3CC[C@H](NC(=O)OC(C)(C)C)CC3)nc12]

Prepared according to Example 13 (Compound 114) step 8 using tert-butyl N-[4-[(6-chloro-8-isopropyl-pyrido[3,2-d]pyrimidin-2-yl)amino]cyclohexyl]carbamate (80 mg, 0.19 mmol), 2-fluoro-4-(4,4,5,5-tetramethyl-1,3,2-dioxaborolan-2-yl)aniline (72 mg, 0.30 mmol), palladium acetate (4.3 mg, 0.02 mmol), tri-o-tolylphosphine (12 mg, 0.04 mmol), sodium carbonate (40 mg, 0.38 mmol), degassed 1,2-dimethoxyethane (1.4 mL) and degassed $H_2O$ (0.4 mL) to provide the title compound (52 mg, 55% yield). LCMS (ESI) $[M+H]^+$=495.1.

Step 8: tert-Butyl ((1,4-trans)-4-((6-(3-fluoro-4-(3,3,3-trifluoropropylsulfonamido)phenyl)-8-isopropylpyrido[3,2-d]pyrimidin-2-yl)amino)cyclohexyl) carbamate

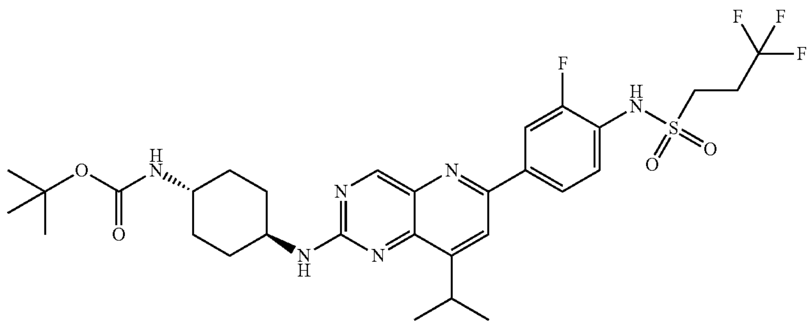 [SMILES: CC(C)c1cc(-c2ccc(NS(=O)(=O)CCC(F)(F)F)c(F)c2)nc2cnc(N[C@H]3CC[C@H](NC(=O)OC(C)(C)C)CC3)nc12]

Prepared according to Example 13 (Compound 114) step 9 using tert-butyl N-[4-[[6-(4-amino-3-fluoro-phenyl)-8-isopropyl-pyrido[3,2-d]pyrimidin-2-yl]amino]cyclohexyl] carbamate (52 mg, 0.11 mmol), pyridine (127 μL, 1.58 mmol), 3,3,3-trifluoropropane-1-sulfonyl chloride (17 μL, 0.14 mmol) and $CH_2Cl_2$ (1.3 mL) to provide the title compound (68 mg, 99% yield). LCMS (ESI) $[M+H]^+$=655.1.

Step 9: N-(4-(2-(((1,4-trans)-4-Aminocyclohexyl) amino)-8-isopropylpyrido[3,2-d]pyrimidin-6-yl)-2-fluorophenyl)-3,3,3-trifluoropropane-1-sulfonamide

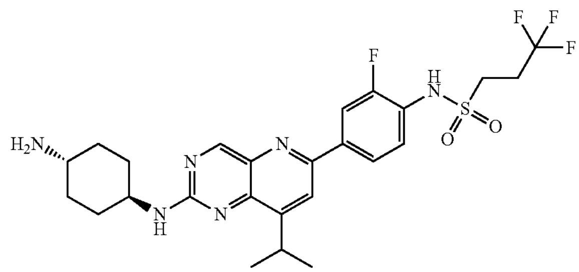 [SMILES: CC(C)c1cc(-c2ccc(NS(=O)(=O)CCC(F)(F)F)c(F)c2)nc2cnc(N[C@H]3CC[C@H](N)CC3)nc12]

Prepared according to Example 13 (Compound 114) step 10 using tert-butyl N-[4-[[6-[3-fluoro-4-(3,3,3-trifluoropropylsulfonylamino)phenyl]-8-isopropyl-pyrido[3,2-d]pyrimidin-2-yl]amino]cyclohexyl]carbamate (68 mg, 0.10 mmol)) trifluoroacetic acid (0.17 mL, 2.16 mmol) and $CH_2Cl_2$ (0.5 mL) to provide the crude title product (69 mg, 100% yield). LCMS (ESI) $[M+H]^+$=555.0.

Step 10: N-(4-(2-(((1,4-trans)-4-(Dimethylamino) cyclohexyl)amino)-8-isopropylpyrido[3,2-d]pyrimidin-6-yl)-2-fluorophenyl)-3,3,3-trifluoropropane-1-sulfonamide

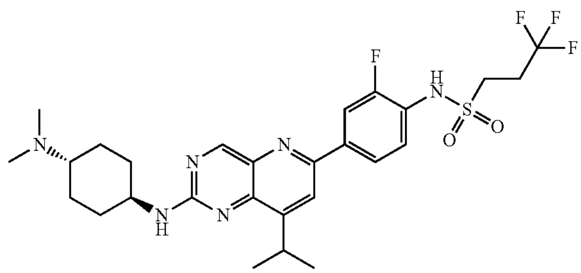 [SMILES: CC(C)c1cc(-c2ccc(NS(=O)(=O)CCC(F)(F)F)c(F)c2)nc2cnc(N[C@H]3CC[C@H](N(C)C)CC3)nc12]

Prepared according to Example 13 (Compound 114) step 11 using N-[4-[2-[(4-aminocyclohexyl)amino]-8-isopropyl-pyrido[3,2-d]pyrimidin-6-yl]-2-fluoro-phenyl]-3,3,3-trifluoro-propane-1-sulfonamide; 2,2,2-trifluoroacetic acid (68 mg, 0.10 mmol), sodium acetate (50 mg, 0.61 mmol), 37% w/w aqueous formaldehyde (120 μL, 1.53 mmol), sodium triacetoxyborohydride (85 mg, 0.41 mmol) and methanol (0.9 mL) to provide the title product (31 mg, 52% yield).

Example 24: N-(5-(2-(((1,4-trans)-4-(Dimethylamino)cyclohexyl)amino)-8-methylpyrido[3,2-d]pyrimidin-6-yl)pyridin-2-yl)-3,3,3-trifluoropropane-1-sulfonamide (Compound 125)

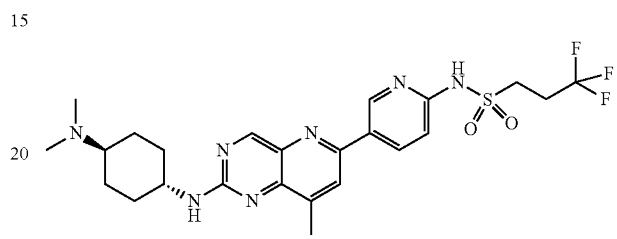

Step 1: tert-Butyl ((1,4-trans)-4-((6-(6-aminopyridin-3-yl)-8-methylpyrido[3,2-d]pyrimidin-2-yl) amino)cyclohexyl)carbamate

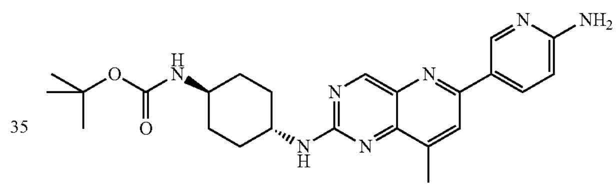

In a 20 mL microwave vial, were added tert-butyl ((1,4-trans)-4-((6-chloro-8-methylpyrido[3,2-d]pyrimidin-2-yl) amino)cyclohexyl)carbamate (100 mg, 0.26 mmol), 2-aminopyridine-5-boronic acid pinacol ester (85 mg, 0.39 mmol) and $K_2CO_3$ (140 mg, 1.01 mmol), 1,4-dioxane (6 mL), and water (1.5 mL). The mixture was degassed 5 minutes before the addition of $Pd(PPh_3)_4$ (45 mg, 0.04 mmol) and then the mixture was irradiated in the microwave for 15 minutes at 150° C. The mixture was diluted with $H_2O$, extracted twice with EtOAc, dried over anhydrous $MgSO_4$, filtered and concentrated under reduced pressure. The crude material was purified by silica flash chromatography (100% EtOAc) to provide the title compound (125 mg, 109% yield). LCMS (ESI) [M+H]+=450.0.

Step 2: tert-Butyl ((1,4-trans)-4-((8-methyl-6-(6-(3,3,3-trifluoropropylsulfonamido)pyridin-3-yl)pyrido [3,2-d]pyrimidin-2-yl)amino)cyclohexyl)carbamate

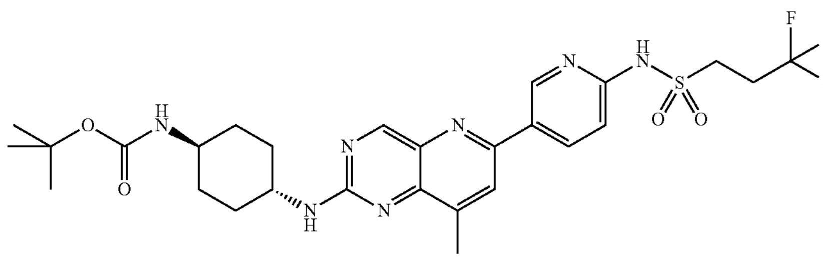

To a mixture of tert-butyl ((1,4-trans)-4-((6-(6-aminopyridin-3-yl)-8-methylpyrido[3,2-d]pyrimidin-2-yl)amino)cyclohexyl)carbamate (94 mg, 0.21 mmol) and DMAP (58 mg, 0.48 mmol), in pyridine (4.7 mL), was added 3,3,3-trifluoropropane-1-sulfonyl chloride (80 μL, 0.63 mmol). The resulting solution was stirred 2 h at rt then pyridine was removed in vacuo. The crude material was purified by flash chromatography through silica gel (0-100% EtOAc/Heptanes) to provide the title compound (73 mg, 57% yield). LCMS (ESI) [M+H]+=610.2.

Step 3: N-(5-(2-(((1,4-trans)-4-Aminocyclohexyl)amino)-8-methylpyrido[3,2-d]pyrimidin-6-yl)pyridin-2-yl)-3,3,3-trifluoropropane-1-sulfonamide

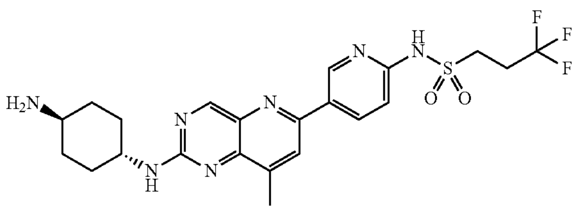 [SMILES: Cc1cc(-c2ccc(NS(=O)(=O)CCC(F)(F)F)nc2)nc2cnc(N[C@H]3CC[C@H](N)CC3)nc12]

TFA (0.5 mL, 6.5 mmol) was added to a solution of tert-butyl ((1,4-trans)-4-((8-methyl-6-(6-(3,3,3-trifluoropropylsulfonamido)pyridin-3-yl)pyrido[3,2-d]pyrimidin-2-yl)amino)cyclohexyl)carbamate (73 mg, 0.12 mmol), in $CH_2Cl_2$ (1 mL). The resulting mixture was stirred 1 h at rt then volatiles were evaporated in vacuo. The residue was purified directly by C18 reverse phase flash chromatography (0-40% MeCN/10 mM aqueous ammonium formate, pH=3.8) to provide 30 mg (49% yield) of the title compound. LCMS (ESI) $[M+H]^+$=507.9.

Step 4: N-(5-(2-(((1,4-trans)-4-(Dimethylamino)cyclohexyl)amino)-8-methylpyrido[3,2-d]pyrimidin-6-yl)pyridin-2-yl)-3,3,3-trifluoropropane-1-sulfonamide

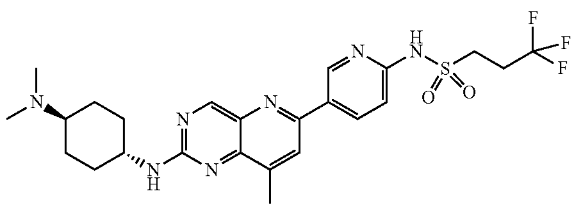 [SMILES: Cc1cc(-c2ccc(NS(=O)(=O)CCC(F)(F)F)nc2)nc2cnc(N[C@H]3CC[C@H](N(C)C)CC3)nc12]

To a solution of N-(5-(2-(((1,4-trans)-4-aminocyclohexyl)amino)-8-methylpyrido[3,2-d]pyrimidin-6-yl)pyridin-2-yl)-3,3,3-trifluoropropane-1-sulfonamide (30 mg, 0.06 mmol), in methanol (1.5 mL), was added 37% w/w aqueous formaldehyde (0.07 mL, 0.87 mmol) followed by sodium triacetoxyborohydride (50 mg, 0.24 mmol). The resulting mixture was stirred at rt. After 8 h, an additional portion of 37% w/w aqueous formaldehyde (0.1 m, 1.24 mmol) and sodium triacetoxyborohydride (25 mg, 0.12 mmol) were added and continued stirring at rt. After a further 16 h, the volatiles were evaporated in vacuo and the residue was directly purified by C18 reverse phase flash chromatography (15-35% MeCN/10 mM aqueous ammonium bicarbonate, pH=10 to provide the title compound (6 mg, 19% yield).

Example 25: N-(5-(2-(((1,4-trans)-4-(Dimethylamino)cyclohexyl)amino)-8-methylpyrido[3,2-d]pyrimidin-6-yl)-6-methylpyridin-2-yl)-3,3,3-trifluoropropane-1-sulfonamide (Compound 126)

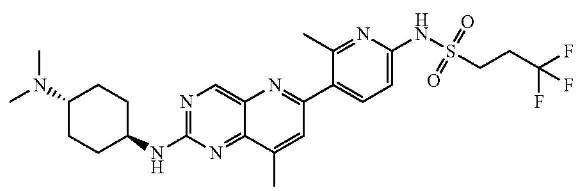 [SMILES: Cc1nc(NS(=O)(=O)CCC(F)(F)F)ccc1-c1cc(C)c2nc(N[C@H]3CC[C@H](N(C)C)CC3)ncc2n1]

Step 1: tert-Butyl ((1,4-trans)-4-((6-(6-amino-2-methylpyridin-3-yl)-8-methylpyrido[3,2-d]pyrimidin-2-yl)amino)cyclohexyl)carbamate

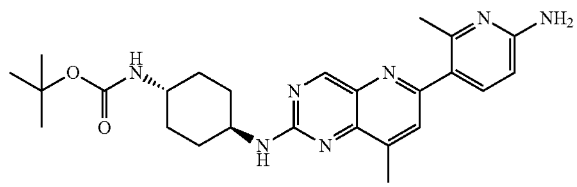 [SMILES: Cc1nc(N)ccc1-c1cc(C)c2nc(N[C@H]3CC[C@H](NC(=O)OC(C)(C)C)CC3)ncc2n1]

In a 20 mL microwave vial was added tert-butyl N-[4-[(6-chloro-8-methyl-pyrido[3,2-d]pyrimidin-2-yl)amino]cyclohexyl]carbamate (200 mg, 0.51 mmol), 6-methyl-5-(4,4,5,5-tetramethyl-1,3,2-dioxaborolan-2-yl)pyridin-2-amine (179 mg, 0.77 mmol), $K_2CO_3$ (282 mg, 2.04 mmol), and $Pd(PPh_3)_4$ (59 mg, 0.05 mmol) in that order. To the mixture was then added 1,4-dioxane (4 mL) and $H_2O$ (1 mL) and the solution was sparged with $N_2$ for 5 min then irradiated 15 minutes at 150° C. in a microwave reactor. The reaction was diluted with EtOAc (40 mL), dried anhydrous $Na_2SO_4$, filtered through Celite and concentrated. The crude material was purified by flash chromatography through silica gel (0-100% EtOAc/heptanes) to provide the title product (207 mg, 87% yield). LCMS (ESI) $[M+H]^+$=464.1.

Step 2: tert-Butyl ((1,4-trans)-4-((8-methyl-6-(2-methyl-6-(3,3,3-trifluoropropylsulfonamido)pyridin-3-yl)pyrido[3,2-d]pyrimidin-2-yl)amino)cyclohexyl) carbamate

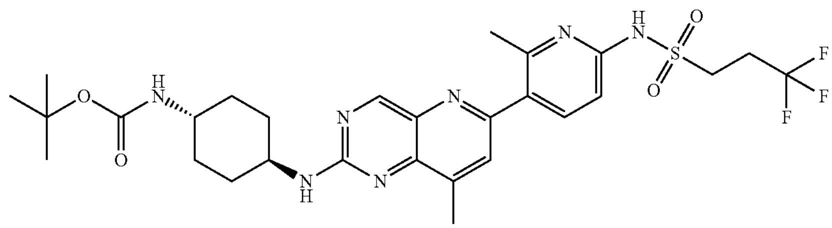 [SMILES: Cc1nc(NS(=O)(=O)CCC(F)(F)F)ccc1-c1cc(C)c2nc(N[C@H]3CC[C@H](NC(=O)OC(C)(C)C)CC3)ncc2n1]

tert-Butyl N-[4-[[6-(6-amino-2-methyl-3-pyridyl)-8-methyl-pyrido[3,2-d]pyrimidin-2-yl]amino]cyclohexyl]carbamate (207 mg, 0.45 mmol) was suspended in $CH_2Cl_2$ (6 mL). 1,8-diazabicyclo[5.4.0]undex-7-ene (0.33 mL, 2.23 mmol) was then added followed by addition of 3,3,3-trifluoropropane-1-sulfonyl chloride (263 mg, 1.34 mmol) in $CH_2Cl_2$ (0.2 mL). The mixture stirred at rt overnight. MeOH (10 mL) was then added and volatiles removed under reduced pressure (repeated ×2). The crude material was purified by silica flash chromatography (0-100% EtOAc/heptanes) to provide the title product (125 mg, 45% yield). LCMS (ESI) $[M+H]^+$=624.1.

Step 3: N-(5-(2-(((1,4-trans)-4-Aminocyclohexyl)amino)-8-methylpyrido[3,2-d]pyrimidin-6-yl)-6-methylpyridin-2-yl)-3,3,3-trifluoropropane-1-sulfonamide 2,2,2-trifluoroacetate

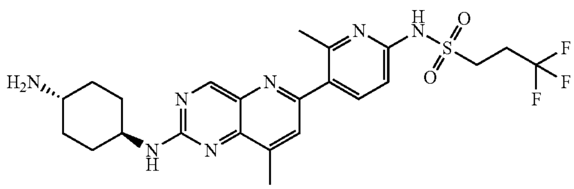 [SMILES: Cc1nc(NS(=O)(=O)CCC(F)(F)F)ccc1-c1cc(C)c2nc(N[C@H]3CC[C@H](N)CC3)ncc2n1]

Prepared according to Example 12 (Compound 113) step 4 using tert-butyl ((1,4-trans)-4-((8-methyl-6-(2-methyl-6-(3,3,3-trifluoropropylsulfonamido)pyridin-3-yl)pyrido[3,2-d]pyrimidin-2-yl)amino)cyclohexyl)carbamate (125 mg, 0.20 mmol), trifluoroacetic acid (0.5 mL) and $CH_2Cl_2$ (2 mL) to provide the crude title product (127 mg, 100% yield).

Step 4: N-(5-(2-(((1,4-trans)-4-(Dimethylamino)cyclohexyl)amino)-8-methylpyrido[3,2-d]pyrimidin-6-yl)-6-methylpyridin-2-yl)-3,3,3-trifluoropropane-1-sulfonamide

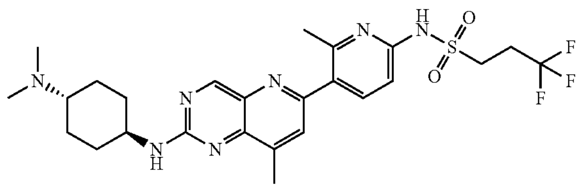 [SMILES: Cc1nc(NS(=O)(=O)CCC(F)(F)F)ccc1-c1cc(C)c2nc(N[C@H]3CC[C@H](N(C)C)CC3)ncc2n1]

Prepared according to Example 12 (Compound 113) step 5 sing N-(5-(2-(((1,4-trans)-4-aminocyclohexyl)amino)-8-methylpyrido[3,2-d]pyrimidin-6-yl)-6-methylpyridin-2-yl)-3,3,3-trifluoropropane-1-sulfonamide 2,2,2-trifluoroacetate (127 mg, 0.2 mmol), 37% w/w aqueous formaldehyde (244 mg, 3.01 mmol), sodium acetate (99 mg, 1.2 mmol), sodium triacetoxyborohydride (168 mg, 0.80 mmol) and methanol (4 mL) to provide the title product (25 mg, 23% yield).

Example 26: N-(4-(2-(((1,4-trans)-4-(Dimethylamino)cyclohexyl)amino)-8-methylpyrido[3,2-d]pyrimidin-6-yl)-2-fluorophenyl)-3-methylbutanamide (Compound 127)

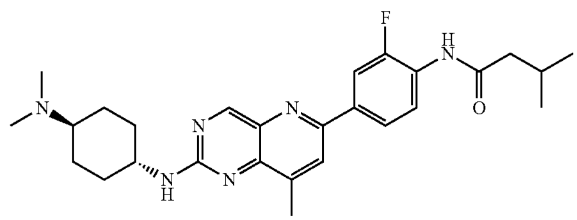 [SMILES: Cc1cc(-c2ccc(NC(=O)CC(C)C)c(F)c2)nc2cnc(N[C@H]3CC[C@H](N(C)C)CC3)nc12]

Step 1: tert-Butyl ((1,4-trans)-4-((6-(3-fluoro-4-(3-methylbutanamido)phenyl)-8-methylpyrido[3,2-d]pyrimidin-2-yl)amino)cyclohexyl)carbamate

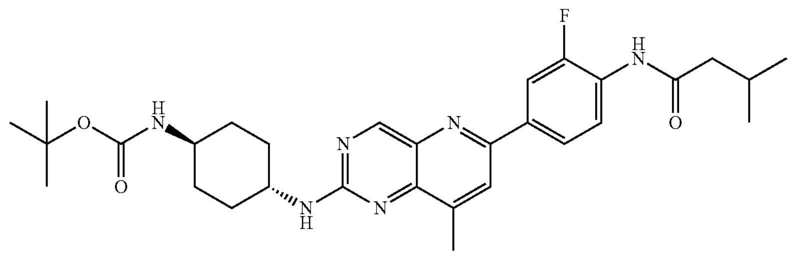 [SMILES: Cc1cc(-c2ccc(NC(=O)CC(C)C)c(F)c2)nc2cnc(N[C@H]3CC[C@H](NC(=O)OC(C)(C)C)CC3)nc12]

tert-Butyl N-[4-[[6-(4-amino-3-fluoro-phenyl)-8-methyl-pyrido[3,2-d]pyrimidin-2-yl]amino]cyclohexyl]carbamate (120 mg, 0.26 mmol) was dissolved in a mixture of $CH_2Cl_2$ (5 mL) and pyridine (0.5 mL). To this mixture was then added isovaleryl chloride (0.09 mL, 0.77 mmol) and the mixture stirred at rt for 16 h. The reaction was diluted with MeOH (5 mL) and concentrated (repeated ×2). The crude material was purified by silica flash chromatography (0-100% EtOAc/heptane) to provide the title product (63 mg, 44% yield). LCMS (ESI) $[M+H]^+$=551.1.

Step 2: N-(4-(2-(((1,4-trans)-4-Aminocyclohexyl)amino)-8-methylpyrido[3,2-d]pyrimidin-6-yl)-2-fluorophenyl)-3-methylbutanamide 2,2,2-trifluoroacetate

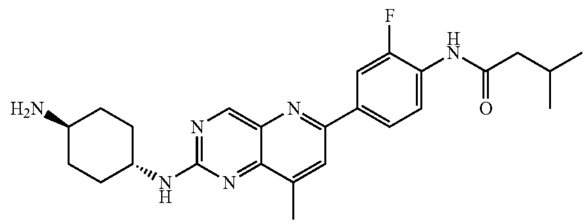 [SMILES: Cc1cc(-c2ccc(NC(=O)CC(C)C)c(F)c2)nc2cnc(N[C@H]3CC[C@H](N)CC3)nc12]

Prepared according to Example 11 (Compound 112) step 4 using tert-butyl ((1,4-trans)-4-((6-(3-fluoro-4-(3-methylbutanamido)phenyl)-8-methylpyrido[3,2-d]pyrimidin-2-yl)amino)cyclohexyl)carbamate (63 mg, 0.11 mmol), trifluoroacetic acid (0.5 mL) and $CH_2Cl_2$ (2 mL) to provide the crude title product (62 mg, 100% yield).

Step 3: N-(4-(2-(((1,4-trans)-4-(Dimethylamino)cyclohexyl)amino)-8-methylpyrido[3,2-d]pyrimidin-6-yl)-2-fluorophenyl)-3-methylbutanamide

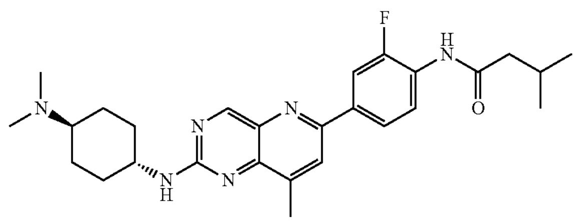 [SMILES: Cc1cc(-c2ccc(NC(=O)CC(C)C)c(F)c2)nc2cnc(N[C@H]3CC[C@H](N(C)C)CC3)nc12]

Prepared according to Example 11 (Compound 12) step 5 using N-(4-(2-(((1,4-trans)-4-aminocyclohexyl)amino)-8-methylpyrido[3,2-d]pyrimidin-6-yl)-2-fluorophenyl)-3-methylbutanamide 2,2,2-trifluoroacetate (62 mg, 0.11 mmol), 37% w/w aqueous formaldehyde (139 mg, 1.72 mmol), sodium acetate (56 mg, 0.69 mmol), sodium triacetoxyborohydride (96 mg, 0.46 mmol) and methanol (3 mL) to provide the title product (9 mg, 16% yield).

Example 27: 2-Chloro-N-(4-(2-(((1,4-trans)-4-(dimethylamino)cyclohexyl)amino)-8-methylpyrido[3,2-d]pyrimidin-6-yl)-2-fluorophenyl)benzenesulfonamide (Compound 128)

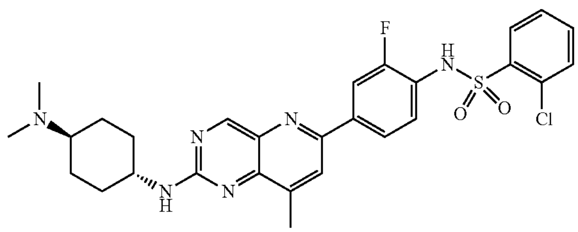 [SMILES: Cc1cc(-c2ccc(NS(=O)(=O)c3ccccc3Cl)c(F)c2)nc2cnc(N[C@H]3CC[C@H](N(C)C)CC3)nc12]

Step 1: tert-Butyl ((1,4-trans)-4-((6-(4-(2-chlorophenylsulfonamido)-3-fluorophenyl)-8-methylpyrido[3,2-d]pyrimidin-2-yl)amino)cyclohexyl)carbamate

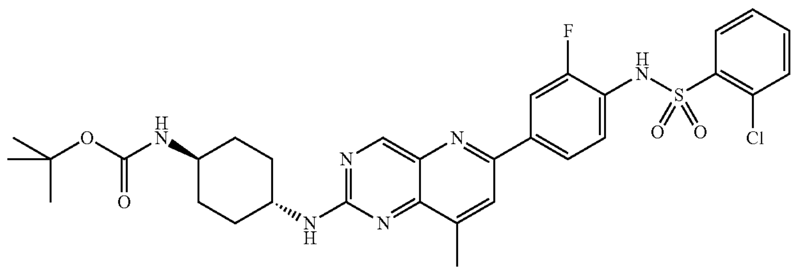 [SMILES: Cc1cc(-c2ccc(NS(=O)(=O)c3ccccc3Cl)c(F)c2)nc2cnc(N[C@H]3CC[C@H](NC(=O)OC(C)(C)C)CC3)nc12]

To a mixture of tert-butyl ((1,4-trans)-4-((6-(4-amino-3-fluorophenyl)-8-methylpyrido[3,2-d]pyrimidin-2-yl)amino)cyclohexyl)carbamate (65 mg, 0.14 mmol) and 2-chlorobenzenesulfonyl chloride (38 mg, 0.18 mmol) in $CH_2Cl_2$ (1 mL), was added pyridine (0.28 mL, 3.47 mmol). The reaction was stirred 1 h at rt then volatiles were removed in vacuo. The crude material was purified by silica flash chromatography (0-20% EtOAc/$CH_2Cl_2$) to provide the title compound (74 mg, 83% yield). LCMS (ESI) $[M+H]^+$ =641.1.

Step 2: N-(4-(2-(((1,4-trans)-4-Aminocyclohexyl)amino)-8-methylpyrido[3,2-d]pyrimidin-6-yl)-2-fluorophenyl)-2-chlorobenzenesulfonamide

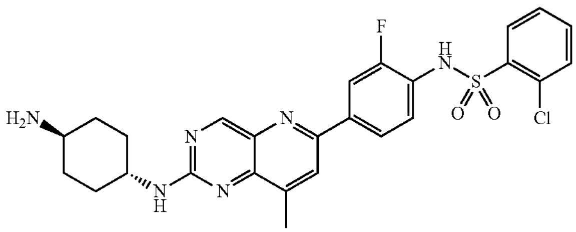 [SMILES: Cc1cc(-c2ccc(NS(=O)(=O)c3ccccc3Cl)c(F)c2)nc2cnc(N[C@H]3CC[C@H](N)CC3)nc12]

To a solution of tert-butyl ((1,4-trans)-4-((6-(4-(2-chlorophenylsulfonamido)-3-fluorophenyl)-8-methylpyrido[3,2-d]pyrimidin-2-yl)amino)cyclohexyl)carbamate (74 mg, 0.12 mmol) in $CH_2Cl_2$ (1 mL) was added TFA (1.0 mL, 13.1 mmol). The resulting mixture was stirred 90 min at rt then volatiles were evaporated in vacuo. The residue was diluted with saturated aqueous sodium bicarbonate and extracted twice with EtOAc. The organic extracts were combined, dried over anhydrous $MgSO_4$, filtered and concentrated in vacuo. The crude material was used without further purification (assumed quantitative yield). LCMS (ESI) [M+H]+=541.0.

Step 3: 2-Chloro-N-(4-(2-(((1,4-trans)-4-(dimethylamino)cyclohexyl)amino)-8-methylpyrido[3,2-d]pyrimidin-6-yl)-2-fluorophenyl)benzenesulfonamide

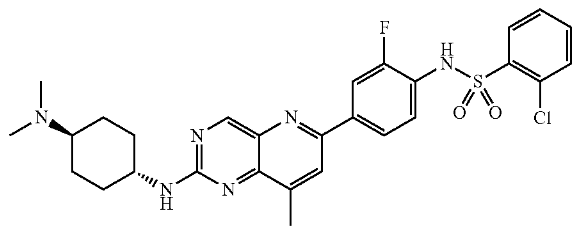 [SMILES: Cc1cc(-c2ccc(NS(=O)(=O)c3ccccc3Cl)c(F)c2)nc2cnc(N[C@H]3CC[C@H](N(C)C)CC3)nc12]

To a solution of N-(4-(2-(((1,4-trans)-4-aminocyclohexyl)amino)-8-methylpyrido[3,2-d]pyrimidin-6-yl)-2-fluorophenyl)-2-chlorobenzenesulfonamide (62 mg, 0.11 mmol), in methanol (1.5 mL), was added 37% w/w aqueous formaldehyde (0.10 mL, 1.16 mmol) followed by sodium triacetoxyborohydride (97 mg, 0.46 mmol). The resulting mixture was stirred 1 h at rt then volatiles were evaporated in vacuo. The residue was purified by C18 reverse phase flash chromatography (0-60% MeCN/10 mM aqueous ammonium bicarbonate, pH=10) to provide the title compound (34 mg, 52% yield).

Example 28: N-(4-(2-(((1,4-trans)-4-(Dimethylamino)cyclohexyl)amino)-8-methylpyrido[3,2-d]pyrimidin-6-yl)-2-fluorophenyl)-1-(4-fluorophenyl)methanesulfonamide (Compound 129)

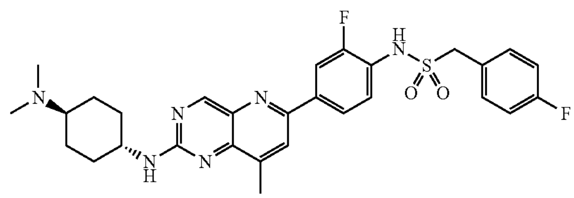 [SMILES: Cc1cc(-c2ccc(NS(=O)(=O)Cc3ccc(F)cc3)c(F)c2)nc2cnc(N[C@H]3CC[C@H](N(C)C)CC3)nc12]

Step 1: tert-Butyl ((1,4-trans)-4-((6-(3-fluoro-4-((4-fluorophenyl)methylsulfonamido)phenyl)-8-methylpyrido[3,2-d]pyrimidin-2-yl)amino)cyclohexyl) carbamate

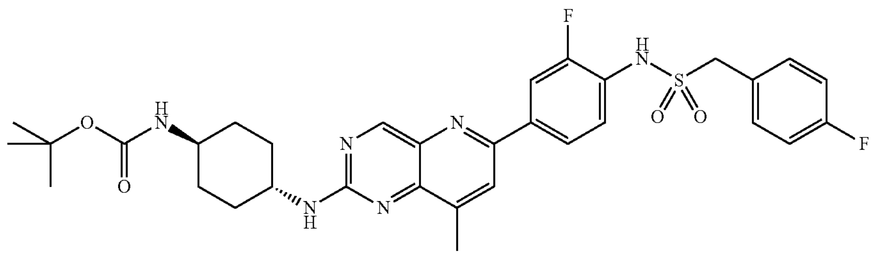 [SMILES: Cc1cc(-c2ccc(NS(=O)(=O)Cc3ccc(F)cc3)c(F)c2)nc2cnc(N[C@H]3CC[C@H](NC(=O)OC(C)(C)C)CC3)nc12]

Prepared according to Example 27 (Compound 128) step 1 using tert-butyl ((1,4-trans)-4-((6-(4-amino-3-fluorophenyl)-8-methylpyrido[3,2-d]pyrimidin-2-yl)amino)cyclohexyl)carbamate (61 mg, 0.13 mmol), (4-fluorophenyl) methanesulfonyl chloride (36 mg, 0.17 mmol) and pyridine (0.27 mL, 3.28 mmol) to provide the title product (38 mg, 56% yield). LCMS (ESI) $[M+H]^+$=639.1.

Step 2: N-(4-(2-(((1,4-trans)-4-Aminocyclohexyl) amino)-8-methylpyrido[3,2-d]pyrimidin-6-yl)-2-fluorophenyl)-1-(4-fluorophenyl)methanesulfonamide

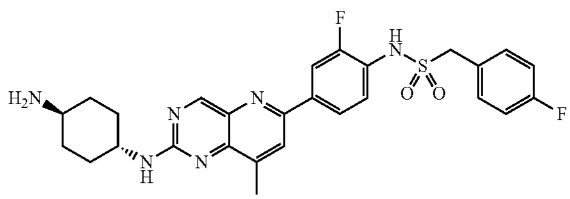 [SMILES: Cc1cc(-c2ccc(NS(=O)(=O)Cc3ccc(F)cc3)c(F)c2)nc2cnc(N[C@H]3CC[C@H](N)CC3)nc12]

Prepared according to Example 27 (Compound 128) step 2 using tert-butyl ((1,4-trans)-4-((6-(3-fluoro-4-((4-fluorophenyl)methylsulfonamido)phenyl)-8-methylpyrido[3,2-d] pyrimidin-2-yl)amino)cyclohexyl)carbamate (38 mg, 0.06 mmol) and TFA (0.5 mL, 6.53 mmol) to provide the crude title compound (assume quantitative yield). LCMS (ESI) [M+H]+=539.0.

Step 3: N-(4-(2-(((1,4-trans)-4-(Dimethylamino) cyclohexyl)amino)-8-methylpyrido[3,2-d]pyrimidin-6-yl)-2-fluorophenyl)-1-(4-fluorophenyl)methanesulfonamide

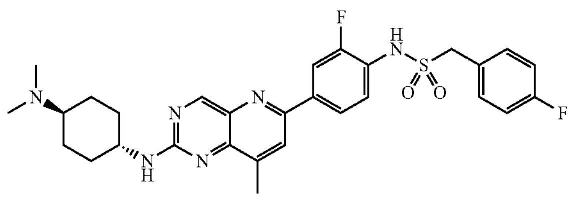 [SMILES: Cc1cc(-c2ccc(NS(=O)(=O)Cc3ccc(F)cc3)c(F)c2)nc2cnc(N[C@H]3CC[C@H](N(C)C)CC3)nc12]

Prepared according to Example 27 (Compound 128) step 3 using N-(4-(2-(((1,4-trans)-4-aminocyclohexyl)amino)-8-methylpyrido[3,2-d]pyrimidin-6-yl)-2-fluorophenyl)-1-(4-fluorophenyl)methanesulfonamide (32 mg, 0.06 mmol), 37% w/w aqueous formaldehyde (0.075 mL, 0.90 mmol) and sodium triacetoxyborohydride (97 mg, 0.46 mmol) to provide the title product (10 mg, 30% yield).

Example 29: N-[4-[2-[[(1,4-trans)-4-(Dimethylamino)cyclohexyl]amino]-8-(fluoromethyl)pyrido[3,2-d]pyrimidin-6-yl]-2-fluoro-phenyl]-1-(4-fluorophenyl)methanesulfonamide (Compound 130)

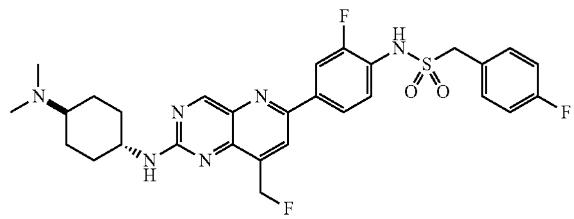 [SMILES: CN(C)[C@H]1CC[C@H](Nc2ncc3nc(-c4ccc(NS(=O)(=O)Cc5ccc(F)cc5)c(F)c4)cc(CF)c3n2)CC1]

Step 1: 8-(Bromomethyl)-2,6-dichloro-pyrido[3,2-d] pyrimidine

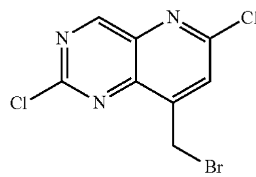

2,6-Dichloro-8-methyl-pyrido[3,2-d]pyrimidine (2.00 g, 9.34 mmol) was suspended in MeCN (30 mL) and to the mixture was added N-bromosuccinimide (4.99 g, 28.0 mmol) followed by benzoyl peroxide (1131 mg, 4.67 mmol) and AcOH (0.07 mL, 1.21 mmol). The mixture was stirred at 82° C. After 4 h, a further 2 equiv. of N-bromosuccinimide and 0.2 equiv. of benzoyl peroxide were added. After a further 4 h, the mixture was concentrated with silica and purified by silica flash column chromatography (0-30% EtOAc/heptanes) to provide the title compound (2.10 g, 77% yield). LCMS (ESI) $[M+H]^+$=291.7.

Step 2: 2,6-Dichloro-8-(iodomethyl)pyrido[3,2-d]pyrimidine

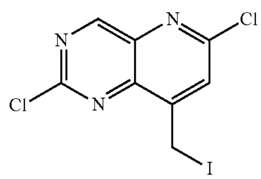 [SMILES: Clc1cc(CI)c2nc(Cl)ncc2n1]

8-(Bromomethyl)-2,6-dichloro-pyrido[3,2-d]pyrimidine (2100 mg, 7.17 mmol) was dissolved in acetone (50 mL) and to the solution was added KI (5949 mg, 35.84 mmol). The reaction was stirred at rt for 20 min then filtered. The filtrate was concentrated then suspended in $CH_2Cl_2$ (100 mL). The mixture was filtered and the filtrate was concentrated in vacuo. The crude material was purified by silica flash column chromatography (0-30% EtOAc/heptanes) to provide the title compound (2100 mg, 86% yield). LCMS (ESI) $[M+H]^+$=337.7.

Step 3: (2,6-Dichloropyrido[3,2-d]pyrimidin-8-yl)methanol

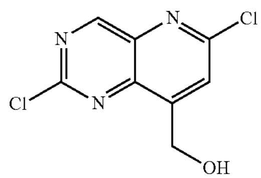 [SMILES: OCc1cc(Cl)nc2cnc(Cl)nc12]

2,6-Dichloro-8-(iodomethyl)pyrido[3,2-d]pyrimidine (2100 mg, 6.18 mmol) was dissolved in ethanol (38 mL) and water (10 mL). Sodium formate (1260 mg, 18.53 mmol) was added and heated to reflux with stirring for 2 h. The reaction was then diluted with toluene and silica gel was added and concentrated. The crude was purified by silica flash column chromatography (0-70% EtOAc/heptanes) to provide the title compound (1100 mg, 77% yield). LCMS (ESI) $[M+H]^+$=229.8.

Step 3: 2,6-Dichloro-8-(fluoromethyl)pyrido[3,2-d]pyrimidine

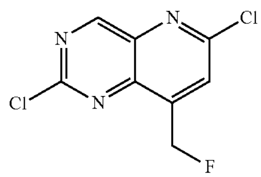 [SMILES: FCc1cc(Cl)nc2cnc(Cl)nc12]

To a solution of (2,6-dichloropyrido[3,2-d]pyrimidin-8-yl)methanol (60 mg, 0.26 mmol) and triethylamine trihydrofluoride (64 μL, 0.39 mmol) in 1,2-dichloroethane (2.6 mL) at rt was added XtalFluor-M (158 mg, 0.65 mmol). The reaction was stirred at 80° C. for 1 h. To the reaction mixture was then added $CH_2Cl_2$ and saturated aqueous sodium bicarbonate (1 mL) and stirring continued for 15 min. The phases were separated and the aqueous phase was extracted with $CH_2Cl_2$ (×3). The organic extracts were combined, dried over $Na_2SO_4$ and concentrated. The crude material was purified by silica flash column chromatography (0-40% EtOAc/heptanes) to provide the title compound (29 mg, 48% yield). $^1H$ NMR (400 MHz, $CDCl_3$) δ 9.43 (s, 1H), 7.91 (t, J=1.4 Hz, 1H), 6.04 (dd, J=46.4, 1.4 Hz, 2H).

Step 4: tert-Butyl 1,4-trans-N-[4-[[6-chloro-8-(fluoromethyl)pyrido[3,2-d]pyrimidin-2-yl]amino]cyclohexyl]carbamate

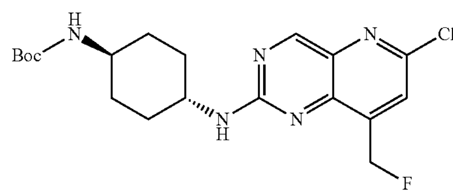 [SMILES: CC(C)(C)OC(=O)N[C@H]1CC[C@H](Nc2ncc3nc(Cl)cc(CF)c3n2)CC1]

2,6-Dichloro-8-(fluoromethyl)pyrido[3,2-d]pyrimidine (35 mg, 0.15 mmol) and N-Boc-trans-1,4-cyclohexanediamine (48 mg, 0.23 mmol) and $NaHCO_3$ (38 mg, 0.45 mmol) were added to DMSO (1 mL) and stirred at 80° C. for 1 h. The mixture was diluted with EtOAc (20 mL) and water (10 mL) and the phases were separated. The organic extract was washed with water, then with saturated aqueous sodium chloride. Silica gel was then added and volatiles were removed under reduced pressure and purified by flash chromatography through silica gel (0-100% EtOAc/heptanes) to provide the title compound (28 mg, 45% yield). LCMS (ESI) $[M+H]^+$=410.2.

Step 5: tert-Butyl 1,4-trans-N-[4-[[6-(4-amino-3-fluoro-phenyl)-8-(fluoromethyl)pyrido[3,2-d]pyrimidin-2-yl]amino]cyclohexyl]carbamate

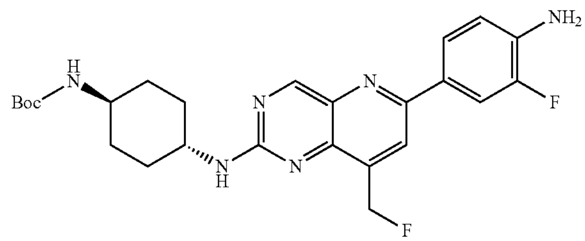 [SMILES: CC(C)(C)OC(=O)N[C@H]1CC[C@H](Nc2ncc3nc(-c4ccc(N)c(F)c4)cc(CF)c3n2)CC1]

A flask was charged with tert-butyl 1,4-trans-N-[4-[[6-chloro-8-(fluoromethyl)pyrido[3,2-d]pyrimidin-2-yl]amino]cyclohexyl]carbamate (28 mg, 0.07 mmol) and 1,2-dimethoxyethane (1 mL) and $H_2O$ (0.25 mL). The mixture was degassed for 10 min with $N_2$ and to this mixture was then added 2-fluoro-4-(4,4,5,5-tetramethyl-1,3,2-dioxaborolan-2-yl)aniline (24 mg, 0.10 mmol), palladium acetate (3 mg, 0.014 mmol), tri-o-tolylphosphine (8.3 mg, 0.028 mmol), and sodium carbonate (14 mg, 0.14 mmol) The reaction was stirred at 100° C. under $N_2$ with a condenser overnight. After 18 h, the reaction was concentrated with silica gel, toluene was added and concentrated again. The crude was purified by silica flash column chromatography (30-90% EtOAc/heptanes) to provide the title compound (15 mg, 45% yield). LCMS (ESI) $[M+H]^+$=485.1.

Step 6: tert-Butyl 1,4-trans-N-[4-[[6-[3-fluoro-4-[(4-fluorophenyl)methylsulfonylamino]phenyl]-8-(fluoromethyl)pyrido[3,2-d]pyrimidin-2-yl]amino]cyclohexyl]carbamate

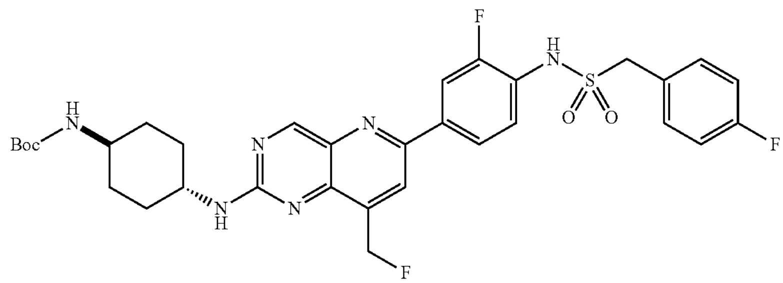 [SMILES: CC(C)(C)OC(=O)N[C@H]1CC[C@H](Nc2ncc3nc(-c4ccc(NS(=O)(=O)Cc5ccc(F)cc5)c(F)c4)cc(CF)c3n2)CC1]

tert-Butyl 1,4-trans-N-[4-[[6-(4-amino-3-fluoro-phenyl)-8-(fluoromethyl)pyrido[3,2-d]pyrimidin-2-yl]amino]cyclohexyl]carbamate (29 mg, 0.06 mmol) was dissolved in $CH_2Cl_2$ (1 mL) and to the solution was added pyridine (141 mg, 1.8 mmol) followed by (4-fluorophenyl)methanesulfonyl chloride (16 mg, 0.08 mmol). The reaction was stirred at rt overnight. To the reaction was added a further 1 equiv. of the sulfonyl chloride and stirred for an additional 2 h at rt. To the reaction was then added toluene and MeOH. The crude was concentrated in vacuo and purified by C18 reverse phase Prep-HPLC (CSH column, from 50-70% MeCN/10 mM aqueous ammonium formate, pH=3.8) to provide the title compound (12 mg, 31% yield). LCMS (ESI) $[M+H]^+$=657.3.

Step 7: N-[4-[2-[[(1,4-trans)-4-(Dimethylamino)cyclohexyl]amino]-8-(fluoromethyl)pyrido[3,2-d]pyrimidin-6-yl]-2-fluoro-phenyl]-1-(4-fluorophenyl)methanesulfonamide

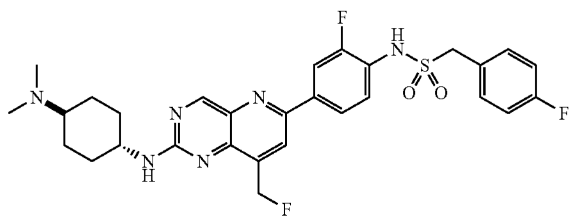 [SMILES: CN(C)[C@H]1CC[C@H](Nc2ncc3nc(-c4ccc(NS(=O)(=O)Cc5ccc(F)cc5)c(F)c4)cc(CF)c3n2)CC1]

tert-Butyl 1,4-trans-N-[4-[[6-[3-fluoro-4-[(4-fluorophenyl)methylsulfonylamino]phenyl]-8-(fluoromethyl)pyrido[3,2-d]pyrimidin-2-yl]amino]cyclohexyl]carbamate (12 mg, 0.02 mmol) was dissolved in TFA (1 mL) and the reaction is stirred at rt for 10 min. To the mixture was added toluene (10 mL) and then the solution was concentrated in vacuo. To the crude amine sale was added methanol (1 mL) and NaOAc (15 mg, 0.19 mmol) followed by 37% w/w aqueous formaldehyde (75 mg, 0.93 mmol). The mixture is stirred at rt for 5 min then sodium triacetoxyborohydride (19 mg, 0.09 mmol) was added. The reaction was stirred at rt for 10 min then directly purified by C18 reverse phase flash column chromatography (0-100% MeCN/10 mM aqueous ammonium formate, pH=3.8) to provide the title compound (7 mg, 64% yield).

Example 30: N-1,4-trans-[4-[8-(Difluoromethyl)-2-[[4-(dimethylamino)cyclohexyl]amino]pyrido[3,2-d]pyrimidin-6-yl]-2-fluoro-phenyl]-1-(4-fluorophenyl)methanesulfonamide (Compound 131)

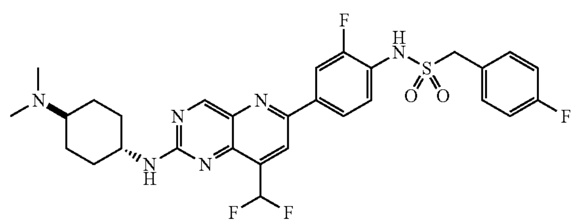 [SMILES: CN(C)[C@H]1CC[C@H](Nc2ncc3nc(-c4ccc(NS(=O)(=O)Cc5ccc(F)cc5)c(F)c4)cc(C(F)F)c3n2)CC1]

Step 1: 2,6-Dichloropyrido[3,2-d]pyrimidine-8-carbaldehyde

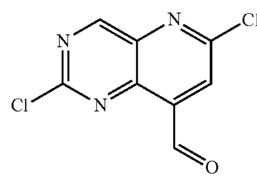 [SMILES: O=Cc1cc(Cl)nc2cnc(Cl)nc12]

(2,6-Dichloropyrido[3,2-d]pyrimidin-8-yl)methanol (200 mg, 0.87 mmol) was dissolved in $CH_2Cl_2$ (5 mL) and to the solution was added Dess Martin periodinane reagent (552 mg, 1.3 mmol). The reaction was stirred at rt for 20 min then purified directly by silica flash column chromatography (0-60% EtOAc/heptanes) to provide the title compound (175 mg, 88% yield). $^1H$ NMR (400 MHz, $CDCl_3$) δ 11.14 (s, 1H), 9.56 (s, 1H), 8.20 (s, 1H).

Step 2: 2,6-Dichloro-8-(difluoromethyl)pyrido[3,2-d]pyrimidine

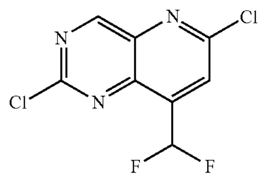 [SMILES: FC(F)c1cc(Cl)nc2cnc(Cl)nc12]

To a solution of 2,6-dichloropyrido[3,2-d]pyrimidine-8-carbaldehyde (175 mg, 0.77 mmol) and triethylamine trihydrofluoride (312 μL, 1.92 mmol) in 1,2-dichloroethane (5.8 mL) was added XtalFluor-M (839 mg, 3.45 mmol). The reaction was stirred at 80° C. for 20 min then MeOH (0.5 mL) was added. The crude was concentrated with silica gel and purified by flash chromatography through silica gel (0-30% EtOAc/heptanes) to provide the title compound (162 mg, 84% yield). $^1$H NMR (400 MHz, $CDCl_3$) δ 9.49 (s, 1H), 8.06 (s, 1H), 7.51 (t, J=53.8 Hz, 1H).

Step 3: tert-Butyl 1,4-trans-N-[4-[[6-chloro-8-(difluoromethyl)pyrido[3,2-d]pyrimidin-2-yl]amino]cyclohexyl]carbamate

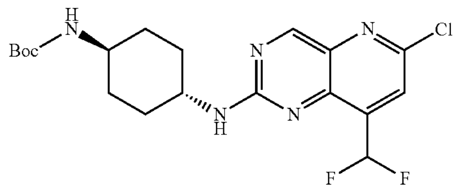 [SMILES: CC(C)(C)OC(=O)N[C@H]1CC[C@H](Nc2ncc3nc(Cl)cc(C(F)F)c3n2)CC1]

2,6-Dichloro-8-(difluoromethyl)pyrido[3,2-d]pyrimidine (162 mg, 0.65 mmol) and N-Boc-trans-1,4-cyclohexanediamine (208 mg, 0.97 mmol) and sodium bicarbonate (163 mg, 1.94 mmol) were combined in DMSO (5 mL) and stirred at 80° C. for 30 min. The reaction was then diluted with EtOAc (50 mL) and water (20 mL), and saturated aqueous citric acid was added and the phases were separated. The organic extract was washed with water then with saturated aqueous sodium chloride and concentrated with silica gel and purified by flash chromatography through silica gel (0-100% EtOAc/heptanes) to provide the title compound (255 mg, 92% yield). LCMS (ESI) $[M+H]^+$=428.1.

Step 4: tert-Butyl 1,4-trans-N-[4-[[6-(4-amino-3-fluoro-phenyl)-8-(difluoromethyl)pyrido[3,2-d]pyrimidin-2-yl]amino]cyclohexyl]carbamate

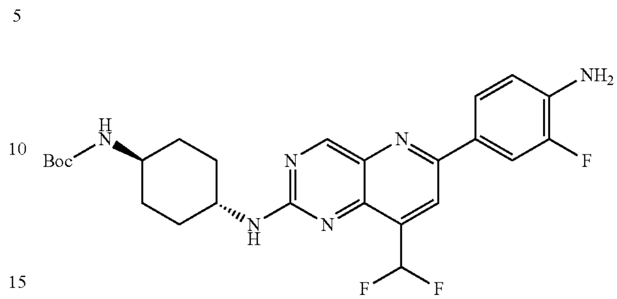

A flask was charged with tert-butyl 1,4-trans-N-[4-[[6-chloro-8-(difluoromethyl)pyrido[3,2-d]pyrimidin-2-yl]amino]cyclohexyl]carbamate (255 mg, 0.60 mmol) and 1,2-dimethoxyethane (10 mL) and $H_2O$ (2.5 mL). The mixture was purged with $N_2$ for 10 min then 2-fluoro-4-(4,4,5,5-tetramethyl-1,3,2-dioxaborolan-2-yl)aniline (212 mg, 0.89 mmol), palladium acetate (27 mg, 0.12 mmol), tri-o-tolylphosphine (72 mg, 0.24 mmol), and sodium carbonate (126 mg, 1.19 mmol) were added in that order. The reaction was heated at 90° C. for 2 h then diluted with toluene (20 mL) and the solution was concentrated with silica gel and purified by flash chromatography through silica gel (10-100% EtOAc/heptanes) to provide the title compound (135 mg, 45% yield). LCMS (ESI) $[M+H]^+$=503.1.

Step 5: tert-Butyl 1,4-trans-N-[4-[[8-(difluoromethyl)-6-[3-fluoro-4-[(4-fluorophenyl)methylsulfonylamino]phenyl]pyrido[3,2-d]pyrimidin-2-yl]amino]cyclohexyl]carbamate

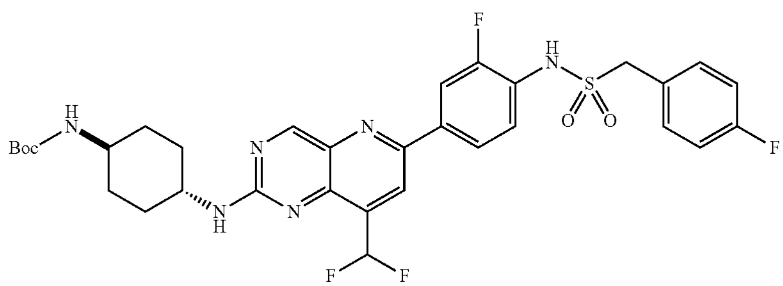 [SMILES: CC(C)(C)OC(=O)N[C@H]1CC[C@H](Nc2ncc3nc(-c4ccc(NS(=O)(=O)Cc5ccc(F)cc5)c(F)c4)cc(C(F)F)c3n2)CC1]

To a suspension of tert-butyl 1,4-trans-N-[4-[[6-(4-amino-3-fluoro-phenyl)-8-(difluoromethyl)pyrido[3,2-d]pyrimidin-2-yl]amino]cyclohexyl]carbamate (135 mg, 0.27 mmol) in pyridine (1 mL) was added (4-fluorophenyl)methanesulfonyl chloride (67 mg, 0.32 mmol). The reaction was stirred at rt overnight then another portion of (4-fluorophenyl)methanesulfonyl chloride (56 mg, 0.27 mmol) was added and continued stirring at rt. After 2 h, the mixture was diluted with toluene and MeOH and concentrated under reduced pressure. The crude was dissolved in DMSO and purified by prep-HPLC (CSH column, 50-70% MeCN/10 mM aqueous ammonium formate, pH=3.8) to provide the title compound (68 mg, 37% yield). LCMS (ESI) $[M+H]^+$=675.3.

Step 6: N-1,4-trans-[4-[8-(Difluoromethyl)-2-[[4-(dimethylamino)cyclohexyl]amino]pyrido[3,2-d]pyrimidin-6-yl]-2-fluoro-phenyl]-1-(4-fluorophenyl)methanesulfonamide

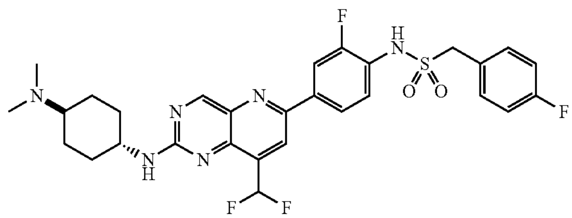 [SMILES: CN(C)[C@H]1CC[C@H](Nc2ncc3nc(-c4ccc(NS(=O)(=O)Cc5ccc(F)cc5)c(F)c4)cc(C(F)F)c3n2)CC1]

Prepared according to Example 29 (Compound 130) step 7 using tert-Butyl 1,4-trans-N-[4-[[8-(difluoromethyl)-6-[3-fluoro-4-[(4-fluorophenyl)methylsulfonylamino]phenyl]pyrido[3,2-d]pyrimidin-2-yl]amino]cyclohexyl]carbamate (70 mg, 0.14 mmol) to provide the title compound (52 mg, 61% yield).

Example 31: N-(4-(2-(((1,4-trans)-4-(Dimethylamino)cyclohexyl)amino)-8-methylpyrido[3,2-d]pyrimidin-6-yl)-2,3-difluorophenyl)-1-(4-fluorophenyl)methanesulfonamide (Compound 132)

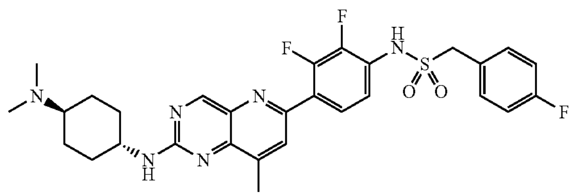 [SMILES: Cc1cc(-c2ccc(NS(=O)(=O)Cc3ccc(F)cc3)c(F)c2F)nc2cnc(N[C@H]3CC[C@H](N(C)C)CC3)nc12]

Step 1: 2,3-Difluoro-4-(4,4,5,5-tetramethyl-1,3,2-dioxaborolan-2-yl)aniline

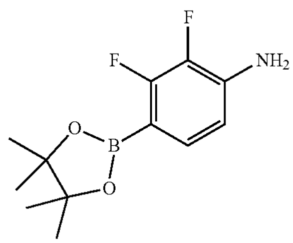 [SMILES: CC1(C)OB(c2ccc(N)c(F)c2F)OC1(C)C]

To a flask containing 4-bromo-2,3-difluoro-aniline (500 mg, 2.40 mmol), bis(pinacolato)diboron (733 mg, 2.89 mmol), potassium acetate (715 mg, 7.21 mmol) and 1,1-bis(diphenylphosphino)ferrocene-palladium dichloride (90 mg, 0.12 mmol) was added $N_2$ degassed 1,4-Dioxane (8 mL). The reaction was heated overnight at 90° C. then diluted with EtOAc and filtered through a pad of celite and concentrated under reduced pressure. The crude material was purified by silica flash chromatography (0-50% $CH_2Cl_2$/heptanes) to provide the title compound (270 mg, 44% yield). $^1H$ NMR (400 MHz, $CDCl_3$) δ 7.26-7.21 (m, 1H), 6.53-6.46 (m, 1H), 4.01 (s, 2H), 1.33 (s, 12H).

Step 2: tert-Butyl ((1,4-trans)-4-((6-(4-amino-2,3-difluorophenyl)-8-methylpyrido[3,2-d]pyrimidin-2-yl)amino)cyclohexyl)carbamate

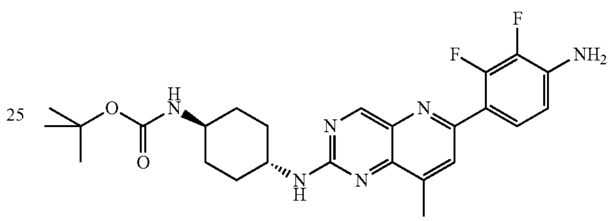

Prepared according to Example 24 (Compound 125) step 1 using tert-butyl ((1,4-trans)-4-((6-chloro-8-methylpyrido[3,2-d]pyrimidin-2-yl)amino)cyclohexyl)carbamate (200 mg, 0.51 mmol), 2,3-difluoro-4-(4,4,5,5-tetramethyl-1,3,2-dioxaborolan-2-yl)aniline (260 mg, 1.02 mmol), potassium carbonate (282 mg, 2.04 mmol) and $Pd(PPh_3)_4$ (88 mg, 0.08 mmol) to provide the title compound (119 mg, 48% yield). LCMS (ESI) [M+H]+=485.0.

Step 3: tert-Butyl ((1,4-trans)-4-((6-(2,3-difluoro-4-((4-fluorophenyl)methylsulfonamido)phenyl)-8-methylpyrido[3,2-d]pyrimidin-2-yl)amino)cyclohexyl)carbamate

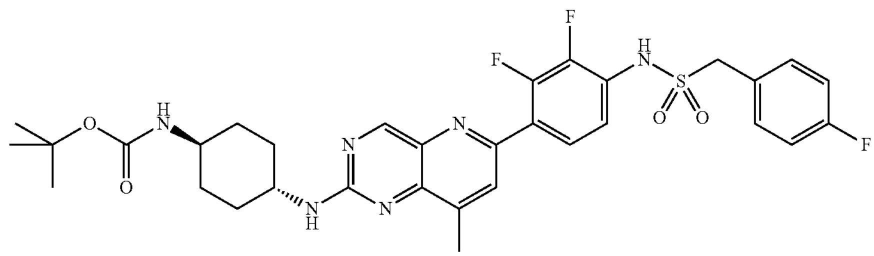 [SMILES: Cc1cc(-c2ccc(NS(=O)(=O)Cc3ccc(F)cc3)c(F)c2F)nc2cnc(N[C@H]3CC[C@H](NC(=O)OC(C)(C)C)CC3)nc12]

Prepared according to Example 27 (Compound 128) step 1 using tert-butyl ((1,4-trans)-4-((6-(4-amino-2,3-difluorophenyl)-8-methylpyrido[3,2-d]pyrimidin-2-yl)amino)cyclohexyl)carbamate (60 mg, 0.12 mmol), (4-fluorophenyl) methanesulfonyl chloride (36 mg, 0.17 mmol) and pyridine (0.25 mL, 3.10 mmol) to provide the title product (39 mg, 48% yield). LCMS (ESI) $[M+H]^+$=657.1.

Step 4: N-(4-(2-(((1,4-trans)-4-(Dimethylamino) cyclohexyl)amino)-8-methylpyrido[3,2-d]pyrimidin-6-yl)-2,3-difluorophenyl)-1-(4-fluorophenyl)methanesulfonamide

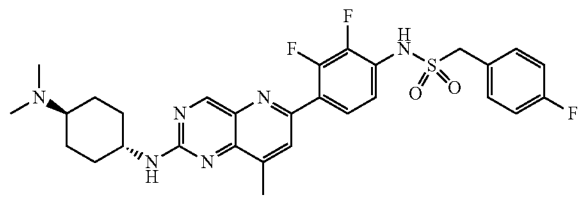 [SMILES: Cc1cc(-c2ccc(NS(=O)(=O)Cc3ccc(F)cc3)c(F)c2F)nc2cnc(N[C@H]3CC[C@H](N(C)C)CC3)nc12]

Prepared according to Example 27 (Compound 128) steps 2-3 using tert-butyl ((1,4-trans)-4-((6-(2,3-difluoro-4-((4-fluorophenyl)methylsulfonamido)phenyl)-8-methylpyrido [3,2-d]pyrimidin-2-yl)amino)cyclohexyl)carbamate (39 mg, 0.06 mmol) to provide the title compound (20 mg, 58% yield).

Example 32: N-(5-(8-(Difluoromethyl)-2-(((1,4-trans)-4-(dimethylamino)cyclohexyl)amino)pyrido [3,2-d]pyrimidin-6-yl)-6-methylpyridin-2-yl)-1-(4-fluorophenyl)methanesulfonamide (Compound 133)

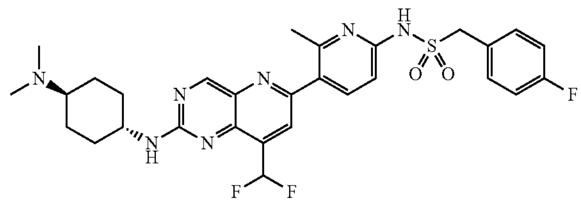 [SMILES: Cc1nc(NS(=O)(=O)Cc2ccc(F)cc2)ccc1-c1cc(C(F)F)c2nc(N[C@H]3CC[C@H](N(C)C)CC3)ncc2n1]

Step 1: tert-Butyl N-1,4-trans-[4-[[6-(6-amino-2-methyl-3-pyridyl)-8-(difluoromethyl)pyrido[3,2-d] pyrimidin-2-yl]amino]cyclohexyl]carbamate

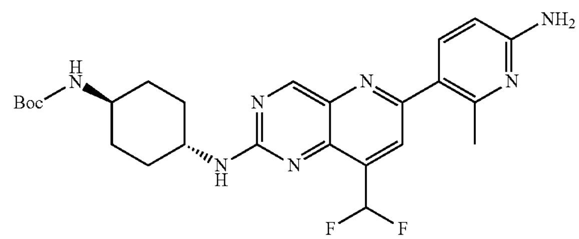 [SMILES: Cc1nc(N)ccc1-c1cc(C(F)F)c2nc(N[C@H]3CC[C@H](NC(=O)OC(C)(C)C)CC3)ncc2n1]

In a glass tube was charged with tert-butyl N-1,4-trans-[4-[[6-chloro-8-(difluoromethyl)pyrido[3,2-d]pyrimidin-2-yl]amino]cyclohexyl]carbamate (100 mg, 0.23 mmol) and 1,2-dimethoxyethane (3.2 mL) and water (0.8 mL). To the reaction vessel was then added 6-methyl-5-(4,4,5,5-tetramethyl-1,3,2-dioxaborolan-2-yl)pyridin-2-amine (109 mg, 0.47 mmol), sodium carbonate (49 mg, 0.47 mmol), palladium acetate (10 mg, 0.05 mmol) and tri-o-tolylphosphine (28 mg, 0.09 mmol). The vessel was purged with $N_2$ for 10 min then stirred at 85° C. for 4 h then concentrated with silica gel and purified by silica flash chromatography (0-10% MeOH/$CH_2Cl_2$) to provide the title compound (82 mg, 70% yield). LCMS (ESI) $[M+H]^+$=500.2.

Step 2: tert-Butyl N-1,4-trans-[4-[[8-(difluoromethyl)-6-[6-[(4-fluorophenyl)methylsulfonylamino]-2-methyl-3-pyridyl]pyrido[3,2-d]pyrimidin-2-yl] amino]cyclohexyl]carbamate

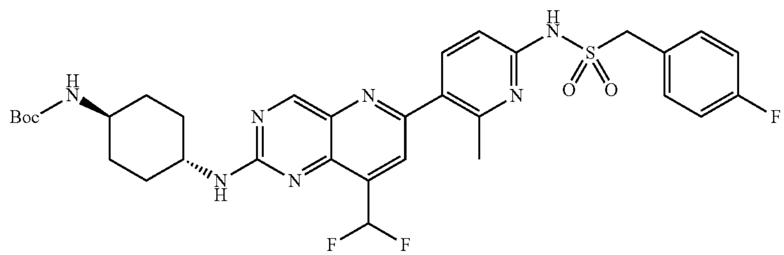 [SMILES: Cc1nc(NS(=O)(=O)Cc2ccc(F)cc2)ccc1-c1cc(C(F)F)c2nc(N[C@H]3CC[C@H](NC(=O)OC(C)(C)C)CC3)ncc2n1]

tert-Butyl N-1,4-trans-[4-[[6-(6-amino-2-methyl-3-pyridyl)-8-(difluoromethyl)pyrido[3,2-d]pyrimidin-2-yl] amino]cyclohexyl]carbamate (102 mg, 0.20 mmol) was suspended in pyridine (806 mg, 10.2 mmol) and to the mixture was added (4-fluorophenyl)methanesulfonyl chloride (51 mg, 0.25 mmol). The reaction was stirred at rt for 2 h then a further portion of (4-fluorophenyl)methanesulfonyl chloride (81 mg, 0.40 mmol) was added. After stirring a further 3 h, diethylamine (100 μL) and DMSO (3 mL) were added and concentrated to remove pyridine. The crude was purified by prep-HPLC (CSH column, 45-65% MeCN/10 mM aqueous ammonium formate, pH=3.8) to provide the title compound (24 mg, 17% yield). LCMS (ESI) $[M+H]^+$=672.3.

Step 3: N-(5-(8-(Difluoromethyl)-2-(((1,4-trans)-4-(dimethylamino)cyclohexyl)amino)pyrido[3,2-d] pyrimidin-6-yl)-6-methylpyridin-2-yl)-1-(4-fluorophenyl)methanesulfonamide

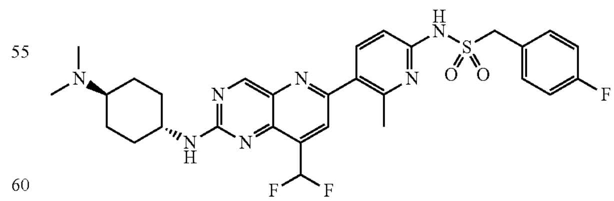

Prepared according to Example 29 (Compound 130) step 7 using tert-butyl N-1,4-trans-[4-[[8-(difluoromethyl)-6-[6-[(4-fluorophenyl)methylsulfonylamino]-2-methyl-3-pyridyl]pyrido[3,2-d]pyrimidin-2-yl]amino]cyclohexyl]carbamate (24 mg, 0.04 mmol) to provide the title compound (16 mg, 75% yield).

Example 33: 2-Chloro-N-(5-(2-(((1,4-trans)-4-(dimethylamino)cyclohexyl)amino)-8-ethylpyrido[3,2-d]pyrimidin-6-yl)-6-methylpyridin-2-yl)benzenesulfonamide (Compound 134)

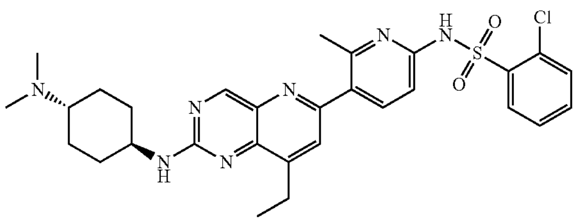 [SMILES: CCc1cc(-c2ccc(NS(=O)(=O)c3ccccc3Cl)nc2C)nc2cnc(N[C@H]3CC[C@H](N(C)C)CC3)nc12]

Step 1: tert-Butyl ((1,4-trans)-4-((6-(6-amino-2-methylpyridin-3-yl)-8-ethylpyrido[3,2-d]pyrimidin-2-yl)amino)cyclohexyl)carbamate

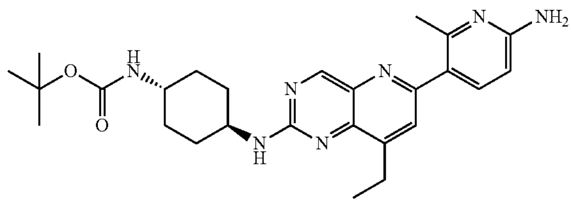 [SMILES: CCc1cc(-c2ccc(N)nc2C)nc2cnc(N[C@H]3CC[C@H](NC(=O)OC(C)(C)C)CC3)nc12]

Prepared according to Example 25 (Compound 126) step 1 using tert-butyl N-[4-[(6-chloro-8-ethyl-pyrido[3,2-d]pyrimidin-2-yl)amino]cyclohexyl]carbamate (360 mg, 0.89 mmol), 6-methyl-5-(4,4,5,5-tetramethyl-1,3,2-dioxaborolan-2-yl)pyridin-2-amine (311 mg, 1.33 mmol), potassium carbonate (490 mg, 3.55 mmol), $Pd(PPh_3)_4$ (102 mg, 0.09 mmol), 1,4-dioxane (5 mL) and $H_2O$ (1.2 mL) to provide the title product (205 mg, 48% yield). LCMS (ESI) $[M+H]^+$=478.1.

Step 2: tert-Butyl ((1,4-trans)-4-((6-(6-(2-chlorophenylsulfonamido)-2-methylpyridin-3-yl)-8-ethylpyrido[3,2-d]pyrimidin-2-yl)amino)cyclohexyl)carbamate

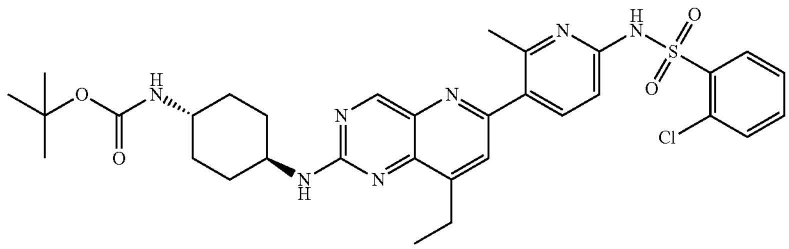

Prepared according to Example 9 (Compound 110) step 3 using tert-butyl ((1,4-trans)-4-((6-(6-amino-2-methylpyridin-3-yl)-8-ethylpyrido[3,2-d]pyrimidin-2-yl)amino)cyclohexyl)carbamate (100 mg, 0.21 mmol), pyridine (2.0 mL), 2-chlorobenzenesulfonyl chloride (66 mg, 0.21 mmol) and 1,8-diazabicyclo[5.4.0]undec-7-ene (0.16 mL, 1.05 mml) to provide the title product (77 mg, 56% yield). LCMS (ESI) $[M+H]^+$=652.1.

Step 3: N-(5-(2-(((1,4-trans)-4-Aminocyclohexyl)amino)-8-ethylpyrido[3,2-d]pyrimidin-6-yl)-6-methylpyridin-2-yl)-2-chlorobenzenesulfonamide 2,2,2-trifluoroacetate

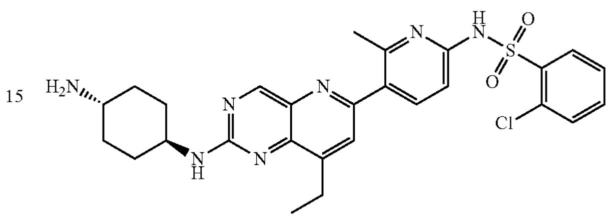

Prepared according to Example 11 (Compound 112) step 4 using tert-butyl ((1,4-trans)-4-((6-(6-(2-chlorophenylsulfonamido)-2-methylpyridin-3-yl)-8-ethylpyrido[3,2-d]pyrimidin-2-yl)amino)cyclohexyl)carbamate (116 mg, 0.18 mmol), trifluoroacetic acid (1.0 mL) and $CH_2Cl_2$ (4 mL) to provide the crude title product (119 mg, 100% yield).

Step 4: 2-Chloro-N-(5-(2-(((1,4-trans)-4-(dimethylamino)cyclohexyl)amino)-8-ethylpyrido[3,2-d]pyrimidin-6-yl)-6-methylpyridin-2-yl)benzenesulfonamide

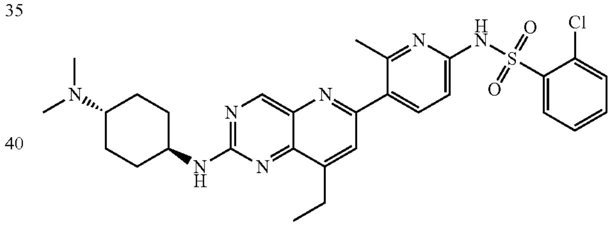

Prepared according to Example 11 (Compound 112) step 5 using N-(5-(2-(((1,4-trans)-4-aminocyclohexyl)amino)-8-ethylpyrido[3,2-d]pyrimidin-6-yl)-6-methylpyridin-2-yl)-2-chlorobenzenesulfonamide 2,2,2-trifluoroacetate (119 mg, 0.18 mmol), 37% w/w aqueous formaldehyde (216 mg, 2.67 mmol), sodium acetate (85 mg, 1.07 mmol), sodium triacetoxyborohydride (149 mg, 0.71 mmol) and methanol (3 mL) to provide the title product (45 mg, 44% yield).

Example 34: 2-Chloro-N-(5-(2-(((1,4-trans)-4-(dimethylamino)cyclohexyl)amino)-8-methylpyrido[3,2-d]pyrimidin-6-yl)pyridin-2-yl)benzenesulfonamide (Compound 135)

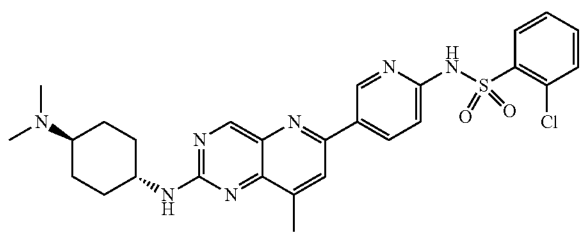 [SMILES: Cc1cc(-c2ccc(NS(=O)(=O)c3ccccc3Cl)nc2)nc2cnc(N[C@H]3CC[C@H](N(C)C)CC3)nc12]

Step 1: tert-Butyl ((1,4-trans)-4-((6-(6-(2-chlorophenylsulfonamido)pyridin-3-yl)-8-methylpyrido[3,2-d]pyrimidin-2-yl)amino)cyclohexyl)carbamate

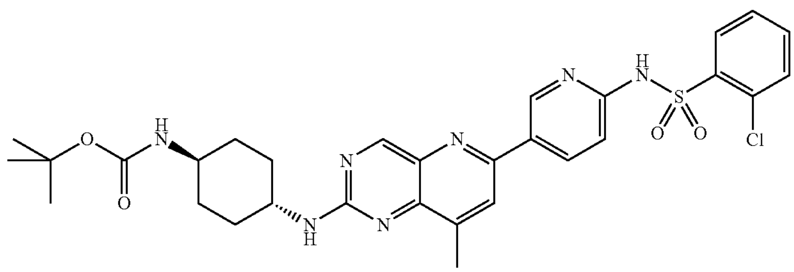 [SMILES: Cc1cc(-c2ccc(NS(=O)(=O)c3ccccc3Cl)nc2)nc2cnc(N[C@H]3CC[C@H](NC(=O)OC(C)(C)C)CC3)nc12]

A mixture of tert-butyl ((1,4-trans)-4-((6-(6-aminopyridin-3-yl)-8-methylpyrido[3,2-d]pyrimidin-2-yl)amino)cyclohexyl)carbamate (60 mg, 0.13 mmol) and 2-chlorobenzenesulfonyl chloride (120 mg, 0.57 mmol), in pyridine (1.0 mL), was stirred overnight at rt. The mixture was then concentrated to dryness and the crude material was purified by flash chromatography through silica gel (0-20% EtOAc/$CH_2Cl_2$) to provide the title compound (40 mg, 48% yield). LCMS (ESI) $[M+H]^+$=624.1.

Step 2: 2-Chloro-N-(5-(2-(((1,4-trans)-4-(dimethylamino)cyclohexyl)amino)-8-methylpyrido[3,2-d]pyrimidin-6-yl)pyridin-2-yl)benzenesulfonamide

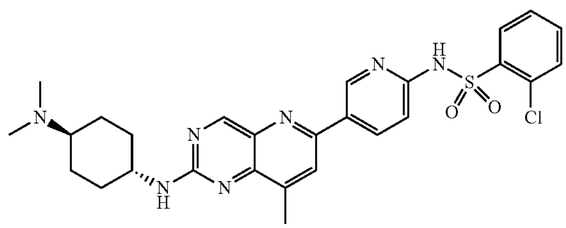 [SMILES: Cc1cc(-c2ccc(NS(=O)(=O)c3ccccc3Cl)nc2)nc2cnc(N[C@H]3CC[C@H](N(C)C)CC3)nc12]

Trifluoroacetic acid (0.5 mL, 6.53 mmol) was added to a solution of tert-butyl ((1,4-trans)-4-((6-(6-(2-chlorophenylsulfonamido)pyridin-3-yl)-8-methylpyrido[3,2-d]pyrimidin-2-yl)amino)cyclohexyl)carbamate (40 mg, 0.06 mmol) in $CH_2Cl_2$ (1 mL) and the mixture was stirred at rt. After 2 h, the mixture was concentrated to dryness then diluted with a saturated aqueous solution of $NaHCO_3$ and extracted twice with 2-MeTHF, then twice with 20% iPrOH/$CHCl_3$. The organic extracts were combined and concentrated under reduced pressure to provide crude N-(5-(2-(((1,4-trans)-4-aminocyclohexyl)amino)-8-methylpyrido[3,2-d]pyrimidin-6-yl)pyridin-2-yl)-2-chlorobenzenesulfonamide. LCMS (ESI) [M+H]+=524.0.

Prepared according to Example 27 (Compound 128) step 3 using N-(5-(2-(((1,4-trans)-4-aminocyclohexyl)amino)-8-methylpyrido[3,2-d]pyrimidin-6-yl)pyridin-2-yl)-2-chlorobenzenesulfonamide (33 mg, 0.06 mmol), 37% w/w aqueous formaldehyde (0.06 mL, 0.73 mmol) and sodium triacetoxyborohydride (68 mg, 0.32 mmol) to provide the title product (11 mg, 31% yield).

Example 35: 2-Chloro-N-(5-(2-(((3S,5S)-5-fluoropiperidin-3-yl)amino)-8-methylpyrido[3,2-d]pyrimidin-6-yl)-6-methylpyridin-2-yl)benzenesulfonamide (Compound 136)

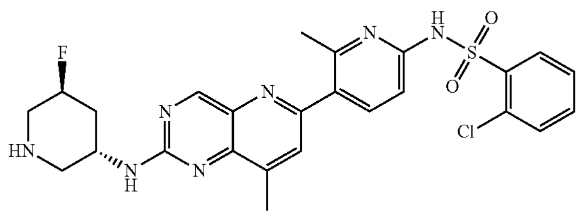 [SMILES: Cc1nc(NS(=O)(=O)c2ccccc2Cl)ccc1-c1cc(C)c2nc(N[C@@H]3CNC[C@@H](F)C3)ncc2n1]

Step 1: (3S,5S)-tert-Butyl 3-((6-(6-amino-2-methylpyridin-3-yl)-8-methylpyrido[3,2-d]pyrimidin-2-yl)amino)-5-fluoropiperidine-1-carboxylate

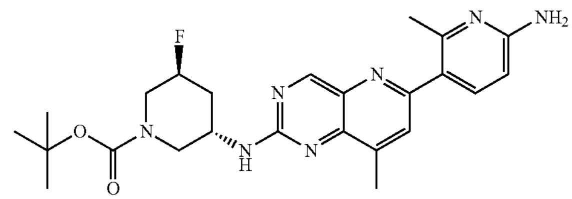 [SMILES: Cc1nc(N)ccc1-c1cc(C)c2nc(N[C@H]3C[C@H](F)CN(C(=O)OC(C)(C)C)C3)ncc2n1]

Prepare according to Example 25 (Compound 126) step 1 using tert-butyl (3S,5S)-3-[(6-chloro-8-methyl-pyrido[3,2-d]pyrimidin-2-yl)amino]-5-fluoro-piperidine-1-carboxylate (350 mg, 0.88 mmol), 6-methyl-5-(4,4,5,5-tetramethyl-1,3,2-dioxaborolan-2-yl)pyridin-2-amine (310 mg, 1.33 mmol), potassium carbonate (489 mg, 3.54 mmol), $Pd(PPh_3)_4$ (102 mg, 0.09 mmol), 1,4-dioxane (5 mL) and $H_2O$ (1.2 mL) to provide the title product (252 mg, 61% yield). LCMS (ESI) $[M+H]^+$=468.1.

Step 2: (3S,5S)-tert-Butyl 3-((6-(6-(2-chlorophenylsulfonamido)-2-methylpyridin-3-yl)-8-methylpyrido[3,2-d]pyrimidin-2-yl)amino)-5-fluoropiperidine-1-carboxylate

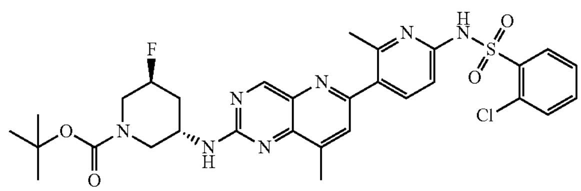 [SMILES: Cc1nc(NS(=O)(=O)c2ccccc2Cl)ccc1-c1cc(C)c2nc(N[C@H]3C[C@H](F)CN(C(=O)OC(C)(C)C)C3)ncc2n1]

Prepared according to Example 9 (Compound 110) step 3 using tert-butyl (3S,5S)-3-[[6-(6-amino-2-methyl-3-pyridyl)-8-methyl-pyrido[3,2-d]pyrimidin-2-yl]amino]-5-fluoro-piperidine-1-carboxylate (125 mg, 0.27 mmol), 2-chlorobenzenesulfonyl chloride (254 mg, 1.2 mmol) and pyridine (2 mL) to provide the title product (69 mg, 40% yield). LCMS (ESI) $[M+H]^+$=642.1.

Step 3: 2-Chloro-N-(5-(2-(((3S,5S)-5-fluoropiperidin-3-yl)amino)-8-methylpyrido[3,2-d]pyrimidin-6-yl)-6-methylpyridin-2-yl)benzenesulfonamide

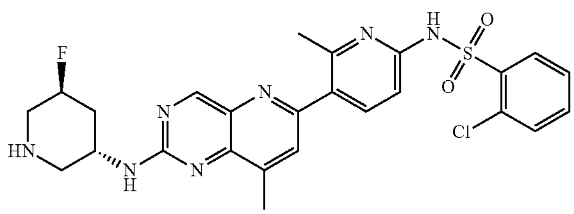 [SMILES: Cc1nc(NS(=O)(=O)c2ccccc2Cl)ccc1-c1cc(C)c2nc(N[C@@H]3CNC[C@@H](F)C3)ncc2n1]

tert-Butyl (3S,5S)-3-[[6-[6-[(2-chlorophenyl)sulfonylamino]-2-methyl-3-pyridyl]-8-methyl-pyrido[3,2-d]pyrimidin-2-yl]amino]-5-fluoro-piperidine-1-carboxylate (69 mg, 0.11 mmol) was dissolved in EtOAc (2 mL) and 4N HCl in dioxanes (2 mL) was added and stirred at rt for 3 h. Volatiles were removed under reduced pressure and the crude residue was purified by C18 reverse phase chromatography (0-100% MeCN/10 mM aqueous ammonium formate, pH=3.8). Appropriate fractions combined and concentrated to remove MeCN then the aqueous mixture was treated with saturated $NaHCO_3$ solution (~10 mL) until pH ~7-8. Organics were extracted with EtOAc (2×40 mL), dried over anhydrous $Na_2SO_4$, filtered and concentrated. The material was then dissolved in MeCN and $H_2O$ and lyophilized to provide the title product (11 mg, 19% yield).

Example 36: N-(4-(2-(((1,4-trans)-4-(Dimethylamino)cyclohexyl)amino)-8-methylpyrido[3,2-d]pyrimidin-6-yl)-2,5-difluorophenyl)-1-(4-fluorophenyl)methanesulfonamide (Compound 137)

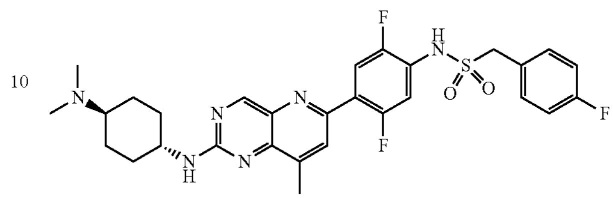

Step 1: 2,5-Difluoro-4-(4,4,5,5-tetramethyl-1,3,2-dioxaborolan-2-yl)aniline

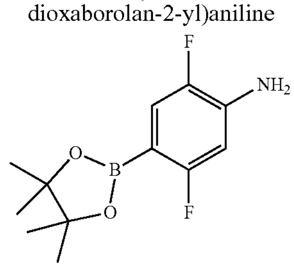

A flask was charged with $Pd_2(dba)_3 \cdot CHCl_3$ (45 mg, 0.04 mmol) and tricyclohexylphosphine (55 mg, 0.20 mmol). Degassed 1,4-Dioxane (10 mL) was added and the resulting mixture was stirred 25 minutes at rt before addition of bis(pinacolato)diboron (700 mg, 2.76 mmol), potassium acetate (715 mg, 7.21 mmol) and 4-Bromo-2,5-difluoroaniline (500 mg, 2.40 mmol) in that order. The reaction mixture was stirred overnight at 120° C. then diluted with EtOAc, filtered through a pad of celite and concentrated under reduced pressure. The crude material was purified by flash chromatography through silica gel (0-100% $CH_2Cl_2$/heptanes) to provide the title compound (524 mg, 85% yield). LCMS (ESI) $[M+H]^+$=256.3.

Step 2: tert-Butyl ((1,4-trans)-4-((6-(4-amino-2,5-difluorophenyl)-8-methylpyrido[3,2-d]pyrimidin-2-yl)amino)cyclohexyl)carbamate

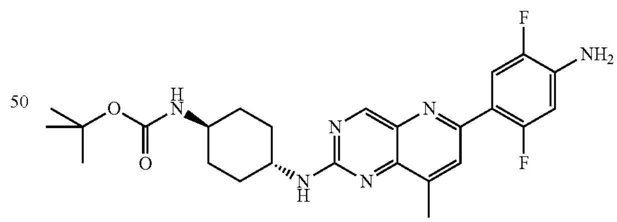

Prepared according to Example 24 (Compound 125) step 1 using tert-butyl ((1,4-trans)-4-((6-chloro-8-methylpyrido[3,2-d]pyrimidin-2-yl)amino)cyclohexyl)carbamate (200 mg, 0.51 mmol), 2,5-difluoro-4-(4,4,5,5-tetramethyl-1,3,2-dioxaborolan-2-yl)aniline (257 mg, 1.01 mmol), potassium carbonate (287 mg, 2.08 mmol) and $Pd(PPh_3)_4$ (89 mg, 0.08 mmol). The reaction mixture was diluted with EtOAc, filtered through celite and the filtrate was evaporated under reduced pressure. To the residue was added $CH_2Cl_2$, $Et_2O$, and heptanes. The resulting solids were filtered to provide the title compound (53 mg, 21% yield). LCMS (ESI) [M+H]+=485.3.

Step 3: tert-Butyl ((1,4-trans)-4-((6-(2,5-difluoro-4-((4-fluorophenyl)methylsulfonamido)phenyl)-8-methylpyrido[3,2-d]pyrimidin-2-yl)amino)cyclohexyl)carbamate

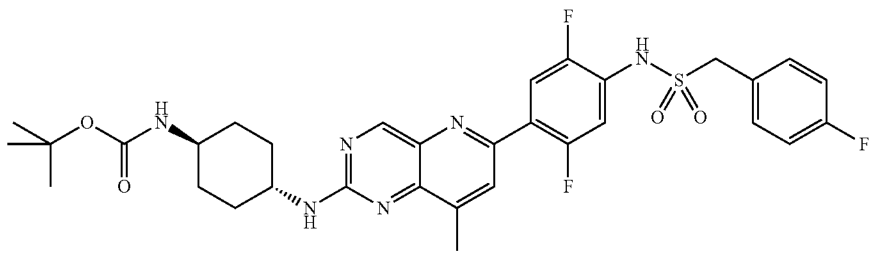 [SMILES: Cc1cc(-c2cc(F)c(NS(=O)(=O)Cc3ccc(F)cc3)cc2F)nc2cnc(N[C@H]3CC[C@H](NC(=O)OC(C)(C)C)CC3)nc12]

Prepared according to Example 34 (Compound 135) step 1 using tert-butyl ((1,4-trans)-4-((6-(4-amino-2,5-difluorophenyl)-8-methylpyrido[3,2-d]pyrimidin-2-yl)amino)cyclohexyl)carbamate (53 mg, 0.11 mmol) and (4-fluorophenyl) methanesulfonyl chloride (46 mg, 0.22 mmol) to provide the title product (47 mg, 65% yield). LCMS (ESI) [M+H]+=657.4.

Step 4: N-(4-(2-(((1,4-trans)-4-Aminocyclohexyl) amino)-8-methylpyrido[3,2-d]pyrimidin-6-yl)-2,5-difluorophenyl)-1-(4-fluorophenyl)methanesulfonamide

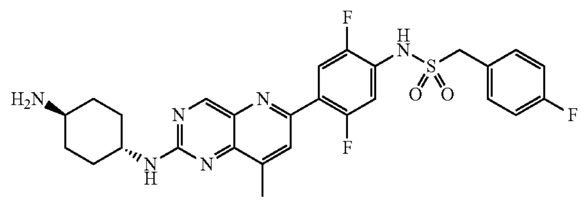 [SMILES: Cc1cc(-c2cc(F)c(NS(=O)(=O)Cc3ccc(F)cc3)cc2F)nc2cnc(N[C@H]3CC[C@H](N)CC3)nc12]

Prepared according to Example 27 (Compound 128) step 2 using tert-butyl ((1,4-trans)-4-((6-(2,5-difluoro-4-((4-fluorophenyl)methylsulfonamido)phenyl)-8-methylpyrido[3,2-d]pyrimidin-2-yl)amino)cyclohexyl)carbamate (47 mg, 0.07 mmol) and TFA (0.5 mL, 6.53 mmol). The solvent was evaporated under reduced pressure and the crude residue was diluted with a saturated aqueous solution of $NaHCO_3$, extracted three times with 2-MeTHF. The organic phases were combined, all the remaining solid on the glassware was solubilized in MeOH and combined with the previous extractions. Solvents were removed under reduced pressure to provide the crude title compound (assumed quantitative yield). LCMS (ESI) $[M+H]^+$=557.0.

Step 5: N-(4-(2-(((1,4-trans)-4-(Dimethylamino) cyclohexyl)amino)-8-methylpyrido[3,2-d]pyrimidin-6-yl)-2,5-difluorophenyl)-1-(4-fluorophenyl)methanesulfonamide

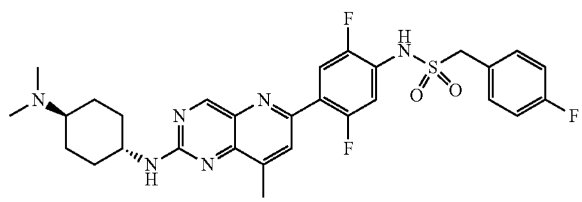 [SMILES: Cc1cc(-c2cc(F)c(NS(=O)(=O)Cc3ccc(F)cc3)cc2F)nc2cnc(N[C@H]3CC[C@H](N(C)C)CC3)nc12]

Prepared according to Example 27 (Compound 128) step 3 using N-(4-(2-(((1,4-trans)-4-aminocyclohexyl)amino)-8-methylpyrido[3,2-d]pyrimidin-6-yl)-2,5-difluorophenyl)-1-(4-fluorophenyl)methanesulfonamide (39 mg, 0.07 mmol), 37% w/w aqueous formaldehyde (0.06 mL, 0.73 mmol) and sodium triacetoxyborohydride (76 mg, 0.36 mmol) to provide the title compound (27 mg, 66% yield).

Example 37: N-(4-(2-(((1,4-trans)-4-(Dimethylamino)cyclohexyl)amino)-8-(methoxymethyl)pyrido[3,2-d]pyrimidin-6-yl)-2-fluorophenyl)-1-(4-fluorophenyl)methanesulfonamide (Compound 138)

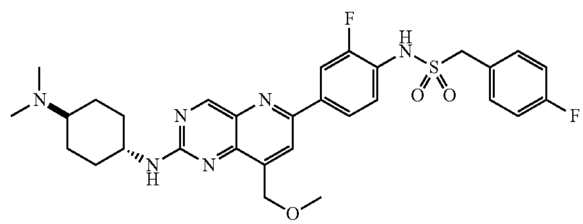 [SMILES: COCc1cc(-c2ccc(NS(=O)(=O)Cc3ccc(F)cc3)c(F)c2)nc2cnc(N[C@H]3CC[C@H](N(C)C)CC3)nc12]

Step 1: 2,6-Dichloro-8-(methoxymethyl)pyrido[3,2-d]pyrimidine

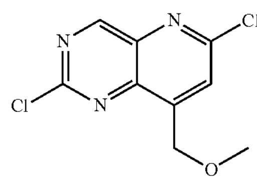

(2,6-Dichloropyrido[3,2-d]pyrimidin-8-yl)methanol (150 mg, 0.65 mmol) was dissolved in $CH_2Cl_2$ (6 mL) and to the solution was added N,N,N',N'-tetramethyl-1,8-naphthalenediamine (209 mg, 0.98 mmol) followed by trimethyloxonium tetrafluoroborate (96 mg, 0.65 mmol). The reaction was stirred at rt for 3 h then diluted with $CH_2Cl_2$ (40 mL) and washed with 1M HCl (10 mL). The organic layer was concentrated with silica gel and purified by flash chromatography through silica gel (0-40% EtOAc/heptanes) to provide the title compound (100 mg, 63% yield). LCMS (ESI) $[M+H]^+$=243.9.

Step 2: tert-Butyl ((1,4-trans)-4-((6-chloro-8-(methoxymethyl)pyrido[3,2-d]pyrimidin-2-yl)amino)cyclohexyl)carbamate

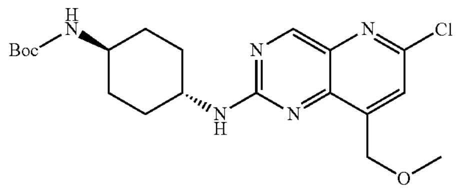 [SMILES: COCc1cc(Cl)nc2cnc(N[C@H]3CC[C@H](NC(=O)OC(C)(C)C)CC3)nc12]

2,6-Dichloro-8-(methoxymethyl)pyrido[3,2-d]pyrimidine (100 mg, 0.41 mmol), N-Boc-trans-1,4-cyclohexanediamine (105 mg, 0.49 mmol) and sodium bicarbonate (138 mg, 1.64 mmol) in DMSO (3 mL) was stirred at 80° C. for 2 h. The reaction was diluted with EtOAc (50 mL) and washed with water (2×20 mL) then with saturated aqueous sodium chloride. The organic layer was concentrated under reduced pressure with silica gel and purified by silica flash chromatography through silica gel (10-100% EtOAc/heptanes) to provide the title compound (140 mg, 81% yield). LCMS (ESI) $[M+H]^+$=422.2.

Step 3: tert-Butyl N-[(1,4-trans)-4-[[6-(4-amino-3-fluoro-phenyl)-8-(methoxymethyl)pyrido[3,2-d]pyrimidin-2-yl]amino]cyclohexyl]carbamate

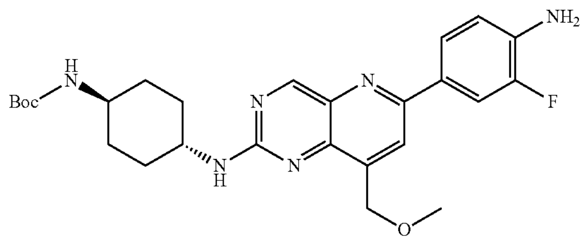 [SMILES: COCc1cc(-c2ccc(N)c(F)c2)nc2cnc(N[C@H]3CC[C@H](NC(=O)OC(C)(C)C)CC3)nc12]

A flask was charged with tert-butyl ((1,4-trans)-4-((6-chloro-8-(methoxymethyl)pyrido[3,2-d]pyrimidin-2-yl)amino)cyclohexyl)carbamate (140 mg, 0.33 mmol) and 1,2-dimethoxyethane (6 mL) and $H_2O$ (1.5 mL). The mixture was purged with $N_2$ for 10 min. To the flask was then added 2-fluoro-4-(4,4,5,5-tetramethyl-1,3,2-dioxaborolan-2-yl)aniline (118 mg, 0.50 mol), palladium acetate (15 mg, 0.07 mmol), tri-o-tolylphosphine (40 mg, 0.13 mmol), sodium carbonate (70 mg, 0.66 mmol) and the mixture was heated at 90° C. for 6 h. Toluene (20 mL) was then added and the mixture was concentrated with silica gel and purified by flash chromatography through silica gel (10-100% EtOAc/heptanes) to provide the title compound (115 mg, 70% yield). LCMS (ESI) $[M+H]^+$=497.1.

Step 4: tert-Butyl N-[(1,4-trans)-4-[[6-[3-fluoro-4-[(4-fluorophenyl)methylsulfonylamino]phenyl]-8-(methoxymethyl)pyrido[3,2-d]pyrimidin-2-yl]amino]cyclohexyl]carbamate

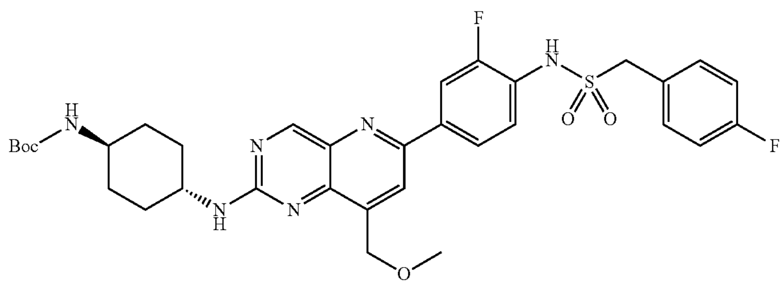 [SMILES: COCc1cc(-c2ccc(NS(=O)(=O)Cc3ccc(F)cc3)c(F)c2)nc2cnc(N[C@H]3CC[C@H](NC(=O)OC(C)(C)C)CC3)nc12]

A flask was charged with tert-butyl ((1,4-trans)-4-((6-chloro-8-(methoxymethyl)pyrido[3,2-d]pyrimidin-2-yl)amino)cyclohexyl)carbamate (100 mg, 0.20 mmol) and pyridine (2 mL). 4-Fluorophenyl)methanesulfonyl chloride (252 mg, 1.21 mmol) was added and stirred at rt for 30 min. MeOH (1 mL) and toluene (10 mL) were then added and the mixture was concentrated with silica gel and purified by flash chromatography through silica gel (0-70% EtOAc/heptanes) to provide the title compound (28 mg, 21% yield). LCMS (ESI) $[M+H]^+$=669.4.

Step 5: N-[(1,4-trans)-4-[2-[[4-(Dimethylamino)cyclohexyl]amino]-8-(methoxymethyl)pyrido[3,2-d]pyrimidin-6-yl]-2-fluoro-phenyl]-1-(4-fluorophenyl)methanesulfonamide

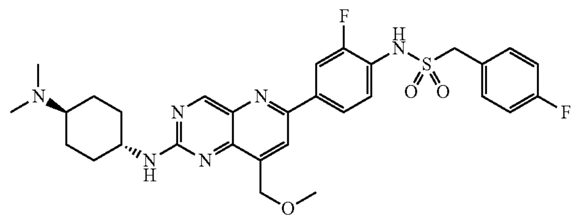 [SMILES: COCc1cc(-c2ccc(NS(=O)(=O)Cc3ccc(F)cc3)c(F)c2)nc2cnc(N[C@H]3CC[C@H](N(C)C)CC3)nc12]

tert-Butyl N-[(1,4-trans)-4-[[6-[3-fluoro-4-[(4-fluorophenyl)methylsulfonylamino]phenyl]-8-(methoxymethyl)pyrido[3,2-d]pyrimidin-2-yl]amino]cyclohexyl]carbamate (28 mg, 0.04 mmol) was treated with TFA (1 mL) and the reaction was stirred at rt for 10 min. Toluene (5 mL) was added and concentrated under reduced pressure. The crude was dissolved in methanol (2 mL) and to solution was added sodium acetate (34 mg, 0.42 mmol) followed by 37% w/w aqueous formaldehyde (34 mg, 0.42 mmol). The mixture was stirred at rt for 10 min then sodium triacetoxyborohydride (44 mg, 0.21 mmol) was added. The reaction was stirred at rt for 10 min then concentrated to half volume and purified directly by C18 reverse phase chromatography (0-100% MeCN/10 mM aqueous ammonium formate, pH=3.8). Appropriate fractions were combined and concentrated to dryness. The residue was dissolved in EtOAc (20 mL) and washed with saturated aqueous sodium bicarbonate (5 mL). The organic layer was dried over $Na_2SO_4$, filtered and concentrated. The residue was dissolved in a mixture of MeCN and water and lyophilized to provide the title compound (17 mg, 68% yield).

Example 38: N-[4-[8-(Difluoromethyl)-2-[[(3S,5S)-5-fluoro-3-piperidyl]amino]pyrido[3,2-d]pyrimidin-6-yl]-2-fluoro-phenyl]-1-(4-fluorophenyl)methanesulfonamide hydrochloride (Compound 139)

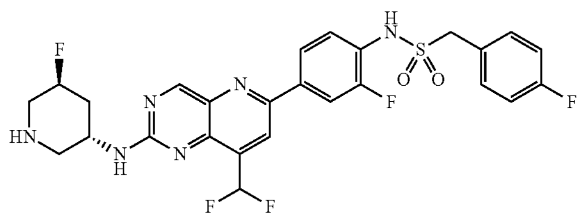 [SMILES: O=S(=O)(Cc1ccc(F)cc1)Nc1ccc(-c2cc(C(F)F)c3nc(N[C@@H]4CNC[C@@H](F)C4)ncc3n2)cc1F]

Step 1: tert-Butyl (3S,5S)-3-[[6-chloro-8-(difluoromethyl)pyrido[3,2-d]pyrimidin-2-yl]amino]-5-fluoro-piperidine-1-carboxylate

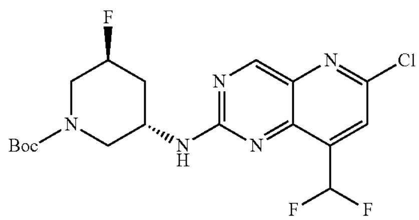 [SMILES: CC(C)(C)OC(=O)N1C[C@@H](F)C[C@H](Nc2ncc3nc(Cl)cc(C(F)F)c3n2)C1]

2,6-Dichloro-8-(difluoromethyl)pyrido[3,2-d]pyrimidine (100 mg, 0.40 mmol) and tert-butyl (3S,5S)-3-amino-5-fluoro-piperidine-1-carboxylate (131 mg, 0.60 mmol) and sodium bicarbonate (100 mg, 1.2 mmol) were combined in DMSO (3 mL) and stirred at 80° C. for 30 min. The mixture was diluted with EtOAc (50 mL) and water (20 mL), and neutralized with saturated aqueous citric acid. The phases were separated and the organic extract was washed with water then with saturated aqueous sodium chloride and concentrated with silica gel and purified by silica flash chromatography (0-100% EtOAc/heptanes) to provide the title compound (120 mg, 69% yield). LCMS (ESI) {[M]-t-Butyl+H}$^+$=376.1.

Step 2: tert-Butyl (3S,5S)-3-[[6-chloro-8-(difluoromethyl)pyrido[3,2-d]pyrimidin-2-yl]amino]-5-fluoro-piperidine-1-carboxylate

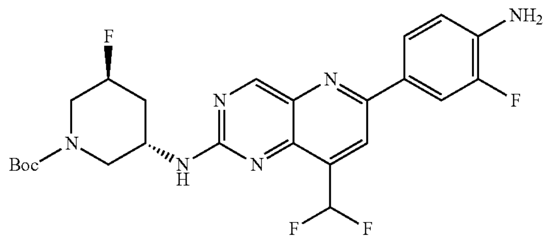 [SMILES: CC(C)(C)OC(=O)N1C[C@@H](F)C[C@H](Nc2ncc3nc(-c4ccc(N)c(F)c4)cc(C(F)F)c3n2)C1]

A flask was charged with tert-butyl (3S,5S)-3-[[6-chloro-8-(difluoromethyl)pyrido[3,2-d]pyrimidin-2-yl]amino]-5-fluoro-piperidine-1-carboxylate (120 mg, 0.28 mmol) and 1,2-dimethoxyethane (6 mL) and $H_2O$ (1.5 mL). The mixture was purged with $N_2$ for 10 min. To this mixture was then added 2-fluoro-4-(4,4,5,5-tetramethyl-1,3,2-dioxaborolan-2-yl)aniline (99 mg, 0.42 mmol), palladium acetate (12 mg, 0.06 mmol), tri-o-tolylphosphine (34 mg, 0.11 mmol), sodium carbonate (59 mg, 0.56 mmol) and the mixture was stirred at 90° C. for 6 h. Toluene (20 mL) was then added and the mixture was concentrated with silica gel and purified by flash chromatography through silica gel (10-100% EtOAc/heptanes) to provide the title compound (76 mg, 54% yield). LCMS (ESI) [M+H]$^+$=507.2.

Step 3: tert-Butyl (3S,5S)-3-[[8-(difluoromethyl)-6-[3-fluoro-4-[(4-fluorophenyl)methylsulfonylamino]phenyl]pyrido[3,2-d]pyrimidin-2-yl]amino]-5-fluoro-piperidine-1-carboxylate

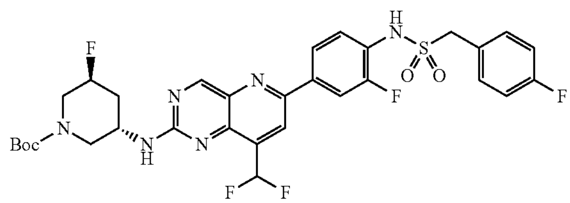 [SMILES: CC(C)(C)OC(=O)N1C[C@@H](F)C[C@H](Nc2ncc3nc(-c4ccc(NS(=O)(=O)Cc5ccc(F)cc5)c(F)c4)cc(C(F)F)c3n2)C1]

tert-Butyl (3S,5S)-3-[[6-chloro-8-(difluoromethyl)pyrido[3,2-d]pyrimidin-2-yl]amino]-5-fluoro-piperidine-1-carboxylate (76 mg, 0.15 mmol) was dissolved in $CH_2Cl_2$ (1 mL) and to the solution was added pyridine (0.5 mL) followed by (4-fluorophenyl)methanesulfonyl chloride (313 mg, 1.5 mmol). The reaction was stirred at rt for 1 h. MeOH (1 mL) and toluene (5 mL) were then added and concentrated to dryness. The crude was dissolved in DMSO and purified by prep-HPLC (CSH column, 50-70% MeCN/10 mM aqueous ammonium formate, pH=3.8) to provide the title compound (35 mg, 34% yield). LCMS (ESI) [M+H]$^+$=679.3.

Step 4: N-[4-[8-(Difluoromethyl)-2-[[(3S,5S)-5-fluoro-3-piperidyl]amino]pyrido[3,2-d]pyrimidin-6-yl]-2-fluoro-phenyl]-1-(4-fluorophenyl)methanesulfonamide hydrochloride

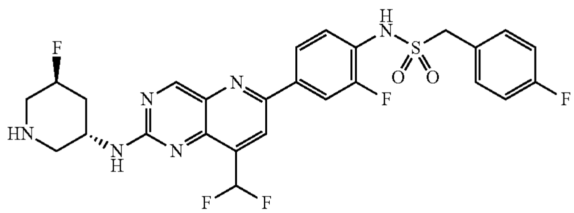 [SMILES: O=S(=O)(Cc1ccc(F)cc1)Nc1ccc(-c2cc(C(F)F)c3nc(N[C@@H]4CNC[C@@H](F)C4)ncc3n2)cc1F]

tert-Butyl (3S,5S)-3-[[8-(difluoromethyl)-6-[3-fluoro-4-[(4-fluorophenyl)methylsulfonylamino]phenyl]pyrido[3,2-d]pyrimidin-2-yl]amino]-5-fluoro-piperidine-1-carboxylate (35 mg, 0.05 mmol) was dissolved in 1,4-dioxane (1 mL) and to the solution was added 2M HCl in dioxane (1 mL, 0.5 mmol). The reaction was stirred at rt for 30 min then diluted with methyl-t-butyl ether (10 mL) and stirred for 5 min. The resulting solids were filtered off, dissolved in water and lyophilized to provide the title compound (20 mg, 63% yield).

Example 39: N-(4-(2-(((1,4-trans)-4-(Dimethylamino)cyclohexyl)amino)-8-methylpyrido[3,2-d]pyrimidin-6-yl)-3,5-difluorophenyl)-1-(4-fluorophenyl)methanesulfonamide (Compound 140)

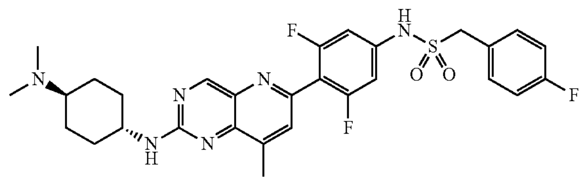 [SMILES: Cc1cc(-c2c(F)cc(NS(=O)(=O)Cc3ccc(F)cc3)cc2F)nc2cnc(N[C@H]3CC[C@H](N(C)C)CC3)nc12]

Step 1: 3,5-Difluoro-4-(4,4,5,5-tetramethyl-1,3,2-dioxaborolan-2-yl)aniline

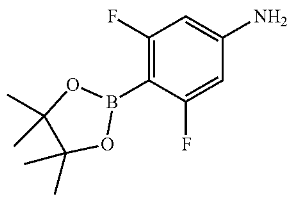 [SMILES: CC1(C)OB(c2c(F)cc(N)cc2F)OC1(C)C]

A flask was charged with $Pd_2(dba)_3 \cdot CHCl_3$ (45 mg, 0.04 mmol) and tricyclohexylphosphine (55 mg, 0.20 mmol). Degassed 1,4-dioxane (10 mL) was added and the resulting mixture was stirred 25 minutes at rt before addition of bis(pinacolato)diboron (700 mg, 2.76 mmol), potassium acetate (715 mg, 7.21 mmol) and 4-bromo-3,5-difluoroaniline (500 mg, 2.40 mmol) in that order. The reaction mixture was stirred overnight at 120° C. then 4 h at 170° C. The reaction mixture was then diluted with EtOAc, filtered through a pad of celite and concentrated under reduced pressure. The crude material was purified by silica flash chromatography (0-100% $CH_2Cl_2$/heptanes) to provide the title compound (252 mg, 41% yield). LCMS (ESI) $[M+H]^+$=256.2.

Step 2: tert-Butyl ((1,4-trans)-4-((6-(4-amino-2,6-difluorophenyl)-8-methylpyrido[3,2-d]pyrimidin-2-yl)amino)cyclohexyl)carbamate

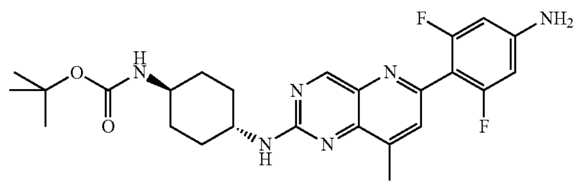 [SMILES: Cc1cc(-c2c(F)cc(N)cc2F)nc2cnc(N[C@H]3CC[C@H](NC(=O)OC(C)(C)C)CC3)nc12]

Prepared according to Example 36 (Compound 137) step 2 using tert-butyl ((1,4-trans)-4-((6-chloro-8-methylpyrido[3,2-d]pyrimidin-2-yl)amino)cyclohexyl)carbamate (196 mg, 0.50 mmol), 3,5-difluoro-4-(4,4,5,5-tetramethyl-1,3,2-dioxaborolan-2-yl)aniline (252 mg, 0.99 mmol), potassium carbonate (282 mg, 2.04 mmol) and $Pd(PPh_3)_4$ (88 mg, 0.08 mmol) to provide the title compound (275 mg, 113% yield). LCMS (ESI) $[M+H]^+$=485.1.

Step 3: tert-Butyl ((1,4-trans)-4-((6-(2,6-difluoro-4-((4-fluorophenyl)methylsulfonamido)phenyl)-8-methylpyrido[3,2-d]pyrimidin-2-yl)amino)cyclohexyl)carbamate

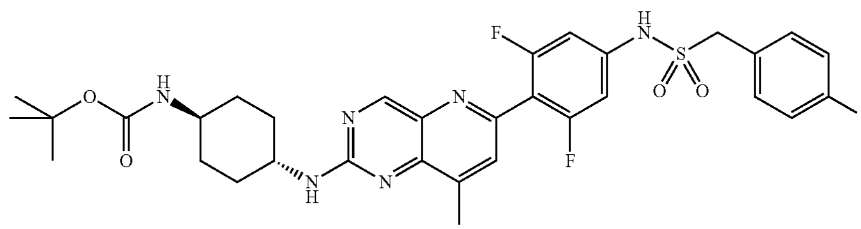

Prepared according to Example 34 (Compound 135) step 1 using tert-butyl ((1,4-trans)-4-((6-(4-amino-2,6-difluorophenyl)-8-methylpyrido[3,2-d]pyrimidin-2-yl)amino)cyclohexyl)carbamate (150 mg, 0.31 mmol) and (4-fluorophenyl) methanesulfonyl chloride (130 mg, 0.62 mmol) to provide the title product (93 mg, 46% yield). LCMS (ESI) $[M+H]^+$=657.2.

Step 4: N-(4-(2-(((1,4-trans)-4-Aminocyclohexyl) amino)-8-methylpyrido[3,2-d]pyrimidin-6-yl)-3,5-difluorophenyl)-1-(4-fluorophenyl)methanesulfonamide

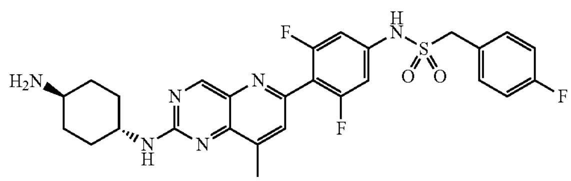 [SMILES: Cc1cc(-c2c(F)cc(NS(=O)(=O)Cc3ccc(F)cc3)cc2F)nc2cnc(N[C@H]3CC[C@H](N)CC3)nc12]

Prepared according to Example 36 (Compound 137) step 2 using tert-butyl ((1,4-trans)-4-((6-(2,6-difluoro-4-((4-fluorophenyl)methylsulfonamido)phenyl)-8-methylpyrido[3,2-d]pyrimidin-2-yl)amino)cyclohexyl)carbamate (93 mg, 0.14 mmol) and TFA (0.5 mL, 6.53 mmol) to provide the title product (assumed quantitative yield). LCMS (ESI) $[M+H]^+$=557.1.

Step 5: N-(4-(2-(((1,4-trans)-4-(Dimethylamino) cyclohexyl)amino)-8-methylpyrido[3,2-d]pyrimidin-6-yl)-3,5-difluorophenyl)-1-(4-fluorophenyl)methanesulfonamide

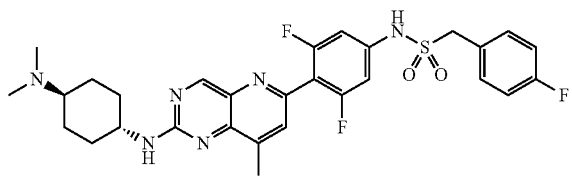 [SMILES: Cc1cc(-c2c(F)cc(NS(=O)(=O)Cc3ccc(F)cc3)cc2F)nc2cnc(N[C@H]3CC[C@H](N(C)C)CC3)nc12]

Prepared according to Example 27 (Compound 128) step 3 using N-(4-(2-(((1,4-trans)-4-aminocyclohexyl)amino)-8-methylpyrido[3,2-d]pyrimidin-6-yl)-3,5-difluorophenyl)-1-(4-fluorophenyl)methanesulfonamide (78 mg, 0.14 mmol), 37% w/w aqueous formaldehyde (0.12 mL, 1.43 mmol) and sodium triacetoxyborohydride (150 mg, 0.71 mmol). The volatiles were evaporated under reduced pressure and the residue was purified by C18 reverse phase flash chromatography (0-50% MeCN/10 mM aqueous ammonium formate, pH=3.8). Appropriate fractions were combined and most of the MeCN and $H_2O$ were evaporated under reduced pressure. The remaining solution was diluted with a saturated aqueous solution of $NaHCO_3$, extracted three times with EtOAc, dried ($MgSO_4$), filtered and concentrated under reduced pressure. The material thus obtained was dissolved in a mixture of MeCN and water and lyophilized to provide the title compound (48 mg, 59% yield).

Example 40: 2-Chloro-N-(5-(2-(((1,4-trans)-4-(dimethylamino)cyclohexyl)amino)-8-ethylpyrido[3,2-d]pyrimidin-6-yl)-6-methoxypyridin-2-yl)benzenesulfonamide (Compound 141)

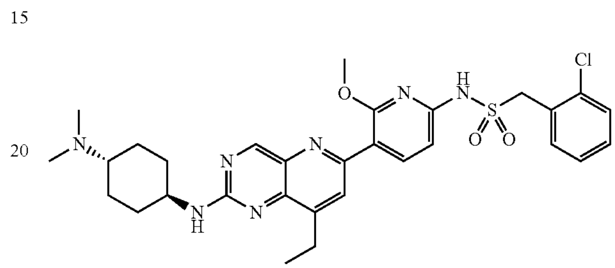

Step 1: tert-Butyl ((1,4-trans)-4-((6-(6-amino-2-methoxypyridin-3-yl)-8-ethylpyrido[3,2-d]pyrimidin-2-yl)amino)cyclohexyl)carbamate

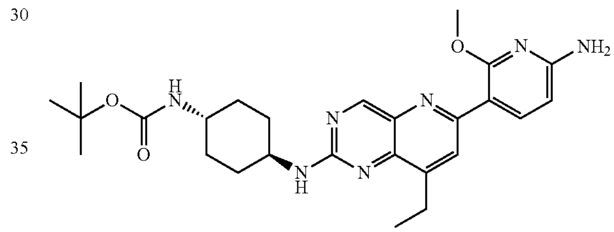

Prepared according to Example 25 (Compound 126) step 1 using tert-butyl N-[4-[(6-chloro-8-ethyl-pyrido[3,2-d]pyrimidin-2-yl)amino]cyclohexyl]carbamate (250 mg, 0.62 mmol), 6-methoxy-5-(4,4,5,5-tetramethyl-1,3,2-dioxaborolan-2-yl)pyridin-2-amine (231 mg, 0.92 mmol), potassium carbonate (340 mg, 2.46 mmol), $Pd(PPh_3)_4$ (71 mg, 0.06 mmol), 1,4-dioxane (4 mL) and $H_2O$ (1 mL) to provide the title compound (290 mg, 95% yield). LCMS (ESI) $[M+H]^+$=494.2.

Step 2: tert-Butyl ((1,4-trans)-4-((6-(6-(2-chlorophenylsulfonamido)-2-methoxypyridin-3-yl)-8-ethylpyrido[3,2-d]pyrimidin-2-yl)amino)cyclohexyl) carbamate

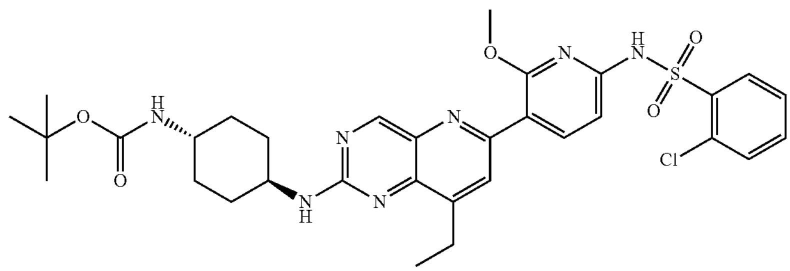 [SMILES: CCc1cc(-c2ccc(NS(=O)(=O)c3ccccc3Cl)nc2OC)nc2cnc(N[C@H]3CC[C@H](NC(=O)OC(C)(C)C)CC3)nc12]

Prepared according to Example 9 (Compound 110) step 3 using tert-butyl ((1,4-trans)-4-((6-(6-amino-2-methoxypyridin-3-yl)-8-ethylpyrido[3,2-d]pyrimidin-2-yl)amino)cyclohexyl)carbamate (145 mg, 0.29 mmol), 2-chlorobenzenesulfonyl chloride (186 mg, 0.88 mmol) and pyridine (2 mL) provide the title product (113 mg, 58% yield). LCMS (ESI) $[M+H]^+$=668.3.

Step 3: N-(5-(2-(((1,4-trans)-4-Aminocyclohexyl)amino)-8-ethylpyrido[3,2-d]pyrimidin-6-yl)-6-methoxypyridin-2-yl)-2-chlorobenzenesulfonamide 2,2,2-trifluoroacetate

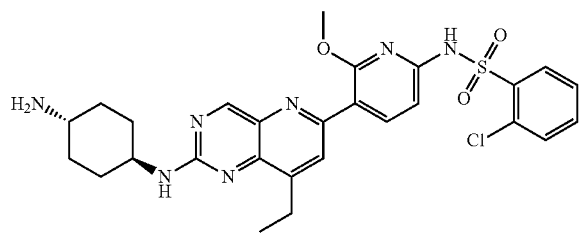 [SMILES: CCc1cc(-c2ccc(NS(=O)(=O)c3ccccc3Cl)nc2OC)nc2cnc(N[C@H]3CC[C@H](N)CC3)nc12]

Prepared according to Example 11 (Compound 112) step 3 using tert-butyl ((1,4-trans)-4-((6-(6-(2-chlorophenylsulfonamido)-2-methoxypyridin-3-yl)-8-ethylpyrido[3,2-d]pyrimidin-2-yl)amino)cyclohexyl)carbamate (113 mg, 0.17 mmol), trifluoroacetic acid (1.0 mL) and $CH_2Cl_2$ (4 mL) to provide the crude title product (116 mg, 100% yield) which was used directly in the next step without further purification.

Step 4: 2-Chloro-N-(5-(2-(((1,4-trans)-4-(dimethylamino)cyclohexyl)amino)-8-ethylpyrido[3,2-d]pyrimidin-6-yl)-6-methoxypyridin-2-yl)benzenesulfonamide

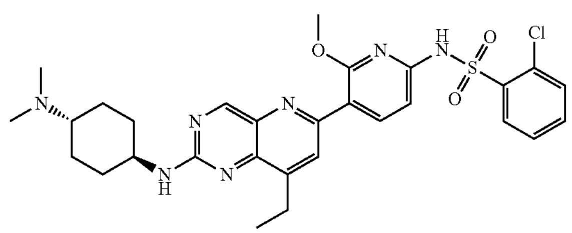 [SMILES: CCc1cc(-c2ccc(NS(=O)(=O)c3ccccc3Cl)nc2OC)nc2cnc(N[C@H]3CC[C@H](N(C)C)CC3)nc12]

Prepared according to Example 11 (Compound 112) step 4 using N-(5-(2-(((1,4-trans)-4-aminocyclohexyl)amino)-8-ethylpyrido[3,2-d]pyrimidin-6-yl)-6-methoxypyridin-2-yl)-2-chlorobenzenesulfonamide 2,2,2-trifluoroacetate (116 mg, 0.17 mmol), MeOH (3 mL), sodium acetate (83 mg, 1.0 mmol), 37% w/w aqueous formaldehyde (206 mg, 2.54 mmol), and sodium triacetoxyborohydride (142 mg, 0.68 mmol) to provide the target compound (25 mg, 25% yield)

Example 41: N-(5-(2-(((1,4-trans)-4-(Dimethylamino)cyclohexyl)amino)-8-ethylpyrido[3,2-d]pyrimidin-6-yl)-6-methoxypyridin-2-yl)-1-(4-fluorophenyl)methanesulfonamide (Compound 142)

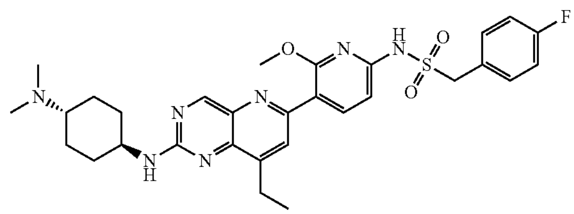 [SMILES: CCc1cc(-c2ccc(NS(=O)(=O)Cc3ccc(F)cc3)nc2OC)nc2cnc(N[C@H]3CC[C@H](N(C)C)CC3)nc12]

Step 1: tert-Butyl ((1,4-trans)-4-((8-ethyl-6-(6-((4-fluorophenyl)methylsulfonamido)-2-methoxypyridin-3-yl)pyrido[3,2-d]pyrimidin-2-yl)amino)cyclohexyl)carbamate

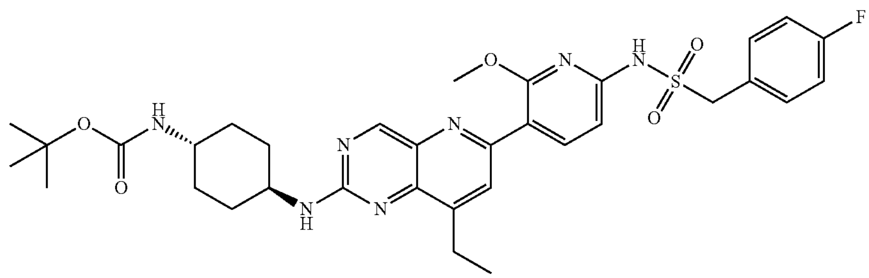 [SMILES: CCc1cc(-c2ccc(NS(=O)(=O)Cc3ccc(F)cc3)nc2OC)nc2cnc(N[C@H]3CC[C@H](NC(=O)OC(C)(C)C)CC3)nc12]

Prepared according to Example 9 (Compound 110) step 3 using tert-butyl N-[4-[[6-(6-amino-2-methoxy-3-pyridyl)-8-ethyl-pyrido[3,2-d]pyrimidin-2-yl]amino]cyclohexyl]carbamate (145 mg, 0.29 mmol) and (4-fluorophenyl)methanesulfonyl chloride (184 mg, 0.88 mmol) and pyridine (2 mL) to provide the title compound (48 mg, 24% yield). LCMS (ESI) $[M+H]^+$=666.2.

Step 2: N-(5-(2-(((1,4-trans)-4-Aminocyclohexyl)amino)-8-ethylpyrido[3,2-d]pyrimidin-6-yl-6-methoxypyridin-2-yl)-1-(4-fluorophenyl)methanesulfonamide 2,2,2-trifluoroacetate

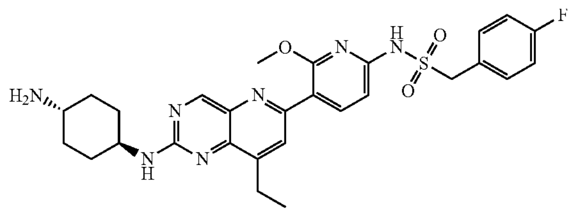 [SMILES: CCc1cc(-c2ccc(NS(=O)(=O)Cc3ccc(F)cc3)nc2OC)nc2cnc(N[C@H]3CC[C@H](N)CC3)nc12]

Prepared according to Example 11 (Compound 112) step 3 using tert-butyl ((1,4-trans)-4-((8-ethyl-6-(6-((4-fluorophenyl)methylsulfonamido)-2-methoxypyridin-3-yl)pyrido[3,2-d]pyrimidin-2-yl)amino)cyclohexyl)carbamate (48 mg, 0.07 mmol), trifluoroacetic acid (0.5 mL) and $CH_2Cl_2$ (2 mL) provide the crude title product (49 mg, 100% yield).

Step 3: N-(5-(2-(((1,4-trans)-4-(Dimethylamino)cyclohexyl)amino)-8-ethylpyrido[3,2-d]pyrimidin-6-yl)-6-methoxypyridin-2-yl)-1-(4-fluorophenyl)methanesulfonamide

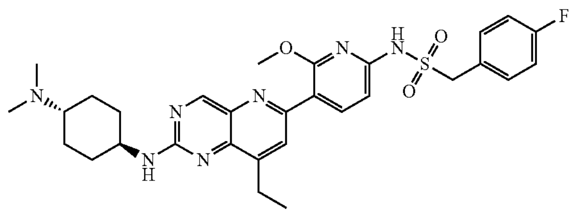 [SMILES: CCc1cc(-c2ccc(NS(=O)(=O)Cc3ccc(F)cc3)nc2OC)nc2cnc(N[C@H]3CC[C@H](N(C)C)CC3)nc12]

Prepared according to Example 11 (Compound 112) step 4 using N-(5-(2-(((1,4-trans)-4-aminocyclohexyl)amino)-8-ethylpyrido[3,2-d]pyrimidin-6-yl)-6-methoxypyridin-2-yl)-1-(4-fluorophenyl)methanesulfonamide 2,2,2-trifluoroacetate (49 mg, 0.07 mmol), sodium acetate (35 mg, 0.43 mmol), 37% w/w aqueous formaldehyde (88 mg, 1.08 mmol), and sodium triacetoxyborohydride (60 mg, 0.29 mmol) to provide the title compound (17 mg, 40% yield).

Example 42: 2-Chloro-N-[(1,4-trans)-4-[8-(difluoromethyl)-2-[[4-(dimethylamino)cyclohexyl]amino]pyrido[3,2-d]pyrimidin-6-yl]-2-fluoro-phenyl]benzenesulfonamide (Compound 143)

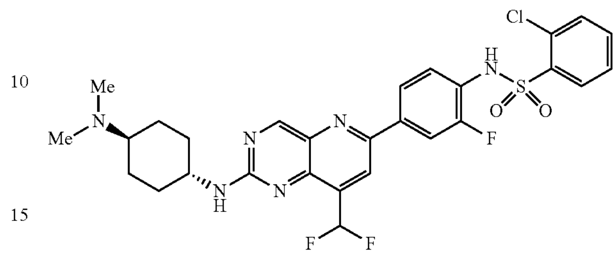

Step 1: tert-Butyl N-[(1,4-trans)-4-[[6-[4-[(2-chlorophenyl)sulfonylamino]-3-fluoro-phenyl]-8-(difluoromethyl)pyrido[3,2-d]pyrimidin-2-yl]amino]cyclohexyl]carbamate

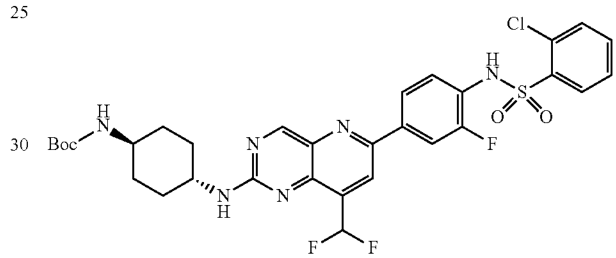

tert-Butyl N-[(1,4-trans)-4-[[6-(4-amino-3-fluoro-phenyl)-8-(difluoromethyl)pyrido[3,2-d]pyrimidin-2-yl]amino]cyclohexyl]carbamate (66 mg, 0.13 mmol) was dissolved in $CH_2Cl_2$ (1 mL) and to the solution was added pyridine (0.5 mL, 1.23 mmol) followed by 2-chlorobenzenesulfonyl chloride (41 mg, 0.20 mmol). The reaction was stirred at rt overnight then a further portion of 2-chlorobenzenesulfonyl chloride (53 mg, 0.26 mmol) was added. After a further 24 h, MeOH (1 mL) and DMSO (1 mL) and toluene (5 mL) were added to the mixture and concentrated under reduced pressure. The crude material was purified by prep-HPLC (CSH column, 55-75% MeCN/10 mM aqueous ammonium formate, pH=3.8) to provide the title compound (42 mg, 47% yield). LCMS (ESI) $[M+H]^+$=677.3.

Step 2: 2-Chloro-N-[(1,4-trans)-4-[8-(difluoromethyl)-2-[[4-(dimethylamino)cyclohexyl]amino]pyrido[3,2-d]pyrimidin-6-yl]-2-fluoro-phenyl]benzenesulfonamide

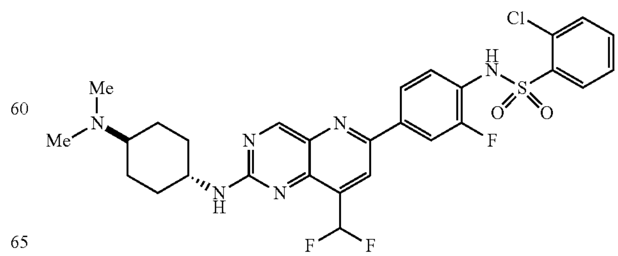

tert-Butyl N-[(1,4-trans)-4-[[6-[4-[(2-chlorophenyl)sulfonylamino]-3-fluoro-phenyl]-8-(difluoromethyl)pyrido[3,2-d]pyrimidin-2-yl]amino]cyclohexyl]carbamate (43 mg, 0.06 mmol) was dissolved in TFA (1 mL) and the reaction was stirred at rt for 10 min. MeOH (1 mL) and toluene (5 mL) were added and concentrated to dryness. The crude deprotected material was dissolved in MeOH (2 mL) and to this was then added sodium acetate (52 mg, 0.64 mmol) and 37% w/w aqueous formaldehyde (51 mg, 0.6 mmol) were added and stirred for 10 min. Sodium triacetoxyborohydride (53 mg, 0.25 mmol) was added and stirred for a further 10 min. The reaction was concentrated to half volume and purified directly by C18 reverse phase chromatography (0-100% 1:1 MeCN:MeOH/10 mM aqueous ammonium bicarbonate, pH=10) to provide the title compound (32 mg, 83% yield).

Example 43: N-[(1,4-trans)-4-[8-(Difluoromethyl)-2-[[4-(dimethylamino)cyclohexyl]amino]pyrido[3,2-d]pyrimidin-6-yl]-2-fluoro-phenyl]-3,3,3-trifluoro-propane-1-sulfonamide (Compound 144)

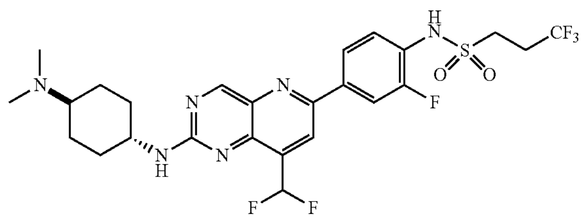 [SMILES: CN(C)[C@H]1CC[C@H](Nc2ncc3nc(-c4ccc(NS(=O)(=O)CCC(F)(F)F)c(F)c4)cc(C(F)F)c3n2)CC1]

Step 1: tert-Butyl N-[(1,4-trans)-4-[[8-(difluoromethyl)-6-[3-fluoro-4-(3,3,3-trifluoropropylsulfonylamino)phenyl]pyrido[3,2-d]pyrimidin-2-yl]amino]cyclohexyl]carbamate

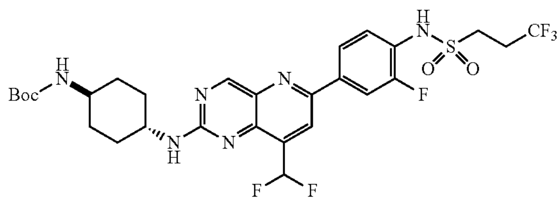 [SMILES: CC(C)(C)OC(=O)N[C@H]1CC[C@H](Nc2ncc3nc(-c4ccc(NS(=O)(=O)CCC(F)(F)F)c(F)c4)cc(C(F)F)c3n2)CC1]

Prepared according to Example 42 (Compound 143) step 1 using tert-Butyl N-[(1,4-trans)-4-[[6-(4-amino-3-fluoro-phenyl)-8-(difluoromethyl)pyrido[3,2-d]pyrimidin-2-yl]amino]cyclohexyl]carbamate (66 mg, 0.13 mmol) and 3,3,3-trifluoropropane-1-sulfonyl chloride (87 mg, 0.46 mmol) to provide the title compound (38 mg, 44% yield). LCMS (ESI) $[M+H]^+$=663.3.

Step 2: N-[4-[8-(Difluoromethyl)-2-[[(1,4-trans)-4-(dimethylamino)cyclohexyl]amino]pyrido[3,2-d]pyrimidin-6-yl]-2-fluoro-phenyl]-3,3,3-trifluoro-propane-1-sulfonamide

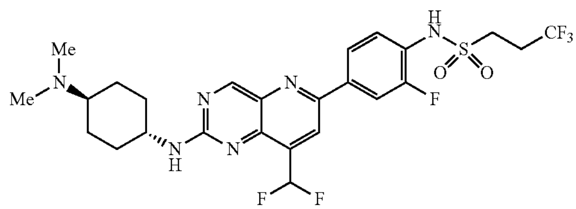 [SMILES: CN(C)[C@H]1CC[C@H](Nc2ncc3nc(-c4ccc(NS(=O)(=O)CCC(F)(F)F)c(F)c4)cc(C(F)F)c3n2)CC1]

Prepared according to Example 42 (Compound 143) step 2 using tert-butyl N-[(1,4-trans)-4-[[8-(difluoromethyl)-6-[3-fluoro-4-(3,3,3-trifluoropropylsulfonylamino)phenyl]pyrido[3,2-d]pyrimidin-2-yl]amino]cyclohexyl]carbamate (39 mg, 0.06 mmol) to provide the title compound (33 mg, 95% yield). LCMS (ESI) $[M+H]^+$=591.3. $^1$H NMR (400 MHz, DMSO-d6) δ 9.18 (s, 1H), 8.33 (s, 1H), 7.90 (d, J=11.3 Hz, 2H), 7.83 (d, J=8.6 Hz, 1H), 7.61 (t, J=56 Hz, 1H), 7.41 (d, J=8.9 Hz, 1H), 4.11-3.66 (m, 1H), 3.09-3.05 (m, 2H), 2.77-2.53 (m, 4H), 2.44 (s, 6H), 2.11-1.88 (m, 5H), 1.52-1.30 (m, 5H).

Example 44: 2-Chloro-N-[5-[8-(difluoromethyl)-2-[[(1,4-trans)-4-(dimethylamino)cyclohexyl]amino]pyrido[3,2-d]pyrimidin-6-yl]-6-methyl-2-pyridyl]benzenesulfonamide (Compound 145)

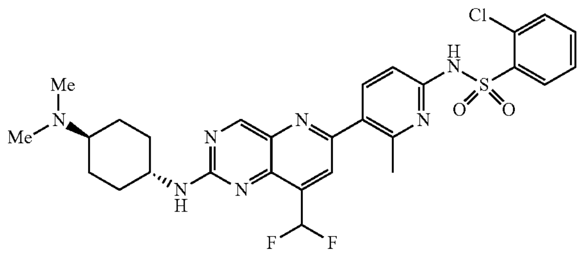 [SMILES: Cc1nc(NS(=O)(=O)c2ccccc2Cl)ccc1-c1cc(C(F)F)c2nc(N[C@H]3CC[C@H](N(C)C)CC3)ncc2n1]

Step 1: tert-Butyl N-[(1,4-trans)-4-[[6-[6-[(2-chlorophenyl)sulfonylamino]-2-methyl-3-pyridyl]-8-(difluoromethyl)pyrido[3,2-d]pyrimidin-2-yl]amino]cyclohexyl]carbamate

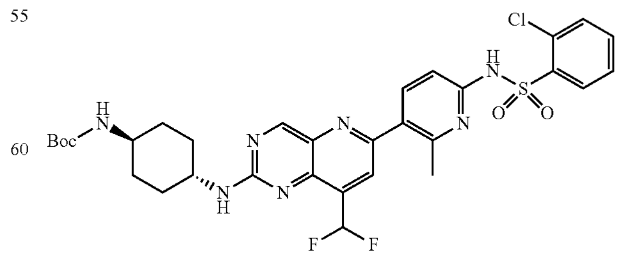

Prepared according to Example 42 (Compound 143) step 1 using tert-butyl N-[(1,4-trans)-4-[[6-(6-amino-2-methyl- 3-pyridyl)-8-(difluoromethyl)pyrido[3,2-d]pyrimidin-2-yl] amino]cyclohexyl]carbamate (25 mg, 0.05 mmol) and 2-chlorobenzenesulfonyl chloride (51 mg, 0.25 mmol) to provide the title compound (21 mg, 62% yield). LCMS (ESI) $[M+H]^+$=674.3.

Step 2: 2-Chloro-N-[5-[8-(difluoromethyl)-2-[[(1,4-trans)-4-(dimethylamino)cyclohexyl]amino]pyrido[3,2-d]pyrimidin-6-yl]-6-methyl-2-pyridyl]benzenesulfonamide

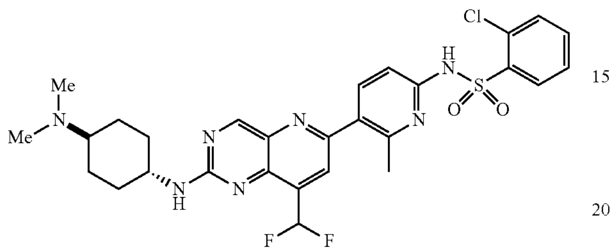

Prepared according to Example 42 (Compound 143) step 2 using tert-butyl N-[(1,4-trans)-4-[[6-[6-[(2-chlorophenyl)sulfonylamino]-2-methyl-3-pyridyl]-8-(difluoromethyl)pyrido[3,2-d]pyrimidin-2-yl]amino]cyclohexyl]carbamate (20 mg, 0.03 mmol) to provide the title compound (17 mg, 95% yield).

Example 45: N-(5-(2-(((1,4-trans)-4-(dimethylamino)cyclohexyl)amino)-8-ethylpyrido[3,2-d]pyrimidin-6-yl)-6-methylpyridin-2-yl)-2-fluorobenzenesulfonamide (Compound 146)

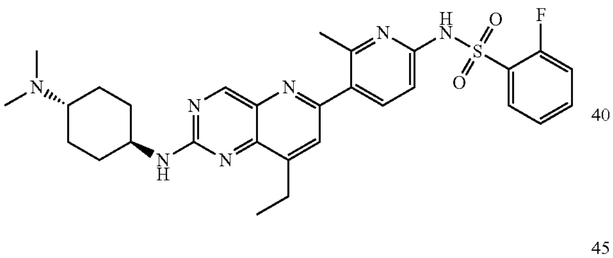

Step 1: tert-Butyl ((1,4-trans)-4-((8-ethyl-6-(6-(2-fluorophenylsulfonamido)-2-methylpyridin-3-yl)pyrido[3,2-d]pyrimidin-2-yl)amino)cyclohexyl)carbamate

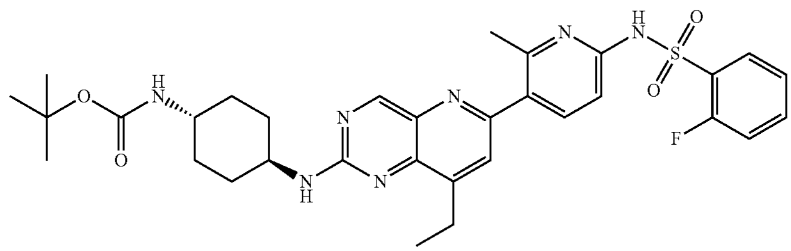

Prepared according to Example 9 (Compound 110) step 3 using tert-butyl N-[4-[[6-(6-amino-2-methyl-3-pyridyl)-8-ethyl-pyrido[3,2-d]pyrimidin-2-yl]amino]cyclohexyl]carbamate (80 mg, 0.17 mmol), pyridine (2.0 mL) and 2-fluorobenzenesulfonyl chloride (98 mg, 0.5 mmol) to provide the title product (82 mg, 77% yield). LCMS (ESI) $[M+H]^+$=636.4.

Step 2: N-(5-(2-(((1,4-trans)-4-Aminocyclohexyl)amino)-8-ethylpyrido[3,2-d]pyrimidin-6-yl)-6-methylpyridin-2-yl)-2-fluorobenzenesulfonamide 2,2,2-trifluoroacetate

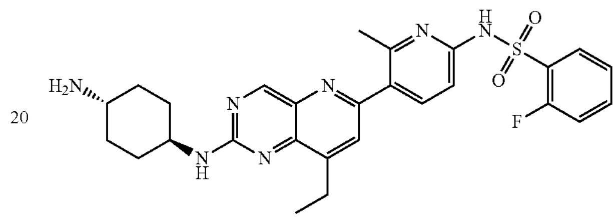

Prepared according to Example 12 (Compound 113) step 4 using tert-butyl ((1,4-trans)-4-((6-(6-(2-fluorophenylsulfonamido)-2-methylpyridin-3-yl)-8-ethylpyrido[3,2-d]pyrimidin-2-yl)amino)cyclohexyl)carbamate (82 mg, 0.13 mmol), trifluoroacetic acid (0.5 mL) and $CH_2Cl_2$ (2 mL) to provide the crude title product (84 mg, 100% yield).

Step 3: N-(5-(2-(((1,4-trans)-4-(Dimethylamino)cyclohexyl)amino)-8-ethylpyrido[3,2-d]pyrimidin-6-yl)-6-methylpyridin-2-yl)-2-fluorobenzenesulfonamide

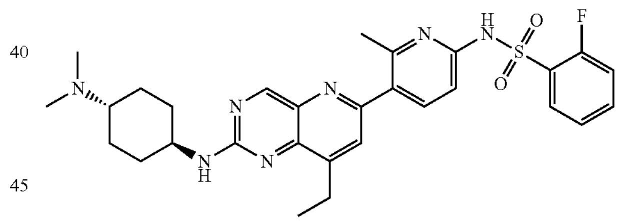

Prepared according to Example 12 (Compound 113) step 5 using N-(5-(2-(((1,4-trans)-4-aminocyclohexyl)amino)-8-ethylpyrido[3,2-d]pyrimidin-6-yl)-6-methylpyridin-2-yl)-2-fluorobenzenesulfonamide 2,2,2-trifluoroacetate (84 mg, 0.13 mmol), 37% w/w aqueous formaldehyde (156 mg, 1.93 mmol), sodium acetate (64 mg, 0.77 mmol), sodium triacetoxyborohydride (108 mg, 0.52 mmol) and methanol (3 mL) to provide the title product (45 mg, 44% yield).

Example 46: 2-(Difluoromethyl)-N-(5-(2-(((1,4-trans)-4-(dimethylamino)cyclohexyl)amino)-8-ethylpyrido[3,2-d]pyrimidin-6-yl)-6-methylpyridin-2-yl)benzenesulfonamide (Compound 147)

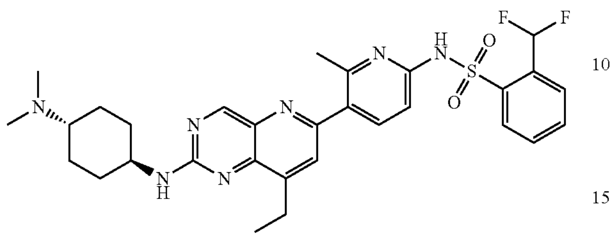

Step 1: tert-Butyl ((1,4-trans)-4-((6-(6-(2-(difluoromethyl)phenylsulfonamido)-2-methylpyridin-3-yl)-8-ethylpyrido[3,2-d]pyrimidin-2-yl)amino)cyclohexyl)carbamate

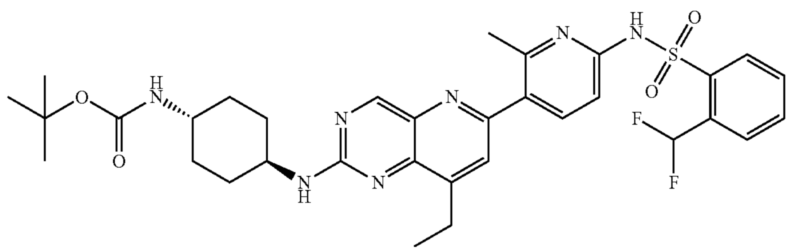 [SMILES: CCc1cc(-c2ccc(NS(=O)(=O)c3ccccc3C(F)F)nc2C)nc2cnc(N[C@H]3CC[C@H](NC(=O)OC(C)(C)C)CC3)nc12]

Prepared according to Example 9 (Compound 110) step 3 using tert-butyl ((1,4-trans)-4-((6-(6-amino-2-methylpyridin-3-yl)-8-ethylpyrido[3,2-d]pyrimidin-2-yl)amino)cyclohexyl)carbamate (70 mg, 0.15 mmol), pyridine (2.0 mL) and 2-(difluoromethyl)benzenesulfonyl chloride (100 mg, 0.44 mmol) to provide the title product (39 mg, 40% yield). LCMS (ESI) $[M+H]^+$=668.3.

Step 2: 2-(Difluoromethyl)-N-(5-(2-(((1,4-trans)-4-(dimethylamino)cyclohexyl)amino)-8-ethylpyrido[3,2-d]pyrimidin-6-yl)-6-methylpyridin-2-yl)benzenesulfonamide

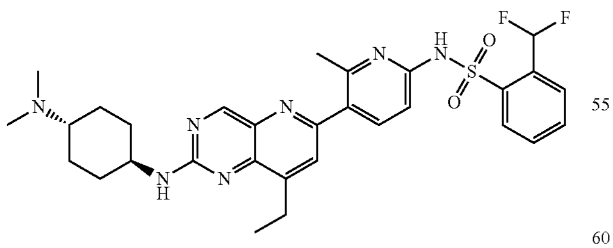

Prepared according to Example 12 (Compound 113) steps 4 and 5 using tert-butyl ((1,4-trans)-4-((6-(6-(2-(difluoromethyl)phenylsulfonamido)-2-methylpyridin-3-yl)-8-ethylpyrido[3,2-d]pyrimidin-2-yl)amino)cyclohexyl)carbamate (39 mg, 0.06 mmol) to provide the title product (9 mg, 25% yield).

Example 47: 2-(Difluoromethoxy)-N-(5-(2-(((1,4-trans)-4-(dimethylamino)cyclohexyl)amino)-8-ethylpyrido[3,2-d]pyrimidin-6-yl)-6-methylpyridin-2-yl)benzenesulfonamide (Compound 148)

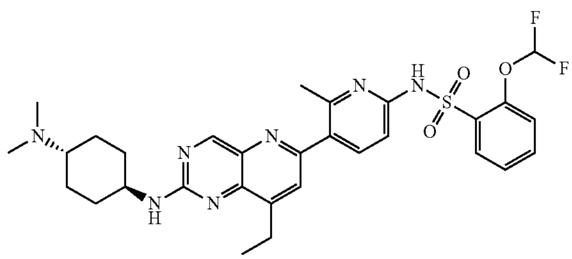 [SMILES: CCc1cc(-c2ccc(NS(=O)(=O)c3ccccc3OC(F)F)nc2C)nc2cnc(N[C@H]3CC[C@H](N(C)C)CC3)nc12]

Step 1: tert-Butyl ((1,4-trans)-4-((6-(6-(2-(difluoromethoxy)phenylsulfonamido)-2-methylpyridin-3-yl)-8-ethylpyrido[3,2-d]pyrimidin-2-yl)amino)cyclohexyl)carbamate

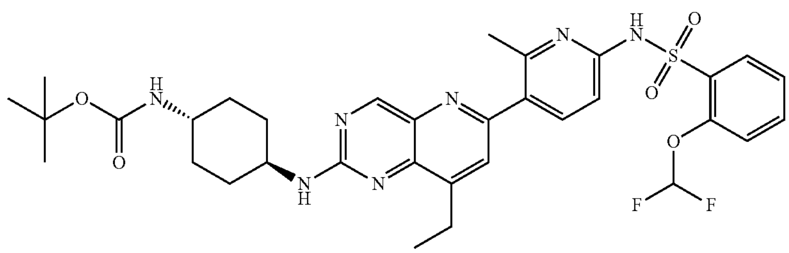 [SMILES: CCc1cc(-c2ccc(NS(=O)(=O)c3ccccc3OC(F)F)nc2C)nc2cnc(N[C@H]3CC[C@H](NC(=O)OC(C)(C)C)CC3)nc12]

Prepared according to Example 9 (Compound 110) step 3 using tert-butyl ((1,4-trans)-4-((6-(6-amino-2-methylpyridin-3-yl)-8-ethylpyrido[3,2-d]pyrimidin-2-yl)amino)cyclohexyl)carbamate (70 mg, 0.15 mmol), pyridine (2.0 mL) and 2-(difluoromethoxy)benzenesulfonyl chloride (107 mg, 0.44 mmol) to provide the title product (59 mg, 59% yield). LCMS (ESI) $[M+H]^+$=684.4.

Step 2: 2-(Difluoromethoxy)-N-(5-(2-(((1,4-trans)-4-(dimethylamino)cyclohexyl)amino)-8-ethylpyrido[3,2-d]pyrimidin-6-yl)-6-methylpyridin-2-yl)benzenesulfonamide

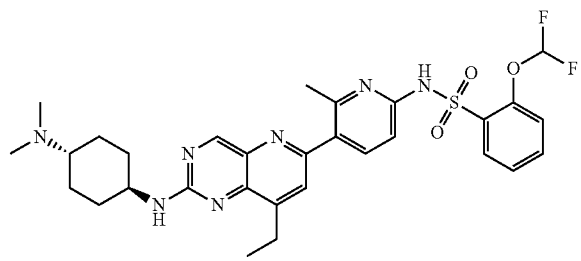 [SMILES: CCc1cc(-c2ccc(NS(=O)(=O)c3ccccc3OC(F)F)nc2C)nc2cnc(N[C@H]3CC[C@H](N(C)C)CC3)nc12]

Prepared according to Example 12 (Compound 113) steps 4 and 5 using tert-butyl ((1,4-trans)-4-((6-(6-(2-(difluoromethoxy)phenylsulfonamido)-2-methylpyridin-3-yl)-8-ethylpyrido[3,2-d]pyrimidin-2-yl)amino)cyclohexyl)carbamate (59 mg, 0.09 mmol) to provide the title product (11 mg, 21% yield).

Example 48: 2-Chloro-N-(5-(2-(((1,4-trans)-4-(dimethylamino)cyclohexyl)amino)-8-methylpyrido[3,2-d]pyrimidin-6-yl)-4-methylpyridin-2-yl)benzenesulfonamide (Compound 149)

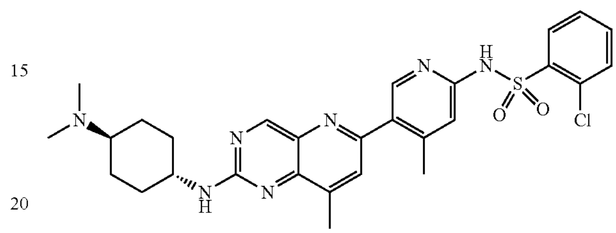

Step 1: 4-Methyl-5-(4,4,5,5-tetramethyl-1,3,2-dioxaborolan-2-yl)pyridin-2-amine

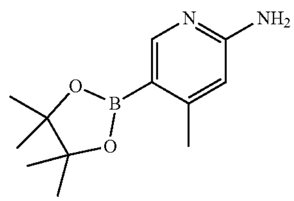 [SMILES: Cc1cc(N)ncc1B1OC(C)(C)C(C)(C)O1]

Prepared according to Example 36 (Compound 137) step 1 using $Pd_2(dba)_3 \cdot CHCl_3$ (50 mg, 0.05 mmol), tricyclohexylphosphine (60 mg, 0.21 mmol), bis(pinacolato)diboron (781 mg, 3.08 mmol), potassium acetate (795 mg, 8.02 mmol) and 5-bromo-4-methyl-pyridin-2-amine (500 mg, 2.67 mmol) to provide the title compound (158 mg, 25% yield). $^1H$ NMR (400 MHz, $CDCl_3$) δ 8.31 (s, 1H), 6.30 (s, 1H), 5.09 (br s, 2H), 2.40 (s, 3H), 1.31 (s, 12H).

Step 2: tert-Butyl ((1,4-trans)-4-((6-(6-amino-4-methylpyridin-3-yl)-8-methylpyrido[3,2-d]pyrimidin-2-yl)amino)cyclohexyl)carbamate

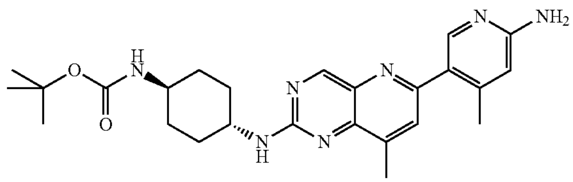 [SMILES: Cc1cc(N)ncc1-c1cc(C)c2nc(N[C@H]3CC[C@H](NC(=O)OC(C)(C)C)CC3)ncc2n1]

Prepared according to Example 36 (Compound 137) step 2 using tert-butyl ((1,4-trans)-4-((6-chloro-8-methylpyrido[3,2-d]pyrimidin-2-yl)amino)cyclohexyl)carbamate (176 mg, 0.45 mmol), 4-methyl-5-(4,4,5,5-tetramethyl-1,3,2-dioxaborolan-2-yl)pyridin-2-amine (158 mg, 0.67 mmol), $K_2CO_3$ (248 mg, 1.79 mmol) and $Pd(PPh_3)_4$ (78 mg, 0.07 mmol). The reaction mixture was diluted with EtOAc and filtered on a pad of celite. The volatiles were evaporated under reduced pressure and the crude material was purified by flash chromatography through silica gel (10-20% MeOH/EtOAc) to provide the title compound (280 mg, 134% yield). LCMS (ESI) $[M+H]^+$=464.1.

Step 3: tert-Butyl ((1,4-trans)-4-((6-(6-(2-chlorophenylsulfonamido)-4-methylpyridin-3-yl)-8-methylpyrido[3,2-d]pyrimidin-2-yl)amino)cyclohexyl)carbamate

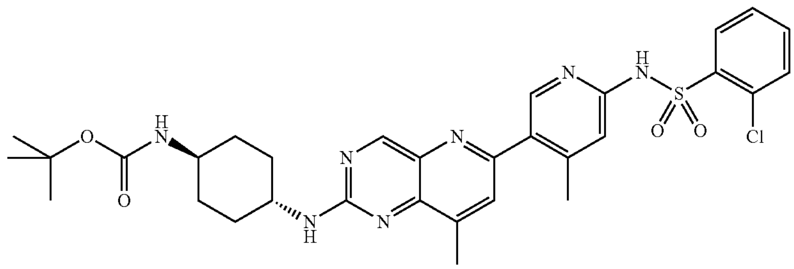 [SMILES: Cc1cc(NS(=O)(=O)c2ccccc2Cl)ncc1-c1cc(C)c2nc(N[C@H]3CC[C@H](NC(=O)OC(C)(C)C)CC3)ncc2n1]

Prepared according to Example 34 (Compound 135) step 1 using tert-butyl ((1,4-trans)-4-((6-(6-amino-4-methylpyridin-3-yl)-8-methylpyrido[3,2-d]pyrimidin-2-yl)amino)cyclohexyl)carbamate (80 mg, 0.17 mmol) and 2-chlorobenzenesulfonyl chloride (145 mg, 0.69 mmol) to provide the title compound (38 mg, 35% yield). LCMS (ESI) $[M+H]^+$ =638.1.

Step 4: N-(5-(2-(((1,4-trans)-4-Aminocyclohexyl)amino)-8-methylpyrido[3,2-d]pyrimidin-6-yl)$_4$-methylpyridin-2-yl)-2-chlorobenzenesulfonamide

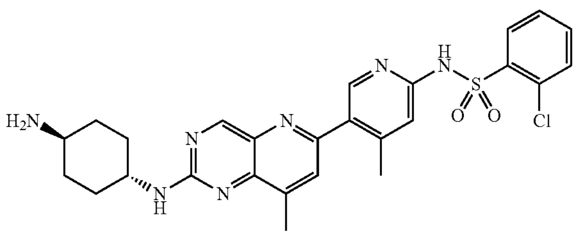 [SMILES: Cc1cc(NS(=O)(=O)c2ccccc2Cl)ncc1-c1cc(C)c2nc(N[C@H]3CC[C@H](N)CC3)ncc2n1]

Prepared according to Example 27 (Compound 128) step 2 using tert-butyl ((1,4-trans)-4-((6-(6-(2-chlorophenylsulfonamido)-4-methylpyridin-3-yl)-8-methylpyrido[3,2-d]pyrimidin-2-yl)amino)cyclohexyl)carbamate (38 mg, 0.06 mmol) and TFA (0.5 mL, 6.53 mmol). Volatiles were evaporated under reduced pressure and the residue was diluted with a saturated aqueous solution of $NaHCO_3$, and extracted twice with 2-MeTHF and three times with a mixture of 20% iPrOH/$CHCl_3$. The organic phases were combined, all the remaining solid on the glassware was solubilized in MeOH and combined with the previous extractions. Solvents were removed under reduced pressure to provide the crude title compound which was used without further purification (assume quantitative yield). LCMS (ESI) $[M+H]^+$=538.1.

Step 5: 2-Chloro-N-(5-(2-(((1,4-trans)-4-(dimethylamino)cyclohexyl)amino)-8-methylpyrido[3,2-d]pyrimidin-6-yl)-4-methylpyridin-2-yl)benzenesulfonamide

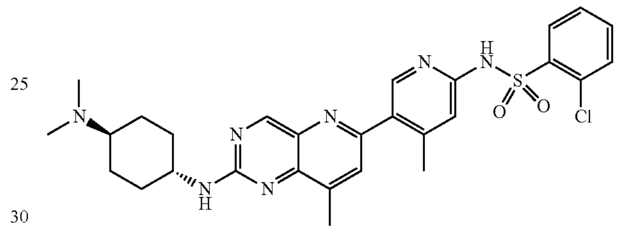

Prepared according to Example 27 (Compound 128) step 3 using N-(5-(2-(((1,4-trans)-4-aminocyclohexyl)amino)-8-methylpyrido[3,2-d]pyrimidin-6-yl)-4-methylpyridin-2-yl)-2-chlorobenzenesulfonamide (32 mg, 0.06 mmol), 37% w/w aqueous formaldehyde (0.05 mL, 0.60 mmol) and sodium triacetoxyborohydride (64 mg, 0.30 mmol) to provide the title product (24 mg, 71% yield).

Example 49: 2-Cyano-N-[(1,4-trans)-4-[2-[[4-(dimethylamino)cyclohexyl]amino]-8-methyl-pyrido[3,2-d]pyrimidin-6-yl]-2-fluoro-phenyl]benzenesulfonamide (Compound 150)

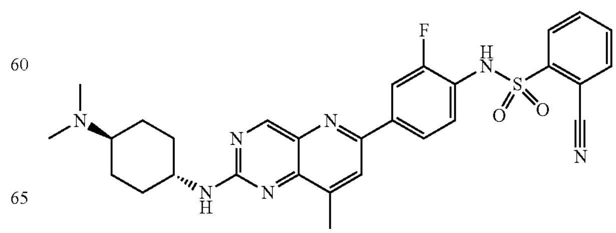

Step 1: tert-Butyl N-[(1,4-trans)-4-[[6-[4-[(2-cyanophenyl)sulfonylamino]-3-fluoro-phenyl]-8-methyl-pyrido[3,2-d]pyrimidin-2-yl]amino]cyclohexyl]carbamate

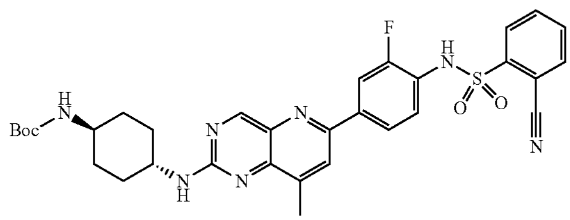 [SMILES: Cc1cc(-c2ccc(NS(=O)(=O)c3ccccc3C#N)c(F)c2)nc2cnc(N[C@H]3CC[C@H](NC(=O)OC(C)(C)C)CC3)nc12]

tert-Butyl N-[(1,4-trans)-4-[[6-(4-amino-3-fluoro-phenyl)-8-methyl-pyrido[3,2-d]pyrimidin-2-yl]amino]cyclohexyl]carbamate (60 mg, 0.13 mmol) was suspended in pyridine (1 mL) and to the solution was added 2-cyanobenzenesulfonyl chloride (31 mg, 0.15 mmol). The reaction was stirred at rt for 1 h then a further portion of 2-cyanobenzenesulfonyl chloride (31 mg, 0.15 mmol) was added and stirred for a further 1 h. MeOH (5 mL) and toluene (10 mL) were then added and the mixture was concentrated under reduced pressure and purified by flash chromatography through silica gel (20-100% EtOAc/heptanes) to provide the title compound (35 mg, 43% yield). LCMS (ESI) $[M+H]^+$ =632.3.

Step 2: 2-Cyano-N-[(1,4-trans)-4-[2-[[4-(dimethylamino)cyclohexyl]amino]-8-methyl-pyrido[3,2-d]pyrimidin-6-yl]-2-fluoro-phenyl]benzenesulfonamide

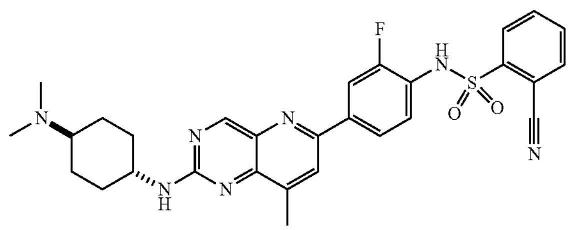 [SMILES: Cc1cc(-c2ccc(NS(=O)(=O)c3ccccc3C#N)c(F)c2)nc2cnc(N[C@H]3CC[C@H](N(C)C)CC3)nc12]

tert-Butyl N-[(1,4-trans)-4-[[6-[4-[(2-cyanophenyl)sulfonylamino]-3-fluoro-phenyl]-8-methyl-pyrido[3,2-d]pyrimidin-2-yl]amino]cyclohexyl]carbamate (35 mg, 0.06 mmol) was dissolved in TFA (1 mL) and stirred at rt for 10 min. To the reaction was added toluene (5 mL) and MeOH (1 mL) and concentrated to dryness. The crude was dissolved in MeOH (2 mL) and to the solution was added NaOAc (45 mg, 0.55 mmol) followed by 37% w/w aqueous formaldehyde (45 mg, 0.55 mmol). The reaction was stirred at rt for 10 min then sodium triacetoxyborohydride (46 mg, 0.22 mmol) was added. Stirring continued for 10 min then concentrated to half volume and directly purified by C18 reverse phase chromatography (0-100% 1:1 MeCN:MeOH/10 mM aqueous ammonium bicarbonate, pH=10) to provide the title compound (21 mg, 67% yield).

Example 50: 6-(2-(((1,4-trans)-4-(Dimethylamino)cyclohexyl)amino)-8-methylpyrido[3,2-d]pyrimidin-6-yl)-3,4-dihydro-1H-benzo[c][1,2]thiazine 2,2-dioxide (Compound 151)

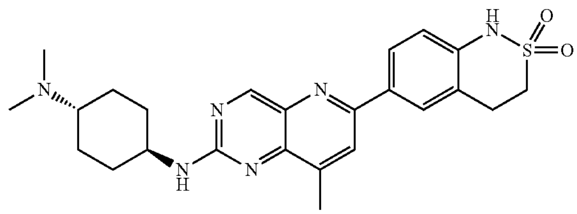 [SMILES: Cc1cc(-c2ccc3c(c2)CCS(=O)(=O)N3)nc2cnc(N[C@H]3CC[C@H](N(C)C)CC3)nc12]

Step 1: 2-(2-Bromo-5-chlorophenyl)ethanol

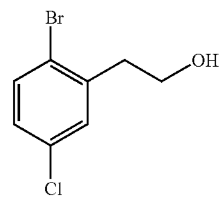 [SMILES: OCCc1cc(Cl)ccc1Br]

To 2-(2-bromo-5-chlorophenyl)acetic acid (10.0 g, 40.1 mmol) in THF (100 mL) at 0° C. was added 1M Borane-THF complex in THF (60.1 mL, 60.1 mmol) slowly and the mixture was slowly warmed up to rt and stirred at rt for 1 h. The reaction was slowly quenched with water, extracted with EtOAc, washed with 2N HCl, dried over anhydrous $Na_2SO_4$, filtered and concentrated to give the title compound (9.45 g, 100% yield). $^1$H NMR (400 MHz, $CDCl_3$) δ 7.47 (d, J=8.5 Hz, 1H), 7.28 (d, J=2.5 Hz, 1H), 7.09 (dd, J=8.5, 2.6 Hz, 1H), 3.89 (t, J=6.6 Hz, 2H), 2.99 (t, J=6.6 Hz, 2H).

Step 2: 1-Bromo-2-(2-bromoethyl)-4-chlorobenzene

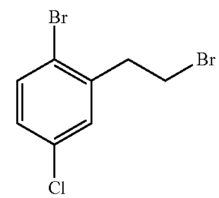 [SMILES: Clc1ccc(Br)c(CCBr)c1]

To 2-(2-bromo-5-chloro-phenyl)ethanol (6.55 g, 27.8 mmol) in $CH_2Cl_2$ (139 mL) was added triphenylphosphine (8.75 g, 33.4 mmol) followed by carbon tetrabromide (3.20 mL, 33.4 mmol) under nitrogen. The mixture was stirred at rt for 22 h then silica gel was added and volatiles were evaporated and purified by silica flash chromatography through silica gel (0-20% EtOAc/heptanes) to provide the title compound (4.38 g, 53% yield). $^1$H NMR (400 MHz, $CDCl_3$) δ 7.47 (d, J=8.5 Hz, 1H), 7.25 (d, J=1.4 Hz, 1H), 7.11 (dd, J=8.5, 2.6 Hz, 1H), 3.57 (t, J=7.4 Hz, 2H), 3.25 (t, J=7.4 Hz, 2H).

Step 3: 2-(2-Bromo-5-chlorophenyl)ethanesulfonic acid

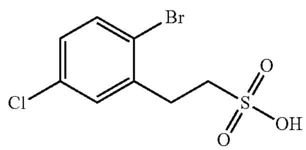 [SMILES: O=S(=O)(O)CCc1cc(Cl)ccc1Br]

A sealed tube was charged with 1-bromo-2-(2-bromoethyl)-4-chloro-benzene (2.98 g, 9.99 mmol), water (15 mL), sodium sulfite (1.30 g, 10.3 mmol) and sodium iodide (0.19 g, 1.27 mmol) and the mixture was heated at 130° C. for 42 h. The mixture was cooled down to rt and the solids filtered off and rinsed with water to provide the title compound (3.01 g, 100% yield). LCMS (ESI) $[M-H]^-$=296.9, 298.9, 300.9. $^1$H NMR (400 MHz, DMSO) δ 7.58 (d, J=8.5 Hz, 1H), 7.41 (d, J=2.6 Hz, 1H), 7.21 (dd, J=8.5, 2.6 Hz, 1H), 2.97 (dd, J=9.9, 6.6 Hz, 2H), 2.67 (dd, J=9.7, 6.8 Hz, 2H).

Step 4: 2-(2-Bromo-5-chlorophenyl)ethanesulfonyl chloride

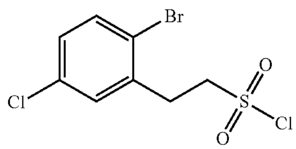 [SMILES: O=S(=O)(Cl)CCc1cc(Cl)ccc1Br]

To 2-(2-bromo-5-chloro-phenyl)ethanesulfonic acid (0.36 g, 1.2 mmol) in toluene (8.0 mL) was added thionyl chloride (5.3 mL, 72 mmol) followed by DMF (80 µL, 0.96 mmol) drop wise then the mixture was stirred at 100° C. for 2 h. The reaction mixture was cooled to room temperature, and filtered to remove inorganic solids. The crude was concentrated to provide the title compound (0.356 g, 93% yield) as a clear oil.

Step 5: 2-(2-Bromo-5-chlorophenyl)-N-(2,4-dimethoxybenzyl)ethanesulfonamide

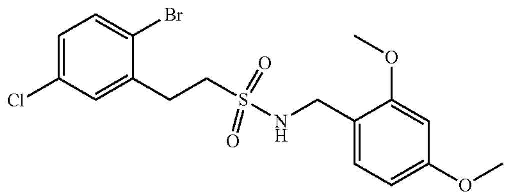 [SMILES: COc1ccc(CNS(=O)(=O)CCc2cc(Cl)ccc2Br)c(OC)c1]

Crude 2-(2-bromo-5-chloro-phenyl)ethanesulfonyl chloride (300 mg, 0.94 mmol) was suspended in $CH_2Cl_2$ (9.4 mL) and to the suspension was added 2,4-dimethoxybenzylamine (283 µL, 1.89 mmol) and pyridine (379 µL, 4.72 mmol) sequentially and the reaction was stirred at rt for 22 h. Aqueous $KHSO_4$ solution was added and the phases were separated. The organic phase was washed with water, then with saturated aqueous sodium chloride, dried over $Na_2SO_4$, filtered and concentrated to dryness. The crude material was purified by silica flash chromatography (0-30% EtOAc/$CH_2Cl_2$) to provide the title product (0.32 g, 76% yield). $^1$H NMR (400 MHz, $CDCl_3$) δ 7.41 (d, J=8.5 Hz, 1H), 7.16 (d, J=8.2 Hz, 1H), 7.06 (dd, J=8.5, 2.5 Hz, 1H), 6.91 (d, J=2.5 Hz, 1H), 6.51-6.41 (m, 2H), 4.93 (t, J=6.3 Hz, 1H), 4.26 (d, J=6.3 Hz, 2H), 3.85 (s, 3H), 3.81 (s, 3H), 3.12-3.06 (m, 2H), 3.01-2.94 (m, 2H).

Step 6: 6-Chloro-1-(2,4-dimethoxybenzyl)-3,4-dihydro-1H-benzo[c][1,2]thiazine 2,2-dioxide

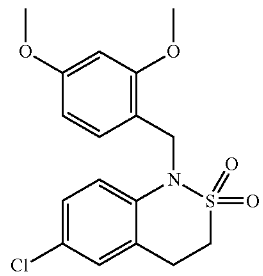 [SMILES: COc1ccc(CN2c3ccc(Cl)cc3CCS2(=O)=O)c(OC)c1]

A solution of 2-(2-bromo-5-chloro-phenyl)-N-[(2,4-dimethoxyphenyl)methyl]ethanesulfonamide (205 mg, 0.46 mmol) in DMSO (4.8 mL) was treated with potassium acetate (227 mg, 2.28 mmol) and copper(I) iodide (175 mg, 0.91 mmol) and stirred at 95° C. for 30 h. After cooling to rt, the reaction mixture was poured into EtOAc, washed with saturated $NH_4Cl$, water, aqueous $Na_2S_2O_3$, then saturated aqueous sodium chloride, dried over $Na_2SO_4$, filtered and concentrated. The crude material was purified by silica flash chromatography (60-80% $CH_2Cl_2$/heptanes) to provide the title product (134 mg, 79% yield). $^1$H NMR (400 MHz, $CDCl_3$) δ 7.26 (d, J=8.6 Hz, 1H), 7.12 (d, J=2.3 Hz, 1H), 7.09 (dd, J=8.8, 2.5 Hz, 1H), 6.81 (d, J=8.8 Hz, 1H), 6.48-6.40 (m, 2H), 4.92 (s, 2H), 3.78 (s, 3H), 3.76 (s, 3H), 3.43 (t, J=6.9 Hz, 2H), 3.29 (t, J=7.0 Hz, 2H).

Step 7: 1-(2,4-Dimethoxybenzyl)-6-(4,4,5,5-tetramethyl-1,3,2-dioxaborolan-2-yl)-3,4-dihydro-1H-benzo[c][1,2]thiazine 2,2-dioxide

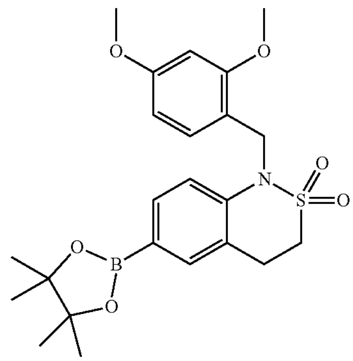 [SMILES: COc1ccc(CN2c3ccc(B4OC(C)(C)C(C)(C)O4)cc3CCS2(=O)=O)c(OC)c1]

A vial was charged with 6-chloro-1-(2,4-dimethoxybenzyl)-3,4-dihydro-1H-benzo[c][1,2]thiazine 2,2-dioxide (61 mg, 0.17 mmol) and 1,4-dioxane (1.7 mL). The solution was degassed with nitrogen for 5 min, then bis(pinacolato) diboron (62.7 mg, 0.25 mmol), potassium acetate (49 mg, 0.50 mmol), 2-dicyclohexylphosphino-2',4',6'-triisopropylbiphenyl (XPhos) (16 mg, 0.03 mmol) and tri(dibenzylideneacetone)dipalladium(0) chloroform adduct (8.6 mg, 0.01 mmol) was added and purged with nitrogen for an additional 2 min. The vial was sealed and the reaction mixture was stirred at 130° C. for 18 h. After cooling to rt, $CH_2Cl_2$ and silica gel were added and volatiles were removed under reduced pressure and purified by silica flash chromatography (10-70% EtOAc/heptanes) to provide the title product (51 mg, 67% yield). $^1$H NMR (400 MHz, $CDCl_3$) δ 7.59 (s, 1H), 7.58-7.51 (m, 1H), 7.24 (d, J=8.5 Hz, 1H), 6.83 (d, J=8.3 Hz, 1H), 6.49-6.39 (m, 2H), 4.98 (s, 2H), 3.81 (s, 3H), 3.77 (s, 3H), 3.50 (t, J=6.8 Hz, 2H), 3.35 (t, J=7.0 Hz, 2H), 1.31 (s, 12H).

Step 8: tert-Butyl ((1,4-trans)-4-((6-(1-(2,4-dimethoxybenzyl)-2,2-dioxido-3,4-dihydro-1H-benzo[c][1,2]thiazin-6-yl)-8-methylpyrido[3,2-d]pyrimidin-2-yl)amino)cyclohexyl)carbamate

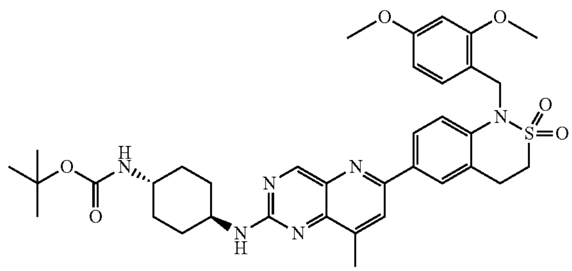 [SMILES: COc1ccc(CN2c3ccc(-c4cc(C)c5nc(N[C@H]6CC[C@H](NC(=O)OC(C)(C)C)CC6)ncc5n4)cc3CCS2(=O)=O)c(OC)c1]

To a microwave vial under nitrogen was added tert-butyl N-[4-[(6-chloro-8-methyl-pyrido[3,2-d]pyrimidin-2-yl) amino]cyclohexyl]carbamate (20 mg, 0.05 mmol), 1-(2,4-dimethoxybenzyl)-6-(4,4,5,5-tetramethyl-1,3,2-dioxaborolan-2-yl)-3,4-dihydro-1H-benzo[c][1,2]thiazine 2,2-dioxide (35 mg, 0.08 mmol) and $K_2CO_3$ (28 mg, 0.20 mmol). To the vial was then added $N_2$ degassed 1,4-dioxane (0.68 mL) and $N_2$ degassed water (0.17 mL). The mixture was $N_2$ degassed for 2 min before the addition of $Pd(PPh_3)_4$ (8.9 mg, 0.01 mmol). The reaction was stirred 20 min at 150° C. in a microwave reactor. The reaction was diluted with EtOAc, silica gel was added and concentrated under reduced pressure and purified by silica flash chromatography (0-100% EtOAc/$CH_2Cl_2$) to provide the title product (32 mg, 91% yield). LCMS (ESI) [M+H]$^+$=689.4.

Step 9: 6-(2-(((1,4-trans)-4-Aminocyclohexyl)amino)-8-methylpyrido[3,2-d]pyrimidin-6-yl)-3,4-dihydro-1H-benzo[c][1,2]thiazine 2,2-dioxide 2,2,2-trifluoroacetate

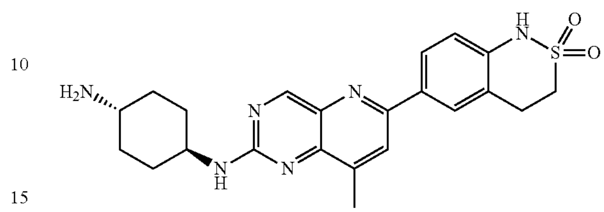

To tert-butyl ((1,4-trans)-4-((6-(1-(2,4-dimethoxybenzyl)-2,2-dioxido-3,4-dihydro-1H-benzo[c][1,2]thiazin-6-yl)-8-methylpyrido[3,2-d]pyrimidin-2-yl)amino)cyclohexyl)carbamate (32 mg, 0.05 mmol) in $CH_2Cl_2$ (0.23 mL) was added trifluoroacetic acid (72 μL, 0.93 mmol) and the reaction was stirred at rt for 15 min. Toluene was then added and the mixture was concentrated to dryness (repeated ×3) to provide the crude title compound (26 mg, 100% yield). LCMS (ESI) [M+H]$^+$=439.3.

Step 10: 6-(2-(((1,4-trans)-4-(Dimethylamino)cyclohexyl)amino)-8-methylpyrido[3,2-d]pyrimidin-6-yl)-3,4-dihydro-1H-benzo[c][1,2]thiazine 2,2-dioxide

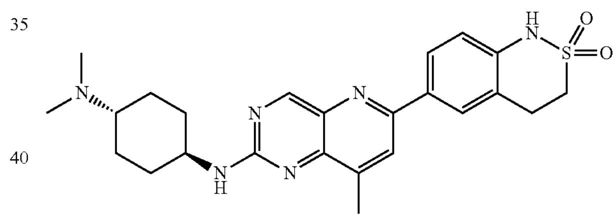

To 6-(2-(((1,4-trans)-4-aminocyclohexyl)amino)-8-methylpyrido[3,2-d]pyrimidin-6-yl)-3,4-dihydro-1H-benzo[c][1,2]thiazine 2,2-dioxide 2,2,2-trifluoroacetate (26 mg, 0.05 mmol) in methanol (1.0 mL) was added 37% w/w aqueous formaldehyde (52 μL, 0.70 mmol) and the reaction was stirred at rt for 18 h. The mixture was concentrated to dryness and the crude material was purified by C18 reverse phase chromatography (10-80% 1:1 MeCN:MeOH/10 mM aqueous ammonium bicarbonate, pH=10) to provide the title product (7 mg, 32% yield). LCMS (ESI) [M+H]$^+$=467.1. $^1$H NMR (400 MHz, DMSO-d6) δ 9.07 (s, 1H), 8.11 (s, 1H), 7.97 (s, 1H), 7.93 (d, J=8.2 Hz, 1H), 7.77-7.63 (m, 1H), 7.47 (s, 1H), 6.76 (d, J=8.3 Hz, 1H), 4.14-4.09 (m, 1H), 2.54 (s, 6H), 2.19 (s, 7H), 1.87 (d, J=13.3 Hz, 2H), 1.27 (dd, J=26.4, 13.9 Hz, 10H), 0.85 (dd, J=9.9, 4.9 Hz, 3H).

Example 51: N-(4-(2-(((1,4-trans)-4-(Dimethylamino)cyclohexyl)amino)-8-ethylpyrido[3,2-d]pyrimidin-6-yl)-2-fluorophenyl)-1-(4-(methylsulfonyl)phenyl)methanesulfonamide (Compound 152)

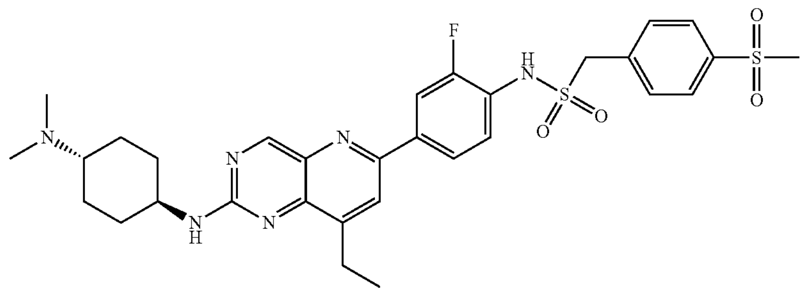

Step 1: Sodium (4-(methylsulfonyl)phenyl)methanesulfonate

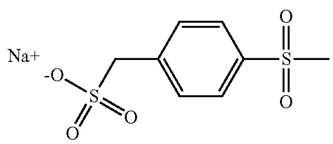

To a sealed tube containing 1-(bromomethyl)-4-methylsulfonyl-benzene (0.75 g, 3.01 mmol) in water (6.0 mL) was added sodium sulfite (0.46 g, 3.61 mmol) and sodium iodide (39.0 mg, 0.26 mmol). The mixture was stirred at 130° C. for 28 h then cooled down to rt and the solids filtered and rinsed with water. The filtrate was concentrated to give the crude title compound (0.82 g, 100% yield) which was used directly in the next step. LCMS (ESI) $[M-H]^-$ 249.0.

Step 2: (4-(Methylsulfonyl)phenyl)methanesulfonyl chloride

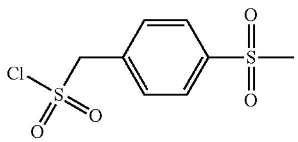

To a solution of sodium (4-methylsulfonylphenyl)methanesulfonate (0.82 g, 3.03 mmol) in 1,2-dichloroethane (15.2 mL) at 0° C. was added oxalyl chloride (4.0 mL, 47 mmol) followed by DMF (76 μL, 0.91 mmol) very slowly and the mixture was stirred at rt for 18 h. The reaction mixture was filtered to remove inorganic material, rinsed with $CH_2Cl_2$ and the filtrate was concentrated to provide the crude title compound (0.81 g, 100% yield) which was used directly in the next step.

Step 3: tert-Butyl ((1,4-trans)-4-((8-ethyl-6-(3-fluoro-4-((4-(methylsulfonyl)phenyl)methylsulfonamido)phenyl)pyrido[3,2-d]pyrimidin-2-yl)amino)cyclohexyl)carbamate

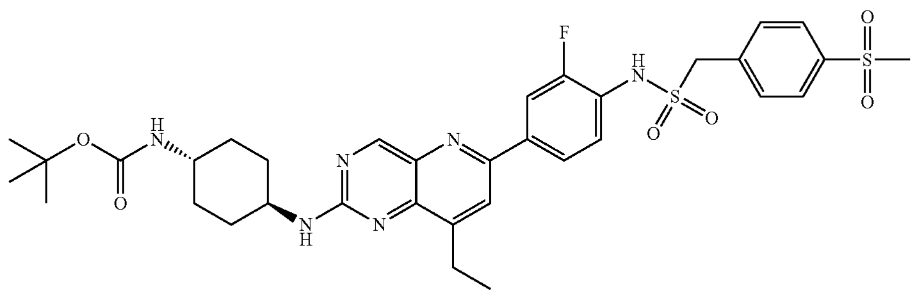 [SMILES: CCc1cc(-c2ccc(NS(=O)(=O)Cc3ccc(S(C)(=O)=O)cc3)c(F)c2)nc2cnc(N[C@H]3CC[C@H](NC(=O)OC(C)(C)C)CC3)nc12]

To tert-butyl N-[4-[[6-(4-amino-3-fluoro-phenyl)-8-ethyl-pyrido[3,2-d]pyrimidin-2-yl]amino]cyclohexyl]carbamate (51 mg, 0.11 mmol) in pyridine (0.27 mL) was added (4-methylsulfonylphenyl)methanesulfonyl chloride (86 mg, 0.32 mmol) and the reaction was stirred at rt for 90 min. MeOH was added and the mixture was concentrated to dryness. The crude was re-dissolved in $CH_2Cl_2$ and silica gel was added and volatiles were removed under reduced pressure and purified by silica flash chromatography (0-100% EtOAc/$CH_2Cl_2$) to provide the title product (60 mg, 79% yield). LCMS (ESI) $[M+H]^+$=713.4.

Step 4: N-(4-(2-(((1,4-trans)-4-Aminocyclohexyl)amino)-8-ethylpyrido[3,2-d]pyrimidin-6-yl)-2-fluorophenyl)-1-(4-(methylsulfonyl)phenyl)methanesulfonamide 2,2,2-trifluoroacetate

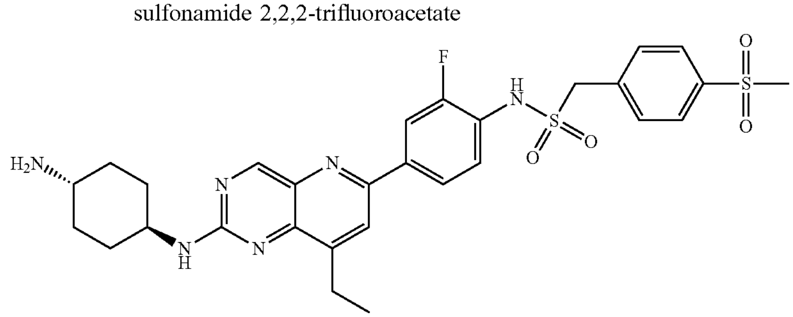

Prepared according to Example 13 (Compound 114) step 10 using tert-butyl ((1,4-trans)-4-((8-ethyl-6-(3-fluoro-4-((4-(methylsulfonyl)phenyl)methylsulfonamido)phenyl)pyrido[3,2-d]pyrimidin-2-yl)amino)cyclohexyl)carbamate (60 mg, 0.08 mmol)), trifluoroacetic acid (0.15 mL, 1.95 mmol) and $CH_2Cl_2$ (0.8 mL) to provide the crude title product (61 mg, 100% yield). LCMS (ESI) $[M+H]^+$=613.2.

Step 5: N-(4-(2-(((1,4-trans)-4-(Dimethylamino)cyclohexyl)amino)-8-ethylpyrido[3,2-d]pyrimidin-6-yl)-2-fluorophenyl)-1-(4-(methylsulfonyl)phenyl)methanesulfonamide

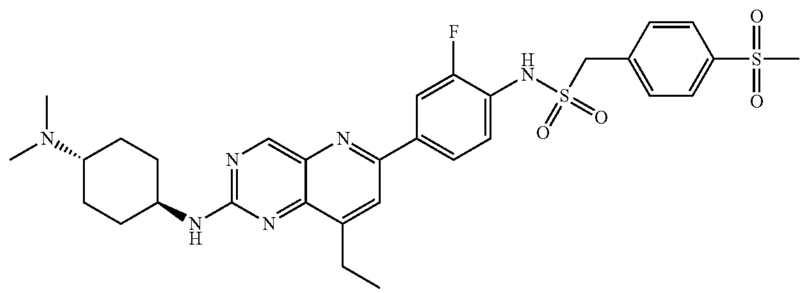

Prepared according to Example 13 (Compound 114) step 11 using N-(4-(2-(((1,4-trans)-4-aminocyclohexyl)amino)-8-ethylpyrido[3,2-d]pyrimidin-6-yl)-2-fluorophenyl)-1-(4-(methylsulfonyl)phenyl)methanesulfonamide 2,2,2-trifluoroacetate (61 mg, 0.08 mmol), sodium acetate (42 mg, 0.50 mmol), 37% w/w aqueous formaldehyde (94 μL, 1.26 mmol), sodium triacetoxyborohydride (71 mg, 0.34 mmol) and methanol (1 mL). The crude was purified by Prep-HPLC (CSH column, 20-40% MeCN/10 mM aqueous ammonium bicarbonate, pH=10) to provide the title compound (34 mg, 63% yield).

-

Example 52: N-(4-(2-(((1,4-trans)-4-(Dimethylamino)cyclohexyl)amino)-8-methylpyrido[3,2-d]pyrimidin-6-yl)-2,3,6-trifluorophenyl)-1-(4-fluorophenyl)methanesulfonamide (Compound 153)

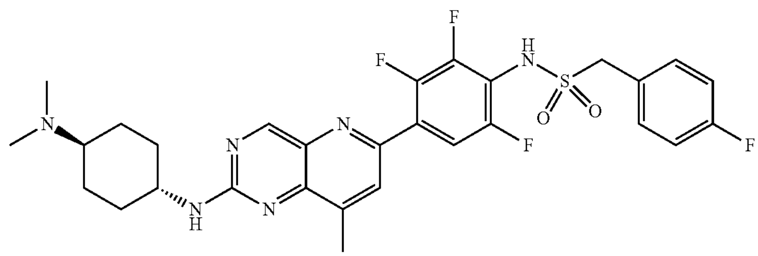 [SMILES: Cc1cc(-c2cc(F)c(NS(=O)(=O)Cc3ccc(F)cc3)c(F)c2F)nc2cnc(N[C@H]3CC[C@H](N(C)C)CC3)nc12]

Step 1: 2,3,6-Trifluoro-4-(4,4,5,5-tetramethyl-1,3,2-dioxaborolan-2-yl)aniline

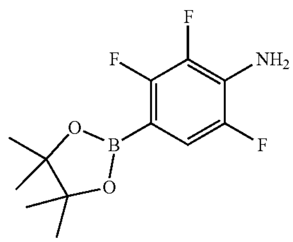 [SMILES: CC1(C)OB(c2cc(F)c(N)c(F)c2F)OC1(C)C]

Prepared according to Example 36 (Compound 137) step 1 using $Pd_2(dba)_3 \cdot CHCl_3$ (41 mg, 0.04 mmol), tricyclohexylphosphine (50 mg, 0.18 mmol), Bis(pinacolato)diboron (646 mg, 2.54 mmol), potassium acetate (657 mg, 6.63 mmol) and 4-bromo-2,3,6-trifluoro-aniline (500 mg, 2.21 mmol) to provide the title compound (260 mg, 43% yield). $^1H$ NMR (400 MHz, $CDCl_3$) δ 7.11 (ddd, J=10.5, 4.3, 2.2 Hz, 1H), 4.03 (br s, 2H), 1.33 (s, 12H).

Step 2: tert-Butyl ((1,4-trans)$_4$-((6-(4-amino-2,3,5-trifluorophenyl)-8-methylpyrido[3,2-d]pyrimidin-2-yl)amino)cyclohexyl)carbamate

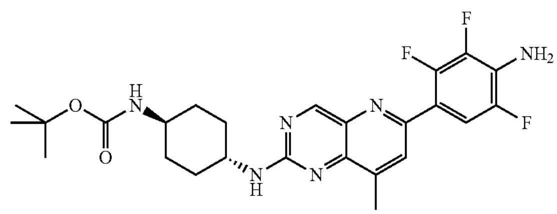 [SMILES: Cc1cc(-c2cc(F)c(N)c(F)c2F)nc2cnc(N[C@H]3CC[C@H](NC(=O)OC(C)(C)C)CC3)nc12]

Prepared according to Example 36 (Compound 137) step 2 using tert-butyl ((1,4-trans)-4-((6-chloro-8-methylpyrido[3,2-d]pyrimidin-2-yl)amino)cyclohexyl)carbamate (250 mg, 0.64 mmol), 2,3,6-trifluoro-4-(4,4,5,5-tetramethyl-1,3,2-dioxaborolan-2-yl)aniline (260 mg, 0.95 mmol), $K_2CO_3$ (352 mg, 2.55 mmol) and $Pd(PPh_3)_4$ (110 mg, 0.10 mmol). The reaction mixture was diluted with EtOAc and filtered on a pad of celite. The volatiles were evaporated under reduced pressure and the residue was triturated in $CH_2Cl_2$ and the precipitate was filtered. A second trituration was performed with MeOH on the filtrate. This second precipitate was filtered and combined with the first batch of solids to provide the title compound (250 mg, 78% yield). LCMS (ESI) [M+H]+=503.3.

Step 3: tert-Butyl ((1,4-trans)-4-((8-methyl-6-(2,3,5-trifluoro-4-((4-fluorophenyl)methylsulfonamido)phenyl)pyrido[3,2-d]pyrimidin-2-yl)amino)cyclohexyl)carbamate

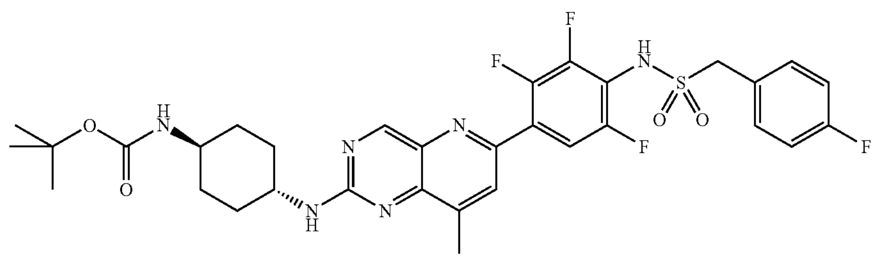 [SMILES: Cc1cc(-c2cc(F)c(NS(=O)(=O)Cc3ccc(F)cc3)c(F)c2F)nc2cnc(N[C@H]3CC[C@H](NC(=O)OC(C)(C)C)CC3)nc12]

A mixture of tert-butyl ((1,4-trans)-4-((6-(4-amino-2,3,5-trifluorophenyl)-8-methylpyrido[3,2-d]pyrimidin-2-yl)amino)cyclohexyl)carbamate (75 mg, 0.15 mmol) and (4-fluorophenyl)methanesulfonyl chloride (125 mg, 0.60 mmol), in pyridine (1.0 mL), was stirred overnight at rt to provide a mixture of the desired sulfonamide as well as undesired bis-sulfonamide. Pyridine was evaporated under reduced pressure and the residue was dissolved in THF (2 mL) and treated with a 1M tetrabutylammonium fluoride in THF (0.15 mL, 0.15 mmol) and stirred at rt until most of the bis-sulfonamide converted to desired mono-sulfonamide. THF was evaporated under reduced pressure and the compound was purified by flash chromatography through silica gel (0-20% EtOAc/$CH_2Cl_2$) to provide the title compound (56 mg, 56% yield). LCMS (ESI) $[M+H]^+$=675.4.

Step 4: N-(4-(2-(((1,4-trans)-4-Aminocyclohexyl)amino)-8-methylpyrido[3,2-d]pyrimidin-6-yl)-2,3,6-trifluorophenyl)-1-(4-fluorophenyl)methanesulfonamide

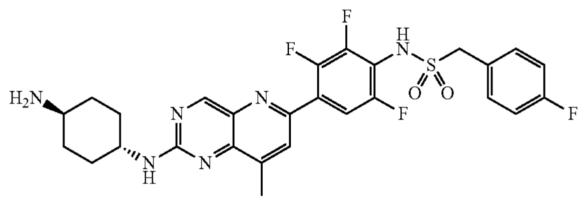 [SMILES: Cc1cc(-c2cc(F)c(NS(=O)(=O)Cc3ccc(F)cc3)c(F)c2F)nc2cnc(N[C@H]3CC[C@H](N)CC3)nc12]

Prepared according to Example 27 (Compound 128) step 2 using tert-butyl ((1,4-trans)-4-((8-methyl-6-(2,3,5-trifluoro-4-((4-fluorophenyl)methylsulfonamido)phenyl)pyrido[3,2-d]pyrimidin-2-yl)amino)cyclohexyl)carbamate (55 mg, 0.08 mmol) and TFA (0.5 mL, 6.53 mmol) to provide the title product (assume quantitative yield). LCMS (ESI) [M+H]+=575.1.

Step 6: N-(4-(2-(((1,4-trans)-4-(Dimethylamino)cyclohexyl)amino)-8-methylpyrido[3,2-d]pyrimidin-6-yl)-2,3,6-trifluorophenyl)-1-(4-fluorophenyl)methanesulfonamide

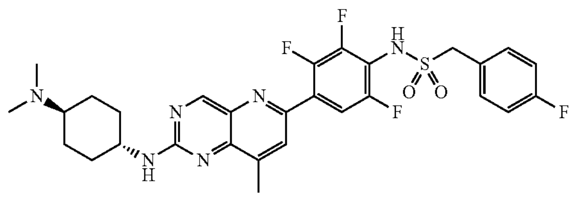 [SMILES: Cc1cc(-c2cc(F)c(NS(=O)(=O)Cc3ccc(F)cc3)c(F)c2F)nc2cnc(N[C@H]3CC[C@H](N(C)C)CC3)nc12]

Prepared according to Example 27 (Compound 128) step 3 using N-(4-(2-(((1,4-trans)-4-aminocyclohexyl)amino)-8-methylpyrido[3,2-d]pyrimidin-6-yl)-2,3,6-trifluorophenyl)-1-(4-fluorophenyl)methanesulfonamide (46 mg, 0.08 mmol), 37% w/w aqueous formaldehyde (0.07 mL, 0.87 mmol) and sodium triacetoxyborohydride (88 mg, 0.42 mmol). The volatiles were evaporated under reduced pressure and the residue was diluted with $H_2O$, extracted five times with 2-MeTHF, dried over anhydrous $MgSO_4$), filtered and concentrated under reduced pressure. The residue was purified by C18 reverse phase chromatography (25-45% MeCN/10 mM aqueous ammonium bicarbonate, pH=10). Appropriate fractions were combined and lyophilized to provide the title compound (13 mg, 27% yield).

Example 53: N-[4-[2-[[(1,4-trans)-4-(Dimethylamino)cyclohexyl]amino]-8-methyl-pyrido[3,2-d]pyrimidin-6-yl]-2-fluoro-phenyl]pyridine-3-sulfonamide (Compound 154)

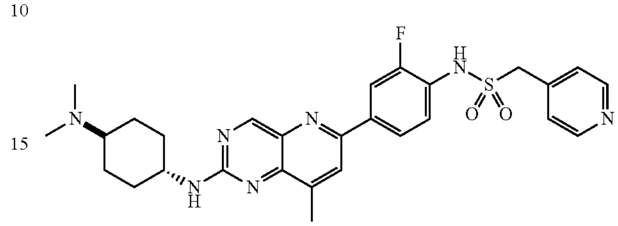

Step 1: tert-Butyl N-[(1,4-trans)-4-[[6-[3-fluoro-4-(3-pyridylsulfonylamino)phenyl]-8-methyl-pyrido[3,2-d]pyrimidin-2-yl]amino]cyclohexyl]carbamate

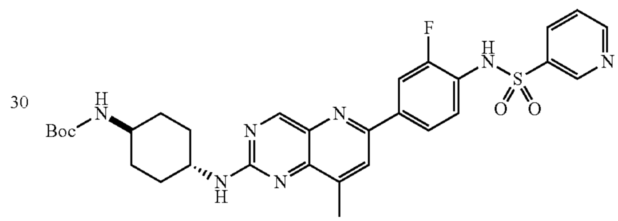

tert-Butyl N-[(1,4-trans)-4-[[6-(4-amino-3-fluoro-phenyl)-8-methyl-pyrido[3,2-d]pyrimidin-2-yl]amino]cyclohexyl]carbamate (80 mg, 0.17 mmol) was suspended in pyridine (1 mL) and to the solution was added pyridine-3-sulfonyl chloride (38 mg, 0.20 mmol). The reaction was stirred at rt for 30 min. The reaction was concentrated with toluene and purified by silica flash chromatography (0-10% MeOH/$CH_2Cl_2$) to provide the title compound (46 mg, 44% in yield). LCMS (ESI) $[M+H]^+$=608.3.

Step 2: N-[4-[2-[[(1,4-trans)-4-(Dimethylamino)cyclohexyl]amino]-8-methyl-pyrido[3,2-d]pyrimidin-6-yl]-2-fluoro-phenyl]pyridine-3-sulfonamide

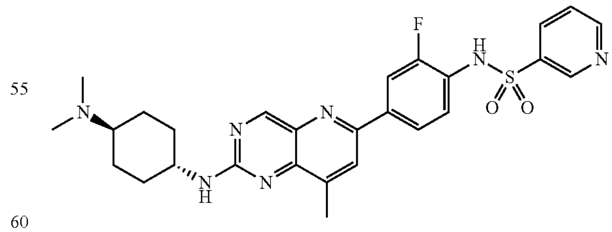

tert-Butyl N-[(1,4-trans)-4-[[6-[3-fluoro-4-(3-pyridylsulfonylamino)phenyl]-8-methyl-pyrido[3,2-d]pyrimidin-2-yl]amino]cyclohexyl]carbamate (46 mg, 0.08 mmol) was dissolved in TFA (1 mL) and stirred at rt for 10 min. To the reaction was added toluene (5 mL) and MeOH (1 mL) and concentrated to dryness. The crude was dissolved in MeOH (2 mL) and to the solution was added NaOAc (62 mg, 0.76 mmol) followed by 37% w/w aqueous formaldehyde (61 mg, 0.76 mmol). The reaction was stirred at rt for 20 min then sodium triacetoxyborohydride (63 mg, 0.30 mmol) was added. Stirring continued for 30 min then the mixture was concentrated to half volume and purified directly by C18 reverse phase chromatography (0-100% 1:1 MeCN:MeOH/10 mM aqueous ammonium bicarbonate, pH=10) to provide the title compound (28 mg, 69% yield).

Example 54: 2-Chloro-N-(4-(2-(((1,4-trans)-4-(dimethylamino)cyclohexyl)amino)-8-methylpyrido[3,2-d]pyrimidin-6-yl)-2,3,6-trifluorophenyl)benzenesulfonamide (Compound 155)

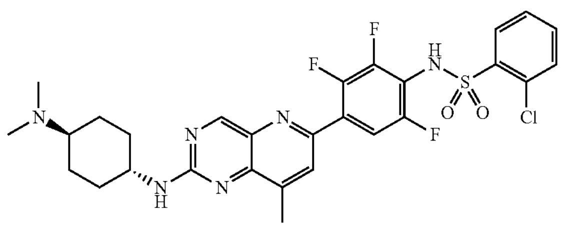 [SMILES: Cc1cc(-c2cc(F)c(NS(=O)(=O)c3ccccc3Cl)c(F)c2F)nc2cnc(N[C@H]3CC[C@H](N(C)C)CC3)nc12]

Step 1: tert-Butyl ((1,4-trans)-4-((6-(4-(2-chlorophenylsulfonamido)-2,3,5-trifluorophenyl)-8-methylpyrido[3,2-d]pyrimidin-2-yl)amino)cyclohexyl)carbamate

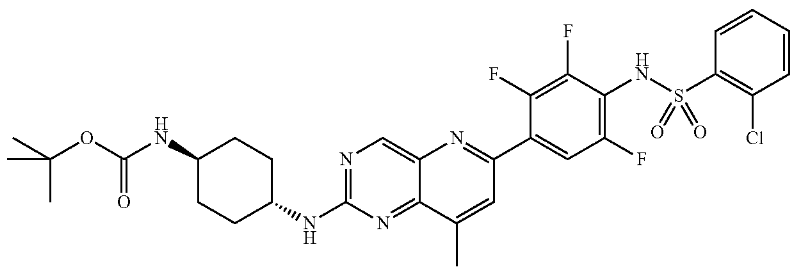 [SMILES: Cc1cc(-c2cc(F)c(NS(=O)(=O)c3ccccc3Cl)c(F)c2F)nc2cnc(N[C@H]3CC[C@H](NC(=O)OC(C)(C)C)CC3)nc12]

Prepared according to Example 52 (Compound 153) step 1 using tert-butyl ((1,4-trans)-4-((6-(4-amino-2,3,5-trifluorophenyl)-8-methylpyrido[3,2-d]pyrimidin-2-yl)amino)cyclohexyl)carbamate (70 mg, 0.14 mmol) and 2-chlorobenzenesulfonyl chloride (88 mg, 0.42 mmol) to provide a mixture of desired mono-sulfonamide and undesired bis-sulfonamide. The residue was dissolved in THF (2 mL) and treated with 1M tetrabutylammonium fluoride in THF (0.30 mL, 0.30 mmol), at rt to convert this bis-sulfonamide to desired mono-sulfonamide. THF was evaporated under reduced pressure and the compound was purified by flash chromatography through silica gel (0-20% EtOAc/$CH_2Cl_2$) to provide the title compound (80 mg, 85% yield). LCMS (ESI) $[M+H]^+$=677.2.

Step 2: N-(4-(2-(((1,4-trans)-4-Aminocyclohexyl)amino)-8-methylpyrido[3,2-d]pyrimidin-6-yl)-2,3,6-trifluorophenyl)-2-chlorobenzenesulfonamide

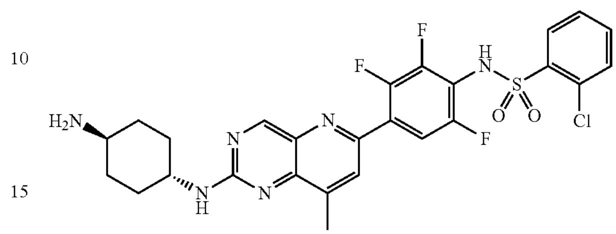

Prepared according to Example 27 (Compound 128) step 2 using tert-butyl ((1,4-trans)-4-((6-(4-(2-chlorophenylsulfonamido)-2,3,5-trifluorophenyl)-8-methylpyrido[3,2-d]pyrimidin-2-yl)amino)cyclohexyl)carbamate (80 mg, 0.12 mmol) and TFA (0.5 mL, 6.53 mmol) to provide the title product (assumed quantitative yield). LCMS (ESI) $[M+H]^+$=577.0.

Step 3: 2-Chloro-N-(4-(2-(((1,4-trans)-4-(dimethylamino)cyclohexyl)amino)-8-methylpyrido[3,2-d]pyrimidin-6-yl)-2,3,6-trifluorophenyl)benzenesulfonamide

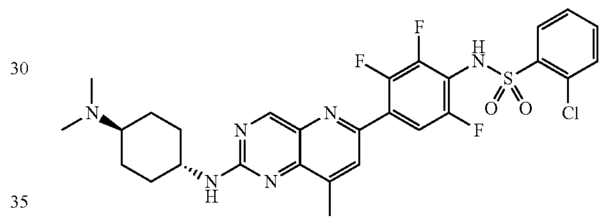

Prepared according to Example 27 (Compound 128) step 3 using N-(4-(2-(((1,4-trans)-4-aminocyclohexyl)amino)-8-methylpyrido[3,2-d]pyrimidin-6-yl)-2,3,6-trifluorophenyl)-2-chlorobenzenesulfonamide (68 mg, 0.12 mmol), 37% w/w aqueous formaldehyde (0.10 mL, 1.23 mmol) and sodium triacetoxyborohydride (125 mg, 0.59 mmol). The volatiles were evaporated under reduced pressure and the residue was purified by C18 reverse phase chromatography (20-40% MeCN/10 mM aqueous ammonium bicarbonate, pH=10) to provide the title compound (47 mg, 66% yield).

Example 55: N-[4-[2-[[(1,4-trans)-4-(Dimethylamino)cyclohexyl]amino]-8-methyl-pyrido[3,2-d]pyrimidin-6-yl]-2-fluoro-phenyl]-4-(trifluoromethyl)pyridine-3-sulfonamide (Compound 156)

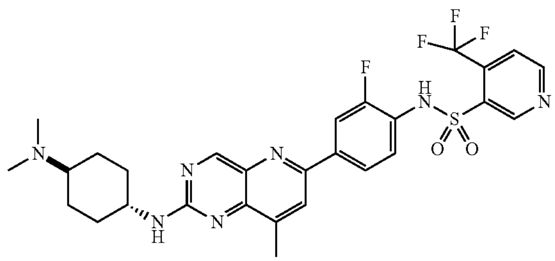 [SMILES: Cc1cc(-c2ccc(NS(=O)(=O)c3cnccc3C(F)(F)F)c(F)c2)nc2cnc(N[C@H]3CC[C@H](N(C)C)CC3)nc12]

Step 1: tert-Butyl N-[(1,4-trans)-4-[[6-[3-fluoro-4-[[4-(trifluoromethyl)-3-pyridyl]sulfonylamino]phenyl]-8-methyl-pyrido[3,2-d]pyrimidin-2-yl]amino]cyclohexyl]carbamate

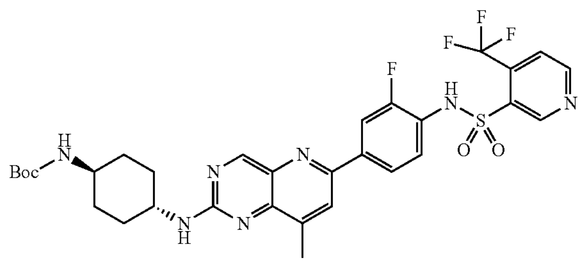 [SMILES: Cc1cc(-c2ccc(NS(=O)(=O)c3cnccc3C(F)(F)F)c(F)c2)nc2cnc(N[C@H]3CC[C@H](NC(=O)OC(C)(C)C)CC3)nc12]

tert-Butyl N-[(1,4-trans)-4-[[6-(4-amino-3-fluoro-phenyl)-8-methyl-pyrido[3,2-d]pyrimidin-2-yl]amino]cyclohexyl]carbamate (80 mg, 0.17 mmol) was suspended in a mixture of pyridine (1 mL) and $CH_2Cl_2$ (2 mL). To the suspension was added 4-(trifluoromethyl)pyridine-3-sulfonyl chloride (84 mg, 0.34 mmol). The reaction was stirred at rt for 2 h then a further portion of 4-(trifluoromethyl)pyridine-3-sulfonyl chloride (84 mg, 0.34 mmol) was added and stirred overnight. To the reaction was added toluene (5 mL) and MeOH (5 mL) and the mixture was concentrated to dryness. The residue was dissolved in DMSO and purified by prep-HPLC (CSH column, 50-70% MeCN/10 mM aqueous ammonium formate, pH=3.8) to provide the title compound (29 mg, 25% yield). LCMS (ESI) $[M+H]^+$=676.4.

Step 2: N-[4-[2-[[(1,4-trans)-4-(Dimethylamino)cyclohexyl]amino]-8-methyl-pyrido[3,2-d]pyrimidin-6-yl]-2-fluoro-phenyl]-4-(trifluoromethyl)pyridine-3-sulfonamide

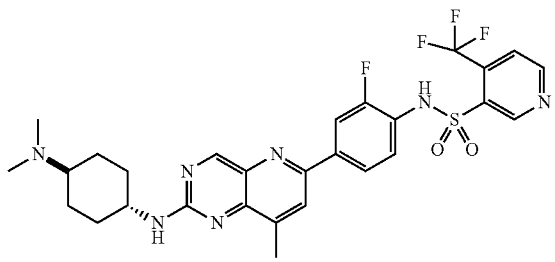 [SMILES: Cc1cc(-c2ccc(NS(=O)(=O)c3cnccc3C(F)(F)F)c(F)c2)nc2cnc(N[C@H]3CC[C@H](N(C)C)CC3)nc12]

tert-Butyl N-[(1,4-trans)-4-[[6-[3-fluoro-4-[[4-(trifluoromethyl)-3-pyridyl]sulfonylamino]phenyl]-8-methyl-pyrido[3,2-d]pyrimidin-2-yl]amino]cyclohexyl]carbamate (29 mg, 0.04 mmol) was dissolved in TFA (1 mL) and reaction was stirred at rt for 10 min. To the reaction was added toluene (5 mL) and MeOH (1 mL) and concentrated to dryness. The crude was dissolved in MeOH (2 mL) and to the solution was added NaOAc (35 mg, 0.43 mmol) followed by 37% w/w aqueous formaldehyde (35 mg, 0.43 mmol). The reaction was stirred at rt for 20 min then sodium triacetoxyborohydride (36 mg, 0.17 mmol) was added. Stirring continued for 30 min then concentrated to half volume and purified by C18 reverse phase chromatography (0-100% 1:1 MeCN:MeOH/10 mM aqueous ammonium bicarbonate, pH=10) to provide the title compound (22 mg, 85% yield).

Example 56: N-[4-[2-[[(1,4-trans)-4-(Dimethylamino)cyclohexyl]amino]-8-methyl-pyrido[3,2-d]pyrimidin-6-yl]-2-fluoro-phenyl]-2-(trifluoromethyl)pyridine-3-sulfonamide (Compound 157)

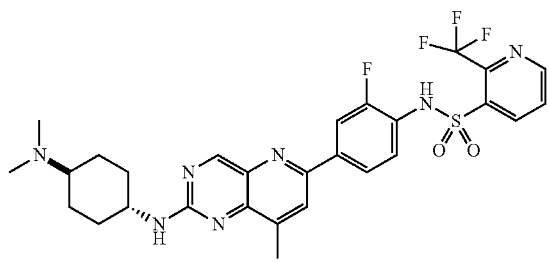 [SMILES: Cc1cc(-c2ccc(NS(=O)(=O)c3cccnc3C(F)(F)F)c(F)c2)nc2cnc(N[C@H]3CC[C@H](N(C)C)CC3)nc12]

Step 1: tert-Butyl N-[(1,4-trans)-4-[[6-[3-fluoro-4-[[2-(trifluoromethyl)-3-pyridyl]sulfonylamino]phenyl]-8-methyl-pyrido[3,2-d]pyrimidin-2-yl]amino]cyclohexyl]carbamate

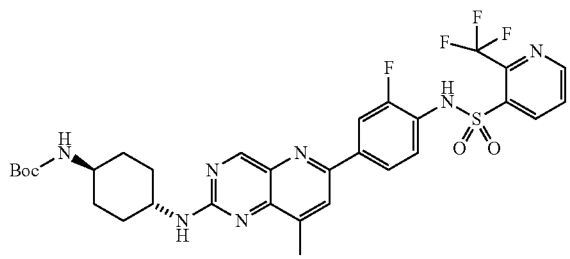

To tert-butyl N-[(1,4-trans)-4-[[6-(4-amino-3-fluoro-phenyl)-8-methyl-pyrido[3,2-d]pyrimidin-2-yl]amino]cyclohexyl]carbamate (75 mg, 0.16 mmol) in $CH_2Cl_2$ (1 mL) was added 2-(trifluoromethyl)pyridine-3-sulfonyl chloride (102 mg, 0.42 mmol) and the reaction was stirred at rt for 16 h. MeOH and silica gel were added and volatiles removed under reduced pressure and purified by flash chromatography through silica gel (0-70% EtOAc/$CH_2Cl_2$) to provide the title compound (100 mg, 92% yield). LCMS (ESI) $[M+H]^+$=676.4.

Step 2: N-[4-[2-[[(1,4-trans)-4-(Dimethylamino) cyclohexyl]amino]-8-methyl-pyrido[3,2-d]pyrimidin-6-yl]-2-fluoro-phenyl]-2-(trifluoromethyl)pyridine-3-sulfonamide

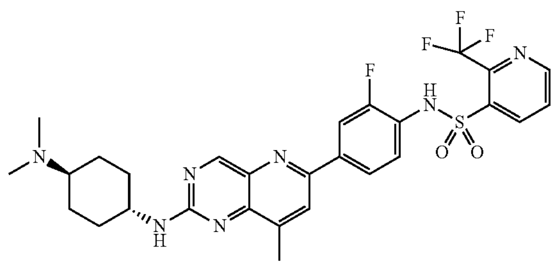 [SMILES: Cc1cc(-c2ccc(NS(=O)(=O)c3cccnc3C(F)(F)F)c(F)c2)nc2cnc(N[C@H]3CC[C@H](N(C)C)CC3)nc12]

tert-Butyl N-[(1,4-trans)-4-[[6-[3-fluoro-4-[[2-(trifluoromethyl)-3-pyridyl]sulfonylamino]phenyl]-8-methyl-pyrido[3,2-d]pyrimidin-2-yl]amino] cyclohexyl]carbamate (121 mg, 0.18 mmol) was dissolved in TFA (1 mL) and the reaction was stirred at rt for 10 min. To the reaction was added toluene (5 mL) and MeOH (1 mL) and concentrated to dryness. The crude was dissolved in MeOH (2 mL) and to the solution was added NaOAc (35 mg, 0.43 mmol) followed by 37% w/w aqueous formaldehyde (105 mg, 0.13 mmol). The reaction was stirred at rt for 20 min then sodium triacetoxyborohydride (108 mg, 0.51 mmol) was added. Stirring continued for 30 min then concentrated to half volume and purified by C18 reverse phase chromatography (0-100% 1:1 MeCN:MeOH/10 mM aqueous ammonium bicarbonate, pH=10) to provide the title compound (44 mg, 40% yield).

Example 57: N-(4-(2-(((1,4-trans)-4-(Dimethylamino)cyclohexyl)amino)-8-methylpyrido[3,2-d]pyrimidin-6-yl)-2-fluorophenyl)pyridine-2-sulfonamide (Compound 158)

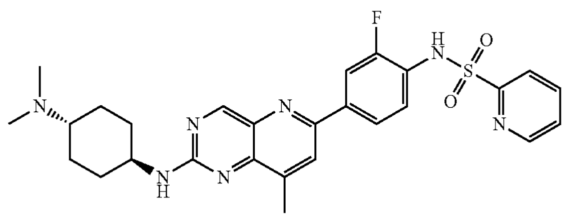 [SMILES: Cc1cc(-c2ccc(NS(=O)(=O)c3ccccn3)c(F)c2)nc2cnc(N[C@H]3CC[C@H](N(C)C)CC3)nc12]

Step 1: tert-Butyl ((1,4-trans)-4-((6-(3-fluoro-4-(pyridine-2-sulfonamido)phenyl)-8-methylpyrido[3,2-d]pyrimidin-2-yl)amino)cyclohexyl)carbamate

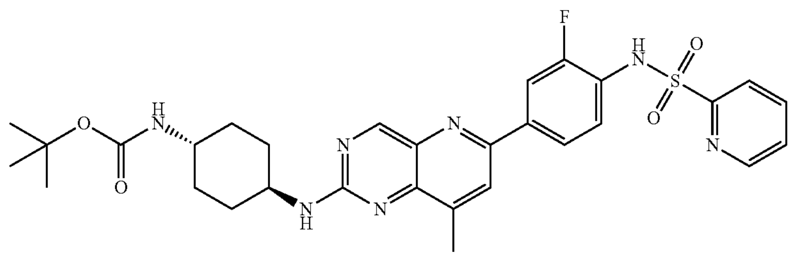 [SMILES: Cc1cc(-c2ccc(NS(=O)(=O)c3ccccn3)c(F)c2)nc2cnc(N[C@H]3CC[C@H](NC(=O)OC(C)(C)C)CC3)nc12]

To a suspension of tert-butyl N-[4-[[6-(4-amino-3-fluoro-phenyl)-8-methyl-pyrido[3,2-d]pyrimidin-2-yl]amino]cyclohexyl]carbamate (70 mg, 0.15 mmol) in pyridine (1 mL) was added pyridine-2-sulfonyl chloride (40 mg, 0.23 mmol). The reaction was stirred at rt for 30 min. To the reaction was added toluene (5 mL) and MeOH (5 mL) and concentrated to dryness. The residue was dissolved in THF (2 mL) and treated with 1M tetrabutylammonium formate in THF (1 mL, 1 mmol) and stirred for 30 min until complete conversion of the bis-sulfonylated product to the mono-sulfonylated product. The reaction was diluted with toluene and concentrated to dryness then purified by flash chromatography through silica gel (20-100% EtOAc/heptanes) to provide the title compound (51 mg, 55.9% yield).

Step 2: N-(4-(2-(((1,4-trans)-4-Aminocyclohexyl)amino)-8-methylpyrido[3,2-d]pyrimidin-6-yl)-2-fluorophenyl)pyridine-2-sulfonamide 2,2,2-trifluoroacetate

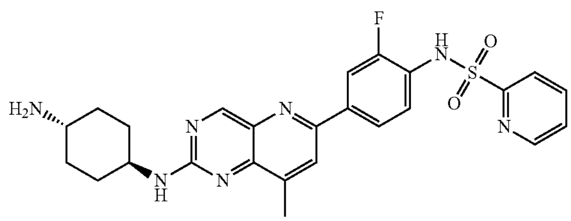 [SMILES: Cc1cc(-c2ccc(NS(=O)(=O)c3ccccn3)c(F)c2)nc2cnc(N[C@H]3CC[C@H](N)CC3)nc12]

Prepared according to Example 12 (Compound 113) step 4 using tert-butyl N-[4-[[6-[3-fluoro-4-(2-pyridylsulfonylamino)phenyl]-8-methyl-pyrido[3,2-d]pyrimidin-2-yl]amino]cyclohexyl]carbamate (51 mg, 0.08 mmol) and trifluoroacetic acid (0.1 mL, 0.08 mmol) provide the crude title product (50 mg, 100% yield).

Step 3: N-(4-(2-(((1,4-trans)-4-(Dimethylamino)cyclohexyl)amino)-8-methylpyrido[3,2-d]pyrimidin-6-yl)-2-fluorophenyl)pyridine-2-sulfonamide

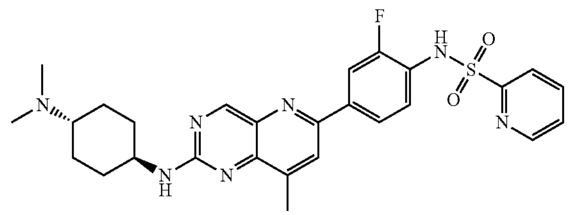 [SMILES: Cc1cc(-c2ccc(NS(=O)(=O)c3ccccn3)c(F)c2)nc2cnc(N[C@H]3CC[C@H](N(C)C)CC3)nc12]

Prepared according to Example 12 (Compound 113) step 5 using N-(4-(2-(((1,4-trans)-4-aminocyclohexyl)amino)-8-methylpyrido[3,2-d]pyrimidin-6-yl)-2-fluorophenyl)pyridine-2-sulfonamide 2,2,2-trifluoroacetate (50 mg, 0.08 mmol), sodium acetate (69 mg, 0.84 mmol), 37% w/w aqueous formaldehyde (68 mg, 0.84 mmol), sodium triacetoxyborohydride (70 mg, 0.34 mmol) and methanol (2 mL). The crude material obtained was purified by C18 reverse phase chromatography (0-100% 1:1 MeCN:MeOH/10 mM aqueous ammonium formate, pH=3.8) to provide the title product (38 mg, 78% yield).

Example 58: 2-Cyano-N-(5-(2-(((1,4-trans)-4-(dimethylamino)cyclohexyl)amino)-8-methylpyrido[3,2-d]pyrimidin-6-yl)-6-methylpyridin-2-yl)benzenesulfonamide (Compound 159)

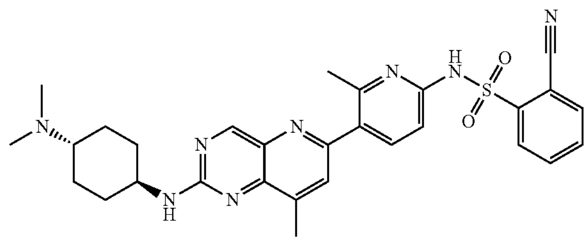 [SMILES: Cc1nc(NS(=O)(=O)c2ccccc2C#N)ccc1-c1cc(C)c2nc(N[C@H]3CC[C@H](N(C)C)CC3)ncc2n1]

Step 1: tert-Butyl ((1,4-trans)-4-((6-(6-(2-cyanophenylsulfonamido)-2-methylpyridin-3-yl)-8-methylpyrido[3,2-d]pyrimidin-2-yl)amino)cyclohexyl) carbamate

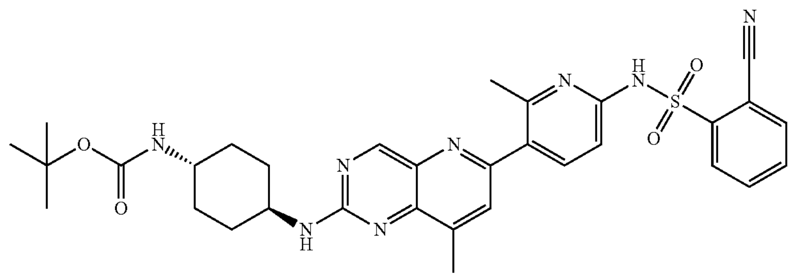 [SMILES: Cc1nc(NS(=O)(=O)c2ccccc2C#N)ccc1-c1cc(C)c2nc(N[C@H]3CC[C@H](NC(=O)OC(C)(C)C)CC3)ncc2n1]

Prepared according to Example 9 (Compound 110) step 3 using tert-butyl ((1,4-trans)-4-((6-(6-amino-2-methylpyridin-3-yl)-8-methylpyrido[3,2-d]pyrimidin-2-yl)amino)cyclohexyl)carbamate (276 mg, 0.60 mmol), pyridine (3.0 mL) and 2-cyanobenzenesulfonyl chloride (360 mg, 1.79 mmol) to provide the title product (194 mg, 51% yield). LCMS (ESI) $[M+H]^+$=629.4.

Step 2: 2-Cyano-N-(5-(2-(((1,4-trans)-4-(dimethylamino)cyclohexyl)amino)-8-methylpyrido[3,2-d]pyrimidin-6-yl)-6-methylpyridin-2-yl)benzenesulfonamide

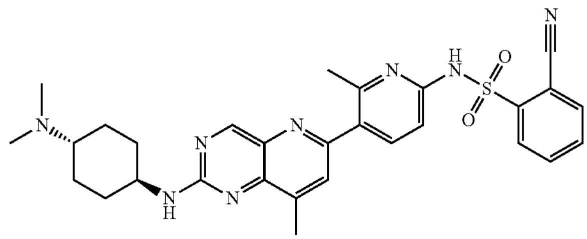 [SMILES: Cc1nc(NS(=O)(=O)c2ccccc2C#N)ccc1-c1cc(C)c2nc(N[C@H]3CC[C@H](N(C)C)CC3)ncc2n1]

Prepared according to Example 12 (Compound 113) steps 4 and 5 tert-butyl ((1,4-trans)-4-((6-(6-(2-cyanophenylsulfonamido)-2-methylpyridin-3-yl)-8-methylpyrido[3,2-d]pyrimidin-2-yl)amino)cyclohexyl)carbamate (194 mg, 0.31 mmol) to provide the title product (13 mg, 8% yield).

Table 3 shows the $^1$H NMR data and synthetic method information for compounds 100-159.

TABLE 3

| Cmpd No. | $^1$H NMR | Synthetic Method |
|---|---|---|
| 100 | (400 MHz, DMSO-$d_6$) δ 9.20 (s, 1H), 8.31 (d, J = 9.0 Hz, 1H), 8.04 (dd, J = 12.3, 2.1 Hz, 1H), 7.94 (dd, J = 8.6, 2.2 Hz, 2H), 7.69 (d, J = 8.3 Hz, 1H), 7.45 (t, J = 8.5 Hz, 1H), 7.40-7.24 (m, 5H), 4.95-4.78 (m, 1H), 4.51 (s, 2H), 4.27 (s, 1H), 3.10 (d, J = 13.1 Hz, 1H), 2.98 (t, J = 12.4 Hz, 1H), 2.80-2.67 (m, 1H), 2.50-2.48 (m, 1H), 2.23-2.15 (m, 1H), 1.94-1.76 (m, 1H). | Ex. 1 |
| 101 | (300 MHz, DMSO-$d_6$) δ 9.27 (s, 1H), 8.99 (s, 1H), 8.32 (s, 1H), 7.97-7.82 (m, 3H), 7.44-7.35 (m, 6H), 4.91-4.78 (m, 1H), 4.51 (s, 2H), 4.27-4.26 (m, 1H), 3.11-2.93 (m, 2H), 2.78-2.68 (m, 2H), 2.25-2.13 (m, 1H), 1.95-1.72 (m, 1H). | Ex. 2 |
| 102 | (400 MHz, $CD_3OD$) δ 8.99 (s, 1H), 8.10 (s, 1H), 7.43-7.37 (m, 2H), 7.37-7.32 (m, 3H), 7.29-7.26 (m, 1H), 7.13-7.10 (m, 1H), 6.06 (t, J = 56.2, 1H), 5.80 (s, 1H), 4.97-4.84 (m, 1H), 4.54 (s, 2H), 4.48 (s, 1H), 3.39-3.35 (m, 1H), 3.17 (t, J = 13.0 Hz, 1H), 2.82 (dd, J = 37.3, 14.5 Hz, 1H), 2.60-2.35 (m, 2H), 1.90 (dt, J = 41.0, 12.9 Hz, 1H), 1.45 (d, J = 6.6 Hz, 3H). | Ex. 3 |
| 103 | (400 MHz, $CD_3OD$) δ 8.99 (s, 1H), 8.10 (s, 1H), 7.42-7.37 (m, 2H), 7.37-7.32 (m, 3H), 7.31-7.25 (m, 1H), 7.13-7.10 (m, 1H), 6.24-5.89 (m, 1H), 5.81 (s, 1H), 4.97-4.85 (m, 1H), 4.54 (s, 2H), 4.53-4.43 (m, 1H), 3.41-3.34 (m, 1H), 3.17 (t, J = 13.1 Hz, 1H), 2.82 (dd, J = 36.9, 14.3 Hz, 1H), 2.59-2.35 (m, 2H), 1.90 (dt, J = 40.8, 12.8 Hz, 1H), 1.45 (d, J = 6.5 Hz, 3H). | Ex. 3 |
| 104 | (300 MHz, $CD_3OD$) δ 8.97 (s, 1H), 8.13 (s, 1H), 7.59-7.50 (m, 2H), 7.44-7.32 (m, 3H), 7.25-7.15 (m, 1H), 5.95-5.85 (m, 1H), 5.01-4.91 (m, 1H), 4.60-4.40 (m, 3H), 4.12-4.09 (m, 1H), 3.97-3.84 (m, 3H), 3.38-3.35 (m, 1H), 3.20 (t, J = 12.9 Hz, 1H), 2.95-2.75 (m, 1H), 2.56 (t, J = 11.7 Hz, 1H), 2.45- 2.25 (m, 2H), 2.21-2.06 (m, 1H), 2.03-1.75 (m, 1H). | Ex. 3 |
| 105 | (300 MHz, $CD_3OD$) δ 8.97 (s, 1H), 8.13 (s, 1H), 7.59-7.50 (m, 2H), 7.44-7.32 (m, 3H), 7.25-7.15 (m, 1H), 5.95-5.85 (m, 1H), 5.01-4.91 (m, 1H), 4.60-4.40 (m, 3H), 4.12-4.09 (m, 1H), 3.97-3.84 (m, 3H), 3.38-3.35 (m, 1H), 3.20 (t, J = 12.9 Hz, 1H), 2.95-2.75 (m, 1H), 2.56 (t, J = 11.7 Hz, 1H), 2.45-2.25 (m, 2H), 2.21-2.06 (m, 1H), 2.03-1.75 (m, 1H). | Ex. 3 |
| 106 | (300 MHz, $CD_3OD$) δ 9.07 (s, 1H), 7.99 (s, 1H), 7.92 (d, J = 12 Hz, 1H), 7.79 (d, J = 18 Hz, 1H), 7.54 (t, | Ex. 5 |

TABLE 3-continued

| Cmpd No. | $^1$H NMR | Synthetic Method |
|---|---|---|
| | J = 8.4 Hz, 1H), 7.43-7.29 (m, 5H), 5.01-4.79 (m, 1H), 4.51 (s, 2H), 4.49-4.38 (m, 1H), 3.43-3.35 (m, 1H), 3.16 (t, J = 13.0 Hz, 1H), 2.94-2.73 (m, 1H), 2.64 (s, 3H), 2.61-2.54 (m, 1H), 2.53-2.39 (m, 1H), 2.00-1.75 (m, 1H). | |
| 107 | (300 MHz, DMSO-$d_6$) δ 9.11 (s, 1H), 8.17 (s, 1H), 7.97-7.83 (m, 2H), 7.56 (s, 1H), 7.46 (t, J = 8.7 Hz, 1H), 3.82 (s, 1H), 3.25-3.10 (m, 2H), 2.80-2.62 (m, 3H), 2.56 (s, 3H), 2.48 (s, 6H), 2.15 (s, 2H), 2.00-1.89 (m, 2H), 1.53-1.29 (m, 4H). | Ex. 5 |
| 108 | (300 MHz, DMSO-$d_6$) δ 9.19 (s, 1H), 8.32 (s, 1H), 8.04-7.93 (m, 2H), 7.80-7.64 (m, 1H), 7.53-7.31 (m, 5H), 6.80-5.85 (brs, 1H), 4.96-4.78 (m, 1H), 4.48 (s, 2H), 4.26 (s, 1H), 3.16 (d, J = 12.6 Hz, 1H), 3.00 (t, J = 12.8 Hz, 1H), 2.89-2.66 (m, 1H), 2.60 (s, 3H), 2.57-2.53 (m, 1H), 2.24 (s, 1H), 2.02-1.73 (m, 1H) | Ex. 5 |
| 109 | (400 MHz, DMSO-d6) δ 9.27-9.15 (m, 2H), 8.54 (s, 1H), 7.84 (d, J = 8.1 Hz, 1H), 7.74 (dd, J = 12.1, 1.8 Hz, 1H), 7.57 (dd, J = 8.4, 1.8 Hz, 1H), 7.43 (t, J = 8.5 Hz, 1H), 7.39-7.30 (m, 5H), 4.84 (d, J = 47.6 Hz, 1H), 4.47 (s, 2H), 4.35-4.17 (m, 1H), 3.15-3.02 (m, 1H), 3.02-2.88 (m, 1H), 2.75 (d, J = 14.0 Hz, 1H), 2.71-2.61 (m, 1H), 2.47-2.41 (m, 1H), 2.28-2.10 (m, 1H), 1.97-1.72 (m, 1H). | Ex. 8 |
| 110 | (400 MHz, DMSO-d6) δ 9.14 (s, 1H), 8.22 (s, 1H), 8.16 (s, 1H), 7.99 (dd, J = 12.5, 1.8 Hz, 1H), 7.93 (dd, J = 8.5, 1.6 Hz, 1H), 7.71-7.61 (m, 1H), 7.49 (t, J = 8.6 Hz, 1H), 4.91 (d, J = 47.8 Hz, 1H), 4.37-4.22 (m, 1H), 3.31-3.23 (m, 2H), 3.23-3.13 (m, 1H), 3.06 (t, J = 12.4 Hz, 1H), 2.92-2.82 (m, 1H), 2.80-2.65 (m, 3H), 2.58 (s, 3H), 2.57-2.53 (m, 1H), 2.31-2.16 (m, 1H), 1.88 (dt, J = 43.3, 12.3 Hz, 1H). | Ex. 9 |
| 111 | (400 MHz, DMSO-d6) δ 9.16 (s, 1H), 8.26 (s, 1H), 8.16 (s, 1H), 8.06 (dd, J = 12.1, 1.7 Hz, 1H), 8.01 (dd, J = 8.5, 1.6 Hz, 1H), 7.77-7.67 (m, 1H), 7.55 (t, J = 8.4 Hz, 1H), 4.92 (d, J = 47.3 Hz, 1H), 4.39-4.20 (m, 1H), 3.30-2.98 (m, 5H), 2.96-2.71 (m, 1H), 2.59 (s, 3H), 2.58-2.53 (m, 1H), 2.32-2.19 (m, 1H), 2.01-1.82 (m, 1H), 1.76 (dq, J = 15.0, 7.5 Hz, 2H), 0.98 (t, J = 7.4 Hz, 3H). | Ex. 10 |
| 112 | (400 MHz, DMSO-d6) δ 9.12 (s, 1H), 8.31-8.17 (m, 2H), 8.03 (dd, J = 12.3, 1.7 Hz, 1H), 7.97 (dd, J = 8.5, 1.6 Hz, 1H), 7.68-7.61 (m, 1H), 7.53 (t, J = 8.5 Hz, 1H), 3.89-3.73 (m, 1H), 3.15-3.06 (m, 2H), 2.57 (s, 3H), 2.43-2.34 (m, 1H), 2.30 (s, 6H), 2.19-1.99 (m, 2H), 1.95-1.83 (m, 2H), 1.82-1.67 (m, 2H), 1.44-1.29 (m, 4H), 0.97 (t, J = 7.4 Hz, 3H). | Ex. 11 |
| 113 | (400 MHz, DMSO-d6) δ 9.11 (s, 1H), 8.22 (s, 1H), 8.20 (s, 1H), 7.99 (dd, J = 12.5, 1.9 Hz, 1H), 7.93 (dd, J = 8.5, 1.8 Hz, 1H), 7.63 (s, 1H), 7.49 (t, J = 8.6 Hz, 1H), 3.80 (bs, 1H), 3.23-3.09 (m, 2H), 2.64 (t, J = 9.8 Hz, 1H), 2.56 (s, 3H), 2.44 (s, 6H), 2.41-2.28 (m, 2H), 2.23-2.08 (m, 2H), 2.02-1.85 (m, 2H), 1.65 (t, J = 19.1 Hz, 3H), 1.52-1.26 (m, 4H). | Ex. 12 |
| 114 | (400 MHz, DMSO-d6) δ 9.09 (s, 1H), 8.08 (s, 1H), 7.87 (d, J = 13.0 Hz, 1H), 7.80 (d, J = 8.3 Hz, 1H), 7.62-7.47 (m, 1H), 7.41 (t, J = 8.8 Hz, 1H), 3.76 (bs, 1H), 3.15-2.87 (m, 4H), 2.78-2.59 (m, 2H), 2.37 (s, 6H), 2.25-2.04 (m, 2H), 2.02-1.84 (m, 2H), 1.50-1.17 (m, 8H). | Ex. 13 |
| 115 | (400 MHz, DMSO-d6) δ 9.15 (br s, 1H), 8.23 (s, 1H), 8.00 (dd, J = 12.4, 2.0 Hz, 1H), 7.92 (dd, J = 8.6 Hz, 1.6 Hz, 1H), 7.64 (br s, 1H), 7.53-7.43 (m, 2H), 7.27 (td, J = 9.9, 2.5 Hz, 1H), 7.12 (td, J = 8.5, 2.6 Hz, 1H), 4.88 (d, J = 47.5 Hz, 1H), 4.48 (s, 2H), 4.27 (br s, 1H), 3.22-3.08 (m, 1H), 3.05-2.94 (m, 1H), 2.89-2.68 (m, 1H), 2.59 (s, 3H), 2.56-2.51 (m, 1H), 2.31-2.15 (m, 1H), 2.01-1.74 (m, 1H). | Ex. 14 |
| 116 | (400 MHz, DMSO-d6) δ 9.15 (br s, 1H), 8.22 (s, 1H), 8.15 (s, 1H), 7.99 (dd, J = 12.5, 1.9 Hz, 1H), 7.93-7.88 (m, 1H), 7.83 (d, J = 8.3 Hz, 2H), 7.66 (br s, 1H), 7.55 (d, J = 8.2 Hz, 2H), 7.47 (t, J = 8.6 Hz, 1H), 4.90 (d, J = 48.0 Hz, 1H), 4.58 (s, 2H), 4.40-4.16 (m, 1H), 3.24-3.10 (m, 1H), 3.03 (t, J = 11.8 Hz, 1H), 2.93-2.69 (m, 1H), 2.59 (s, 3H), 2.63-2.54 (m, 1H), 2.31-2.16 (m, 1H), 2.00-1.74 (m, 1H). | Ex. 15 |
| 117 | (400 MHz, DMSO-d6) δ 9.09 (s, 1H), 8.20 (s, 1H), 8.15 (s, 1H), 7.86 (dd, J = 12.9, 1.6 Hz, 1H), 7.81 (dd, J = 8.6, 1.5 Hz, 1H), 7.56 (s, 1H), 7.44 (t, J = 8.7 Hz, 1H), 3.90-3.76 (m, 1H), 3.57 (t, J = 14.1 Hz, 2H), 2.76-2.64 (m, 1H), 2.55 (s, 3H), 2.47 (s, 6H), 2.23-2.05 (m, 4H), 2.01-1.88 (m, 2H), 1.53-1.29 (m, 4H), 0.93 (t, J = 7.5 Hz, 3H). | Ex. 16 |
| 118 | (400 MHz, DMSO-d6) δ 9.24 (s, 1H), 8.21 (s, 1H), 7.96 (dd, J = 12.8, 2.0 Hz, 1H), 7.90 (dd, J = 8.5, 1.9 Hz, 1H), 7.45 (t, J = 8.7 Hz, 1H), 7.28 (s, 1H), 6.55 (d, J = 8.8 Hz, 1H), 4.08 (s, 3H), 3.85-3.71 (m, 1H), 3.19-3.05 (m, 2H), 2.78-2.56 (m, 3H), 2.43 (s, 6H), 2.11 (d, J = 11.8 Hz, 2H), 2.02-1.81 (m, 2H), 1.66-1.37 (m, 4H). | Ex. 17 |
| 119 | (400 MHz, DMSO-d6) δ 9.14 (br s, 1H), 8.18 (s, 1H), 8.14 (s, 1H), 7.96 (d, J = 12.6 Hz, 1H), 7.90 (d, J = 8.3 Hz, 1H), 7.61 (br s, 1H), 7.47 (t, J = 8.6 Hz, 1H), 4.88 (d, J = 47.2 Hz, 1H), 4.23 (s, 1H), 3.26-3.10 (m, 3H), 3.08-2.93 (m, 3H), 2.87-2.64 (m, 3H), 2.62-2.53 (m, 1H), 2.32-2.14 (m, 1H), 1.99-1.75 (m, 1H), 1.33 (t, J = 7.4 Hz, 3H). | Ex. 18 |
| 120 | (400 MHz, DMSO-d6) δ 9.09 (s, 1H), 8.17-8.08 (m, 2H), 7.86 (d, J = 7.8 Hz, 1H), 7.54 (s, 1H), 7.42 (d, J = 8.6 Hz, 1H), 3.95-3.73 (m, 1H), 3.04-2.94 (m, 2H), 2.94-2.79 (m, 1H), 2.73-2.63 (m, 2H), 2.62-2.53 (m, 10H), 2.26-2.10 (m, 1H), 2.07-1.93 (m, 2H), 1.61-1.30 (m, 4H). | Ex. 19 |
| 121 | (400 MHz, DMSO-d6) δ 9.14 (br s, 1H), 8.22 (s, 1H), 8.18 (s, 1H), 7.99 (dd, J = 12.4, 1.8 Hz, 1H), 7.91 (dd, J = 8.5, 1.7 Hz, 1H), 7.62 (br s, 1H), 7.47-7.34 (m, 3H), 7.24-7.12 (m, 2H), 4.85 (d, J = 46.4 Hz, 1H), 4.45 (s, 2H), 4.36-4.16 (m, 1H), 3.21-3.05 (m, 1H), 2.96 (t, J = 12.7 Hz, 1H), 2.84-2.64 (m, 1H), 2.58 (s, 3H), 2.60-2.52 (m, 1H), 2.32-2.14 (m, 1H), 2.01-1.76 (m, 1H). | Ex. 20 |
| 122 | (400 MHz, DMSO-d6) δ 9.16 (br s, 1H), 8.19 (s, 1H), 8.17 (s, 1H), 8.03 (d, J = 12.4 Hz, 1H), 7.94 (d, J = 8.4 Hz, 1H), 7.64 (br s, 1H), 7.43 (t, J = 8.5 Hz, 1H), 7.39-7.29 (m, 5H), 4.85 (d, J = 47.4 Hz, 1H), 4.48 (s, 2H), 4.33-4.12 (m, 1H), 3.23-2.89 (m, 4H), 2.86-2.64 (m, 1H), 2.62-2.51 (m, 1H), 2.29-2.11 (m, 1H), 1.99-1.76 (m, 1H), 1.34 (t, J = 7.4 Hz, 3H). | Ex. 21 |
| 123 | (400 MHz, DMSO-d6) δ 9.10 (br s, 1H), 8.13 (s, 1H), 8.07 (s, 1H), 7.94 (dd, J = 7.8, 1.6 Hz, 1H), 7.85 (dd, J = 12.6, 1.9 Hz, 1H), 7.76 (d, J = 8.6 Hz, 1H), 7.66 (br s, 1H), 7.55 (d, J = 7.8 Hz, 1H), 7.52-7.46 (m, 1H), 7.44-7.37 (m, 1H), 7.26 (t, J = 8.6 Hz, 1H), 4.96 (d, J = 47.4 Hz, 1H), 4.26 (s, 1H), 3.27-3.05 (m, 2H), 3.06-2.78 (m, 3H), 2.70-2.54 (m, 1H), 2.35-2.18 (m, 1H), 2.02-1.74 (m, 1H), 1.29 (t, J = 7.5 Hz, 3H). | Ex. 22 |
| 124 | (400 MHz, DMSO-d6) δ 9.11 (s, 1H), 8.17 (s, 1H), 8.04 (s, 1H), 7.93 (d, J = 11.0 Hz, 1H), 7.86 (d, J = 8.6 Hz, 1H), 7.59 (bs, 1H), 7.44 (t, J = 8.7 Hz, 1H), 3.80 (bs, 2H), 3.18-3.06 (m, 2H), 2.79-2.63 (m, 2H), 2.43 (s, 6H), 2.23-2.04 (m, 2H), 2.04-1.77 (m, 2H), 1.51-1.21 (m, 11H). | Ex. 23 |
| 125 | (400 MHz, DMSO-d6) δ 9.05 (br s, 1H), 8.78 (d, J = 2.2 Hz, 1H), 8.15 (dd, J = 8.6, 2.5 Hz, 1H), 8.12 (s, 1H), 7.44 (br s, 1H), 6.62 (d, J = 8.7 Hz, 1H), 3.88-3.70 (m, 1H), 3.25-3.11 (m, 1H), 2.65-2.52 (m, 2H), 2.54 (s, 3H), 2.22 (s, 6H), 2.16-2.00 (m, 2H), 1.91-1.78 (m, 2H), 1.43-1.19 (m, 6H). | Ex. 24 |
| 126 | (400 MHz, DMSO) δ 9.08 (s, 1H), 7.85 (d, J = 8.0 Hz, 1H), 7.76 (s, 1H), 7.66-7.55 (m, 1H), 7.02-6.91 (m, 1H), 3.89-3.71 (m, 1H), 3.59-3.43 (m, 2H), 2.80-2.62 (m, 3H), 2.55 (s, 3H), 2.36-2.21 (m, 9H), 2.18-2.06 (m, 1H), 1.94-1.82 (m, 2H), 1.44-1.22 (m, 5H). | Ex. 25 |
| 127 | (400 MHz, DMSO-d6) δ 9.82 (s, 1H), 9.13 (s, 1H), 8.25 (s, 1H), 8.14-7.95 (m, 3H), 7.68 (s, 1H), 3.93-3.73 (m, 1H), 3.32-3.29 (m, 1H), 2.58 (s, 6H), 2.36-2.26 (m, 4H), 2.24-1.94 (m, 6H), 1.61-1.30 (m, 4H), 0.95 (d, J = 6.6 Hz, 6H). | Ex. 26 |
| 128 | (400 MHz, DMSO-d6) δ 9.04 (br s, 1H), 8.06 (s, 1H), 7.96 (d, J = 6.3 Hz, 1H), 7.75 (d, J = 14.2 Hz, 1H), 7.60 (d, J = 9.0 Hz, 1H), 7.55-7.30 (m, 4H), 7.18 (t, J = 8.7 Hz, 1H), 3.91-3.70 (m, 1H), 3.29-3.16 (m, 1H), 2.72-2.58 (m, 1H), 2.54 (s, 3H), 2.45 (s, 6H), | Ex. 27 |

TABLE 3-continued

| Cmpd No. | $^1$H NMR | Synthetic Method |
|---|---|---|
| | 2.22-2.05 (m, 1H), 2.02-1.86 (m, 2H), 1.53-1.27 (m, 4H). | |
| 129 | (400 MHz, DMSO-d6) δ 9.07 (br s, 1H), 8.14 (s, 1H), 7.88 (d, J = 12.8 Hz, 1H), 7.81 (d, J = 8.8 Hz, 1H), 7.53 (br s, 1H), 7.40 (t, J = 8.7 Hz, 1H), 7.34 (dd, J = 8.6, 5.6 Hz, 2H), 7.13 (t, J = 8.9 Hz, 2H), 4.29 (s, 2H), 3.92-3.67 (m, 1H), 3.23-3.15 (m, 1H), 2.54 (s, 3H), 2.35-2.26 (m, 1H), 2.25 (s, 6H), 2.17-2.00 (m, 1H), 1.93-1.78 (m, 2H), 1.41-1.23 (m, 4H). | Ex. 28 |
| 130 | (400 MHz, DMSO-d6) δ 9.13 (s, 1H), 8.22 (s, 2H), 7.88 (d, J = 12.8 Hz, 1H), 7.79 (d, J = 8.7 Hz, 1H), 7.42 (t, J = 8.2 Hz, 1H), 7.36-7.31 (m, 2H), 7.12 (t, J = 8.5 Hz, 2H), 5.96 (s, 1H), 5.84 (s, 1H), 4.23 (s, 2H), 3.73-3.68 (m, 1H), 2.27 (s, 6H), 2.13-2.02 (m, 2H), 1.92-1.86 (m, 3H), 1.38-1.31 (m, 5H). | Ex. 29 |
| 131 | (400 MHz, DMSO-d6) δ 9.25 (m, 1H), 8.37 (s, 1H), 8.21 (s, 1H), 8.07-7.83 (m, 3H), 7.66-6.23 (m, 4H), 7.15 (t, J = 8.8 Hz, 2H), 4.40 (s, 2H), 3.88-3.79 (m, 1H), 2.66-2.60 (m, 1H), 2.43 (s, 6H), 2.14-2.08 (m, 1H), 1.95-1.89 (m, 2H), 1.47-1.36 (m, 4H). | Ex. 30 |
| 132 | (400 MHz, DMSO-d6) δ 9.07 (br s, 1H), 7.85 (s, 1H), 7.50 (br s, 1H), 7.44 (t, J = 9.2 Hz, 1H), 7.29 (dd, J = 8.5, 5.8 Hz, 2H), 7.23 (t, J = 8.2 Hz, 1H), 7.09 (t, J = 8.9 Hz, 2H), 4.02 (s, 2H), 3.91-3.70 (m, 1H), 3.48-3.38 (m, 1H), 2.54 (s, 3H), 2.22 (s, 6H), 2.29-2.01 (m, 2H), 1.91-1.78 (m, 2H), 1.40-1.25 (m, 4H). | Ex. 31 |
| 133 | (400 MHz, DMSO-d6) δ 9.25 (s, 1H), 8.09-7.97 (m, 2H), 7.88 (d, J = 8.6 Hz, 1H), 7.60 (t, J = 54.0 Hz, 1H), 7.33 (dd, J = 8.3, 5.8 Hz, 2H), 7.17 (t, J = 8.8 Hz, 2H), 6.89 (d, J = 8.5 Hz, 1H), 6.69 (s, 1H, NH), 4.73 (s, 2H), 3.81-3.72 (m, 1H).2.56 (s, 3H), 2.24 (s, 6H), 2.13-2.03 (m, 2H), 1.91-1.86 (m, 2H), 1.38-1.29 (m, 4H). | Ex. 32 |
| 134 | (400 MHz, DMSO-d6) δ 9.06 (s, 1H), 8.13 (d, J = 6.9 Hz, 1H), 7.87 (d, J = 8.7 Hz, 1H), 7.69 (s, 1H), 7.66-7.59 (m, 1H), 7.58-7.46 (m, 3H), 7.06 (d, J = 7.3 Hz, 1H), 3.87-3.68 (m, 1H), 2.99 (q, J = 7.2 Hz, 2H), 2.44 (s, 3H), 2.36-2.29 (m, 1H), 2.25 (s, 6H), 2.16-2.04 (m, 2H), 1.93-1.82 (m, 2H), 1.42-1.24 (m, 7H). | Ex. 33 |
| 135 | (400 MHz, DMSO-d6) δ 9.00 (br s, 1H), 8.63 (s, 1H), 8.07-7.95 (m, 2H), 7.73-7.50 (m, 2H), 7.44-7.27 (m, 3H), 6.67 (d, J = 9.2 Hz, 1H), 3.84-3.68 (m, 1H), 2.52 (s, 3H), 2.18 (s, 6H), 2.20-2.17 (m, 1H), 1.89-1.75 (m, 2H), 1.41-1.18 (m, 6H). | Ex. 34 |
| 136 | (400 MHz, DMSO-d6) δ 9.07 (s, 1H), 8.13 (d, J = 6.5 Hz, 1H), 7.96 (d, J = 6.8 Hz, 1H), 7.84 (t, J = 5.7 Hz, 1H), 7.74 (s, 1H), 7.71-7.64 (m, 1H), 7.57-7.47 (m, 3H), 7.05 (s, 1H), 4.81 (d, J = 49.5 Hz, 1H), 4.31-4.08 (m, 1H), 3.25-3.19 (m, 3H), 2.84-2.74 (m, 2H), 2.45 (s, 3H), 1.64-1.56 (m, 1H), 1.55-1.40 (m, 3H). | Ex. 35 |
| 137 | (400 MHz, DMSO-d6) δ 9.07 (br s, 1H), 7.88 (s, 1H), 7.57 (dd, J = 12.7, 8.1 Hz, 1H), 7.48 (brs, 1H), 7.30 (dd, J = 8.6, 5.7 Hz, 2H), 7.18-7.01 (m, 3H), 4.00 (s, 2H), 3.91-3.67 (m, 1H), 3.26-3.19 (m, 1H), 2.53 (s, 3H), 2.19 (s, 6H), 2.16-2.04 (m, 2H), 1.90-1.77 (m, 2H), 1.40- 1.26 (m, 4H). | Ex. 36 |
| 138 | (400 MHz, DMSO-d6) δ 9.13 (s, 1H), 8.11 (s, 1H), 7.90 (d, J = 12.7 Hz, 1H), 7.81 (d, J = 8.7 Hz, 1H), 1.63-7.59 (s, 1H, br), 7.43 (t, J = 8.6 Hz, 1H), 7.36 (dd, J = 8.5, 5.6 Hz, 2H), 7.15 (t, J = 8.9 Hz, 2H), 4.86 (s, 2H), 4.37 (s, 2H), 3.75-3.70 (m, 1H), 3.48 (s, 3H), 2.39-3.33 (m, 1H), 2.30 (s, 6H), 2.15-2.09 (m, 1H), 1.90-1.83 (m, 2H), 1.39-1.27 (m, 4H). | Ex. 37 |
| 139 | (400 MHz, DMSO-d6) δ 9.95 (s, 1H), 9.44 (s, br, 1H), 9.34 (s, 1H), 9.24 (s, br, 1H), 8.51 (s, 1H), 8.35 (d, J = 6.8 Hz, 1H), 8.13 (dd, J = 12.1, 1.8 Hz, 1H), 8.02 (d, J = 8.5 Hz, 1H), 7.73 (t, J = 54.2 Hz, 1H), 7.47-7.35 (m, 3H), 7.19 (t, J = 8.8 Hz, 2H), 5.26 (d, J = 45.1 Hz, 1H), 4.58 (s, 2H), 4.41 (s, 1H), 3.56-3.50 (m, 2H), 2.83-2.78 (m, 1H), 2.39-2.35 (m, 1H), 2.14-1.78 (m, 1H). | Ex. 38 |
| 140 | (400 MHz, DMSO-d6) δ 9.09 (br s, 1H), 7.70 (br s, 1H), 7.64 (s, 1H), 7.33 (dd, J = 8.6, 5.6 Hz, 2H), 7.19 (t, J = 8.9 Hz, 2H), 6.77 (d, J = 10.3 Hz, 2H), 4.47 (s, 2H), 3.92-3.74 (m, 1H), 3.46-3.36 (m, 1H), 2.55 (s, 3H), 2.37 (s, 6H), 2.23-1.83 (m, 4H), 1.50-1.30 (m, 4H). | Ex. 39 |
| 141 | (400 MHz, DMSO-d6) δ 9.06 (s, 1H), 8.24 (d, J = 7.3 Hz, 1H), 8.07 (d, J = 7.8 Hz, 1H), 7.96 (s, 1H), 7.66-7.47 (m, 4H), 6.61-6.48 (m, 1H), 3.87-3.70 (m, 1H), 3.53 (s, 3H), 3.51-3.46 (m, 1H), 2.96 (q, J = 6.7 Hz, 2H), 2.61 (s, 6H), 2.27-1.93 (m, 4H), 1.59-1.45 (m, 2H), 1.44-1.33 (m, 2H), 1.26 (t, J = 7.2 Hz, 3H). | Ex. 40 |
| 142 | (400 MHz, DMSO-d6) δ 9.08 (s, 1H), 8.18-8.07 (m, 2H), 7.49 (s, 1H), 7.34 (dd, J = 8.2, 5.9 Hz, 2H), 7.17 (t, J = 8.7 Hz, 2H), 6.43 (d, J = 7.7 Hz, 1H), 4.76 (s, 2H), 4.03 (s, 3H), 3.86-3.69 (m, 1H), 3.59-3.48 (m, 1H), 3.01 (t, J = 7.3 Hz, 2H), 2.24 (s, 6H), 2.17-2.04 (m, 2H), 1.94-1.80 (m, 2H), 1.42-1.27 (m, 7H). | Ex. 41 |
| 143 | (400 MHz, DMSO-d6) δ 9.24-9.11 (d, J = 31.4 Hz, 1H), 8.26 (s, 1H), 7.95 (dd, J = 7.6, 1.7 Hz, 1H), 7.90 (d, J = 7.5 Hz, 1H), 7.81 (d, J = 13.0 Hz, 1H), 7.66 (d, J = 6.8 Hz, 1H), 7.55-7.32 (m, 4H), 7.21 (t, J = 8.8 Hz, 1H), 3.88-3.76 (m, 1H), 2.89-2.83 (m, 1H), 2.56 (s, 6H), 2.16-1.91 (m, 4H), 1.55-1.31 (m, 4H). | Ex. 42 |
| 144 | (400 MHz, DMSO-d6) δ 9.18 (s, 1H), 8.33 (s, 1H), 7.90 (d, J = 11.3 Hz, 2H), 7.83 (d, J = 8.6 Hz, 1H), 7.61 (t, J = 56 Hz, 1H), 7.41 (d, J = 8.9 Hz, 1H), 4.11-3.66 (m, 1H), 3.09-3.05 (m, 2H), 2.77-2.53 (m, 4H), 2.44 (s, 6H), 2.11-1.88 (m, 5H), 1.52-1.30 (m, 5H). | Ex. 43 |
| 145 | (400 MHz, DMSO-d6) δ 9.26-9.12 (m, 1H), 8.12 (d, J = 6.9 Hz, 1H), 7.97 (s, 2H), 7.88-7.83 (m, 1H), 7.56 (s, J = 52.0 Hz, 1H), 7.53-7.41 (m, 3H), 7.03 (s, br, 1H), 3.74-3.70 (m, 1H), 2.44-2.39 (m, 4H), 2.33-2.29 (m, 1H), 2.26 (s, 6H), 2.11-2.04 (m, 1H), 1.89-1.82 (m, 2H), 1.39-1.27 (m, 4H). | Ex. 44 |
| 146 | (400 MHz, DMSO-d6) δ 9.06 (s, 1H), 7.99-7.85 (m, 2H), 7.69 (s, 1H), 7.66-7.53 (m, 2H), 7.32 (dd, J = 16.2, 8.3 Hz, 2H), 7.16-7.06 (m, 1H), 3.84-3.66 (m, 1H), 3.42-3.36 (m, 1H), 2.99 (q, J = 7.4 Hz, 2H), 2.45 (s, 3H), 2.26 (s, 6H), 2.17-2.04 (m, 2H), 1.93-1.81 (m, 2H), 1.43-1.20 (m, 7H). | Ex. 45 |
| 147 | (400 MHz, DMSO-d6) δ 9.04 (s, 1H), 8.07-8.01 (m, 1H), 7.91 (s, 1H), 7.81-7.70 (m, 2H), 7.69-7.55 (m, 4H), 6.97-6.69 (m, 1H), 3.87-3.66 (m, 1H), 3.26-3.19 (m, 1H), 2.98 (q, J = 7.5 Hz, 2H), 2.40 (s, 3H), 2.30 (s, 6H), 2.19-2.05 (m, 2H), 1.95-1.84 (m, 2H), 1.41-1.31 (m, 3H), 1.31-1.21 (m, 4H). | Ex. 46 |
| 148 | (400 MHz, DMSO-d6) δ 9.06 (s, 1H), 8.02 (d, J = 7.2 Hz, 1H), 7.88 (s, 1H), 7.69 (s, 1H), 7.67-7.55 (m, 2H), 7.47-7.20 (m, 3H), 7.21-6.99 (m, 1H), 3.84-3.68 (m, 1H), 3.47-3.40 (m, 1H), 2.99 (q, J = 6.9 Hz, 2H), 2.45 (s, 3H), 2.26 (s, 6H), 2.16-2.04 (m, 2H), 1.94-1.82 (m, 2H), 1.40-1.24 (m, 7H). | Ex. 47 |
| 149 | (400 MHz, DMSO-d6) δ 9.05 (br s, 1H), 8.12 (d, J = 6.9 Hz, 1H), 8.03 (s, 1H), 7.74 (s, 1H), 7.65-7.43 (m, 4H), 6.95 (s, 1H), 3.88-3.70 (m, 1H), 3.54-3.49 (m, 1H), 2.51 (s, 3H), 2.44-2.35 (m, 1H), 2.34 (s, 3H), 2.30 (s, 6H), 2.17-2.07 (m, 1H), 1.95-1.83 (m, 2H), 1.43-1.27 (m, 4H). | Ex. 48 |
| 150 | (400 MHz, DMSO-d6) δ 9.01 (s, 1H), 8.03 (s, 1H), 7.91 (d, J = 7.4 Hz, 1H), 7.80 (d, J = 7.6 Hz, 1H), 7.73-7.62 (m, 2H), 7.58-7.48 (m, 2H), 7.17 (t, J = 8.9 Hz, 1H), 2.17 (s, 6H), 1.88-1.79 (m, 2H), 1.38-1.19 (m, 6H). | Ex. 49 |
| 151 | (400 MHz, DMSO-d6) δ 9.07 (s, 1H), 8.11 (s, 1H), 7.97 (s, 1H), 7.93 (d, J = 8.2 Hz, 1H), 7.77-7.63 (m, 1H), 7.47 (s, 1H), 6.76 (d, J = 8.3 Hz, 1H), 4.14-4.09 (m, 1H), 2.54 (s, 6H), 2.19 (s, 7H), 1.87 (d, J = 13.3 Hz, 2H), 1.27 (dd, J = 26.4, 13.9 Hz, 10H), 0.85 (dd, J = 9.9, 4.9 Hz, 3H). | Ex. 50 |
| 152 | (400 MHz, DMSO-d6) δ 9.15 (s, 1H), 8.16 (s, 1H), 8.03 (d, J = 12.2 Hz, 1H), 8.00-7.87 (m, 3H), 7.72 (bs, 1H), 7.63 (d, J = 8.2 Hz, 2H), 7.48 (t, J = 8.5 Hz, 1H), 4.67 (s, 2H), 3.19 (s, 3H), 3.10-2.92 (m, 3H), 2.67 (s, 6H), 2.45 (s, 1H), 2.27-2.11 (m, 2H), 2.11-1.90 (m, 2H), 1.54 (dd, J = 20.2, 6.9 Hz, 2H), 1.48-1.26 (m, 5H). | Ex. 51 |
| 153 | (400 MHz, DMSO-d6) δ 9.11 (br s, 1H), 7.92 (s, 1H), 7.74-7.55 (m, 1H), 7.51-7.33 (m, 3H), 7.11 (t, J = 8.9 Hz, 2H), 4.11 (s, 2H), 3.91-3.74 (m, 1H), 3.53-3.42 (m, 1H), 2.56 (s, 3H), 2.40 (s, 6H), 2.46-2.30 (m, 1H), 2.24-2.09 (m, 1H), 1.98-1.84 (m, 2H), 1.53-1.28 (m, 4H). | Ex. 52 |

TABLE 3-continued

| Cmpd No. | $^1$H NMR | Synthetic Method |
|---|---|---|
| 154 | (400 MHz, DMSO-d6) δ 9.03 (s, 1H), 8.84 (d, J = 1.7 Hz, 1H), 8.57 (d, J = 3.8 Hz, 1H), 8.04 (d, J = 10.1 Hz, 2H), 7.73 (d, J = 13.0 Hz, 1H), 7.63 (d, J = 9.0 Hz, 1H), 7.51 (s, 1H), 7.43 (dd, J = 7.8, 4.8 Hz, 1H), 7.25 (t, J = 8.8 Hz, 1H), 3.78-3.69 (m, 1H), 2.88-2.80 (m, 1H), 2.54 (s, 6H), 2.26-2.10 (m, 2H), 1.99-1.83 (m, 2H), 1.57-1.29 (m, 4H). | Ex. 53 |
| 155 | (400 MHz, DMSO-d6) δ 9.07 (br s, 1H), 7.95 (d, J = 6.9 Hz, 1H), 7.87 (s, 1H), 7.61 (br s, 1H), 7.40 (d, J = 7.5 Hz, 1H), 7.36-7.22 (m, 3H), 3.87-3.70 (m, 1H), 3.43-3.34 (m, 1H), 2.52 (s, 3H), 2.39 (s, 6H), 2.21-2.04 (m, 2H), 1.98-1.82 (m, 2H), 1.49-1.24 (m, 4H). | Ex. 54 |
| 156 | (400 MHz, DMSO-d6) δ 9.16 (s, 1H), 9.01 (s, 1H), 8.79-8.71 (m, 1H), 8.03 (s, 1H), 7.72 (dd, J = 7.1, 3.6 Hz, 2H), 7.55 (d, J = 8.6 Hz, 1H), 7.43 (s, 1H), 7.12 (t, J = 8.9 Hz, 1H), 3.80-3.71 (m, 1H), 2.38-2.34 (m, 1H), 2.29 (s, 6H), 2.14-2.03 (m, 1H), 1.89-1.82 (m, 2H), 1.38-1.32 (m, 4H). | Ex. 55 |
| 157 | (400 MHz, DMSO-d6) δ 9.05 (s, 1H), 8.68 (d, J = 3.7 Hz, 1H), 8.40 (d, J = 8.1 Hz, 1H), 8.06 (s, 1H), 7.75 (dd, J = 13.1, 2.1 Hz, 1H), 7.70 (dd, J = 8.1, 4.6 Hz, 1H), 7.56 (dd, J = 8.6, 1.9 Hz, 2H), 7.50 (br, 1H), 7.07 (t, J = 8.9 Hz, 1H), 3.81 (s, 1H), 3.05-2.89 (m, 1H), 2.64 (s, 6H), 2.51 (s, 3H), 2.25-2.07 (m, 2H), 1.99 (d, J = 9.8 Hz, 2H), 1.52 (dd, J = 22.7, 12.1 Hz, 2H), 1.43-1.29 (m, 2H). | Ex. 56 |
| 158 | (400 MHz, DMSO-d6) δ 9.04 (s, 1H), 8.60 (d, J = 4.3 Hz, 1H), 8.09 (s, 1H), 7.93 (t, J = 7.6 Hz, 1H), 7.86 (d, J = 7.8 Hz, 1H), 7.78 (d, J = 12.7 Hz, 1H), 7.70 (d, J = 8.5 Hz, 1H), 7.59-7.45 (m, 2H), 7.39 (t, J = 8.7 Hz, 1H), 3.81-3.75 (m, 1H), 2.74-2.65 (m, 2H), 2.51 (s, 3H), 2.47 (s, 6H), 2.17-2.04 (m, 2H), 1.97-1.90 (m, 2H), 1.49-1.28 (m, 4H). | Ex. 57 |
| 159 | (400 MHz, DMSO-d6) δ 9.05 (s, 1H), 8.11 (d, J = 8.1 Hz, 1H), 7.93 (d, J = 7.2 Hz, 1H), 7.84-7.76 (m, 2H), 7.71 (s, H), 7.69-7.62 (m, 1H), 7.61-7.54 (m, 1H), 7.08-6.91 (m, 1H), 3.88-3.73 (m, 1H), 3.22-3.12 (m, 1H), 2.43 (s, 3H), 2.33 (s, 6H), 2.20-2.08 (m, 2H), 1.94-1.86 (m, 2H), 1.44-1.31 (m, 4H). [one methyl signal hidden under DMSO peak]. | Ex. 58 |

Example 59. IRE1α TR-FRET Competition Binding Assay

To determine the affinity of compound binding to the kinase domain of IRE1α, a time-resolved fluorescence resonance energy transfer (TR-FRET) competition assay was used.

A His-tagged IRE1α kinase dead construct containing the kinase and RNase domains (KR, AA G547-L977, D688N) was expressed in Sf9 insect cells. The purified protein (final concentration 0.25 nM) was pre-incubated with anti-His Europium labeled antibody (Life Technologies PV5596, final concentration 2 nM) for one hour at 4° C. in TR-FRET Assay Buffer (50 mM HEPES, pH 7.5, 10 mM MgCl2, 0.083 mM Brij 35, 1 mM DTT, and 0.1% bovine gamma globulin) prior to addition to test compounds. An Alexa fluor 647-labeled probe based on an ATP competitive inhibitor was added to a final concentration of 2 nM. Reactions were carried out for one hour at room temperature in a final volume of 20 μL in 384 well white ProxiPlates (Perkin Elmer 6008289). Binding of the probe to the IRE1α protein was detected in an Envision instrument (PerkinElmer) equipped with a TRF laser option and a LANCE/Delfia Dual/Bias D400/D630 mirror (Ex 347 nm, 1st Em 665 nm, 2nd Em 615 nm).

Example 60. IRE1α RNase Activity Assay

Inhibitors of the RNase activity of IRE1α were assessed by using a mini-XBP-1 stem-loop RNA as a substrate for the IRE1α RNase activity. A 5'-Carboxyfluorescein (FAM)- and 3'-Black Hole Quencher (BHQ)-labeled XBP1 single stem-loop mini-substrate (5'FAM-CAUGUCCGCAGCGCAUG-3'BHQ) (SEQ ID NO: 1) is cleaved by IRE1α. When the oligo is intact, the fluorescence signal is quenched by BHQ. Upon cleavage, the fluorescence is no longer quenched and can be quantified.

An IRE1α construct corresponding to the linker, kinase and RNase domains (LKR, AA Q470-L977) was expressed in Sf9 insect cells. All reagent preparation and procedures were done under RNase free conditions. Test compounds and purified enzyme were combined in RNase Assay Buffer (20 mM HEPES, pH 7.5, 50 mM KAc, 1 mM MgAc, 1 mM DTT, and 0.05% Triton X-100) in a 384 well white Proxi-Plate (Perkin Elmer 6008289). Upon addition of the RNA substrate (final assay volume 20 μL), the plates were placed into a Flexstation 3 instrument (Molecular Devices) for kinetic fluorescence reading at 2 minute intervals (Ex 485, Em 535). The velocity of the reaction, using the first 50 minutes, was used to calculate the RNase activity and inhibition of test compounds.

Example 61: IRE1α Ribonuclease Luciferase Reporter Assay

HEK293 cells expressing a pBABE.puro_HA-2xXBP1delta DBD firefly luciferase reporter, obtained from the University of California at San Francisco (UCSF, Walter lab), were cultured in DMEM high glucose media containing L-glutamine, 10% fetal bovine serum, 100 units/mL of penicillin and 100 μg/mL of streptomycin, plus 2 μg/ml puromycin to maintain selective pressure. Upon stimulation of IRE1 and activation of the endogenous RNase activity, a 26 nt intron is removed from XBP1 resulting in a frame shift allowing the transcription of the luciferase.

Cells were seeded without puromycin at 10,000/well in 384 well clear bottom white tissue culture plates (Corning 3707), 25 μL volume. The following morning, test compounds were added and incubated for one hour at 37° C. prior to stimulation of the cells with thapsigargin at 50 μM final concentration for an additional 5 hours. After equilibration to room temperature, 25 μL of One-Glo luciferase detection reagent (Promega cat #E6120) was added, plates sealed and shaken for 5 minutes to lyse cells, then luciferase quantified by luminescence detection using an Envision instrument (PerkinElmer).

Reference for the XBP1s reporter cell line: Mendez A S, Alfaro J, Morales-Soto M A, Dar A C, McCullagh E, Gotthardt K, Li H, Acosta-Alvear D, Sidrauski C, Korennykh A V, Bernales S, Shokat K M, Walter P. 2015. Endoplasmic reticulum stress-independent activation of unfolded protein response kinases by a small molecule ATP-mimic. eLife 2015; 4:e05434

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A compound having formula (II):

(II)

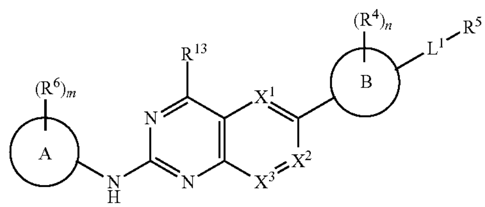

or a stereoisomer, tautomer or pharmaceutically acceptable salt thereof, wherein:

Ring B is $C_{3-7}$ cycloalkyl, 3 to 7 membered heterocycloalkyl, $C_{5-7}$ aryl, or 5 to 7 membered heteroaryl;

$L^1$ is —$NHSO_2$—, —$SO_2NH$—, —NH—, or pyrrolidin-2-one;

$X^1$ and $X^2$ are independently —N— or —$CR^2$—;

$X^3$ is —N— or —$CR^3$—, wherein one of $X^1$, $X^2$, and $X^3$ is —N—;

Ring A is $C_{3-6}$ cycloalkyl or 3 to 6 membered heterocycloalkyl;

m is 0, 1, 2, 3, 4, or 5;

each $R^2$ is independently hydrogen, halogen, —$OR^7$, $R^{10}$-substituted or unsubstituted $C_{1-6}$ alkyl, $R^{10}$-substituted or unsubstituted $C_{3-7}$ cycloalkyl, or $R^{10}$-substituted or unsubstituted 3 to 7 membered heterocycloalkyl, $R^3$ is hydrogen, halogen, —CN, —$OR^7$, —$NO_2$, —$C(O)R^7$, —$C(O)OR^7$, —$C(O)NR^{7A}R^{7B}$, —$OC(O)R^7$, —$OC(O)NR^{7A}R^{7B}$, —$SR^{7A}$, —$S(O)R^7$, —$S(O)_2R^7$, —$S(O)(=NR^{7A})R^{7B}$, —$S(O)_2NR^{7A}R^{7B}$, —$NR^{7A}R^{7B}$, —$NR^{7A}C(O)R^7$, —$NR^{7A}C(O)OR^7$, —$N(R^{7A})C(O)NR^{7A}R^{7B}$, —$NR^{7A}S(O)_2R^7$, —$NR^{7A}S(O)_2NR^{7A}R^{7B}$, —$P(O)(R^7)_2$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, $R^{10}$-substituted or unsubstituted 3 to 7 membered heterocycloalkyl, $R^{10}$-substituted or unsubstituted $C_{5-7}$ aryl, or $R^{10}$-substituted or unsubstituted 5 to 7 membered heteroaryl;

each $R^4$ is hydrogen, halogen, —$OR^7$, —CN, —$S(O)_2R^7$, $R^{10}$-substituted or unsubstituted $C_{1-6}$ alkyl, $R^{10}$-substituted or unsubstituted $C_{1-6}$ haloalkyl, or $R^{10}$-substituted or unsubstituted $C_{3-7}$ cycloalkyl;

n is 0, 1, 2, 3, or 4;

$R^5$ is $R^{10}$-substituted or unsubstituted $C_{1-6}$ alkyl, $R^{10}$-substituted or unsubstituted $C_{1-6}$ haloalkyl, $R^{10}$-substituted or unsubstituted 3 to 7 membered heterocycloalkyl, $R^{10}$-substituted or unsubstituted benzyl, $R^{10}$-substituted or unsubstituted pyrrolidinyl, $R^{10}$-substituted or unsubstituted piperidinyl, or $R^{10}$-substituted or unsubstituted $C_{3-7}$ membered cycloalkyl;

or, wherein an atom on $R^5$, together with $L^1$ and an atom on ring B, form a 4 to 7 membered heterocycloalkyl or 5 to 7 membered heteroaryl;

each $R^6$ is independently hydrogen, halogen, —$OR^7$, —$NR^{6A}R^{6B}$, $R^{10}$-substituted or unsubstituted $C_{1-6}$ alkyl, or $R^{10}$-substituted or unsubstituted $C_{1-6}$ haloalkyl;

$R^{6A}$ and $R^{6B}$ are independently hydrogen or $R^{10}$-substituted or unsubstituted $C_{1-6}$ alkyl, or $R^{6A}$ and $R^{6B}$ are taken together with the nitrogen atom to which they are attached to form a $R^{10}$-substituted or unsubstituted 4 to 7 membered heterocycloalkyl, each $R^7$ is independently hydrogen, $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl, each $R^{7A}$ and $R^{7B}$ is independently hydrogen, $R^{8A}$-substituted or unsubstituted $C_{1-6}$ alkyl, $R^{8A}$-substituted or unsubstituted $C_{1-6}$ haloalkyl, $R^{8A}$-substituted or unsubstituted $C_{3-7}$ cycloalkyl, or $R^{8A}$-substituted or unsubstituted 3 to 7 membered heterocycloalkyl, each $R^{8A}$ is independently hydrogen, halogen, oxo, —CN, —$NO_2$, —C(O)H, —$C(O)CH_3$, —C(O)OH, —$C(O)OCH_3$, —$C(O)NH_2$, —OH, —$OCH_3$, —$OCF_3$, —OC(O)H, —OC(O) $CH_3$, —$OC(O)NH_2$, —SH, —S(O)H, —$S(O)_2H$, —S(O)(=NH)H, —$S(O)_2NH_2$, —$NH_2$, —$NH(CH_3)$, —$N(CH_3)_2$, —NHC(O)H, —NHC(O)

OH, $—N(H)C(O)NH_2$, $—NHS(O)_2H$, $—NHS(O)_2NH_2$, or $—P(O)(CH_3)_2$, $—CF_3$, $—CHF_2$, $—CH_2F$, $—C(CH_3)_2F$, $—C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^8$ is independently hydrogen, halogen, oxo, —CN, $—OR^{8B}$, $—NO_2$, $—C(O)R^{8B}$, $—C(O)OR^{8B}$, $—C(O)NR^{8C}R^{8D}$, $—OC(O)R^{8B}$, $—OC(O)NR^{8C}R^{8D}$, $—SR^{8C}$, $—S(O)R^{8B}$, $—S(O)_2R^{8B}$, $—S(O)(=NR^{8C})R^{8D}$, $—S(O)_2NR^{8C}R^{8D}$, $—NR^{8C}R^{8D}$, $—NR^{8C}C(O)R^{8B}$, $—NR^{8C}C(O)OR^{8B}$, $—N(R^{8C})C(O)NR^{8C}R^{8D}$, $—NR^{8C}S(O)_2R^{8B}$, $—NR^{8C}S(O)_2NR^{8C}R^{8D}$, $—P(O)(R^{8B})_2$, $R^9$-substituted or unsubstituted $C_{1-6}$ alkyl, $R^9$-substituted or unsubstituted $C_{1-6}$ haloalkyl, $R^9$-substituted or unsubstituted $C_{3-7}$ cycloalkyl, $R^9$-substituted or unsubstituted 3 to 6 membered heterocycloalkyl, $R^9$-substituted or unsubstituted $C_{5-7}$ aryl, or $R^9$-substituted or unsubstituted 5 to 7 membered heteroaryl;

each $R^{8B}$, $R^{8C}$, and $R^{8D}$ is independently hydrogen, $R^{9A}$-substituted or unsubstituted $C_{1-6}$ alkyl, $R^{9A}$-substituted or unsubstituted $C_{1-6}$ haloalkyl, $R^{9A}$-substituted or unsubstituted $C_{3-7}$ cycloalkyl, or $R^{9A}$-substituted or unsubstituted 3 to 7 membered heterocycloalkyl, each $R^{9A}$ is independently hydrogen, halogen, oxo, —CN, $—NO_2$, —C(O)H, $—C(O)CH_3$, —C(O)OH, $—C(O)OCH_3$, $—C(O)NH_2$, —OH, $—OCH_3$, $—OCF_3$, —OC(O)H, —OC(O) $CH_3$, $—OC(O)NH_2$, —SH, —S(O)H, $—S(O)_2H$, —S(O)(=NH)H, $—S(O)_2NH_2$, $—NH_2$, $—NH(CH_3)$, $—N(CH_3)_2$, —NHC(O)H, —NHC(O)OH, $—N(H)C(O)NH_2$, $—NHS(O)_2H$, $—NHS(O)_2NH_2$, or $—P(O)(CH_3)_2$, $—CF_3$, $—CHF_2$, $—CH_2F$, $—C(CH_3)_2F$, $—C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^9$ is independently hydrogen, halogen, oxo, —CN, $—OR^{9B}$, $—NO_2$, $—C(O)R^{9B}$, $C(O)OR^{9B}$, $—C(O)NR^{9C}R^{9D}$, $—OC(O)R^{9B}$, $—OC(O)NR^{9C}R^{9D}$, $—SR^{9C}$, $—S(O)R^{9B}$, $—S(O)_2R^{9B}$, $—S(O)(=NR^{9C})R^{9D}$, $—S(O)_2NR^{9C}R^{9D}$, $—NR^{9C}R^{9D}$, $—NR^{9C}C(O)R^{9B}$, $—NR^{9C}C(O)OR^{9B}$, $—N(R^{9C})C(O)NR^{9C}R^{9D}$, $—NR^{9C}S(O)_2R^{9B}$, $—NR^{9C}S(O)_2NR^{9C}R^{9D}$, $—P(O)(R^{9B})_2$, $R^{12}$-substituted or unsubstituted $C_{1-6}$ alkyl, $R^{12}$-substituted or unsubstituted $C_{1-6}$ haloalkyl, $R^{12}$-substituted or unsubstituted $C_{3-7}$ cycloalkyl, $R^{12}$-substituted or unsubstituted 3 to 6 membered heterocycloalkyl, $R^{12}$-substituted or unsubstituted $C_{5-7}$ aryl, or $R^{12}$-substituted or unsubstituted 5 to 7 membered heteroaryl;

each $R^{9B}$, $R^{9C}$, and $R^{9D}$ is independently hydrogen, $R^{10A}$-substituted or unsubstituted $C_{1-6}$ alkyl, $R^{10A}$-substituted or unsubstituted $C_{1-6}$ haloalkyl, $R^{10A}$-substituted or unsubstituted $C_{3-7}$ cycloalkyl, or $R^{10A}$-substituted or unsubstituted 3 to 7 membered heterocycloalkyl, each $R^{10A}$ is independently hydrogen, halogen, oxo, —CN, $—NO_2$, —C(O)H, $—C(O)CH_3$, —C(O)OH, $—C(O)OCH_3$, $—C(O)NH_2$, —OH, $—OCH_3$, $—OCF_3$, —OC(O)H, —OC(O) $CH_3$, $—OC(O)NH_2$, —SH, —S(O)H, $—S(O)_2H$, —S(O)(=NH)H, $—S(O)_2NH_2$, $—NH_2$, $—NH(CH_3)$, $—N(CH_3)_2$, —NHC(O)H, —NHC(O)OH, $—N(H)C(O)NH_2$, $—NHS(O)_2H$, $—NHS(O)_2NH_2$, or $—P(O)(CH_3)_2$, $—CF_3$, $—CHF_2$, $—CH_2F$, $—C(CH_3)_2F$, $—C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^{10}$ is independently hydrogen, halogen, oxo, —CN, $—OR^{11A}$, $—NO_2$, $—C(O)R^{11A}$, $—C(O)OR^{11A}$, $—C(O)NR^{11B}R^{11C}$, $—OC(O)R^{11A}$, $—OC(O)NR^{11B}R^{11C}$, $—SR^{11B}$, $—S(O)R^{11A}$, $—S(O)_2R^{11A}$, $—S(O)(=NR^{11B})R^{11C}$, $—S(O)_2NR^{11B}R^{11C}$, $—NR^{11B}R^{11C}$, $—NR^{11B}C(O)R^{11A}$, $—NR^{11B}C(O)OR^{11A}$, $—N(R^{11B})C(O)NR^{11B}R^{11C}$, $—NR^{11B}S(O)_2R^{11A}$, $—NR^{11B}S(O)_2NR^{11B}R^{11C}$, $—P(O)(R^{11A})_2$, $R^{11}$-substituted or unsubstituted $C_{1-6}$ alkoxy, $R^{11}$-substituted or unsubstituted $C_{1-6}$ alkyl, $R^{11}$-substituted or unsubstituted $C_{1-6}$ haloalkyl, $R^{11}$-substituted or unsubstituted $C_3$-7 cycloalkyl, $R^{11}$-substituted or unsubstituted 3 to 6 membered heterocycloalkyl, $R^{11}$-substituted or unsubstituted $C_{5-7}$ aryl, or $R^{11}$-substituted or unsubstituted 5 to 7 membered heteroaryl;

each $R^{11A}$, $R^{11B}$, and $R^{11C}$ is independently hydrogen, $R^{12A}$-substituted or unsubstituted $C_{1-6}$ alkyl, $R^{12A}$-substituted or unsubstituted $C_{1-6}$ haloalkyl, $R^{12A}$-substituted or unsubstituted $C_{3-7}$ cycloalkyl, or $R^{12A}$-substituted or unsubstituted 3 to 7 membered heterocycloalkyl, each $R^{12A}$ is independently hydrogen, halogen, oxo, —CN, $—NO_2$, —C(O)H, $—C(O)CH_3$, —C(O)OH, $—C(O)OCH_3$, $—C(O)NH_2$, —OH, $—OCH_3$, $—OCF_3$, —OC(O)H, —OC(O) $CH_3$, $—OC(O)NH_2$, —SH, —S(O)H, $—S(O)_2H$, —S(O)(=NH)H, $—S(O)_2NH_2$, $—NH_2$, $—NH(CH_3)$, $—N(CH_3)_2$, —NHC(O)H, —NHC(O)OH, $—N(H)C(O)NH_2$, $—NHS(O)_2H$, $—NHS(O)_2NH_2$, or $—P(O)(CH_3)_2$, $—CF_3$, $—CHF_2$, $—CH_2F$, $—C(CH_3)_2F$, $—C(CH_3)F_2$, unsubstituted $C_{1-6}$ alkoxy, unsubstituted $C_{1-6}$ alkyl, unsubstituted $C_{1-6}$ haloalkyl, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl;

each $R^{11}$ is independently hydrogen, halogen, oxo, —CN, $—OR^{12B}$, $—NO_2$, $—C(O)R^{12B}$, $C(O)OR^{12B}$, $—C(O)NR^{12C}R^{12D}$, $—OC(O)R^{12B}$, $—OC(O)NR^{12C}R^{12D}$, $—SR^{12C}$, $—S(O)R^{12B}$, $—S(O)_2R^{12B}$, $—S(O)(=NR^{12C})R^{12D}$, $—S(O)_2NR^{12C}R^{12D}$, $—NR^{12C}R^{12D}$, $—NR^{12C}C(O)R^{12B}$, $—NR^{12C}C(O)OR^{12B}$, $—N(R^{12C})C(O)NR^{12C}R^{12D}$, $—NR^{12C}S(O)_2R^{12B}$, $—NR^{12C}S(O)_2NR^{12C}R^{12D}$, $—P(O)(R^{12B})_2$, $R^{12}$-substituted or unsubstituted $C_{1-6}$ alkyl, $R^{12}$-substituted or unsubstituted $C_{1-6}$ haloalkyl, $R^{12}$-substituted or unsubstituted $C_{3-7}$ cycloalkyl, $R^{12}$-substituted or unsubstituted 3 to 6 membered heterocycloalkyl, $R^{12}$-substituted or unsubstituted $C_{5-7}$ aryl, or $R^{12}$-substituted or unsubstituted 5 to 7 membered heteroaryl;

each $R^{12B}$, $R^{12C}$, and $R^{12D}$ is independently hydrogen, unsubstituted $C_{1-6}$ alkyl, unsubstituted $C_{1-6}$ haloalkyl, unsubstituted $C_{3-7}$ cycloalkyl, or unsubstituted 3 to 7 membered heterocycloalkyl, each $R^{12}$ is independently hydrogen, halogen, oxo, —CN, $—NO_2$, —C(O)H, $—C(O)CH_3$, —C(O)OH, $—C(O)OCH_3$, $—C(O)NH_2$, —OH, $—OCH_3$, $—OCF_3$, —OC(O)H, $—OC(O)CH_3$, $—OC(O)NH_2$, —SH, —S(O)H, $—S(O)_2H$, —S(O)(=NH)H, $—S(O)_2NH_2$, $—NH_2$, $—NH(CH_3)$, $—N(CH_3)_2$, —NHC(O)H, —NHC(O)OH, $—N(H)C(O)NH_2$, $—NHS(O)_2H$, $—NHS(O)_2NH_2$, or $—P(O)(CH_3)_2$, $—CF_3$, $—CHF_2$, $—CH_2F$, $—C(CH_3)_2F$, $—C(CH_3)F_2$, unsubstituted $C_{1-6}$ alkoxy, unsubstituted $C_{1-6}$ alkyl, unsubstituted $C_{1-6}$ alkoxy, unsubstituted $C_{1-6}$ haloalkyl, unsubstituted $C_{1-6}$ haloalkoxy, unsubstituted $C_{3-7}$ cycloalkyl, unsubstituted 3 to 6 membered heterocycloalkyl, unsubstituted $C_{5-7}$ aryl, or unsubstituted 5 to 7 membered heteroaryl; and $R^{13}$ is hydrogen, halogen, or $R^{10}$-substituted or unsubstituted $C_{1-6}$ alkyl.

2. The compound, stereoisomer, tautomer, or pharmaceutically acceptable salt thereof of claim 1, wherein the compound has the formula:

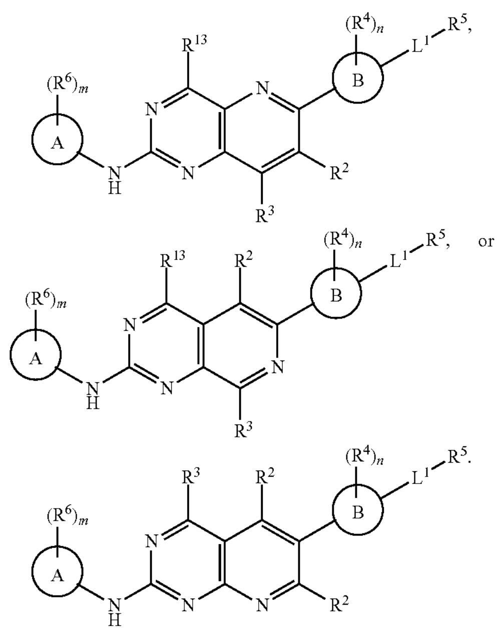

or

3. The compound, stereoisomer, tautomer, or pharmaceutically acceptable salt thereof of claim 1, wherein $R^2$ is independently hydrogen, $—OR^7$, or $R^{10}$-substituted or unsubstituted $C_{1-6}$ alkyl.

4. The compound, stereoisomer, tautomer, or pharmaceutically acceptable salt thereof of claim 3, wherein $R^7$ is hydrogen, $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl.

5. The compound, stereoisomer, tautomer, or pharmaceutically acceptable salt thereof of claim 1, wherein $R^3$ is hydrogen, halogen, $—OR^7$, $—NR^{7A}R^{7B}$, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-7}$ cycloalkyl, or $R^{10}$-substituted or unsubstituted 3 to 7 membered heterocycloalkyl.

6. The compound, stereoisomer, tautomer, or pharmaceutically acceptable salt thereof of claim 5, wherein $R^7$ is $R^8$-substituted or unsubstituted $C_{1-6}$ alkyl, $R^8$-substituted or unsubstituted $C_{1-6}$ haloalkyl, $R^8$-substituted or unsubstituted $C_{3-7}$ cycloalkyl, or $R^8$-substituted or unsubstituted 3 to 7 membered heterocycloalkyl, and wherein $R^{7A}$ and $R^{7B}$ are independently hydrogen or $R^{8A}$-substituted or unsubstituted $C_{1-6}$ alkyl.

7. The compound, stereoisomer, tautomer, or pharmaceutically acceptable salt thereof of claim 5, wherein $R^3$ is methyl, ethyl, propyl isopropyl, $—C(CH_3)_2F$, $—C(CH_3)F_2$, $—CH_2F$, $—CHF_2$, or $—CF_3$.

8. The compound, stereoisomer, tautomer, or pharmaceutically acceptable salt thereof of claim 1, wherein $R^4$ is halogen and n is 1, 2, or 3.

9. The compound, stereoisomer, tautomer, or pharmaceutically acceptable salt thereof of claim 1, wherein $R^4$ is F and n is 1, 2, or 3; or, wherein $R^4$ is $—OR^7$ and n is 1.

10. The compound, stereoisomer, tautomer, or pharmaceutically acceptable salt thereof of claim 1, wherein $L^1$ is $—NHSO_2—$ or pyrrolidin-2-one.

11. The compound, stereoisomer, tautomer, or pharmaceutically acceptable salt thereof of claim 1, wherein $R^5$ is $R^{10}$-substituted or unsubstituted benzyl, $R^{10}$-substituted or unsubstituted pyrrolidinyl, $R^{10}$-substituted or unsubstituted piperidinyl, $R^{10}$-substituted or unsubstituted $C_{1-6}$ haloalkyl, or $R^{10}$-substituted or unsubstituted $C_{1-6}$ alkyl.

12. The compound, stereoisomer, tautomer, or pharmaceutically acceptable salt thereof of claim 11, wherein $R^{10}$ is hydrogen, halogen —OH, —CN, $—CF_3$, $—CHF_2$, $—CH_2F$, $—C(CH_3)_2F$, $—C(CH_3)F_2$, methyl, propyl, or ethyl.

13. The compound, stereoisomer, tautomer, or pharmaceutically acceptable salt thereof of claim 1, wherein $R^6$ is independently hydrogen, halogen, $R^{10}$-substituted or unsubstituted $C_{1-6}$ alkyl, $R^{10}$-substituted or unsubstituted $C_{1-6}$ haloalkyl, or $—NR^{6A}R^{6B}$.

14. The compound, stereoisomer, tautomer, or pharmaceutically acceptable salt thereof of claim 13, wherein at least one $R^6$ is $—NR^{6A}R^{6B}$, wherein $R^{6A}$ and $R^{6B}$ are each $R^{10}$-substituted or unsubstituted $C_{1-6}$ alkyl.

15. The compound, stereoisomer, tautomer, or A pharmaceutically acceptable salt thereof of claim 1, wherein Ring A is $R^6$-substituted cyclohexyl or $R^6$-substituted piperidinyl.

16. The compound, stereoisomer, tautomer, or pharmaceutically acceptable salt thereof of claim 1, wherein Ring A has the formula:

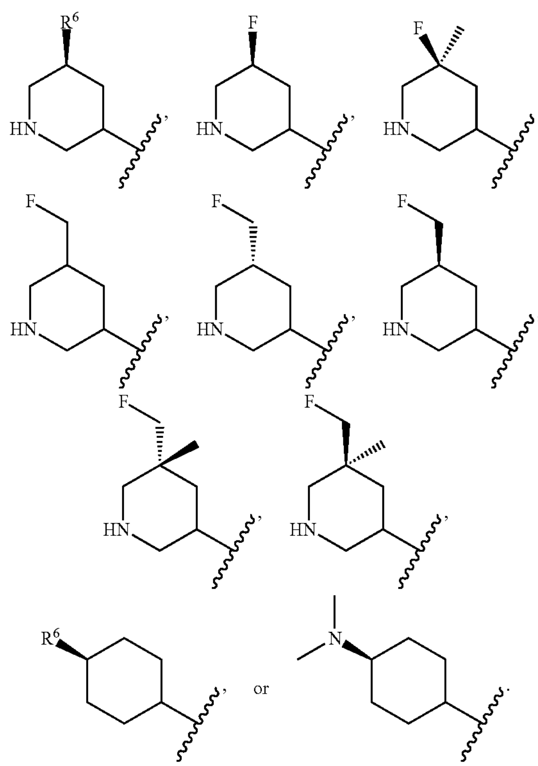

or

17. The compound, stereoisomer, tautomer, or pharmaceutically acceptable salt thereof of claim 1, wherein Ring B is $R^4$-substituted or unsubstituted $C_{5-7}$ aryl.

18. The compound, stereoisomer, tautomer, or pharmaceutically acceptable salt thereof of claim 17, wherein Ring B has the formula:

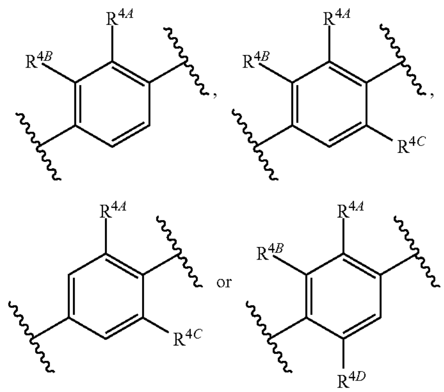

wherein $R^{4A}$, $R^{4B}$, $R^{4C}$, and $R^{4D}$ are each independently hydrogen, halogen, —CN, $R^{10}$-substituted or unsubstituted $C_{1-6}$ alkyl, $R^{10}$-substituted or unsubstituted $C_{1-6}$ haloalkyl, $R^{10}$-substituted or unsubstituted $C_{3-6}$ cycloalkyl, $R^{10}$-substituted or unsubstituted $C_{1-6}$ alkoxy, or $R^{10}$-substituted or unsubstituted $C_{1-6}$ haloalkoxy.

19. The compound, stereoisomer, tautomer, or pharmaceutically acceptable salt thereof of claim 1, wherein the compound has the formula:

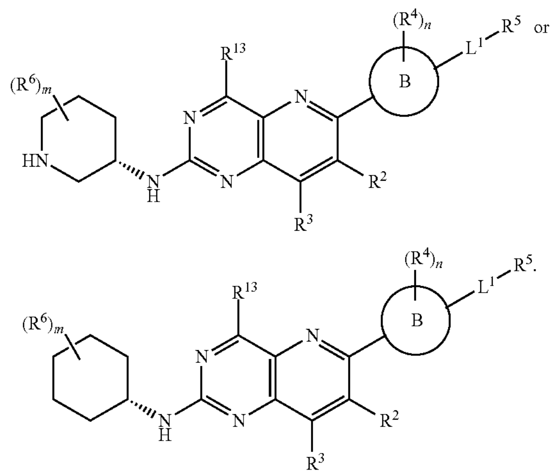

20. The compound, stereoisomer, tautomer, or pharmaceutically acceptable salt thereof of claim 1, wherein the compound has the formula:

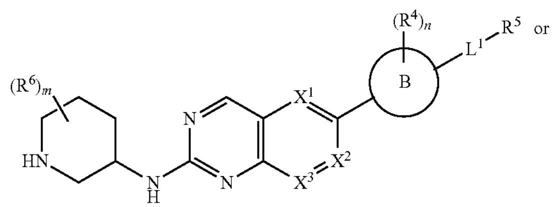

-continued

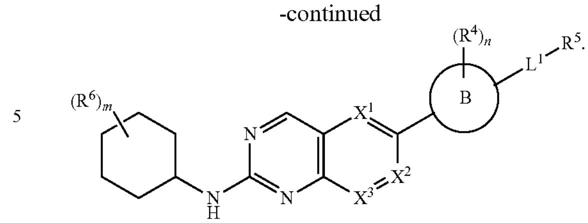

21. The compound, stereoisomer, tautomer, or pharmaceutically acceptable salt thereof of claim 1, wherein the compound has the formula:

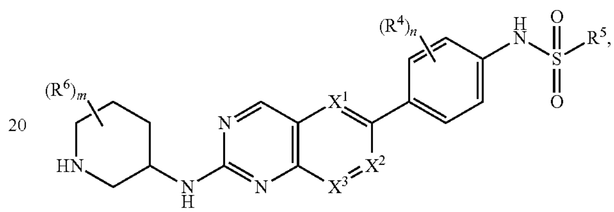

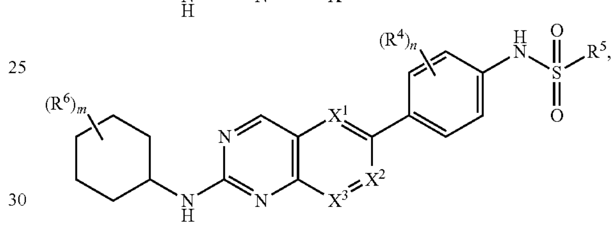

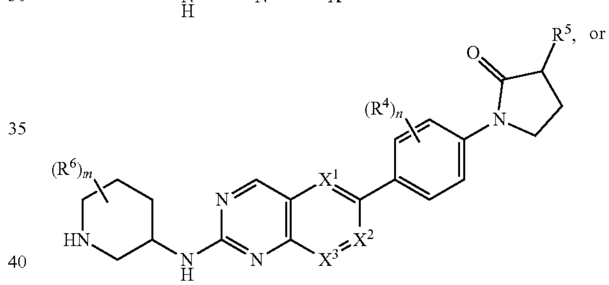

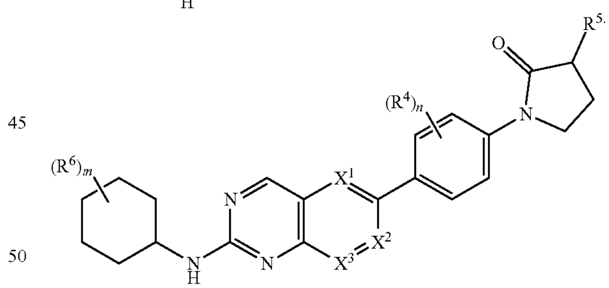

22. The compound, stereoisomer, tautomer, or pharmaceutically acceptable salt thereof of claim 21, wherein the compound has the formula:

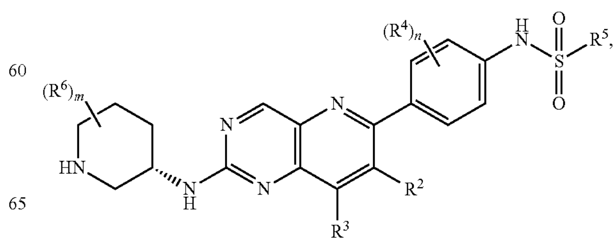

-continued
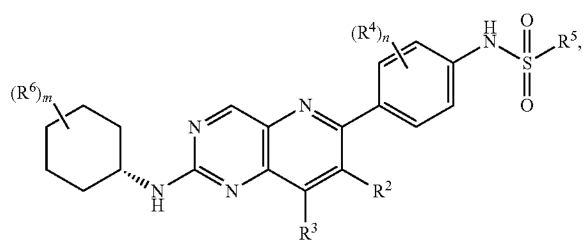
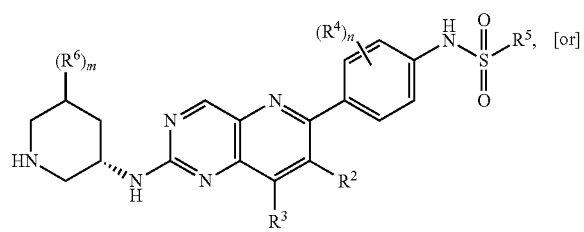
[or]
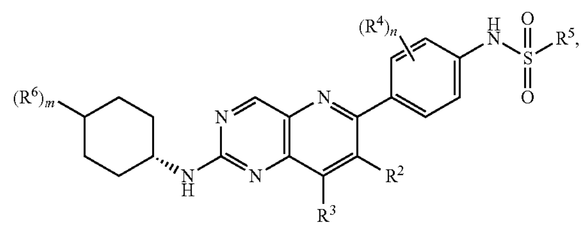
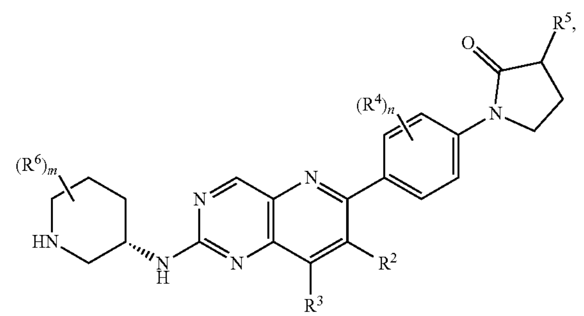
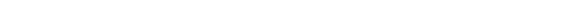
-continued
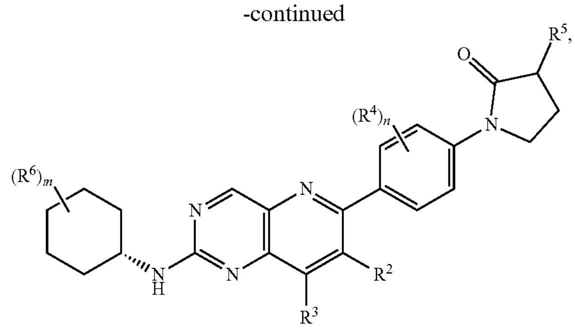
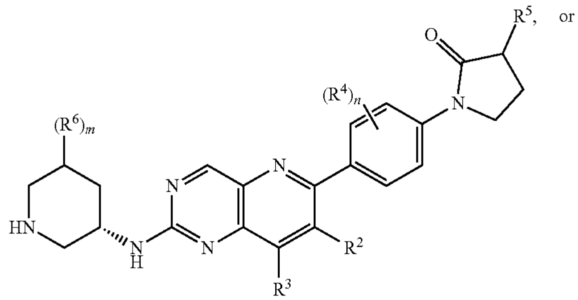
or
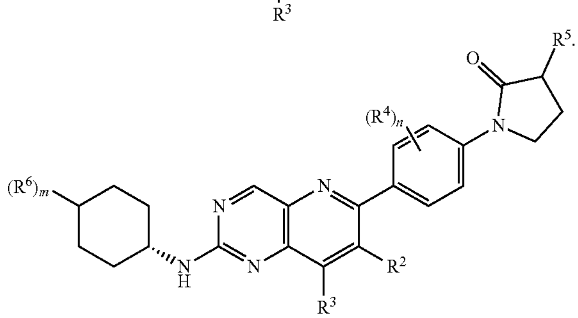
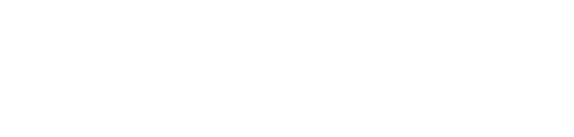
23. The compound of claim 1 or pharmaceutically acceptable salt thereof selected from the group consisting of:
| Cmpd No. | Structure |
| --- | --- |
| 100 | 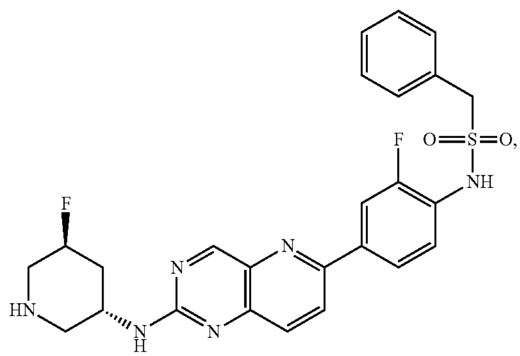 [SMILES: O=S(=O)(Cc1ccccc1)Nc1ccc(-c2ccc3nc(N[C@@H]4CNC[C@@H](F)C4)ncc3n2)cc1F] |

-continued
| Cmpd No. | Structure |
|---|---|
| 101 | 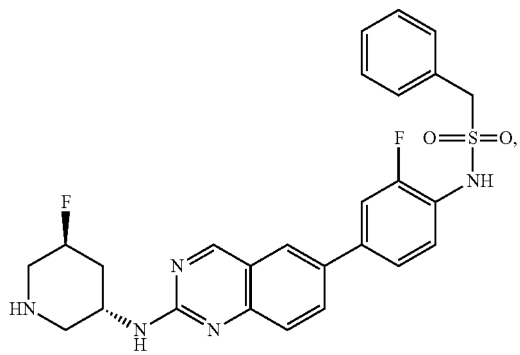 [SMILES: O=S(=O)(Cc1ccccc1)Nc1ccc(-c2ccc3nc(N[C@@H]4CNC[C@@H](F)C4)ncc3c2)cc1F] |
| 102 | 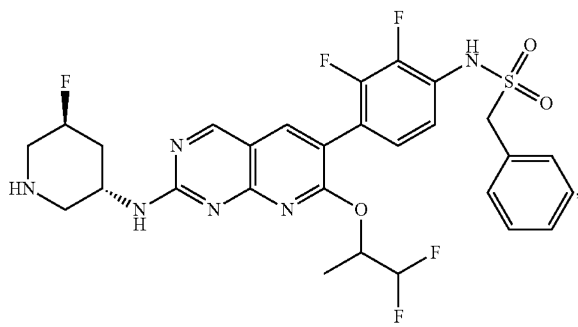 [SMILES: CC(Oc1nc2nc(N[C@@H]3CNC[C@@H](F)C3)ncc2cc1-c1ccc(NS(=O)(=O)Cc2ccccc2)c(F)c1F)C(F)F] |
| 103 | 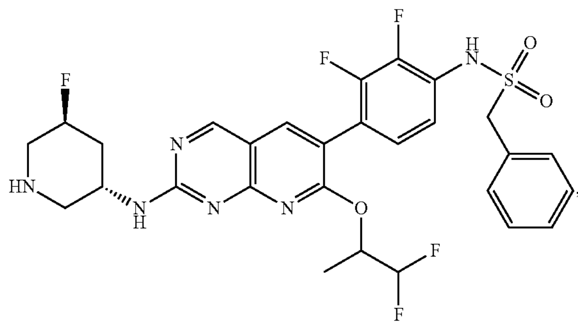 [SMILES: CC(Oc1nc2nc(N[C@@H]3CNC[C@@H](F)C3)ncc2cc1-c1ccc(NS(=O)(=O)Cc2ccccc2)c(F)c1F)C(F)F] |
| 104 | 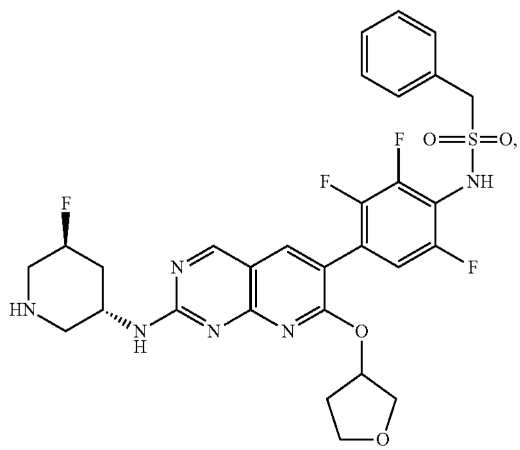 [SMILES: O=S(=O)(Cc1ccccc1)Nc1c(F)cc(-c2cc3cnc(N[C@@H]4CNC[C@@H](F)C4)nc3nc2OC2CCOC2)c(F)c1F] |

-continued
| Cmpd No. | Structure |
|---|---|
| 105 | 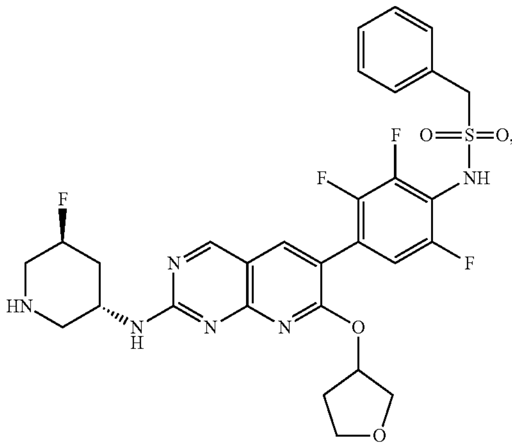 [SMILES: O=S(=O)(Cc1ccccc1)Nc1c(F)cc(-c2cc3cnc(N[C@@H]4CNC[C@@H](F)C4)nc3nc2OC2CCOC2)c(F)c1F] |
| 106 | 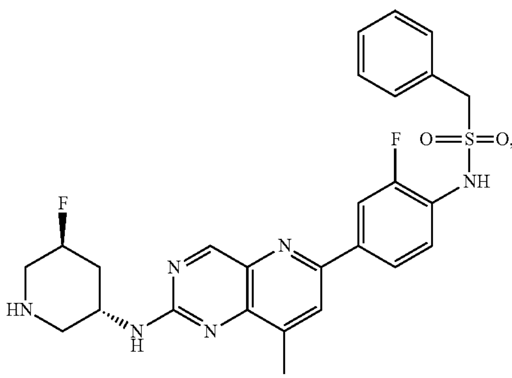 [SMILES: Cc1cc(-c2ccc(NS(=O)(=O)Cc3ccccc3)c(F)c2)nc2cnc(N[C@@H]3CNC[C@@H](F)C3)nc12] |
| 107 | 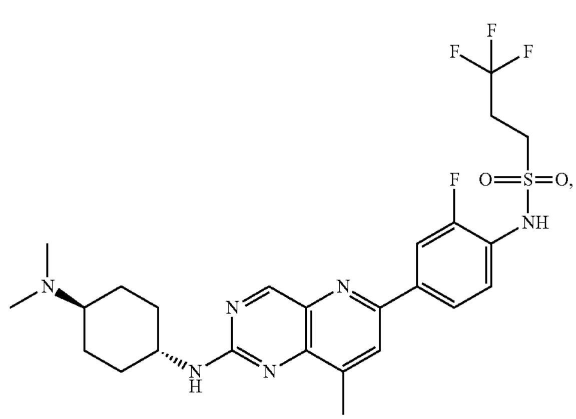 [SMILES: Cc1cc(-c2ccc(NS(=O)(=O)CCC(F)(F)F)c(F)c2)nc2cnc(N[C@H]3CC[C@H](N(C)C)CC3)nc12] |
| 108 | 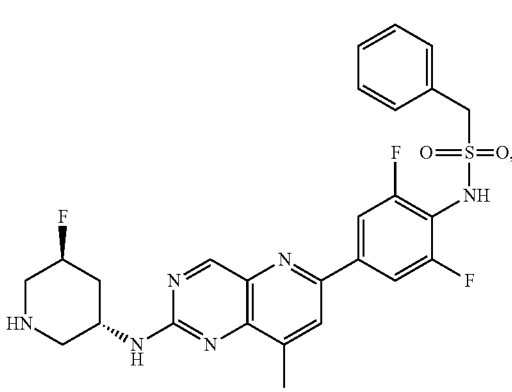 [SMILES: Cc1cc(-c2cc(F)c(NS(=O)(=O)Cc3ccccc3)c(F)c2)nc2cnc(N[C@@H]3CNC[C@@H](F)C3)nc12] |

-continued
| Cmpd No. | Structure |
|---|---|
| 109 | 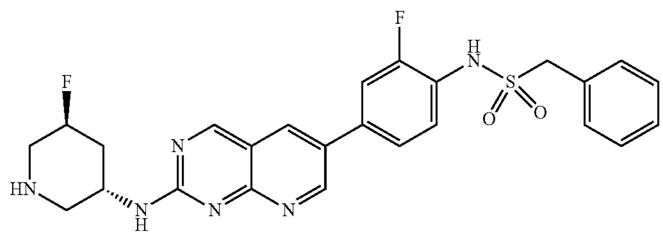 [SMILES: O=S(=O)(Cc1ccccc1)Nc1ccc(-c2cnc3nc(N[C@@H]4CNC[C@@H](F)C4)ncc3c2)cc1F] , |
| 110 | 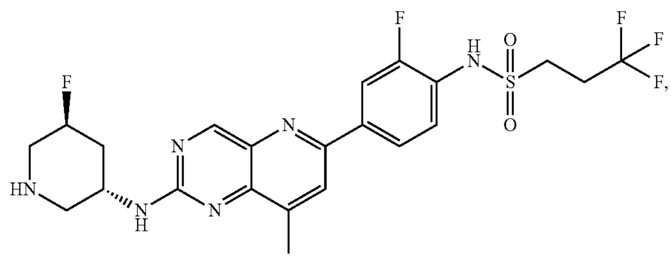 [SMILES: Cc1cc(-c2ccc(NS(=O)(=O)CCC(F)(F)F)c(F)c2)nc2cnc(N[C@@H]3CNC[C@@H](F)C3)nc12] , |
| 111 | 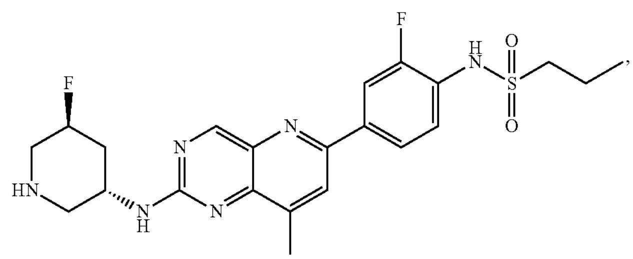 [SMILES: CCCS(=O)(=O)Nc1ccc(-c2cc(C)c3nc(N[C@@H]4CNC[C@@H](F)C4)ncc3n2)cc1F] , |
| 112 | 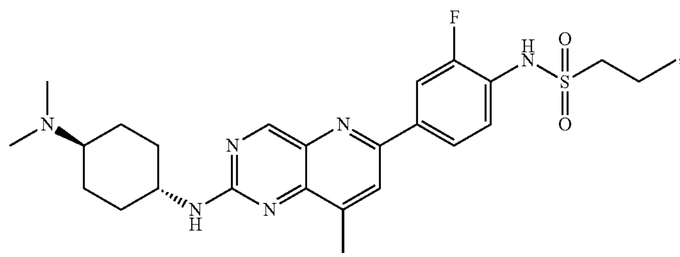 [SMILES: CCCS(=O)(=O)Nc1ccc(-c2cc(C)c3nc(N[C@H]4CC[C@H](N(C)C)CC4)ncc3n2)cc1F] , |
| 113 | 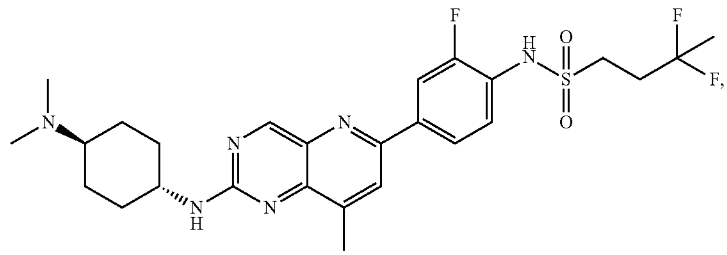 [SMILES: Cc1cc(-c2ccc(NS(=O)(=O)CCC(C)(F)F)c(F)c2)nc2cnc(N[C@H]3CC[C@H](N(C)C)CC3)nc12] , |

-continued
| Cmpd No. | Structure |
| --- | --- |
| 114 | 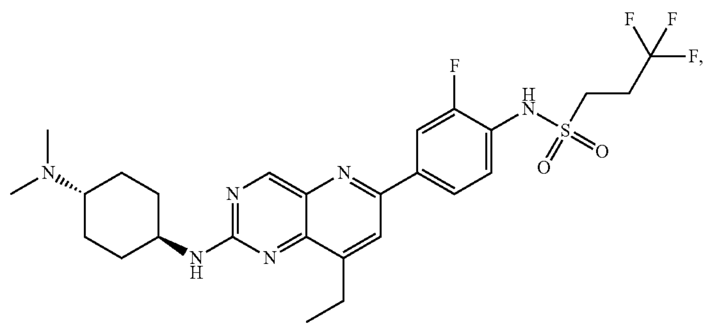 [SMILES: CCc1cc(-c2ccc(NS(=O)(=O)CCC(F)(F)F)c(F)c2)nc2cnc(N[C@H]3CC[C@H](N(C)C)CC3)nc12] |
| 115 | 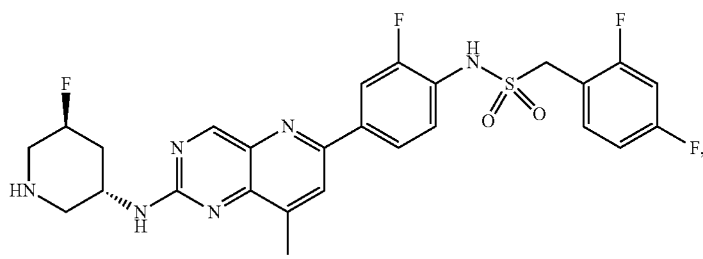 [SMILES: Cc1cc(-c2ccc(NS(=O)(=O)Cc3ccc(F)cc3F)c(F)c2)nc2cnc(N[C@@H]3CNC[C@@H](F)C3)nc12] |
| 116 | 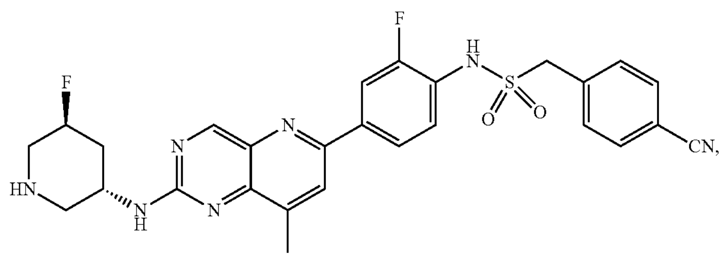 [SMILES: Cc1cc(-c2ccc(NS(=O)(=O)Cc3ccc(C#N)cc3)c(F)c2)nc2cnc(N[C@@H]3CNC[C@@H](F)C3)nc12] |
| 117 | 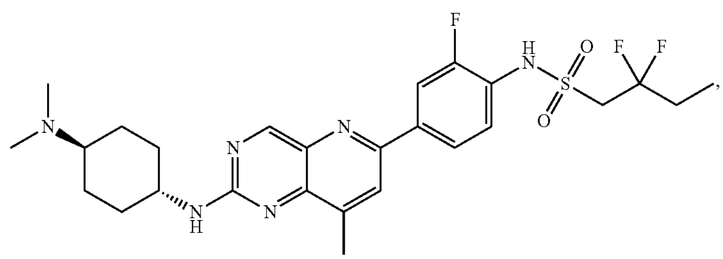 [SMILES: CCC(F)(F)CS(=O)(=O)Nc1ccc(-c2cc(C)c3nc(N[C@H]4CC[C@H](N(C)C)CC4)ncc3n2)cc1F] |
| 118 | 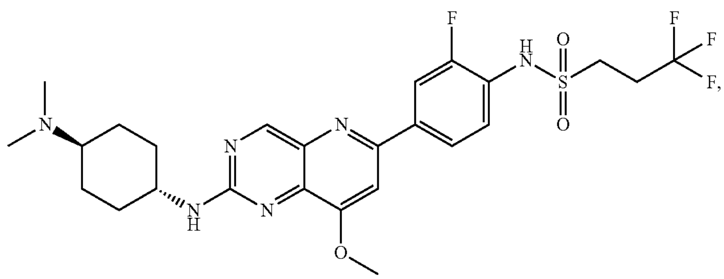 [SMILES: COc1cc(-c2ccc(NS(=O)(=O)CCC(F)(F)F)c(F)c2)nc2cnc(N[C@H]3CC[C@H](N(C)C)CC3)nc12] |

-continued
| Cmpd No. | Structure |
| --- | --- |
| 119 | 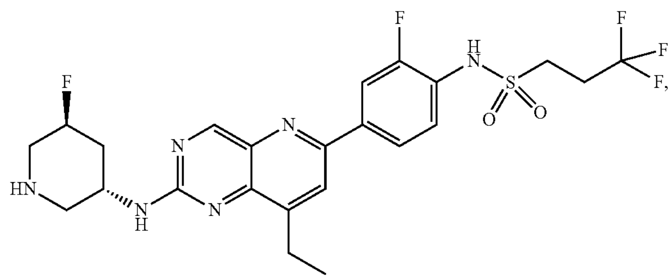 [SMILES: CCc1cc(-c2ccc(NS(=O)(=O)CCC(F)(F)F)c(F)c2)nc2cnc(N[C@@H]3CNC[C@@H](F)C3)nc12] |
| 120 | 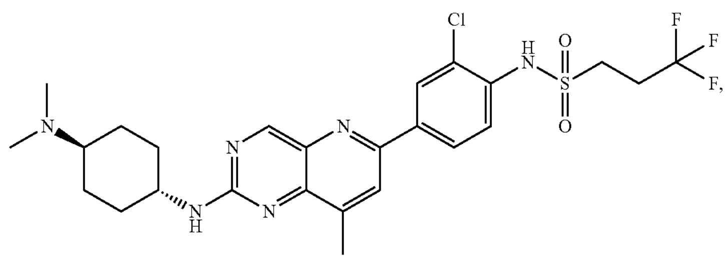 |
| 121 | 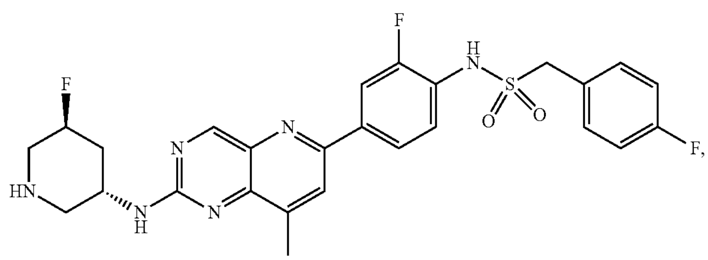 [SMILES: Cc1cc(-c2ccc(NS(=O)(=O)Cc3ccc(F)cc3)c(F)c2)nc2cnc(N[C@@H]3CNC[C@@H](F)C3)nc12] |
| 122 | 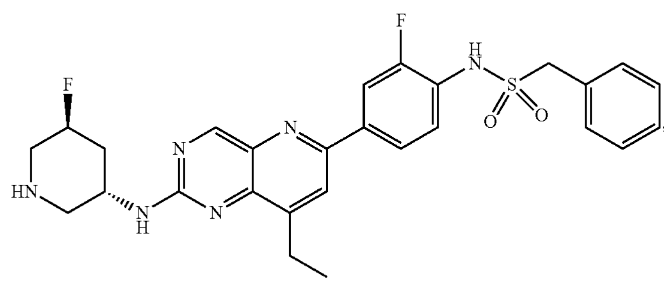 [SMILES: CCc1cc(-c2ccc(NS(=O)(=O)Cc3ccccc3)c(F)c2)nc2cnc(N[C@@H]3CNC[C@@H](F)C3)nc12] |
| 124 | 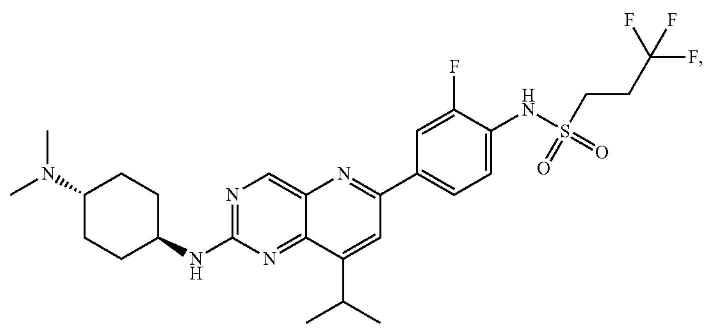 [SMILES: CC(C)c1cc(-c2ccc(NS(=O)(=O)CCC(F)(F)F)c(F)c2)nc2cnc(N[C@H]3CC[C@H](N(C)C)CC3)nc12] |

-continued
| Cmpd No. | Structure |
|---|---|
| 125 | 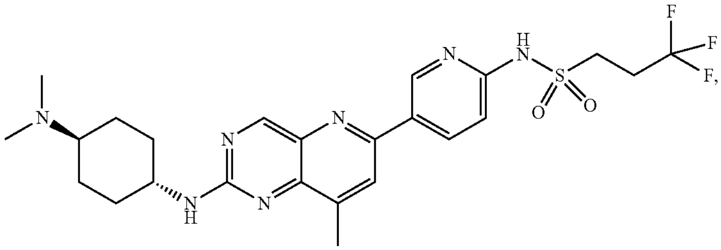 [SMILES: Cc1cc(-c2ccc(NS(=O)(=O)CCC(F)(F)F)nc2)nc2cnc(N[C@H]3CC[C@H](N(C)C)CC3)nc12] |
| 126 | 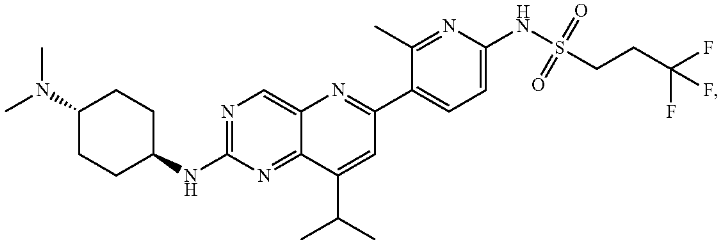 [SMILES: Cc1nc(NS(=O)(=O)CCC(F)(F)F)ccc1-c1cc(C(C)C)c2nc(N[C@H]3CC[C@H](N(C)C)CC3)ncc2n1] |
| 127 | 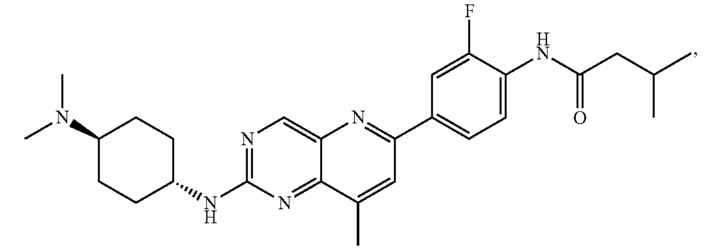 [SMILES: Cc1cc(-c2ccc(NC(=O)CC(C)C)c(F)c2)nc2cnc(N[C@H]3CC[C@H](N(C)C)CC3)nc12] |
| 129 | 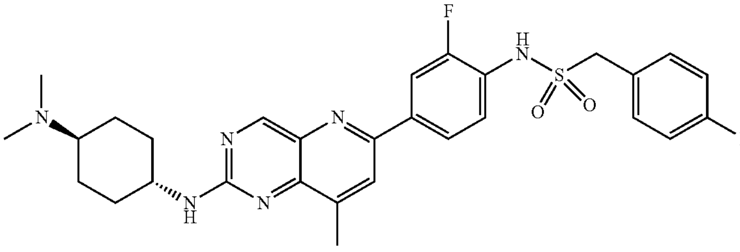 |
| 130 | 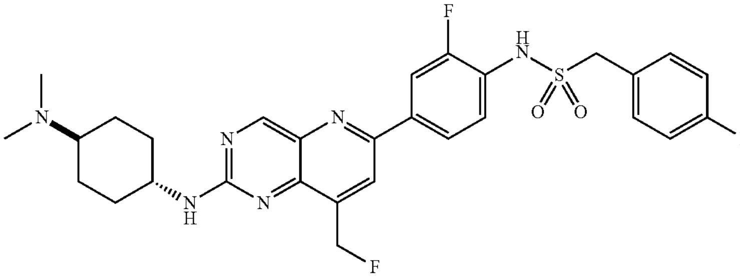 |
| 131 | 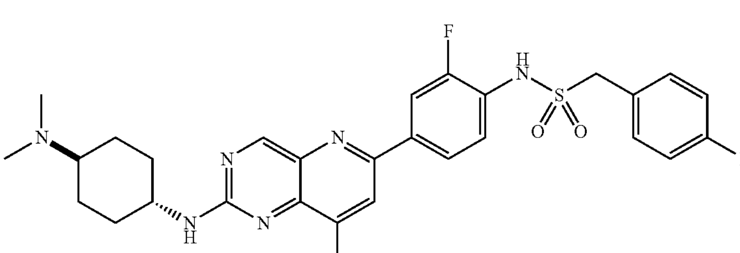 |

-continued
| Cmpd No. | Structure |
|---|---|
| 132 | 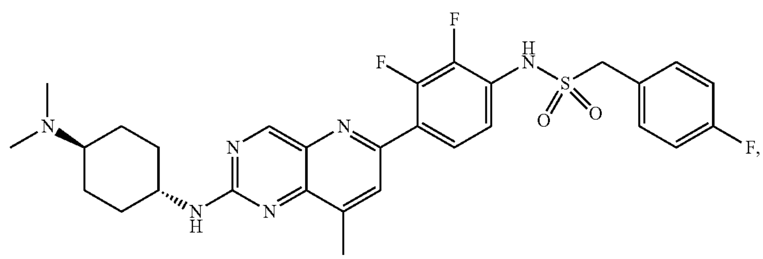 [SMILES: Cc1cc(-c2ccc(NS(=O)(=O)Cc3ccc(F)cc3)c(F)c2F)nc2cnc(N[C@H]3CC[C@H](N(C)C)CC3)nc12] |
| 137 | 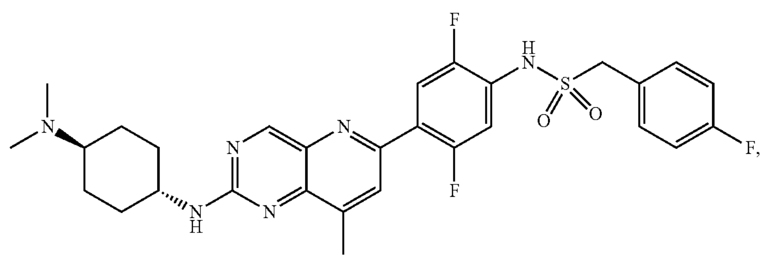 [SMILES: Cc1cc(-c2cc(F)c(NS(=O)(=O)Cc3ccc(F)cc3)cc2F)nc2cnc(N[C@H]3CC[C@H](N(C)C)CC3)nc12] |
| 138 | 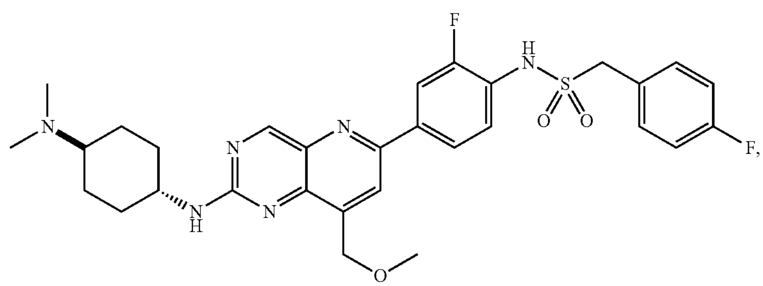 [SMILES: COCc1cc(-c2ccc(NS(=O)(=O)Cc3ccc(F)cc3)c(F)c2)nc2cnc(N[C@H]3CC[C@H](N(C)C)CC3)nc12] |
| 139 | 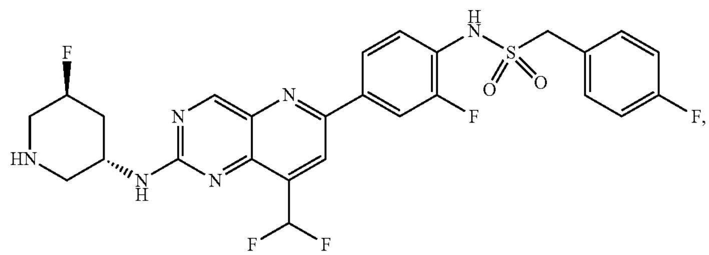 [SMILES: O=S(=O)(Cc1ccc(F)cc1)Nc1ccc(-c2cc(C(F)F)c3nc(N[C@@H]4CNC[C@@H](F)C4)ncc3n2)cc1F] |
| 140 | 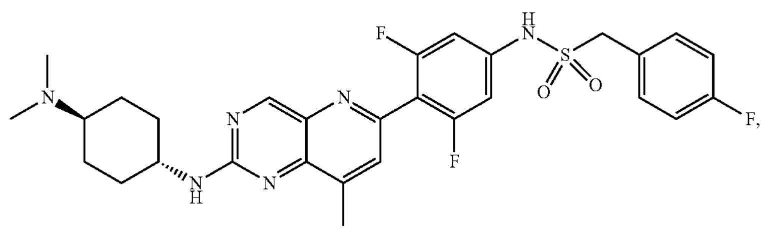 [SMILES: Cc1cc(-c2c(F)cc(NS(=O)(=O)Cc3ccc(F)cc3)cc2F)nc2cnc(N[C@H]3CC[C@H](N(C)C)CC3)nc12] |
| 142 | 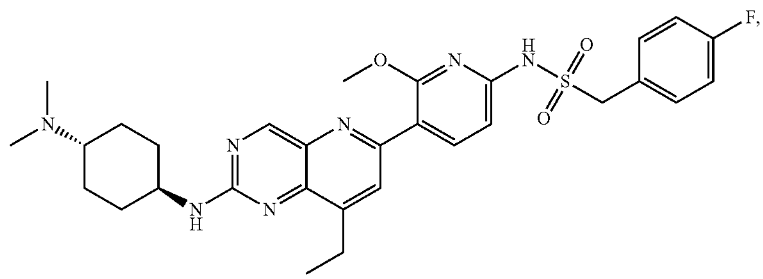 [SMILES: CCc1cc(-c2ccc(NS(=O)(=O)Cc3ccc(F)cc3)nc2OC)nc2cnc(N[C@H]3CC[C@H](N(C)C)CC3)nc12] |

-continued
| Cmpd No. | Structure |
| --- | --- |
| 144 | 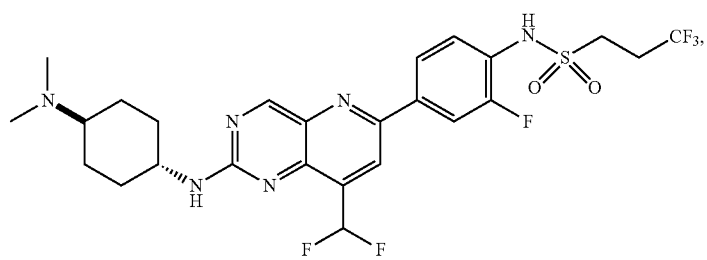 [SMILES: CN(C)[C@H]1CC[C@H](Nc2ncc3nc(-c4ccc(NS(=O)(=O)CCC(F)(F)F)c(F)c4)cc(C(F)F)c3n2)CC1] |
| 151 | 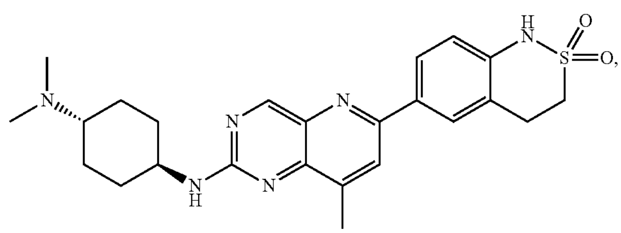 [SMILES: Cc1cc(-c2ccc3c(c2)CCS(=O)(=O)N3)nc2cnc(N[C@H]3CC[C@H](N(C)C)CC3)nc12] |
| 152 | 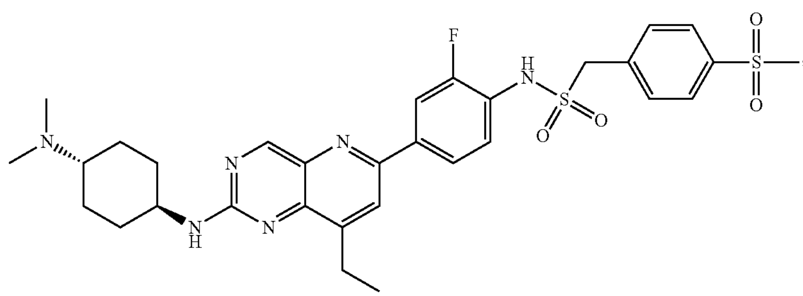 |
| 153 | 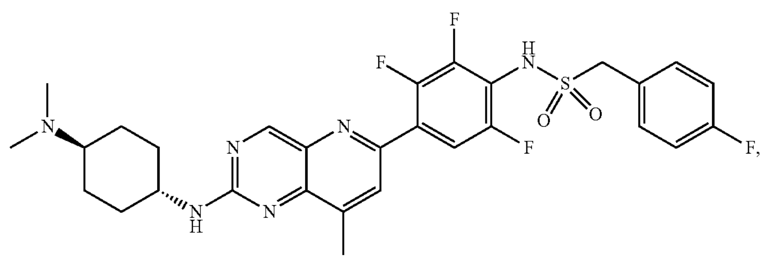 [SMILES: Cc1cc(-c2cc(F)c(NS(=O)(=O)Cc3ccc(F)cc3)c(F)c2F)nc2cnc(N[C@H]3CC[C@H](N(C)C)CC3)nc12] |
| 154 | 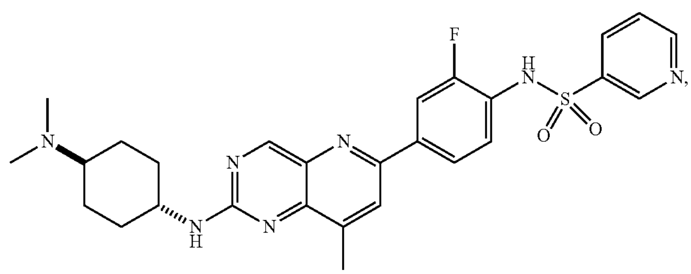 [SMILES: Cc1cc(-c2ccc(NS(=O)(=O)c3cccnc3)c(F)c2)nc2cnc(N[C@H]3CC[C@H](N(C)C)CC3)nc12] |

-continued
| Cmpd No. | Structure |
|---|---|
| 156 | 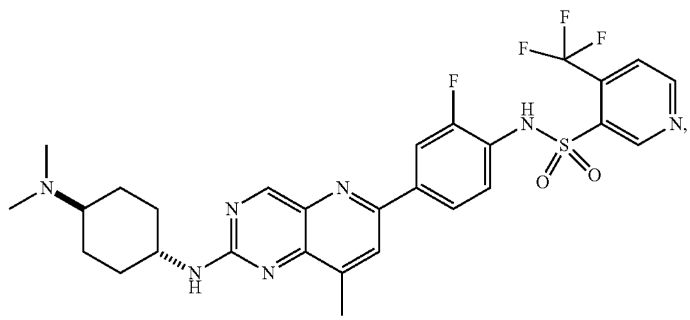 [SMILES: Cc1cc(-c2ccc(NS(=O)(=O)c3cnccc3C(F)(F)F)c(F)c2)nc2cnc(N[C@H]3CC[C@H](N(C)C)CC3)nc12] |
| 157 | 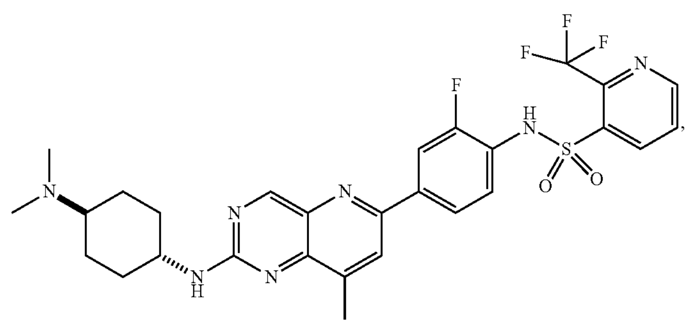 [SMILES: Cc1cc(-c2ccc(NS(=O)(=O)c3cccnc3C(F)(F)F)c(F)c2)nc2cnc(N[C@H]3CC[C@H](N(C)C)CC3)nc12] |
| 158 | 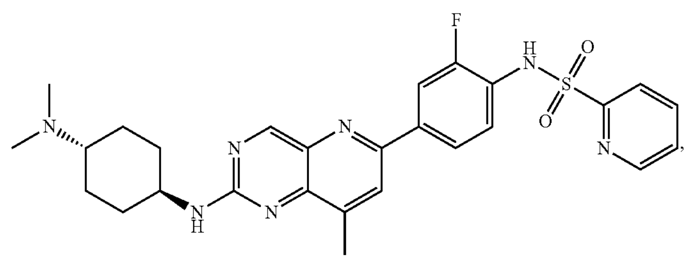 [SMILES: Cc1cc(-c2ccc(NS(=O)(=O)c3ccccn3)c(F)c2)nc2cnc(N[C@H]3CC[C@H](N(C)C)CC3)nc12] |
| 201 | 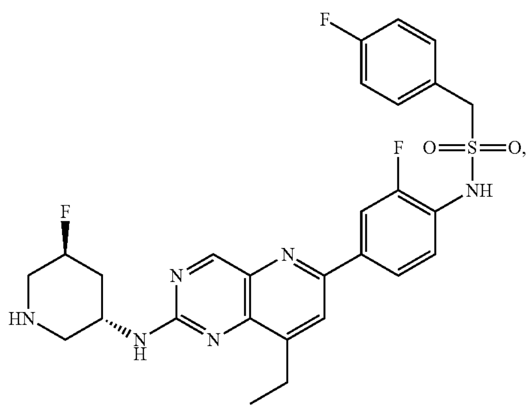 [SMILES: CCc1cc(-c2ccc(NS(=O)(=O)Cc3ccc(F)cc3)c(F)c2)nc2cnc(N[C@@H]3CNC[C@@H](F)C3)nc12] |

-continued
| Cmpd No. | Structure |
| --- | --- |
| 202 | 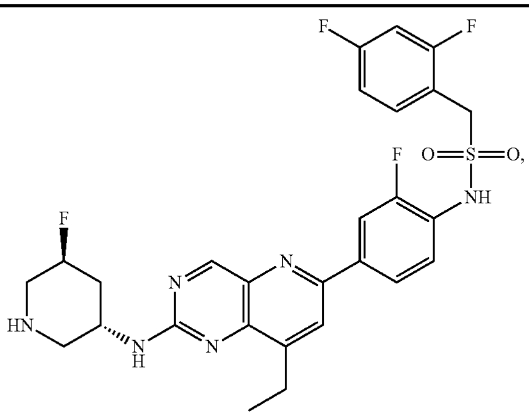 |
| 203 | 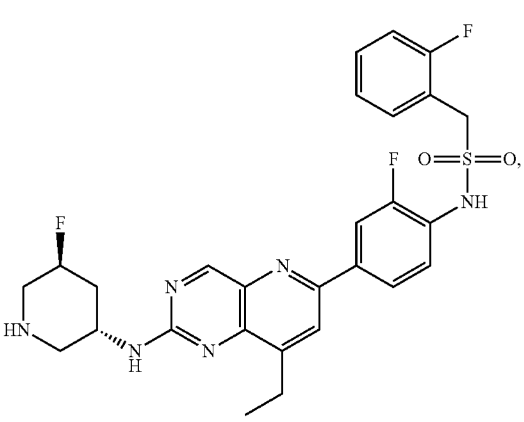 [SMILES: CCc1cc(-c2ccc(NS(=O)(=O)Cc3ccccc3F)c(F)c2)nc2cnc(N[C@@H]3CNC[C@@H](F)C3)nc12] |
| 204 | 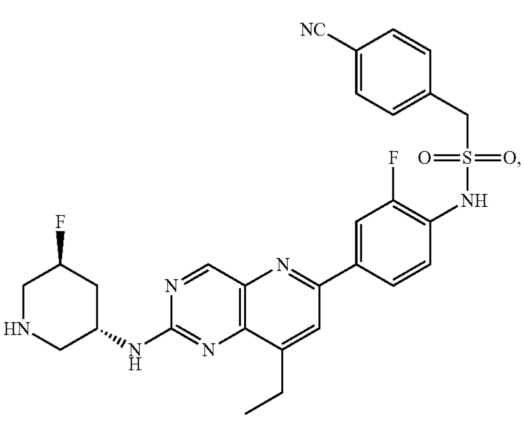 [SMILES: CCc1cc(-c2ccc(NS(=O)(=O)Cc3ccc(C#N)cc3)c(F)c2)nc2cnc(N[C@@H]3CNC[C@@H](F)C3)nc12] |
| 205 | 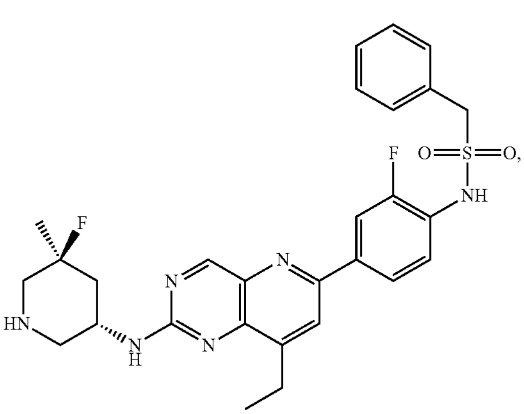 [SMILES: CCc1cc(-c2ccc(NS(=O)(=O)Cc3ccccc3)c(F)c2)nc2cnc(N[C@@H]3CNC[C@@](C)(F)C3)nc12] |

-continued
| Cmpd No. | Structure |
|---|---|
| 206 | 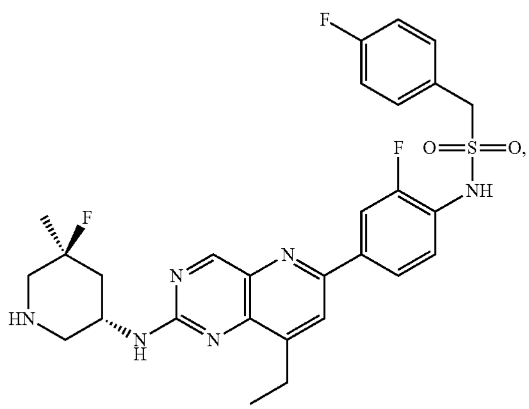 [SMILES: CCc1cc(-c2ccc(NS(=O)(=O)Cc3ccc(F)cc3)c(F)c2)nc2cnc(N[C@@H]3CNC[C@@](C)(F)C3)nc12] |
| 207 | 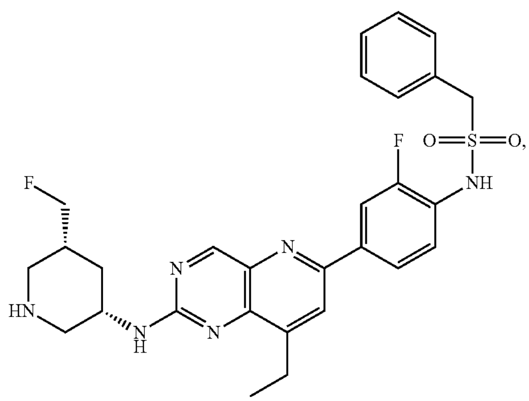 [SMILES: CCc1cc(-c2ccc(NS(=O)(=O)Cc3ccccc3)c(F)c2)nc2cnc(N[C@@H]3CNC[C@H](CF)C3)nc12] |
| 208 | 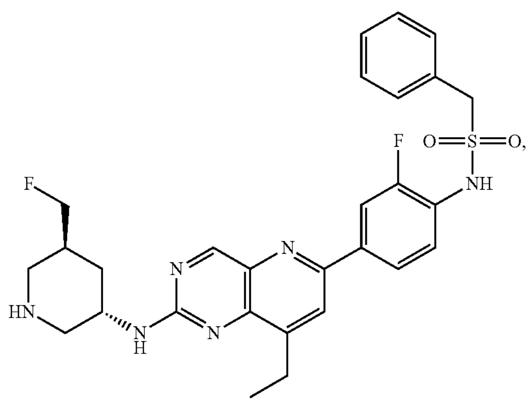 [SMILES: CCc1cc(-c2ccc(NS(=O)(=O)Cc3ccccc3)c(F)c2)nc2cnc(N[C@@H]3CNC[C@@H](CF)C3)nc12] |

-continued
| Cmpd No. | Structure |
|---|---|
| 209 | 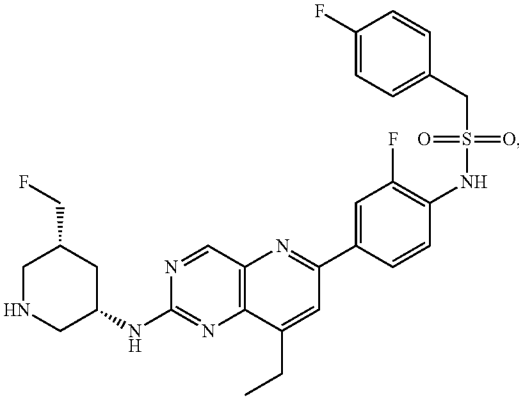 [SMILES: CCc1cc(-c2ccc(NS(=O)(=O)Cc3ccc(F)cc3)c(F)c2)nc2cnc(N[C@@H]3CNC[C@H](CF)C3)nc12] |
| 210 | 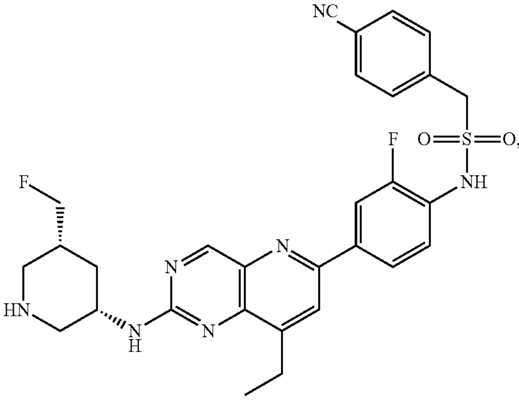 |
| 211 | 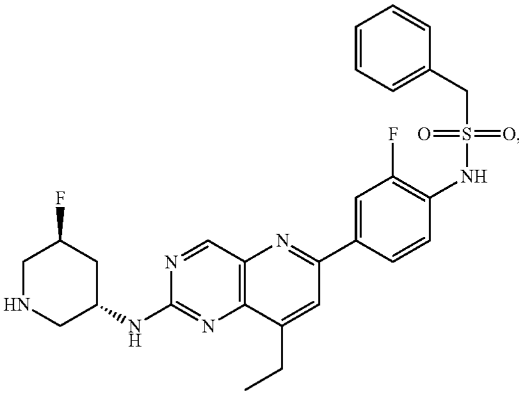 [SMILES: CCc1cc(-c2ccc(NS(=O)(=O)Cc3ccccc3)c(F)c2)nc2cnc(N[C@@H]3CNC[C@@H](F)C3)nc12] |
| 212 | 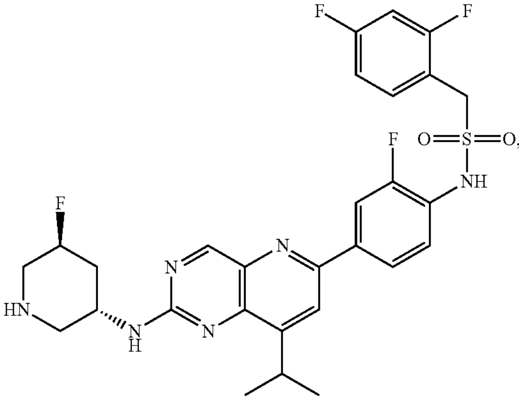 [SMILES: CC(C)c1cc(-c2ccc(NS(=O)(=O)Cc3ccc(F)cc3F)c(F)c2)nc2cnc(N[C@@H]3CNC[C@@H](F)C3)nc12] |

-continued
| Cmpd No. | Structure |
|---|---|
| 213 | 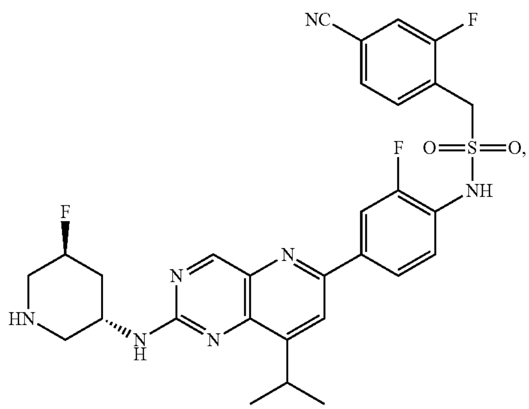 [SMILES: CC(C)c1cc(-c2ccc(NS(=O)(=O)Cc3ccc(C#N)cc3F)c(F)c2)nc2cnc(N[C@@H]3CNC[C@@H](F)C3)nc12] |
| 214 | 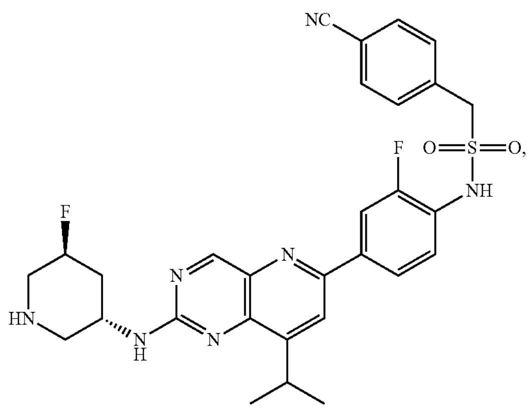 [SMILES: CC(C)c1cc(-c2ccc(NS(=O)(=O)Cc3ccc(C#N)cc3)c(F)c2)nc2cnc(N[C@@H]3CNC[C@@H](F)C3)nc12] |
| 215 | 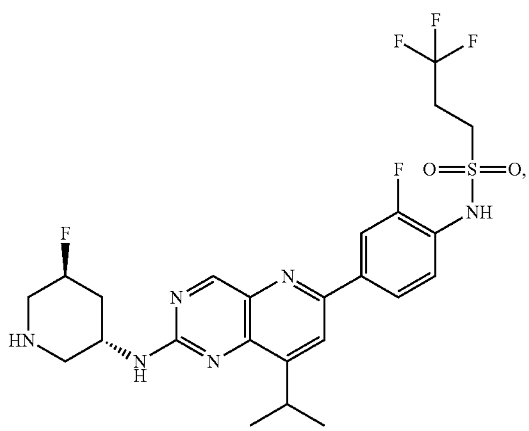 [SMILES: CC(C)c1cc(-c2ccc(NS(=O)(=O)CCC(F)(F)F)c(F)c2)nc2cnc(N[C@@H]3CNC[C@@H](F)C3)nc12] |

-continued
| Cmpd No. | Structure |
|---|---|
| 216 | 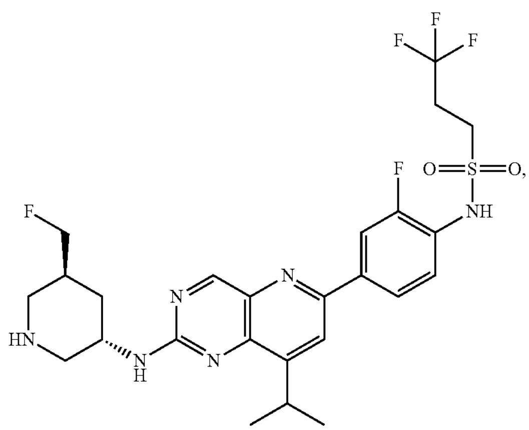 [SMILES: CC(C)c1cc(-c2ccc(NS(=O)(=O)CCC(F)(F)F)c(F)c2)nc2cnc(N[C@@H]3CNC[C@@H](CF)C3)nc12] |
| 217 | 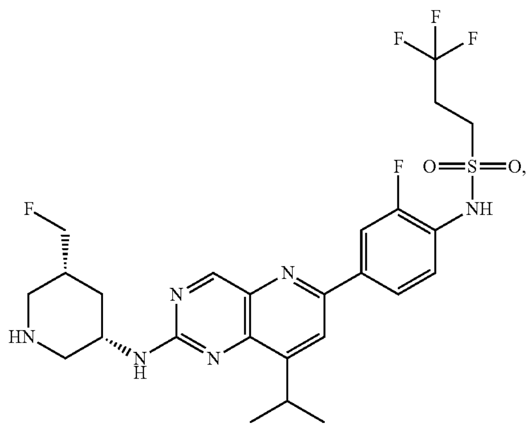 [SMILES: CC(C)c1cc(-c2ccc(NS(=O)(=O)CCC(F)(F)F)c(F)c2)nc2cnc(N[C@@H]3CNC[C@H](CF)C3)nc12] |
| 218 | 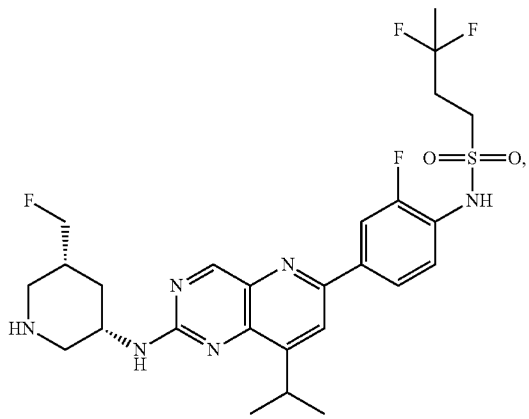 [SMILES: CC(C)c1cc(-c2ccc(NS(=O)(=O)CCC(C)(F)F)c(F)c2)nc2cnc(N[C@@H]3CNC[C@H](CF)C3)nc12] |

-continued
| Cmpd No. | Structure |
| --- | --- |
| 219 | 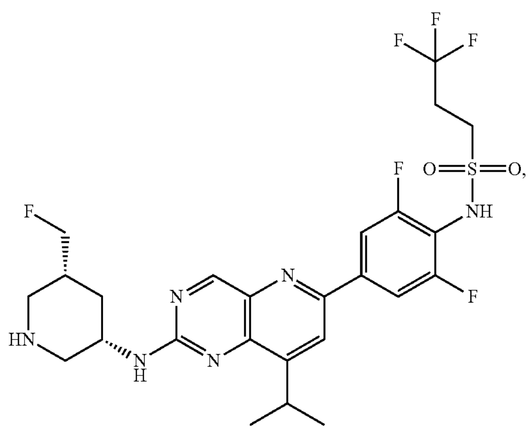 [SMILES: CC(C)c1cc(-c2cc(F)c(NS(=O)(=O)CCC(F)(F)F)c(F)c2)nc2cnc(N[C@@H]3CNC[C@H](CF)C3)nc12] |
| 220 | 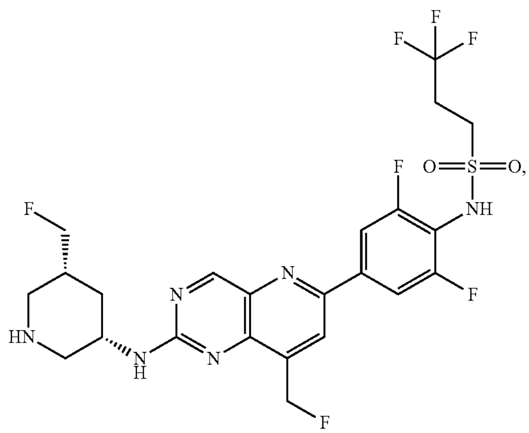 [SMILES: O=S(=O)(CCC(F)(F)F)Nc1c(F)cc(-c2cc(CF)c3nc(N[C@@H]4CNC[C@H](CF)C4)ncc3n2)cc1F] |
| 221 | 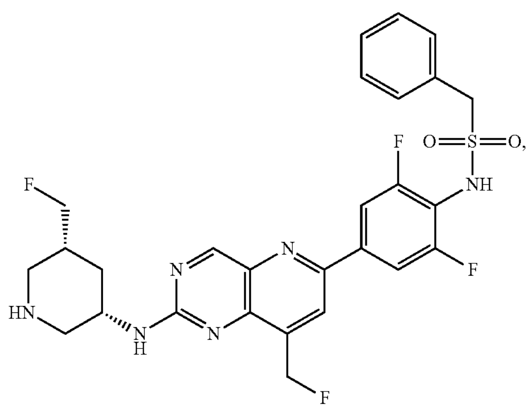 [SMILES: O=S(=O)(Cc1ccccc1)Nc1c(F)cc(-c2cc(CF)c3nc(N[C@@H]4CNC[C@H](CF)C4)ncc3n2)cc1F] |

-continued
| Cmpd No. | Structure |
|---|---|
| 222 | 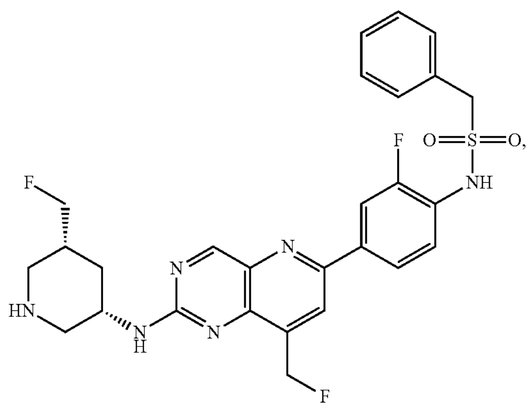 [SMILES: O=S(=O)(Cc1ccccc1)Nc1ccc(-c2cc(CF)c3nc(N[C@@H]4CNC[C@H](CF)C4)ncc3n2)cc1F] |
| 230 | 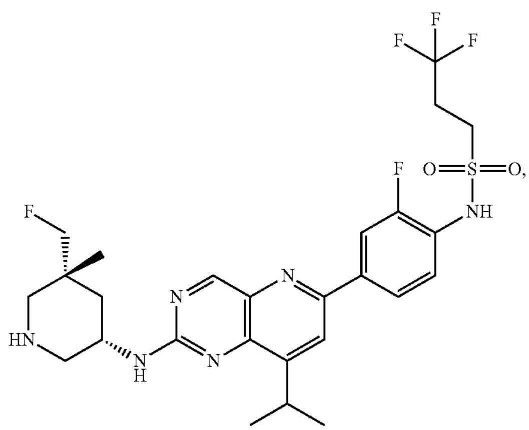 [SMILES: CC(C)c1cc(-c2ccc(NS(=O)(=O)CCC(F)(F)F)c(F)c2)nc2cnc(N[C@@H]3CNC[C@](C)(CF)C3)nc12] |
| 231 | 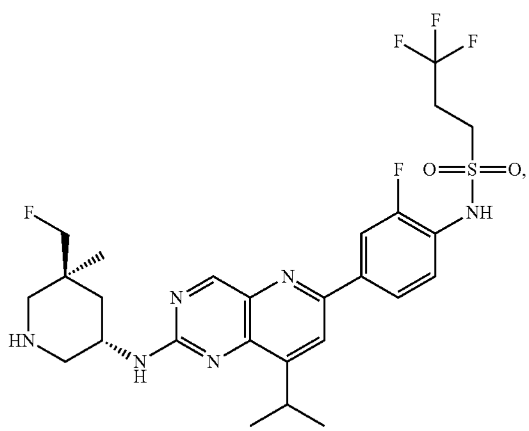 [SMILES: CC(C)c1cc(-c2ccc(NS(=O)(=O)CCC(F)(F)F)c(F)c2)nc2cnc(N[C@@H]3CNC[C@@](C)(CF)C3)nc12] |

-continued
| Cmpd No. | Structure |
|---|---|
| 232 | 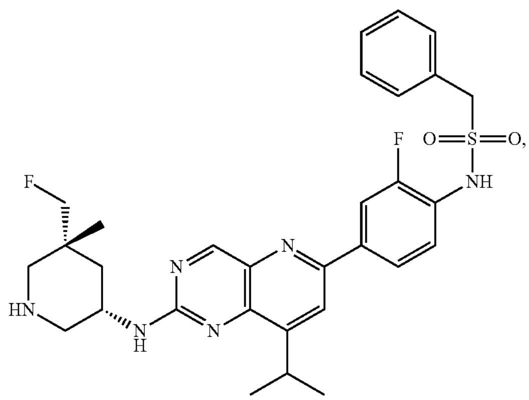 [SMILES: CC(C)c1cc(-c2ccc(NS(=O)(=O)Cc3ccccc3)c(F)c2)nc2cnc(N[C@@H]3CNC[C@](C)(CF)C3)nc12] |
| 233 | 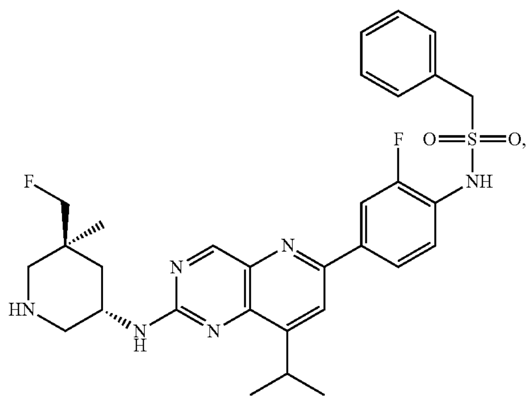 [SMILES: CC(C)c1cc(-c2ccc(NS(=O)(=O)Cc3ccccc3)c(F)c2)nc2cnc(N[C@@H]3CNC[C@@](C)(CF)C3)nc12] |
| 234 | 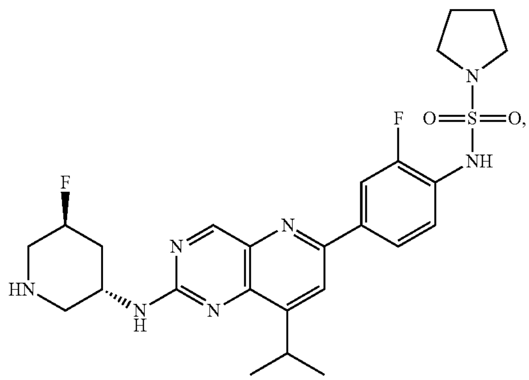 [SMILES: CC(C)c1cc(-c2ccc(NS(=O)(=O)N3CCCC3)c(F)c2)nc2cnc(N[C@@H]3CNC[C@@H](F)C3)nc12] |
| 235 | 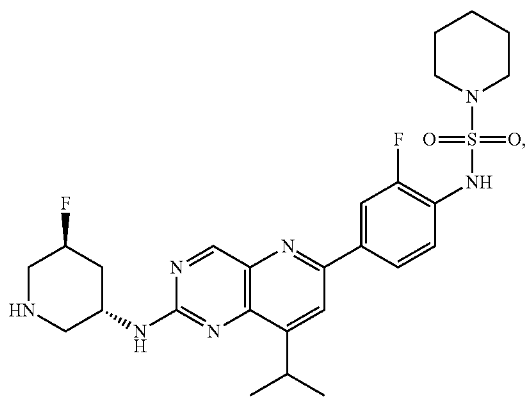 [SMILES: CC(C)c1cc(-c2ccc(NS(=O)(=O)N3CCCCC3)c(F)c2)nc2cnc(N[C@@H]3CNC[C@@H](F)C3)nc12] |

-continued
| Cmpd No. | Structure |
|---|---|
| 236 | 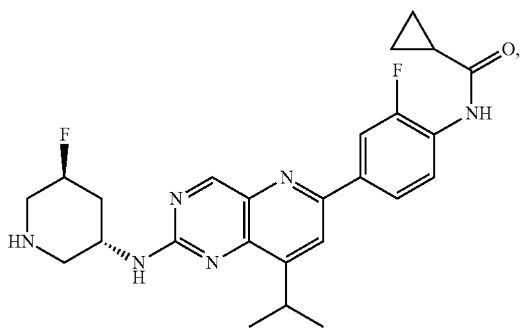 [SMILES: CC(C)c1cc(-c2ccc(NC(=O)C3CC3)c(F)c2)nc2cnc(N[C@@H]3CNC[C@@H](F)C3)nc12] |
| 237 | 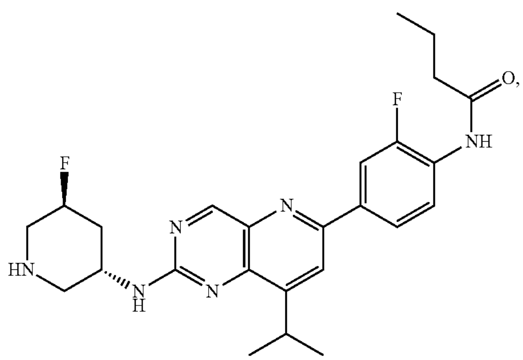 [SMILES: CCCC(=O)Nc1ccc(-c2cc(C(C)C)c3nc(N[C@@H]4CNC[C@@H](F)C4)ncc3n2)cc1F] |
| 238 | 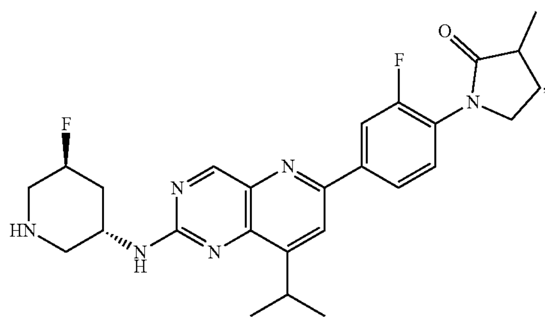 [SMILES: CC1CCN(c2ccc(-c3cc(C(C)C)c4nc(N[C@@H]5CNC[C@@H](F)C5)ncc4n3)cc2F)C1=O] |
| 239 | 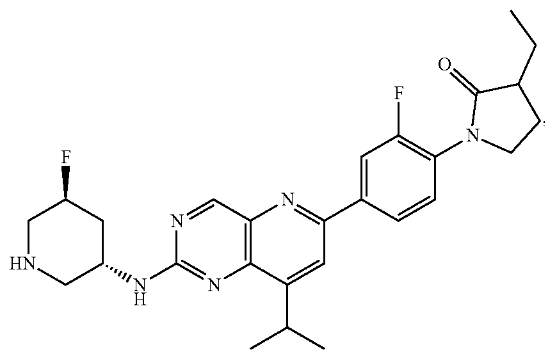 [SMILES: CCC1CCN(c2ccc(-c3cc(C(C)C)c4nc(N[C@@H]5CNC[C@@H](F)C5)ncc4n3)cc2F)C1=O] |

-continued
| Cmpd No. | Structure |
|---|---|
| 240 | 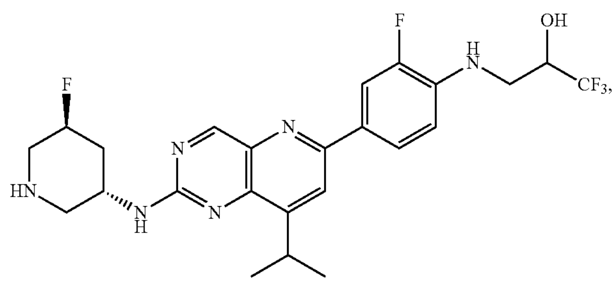 [SMILES: CC(C)c1cc(-c2ccc(NCC(O)C(F)(F)F)c(F)c2)nc2cnc(N[C@@H]3CNC[C@@H](F)C3)nc12] |
| 241 | 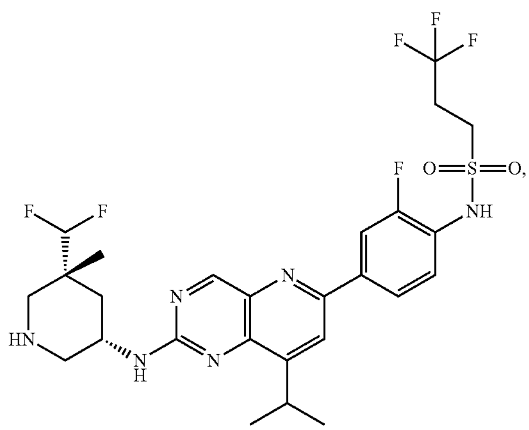 [SMILES: CC(C)c1cc(-c2ccc(NS(=O)(=O)CCC(F)(F)F)c(F)c2)nc2cnc(N[C@@H]3CNC[C@](C)(C(F)F)C3)nc12] |
| 242 | 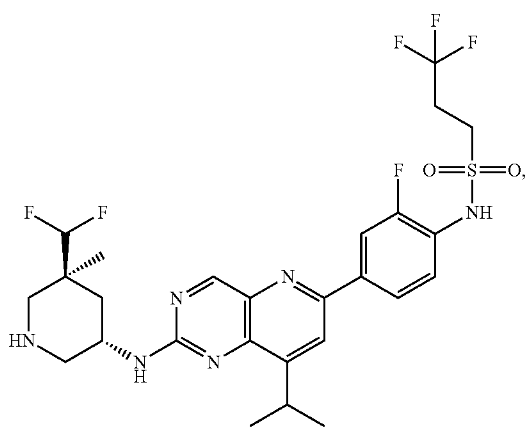 [SMILES: CC(C)c1cc(-c2ccc(NS(=O)(=O)CCC(F)(F)F)c(F)c2)nc2cnc(N[C@@H]3CNC[C@@](C)(C(F)F)C3)nc12] |
| 243 | 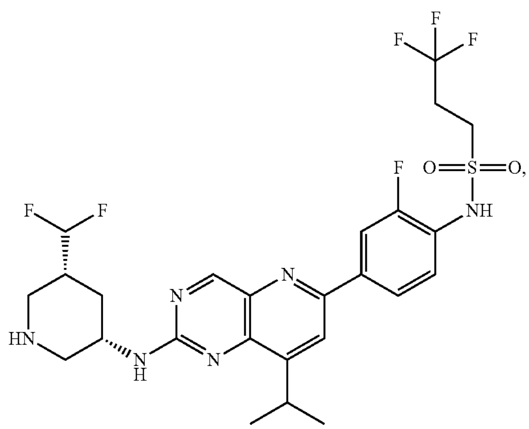 [SMILES: CC(C)c1cc(-c2ccc(NS(=O)(=O)CCC(F)(F)F)c(F)c2)nc2cnc(N[C@@H]3CNC[C@H](C(F)F)C3)nc12] |

-continued
| Cmpd No. | Structure |
| --- | --- |
| 244 | 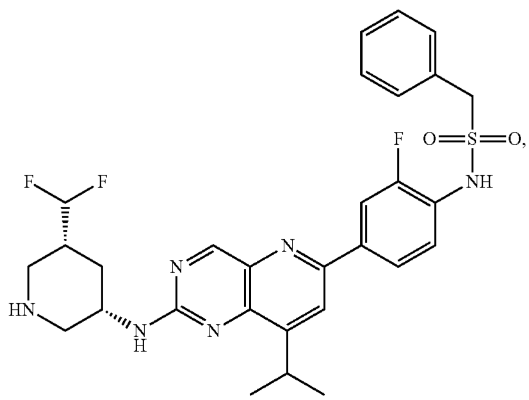 [SMILES: CC(C)c1cc(-c2ccc(NS(=O)(=O)Cc3ccccc3)c(F)c2)nc2cnc(N[C@@H]3CNC[C@H](C(F)F)C3)nc12] |
| 245 | 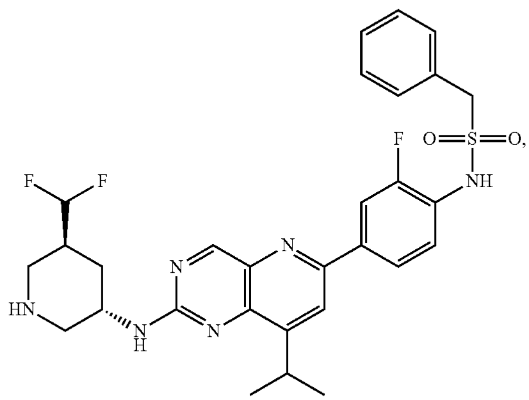 [SMILES: CC(C)c1cc(-c2ccc(NS(=O)(=O)Cc3ccccc3)c(F)c2)nc2cnc(N[C@@H]3CNC[C@@H](C(F)F)C3)nc12] |
| 246 | 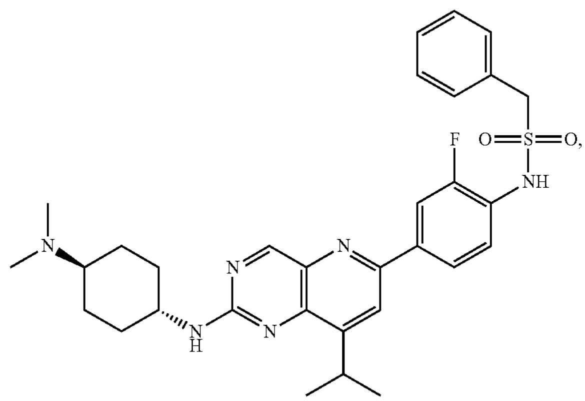 [SMILES: CC(C)c1cc(-c2ccc(NS(=O)(=O)Cc3ccccc3)c(F)c2)nc2cnc(N[C@H]3CC[C@H](N(C)C)CC3)nc12] |
| 247 | 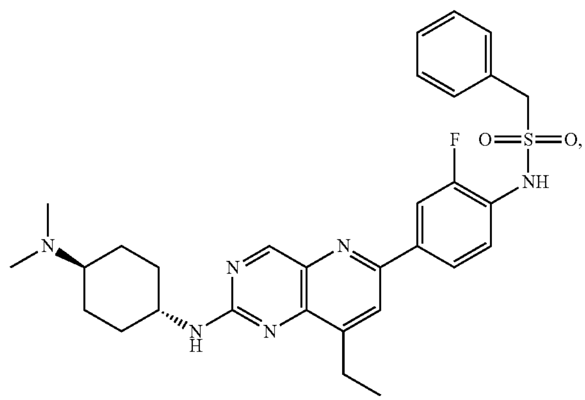 [SMILES: CCc1cc(-c2ccc(NS(=O)(=O)Cc3ccccc3)c(F)c2)nc2cnc(N[C@H]3CC[C@H](N(C)C)CC3)nc12] |

-continued
| Cmpd No. | Structure |
|---|---|
| 248 | 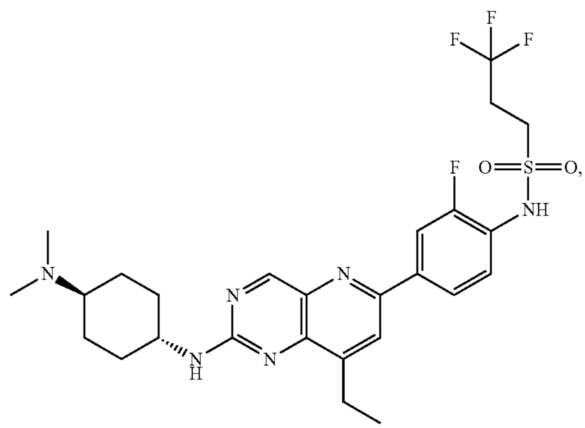 [SMILES: CCc1cc(-c2ccc(NS(=O)(=O)CCC(F)(F)F)c(F)c2)nc2cnc(N[C@H]3CC[C@H](N(C)C)CC3)nc12] |
| 249 | 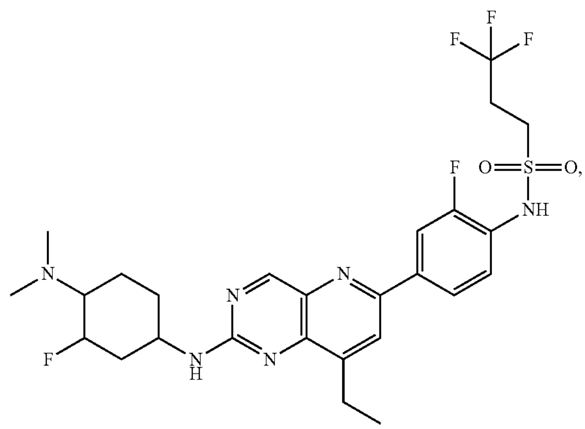 [SMILES: CCc1cc(-c2ccc(NS(=O)(=O)CCC(F)(F)F)c(F)c2)nc2cnc(NC3CCC(N(C)C)C(F)C3)nc12] |
| 259 | 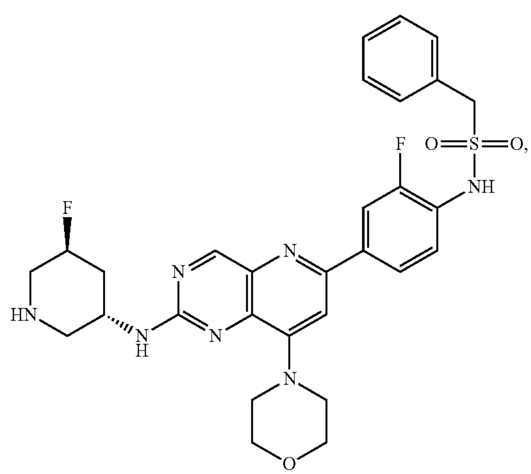 [SMILES: O=S(=O)(Cc1ccccc1)Nc1ccc(-c2cc(N3CCOCC3)c3nc(N[C@@H]4CNC[C@@H](F)C4)ncc3n2)cc1F] |

-continued
| Cmpd No. | Structure |
|---|---|
| 260 | 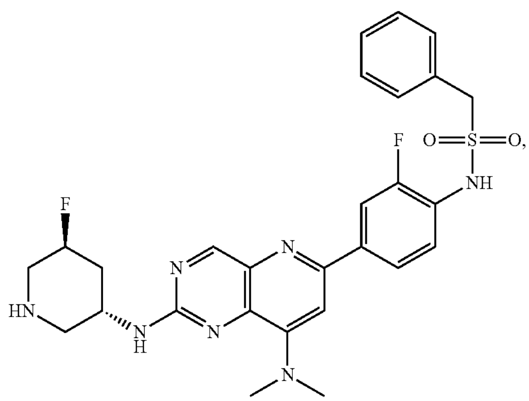 [SMILES: CN(C)c1cc(-c2ccc(NS(=O)(=O)Cc3ccccc3)c(F)c2)nc2cnc(N[C@@H]3CNC[C@@H](F)C3)nc12] |
| 261 | 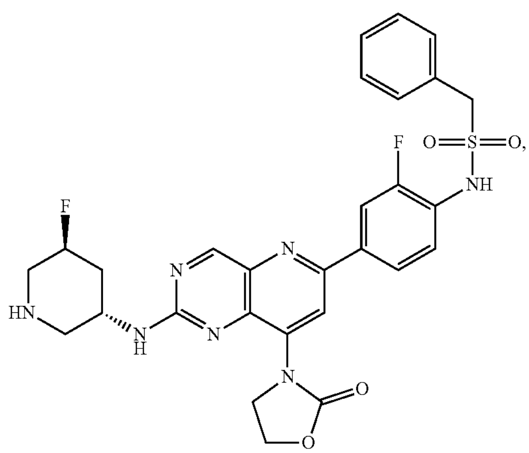 [SMILES: O=C1OCCN1c1cc(-c2ccc(NS(=O)(=O)Cc3ccccc3)c(F)c2)nc2cnc(N[C@@H]3CNC[C@@H](F)C3)nc12] |
| 262 | 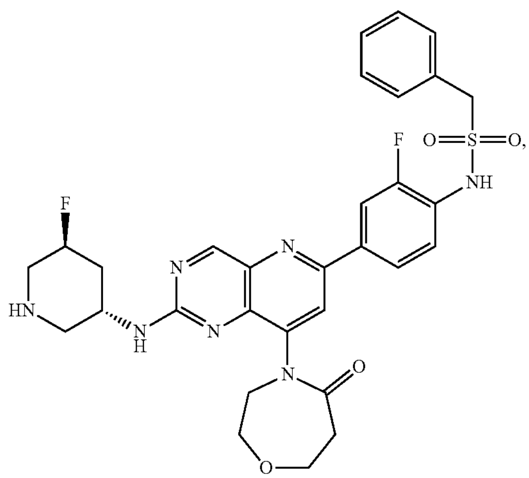 [SMILES: O=C1CCOCCN1c1cc(-c2ccc(NS(=O)(=O)Cc3ccccc3)c(F)c2)nc2cnc(N[C@@H]3CNC[C@@H](F)C3)nc12] |

-continued
| Cmpd No. | Structure |
|---|---|
| 263 | 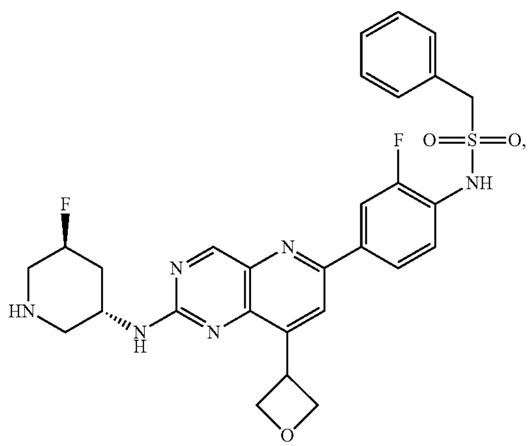 [SMILES: O=S(=O)(Cc1ccccc1)Nc1ccc(-c2cc(C3COC3)c3nc(N[C@@H]4CNC[C@@H](F)C4)ncc3n2)cc1F] , |
| 264 | 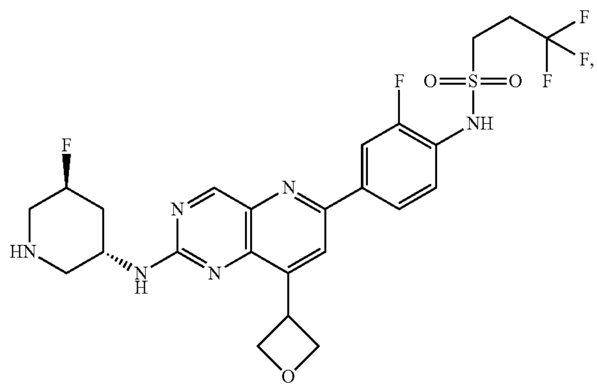 [SMILES: O=S(=O)(CCC(F)(F)F)Nc1ccc(-c2cc(C3COC3)c3nc(N[C@@H]4CNC[C@@H](F)C4)ncc3n2)cc1F] , |
| 265 | 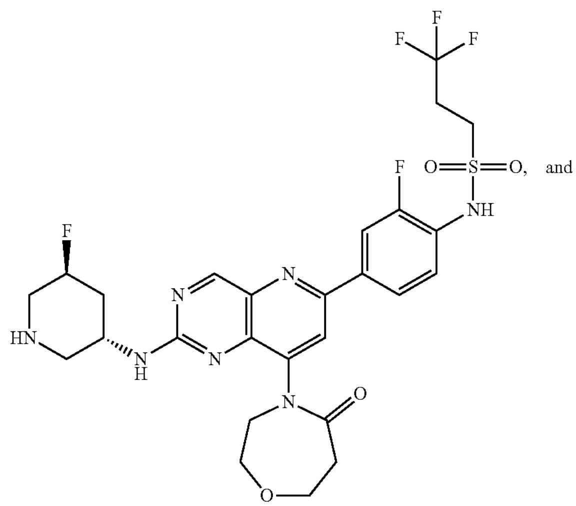 [SMILES: O=C1CCOCCN1c1cc(-c2ccc(NS(=O)(=O)CCC(F)(F)F)c(F)c2)nc2cnc(N[C@@H]3CNC[C@@H](F)C3)nc12 ; "and"] , and |

-continued

| Cmpd No. | Structure |
| --- | --- |
| 266 | 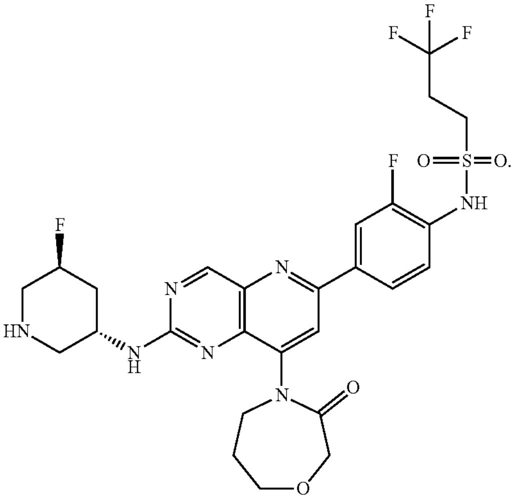 [SMILES: O=C1COCCCN1c1cc(-c2ccc(NS(=O)(=O)CCC(F)(F)F)c(F)c2)nc2cnc(N[C@@H]3CNC[C@@H](F)C3)nc12] |

24. A pharmaceutical composition comprising a compound or pharmaceutically acceptable salt thereof of claim 1 and one or more pharmaceutically acceptable excipients.

25. A method of treating an IRE1-related disease or disorder, wherein the IRE1-related disease or disorder is cancer, the method comprising administering to a subject having an IRE1-related disease or disorder an effective amount of the compound of claim 1 or a pharmaceutically acceptable salt thereof, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, head and neck cancer, lymphoma, lymphocytic leukemia, multiple myeloma (MM), acute myelogenous leukemia (AML), chronic myelogenous leukemia (CML), myelodysplastic syndrome (MDS), myeloproliferative disease (MPD), or triple-negative breast cancer (TNBC).

* * * * *

SEQUENCE LISTING

```
<160> NUMBER OF SEQ ID NOS: 1

<210> SEQ ID NO 1
<211> LENGTH: 17
<212> TYPE: RNA
<213> ORGANISM: Artificial Sequence
<220> FEATURE:
<223> OTHER INFORMATION: Synthetic

<400> SEQUENCE: 1

cauguccgca gcgcaug                                                 17
```